(12) United States Patent
Chinnaiyan

(10) Patent No.: US 7,700,293 B2
(45) Date of Patent: *Apr. 20, 2010

(54) EXPRESSION PROFILE OF PROSTATE CANCER

(75) Inventor: Arul M. Chinnaiyan, Plymouth, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 2 days.

This patent is subject to a terminal disclaimer.

(21) Appl. No.: 11/924,415

(22) Filed: Oct. 25, 2007

(65) Prior Publication Data

US 2008/0222741 A1  Sep. 11, 2008

Related U.S. Application Data

(60) Continuation-in-part of application No. 11/343,797, filed on Jan. 31, 2006, which is a division of application No. 10/210,120, filed on Aug. 1, 2002, now Pat. No. 7,229,774.

(60) Provisional application No. 60/309,581, filed on Aug. 2, 2001, provisional application No. 60/334,468, filed on Nov. 15, 2001.

(51) Int. Cl.
*C12Q 1/68* (2006.01)

(52) U.S. Cl. .................................................. 435/6

(58) Field of Classification Search ................ None
See application file for complete search history.

(56) References Cited

U.S. PATENT DOCUMENTS

| | | | |
|---|---|---|---|
| 5,871,960 | A | 2/1999 | Smith |
| 5,871,961 | A | 2/1999 | Smith |
| 5,981,830 | A | 11/1999 | Wu |
| 6,335,170 | B1 | 1/2002 | Orntoft |
| 6,465,611 | B1 | 10/2002 | Xu |
| 6,518,028 | B1 | 2/2003 | O'Brien |
| 6,620,922 | B1 | 9/2003 | Xu |
| 6,630,305 | B1 | 10/2003 | Xu |
| 6,664,377 | B1 | 12/2003 | Xu |
| 6,759,515 | B1 | 7/2004 | Xu |
| 6,800,746 | B2 | 10/2004 | Xu |
| 6,818,751 | B1 | 11/2004 | Xu |
| 7,229,774 | B2 * | 6/2007 | Chinnaiyan et al. .......... 435/7.1 |
| 2002/0123081 | A1 | 9/2002 | Richardson |
| 2003/0108963 | A1 | 6/2003 | Schlegel |

FOREIGN PATENT DOCUMENTS

| | | |
|---|---|---|
| WO | 9718825 | 5/1997 |
| WO | 0125272 | 4/2001 |
| WO | 0157194 | 8/2001 |
| WO | 0162271 | 8/2001 |
| WO | 0173032 | 10/2001 |
| WO | 0177389 | 10/2001 |
| WO | 0227324 | 4/2002 |
| WO | 02059373 | 8/2002 |

OTHER PUBLICATIONS

Abel et al., "Characterization of EZH1, a human homolog of Drosophila Enhancer of zeste near BRCA1.," Genomics 37:161 (1996).
Alizadeh et al., "Distinct types of diffuse large B-cell lymphoma identified by gene expression profiling," Nature 403:503 [2000].
An et al., Proceedings of the Annual Mtg. of An Assoc for Cancer Research 40:235-236 (Apr. 10-14, 1999), Philadelphia, PA, USA.
Breuer et al., "Very high frequency of lymphoma induction by a chemical carcinogen in pim-1 transgenic mice," Nature 340:61 [1989].
Brichory et al., "An immune response manifested by the common occurrence of annexins I and II autoantibodies and high circulating levels of IL-6 in lung cancer," PNAS 98:9824-9829 (2001).
Brock et al., "The Polycomb group—no longer an exclusive club?," Curr. Opin. Genet. Dev. 11:175 [2001].
Brown and Botstein, "Exploring the new world of the genome with DNA microarrays," Nat. Gent., 21:33 [1999].
Chan et al., "Annexin IV inhibits calmodulin-dependent protein kinase II-activated chloride conductance. A novel mechanism for ion channel regulation," J. Biol. Chem. 269:32464 [1994].
Chen et al., "Cloning of a human homolog of the Drosophila enhancer of zeste gene (EZH2) that maps to chromosome 21q22.2," Genomics 38:30 (1996).
Chinnadurai, "CtBP, an unconventional transcriptional corepressor in development and oncogenesis," Mol Cell. 9: 213 [2002].
Clayton et al., "Clinical consequences of defects in peroxisomal beta-oxidation," Biochem. Soc. Trans. 29:298 [2001].
Cohly, et al., Pilot-Study: A Non-Invasive Urine Test ofr Potential Prostate Abnormalities; Int. J. Mol. Sci. (2002), vol. 3, pp. 1039-1047.
Cuypers et al., "Murine leukemia virus-induced T-cell lymphomagenesis: integration of proviruses in a distinct chromosomal region," Cell 37:141 [1984].
De Marzo et al., "Proliferative inflammatory atrophy of the prostate: implications for prostatic carcinogenesis," Am J Pathol 155:1985 [1999].
Debril et al., "The pleiotropic functions of peroxisome proliferator-activated receptor gamma," J. Mol. Med. 79:30 [2001].
Dhanasekaran et al., "Delineation of prognostic biomarkers in prostate cancer," Nature 412: 822 [2001].
Eisen et al., "Cluster analysis and display of genome-wide expression patterns," PNAS 95:14863 [1998].
Elek et al., "Microarray-based expression profiling in prostate tumors," Int. J. of In vivo Res 14:173 (2000).
Emmert Buck et al., "Molecular profiling of clinical tissue specimens: feasibility and applications," Am. J. Pathol., 156:1109 [2000].
Epstein and Potter, "The pathological interpretation and significance of prostate needle biopsy findings: implications and current controversies," J. Urol., 166:402 [2001].

(Continued)

*Primary Examiner*—Young J Kim
(74) *Attorney, Agent, or Firm*—Casimir Jones, S.C.

(57) ABSTRACT

The present invention relates to compositions and methods for cancer diagnostics, including but not limited to, cancer markers. In particular, the present invention provides gene expression profiles associated with prostate cancers. Genes identified as cancer markers using the methods of the present invention find use in the diagnosis and characterization of prostate cancer. In addition, the genes provide targets for cancer drug screens and therapeutic applications.

9 Claims, 136 Drawing Sheets

OTHER PUBLICATIONS

Etzioni et al., "Cancer surveillance series: interpreting trends in prostate cancer—part III: Quantifying the link between population prostate-specific antigen testing and recent declines in prostate cancer mortality," J. Natl. Cancer Inst., 91:1033 [1999].

Ferdinandusse et al., "Mutations in the gene encoding peroxisomal alpha-methylacyl-CoA racemase cause adult-onset sensory motor neuropathy," Nat. Genet., 24:188 [2000].

Ferdinandusse et al., Plasma analysis of di- and trihydroxycholestanoic acid diastereoisomers in peroxisomal alpha-methylacyl-CoA racemase deficienc J Lipid Res 42:137 [2001].

Ferdinandusse et al., "Subcellular localization and physiological role of alpha-methylacyl-CoA racemase," J. Lipid Res., 41:1890 [2000].

Fox Chase Center, Publication Online, Apr. 20, 2000, 2 pages at http:///:www.sciencedaily.com/releases/2000/04/000406090853.htm.

Francis et al., "In vitro studies on L-771,688 (SNAP 6383), a new potent and selective alpha1A-adrenoceptor antagonist," Eur J Pharmacol 2:409 [2001].

Grande et al., "Prognostic value of serial tissue prostate-specific antigen measurements during different hormonal treatments in prostate cancer patients," Clin Cancer Res., 6:1790 (2000).

Grover, et al., "Highi resolution two-dimesional electrophoretic analysis of urinary proteins of patients with prostatic cancer," Electrophoresis, vol. 18, pp. 814-818 (1997).

Gunster eta l., "Differential expression of human Polycomb group proteins in various tissues and cell types," J. Cell Biochem. Supl. 36:129 (2001).

Hammond et al., "An RNA-directed nuclease mediates post-transcriptional gene silencing in Drosophila cells," Nature 404:293 [2000].

Hinoi et al., "Loss of CDX2 expression and microsatellite instability are prominent features of large cell minimally differentiated carcinomas of the colon," Am. J. Pathol. 159:2239 [2001].

Hisatake et al., "Down-Regulation of prostate-specific antigen expression by ligands for peroxisome proliferator-activated receptor gamma in human prostate cancer," Cancer Res. 60:5494 [2000].

Hubaishy et al., "Modulation of annexin II tetramer by tyrosine phosphorylation," Biochemistry 34:14527 [1995].

Jacobs et al., "The oncogene and Polycomb-group gene bmi-1 regulates cell proliferation and senescence through the ink4a locus.," Nature 397:164 [1999].

Jacobsen et al., "Incidence of prostate cancer diagnosis in the eras before and after serum prostate-specific antigen testing," JAMA 274:1445 [1995].

Jenuwein et al., "Set domain proteins modulate chromatin domains in eu- and heterochromatin," Cell. Mol. Life Sci. 54:80 [1998].

Jiang, et al., Expression of a π-Methylacyl-CoA Racemase (P504S) in various Malignant Neoplasms and Normal Tissues: Hum. Pathol., (2003) vol. 34, No. 8, pp. 792-796.

Kazama et al., "Hepsin, a putative membrane-associated serine protease, activates human factor VII and initiates a pathway of blood coagulation on the cell surface leading to thrombin formation," J. Biol. Chem., 270:66 [1995].

Kotti et al., "In mouse alpha -methylacyl-CoA racemase, the same gene product is simultaneously located in mitochondria and peroxisomes," J. Biol.Chem., 275:20887 [2000].

Kubota et al., "Ligand for peroxisome proliferator-activated receptor gamma (troglitazone) has potent antitumor effect against human prostate cancer both in vitro and in vivo," Cancer Res. 58:3344 [1998].

Kuefer et al., "α-Methyacyl-CoA Racemase: Expression Levels of this Novel Cancer Biomarker Depend on Tumor," Am. J. Pathol. (2002), vol. 161, No. 3, pp. 841-848.

Kumar Smith et al., "Base excess and lactate as prognostic indicators for patients admitted to intensive care.," J. Biol. Chem. 276(24)21039-45 [2001].

Kurachi et al., "Hepsin," Methods Enzymol., 244:100 [1994].

Laible et al., "Mammalian homologues of the Polycomb-group gene Enhancer of zeste mediate gene silencing in Drosophila heterochromatin and at S. cerevisiae telomeres," Embo. J. 16:3219 [1997].

Luo et al., "Human prostate cancer and benign prostatic hyperplasia: molecular dissection by gene expression pro," Cancer Res. 61:4683 [2001].

Maattanen et al., "European randomized study of prostate cancer screening: first-year results of the Finnish trial", Br. J. Cancer 79:1210 [1999].

Macejak et al., "Inhibition of hepatitis C virus (HCV)-RNA-dependent translation and replication of a chimeric HCV poliovirus using synthetic stabilized ribozymes," Hepatology 31:769 [2000].

Magee et al., "Expression profiling reveals hepsin overexpression in prostate cancer," Cancer Res. 61:5692 [2001].

Mahmoudi et al., "Chromatin silencing and activation by Polycomb and trithorax group proteins," Oncogene 20:3055 [2001].

Mailliard et al., "Calcium-dependent binding of S100C to the N-terminal domain of annexin I," J Biol. Chem. 271:719 [1996].

Matikainen et al., "Interferon-alpha activates multiple STAT proteins and upregulates proliferation-associated IL-2Ralpha, c-myc, and pim-1 genes in human T cells," Blood 93:1980 [1999].

McNeal and Bostwick, "Intraductal dysplasia: a premalignant lesion of the prostate," Hum Pathol 17:64 [1986].

McNeal et al., "Patterns of progression in prostate cancer," Lancet 1:60 [1986].

Moyad, "Fat reduction to prevent prostate cancer: waiting for more evidence?," Curr Opin Urol 11:457 [2001].

Mueller et al., "Effects of ligand activation of peroxisome proliferator-activated receptor gamma in human prostate cancer," PNAS 97:10990 [2000].

Nelson et al., "Contemporary preoperative parameters predict cancer-free survival after radical prostatectomy: a tool to facilitate treatment decisions," Urol. Oncol. 21:213-8 [2003].

Nelson et al., "Preoperative parameters for predicting early prostate cancer recurrence after radical prostatectomy.," Urology 59:740-5; discussion 745-6 [2002].

O'Carroll et al., "The polycomb-group gene Ezh2 is required for early mouse development," Mol. Cell. Biol. 21:4330 [2001].

Paweletz et al., "Loss of annexin 1 correlates with early onset of tumorigenesis in esophageal and prostate carcinoma," Cancer Res. 60:6293 [2000].

Pepinsky et al., "Epidermal growth factor-dependent phosphorylation of lipocortin," Nature 321:81 [1986].

Riefler et al., "Binding of neuronal nitric-oxide synthase (nNOS) to carboxyl-terminal-binding protein (CtBP) changes the localization of CtBP from the nucleus to the cytosol: a novel function for targeting by the PDZ domain of nNOS," J. Biol. Chem. 276:48262 [2001].

Rogers, CG, "Prostate Cancer Detection on Urinalysis for α-Methylacyl Coenzyme a Racemase Protein," The Journal of Urology, vol. 172, pp. 1502-1503, Oct. 2004.

Rubin et al., "alpha-Methylacyl coenzyme A racemase as a tissue biomarker for prostate cancer," JAMA 287 (13):1662-70 [2002].

Rubin, et al., Quantiative Determination of Expression of the Prostate Cancer Protein π-Methylacyl CoA Racemase; Am. J. Pathol. Mar. 3, 2004, vol. 164, No. 3, pp. 831-840.

Saez et al., "Activators of the nuclear receptor PPARgamma enhance colon polyp formation,"Nat. Med. 4:1058 [1998].

Satijin et al., "The polycomb group protein EED interacts with YY1, and both proteins induce neural tissue in Xenopus embryos," Mol. Cell. Biol. 21:1360 [2001].

Satijn et al., "Polycomb group protein complexes: do different complexes regulate distinct target genes?," Biochim. Biophys. Acta. 1447:1 [1999], pp. 1-16.

Scheurle et al., "HER-2/neu expression in archival non-small cell lung carcinomas using FDA-approved Hercep test," Anticancer Res. 20:2091 (2000).

Schmitz et al., "Purification and characterization of an alpha-methylacyl-CoA racemase from human liver," Eur J Biochem 231:815 [1995].

Schroder et al., "Evaluation of the digital rectal examination as a screening test for prostate cancer. Rotterdam section of the European Randomized Study of Screening for Prostate Can," J. Natl. Cancer Inst., 90:1817 [1998].

Selbert et al., "Annexin VII relocalization as a result of dystrophin deficiency," Exp. Cell. Res. 222:199 [1996].

Sewalt et al., "Characterization of interactions between the mammalian polycomb-group proteins Enx1/EZH2 and EED suggests the existence of different mammalian polycomb-group protein complexes," Mol. Cell. Biol. 18:3586 [1998].

Shah et al., "Postatrophic hyperplasia of the prostate gland: neoplastic precursor or innocent bystander?," Am J Pathol 158:1767 [2001].

Shappell et al "15S-Hydroxyeicosatetraenoic acid activates peroxisome proliferator-activated receptor gamma and inhibits proliferation in PC3 prostate carcinoma cells," Cancer Res. 61:497 [2001].

Shirogane, et al., "Synergistic roles for Pim-1 and c-Myc in STAT3-mediated cell cycle progression and antiapoptosis," Immunity 11:709 [1999].

Shurbaji et al., "Immunohistochemical detection of a fatty acid synthase (OA-519) as a predictor of progression of prostate cancer," Hum. Pathol., 27:917 [1996].

Sinclair et al., "Enhancer of Polycomb is a suppressor of position-effect variegation in Drosophila melanogaster," Genetics 148:211 [1998].

Smith et al., "Structural evolution of the annexin supergene family," Trends. Genet. 10:241 [1994].

Sreekumar et al, "Humoral Immune Response to α-Methylacyl-CoA Racemase and Prostate Cancer," The Journal of Cancer Institute, vol. 96, No. 11, Jun. 2, 2004.

Stamey et al., "Molecular genetic profiling of Gleason grade 4/5 prostate cancers compared to benign prostatic hyperplasia," J. Urology vol. 166, No. 6, pp. 2171-2177 (2001).

Tanimoto et al., "Hepsin, a cell surface serine protease identified in hepatoma cells, is overexpressed in ovarian cancer," Cancer Res., 57:2884 [1997].

Tomita et al., "Cadherin switching in human prostate cancer progression." Cancer Res., 60:3650 [2000].

Torres Rosado et al., "Hepsin, a putative cell-surface serine protease, is required for mammalian cell growth," PNAS, 90:7181 [1993].

Tsao and Shibata, "Further evidence that one of the earliest alterations in colorectal carcinogenesis involves APC," Am J Pathol 145: 531 [1994].

Tsuji et al., "Hepsin, a cell membrane-associated protease. Characterization, tissue distribution, and gene localization," J. Biol. Chem., 266:16948 [1991].

van Lohuizzen et al., "Identification of cooperating oncogenes in E mu-myc transgenic mice by provirus tagging," Cell 65:737 [1991].

Visser et al., "The Polycomb group protein EZH2 is upregulated in proliferating, cultured human mantle cell lymphoma," Br. J. Hematol. 112:950 [2001].

Wallner et al., "Cloning and expression of human lipocortin, a phospholipase A2 inhibitor with potential anti-inflammatory activity," Nature 320:77 [1986].

Webber et al., "Acinar differentiation by non-malignant immortalized human prostatic epithelial cells and its loss by malignant cells," Carcinogenesis 18:1225 [1997].

Weigart et al., "CIBP/BARS induces fission of Golgi membranes by acylating tysophosphatidic acid," Nature 402:429 [1999].

Welsh et al., "Analysis of gene expression identifies candidate markers and pharmacological targets in prostate cancer," Cancer Res. 61:5974 [2001].

Willett, "Diet and cancer," Oncologist 5:393 [2000].

Yeldandi et al., "Hydrogen peroxide generation in peroxisome proliferator-induced oncogenesis," Mutat. Res. 448:159 [2000].

Yu et al., "Altered Hox expression and segmental identity in MII-mutant mice," Nature 378:505 [1995].

Zhou, et al., Expression and Diagnostic Utility of Alpha-Methylacyl-CoA-Racemase (P504S) in Foamy Gland and Pseudohyperplastic; Am. J. Syrg. Pathol., (2003), vol. 27, No. 6.

Zielie, PJ, "A Novel Diagnostic Test for Prostate Cancer Emerges from the Determination of α-Methylacyl-Coenzyme a Racemase in Prostatic Secretions," The Journal of Urology, vol. 172, pp. 1130-1133, Sep. 2004.

Zomer et al., "Pristanic acid and phytanic acid: naturally occurring ligands for the nuclear receptor peroxisome proliferator-activated receptor alpha," J. Lipid Res. 41:1801 [2000].

Raaphorst, Frank M., et al.; "Coexpression of BMI-1 and EZH2 Polycomb Group Genes in Reed-sternberg Cells of Hodgkin's Disease"; American Journal of Pathology, vol. 157, No. 3, Sep. 2000; pp. 709-715.

* cited by examiner

Figure 9

| SEQ ID NO | Name | Accession Number |
|---|---|---|
| 1 | Hepsin | M18930 |
| 2 | pim-1 | M54915 |
| 3 | FKBP5 | XM_004288 |
| 4 | FASN | NM_004104 |
| 5 | FOLH1 | M99487 |
| 6 | TNFSF10 | XM_045049 |
| 7 | PCM1 | XM_044711 |
| 8 | S100A11 | XM_047223 |
| 9 | IGFBP3 | XM_004689 |
| 10 | SLUG | XM_011634 |
| 11 | GSTM3 | J05459 |
| 12 | IL1R2 | X59770 |
| 13 | ITGB4 | X53587 |
| 14 | CCND2 | XM_034568 |
| 15 | EDNRB | S57283 |
| 16 | APP | X06989 |
| 17 | THROMBOSPONDIN 1 | X04665 |
| 18 | ANNEXIN A1 | XM_005665 |
| 19 | EPHA1 | M18391 |
| 20 | NCK1 | XM_051968 |
| 21 | MAPK6 | XM_017662 |
| 22 | SGK | XM_037045 |
| 23 | HEVIN | XM_011533 |
| 24 | MEIS2 | XM_012430 |
| 25 | MYLK | XM_042191 |
| 26 | FZD7 | NM_003507 |
| 27 | CAVEOLIN 2 | XM_004966 |
| 28 | TACC1 | XM_049505 |
| 29 | ARHB | XM_002689 |
| 30 | PSG9 | NM_002784 |
| 31 | GSTM1 | NM_000561 |
| 32 | Keratin 5 | XM_006847 |
| 33 | TIMP2 | XM_027036 |
| 34 | GELSOLIN | XM_016545 |
| 35 | ITM2C | AA034213 |
| 36 | GSTM5 | XM_002154 |
| 37 | VINCULIN | XM_011883 |
| 38 | FHL1 | XM_042931 |

Figure 9 (cont.)

| 39 | GSTP1 | XM_040116 |
|---|---|---|
| 40 | MEIS1 | XM_010880 |
| 41 | ETS2 | XM_009766 |
| 42 | PPP2CB | XM_005121 |
| 43 | CATHEPSIN B | XM_005133 |
| 44 | COL1A2 | XM_029246 |
| 45 | RIG | XM_006029 |
| 46 | VIMENTIN | XM_042952 |
| 47 | MOESIN | XM_013042 |
| 48 | MCAM | XM_006077 |
| 49 | FIBRONECTIN 1 | XM_030549 |
| 50 | NBL1 | XM_001434 |
| 51 | ANNEXIN A4 | XM_031594 |
| 52 | ANNEXIN A11 | XM_035906 |
| 53 | IL1R1 | XM_002686 |
| 54 | IGFBP5 | XM_046731 |
| 55 | CYSTATIN C | XM_009599 |
| 56 | COL15A1 | XM_005592 |
| 57 | ADAMTS1 | XM_047796 |
| 58 | SKI | XM_001535 |
| 59 | EGR1 | XM_033546 |
| 60 | FOSB | NM_006732 |
| 61 | CFLAR | XM_027980 |
| 62 | JUN | XM_001472 |
| 63 | YWHAB | XM_009519 |
| 64 | NRAS | XM_001317 |
| 65 | C7 | J03507 |
| 66 | SCYA2 | XM_038982 |
| 67 | ITGA1 | XM_032902 |
| 68 | LUMICAN | XM_006900 |
| 69 | C1S | XM_032536 |
| 70 | C4BPA | XM_052053 |
| 71 | COL3A1 | XM_044878 |
| 72 | FAT | XM_003477 |
| 73 | MMECD10 | XM_030168 |
| 74 | CLUSTERIN | XM_005113 |
| 75 | PLA2G2A | XM_027887 |
| 76 | MADH4 | XM_030100 |
| 77 | SEPP1 | XM_011306 |
| 78 | RAB2 | XM_037653 |
| 79 | PP1CB | NM_002709 |
| 80 | MPDZ | XM_051281 |

Figure 9 (cont.)

| 81 | PRKCL2 | XM_001880 |
|---|---|---|
| 82 | ATF2 | XM_027217 |
| 83 | RAB5A | NM_004162 |
| 84 | Cathepsin H | XM_007633 |
| 85 | CTBP1 | XM_003445 |
| 86 | MAP3K10 | XM_042665 |
| 87 | TBXA2R | XM_047633 |
| 88 | MTA1 | NM_004689 |
| 89 | RAP2 | NM_002886 |
| 90 | TRAP1 | XM_036666 |
| 91 | TFCP2 | XM_051171 |
| 92 | E2-EPF | XM_012615 |
| 93 | UBCH10 | XM_009488 |
| 94 | TASTIN | XM_006826 |
| 95 | EZH2 | XM_004774; NM004456 |
| 96 | FLS353 | AB024704 |
| 97 | MYBL2 | XM_009492 |
| 98 | LIMK1 | XM_051836 |
| 99 | TRAF4 | XM_031428 |
| 104 | AMACR | XM_043772; NM01324 |
| 114 | GP73 | AF236056 |
| 115 | CTBP2 | AF016507 |
| 116 | Annexin A2 | NM_004039 |
| 117 | Annexin A4 | XM_031596 |
| 118 | Annexin A11 | NM_001157 |
| 119 | ABCC5 (MDR5) | XM_002914 |
| 120 | ASNS | M27396 |
| 121 | TOP2A | NM_001067 |
| 122 | VaV2 | XM_005638 |

Figure 10

```
SEQ ID NO:1
1      tcgagcccgc tttccaggga ccctacctga gggcccacag gtgaggcagc ctggcctagc
61     aggccccacg ccaccgcctc tgcctccagg ccgcccgctg ctgcggggcc accatgctcc
121    tgcccaggcc tggagactga cccgaccccg gcactacctc gaggctccgc ccccacctgc
181    tggaccccag ggtcccaccc tggcccagga ggtcagccag ggaatcatta acaagaggca
241    gtgacatggc gcagaaggag ggtggccgga ctgtgccatg ctgctccaga cccaaggtgg
301    cagctctcac tgcggggacc ctgctacttc tgacagccat cggggcggca tcctgggcca
361    ttgtggctgt tctcctcagg agtgaccagg agccgctgta cccagtgcag gtcagctctg
421    cggacgctcg gctcatggtc tttgacaaga cggaagggac gtggcggctg ctgtgctcct
481    cgcgctccaa cgccagggta gccggactca gctgcgagga gatgggcttc ctcaggcac
541    tgacccactc cgagctggac gtgcgaacgg cgggcgccaa tggcacgtcg ggcttcttct
601    gtgtggacga ggggaggctg ccccacaccc agaggctgct ggaggtcatc tccgtgtgtg
661    attgccccag aggccgtttc ttggccgcca tctgccaaga ctgtggccgc aggaagctgc
721    ccgtggaccg catcgtggga ggccgggaca ccagcttggg ccggtggccg tggcaagtca
781    gccttcgcta tgatggagca caactctgtg ggggatccct gctctccggg gactgggtgc
841    tgacagccgc ccactgcttc ccggagcgga accgggtcct gtcccgatgg cgagtgtttg
901    ccggtgccgt ggcccaggcc tctccccacg gtctgcagct gggggtgcag gctgtggtct
961    accacggggg ctatcttccc tttcgggacc ccaacagcga ggagaacagc aacgatattg
1021   ccctggtcca cctctccagt ccctgcccc tcacagaata catccagcct gtgtgcctcc
1081   cagctgccgg ccaggccctg gtggatggca agatctgtac cgtgacgggc tggggcaaca
1141   cgcagtacta tggccaacag gccggggtac tccaggaggc tcgagtcccc ataatcagca
1201   atgatgtctg caatggcgct gacttctatg gaaaccagat caagcccaag atgttctgtg
1261   ctggctaccc cgagggtggc attgatgcct gccagggcga cagcggtggt cccttctgtg
1321   gtgaggacag catctctcgg acgccacgtt ggcggctgtg tggcattgtg agttggggca
1381   ctggctgtgc cctggcccag aagccaggcg tctacaccaa agtcagtgac ttccggggagt
1441   ggatcttcca ggccataaag actcactccg aagccagcgg catggtgacc cagctctgac
1501   cggtggcttc tcgctgcgca gcctccaggg cccgaggtga tcccggtggt gggatccacg
1561   ctgggccgag gatgggacgt ttttcttctt gggcccggtc cacaggtcca aggacccct
1621   ccctccaggg tcctctcttc cacagtggcg ggccactca gccccgagac cacccaacct
1681   cacccctcctg acccccatgt aaatattgtt ctgctgtctg ggactcctgt ctaggtgccc
1741   ctgatgatgg gatgctcttt aaataataaa gatggtcttg att SEQ ID NO:2
1      gaggaggccc gagaggagtc ggtggcagcg gcggcggcgg gaccggcagc agcagcagca
61     gcagcagcag caaccactag cctcctgccc cgcggcgttg cgacgagccc cacgagccgc
121    tcaccccgcc gttctcagcg ctgcccgacc ccgctggcgc gcctccgcc gcagtccgg
181    cagcgcctca gttgtcctcc gactcgccct cggccttcgc gcagcgcagc acagccgcac
241    gcaccgcagc acagcacagc acagccagg catagcttcg gcacagcccc ggctccggct
301    cctgcggcag ctcctctggc acgtccctgc gccgacattc tggaggttgg atgctcttgt
361    ccaaaatcaa ctcgcttgcc cacctgcgcg ccgcgccctg caacgacctg cacgccacca
421    agctggcgcc cggcaaggag aaggagcccc tggagtcgca gtaccaggtg ggcccgctac
481    tgggcagcgg cggcttcggc tcggtctact caggcatccg cgtctccgac aacttgccgg
541    tggccatcaa acacgtggag aaggaccgga tttccgactg gggagagctg cctaatggca
601    ctcgagtgcc catggaagtg gtcctgctga gaaggtgag ctcgggtttc tccggcgtca
661    ttaggctcct ggactggttc gagaggcccg acagtttcgt cctgatcctg gagaggccg
721    agccggtgca agatctcttc gacttcatca cggaaagggg agccctgcaa gaggagctgg
781    cccgcagctt cttctggcag gtgctggagg ccgtgcggca ctgccacaac tgcggggtgc
```

Figure 10 (cont.)

```
 841    tacaccgcga catcaaggac gaaaacatcc ttatcgacct caatcgcggc gagctcaagc
 901    tcatcgactt cgggtcgggg gcgctgctca aggacaccgt ctacacggac ttcgatggga
 961    cccgagtgta tagccctcca gagtggatcc gctaccatcg ctaccatggc aggtcggcgg
1021    cagtctggtc cctggggatc ctgctgtatg atatggtgtg tggagatatt cctttcgagc
1081    atgacgaaga gatcatcagg ggccaggttt tcttcaggca gagggtctct tcagaatgtc
1141    agcatctcat tagatggtgc ttggccctga gaccatcaga taggccaacc ttcgaagaaa
1201    tccagaacca tccatggatg caagatgttc tcctgcccca ggaaactgct gagatccacc
1261    tccacagcct gtcgccgggg cccagcaaat agcagccttt ctggcaggtc ctccctctc
1321    ttgtcagatg cccgagggag gggaagcttc tgtctccagc ttcccgagta ccagtgacac
1381    gtctcgccaa gcaggacagt gcttgataca ggaacaacat ttacaactca ttccagatcc
1441    caggcccctg gaggctgcct cccaacagtg gggaagagtg actctccagg ggtcctaggc
1501    ctcaactcct cccatagata ctctcttctt ctcataggtg tccagcattg ctggactctg
1561    aaatatcccg ggggtggggg gtggggtgg gcagaaccct gccaatggaa ctctttcttc
1621    atcatgagtt ctgctgaatg ccgcgatggg tcaggtaggg gggaaacagg ttgggatggg
1681    ataggactag cacattttaa gtccctgtca cctcttccga ctctttctga gtgccttctg
1741    tggggactcc ggctgtgctg ggagaaatac ttgaacttgc ctcttttacc tgctgcttct
1801    ccaaaaatct gcctgggttt tgttccctat ttttctctcc tgtcctccct caccccctcc
1861    ttcatatgaa aggtgccatg gaagaggcta cagggccaaa cgctgagcca cctgcccttt
1921    tttctgcctc ctttagtaaa actccgagtg aactggtctt cctttttggt ttttacttaa
1981    ctgtttcaaa gccaagacct cacacacaca aaaaaatgca caaccaagc aatcaacaga
2041    aaagctgtaa atgtgtgtac agttggcatg gtagtataca aaaagattgt agtggatcta
2101    attttttaaga aattttgcct ttaagttatt ttacctgttt ttgtttcttg ttttgaaaga
2161    tgcgcattct aacctggagg tcaatgttat gtatttattt atttatttat ttggttccct
2221    tcctattcca agcttccata gctgctgccc tagttttctt tcctcctttc ctcctctgac
2281    ttggggacct tttgggggag ggctgcgacg cttgctctgt ttgtggggtg acgggactca
2341    ggcgggacag tgctgcagct ccctggcttc tgtggggccc ctcacctact tacccaggtg
2401    ggtcccggct ctgtgggtga tgggaggggc cattgctgac tgtgtatata ggataattat
2461    gaaacacagt tctggatggt gtgccttcca gatcctctct ggggctgtgt tttgagcagc
2521    aggtagcctg ctggttttat ctgagtgaaa tactgtacag gggaataaaa gagatcttat
2581    tttttttta tacttgcgtt tggaataaaa acccttggc ttt SEQ ID NO:3
   1    gaacaatgaa gaaagcccca cagccactgt tgctgagcag ggagaggata ttacctccaa
  61    aaaagacagg ggagtattaa agattgtcaa aagagtgggg aatggtgagg aaacgccgat
 121    gattggagac aaagtttatg tccattacaa aggaaaattg tcaaatggaa agaagtttga
 181    ttccagtcat gatagaaatg aaccatttgt ctttagtctt ggcaaaggcc aagtcatcaa
 241    ggcatgggac attggggtgg ctaccatgaa gaaaggagag atatgccatt tactgtgcaa
 301    accagaatat gcatatggct cggctggcag tctccctaaa attccctcga atgcaactct
 361    ctttttgag attgagctcc ttgatttcaa aggagaggat ttatttgaag atggaggcat
 421    tatccggaga accaaacgga aggagaggg atattcaaat ccaaacgaag gagcaacagt
 481    agaaatccac ctggaaggcc gctgtggtgg aaggatgttt gactgcagag atgtggcatt
 541    cactgtgggc gaaggagaag accacgacat tccaattgga attgacaaag ctctggagaa
 601    aatgcagcgg gaagaacaat gtatttata tcttggacca agatatggtt tggagaggc
 661    agggaagcct aaatttggca ttgaacctaa tgctgagctt atatatgaag ttacacttaa
 721    gagcttcgaa aaggccaaag aatcctggga gatggatacc aaagaaaaat tggagcaggc
 781    tgccattgtc aaagagaagg gaaccgtata cttcaaggga ggcaaataca tgcaggcggt
 841    gattcagtat gggaagatag tgtcctggtt agagatggaa tatggtttat cagaaaagga
 901    atcgaaagct tctgaatcat ttctccttgc tgcctttctg aacctggcca tgtgctacct
 961    gaagcttaga gaatacacca agctgttga atgctgtgac aaggcccttg gactggacag
1021    tgccaatgag aaaggcttgt ataggagggg tgaagcccag ctgctcatga acgagtttga
1081    gtcagccaag ggtgactttg agaaagtgct ggaagtaaac cccagaata aggctgcaag
1141    actgcagatc tccatgtgcc agaaaaaggc caaggagcac aacgagcggg accgcaggat
1201    atacgccaac atgttcaaga gtttgcaga gcaggatgcc aaggaagagg ccaataaagc
1261    aatgggcaag aagacttcag aagggtcac taatgaaaaa ggaacagaca gtcaagcaat
```

Figure 10 (cont.)

```
1321    ggaagaagag aaacctgagg gccacgtatg acgccacgcc aaggagggaa gagtcccagt
1381    gaactcggcc cctcctcaat gggctttccc ccaactcagg acagaacagt gtttaatgta
1441    aagtttgtta tagtctatgt gattctggaa gcaaatggca aaaccagtag cttcccaaaa
1501    acagccccc  tgctgctgcc cggagggttc actgaggggt ggcacgggac cactccaggt
1561    ggaacaaaca gaaatgactg tggtgtggag ggagtgagcc agcagcttaa gtccagctca
1621    tttcagtttc tatcaacctt caagtatcca attcagggtc cctggagatc atcctaacaa
1681    tgtggggctg ttaggtttta cctttgaact ttcatagcac tgcagaaacc tttaaaaaaa
1741    aaatgcttca tgaatttctc ctttcctaca gttgggtagg gtaggggaag gaggataagc
1801    ttttgttttt taaatgactg aagtgctata aatgtagtct gttgcatttt taaccaacag
1861    aacccacagt agaggggtct catgtctccc cagttccaca gcagtgtcac agacgtgaaa
1921    gccagaacct cagaggccac ttgcttgctg acttagcctc ctcccaaagt cccctcctc
1981    agccagcctc cttgtgagag tggctttcta ccacacacag cctgtccctg ggggagtaat
2041    tctgtcattc ctaaaacacc cttcagcaat gataatgagc agatgagagt ttctggatta
2101    gcttttccta ttttcgatga agttctgaga tactgaaatg tgaaagagc  aatcagaatt
2161    gtgctttttc tcccctcctc tattccttt  agggaataat attcaataca cagtacttcc
2221    tcccag
```

SEQ ID NO:4

```
1       atggaggagg tggtgattgc cggcatgttc gggaagctgc cagagtcgga gaacttgcag
61      gagttctggg acaacctcat cggcggtgtg gacatggtca cggacgatga ccgtcgctgg
121     aaggctgggc tctacggcct gccccggcgg tccggcaagc tgaaggacct gtctaggttt
181     gatgcctcct tcttcggagt ccaccccaag caggcacaca cgatggaccc tcagctgcgg
241     ctgctgctgg aagctaccta tgaagccatc gtggacggag gcatcaaccc agattcactc
301     cgaggaacac acactggcgt ctgggtgggc gtgagcggct ctgagacctc ggaggccctg
361     agccgagacc ccgagacact cgtgggctac agcatggtgg gctgccagcg agcgatgatg
421     gccaaccggc tctccttctt cttcgacttc agagggccca gcatcgcact ggacacagcc
481     tgctcctcca gcctgatggc cctgcagaac gcctaccagg ccatccacag cgggcagtgc
541     cctgccgcca tcgtgggggg catcaacgtc ctgctgaagc ccaacacctc cgtgcagttc
601     ttgaggctgg ggatgctcag ccccgagggc acctgcaagg ccttcgacac agcggggaat
661     gggtactgcc gctcggaggg tgtggtggct gtcctgctga ccaagaagtc cctggcccgg
721     aaggtctaca ccaccatcct gaacaaaggc accaatacag atggcttcaa ggagcaaggc
781     gtgaccttcc ctcaggatat ccaggagcag cctatccgct cgttgtacca gtcggccgga
841     gtggcccctg agtcatttga atacatcgaa gcccacggac caggcaccaa ggtgggcgac
901     ccccaggagc gtaatggcat cacccgagcc ctgtgcgcca cccgccagga gccgctgctc
961     atcggctcca ccaagtccaa catgggccac ccggagccag cctcggggct cgacgccctg
1021    gccaaggtgc tgctgtccct ggagcacggg ctctgggccc caacctgca  cttccatagc
1081    cccaaccctg agatcccagc gctgttggat gggcggctgc aggtggtgga ccagccctg
1141    cccgtccgtg gcggcaacgt gggcatcaac tcctttggct cgggggctc  caacatgcac
1201    atcatcctga gcccaacac  gcagtccgcc ccgcacccg  cccacatgc  caccctgccc
1261    cgtctgctgc gggccagcgg acgcaccct  gaggccgtgc agaagctgct ggagcagggc
1321    ctccggcaca gccagggcct ggctttcctg agcatgctga acgacatcgc ggctgtcccc
1381    gccaccgcca tgcccttccg tggctacgct gtgctgggtg gtgagacgcg gtggcccaga
1441    gtgcagcagg tgcccgctgg cgagcgcccg ctctggttca tctgctctgg gatgggcaca
1501    cagtggcgtg aatggggct  gagccttatg cgcctggacc gcttccgaga ttccatccta
1561    cgctccgatg aggctgtgaa ccgattcggc ctgaaggtgt cacagctgct gctgagcaca
1621    gacgagagca ccctttgatga catcgtccat tcgtttgtga gcctgactgc catccagata
1681    ggcctcatag acctgctgag ctgcatggga cctgaggcag atggcatcgt cggccactcc
1741    ctgggggagt ggctgtcggt acgcgacggc tgcctgtccc aggaggaggc cgtcctcgct
1801    gcctactgga ggggacagtg catcaaagaa gccccacttc ccgccggcgc catggcagcc
1861    gtgggcttgt cctggggagga gtgtaaacag cgctgccccc ctgcggtggt gcccgctgc
1921    cacaactcca aggacacagt caccatctcg ggacctcagg cccggtgtt  tgagttcgtg
1981    gagcagctga ggaaggaggg tgtgtttgcc aaggaggtgc ggaccggcgg tatggccttc
2041    cactcctact tcatggaggc catcgcaccc cactgctgc  aggagctcaa gaaggtgatc
2101    cgggagccga agccacgttc agcccgctgg ctcagcacct ctatccccga ggccagtgg
```

Figure 10 (cont.)

```
2161  cacagcagcc tggcacgcac gtcttccgcc gagtacaatg tcaacaacct ggtgagccct
2221  gtgctgttcc aggaggccct gtggcacgtg cctgagcacg cggtggtgct ggagatcgcc
2281  ccgaccccgt gccctcaggc tgtcctgaag cgggtccgta agccgagctg caccatcatc
2341  ccccgtatga agaaggatca cagggacaac ctggagttct tcctggccgg catcggcagg
2401  ctgcacctct caggcatcga cgccaacccc aatgccttgt tcccacctgt ggagtcccca
2461  gctccccgag gaactcccct catctcccca ctcatcaagt gggaccacag cctggcctgg
2521  gacgcgcgg ccgccgagga cttccccaac ggttcaggtt cccctcagc caccatctac
2581  acatgcacac aagctccga gtctcctgac cgctacctgg tggaccacac catcgacggt
2641  cgcgtcctct tccccgccac tggctacctg agcatagtgt ggaagacgct ggccgcgcc
2701  tgggctgggc tcgagcagct gcctgtggtg tttgaggatg tggtgcagca ccaggccacc
2761  atcctgccca agactgggac agtgtccttg gaggtacggc tcctggaggc caccggtgcc
2821  ttcgaggtgt cagagaacgg caacctggta gtgagtggga aggtgtacca gtgggatgac
2881  cctgacccca ggctcttcga ccacccggaa agtcccacc ccaattcccc acggagtccc
2941  ctcttcctgg cccaggcaga agtttacaag gagctgcgtc tgcgtggcta cgactacggc
3001  cctcatttcc agggcatcct ggaggccagc ctggaaggtg actcggggag gctgctgtgg
3061  aaggataact gggtgagctt catggacacc atgctgcaga tgtccatcct gggctcggcc
3121  aagcacggcc tgtacctacc caccgtgtc accgccatcc acatcgaccc tgccacccac
3181  aggcagaagc tgtacacact gcaggacaag gcccaagtgg ctgacgtggt ggtgagcagg
3241  tggccgaggg tcacagtggc gggaggcgtc cacatctccg ggctccacac tgagtcggcc
3301  ccgcggcggc acgaggagca gcaggtgccc atcctggaga agttttgctt cactccccac
3361  acggaggagg ggtgcctgtc tgagcacgct gccctcgagg aggagctgca actgtgcaag
3421  gggctggtcg aggcactcga gaccaaggtg acccagcagg gctgaagat ggtggtgccg
3481  gactggacgg ggcccagatc cccccgggac ccctcacagc aggaactgcc ccggctgttg
3541  tcggctgcct gcaggcttca gctcaacggg aacctgcagc tggagctggc gcaggtgctg
3601  gcccaggaga ggcccaaget gccagaggac cctctgctca gcggcctcct ggactcccg
3661  gcactcaagg cctgcctgga cactgccgtg gagaacatgc ccagcctgaa gatgaaggtg
3721  gtggaggtgc tggccggcca cggtcacctg tattcccgca tcccaggcct gctcagcccc
3781  catcccctgc tgcagctgag ctacacggcc accgaccgcc accccaggc cctggaggct
3841  gcccaggccg agctgcagca gcacgacgtt gcccagggcc agtgggatcc cgcagaccct
3901  gcccccagcg ccctgggcag cgcggacctc ctggtgtgca actgtgctgt ggctgccctc
3961  ggggaccgg cctcagctct cagcaacatg gtggctgccc tgagagaagg gggctttctg
4021  ctcctgcaca cactgctccg ggggcaccct cgggacatcg tggccttcct cacctccact
4081  gagccgcagt atggccaggg catcctgagc caggacgcgt gggagagcct cttctccagg
4141  gtgtcgctgc gcctggtggg cctgaagaag tccttctacg gcgccacgct cttcctgtgc
4201  cgccggccca ccccgcagga cagccccatc ttcctgccgg tggacgatac cagcttccgc
4261  tgggtggagt ctctgaaggg catcctggct gacgaagact cttcccggcc tgtgtggctg
4321  aaggccatca actgtgccac ctcgggcgtg gtgggcttgg tgaactgtct ccgccgagag
4381  cccggcggaa ccgtccggtg tgtgctgctc tccaacctca gcagcacctc ccacgtcccg
4441  gaggtggacc cgggctccgc agaactgcag aaggtgttgc agggagacct ggtgatgaac
4501  gtctaccgcg acggggcctg gggggttttc cgccacttcc tgctggagga caagcctgag
4561  gagccgacgg cacatgcctt tgtgagcacc ctcaccgggg gggacctgtc ctccatccgc
4621  tgggtctgct cctcgctgcg ccatgcccag cccacctgcc ctggcgccca gctctgcacg
4681  gtctactacg cctccctcaa cttccgcgac atcatgctgg ccactggcaa gctgtccct
4741  gatgccatcc cagggaagtg gacctcccag gacagcctgc taggtatgga gttctcgggc
4801  cgagacgcca gcggcaagcg tgtgatggga ctggtgcctg ccaagggcct ggccacctct
4861  gtcctgctgt caccggactt cctctgggat gtgccttcca actggacgct ggaggaggcg
4921  gcctcggtgc ctgtcgtcta cagcacggcc tactacgcgc tggtggtgcg tgggcgggtg
4981  cgccccgggg acgctgct catccactcg ggctcgggcg gcgtgggcca ggccgccatc
5041  gccatcgccc tcagtctggg ctgccgcgtc ttcaccaccg tggggtcggc tgagaagcgg
5101  gcgtacctcc aggccaggtt ccccccagctc gacagcacca gcttcgccaa ctcccgggac
5161  acatccttcg agcagcatgt gctgtggcac acgggcggga agggcgttga cctggtcttg
5221  aactccttgg cggaagagaa gctgcaggcc agcgtgaggt gcttcggtac gcacggtcgc
5281  ttcctggaaa ttggcaaatt cgacctttct cagaaccacc cgctcggcat ggctatcttc
5341  ctgaagaacg tgacattcca cggggtccta ctggatgcgt tcttcaacga gagcagtgct
```

Figure 10 (cont.)

```
5401   gactggcggg aggtgtgggc gcttgtcgag gccgccatcc gggatggggt ggtacggccc
5461   ctcaagtgca cggtgttcca tggggcccag gtggaggacg ccttccgcta catggcccaa
5521   gggaagcaca ttggcaaagt cgtcgtgcag gtgcttgcgg aggagccggc agtgctgaag
5581   ggggccaaac ccaagctgat gtcggccatc tccaagacct tctgccggc ccacaagagc
5641   tacatcatcg ctggtggtct gggtggcttc ggcctggagt tggcgcagtg gctgatacag
5701   cgtggggtgc agaagctcgt gttgacttct cgctccggga tccggacagg ctaccaggcc
5761   aagcaggtcc gccgtggag cgccagggg ctacaggtgc aggtgtccac cagcaacatc
5821   agctcactgg aggggcccg gggcctcatt gccgaggcgg cgcagcttgg gcccgtgggg
5881   ggcgtcttca acctggccgt ggtcttgaga gatggcttgc tggagaacca gaccccagag
5941   ttcttccagg acgtctgcaa gcccaagtac agcggcaccc tgaacctgga cagggtgacc
6001   cgagaggcgt gccctgagct ggactacttt gtggtcttct cctctgtgag ctgcgggcgt
6061   ggcaatgcgg gacagagcaa ctacggcttt gccaattccg ccatggagcg tatctgtgag
6121   aaacgccggc acgaaggcct cccaggcctg gccgtgcagt ggggcgccat cggcaccgtg
6181   ggcattttgg tggagacgat gagcaccaac gacacgatcg tcagtggcac gctgcccacg
6241   cgcattggcg tccttggcct ggaggtgctg gacctcttcc tgaaccagcc ccacatggtc
6301   ctgagcagct ttgtgctggc tgagaaggct gcggcctata gggacaggga cagccagcgg
6361   gacctggtgg aggccgtggc acacatcctg ggcatccgcg acttggctgc tgtcaacctg
6421   ggcggctcac tggcggacct gggcctggac tcgctcatga gcgcgccggt gcgccagacg
6481   ctggagcgtg agctcaacct ggtgctgtcc gtgcgcgagg tgcggcaact cacgctccgg
6541   aaactgcagg agctgtcctc aaaggcggat gaagccagcg agctggcatg ccccacgccc
6601   aaggaggatg gtctggccca gcagcagact cagctgaacc tgcgctccct gctggtgaaa
6661   ccggagggcc ccaccctgat gcggctcaac tccgtgcaga gctcggagcg gcccctgttc
6721   ctggtgcacc caatcgaggc taccaccgtg ttccacagcc tcggtcccgg tctcagcatc
6781   cccacctatg gcctgcagtg caccccggct gcgccccttg acagcatcca cagcctggct
6841   gcctactaca tcgactgcat caggcaggtg cagcccgagg gccctaccg cgtggccggc
6901   tactcctacg gggcctgcgt ggcctttgaa atgtgctccc agctgcaggc ccagcagagc
6961   ccagccccca cccacaacag cctcttcctg ttcgacggct cgcccaccta cgtactggcc
7021   tacacccaga gctaccgggc aaagctgacc ccaggctgta aggctgaggc tgagacggag
7081   gccatatgct tcttcgtgca gcagttcacg gacatggagc acaacagggt gctggaggcg
7141   ctgctgccgc tgaagggcct agaggagcgt gtggcagccg ccgtggacct gatcatcaag
7201   agccaccagg gcctggaccg ccaggagctg agctttgcgg cccggtcctt ctactacagg
7261   ctgcgtgccg ctgaccagta tacacccaag gccaagtaca gtggcaacgt gatgctactg
7321   cgggccaaga cgggtggccg ctacggcgag gacctgggcg cggactacaa cctctcccag
7381   gtatgcgacg ggaaagtatc cgtccatatc atcgagggtg accaccgcac gctgctggag
7441   ggcagcggcc tggagtccat catcagcatc atccacagct ccctggctga gccacgtgtg
7501   agtcgggagg gctag SEQ ID NO:5
1      ctcaaaaggg gccggatttc cttctcctgg aggcagatgt tgcctctctc tctcgctcgg
61     attggttcag tgcactctag aaacactgct gtggtggaga aactggaccc caggtctgga
121    gcgaattcca gcctgcaggg ctgataagcg aggcattagt gagattgaga gagactttac
181    cccgccgtgg tggttggagg gcgcgcagta gagcagcagc acaggcgcgg gtcccgggag
241    gccggctctg ctcgcgccga gatgtggaat ctccttcacg aaaccgactc ggctgtggcc
301    accgcgcgcc gcccgcgctg gctgtgcgct ggggcgctgg tgctggcggg tggcttcttt
361    ctcctcggct tcctcttcgg gtggtttata aaatcctcca atgaagctac taacattact
421    ccaaagcata atatgaaagc attttggat gaattgaaag ctgagaacat caagaagttc
481    ttatataatt ttacacagat accacattta gcaggaacag aacaaaactt tcagcttgca
541    aagcaaattc aatcccagtg gaaagaattt ggcctggatt ctgttgagct agcacattat
601    gatgtcctgt tgtcctaccc aaataagact catcccaact acatctcaat aattaatgaa
661    gatggaaatg agatttcaa cacatcatta tttgaaccac ctcctccagg atatgaaaat
721    gtttcggata ttgtaccacc tttcagtgct ttctctcctc aaggaatgcc agagggcgat
781    ctagtgtatg ttaactatgc acgaactgaa gacttcttta aattggaacg ggacatgaaa
841    atcaattgct ctgggaaaat tgtaattgcc agatatggga aagttttcag aggaaataag
901    gttaaaaatg cccagctggc aggggccaaa ggagtcattc tctactccga ccctgctgac
```

Figure 10 (cont.)

```
 961   tactttgctc ctggggtgaa gtcctatcca gatggttgga atcttcctgg aggtggtgtc
1021   cagcgtggaa atatcctaaa tctgaatggt gcaggagacc ctctcacacc aggttaccca
1081   gcaaatgaat atgcttatag gcgtggaatt gcagaggctg ttggtcttcc aagtattcct
1141   gttcatccaa ttggatacta tgatgcacag aagctcctag aaaaaatggg tggctcagca
1201   ccaccagata gcagctggag aggaagtctc aaagtgccct acaatgttgg acctggcttt
1261   actggaaact tttctacaca aaaagtcaag atgcacatcc actctaccaa tgaagtgaca
1321   agaatttaca atgtgatagg tactctcaga ggagcagtgg aaccagacag atatgtcatt
1381   ctgggaggtc accgggactc atgggtgttt ggtggtattg accctcagag tggagcagct
1441   gttgttcatg aaattgtgag gagctttgga acactgaaaa aggaagggtg gagacctaga
1501   agaacaattt tgtttgcaag ctgggatgca gaagaatttg gtcttcttgg ttctactgag
1561   tggcagagg  agaattcaag actccttcaa gagcgtggcg tggcttatat taatgctgac
1621   tcatctatag aaggaaacta cactctgaga gttgattgta caccgctgat gtacagcttg
1681   gtacacaacc taacaaaaga gctgaaaagc cctgatgaag gctttgaagg caaatctctt
1741   tatgaaagtt ggactaaaaa aagtccttcc ccagagttca gtggcatgcc caggataagc
1801   aaattgggat ctggaaatga ttttgaggtg ttcttccaac gacttggaat tgcttcaggc
1861   agagcacggt atactaaaaa ttgggaaaca aacaaattca gcggctatcc actgtatcac
1921   agtgtctatg aaacatatga gttggtggaa aagttttatg atccaatgtt taaatatcac
1981   ctcactgtgg cccaggttcg aggagggatg gtgtttgagc tagccaattc catagtgctc
2041   ccttttgatt gtcgagatta tgctgtagtt ttaagaaagt atgctgacaa aatctacagt
2101   atttctatga aacatccaca ggaaatgaag acatacagtg tatcatttga ttcactttt
2161   tctgcagtaa agaattttac agaaattgct tccaagttca gtgagagact ccaggacttt
2221   gacaaaagca acccaatagt attaagaatg atgaatgatc aactcatgtt tctggaaaga
2281   gcatttattg atccattagg gttaccagac aggccttttt ataggcatgt catctatgct
2341   ccaagcagcc acaacaagta tgcaggggag tcattcccag gaatttatga tgctctgttt
2401   gatattgaaa gcaaagtgga cccttccaag gcctggggag aagtgaagag acagatttat
2461   gttgcagcct tcacagtgca ggcagctgca gagactttga gtgaagtagc ctaagaggat
2521   tctttagaga atccgtattg aatttgtgtg gtatgtcact cagaaagaat cgtaatgggt
2581   atattgataa attttaaaat tggtatattt gaaataaagt tgaatattat atataaaaaa
2641   aaaaaaaaaa aaa
```

SEQ ID NO:6
```
   1   cctcactgac tataaaagaa tagagaagga agggcttcag tgaccggctg cctggctgac
  61   ttacagcagt cagactctga caggatcatg gctatgatgg aggtccaggg gggacccagc
 121   ctgggacaga cctgcgtgct gatcgtgatc ttcacagtgc tcctgcagtc tctctgtgtg
 181   gctgtaactt acgtgtactt taccaacgag ctgaagcaga tgcaggacaa gtactccaaa
 241   agtggcattg cttgtttctt aaaagaagat gacagttatt gggaccccaa tgacgaagag
 301   agtatgaaca gcccctgctg gcaagtcaag tgcaactcc gtcagctcgt tagaaagatg
 361   attttgagaa cctctgagga aaccatttct acagttcaag aaaagcaaca aaatatttct
 421   cccctagtga gagaagagg tcctcagaga gtagcagctc acataactgg gaccagagga
 481   agaagcaaca cattgtcttc tccaaactcc aagaatgaaa aggctctggg ccgcaaaata
 541   aactcctggg aatcatcaag gagtgggcat tcattcctga gcaacttgca cttgaggaat
 601   ggtgaactgg tcatccatga aaagggtttt tactacatct attcccaaac atactttcga
 661   tttcaggagg aaataaaaga aacacaaag aacgacaaac aaatggtcca atatatttac
 721   aaatacacaa gttatcctga ccctatattg ttgatgaaaa gtgctagaaa tagttgttgg
 781   tctaaagatg cagaatatgg actctattcc atctatcaag ggggaatatt tgagcttaag
 841   gaaaatgaca gaattttttgt ttctgtaaca aatgagcact tgatagacat ggaccatgaa
 901   gccagttttt tggggccttt tttagttggc taactgacct ggaagaaaaa gcaataacc
 961   tcaaagtgac tattcagttt tcaggatgat acactatgaa gatgtttcaa aaaatctgac
1021   caaaacaaac aaacagaaaa cagaaaacaa aaaacctct atgcaatctg agtagagcag
1081   ccacaaccaa aaaattctac aacacacact gttctgaaag tgactcactt atcccaagag
1141   aatgaaattg ctgaaagatc tttcaggact ctacctcata tcagtttgct agcagaaatc
1201   tagaagactg tcagcttcca aacattaatg caatggttaa catcttctgt ctttataatc
1261   tactccttgt aaagactgta gaagaagag caacaatcca tctctcaagt agtgtatcac
1321   agtagtagcc tccaggtttc cttaagggac aacatcctta agtcaaaaga gagaagaggc
```

Figure 10 (cont.)

```
1381 accactaaaa gatcgcagtt tgcctggtgc agtggctcac acctgtaatc ccaacatttt
1441 gggaacccaa ggtgggtaga tcacgagatc aagagatcaa gaccatagtg accaacatag
1501 tgaaacccca tctctactga aagtacaaaa attagctggg tgtgttggca catgcctgta
1561 gtcccagcta cttgagaggc tgaggcaaga gaattgtttg aacccgggag gcagaggttg
1621 cagtgtggtg agatcatgcc actacactcc agcctggcga cagagcgaga cttggtttca
1681 aaaaaaaaaa aaaaaaaaac ttcagtaagt acgtgttatt tttttcaata aaattctatt
1741 acagtatgtc
```

SEQ ID NO:7

```
   1 ggtcacatga ctccagtcta gctcgcattg cggctcccgc ccgggcgagt tctcgccccc
  61 gcgcggccgt tgccgaggag acggcgcatg tcccgccgcg cgttgccccc tctgcagtac
 121 ccccgcccct cttctcccac cacaatgaga tcctaagatg gcggtggctg cggcggttgg
 181 cgctgcgtag ctgaggtcga aaaggcggcc actggggccg aggcagccag gaaacgtgtg
 241 ggcctctctg ctgcggtctc cgagggccga ccgctgccgg cggcgggtcg tgggggctga
 301 ctgtcgctct gcctttgaca ggagaggctg cttcttgtag aggaaacagc tttgaagtgt
 361 ggagcgggaa aggagcagtt tctgagctgc aaaaactagt ttctaaacag agagttaatt
 421 gttaaatcca gtatggccac aggaggaggt ccctttgaag atggcatgaa tgatcaggat
 481 ttaccaaact ggagtaatga gaatgttgat gacaggctca acaatatgga ttggggtgcc
 541 caacagaaga aagcaaatag atcatcagaa aagaataaga aaaagtttgg tgtagaaagt
 601 gataaaagag taaccaatga tatttctccg gagtcgtcac caggagttgg aaggcgaaga
 661 acaaagactc cacatacgtt cccacacagt agatacatga gtcagatgtc tgtcccagag
 721 caggcagaat tagagaaact gaaacagcgg ataaacttca gtgatttaga tcagagaagc
 781 attggaagtg attcccaagg tagagcaaca gctgctaaca acaaacgtca gcttagtgaa
 841 aaccgaaagc ccttcaactt tttgcctatg cagattaata ctaacaagag caaagatgca
 901 tctacaagtc ccccaaacag agaaacgatt ggatcagcac agtgtaaaga gttgtttgct
 961 tctgctttaa gtaatgacct cttgcaaaac tgtcaggtgt ctgaagaaga tgggagggga
1021 gaacctgcaa tggagagcag ccagattgta agcaggcttg ttcaaattcg cgattatatt
1081 actaaagcta gttccatgcg ggaagatctt gtagagaaaa atgagagatc tgctaatgtt
1141 gagcgcctta ctcatctaat agatcaccct aaagaacaag agaagtcata tatgaaattt
1201 cttaaaaaaa tccttgccag agatcctcag caggagccta tggaagagat agaaaatttg
1261 aagaaacaac atgatttatt aaaaagaatg ttacaacagc aggagcaact aagagctcta
1321 cagggacggc aggctgcact tctagctctg caacataaag cagagcaagc tattgcagtg
1381 atggatgatt ctgttgttgc agaaactgca ggtagcttat ctggcgtcag tatcacatct
1441 gaactaaatg aagaattgaa tgacttaatt cagcgttttc ataatcagct tcgtgattct
1501 cagcctccag ctgttccaga caatagaaga caggcagaaa gtctttcatt aactagggag
1561 gtttcccaga gcaggaaacc atcagcttca gaacgtttac ctgatgagaa agtcgaactt
1621 tttagcaaaa tgagagtgct acaggaaaag aaacaaaaaa tggacaaatt gcttggagaa
1681 cttcatacac ttcgagatca gcatcttaac aattcatcat cctctccaca aaggagtgtc
1741 gatcagagaa gtacttcagc tccctctgct tctgtaggct tggcaccggt tgtcaatgga
1801 gaatccaata gcctcacatc atctgttcct tatcctactg cttctctagt atctcagaat
1861 gagagtgaaa acgaaggcca cctcaatcca tctgaaaaac tccagaagtt aaatgaagtt
1921 cgaaagagat tgaatgagct aagagaatta gttcattatt atgaacaaac gtcagacatg
1981 atgacagatg ctgtgaatga aaacaggaaa gatgaagaaa ctgaagagtc agaatatgat
2041 tctgagcatg aaaattccga gcctgttact aacattcgaa atccacaagt agcttccact
2101 tggaatgaag taaatagtca tagtaatgca cagtgtgttt ctaataatag agatgggcga
2161 acagttaatt ctaattgtga aattaacaac agatctgctg ccaacataag ggctctaaac
2221 gtgcctcctt ctttagattg tcgatataat agagaagggg aacaggagat tcatgttgca
2281 caaggtgaag atgatgagga ggaggaggaa gaagcagaag aggagggagt cagtggagct
2341 tcattatcta gtcacaggag cagtctggtt gatgagcatc agaagatgc tgaatttgaa
2401 cagaagatca accgacttat ggctgcaaaa cagaaactta gacagttaca agatcttgtt
2461 gctatggtac aggatgatga tgcagctcaa ggagttatct ctgccagtgc atcaaatttg
2521 gatgatttct acccagcaga agaagacacc aagcaaaatt caaataacac tagaggaaat
2581 gccaataaaa cacagaaaga tactggagta aatgaaaagg caagagagaa attttatgag
2641 gctaaactac agcagcaaca gagagagcta aaacaattgc aggaagaaag aaagaaactg
```

Figure 10 (cont.)

```
2701 attgacattc aggagaaaat tcaagcattg caaacggcat gccctgactt acagctgtca
2761 gctgctagtg tgggtaactg tcccaccaaa aaatatatgc cagctgttac ttcaacccca
2821 actgttaatc aacacgagac cagtacaagc aaatctgttt ttgagcctga agattcttca
2881 atagtagata atgagttgtg gtcagaaatg agaagacatg aaatgttgag ggaggagctg
2941 cgacagagaa gaaagcagct tgaagctctg atggctgaac atcagaggag gcaaggtcta
3001 gctgaaactg catctccagt ggctgtgtca ttgagaagtg atggatctga gaacctatgt
3061 actcctcagc aaagtagaac agaaaaaacg atggcaactt ggggagggtc tacccagtgt
3121 gcactagatg aagaaggaga tgaagacggt tacctttctg aaggaattgt tcggacagat
3181 gaagaggagg aagaagagca agatgccagt tccaatgata actttttctgt gtgtccttct
3241 racagtgtga atcataactc ctacaatgga aaggaaacta aaaataggtg gaagaacaat
3301 tgcccttttt cggcagatga aaattatcgt cctttagcca agacaaggca acagaatatc
3361 agcatgcaac ggcaagaaaa ccttcgttgg gtgtcagagc tctcttacgt agaagagaaa
3421 gaacaatggc aagaacaaat caatcagcta aagaaacagc ttgatttag tgtcagtatt
3481 tgtcagactt tgatgcaaga ccagcagact ctatcttgtc tgctacaaac tcttctcacg
3541 ggtccttaca gtgttatgcc cagcaatgtt gcatctcctc aagtacactt cataatgcac
3601 cagttgaacc agtgctatac tcagctaaca tggcaacaga ataatgttca gaggttgaaa
3661 caaatgctaa atgaacttat gcgccagcaa aatcagcatc cagaaaaacc tggaggcaag
3721 gaaagaggca gtagtgcatc gcacctcct tctcccagtt tatttgtcc tttcagcttt
3781 ccaacacagc ctgtaaatct cttcaatata cctggattta ctaacttttc atcatttgca
3841 ccaggtatga atttcagccc tttatttcct tctaattttg gagattttc tcagaatatc
3901 tctacaccca gtgaacagca gcaaccctta gcccagaatt cttcaggaaa aacagaatat
3961 atggcttttc caaaaccttt tgaaagcagt tcctctattg gagcagagaa accaaggaat
4021 aaaaaactgc ctgaagagga ggtggaaagc agtaggacac catggttata tgaacaagaa
4081 ggtgaagtag agaaaccatt tatcaagact ggatttcag tgtctgtaga aaaatctaca
4141 agtagtaacc gcaaaaatca attagataca aacggaagaa gacgccagtt tgatgaagaa
4201 tcactggaaa gctttagcag tatgcctgat ccagtagatc caacaacagt gactaaaaca
4261 ttcaagacaa gaaaagcgtc tgcacaggcc agcctggcat ctaaagataa aactcccaag
4321 tcaaaaagta agaagaggaa ttctactcag ctgaaaagca gagttaaaaa catcaggtat
4381 gaaagtgcca gtatgtctag cacatgtgaa ccttgcaaaa gtaggaacag acattcagcc
4441 cagactgaag agcctgttca agcaaaagta ttcagcagaa agaatcatga gcaactggaa
4501 aaaataataa aatgtaatag gtctacagaa atatcttcag aaactgggag tgatttttcc
4561 atgtttgaag ctttgcgaga tactatttat tctgaagtag ctacattaat ttctcaaaat
4621 gaatctcgtc cacatttcct tattgaactc ttccatgagc tgcagctact aaacacagac
4681 tacttgagac agagggcttt atatgcattg caggacatag tatccagaca tatttctgag
4741 agccatgaaa aaggagaaaa tgtaaagtca gtaaactctg gtacttggat agcatcaaac
4801 tcagaactta ctcctagtga gagccttgct actactgatg atgaaacttt tgagaagaac
4861 tttgaaagag aaacccataa aataagtgag caaaatgatg ctgataatgc tagtgtcctg
4921 tctgtatcat caaattttga gcctttgca acagatgatc taggtaacac cgtgattcac
4981 ttagatcaag cattagccag aatgagagaa tatgagcgta tgaagactga ggctgaaagt
5041 aactcaaata tgagatgcat ctgcaggatt attgaggatg gagatggtgc tggtgcaggt
5101 actacagtta ataatttaga agaaactccc gttattgaaa atcgtagttc acaacaacct
5161 gtaagtgaag ttctaccat cccatgtcct agaattgata ctcagcagct ggaccggcaa
5221 attaaagcaa ttatgaaaga agtcattcct ttttgaagg agcacatgga tgaagtatgc
5281 tcctcgcagc ttctaacttc agtaaggcgc atggttttga cccttaccca gcaaaatgat
5341 gagagcaaag agtttgtaaa gttctttcat aaacaacttg aagtatatt acaggattca
5401 ctggcaaaat tgctggcag aaaactgaaa gactgtggag aagatcttct tgtagagata
5461 tctgaagtgt tgttcaatga attggcttc tttaagctta tgcaagattt ggataataat
5521 agtataactg ttaaacagag atgcaaaagg aaaatagaag caactggagt gatacaatct
5581 tgtgccaaag agctaaaagg attcttgaag atcatggctc acctgctgga gagattgatg
5641 atgaagacaa agacaaggat gaaactgaaa cagttaagca gactcaaaca tctgaggtgt
5701 atgatggtcc caaaaatgta agatctgata tttctgatca agaggaagat gaagaaagtg
5761 aaggatgtcc agtgtctatt aatttgtcta agctgaaac tcaggcttta actaattatg
5821 gaagtggaga agatgaaaat gaggatgaag aaatggaaga atttgaagaa ggccctgtgg
5881 atgtccagac ttccctccag gctaacactg aagctactga agaaaatgaa catgatgaac
```

Figure 10 (cont.)

```
5941 aggtcctaca acgtgacttt aaaaagacag cagaaagcaa aaatgtccca ttggaacgag
6001 aagccactag taaaaatgac caaaataact gtcctgtgaa accctgttac ctcaatatct
6061 tggaagatga gcaacccttta aatagtgctg cccataagga gtcacctcct actgttgatt
6121 caactcaaca gcctaaccct ttgccgttac gtttacctga aatggaaccc ttagtgccta
6181 gagtcaaaga agttaaatct gctcaggaaa ctcctgaaag ctctctggct ggaagtcctg
6241 atactgaatc tccagtgtta gtgaatgact atgaagcaga atctggtaat ataagtcaaa
6301 agtctgatga agaagatttt gtaaaagttg aagatttacc actgaaactg acaatatatt
6361 cagaggcaga tctaagaaag aaaatggtag aagaagaaca gaaaaaccat ttatctggtg
6421 aaatatgtga aatgcagacc gaagaattag ctggaaattc tgagacacta aaagaacctg
6481 aaacggtggg agcccagagt atatgagatg tcttcagagg ctcatctaac tctgtcctta
6541 catactcaat gcatatatga aaacaatact aaataaacat ctgatctgta taaaaat
```

SEQ ID NO:8
```
  1 ctccaaaggc aaaaatctcc agccctacag agactgagcg gtgcatcgag tccctgattg
 61 ctgtcttcca gaagtatgct ggaaaggatg gttataacta cactctctcc aagacagagt
121 tcgtaagctt catgaataca gaactagctg ccttcacaaa gaaccagaag gaccctggtg
181 tccttgaccg catgatgaag aaactggaca ccaacagtga tggtcagcta gatttctcag
241 aatttcttaa tctgattggt ggcctagcta tggcttgcca tgactccttc ctcaaggctg
301 tccttccca gaagcggacc tgaggacccc ttggccctgg ccttcaaacc caccccttt
361 ccttccagcc tttctgtcat catctccaca gcccacccat ccctgagca cactaaccac
421 ctcatgcagg ccccacctgc caatagtaat aaagcaatgt cacttttta aaacatgaa
```

SEQ ID NO:9
```
   1 gccgcttcct gcctggattc cacagcttcg cgccgtgtac tgtcgcccca tccctgcgcg
  61 cccagcctgc caagcagcgt gccccggttg caggcgtcat gcagcgggcg cgacccacgc
 121 tctgggccgc tgcgctgact ctgctggtgc tgctccgcgg gccgccggtg gcgcgggctg
 181 gcgcgagctc ggcgggcttg ggtcccgtgg tgcgctgcga gccgtgcgac gcgcgtgcac
 241 tggcccagtg cgcgcctccg cccgccgtgt gcgcggagct ggtgcgcgag ccgggctgcg
 301 gctgctgcct gacgtgcgca ctgagcgagg gccagccgtg cggcatctac accgagcgct
 361 gtggctccgg ccttcgctgc cagccgtcgc ccgacgaggc gcgaccgctg caggcgctgc
 421 tggacggccg cgggctctgc gtcaacgcta gtgccgtcag ccgcctgcgc gcctacctgc
 481 tgccagcgcc gccagctcca ggaaatgcta gtgagtcgga ggaagaccgc agcgccggca
 541 gtgtggagag cccgtccgtc tccagcacgc accgggtgtc tgatcccaag ttccaccccc
 601 tccattcaaa gataatcatc atcaagaaag ggcatgctaa agacagccag cgctacaaag
 661 ttgactacga gtctcagagc acagataccc agaacttctc ctccgagtcc aagcgggaga
 721 cagaatatgg tccctgccgt agagaaatgg aagacacact gaatcacctg aagttcctca
 781 atgtgctgag tcccaggggt gtacacattc caactgtga caagaaggga tttttataaga
 841 aaaagcagtg tcgcccttcc aaaggcagga agcggggctt ctgctggtgt gtggataagt
 901 atggcagcc tctcccaggc tacaccacca aggggaagga ggacgtgcac tgctacagca
 961 tgcagagcaa gtagacgcct gccgcaaggt taatgtggag ctcaaatatg ccttatttttg
1021 cacaaaagac tgccaaggac atgaccagca gctggctaca gcctcgattt atatttctgt
1081 ttgtggtgaa ctgatttttt ttaaaccaaa gtttagaaag aggttttga aatgcctatg
1141 gtttctttga atggtaaact tgagcatctt ttcactttcc agtagtcagc aaagagcagt
1201 ttgaattttc ttgtcgcttc ctatcaaaat attcagagac tcgagcacag cacccagact
1261 tcatgcgccc gtgaatgct caccacatgt tggtcgaagc ggccgaccac tgactttgtg
1321 acttaggcgg ctgtgttgcc tatgtagaga acacgcttca ccccactcc ccgtacagtg
1381 cgcacaggct ttatcgagaa taggaaaacc tttaaacccc ggtcatccgg acatcccaac
1441 gcatgctcct ggagctcaca gccttctgtg gtgtcatttc tgaaacaagg gcgtggatcc
1501 ctcaaccaag aagaatgttt atgtcttcaa gtgacctgta ctgcttgggg actattggag
1561 aaaataaggt ggagtcctac ttgttaaaaa aatatgtatc taagaatgtt ctagggcact
1621 ctgggaacct ataaaggcag gtatttcggg ccctcctctt caggaatctt cctgaagaca
1681 tgcccagtc gaaggccag gatggcttt gctgcggccc cgtggggtag gagggacaga
1741 gagacaggga gagtcagcct ccacattcag aggcatcaca agtaatggca caattcttcg
1801 gatgactgca gaaaatagtg ttttgtagtt caacaactca agacgaagct tatttctgag
```

Figure 10 (cont.)

```
1861 gataagctct ttaaaggcaa agctttattt tcatctctca tcttttgtcc tccttagcac
1921 aatgtaaaaa agaatagtaa tatcagaaca ggaaggagga atggcttgct ggggagccca
1981 tccaggacac tgggagcaca tagagattca cccatgtttg ttgaacttag agtcattctc
2041 atgcttttct ttataattca cacatatatg cagagaagat atgttcttgt taacattgta
2101 tacaacatag ccccaaatat agtaagatct atactagata atcctagatg aaatgttaga
2161 gatgctattt gatacaactg tggccatgac tgaggaaagg agctcacgcc cagagactgg
2221 gctgctctcc cggaggccaa acccaagaag gtctggcaaa gtcaggctca gggagactct
2281 gccctgctgc agacctcggt gtggacacac gctgcataga gctctccttg aaaacagagg
2341 ggtctcaaga cattctgcct acctattagc ttttctttat ttttttaact ttttgggggg
2401 aaaagtattt ttgagaagtt tgtcttgcaa tgtatttata aatagtaaat aaagttttta
2461 ccatt
```

SEQ ID NO:10
```
  1 atgccgcgct ccttcctggt caagaagcat ttcaacgcct ccaaaaagcc aaactacagc
 61 gaactggaca cacatacagt gattatttcc ccgtatctct atgagagtta ctccatgcct
121 gtcataccac aaccagagat cctcagctca ggagcataca gccccatcac tgtgtggact
181 accgctgctc cattccacgc ccagctaccc aatggcctct ctcctctttc cggatactcc
241 tcatctttgg ggcgagtgag tcccccctcct ccatctgaca cctcctccaa ggaccacagt
301 ggctcagaaa gccccattag tgatgaagag gaaagactac agtccaagct ttcagacccc
361 catgccattg aagctgaaaa gtttcagtgc aatttatgca ataagaccta ttcaactttt
421 tctgggctgg ccaaacataa gcagctgcac tgcgatgccc agtctagaaa atctttcagc
481 tgtaaatact gtgacaagga atatgtgagc ctgggcgccc tgaagatgca tattcggacc
541 cacacattac cttgtgtttg caagatctgc ggcaaggcgt tttccagacc ctggttgctt
601 caaggacaca ttagaactca cacgggggag aagcctttt cttgccctca ctgcaacaga
661 gcatttgcag acaggtcaaa tctgagggct catctgcaga cccattctga tgtaaagaaa
721 taccagtgca aaaactgctc caaaaccttc tccagaatgt ctctcctgca caaacatgag
781 gaatctggct gctgtgtagc acactga
```

SEQ ID NO:11
```
  1 ctcggaagcc cgtcaccatg tcgtgcgagt cgtctatggt tctcgggtac tgggatattc
 61 gtgggctggc gcacgccatc cgcctgctcc tggagttcac ggataccttt tatgaggaga
121 aacggtacac gtgcggggaa gctcctgact atgatcgaag ccaatggctg gatgtgaaat
181 tcaagctaga cctggacttt cctaatctgc cctacctcct ggatgggaag aacaagatca
241 cccagagcaa tgccatcctg cgctacatcg ctcgcaagca caacatgtgt ggtgagactg
301 aagaagaaaa gattcgagtg gacatcatag agaaccaagt aatggatttc cgcacacaac
361 tgataaggct ctgttacagc tctgaccacg aaaaactgaa gcctcagtac ttggaagagc
421 tacctggaca actgaaacaa ttctccatgt ttctgtggaa attctcatgg tttgccgggg
481 aaaagctcac ctttgtggat tttctcacct atgatatctt ggatcagaac cgtatatttg
541 accccaagtg cctggatgag ttcccaaacc tgaaggcttt catgtgccgt tttgaggctt
601 tggagaaaat cgctgcctac ttacagtctg atcagttctg caagatgccc atcaacaaca
661 agatggccca gtggggcaac aagcctgtat gctgagcagg aggcagactt gcagagcttg
721 ttttgtttca tcctgtccgt aagggtcag cgctcttgct ttgctctttt caatgaatag
781 cacttatgtt actggtgtcc agctgagttt ctcttgggta taaaggctaa aagggaaaaa
841 ggatatgtgg agaatcatca agatatgaat tgaatcgctg cgatactgtg gcatttccct
901 actcccaac tgagttcaag ggctgtaggt tcatgcccaa gccctgagag tgggtactag
961 aaaaaacgag attgcacagt tggagagagc aggtgtgtta aatggactgg agtccctgtg
1021 aagactgggt gaggataaca caagtaaaac tgtggtactg atggacttaa ccggagttcg
1081 gaaaccgtcc tgtgtacaca tgggagttta gtgtgataaa ggcagtattt cagactggtg
1141 ggctagccaa tagagttggc aattgcttat tgaaactcat taaaaataat agagcccccac
1201 ttgacactat tcactaaaat taatctggaa tttaaggccc aacattaaac acaaagctgt
1261 attgat
```

SEQ ID NO:12
```
  1 gccacgtgct gctgggtctc agtcctccac ttcccgtgtc ctctggaagt tgtcaggagc
```

Figure 10 (cont.)

```
  61 aatgttgcgc ttgtacgtgt tggtaatggg agtttctgcc ttcacccttc agcctgcggc
 121 acacacaggg gctgccagaa gctgccggtt tcgtgggagg cattacaagc gggagttcag
 181 gctggaaggg gagcctgtag ccctgaggtg cccccaggtg ccctactggt tgtgggcctc
 241 tgtcagcccc cgcatcaacc tgacatggca taaaaatgac tctgctagga cggtcccagg
 301 agaagaagag acacggatgt gggcccagga cggtgctctg tggcttctgc cagccttgca
 361 ggaggactct ggcacctacg tctgcactac tagaaatgct tcttactgtg acaaaatgtc
 421 cattgagctc agagtttttg agaatacaga tgctttcctg ccgttcatct catacccgca
 481 aattttaacc ttgtcaacct ctggggtatt agtatgccct gacctgagtg aattcacccg
 541 tgacaaaact gacgtgaaga ttcaatggta caaggattct cttcttttgg ataaagacaa
 601 tgagaaattt ctaagtgtga ggggaccac tcacttactc gtacacgatg tggccctgga
 661 agatgctggc tattaccgct gtgtcctgac atttgcccat gaaggccagc aatacaacat
 721 cactaggagt attgagctac gcatcaagaa aaaaaagaa gagaccattc ctgtgatcat
 781 ttccccctc aagaccatat cagcttctct ggggtcaaga ctgacaatcc cgtgtaaggt
 841 gtttctggga accggcacac ccttaaccac catgctgtgg tggacggcca atgacaccca
 901 catagagagc gcctaccgg gaggcgcgt gaccgagggg ccacgccagg aatattcaga
 961 aaataatgag aactacattg aagtgccatt gattttgat cctgtcacaa gagaggattt
1021 gcacatggat tttaaatgtg ttgtccataa taccctgagt tttcagacac tacgcaccac
1081 agtcaaggaa gcctcctcca cgttctcctg gggcattgtg ctggccccac tttcactggc
1141 cttcttggtt ttgggggaa tatggatgca cagacggtgc aaacacagaa ctggaaaagc
1201 agatggtctg actgtgctat ggcctcatca tcaagacttt caatcctatc ccaagtgaaa
1261 taaatggaat gaaataattc aaacacaaaa aaaaaaaaa aaaaaaaa
```

SEQ ID NO:13
```
   1 gcgctgcccg cctcgtcccc accccccaac cccccgcgcc cgccctcgga cagtccctgc
  61 tcgcccgcgc gctgcagccc catctcctag cggcagccca ggcgcggagg gagcgagtcc
 121 gccccgaggt aggtccagga cgggcgcaca gcagcagccg aggctggccg ggagagggag
 181 gaagaggatg gcagggccac gcccagccc atgggccagg ctgctcctgg cagccttgat
 241 cagcgtcagc ctctctggga ccttggcaaa ccgctgcaag aaggccccag tgaagagctg
 301 cacggagtgt gtccgtgtgg ataaggactg cgcctactgc acagacgaga tgttcaggga
 361 ccggcgctgc aacacccagg cggagctgct ggccgcgggc tgccagcggg agagcatcgt
 421 ggtcatggag agcagcttcc aaatcacaga ggagacccag attgacacca ccctgcggcg
 481 cagccagatg tccccccaag gcctgcgggt ccgtctgcgg cccggtgagg agcggcattt
 541 tgagctggag gtgtttgagc cactggagag cccgtggac ctgtacatcc tcatggactt
 601 ctccaactcc atgtccgatg atctggacaa cctcaagaag atggggcaga acctggctcg
 661 ggtcctgagc cagctcacca gcgactacac tattggattt ggcaagtttg tggacaaagt
 721 cagcgtcccg cagacggaca tgaggcctga aagctgaag gagccctggc ccaacagtga
 781 ccccccttc tccttcaaga acgtcatcag cctgacagaa gatgtggatg agttccggaa
 841 taaactgcag ggagagcgga tctcaggcaa cctggatgct cctgagggcg gcttcgatgc
 901 catcctgcag acagctgtgt gcacgaggga cattggctgg cgcccggaca gcacccacct
 961 gctggtcttc tccaccgagt cagccttcca ctatgaggct gatggcgcca acgtgctggc
1021 tggcatcatg agccgcaacg atgaacggtg ccacctggac accacgggca cctacaccca
1081 gtacaggaca caggactacc cgtcggtgcc caccctggtg cgcctgctcg ccaagcacaa
1141 catcatcccc atctttgctg tcaccaacta ctcctatagc tactacgaga gcttcacac
1201 ctatttccct gtctcctcac tggggtgct gcaggaggac tcgtccaaca tcgtggagct
1261 gctggaggag gccttcaatc ggatccgctc caacctggac atccgggccc tagacagccc
1321 ccgaggcctt cggacagagg tcacctccaa gatgttccag aagacgagga ctgggtcctt
1381 tcacatccgg cgggggaag tgggtatata ccaggtgcag ctgcgggccc ttgagcacgt
1441 ggatgggacg cacgtgtgcc agctgccgga ggaccagaag ggcaacatcc atctgaaacc
1501 ttccttctcc gacggcctca agatggacgc gggcatcatc tgtgatgtgt gcacctgcga
1561 gctgcaaaaa gaggtgcggt cagctcgctg cagcttcaac ggagacttcg tgtgcggaca
1621 gtgtgtgtgc agcgagggct ggagtggcca gacctgcaac tgctccaccg gctctctgag
1681 tgacattcag ccctgcctgc ggggaggcga ggacaagccg tgctccggcc gtggggagtg
1741 ccagtgcggg cactgtgtgt gctacggcga aggccgctac gagggtcagt tctgcgagta
1801 tgacaacttc cagtgtcccc gcacttccgg gttcctgtgc aatgaccgag gacgctgctc
```

Figure 10 (cont.)

```
1861 catgggccag tgtgtgtgtg agcctggttg gacaggccca agctgtgact gtccctcag
1921 caatgccacc tgcatcgaca gcaatggggg catctgtaat ggacgtggcc actgtgagtg
1981 tggccgctgc cactgccacc agcagtcgct ctacacggac accatctgcg agatcaacta
2041 ctcggcgatc cacccgggcc tctgcgagga cctacgctcc tgcgtgcagt gccaggcgtg
2101 gggcaccggc gagaagaagg ggcgcacgtg tgaggaatgc aacttcaagg tcaagatggt
2161 ggacgagctt aagagagccg aggaggtggt ggtgcgctgc tccttccggg acgaggatga
2221 cgactgcacc tacagctaca ccatggaagg tgacggcgcc cctgggccca acagcactgt
2281 cctggtgcac aagaagaagg actgccctcc gggctccttc tggtggctca tccccctgct
2341 cctcctcctc ctgccgctcc tggccctgct actgctgcta tgctggaagt actgtgcctg
2401 ctgcaaggcc tgcctggcac ttctcccgtg ctgcaaccga ggtcacatgg tgggctttaa
2461 ggaagaccac tacatgctgc gggagaacct gatggcctct gaccacttgg acacgcccat
2521 gctgcgcagc gggaacctca agggcgtga cgtggtccgc tggaaggtca ccaacaacat
2581 gcagcggcct ggctttgcca ctcatgccgc cagcatcaac ccacagagc tggtgcccta
2641 cgggctgtcc ttgcgcctgg cccgcctttg caccgagaac ctgctgaagc ctgacactcg
2701 ggagtgcgcc cagctgcgcc aggaggtgga ggagaacctg aacgaggtct acaggcagat
2761 ctccggtgta cacaagctcc agcagaccaa gttccggcag cagcccaatg ccgggaaaaa
2821 gcaagaccac accattgtgg acacagtgct gatggcgccc cgctcggcca agccggccct
2881 gctgaagctt acagagaagc aggtggaaca gagggccttc cacgacctca aggtggcccc
2941 cggctactac accctcactg cagaccagga cgcccgggc atggtggagt tccaggaggg
3001 cgtggagctg gtggacgtac gggtgcccct ctttatccgg cctgaggatg acgacgagaa
3061 gcagctgctg gtggaggcca tcgacgtgcc cgcaggcact gccaccctcg gccgccgcct
3121 ggtaaacatc accatcatca aggagcaagc cagagacgtg gtgtcctttg agcagcctga
3181 gttctcggtc agccgcgggg accaggtggc ccgcatccct gtcatccggc gtgtcctgga
3241 cggcgggaag tcccaggtct cctaccgcac acaggatggc accgcgcagg caaccgggga
3301 ctacatcccc gtggagggtg agctgctgtt ccagcctggg gaggcctgga agagctgca
3361 ggtgaagctc ctggagctgc aagaagttga ctccctcctg cggggccgcc aggtccgcg
3421 tttccacgtc cagctcagca ccctaagtt tggggcccac ctgggccagc ccactccac
3481 caccatcatc atcagggacc cagatgaact ggaccggagc ttcacgagtc agatgttgtc
3541 atcacagcca ccccctcacg gcgacctggg cgccccgcag aaccccaatg ctaaggccgc
3601 tgggtccagg aagatccatt tcaactggct gccccttct ggcaagccaa tggggtacag
3661 ggtaaagtac tggattcagg gcgactccga atccgaagcc cacctgctcg acagcaaggt
3721 gccctcagtg gagctcacca acctgtaccc gtattgcgac tatgagatga aggtgtgcgc
3781 ctacgggct cagggcgagg gaccctacag ctccctggtg tcctgccgca ccaccagga
3841 agtgcccagc gagccagggc gtctggcctt caatgtcgtc tcctccacgg tgacccagct
3901 gagctgggct gagccggctg agaccaacgg tgagatcaca gcctacgagg tctgctatgg
3961 cctggtcaac gatgacaacc gacctattgg gcccatgaag aaagtgctgg ttgacaaccc
4021 taagaaccgg atgctgctta ttgagaacct tcgggagtcc cagccctacc gctacacggt
4081 gaaggcgcgc aacggggccg gctgggggcc tgagcgggag gccatcatca acctggccac
4141 ccagcccaag aggcccatgt ccatcccat catccctgac atccctatcg tggacgccca
4201 gagcggggag gactacgaca gcttccttat gtacagcgat gacgttctac gctctccatc
4261 gggcagccag aggcccagcg tctccgatga cactggctgc ggctggaagt tcgagcccct
4321 gctggggggg gagctggacc tgcggcgcgt cacgtggcgg ctgccccgg agctcatccc
4381 gcgcctgtcg gccagcagcg ggcgctcctc cgacgccgag gccccacgg ccccccggac
4441 gacggcggcg cgggcgggaa gggcggcagc cgtgccccgc agtgcgacac ccgggccccc
4501 cggagagcac ctggtgaatg gcggatgga ctttgccttc ccgggcagca ccaactcct
4561 gcacaggatg accacgacca gtgctgctgc ctatggcacc cacctgagcc cacacgtgcc
4621 ccaccgcgtg ctaagcacat cctccaccct cacacgggac tacaactcac tgacccgctc
4681 agaacactca cactcgacca cactgcccag ggactactcc accctcacct ccgtctcctc
4741 ccacgactct cgcctgactg ctggtgtgcc cgacacgccc accgcctgg tgttctctgc
4801 cctggggccc acatctctca gagtgagctg gcaggagccg cggtgcgagc ggccgctgca
4861 gggctacagt gtggagtacc agctgctgaa cggcggtgag ctgcatcggc tcaacatccc
4921 caaccctgcc cagacctcgg tggtggtgga agacctcctg cccaaccact cctacgtgtt
4981 ccgcgtgcgg gcccagagcc aggaaggctg gggccgagag cgtgagggtg tcatcaccat
5041 tgaatcccag gtgcacccgc agagcccact gtgtccctg ccaggctccg ccttcacttt
```

Figure 10 (cont.)

```
5101 gagcactccc agtgccccag gcccgctggt gttcactgcc ctgagcccag actcgctgca
5161 gctgagctgg gagcggccac ggaggcccaa tggggatatc gtcggctacc tggtgacctg
5221 tgagatggcc caaggaggag ggccagccac cgcattccgg gtggatggag acagcccga
5281 gagccggctg accgtgccgg gcctcagcga aacgtgccc tacaagttca aggtgcaggc
5341 caggaccact gagggcttcg ggccagagcg cgagggcatc atcaccatag agtcccagga
5401 tggaggaccc ttcccgcagc tgggcagccg tgccgggctc ttccagcacc cgctgcaaag
5461 cgagtacagc agcatcacca ccacccacac cagcgccacc gagcccttcc tagtggatgg
5521 gctgaccctg ggggcccagc acctggaggc aggcggctcc ctcaccggc atgtgaccca
5581 ggagtttgtg agccggacac tgaccaccag cggaacccct agcacccaca tggaccaaca
5641 gttcttccaa acttgaccgc accctgcccc acccccgcca tgtcccacta ggcgtcctcc
5701 cgactcctct cccggagcct cctcagctac tccatccttg caccctggg ggcccagccc
5761 acccgcatgc acagagcagg ggctaggtgt ctcctgggag gcatgaaggg ggcaaggtcc
5821 gtcctctgtg ggcccaaacc tatttgtaac caaagagctg ggagcagcac aaggacccag
5881 cctttgttct gcacttaata aatggttttg ctactgctaa aaaaaaaaaa aaaaaaaaaa
5941 aaaaaaaaaa aaaaaaaaaa aaaaaaaaaa aaaaaaaaaa aaaaaaaaaa aaaa SEQ ID NO:14
    1 ccgccgggct ggccatggag ctgctgtgcc acgaggtgga cccggtccgc agggccgtgc
   61 gggaccgcaa cctgctccga gacgaccgcg tcctgcagaa cctgctcacc atcgaggagc
  121 gctaccttcc gcagtgctcc tacttcaagt gcgtgcagaa ggacatccaa ccctacatgc
  181 gcagaatggt ggccacctgg atgctggagg tctgtgagga acagaagtgc gaagaagagg
  241 tcttccctct ggccatgaat tacctggacc gtttcttggc tggggtcccg actccgaagt
  301 cccatctgca actcctgggt gctgtctgca tgttcctggc ctccaaactc aaagagacca
  361 gcccgctgac cgcggagaag ctgtgcattt acaccgacaa ctccatcaag cctcaggagc
  421 tgctggagtg ggaactggtg gtgctgggga gttgaagtg gaacctggca gctgtcactc
  481 ctcatgactt cattgagcac atcttgcgca agctgcccca gcagcgggag aagctgtctc
  541 tgatccgcaa gcatgctcag accttcattg ctctgtgtgc caccgacttt aagtttgcca
  601 tgtacccacc gtcgatgatc gcaactggaa gtgtgggagc agccatctgt gggctccagc
  661 aggatgagga agtgagctcg ctcacttgtg atgccctgac tgagctgctg gctaagatca
  721 ccaacacaga cgtggattgt ctcaaagctt gccaggagca gattgaggcg gtgctcctca
  781 atagcctgca gcagtaccgt caggaccaac gtgacggatc caagtcggag gatgaactgg
  841 accaagccag caccctaca gacgtgcggg atatcgacct gtgaggatgc cagttgggcc
  901 gaaagagaga gacgcgtcca taatctggtc tcttcttctt tctggttgtt tttgttcttt
  961 gtgtttagg gtgaaactta aaaaaaaat tctgccccca cctagatcat atttaaagat
 1021 cttttagaag tgagagaaaa aggtcctacg aaacggaat aataaaagc atttggtgcc
 1081 tatttgaagt acagcataag ggaatccctt gtatatgcga acagttattg tttgattatg
 1141 taaaagtaat agtaaaatgc ttacaggaaa acctgcagag tagttagaga atatgtatgc
 1201 ctgcaatatg ggaacaaatt agaggagact tttttttttc atgttatgag ctagcacata
 1261 cacccccttg tagtataatt tcaaggaact gtgtacgcca tttatggcat gattagattg
 1321 caaagcaatg aactcaagaa ggaattgaaa taaggaggga catgatgggg aaggagtaca
 1381 aaacaatctc tcaacatgat tgaaccattt gggatggaga agcaccttg ctctcagcca
 1441 cctgttacta agtcaggagt gtagttggat ctctacatta atgtcctctt gctgtctaca
 1501 gtagctgcta cctaaaaaaa gatgttttat tttgccagtt ggacacaggt gattggctcc
 1561 tgggtttcat gttctgtgac atcctgcttc ttcttccaaa tgcagttcat tgcagacacc
 1621 accatattgc tatctaatgg ggaaatgtag ctatgggcca taaccaaaac tcacatgaaa
 1681 cggaggcaga tggagaccaa gggtgggatc cagaatggag tctttttctgt tattgtattt
 1741 aaaagggtaa tgtggccttg gcatttcttc ttagaaaaaa actaatttt ggtgctgatt
 1801 ggcatgtctg gttcacagtt tagcattgtt ataaaccatt ccattcgaaa agcactttga
 1861 aaaattgttc ccgagcgata gatgggatgg tttatgca SEQ ID NO:15
    1 gagacattcc ggtgggggac tctggccagc ccgagcaacg tggatcctga gagcactccc
   61 aggtaggcat ttgccccggt gggacgcctt gccagagcag tgtgtggcag gccccgtgg
  121 aggatcaaca cagtggctga acactgggaa ggaactggta cttggagtct ggacatctga
```

Figure 10 (cont.)

```
 181 aacttggctc tgaaactgcg cagcggccac cggacgcctt ctggagcagg tagcagcatg
 241 cagccgcctc caagtctgtg cggacgcgcc ctggttgcgc tggttcttgc ctgcggcctg
 301 tcgcggatct ggggagagga gagaggcttc ccgcctgaca gggccactcc gcttttgcaa
 361 accgcagaga taatgacgcc acccactaag accttatggc caagggttc caacgccagt
 421 ctggcgcggt cgttggcacc tgcggaggtg cctaaaggag acaggacggc aggatctccg
 481 ccacgcacca tctcccctcc cccgtgccaa ggacccatcg agatcaagga gacttcaaa
 541 tacatcaaca cggttgtgtc ctgccttgtg ttcgtgctgg ggatcatcgg gaactccaca
 601 cttctgagaa ttatctacaa gaacaagtgc atgcgaaacg gtcccaatat cttgatcgcc
 661 agcttggctc tgggagacct gctgcacatc gtcattgaca tccctatcaa tgtctacaag
 721 ctgctggcag aggactggcc atttggagct gagatgtgta agctggtgcc tttcatacag
 781 aaagcctccg tgggaatcac tgtgctgagt ctatgtgctc tgagtattga cagatatcga
 841 gctgttgctt cttggagtag aattaaagga attggggttc caaaatggac agcagtagaa
 901 attgttttga tttgggtggt ctctgtggtt ctggctgtcc ctgaagccat aggttttgat
 961 ataattacga tggactacaa aggaagttat ctgcgaatct gcttgcttca tcccgttcag
1021 aagacagctt tcatgcagtt tacaagaca gcaaagatt ggtggctgtt cagtttctat
1081 ttctgcttgc cattggccat cactgcattt ttttatacac taatgacctg tgaaatgttg
1141 agaaagaaaa gtggcatgca gattgcttta aatgatcacc taaagcagag acgggaagtg
1201 gccaaaaccg tcttttgcct ggtccttgtc tttgccctct gctggcttcc ccttcacctc
1261 agcaggattc tgaagctcac tctttataat cagaatgatc ccaatagatg tgaactttg
1321 agctttctgt tggtattgga ctatattggt atcaacatgg cttcactgaa ttcctgcatt
1381 aacccaattg ctctgtattt ggtgagcaaa agattcaaaa actgctttaa gtcatgctta
1441 tgctgctggt gccagtcatt tgaagaaaaa cagtccttgg aggaaaagca gtcgtgctta
1501 aagttcaaag ctaatgatca cggatatgac aacttccgtt ccagtaataa atacagctca
1561 tcttgaaaga agaactattc actgtatttc attttcttta tattggaccg aagtcattaa
1621 aacaaaatga aacatttgcc aaaacaaaac aaaaaactat gtatttgcac agcacactat
1681 taaaatatta agtgtaatta ttttaacact cacagctaca tatgacattt tatgagctgt
1741 ttacggcatg gaaagaaaat cagtgggaat taagaaagcc tcgtcgtgaa agcacttaat
1801 tttttacagt tagcacttca acatagctct taacaacttc caggatattc acacaacact
1861 taggcttaaa aatgagctca ctcagaattt ctattctttc taaaagaga tttatttta
1921 aatcaatggg actctgatat aaaggaagaa taagtcactg taaaacagaa cttttaaatg
1981 aagcttaaat tactcaattt aaaatttaa aatcctttaa aacaacttt caattaatat
2041 tatcacacta ttatcagatt gtaattagat gcaaatgaga gagcagttta gttgttgcat
2101 ttttcggaca ctggaaacat ttaaatgatc aggagggagt aacagaaaga gcaaggctgt
2161 ttttgaaaat cattacactt tcactagaag cccaaacctc agcattctgc aatatgtaac
2221 caacatgtca caaacaagca gcatgtaaca gactggcaca tgtgccagct gaatttaaaa
2281 tataatactt ttaaaagaa aattattaca tcctttacat tcagttaaga tcaaacctca
2341 caaagagaaa tagaatgttt gaaggctat cccaaaagac ttttttgaat ctgtcattca
2401 catccctgt gaagacaata ctatctacaa tttttcagg attattaaaa tcttcttttt
2461 tcactatcgt agcttaaact ctgttggtt ttgtcatctg taaatactta cctacataca
2521 ctgcatgtag atgattaaat gagggcaggc cctgtgctca tagctttacg atggagagat
2581 gccagtgacc tcataataaa gactgtgaac tgcctggtgc agtgtccaca tgacaaaggg
2641 gcaggtagca ccctctctca cccatgctgt ggttaaaatg gtttctagca tatgtataat
2701 gctatagtta aaatactatt tttcaaaatc atacagatta gtacatttaa cagctacctg
2761 taaagcttat tactaatttt tgtattattt ttgtaaatag ccaatagaaa agtttgcttg
2821 acatggtgct tttctttcat ctagaggcaa aactgctttt tgagaccgta agaacctctt
2881 agctttgtgc gttcctgcct aatttttata tcttctaagc aaagtgcctt aggatagctt
2941 gggatgagat gtgtgtgaaa gtatgtacaa gagaaacgg aagagagagg aaatgaggtg
3001 gggttggagg aaacccatgg ggacagattc ccattcttag cctaacgttc gtcattgcct
3061 cgtcacatca atgcaaaagg tcctgatttt gttccagcaa aacacagtgc aatgttctca
3121 gagtgacttt cgaaataaat tgggcccaag agcttaact cggtcttaaa atatgcccaa
3181 attttactt tgttttctt ttaataggct gggccacatg ttggaaataa gctagtaatg
3241 ttgttttctg tcaatattga atgtgatggt acagtaaacc aaaacccaac aatgtggcca
3301 gaaagaaaga gcaataataa ttaattcaca caccatatgg attctattta taaatcaccc
3361 acaaacttgt tctttaattt catcccaatc acttttcag aggcctgtta tcatagaagt
```

Figure 10 (cont.)

```
3421 cattttagac tctcaattttt aaattaatttt tgaatcacta atattttcac agtttattaa
3481 tatatttaat ttctatttaa attttagatt attttattta ccatgtactg aattttttaca
3541 tcctgatacc ctttccttct ccatgtcagt atcatgttct ctaattatct tgccaaattt
3601 tgaaactaca cacaaaaagc atacttgcat tatttataat aaaattgcat tcagtggctt
3661 tttaaaaaaa atgtttgatt caaaacttta acatactgat aagtaagaaa caattataat
3721 ttctttacat actcaaaacc aagatagaaa aaggtgctat cgttcaactt caaaacatgt
3781 ttcctagtat taaggactt  aatatagcaa cagacaaaat tattgttaac atggatgtta
3841 cagctcaaaa gatttataaa agattttaac ctattttctc ccttattatc cactgctaat
3901 gtggatgtat gttcaaacac cttttagtat tgatagctta catatggcca aaggaataca
3961 gtttatagca aaacatgggt atgctgtagc taacttatta aaagtgtaat ataacaatgt
4021 aaaaaattat atatctggga ggattttttg gttgcctaaa gtggctatag ttactgattt
4081 tttattatgt aagcaaaacc aataaaaatt taagttttttt taacaactac cttattttc
4141 actgtacaga cactaattca ttaaatacta attgattgtt taaaagaaat ataaatgtga
4201 caagtggaca ttatttatgt taaatataca attatcaagc aagtatgaag ttattcaatt
4261 aaaatgccac atttctggtc tctggg
```

SEQ ID NO:16

```
   1 gaattcccgc ggagcagcgt gcgcggggcc ccgggagacg gcggcggtag cggcgcgggc
  61 agagcaagga cgcggcggat cccactcgca cagcagcgca ctcggtgccc cgcgcagggt
 121 cgcgatgctg cccggtttgg cactgctcct gctggccgcc tggacggctc gggcgctgga
 181 ggtacccact gatggtaatg ctggcctgct ggctgaaccc cagattgcca tgttctgtgg
 241 cagactgaac atgcacatga atgtccagaa tgggaagtgg gattcagatc catcagggac
 301 caaaacctgc attgatacca aggaaggcat cctgcagtat tgccaagaag tctaccctga
 361 actgcagatc accaatgtgg tagaagccaa ccaaccagtg accatccaga actggtgcaa
 421 gcggggccgc aagcagtgca gacccatcc  ccactttgtg attccctacc gctgcttagt
 481 tggtgagttt gtaagtgatg cccttctcgt tcctgacaag tgcaaattct tacaccagga
 541 gaggatggat gtttgcgaaa ctcatcttca ctggcacacc gtcgccaaag agacatgcag
 601 tgagaagagt accaacttgc atgactacgg catgttgctg ccctgcggaa ttgacaagtt
 661 ccgaggggta gagtttgtgt gttgcccact ggctgaagaa agtgacaatg tggattctgc
 721 tgatgcggag gaggatgact cggatgtctg gtggggcgga gcagacacag actatgcaga
 781 tgggagtgaa gacaaagtag tagaagtagc agaggaggaa gaagtggctg aggtggaaga
 841 agaagaagcc gatgatgacg aggacgatga ggatggtgat gaggtagagg aagaggctga
 901 ggaaccctac gaagaagcca cagagagaac caccagcatt gccaccacca ccaccaccac
 961 cacagagtct gtggaagagg tggttcgaga ggtgtgctct gaacaagccg agacggggcc
1021 gtgccgagca atgatctccc gctggtactt tgatgtgact gaaggaagt  gtgccccatt
1081 cttttacggc ggatgtggcg gcaaccggaa caactttgac acagaagagt actgcatggc
1141 cgtgtgtggc agcgccattc ctacaacagc agccagtacc cctgatgccg ttgacaagta
1201 tctcgagaca cctgggatg  agaatgaaca tgcccattc  cagaaagcca agagagggct
1261 tgaggccaag caccgagaga aatgtccca  ggtcatgaga gaatgggaag aggcagaacg
1321 tcaagcaaag aacttgccta aagctgataa gaaggcagtt atccagcatt tccaggagaa
1381 agtggaatct ttggaacagg aagcagccaa cgagagacag cagctggtgg agacacacat
1441 ggccagagtg gaagccatgc tcaatgaccg ccgccgcctg gccctggaga actacatcac
1501 cgctctgcag gctgttcctc ctcggcctcg tcacgtgttc aatatgctaa agaagtatgt
1561 ccgcgcagaa cagaaggaca gacagcacac cctaaagcat ttcgagcatg tgcgcatggt
1621 ggatcccaag aaagccgctc agatccggtc ccaggttatg acacacctcc gtgtgattta
1681 tgagcgcatg aatcagtctc tctccctgct ctacaacgtg cctgcagtgg ccgaggagat
1741 tcaggatgaa gttgatgagc tgcttcagaa agagcaaaac tattcagatg acgtcttggc
1801 caacatgatt agtgaaccaa ggatcagtta cggaaacgat gctctcatgc catctttgac
1861 cgaaacgaaa accaccgtgg agctccttcc cgtgaatgga gagttcagcc tggacgatct
1921 ccagccgtgg cattctttgt gggctgactc tgtgccagcc aacacagaaa acgaagttga
1981 gcctgttgat gcccgccctg ctgccgaccg aggactgacc actcgaccag gttctggtt
2041 gacaaatatc aagacggagg agatctctga agtgaagatg gatcagaat  tcgacatga
2101 ctcaggatat gaagttcatc atcaaaaatt ggtgttctt  gcagaagatg tgggttcaaa
2161 caaaggtgca atcattggac tcatggtggg cggtgttgtc atagcgacag tgatcgtcat
```

Figure 10 (cont.)

```
2221 caccttggtg atgctgaaga agaaacagta cacatccatt catcatggtg tggtggaggt
2281 tgacgccgct gtcaccccag aggagcgcca cctgtccaag atgcagcaga acggctacga
2341 aaatccaacc tacaagttct ttgagcagat gcagaactag accccgcca cagcagcctc
2401 tgaagttgga cagcaaaacc attgcttcac tacccatcgg tgtccattta tagaataatg
2461 tgggaagaaa caaacccgtt ttatgattta ctcattatcg ccttttgaca gctgtgctgt
2521 aacacaagta gatgcctgaa cttgaattaa tccacacatc agtaatgtat tctatctctc
2581 tttacatttt ggtctctata ctacattatt aatgggtttt gtgtactgta aagaatttag
2641 ctgtatcaaa ctagtgcatg aatagattct ctcctgatta tttatcacat agccccttag
2701 ccagttgtat attattcttg tggtttgtga cccaattaag tcctacttta catatgcttt
2761 aagaatcgat gggggatgct tcatgtgaac gtgggagttc agctgcttct cttgcctaag
2821 tattccttc ctgatcacta tgcattttaa agttaaacat ttttaagtat ttcagatgct
2881 ttagagagat ttttttttcca tgactgcatt ttactgtaca gattgctgct tctgctatat
2941 ttgtgatata ggaattaaga ggatacacac gtttgtttct tcgtgcctgt tttatgtgca
3001 cacattaggc attgagactt caagcttttc ttttttttgtc cacgtatctt tgggtctttg
3061 ataaagaaaa gaatccctgt tcattgtaag cacttttacg gggcgggtgg ggaggggtgc
3121 tctgctggtc ttcaattacc aagaattc
```

SEQ ID NO:17
```
   1 gccgccctcg ccaccgctcc cggccgccgc gctccggtac acacaggatc cctgctgggc
  61 accaacagct ccaccatggg gctggcctgg ggactaggcg tcctgttcct gatgcatgtg
 121 tgtggcacca accgcattcc agagtctggc ggagacaaca gcgtgtttga catctttgaa
 181 ctcaccgggg ccgccgcaa ggggtctggg cgccgactgg tgaagggccc cgaccttcc
 241 agccagctt tccgcatcga ggatgccaac ctgatccccc ctgtgcctga tgacaagttc
 301 caagacctgg tggatgctgt gcggacagaa aagggttcc tccttctggc atccctgagg
 361 cagatgaaga agacccgggg cacgctgctg gccctggagc ggaaagacca ctctggccag
 421 gtcttcagcg tggtgtccaa tggcaaggcg ggcaccctgg acctcagcct gaccgtccaa
 481 ggaaagcagc acgtggtgtc tgtggaagaa gctctcctgg caaccggcca gtggaagagc
 541 atcaccctgt ttgtgcagga agacagggcc cagctgtaca tcgactgtga aaagatggag
 601 aatgctgagt tggacgtccc catccaaagc gtcttcacca gagacctggc cagcatcgcc
 661 agactccgca tcgcaaaggg gggcgtcaat gacaatttcc aggggggtgct gcagaatgtg
 721 aggtttgtct ttggaaccac accagaagac atcctcagga caaaggctg ctccagctct
 781 accagtgtcc tcctcaccct tgacaacaac gtggtgaatg gttccagccc tgccatccgc
 841 actaactaca ttggccacaa gacaaaggac ttgcaagcca tctgcggcat ctcctgtgat
 901 gagctgtcca gcatggtcct ggaactcagg ggcctgcgca ccattgtgac cacgctgcag
 961 gacagcatcc gcaaagtgac tgaagagaac aaagagttgg ccaatgagct gaggcggcct
1021 ccctatgct atcacaacgg agttcagtac agaaataacg aggaatggac tgttgatagc
1081 tgcactgagt gtcactgtca gaactcagtt accatctgca aaaaggtgtc ctgccccatc
1141 atgccctgct ccaatgccac agttcctgat ggagaatgct gtcctcgctg ttggcccagc
1201 gactctgcgg acgatggctg gtctccatgg tccagtgga cctcctgttc tacgagctgt
1261 ggcaatggaa ttcagcagcg cggccgctcc tgcgatagcc tcaacaaccg atgtgagggc
1321 tcctcggtcc agacacggac ctgccacatt caggagtgtg acaagagatt taaacaggat
1381 ggtggctgga gccactggtc cccgtggtca tcttgttctg tgacatgtgg tgatggtgtg
1441 atcacaagga tccggctctg caactctccc agccccaga tgaacgggaa accctgtgaa
1501 ggcgaagcgc gggagaccaa agcctgcaag aaagacgcct gccccatcaa tggaggctgg
1561 ggtccttggt caccatggga catctgttct gtcacctgtg gaggagggt acagaaacgt
1621 agtcgtctct gcaacaaccc cacacccag tttggaggca aggactcgt tggtgatgta
1681 acagaaaacc agatctgcaa caagcaggac tgtccaattg atggatgcct gtccaatccc
1741 tgctttgccg gcgtgaagtg tactagctac cctgatggca gctggaaatg tggtgcttgt
1801 ccctggtt acagtggaaa tggcatccag tgcacagatt ttgatgagtg caaagaagtg
1861 cctgatgcct gcttcaacca caatggagag caccggtgtg agaacacgga cccggctac
1921 aactgcctgc cctgccccc acgcttcacc ggctcacagc cttcggcca gggtgtcgaa
1981 catgccacgg ccaacaaaca ggtgtgcaag ccccgtaacc ctgcacgga tgggacccac
2041 gactgcaaca gaacgccaa gtgcaactac ctgggccact atagcgaccc catgtaccgc
2101 tgcgagtgca agcctggcta cgctggcaat ggcatcatct gcgggagga cacagacctg
```

Figure 10 (cont.)

```
2161 gatggctggc ccaatgagaa cctggtgtgc gtggccaatg cgacttacca ctgcaaaaag
2221 gataattgcc ccaaccttcc caactcaggg caggaagact atgacaagga tggaattggt
2281 gatgcctgtg atgatgacga tgacaatgat aaaattccag atgacaggga caactgtcca
2341 ttccattaca acccagctca gtatgactat gacagagatg atgtgggaga ccgctgtgac
2401 aactgtccct acaaccacaa cccagatcag gcagacacag acaacaatgg ggaaggagac
2461 gcctgtgctg cagacattga tggagacggt atcctcaatg aacgggacaa ctgccagtac
2521 gtctacaatg tggaccagag agacactgat atggatgggg ttggagatca gtgtgacaat
2581 tgcccttgg aacacaatcc ggatcagctg gactctgact cagaccgcat tggagatacc
2641 tgtgacaaca atcaggatat tgatgaagat ggccaccaga acaatctgga caactgtccc
2701 tatgtgccca atgccaacca ggctgaccat gacaagatg gcaagggaga tgcctgtgac
2761 cacgatgatg acaacgatgg cattcctgat gacaaggaca actgcagact cgtgcccaat
2821 cccgaccaga aggactctga cggcgatggt cgaggtgatg cctgcaaaga tgattttgac
2881 catgacagtg tgccagacat cgatgacatc tgtcctgaga atgttgacat cagtgagacc
2941 gatttccgcc gattccagat gattcctctg gaccccaaag ggacatccca aaatgaccct
3001 aactgggttg tacgccatca gggtaaagaa ctcgtccaga ctgtcaactg tgatcctgga
3061 ctcgctgtag gttatgatga gtttaatgct gtggacttca gtggcaccct cttcatcaac
3121 accgaaaggg acgatgacta tgctggattt gtctttggct accagtccag cagccgcttt
3181 tatgttgtga tgtggaagca agtcacccag tcctactggg acaccaaccc cacgagggct
3241 cagggatact cgggcctttc tgtgaaagtt gtaaactcca ccacagggcc tggcgagcac
3301 ctgcggaacg ccctgtggca cacaggaaac accctggcc aggtgcgcac cctgtggcat
3361 gaccctcgtc acataggctg gaaagatttc accgcctaca gatggcgtct cagccacagg
3421 ccaaagacgg gtttcattag agtggtgatg tatgaaggga agaaaatcat ggctgactca
3481 ggacccatct atgataaaac ctatgctggt ggtagactag ggttgtttgt cttctctcaa
3541 gaaatggtgt tcttctctga cctgaaatac gaatgtagag atccctaatc atcaaattgt
3601 tgattgaaag actgatcata aaccaatgct ggtattgcac cttctggaac tatgggcttg
3661 agaaaccccc caggatcact tctccttggc ttccttcttt tctgtgcttg catcagtgtg
3721 gactcctaga acgtgcgacc tgcctcaaga aaatgcagtt ttcaaaaaca gactcagcat
3781 tcagcctcca atgaataaga catcttccaa gcatataaac aattgctttg gtttcctttt
3841 gaaaaagcat ctacttgctt cagttgggaa ggtgcccatt ccactctgcc tttgtcacag
3901 agcagggtgc tattgtgagg ccatctctga gcagtggact caaaagcatt ttcaggcatg
3961 tcagagaagg gaggactcac tagaattagc aaacaaaacc accctgacat cctccttcag
4021 gaacacgggg agcagaggcc aaagcactaa ggggagggcg catcccgag acgattgtat
4081 gaagaaaata tggaggaact gttacatgtt cggtactaag tcattttcag gggattgaaa
4141 gactattgct ggatttcatg atgctgactg gcgttagctg attaacccat gtaaataggc
4201 acttaaatag aagcaggaaa gggagacaaa gactggcttc tggacttcct ccctgatccc
4261 caccccttact catcacctgc agtggccaga attagggaat cagaatcgaa accagtgtaa
4321 ggcagtgctg gctgccattg cctggtcaca ttgaaattgg tggcttcatt ctagatgtag
4381 cttgtgcaga tgtagcagga aataggaaa acctaccatc tcagtgagca ccag
```

SEQ ID NO:18

```
  1 atttctcttt agttctttgc aagaaggtag agataaagac acttttcaa aaatggcaat
 61 ggtatcagaa ttcctcaagc aggcctggtt tattgaaaat gaagagcagg aatatgttca
121 aactgtgaag tcatccaaag gtggtccgg atcagcggtg agccctatc ctaccttcaa
181 tccatcctcg gatgtcgctg ccttgcataa ggccataatg gttaaaggtg tggatgaagc
241 aaccatcatt gacattctaa ctaagcgaaa caatgcacag cgtcaacaga tcaaagcagc
301 atatctccag gaaacaggaa agccctgga tgaaacactg aagaaagccc ttacaggtca
361 ccttgaggag gttgttttag ctctgctaaa aactccagcg caatttgatg ctgatgaact
421 tcgtgctgcc atgaagggcc ttggaactga tgaagatact ctaattgaga ttttggcatc
481 aagaactaac aaagaaatca gagacattaa cagggtctac agagaggaac tgaagagaga
541 tctggccaaa gacataacct cagacacatc tggagatttt cggaacgctt tgctttctct
601 tgctaagggt gaccgatctg aggactttgg tgtaatgaa gacttggctg attcagatgc
661 cagggccttg tatgaagcag gagaaaggag aaagggaca gacgtaaacg tgttcaatac
721 catccttacc accagaagct atccacaact tcgcagagtg tttcagaaat acaccaagta
781 cagtaagcat gacatgaaca aagttctgga cctggagttg aaaggtgaca ttgagaaatg
```

Figure 10 (cont.)

```
 841 cctcacagct atcgtgaagt gcgccacaag caaaccagct ttctttgcag agaagcttca
 901 tcaagccatg aaggtgttg gaactcgcca taaggcattg atcaggatta tggtttcccg
 961 ttctgaaatt gacatgaatg atatcaaagc attctatcag aagatgtatg gtatctccct
1021 ttgccaagcc atcctggatg aaaccaaagg agattatgag aaaatcctgg tggctctttg
1081 tggaggaaac taaacattcc cttgatggtc tcaagctatg atcagaagac tttaattata
1141 tatttcatc ctataagctt aaataggaaa gtttcttcaa caggattaca gtgtagctac
1201 ctacatgctg aaaaatatag ccttttaaatc atttttatat tataactctg tataatagag
1261 ataagtccat tttttaaaaa tgtttccccc aaaccataaa accctataca agttgttcta
1321 gtaacaatac atgagaaaga tgtctatgta gctgaaaata aaatgacgtc acaagac
```

SEQ ID NO:19
```
   1 gcccccgccc ggcccgcccc gctctcctag tcccttgcaa cctggcgctg catccgggcc
  61 actgtcccag gtccaggtc ccggcccgga gctatggagc ggcgctggcc cctggggcta
 121 gggctggtgc tgctgctctg cgccccgctg ccccggggg cgcgcgccaa ggaagttact
 181 ctgatggaca caagcaaggc acagggagag ctgggctggc tgctggatcc cccaaaagat
 241 gggtggagtg aacagcaaca gatactgaat gggacacccc tctacatgta ccaggactgc
 301 ccaatgcaag gacgcagaga cactgaccac tggcttcgct ccaattggat ctaccgcggg
 361 gaggaggctt cccgcgtcca cgtggagctg cagttcaccg tgcgggactg caagagtttc
 421 cctgggggag ccgggcctct gggctgcaag gagaccttca accttctgta catggagagt
 481 gaccaggatg tgggcattca gctccgacgg cccttgttcc agaaggtaac cacggtggct
 541 gcagaccaga gcttcaccat tgagaccctt gcgtctggct ccgtgaagct gaatgtggag
 601 cgctgctctc tgggccgcct gacccgccgt ggcctctacc tcgctttcca aacccgggt
 661 gcctgtgtgg ccctggtgtc tgtccgggtc ttctaccagc gctgtcctga gaccctgaat
 721 ggcttggccc aattcccaga cactctgcct ggccccgctg ggttggtgga agtggcgggc
 781 acctgcttgc cccacgcgcg ggccagcccc aggccctcag gtgcaccccg catgcactgc
 841 agccctgatg gcgagtggct ggtgcctgta ggacggtgcc actgtgagcc tggctatgag
 901 gaaggtggca gtggcgaagc atgtgttgcc tgcccagcg gctcctaccg gatggacatg
 961 gacacacccc attgtctcac gtgccccag cagagcactg ctgagtctga ggggccacc
1021 atctgtacct gtgagagcgg ccattacaga gctccggggg agggccccca ggtggcatgc
1081 acaggtcccc cctcggcccc ccgaaacctg agcttctctg cctcagggac tcagctctcc
1141 ctgcgttggg aaccccagc agatacgggg ggacgccagg atgtcagata cagtgtgagg
1201 tgttcccagt gtcagggcac agcacaggac ggggggcct gccagccctg tgggtgggc
1261 gtgcacttct cgccgggggc ccgggcgctc accacacctg cagtgcatgt caatgccctt
1321 gaaccttatg ccaactacac ctttaatgtg gaagcccaaa atggagtgtc agggctgggc
1381 agctctggcc atgccagcac ctcagtcagc atcagcatgg ggcatgcaga gtcactgtca
1441 ggcctgtctc tgagactggt gaagaaagaa ccgaggcaac tagagctgac ctgggcgggg
1501 tcccggcccc gaagccctgg ggcgaacctg acctatgagc tgcacgtgct gaaccaggat
1561 gaagaacggt accagatggt tctagaaccc agggtcttgc tgacagagct gcagcctgac
1621 accacataca tcgtcagagt ccgaatgctg acccactgg gtcctggcc tttctcccct
1681 gatcatgagt ttcggaccag cccaccagtg tccaggggcc tgactggagg agagattgta
1741 gccgtcatct tgggctgct gcttggtgca gccttgctgc ttgggattct cgttttccgg
1801 tccaggagag cccagcggca gaggcagcag aggcacgtga ccgcgccacc gatgtggatc
1861 gagaggacaa gctgtgctga agccttatgt ggtacctcca ggcatacgag gaccctgcac
1921 agggagcctt ggactttacc cggaggctgg tctaattttc cttcccggga gcttgatcca
1981 gcgtggctga tggtggacac tgtcatagga gaggagagt ttggggaagt gtatcgaggg
2041 accctcaggc tccccagcca ggactgcaag actgtggcca ttaagaccct aaaagacaca
2101 tccccaggtg gccagtggtg gaacttcctt cgagaggcaa ctatcatggg ccagtttagc
2161 cacccgcata ttctgcatct ggaaggcgtc gtcacaaagc gaaagccgat catgatcatc
2221 acagaattta tggagaatgc agccctggat gccttcctga gggagcggga ggaccagctg
2281 gtccctgggc agctagtggc catgctgcag ggcatagcat ctggcatgaa ctacctcagt
2341 aatcacaatt atgtccaccg ggacctggct gccagaaaca tcttggtgaa tcaaaacctg
2401 tgctgcaagg tgtctgactt tggcctgact cgcctcctgg atgactttga tggcacatac
2461 gaaacccagg gaggaaagat ccctatccgt tggacagccc ctgaagccat tgcccatcgg
2521 atcttcacca cagccagcga tgtgtgggagc tttgggattg tgatgtggga ggtgctgagc
```

Figure 10 (cont.)

```
2581 tttggggaca agccttatgg ggagatgagc aatcaggagg ttatgaagag cattgaggat
2641 gggtaccggt tgccccctcc tgtggactgc cctgcccctc tgtatgagct catgaagaac
2701 tgctgggcat atgaccgtgc ccgccggcca cacttccaga agcttcaggc acatctggag
2761 caactgcttg ccaaccccca ctccctgcgg accattgcca actttgaccc cagggtgact
2821 cttcgcctgc ccagcctgag tggctcagat gggatcccgt atcgaaccgt ctctgagtgg
2881 ctcgagtcca tacgcatgaa acgctacatc ctgcacttcc actcggctgg gctggacacc
2941 atggagtgtg tgctggagct gaccgctgag gacctgacgc agatgggaat cacactgccc
3001 gggcaccaga agcgcattct ttgcagtatt cagggattca aggactgatc cctcctctca
3061 ccccatgccc aatcagggtg caaggagcaa ggacgggcc aaggtcgctc atggtcactc
3121 cctgcgcccc ttcccacaac ctgccagact aggctatcgg tgctgcttct gcccgcttta
3181 aggagaaccc tgctctgcac cccagaaaac ctctttgttt taaaagggag gtggggtag
3241 aagtaaaagg atgatcatgg gagggagctc aggggttaat atatatacat acatacacat
3301 atatatattg ttgtaaataa acaggaaatg attttctgcc tccatcccac ccatcagggc
3361 tgcaggcact
```

SEQ ID NO:20

```
   1 ccaagagcta cgcggcggcg gcggagcgca ggcctcgtgc cgttacggcc atcacggcgg
  61 ccgcagtggc gtcctggagc cctcctcagt gctgaagctg ctgaaagatg gcagaagaag
 121 tggtggtagt agccaaattt gattatgtgg cccaacaaga acaagagttg gacatcaaga
 181 agaatgagag attatggctt ctggatgatt ctaagtcctg gtggcgagtt cgaaattcca
 241 tgaataaaac aggttttgtg ccttctaact atgtggaaag gaaaaacagt gctcggaaag
 301 catctattgt gaaaaaccta aaggatacct taggcattgg aaaagtgaaa agaaaaccta
 361 gtgtgccaga ttctgcatct cctgctgatg atagtttcgt tgacccaggg gaacgtctct
 421 atgacctcaa catgcccgct tatgtgaaat ttaactacat ggctgagaga gaggatgaat
 481 tatcattgat aaaggggaca aaggtgatcg tcatggagaa atgcagtgat gggtggtggc
 541 gtggtagcta caatggacaa gttggatggt tccttcaaa ctatgtaact gaagaaggtg
 601 acagtccttt gggtgaccat gtgggttctc tgtcagagaa attagcagca gtcgtcaata
 661 acctaaatac tgggcaagtg ttgcatgtgg tacaggctct ttacccattc agctcatcta
 721 atgatgaaga acttaatttc gagaaaggag atgtaatgga tgttattgaa aaacctgaaa
 781 atgacccaga gtggtggaaa tgcaggaaga tcaatggtat ggttggtcta gtaccaaaaa
 841 actatgttac cgttatgcag aataatccat taacttcagg tttggaacca tcacctccac
 901 agtgtgatta cattaggcct tcactcactg gaaagtttgc tggcaatcct tggtattatg
 961 gcaaagtcac caggcatcaa gcagaaatgg cattaaatga aagaggacat gaaggggatt
1021 tcctcattcg tgatagtgaa tcttcgccaa atgatttctc agtatcacta aaagcacaag
1081 ggaaaaacaa gcatttaaa gtccaactaa aagagactgt ctactgcatt gggcagcgta
1141 aattcagcac catggaagaa cttgtagaac attacaaaaa ggaccaatt tttacaagtg
1201 aacaaggaga aaaattatat cttgtcaagc atttatcatg atactgctga ccagaagtga
1261 ctgctgtgta gctgtaattt gtcatgtaat tgaagactga gaaatgttg ggtccagtcg
1321 tgcttgattg gaaattgttg tttctaaatc tatatgagaa ttgacaataa gtattttat
1381 tataactcag cccatacata tatactatgt atgcagtgca tctgcataga acagttcctt
1441 atccttggcc ttctgtttta ttgttttttt ctttgctgtt ttccctttgc ttctaatatt
1501 acagttttgt attttgtaaa caaaaatcaa ataatgcata tcagaatctt tatatggaag
1561 aaatcccttta ttgcctttcc tttgtttcct tgtaaaggca ccctgttctg ttatggtttt
1621 tcattatata aaattattat atctatatat gacatatgct aaaattctt ggagagtgtt
1681 aatcttttct gtgactaaat agcaataata agtggaaat tagaaattat ttccaggtat
1741 tatatttgtc acaggccatt gtaaatacca agtatattgt gtctgccata atttttaaaa
1801 atacattcat tgtcttcagt catacagcaa gacacatgag acatagatta gaaaacatgt
1861 tgtacaattt taatttacaa ctgttggaaa taaaaatcac ttaatttttt tcc
```

SEQ ID NO:21

```
   1 catggcggcg actgcggcaa agcgagagcc tcggagacgc cgctgccgcc agcacagccg
  61 gagacctgag ccgacactgg gggcagtccg cgagccccgc actctctcga tgagtcggag
 121 aagtcccgtt gtatcagagt aagatggacg gtagctttga ttgtgattgt ggtgagctgg
 181 agccacctga tcactaacaa aagacatctt ctgttaacca acagccgcca gggcttcctg
```

Figure 10 (cont.)

```
 241 ttgaaataaa tatatagcaa caaaggaaaa aaagaagcaa aacggaaata gtgcttacca
 301 gcaccttaga atgatgctgc tcaggaccag tccaacactg aatgtatctg cactgtgagg
 361 agaatgttca tagaagcctg ttgtgtgcat atttattcac atttttgtta aatgttaaat
 421 cgtttagcac ggtaatctga gtgcacagta tgtcatttca ttccgtttga gtttcttgtt
 481 ttcgttaaat gtctgcagag ttgctgcccc tttcttgaac tatgagtact gcaatcttt
 541 taattctcaa tatgaataga gcttttgag ctttaaatct aaggggaact cgacaggcct
 601 gtttggcata tgcaatgaac atcaagaaac catcttgctg tggaagcata attatttttc
 661 ttctcccttt ttgaaagatc tttccttttg atgccagttt tcttccttgt ttacacaagt
 721 tcaatttgaa aggaaaaggc aatagtaagg gtttcaaaat ggcagagaaa tttgaaagtc
 781 tcatgaacat tcatggtttt gatctgggct ctaggtatat ggacttaaaa ccattgggtt
 841 gtggaggcaa tggcttggtt ttttctgctg tagacaatga ctgtgacaaa agagtagcca
 901 tcaagaaaat tgtccttact gatccccaga gtgtcaaaca tgctctacgt gaaatcaaaa
 961 ttattagaag acttgaccat gataacattg tgaaagtgtt tgagattctt ggtcccagtg
1021 gaagccaatt aacagacgat gtgggctctc ttacggaact gaacagtgtt tacattgttc
1081 aggagtacat ggagacagac ttggctaatg tgctggagca gggccctta ctggaagagc
1141 atgccaggct tttcatgtat cagctgctac ggggctcaa gtatattcac tctgcaaatg
1201 tactgcacag agatctcaaa ccagctaatc ttttcattaa tacggaagac ttggtgctga
1261 agataggtga ctttggtctt gcacggatca tggatcctca ttattcccat aagggtcatc
1321 tttctgaagg attggttact aaatggtaca gatctccacg tcttttactt tctcctaata
1381 attatactaa agccattgac atgtgggctg caggctgcat ctttgctgaa atgctgactg
1441 gtaaaaccct ttttgcaggt gcacatgaac ttgaacagat gcagctgatt ttagaatcta
1501 ttcctgttgt acatgaggaa gatcgtcagg agcttctcag cgtaattcca gtttacatta
1561 gaaatgacat gactgagcca cacaaacctt taactcagct gcttccagga attagtcgag
1621 aagcactgga tttcctggaa caaattttga catttagccc catggatcgg ttaacagcag
1681 aagaagcact ctcccatcct tacatgagca tatattcttt tccaatggat gagccaattt
1741 caagccatcc ttttcatatt gaagatgaag ttgatgatat tttgcttatg gatgaaactc
1801 acagtcacat ttataactgg gaaaggtatc atgattgtca gttttcagag catgattggc
1861 ctgtacataa caactttgat attgatgaag ttcagcttga tccaagagct ctgtccgatg
1921 tcactgatga agaagaagta caagttgatc ccgaaaata tttggatgga gatcgggaaa
1981 agtatctgga ggatcctgct tttgatacca attactctac tgagccttgt tggcaatact
2041 cagatcatca tgaaaacaaa tattgtgatc tggagtgtag ccatacttgt aactacaaaa
2101 cgaggtcatc atcatattta gataacttag tttggagaga gagtgaagtt aaccattact
2161 atgaacccaa gcttattata gatctttcca attggaaaga acaaagcaaa gaaaaatctg
2221 ataagaaagg caaatcaaaa tgtgaaagga atggattggt taaagcccag atagcgctag
2281 aggaagcatc acagcaactg gctggaaaag aaagggaaaa gaatcaggga tttgattttg
2341 attcctttat tgcaggaact attcagctta gttcccagca tgagcctact gatgttgttg
2401 ataaattaaa tgacttgaat agctcagtgt cccaactaga attgaaaagt ttgatatcaa
2461 agtcagtaag ccaagaaaaa caggaaaaag gaatggcaaa tctggctcaa ttagaagcct
2521 tgtaccagtc ttcttgggac agccagtttg tgagtggtgg ggaggactgt ttttcataa
2581 atcagttttg tgaggtaagg aaggatgaac aagttgagaa ggaaaacact tacactagtt
2641 acttggacaa gttctttagc aggaaagaag atactgaaat gctagaaact gagccagtag
2701 aggatgggaa gcttggggag agaggacatg aggaaggatt tctgaacaac agtggggagt
2761 tcctctttaa caagcagctc gagtccatag gcatcccaca gtttcacagt ccagttgggt
2821 caccacttaa gtcaatacag gccacattaa caccttctgc tatgaaatct tcccctcaaa
2881 ttcctcatca aacatacagc agcattctga aacatctgaa ctaaaacact cagcagacat
2941 ttatctttgt attcttcatg aaatgtgttt tgtcttttt tattactagt gtttaagtca
3001 ttttttactt gaatcagatg gtgtcattta gtaaggattt tatgagttct tgttttttaa
3061 aatccagact ttcttttct acatgtgaga tagttttcat tttaactggc atgtcatttg
3121 cacacaaaaa taaagactag agcaaaataa tgcaacgcag gaggagaaaa gaaatgcact
3181 aagacaagaa cattctctca tagaacattg atctgtttta caggaaacaa accttgcctt
3241 gaaatttaca cagtgag
```

SEQ ID NO:22

```
   1 ggtctttgag cgctaacgtc tttctgtctc cccgcggtgg tgatgacggt gaaaactgag
```

Figure 10 (cont.)

```
  61 gctgctaagg gcaccctcac ttactccagg atgaggggca tggtggcaat tctcatcgct
 121 ttcatgaagc agaggaggat gggtctgaac gactttattc agaagattgc caataactcc
 181 tatgcatgca aacaccctga agttcagtcc atcttgaaga tctcccaacc tcaggagcct
 241 gagcttatga atgccaaccc ttctcctcca ccaagtcctt ctcagcaaat caaccttggc
 301 ccgtcgtcca atcctcatgc taaaccatct gactttcact tcttgaaagt gatcggaaag
 361 ggcagttttg gaaaggttct tctagcaaga cacaaggcag aagaagtgtt ctatgcagtc
 421 aaagttttac agaagaaagc aatcctgaaa aagaaagagg agaagcatat tatgtcggag
 481 cggaatgttc tgttgaagaa tgtgaagcac cctttcctgg tgggccttca cttctctttc
 541 cagactgctg acaaattgta ctttgtccta gactacatta atggtggaga gttgttctac
 601 catctccaga gggaacgctg cttcctggaa ccacgggctc gtttctatgc tgctgaaata
 661 gccagtgcct tgggctacct gcattcactg aacatcgttt atagagactt aaaaccagag
 721 aatattttgc tagattcaca gggacacatt gtccttactg acttcggact ctgcaaggag
 781 aacattgaac acaacagcac aacatccacc ttctgtggca cgccggagta tctcgcacct
 841 gaggtgcttc ataagcagcc ttatgacagg actgtggact ggtggtgcct gggagctgtc
 901 ttgtatgaga tgctgtatgg cctgccgcct ttttatagcc gaaacacagc tgaaatgtac
 961 gacaacattc tgaacaagcc tctccagctg aaaccaaata ttacaaattc cgcaagacac
1021 ctcctggagg gcctcctgca gaaggacagg acaaagcggc tcggggccaa ggatgacttc
1081 atggagatta agagtcatgt cttcttctcc ttaattaact gggatgatct cattaataag
1141 aagattactc cccctttttaa cccaaatgtg agtgggccca acgacctacg gcactttgac
1201 cccgagttta ccgaagagcc tgtccccaac tccattggca gtcccctga cagcgtcctc
1261 gtcacagcca gcgtcaagga agctgccgag gctttcctag gcttttccta tgcgcctccc
1321 acggactctt tcctctgaac cctgttaggg cttggtttta aaggatttta tgtgtgtttc
1381 cgaatgtttt agttagcctt ttggtggagc cgccagctga caggacatct tacaagagaa
1441 tttgcacatc tctggaagct tagcaatctt attgcacact gttcgctgga agcttttga
1501 agagcacatt ctcctcagtg agctcatgag gttttcattt ttattcttcc ttccaacgtg
1561 gtgctatctc tgaaacgagc gttagagtgc cgccttagac ggaggcagga gtttcgttag
1621 aaagcggacg ctgttctaaa aaaggtctcc tgcagatctg tctgggctgt gatgacgaat
1681 attatgaaat gtgccttttc tgaagagatt gtgttagctc caaagctttt cctatcgcag
1741 tgtttcagtt ctttattttc ccttgtggat atgctgtgtg aaccgtcgtg tgagtgtggt
1801 atgcctgatc acagatggat tttgttataa gcatcaatgt gacacttgca ggacactaca
1861 acgtgggaca ttgtttgttt cttccatatt tggaagataa atttatgtgt agactttttt
1921 gtaagatacg gttaataact aaaatttatt gaaatggtct tgcaatgact cgtattcaga
1981 tgcttaaaga aagcattgct gctacaaata tttctatttt tagaaagggt ttttatggac
2041 caatgcccca gttgtcagtc agagccgttg gtgttttca ttgtttaaaa tgtcacctgt
2101 aaaatgggca ttatttatgt tttttttttt gcattcctga taattgtatg tattgtataa
2161 agaacgtctg tacattgggt tataacacta gtatatttaa acttacaggc ttatttgtaa
2221 tgtaaaccac cattttaatg tactgtaatt aacatggtta taatacgtac aatccttccc
2281 tcatcccatc acacaacttt ttttgtgtgt gataaactga ttttggtttg caataaaacc
2341 ttgaaaaata ttta
```

SEQ ID NO:23
```
  1 gagcagcaga atttcaactc cagtagactt gaatatgcct ctgggcaaag aagcagagct
 61 aacgaggaaa gggatttaaa gagttttct tgggtgtttg tcaaactttt attccctgtc
121 tgtgtgcaga gggattcaa cttcaatttt tctgcagtgg ctctgggtcc agcccttac
181 ttaaagatct ggaaagcatg aagactgggc ttttttcct atgtctcttg ggaactgcag
241 ctgcaatccc gacaaatgca agattattat ctgatcattc caaaccaact gctgaaacgg
301 tagcacctga caacactgca atccccagtt taagggctga agctgaagaa aatgaaaaag
361 aaacagcagt atccacagaa gacgattccc accataagc tgaaaaatca tcagtactaa
421 agtcaaaaga ggaaagccat gaacagtcag cagaacaggg caagagttct agccaagagc
481 tgggattgaa ggatcaagag gacagtgatg gtcacttaag tgtgaatttg gagtatgcac
541 caactgaagg tacattggac ataaaagaag atatgagtga gcctcaggag aaaaaactct
601 cagagaacac tgattttttg gctcctggtg ttagttcctt cacagattct aaccaacaag
661 aaagtatcac aaagagagag gaaaaccaag aacaacctag aaattattca catcatcagt
721 tgaacaggag cagtaaacat agccaaggcc taagggatca aggaaaccaa gagcaggatc
```

Figure 10 (cont.)

```
 781 caaatatttc caatggagaa gaggaagaag aaaaagagcc aggtgaagtt ggtacccaca
 841 atgataacca agaaagaaag acagaattgc ccagggagca tgctaacagc aagcaggagg
 901 aagacaatac ccaatctgat gatattttgg aagagtctga tcaaccaact caagtaagca
 961 agatgcagga ggatgaattt gatcagggta accaagaaca agaagataac tccaatgcag
1021 aaatggaaga ggaaaatgca tcgaacgtca ataagcacat tcaagaaact gaatggcaga
1081 gtcaagaggg taaaactggc ctagaagcta tcagcaacca caaagagaca gaagaaaaga
1141 ctgtttctga ggctctgctc atggaaccta ctgatgatgg taataccacg cccagaaatc
1201 atggagttga tgatgatggc gatgatgatg gcgatgatgg cggcactgat ggccccaggc
1261 acagtgcaag tgatgactac ttcatcccaa gccaggcctt tctggaggcc gagagagctc
1321 aatccattgc ctatcacctc aaaattgagg agcaaagaga aaaagtacat gaaaatgaaa
1381 ataggtac cactgagcct ggagagcacc aagaggccaa gaaagcagag aactcatcaa
1441 atgaggagga aacgtcaagt gaaggcaaca tgagggtgca tgctgtggat tcttgcatga
1501 gcttccagtg taaagaggc cacatctgta aggcagacca acagggaaaa cctcactgtg
1561 tctgccagga tccagtgact tgtcctccaa caaaccct tgatcaagtt tgtggcactg
1621 acaatcagac ctatgctagt tcctgtcatc tattcgctac taaatgcaga ctggaggga
1681 ccaaaaaggg gcatcaactc cagctggatt attttggagc ctgcaaat
```

SEQ ID NO:24

```
   1 cggataagga caaaaaacgc cagaagaaaa gaggcatttt ccccaaagta gcaacaaata
  61 tcatgagagc atggctcttc cagcatctca cacatccgta cccttccgaa gagcagaaga
 121 aacagttagc gcaagacaca ggacttacaa ttctccaagt aaacaactgg tttattaatg
 181 ccagaagaag aatagtacag cccatgattg accagtcaaa tcgagcagtg agccaaggag
 241 cagcatatag tccagagggt cagcccatgg ggagctttgt gttggatggt cagcaacaca
 301 tggggatccg gcctgcagga cctatgagtg gaatgggcat gaatatgggc atggatgggc
 361 aatggcacta catgtaacct tcatcatgta aagcaatcgc aaagcaaggg ggaagtttgc
 421 agagcatgcc aggggactac gtttctcagg gtggtcctat gggaatgagt atggcacagc
 481 caagttacac tcctccccag atgacccac accctactca attaagacat ggacccccaa
 541 tgcattcata tttgccaagc catcccacc cccagccat gatgatgcac ggaggacccc
 601 ctacccaccc tggaatgact atgtcagcac agagccccac aatgttaaat tctgtagatc
 661 ccaatgttgg cggacaggtt atggacattc atgcccaata gtataaggga actcaaggga
 721 aaaggaaaca cacgcaaaaa ctattttaag actttctgaa ctttgaccag atgttgacac
 781 ttaatatgaa attccagaca gctgtgatta ttttttactt ttgtcatttt tcatcaagca
 841 acagaggacc aatgcaacaa gaacacaaat gtgaaatcat gggctgactg agacaattct
 901 gtccatgtaa agatcctctg gaaaaagact ccgagagtta taactactgt agtataaata
 961 taggaactaa gttaaacttg tacatttctg ttgatcacgc cgttatgttg cctcaaatag
1021 ttttagaaga gaaaaaaaaa tatatccttg ttttccacac tatgtgtgtt gttcccaaaa
1081 gaatgactgt tttggttcat cagtgaattc accatccagg agagactgtg gtatatattt
1141 taaacctgtt gggccaatga gaaagaacc acactggaga tcatgatgaa cttttggctg
1201 aacctcatca ctcgaactcc agcttcaaga atgtgttttc atgcccggcc tttgttcctc
1261 cataaatgtg tcctttagtt tcaaacagat ctttatagtt cgtgcttcat aagccaattc
1321 ttattattat ttttggggga ctcttcttca aagagcttgc caatgaagat ttaaagacag
1381 agcaggagct tcttccagga gttctgagcc ttggttgtgg acaaaacaat cttaagttgg
1441 gcagctttcc tcaacacaaa aaaagttat taatggtcat tgaaccataa ctaggacttt
1501 atcagaaact caaagcttgg gggataaaaa ggagcaagag aatactgtaa caaacttcgt
1561 acagagttcg gtctattaat tgtttcatgt tagatattct atgtgtttac ctcaattgaa
1621 aaaaaaaga atgttttgc tagtatcaga tctgctgtgg aattggtatt gtatgtccat
1681 gaattcttct tttctcagca cgtgttcctc actagaagaa aatgctgtta cctttaagct
1741 ttgtcaaatt tacattaaaa tacttgtatg aggactgtga cgttatgtta aaaaaaaaa
1801 ggtgttaagt cacaaaaagc ggtaataaat atttcatttt tgatttt
```

SEQ ID NO:25

```
  1 agcacactga ggaggcgatc cgccagcagg aggtggagca gctggacttc cgagacctcc
 61 tggggaagaa ggtgagtaca aagacctat cggaagacga cctgaaggag atcccagccg
121 agcagatgga tttccgtgcc aacctgcagc ggcaagtgaa gccaaagact gtgtctgagg
```

Figure 10 (cont.)

```
 181 aagagaggaa ggtgcacagc ccccagcagg tcgattttcg ctctgtcctg gccaagaagg
 241 ggacttccaa gaccccgtg cctgagaagg tgccaccgcc aaaacctgcc accccggatt
 301 ttcgctcagt gctgggtggc aagaagaaat taccagcaga gaatggcagc agcagtgccg
 361 agaccctgaa tgccaaggca gtggagagtt ccaagcccct gagcaatgca cagccttcag
 421 ggcccttgaa acccgtgggc aacgccaagc ctgctgagac cctgaagcca atgggcaacg
 481 ccaagcctgc cgagaccctg aagcccatgg gcaatgccaa gcctgatgag aacctgaaat
 541 ccgctagcaa agaagaactc aagaaagacg ttaagaatga tgtgaactgc aagagaggcc
 601 atgcagggac cacagataat gaaaagagat cagagagcca ggggacagcc ccagccttca
 661 agcagaagct gcaagatgtt catgtggcag agggcaagaa gctgctgctc cagtgccagg
 721 tgtcttctga ccccccagcc accatcatct ggacgctgaa cggaaagacc atcaagacca
 781 ccaagttcat catcctctcc caggaaggct cactctgctc cgtctccatc gagaaggcac
 841 tgcctgagga cagaggctta tacaagtgtg tagccaagaa tgacgctggc caggcggagt
 901 gctcctgcca agtcaccgtg gatgatgctc cagccagtga gaacaccaag gccccagaga
 961 tgaaatcccg gaggcccaag agctctcttc ctcccgtgct aggaactgag agtgatgcga
1021 ctgtgaaaaa gaaacctgcc cccaagacac ctccgaaggc agcaatgccc cctcagatca
1081 tccagttccc tgaggaccag aaggtacgcg caggagagtc agtggagctg tttggcaaag
1141 tgacaggcac tcagcccatc acctgtacct ggatgaagtt ccgaaagcag atccaggaaa
1201 gcgagcacat gaaggtggag aacagcgaga tggcagcaa gctcaccatc ctggccgcgc
1261 gccaggagca ctgcggctgc tacacactgc tggtggagaa caagctgggc agcaggcagg
1321 cccaggtcaa cctcactgtc gtggataagc cagaccccc agctggcaca ccttgtgcct
1381 ctgacattcg gagctcctca ctgaccctgt cctggtatgg ctcctcatat gatggggca
1441 gtgctgtaca gtcctacagc atcgagatct gggactcagc caacaagacg tggaaggaac
1501 tagccacatg ccgcagcacc tctttcaacg tccaggacct gctgcctgac cacgaatata
1561 agttccgtgt acgtgcaatc aacgtgtatg gaaccagtga gccaagccag gagtctgaac
1621 tcacaacggt aggagagaaa cctgaagagc cgaaggatga gtggaggtg tcagacgatg
1681 atgagaagga gcccgaggtt gattaccgga cagtgacaat caatactgaa caaaaagtat
1741 ctgacttcta cgacattgag gagagattag gatctggaa atttggacag gtctttcgac
1801 ttgtagaaaa gaaaactcga aaagtctggg cagggaagtt cttcaaggca tattcagcaa
1861 aagagaaaga gaatatccgg caggagatta gcatcatgaa ctgcctccac caccctaagc
1921 tggtccagtg tgtggatgcc tttgaagaaa aggccaacat cgtcatggtc ctggagatcg
1981 tgtcaggagg ggagctgttt gagcgcatca ttgacgagga ctttgagctg acggagcgtg
2041 agtgcatcaa gtacatgcgg cagatctcgg agggagtgga gtacatccac aagcagggca
2101 tcgtgcacct ggacctcaag ccggagaaca tcatgtgtgt caacaagacg ggcaccagga
2161 tcaagctcat cgactttggt ctggccagga ggctggagaa cgcggggtct ctgaaggtcc
2221 tctttggcac cccagaattt gtggctcctg aagtgatcaa ctatgagccc atcggctacg
2281 ccacagacat gtggagcatc ggggtcatct gctacatcct agtcagtggc ctttccccct
2341 tcatgggaga caacgataac gaaaccttgg ccaacgttac ctcagccacc tgggacttcg
2401 acgacgaggc attcgatgag atctccgacg atgccaagga tttcatcagc aatctgctga
2461 agaaagatat gaaaaccgc ctggactgca gcagtgcct tcagcatcca tggctaatga
2521 aagataccaa gaacatggag gccaagaaac tctccaagga ccggatgaag aagtacatgg
2581 caagaaggaa atggcagaaa acgggcaatg ctgtgagagc cattggaaga ctgtcctcta
2641 tggcaatgat ctcagggctc agtggcagga aatcctcaac agggtcacca accagcccgc
2701 tcaatgcaga aaaactagaa tctgaagaag atgtgtccca agctttcctt gaggctgttg
2761 ctgaggaaaa gcctcatgta aaaccctatt tctctaagac cattcgcgat ttagaagttg
2821 tggagggaag tgctgctaga tttgactgca agattgaagg atacccagac ccgaggttg
2881 tctggttcaa agatgaccag tcaatcaggg agtcccgcca cttccagata gactacgatg
2941 aggacgggaa ctgctcttta attattagtg atgtttgcgg ggatgacgat gccaagtaca
3001 cctgcaaggc tgtcaacagt cttggagaag ccacctgcac agcagagctc attgtggaaa
3061 cgatggagga aggtgaaggg gaagggaag aggaagaaga gtgaaacaaa gccagagaaa
3121 agcagtttct aagtcatatt aaaaggacta tttctctaaa actc
```

SEQ ID NO:26

```
  1 ctctcccaac cgcctcgtcg cactcctcag gctgagagca ccgctgcact cgcggccggc
 61 gatgcgggac cccggcgcgg ccgctccgct ttcgtccctg ggcctctgtg ccctggtgct
```

Figure 10 (cont.)

```
 121 ggcgctgctg ggcgcactgt ccgcgggcgc cggggcgcag ccgtaccacg gagagaaggg
 181 catctccgtg ccggaccacg gcttctgcca gcccatctcc atcccgctgt gcacggacat
 241 cgcctacaac cagaccatcc tgcccaacct gctgggccac acgaaccaag aggacgcggg
 301 cctcgaggtg caccagttct acccgctggt gaaggtgcag tgttctcccg aactccgctt
 361 tttcttatgc tccatgtatg cgcccgtgtg caccgtgctc gatcaggcca tcccgccgtg
 421 tcgttctctg tgcgagcgcg cccgccaggg ctgcgaggcg ctcatgaaca agttcggctt
 481 ccagtggccc gagcggctgc gctgcgagaa cttcccggtg cacggtgcgg gcgagatctg
 541 cgtgggccag aacacgtcgg acggctccgg gggcccaggc ggcggcccca ctgcctaccc
 601 taccgcgccc tacctgccgg acctgccctt caccgcgctg ccccgggggg cctcagatgg
 661 caggggcgt cccgccttcc ccttctcatg ccccgtcag ctcaaggtgc ccccgtacct
 721 gggctaccgc ttcctgggtg agcgcgattg tggcgcccg tgcgaaccgg gccgtgccaa
 781 cggcctgatg tactttaagg aggaggagag gcgcttcgcc cgcctctggg tgggcgtgtg
 841 gtccgtgctg tgctgcgcct cgacgctctt taccgttctc acctacctgg tggacatgcg
 901 gcgcttcagc tacccagagc ggcccatcat cttcctgtcg ggctgctact tcatggtggc
 961 cgtggcgcac gtggccggct tccttctaga ggaccgcgcc gtgtgcgtgg agcgcttctc
1021 ggacgatggc taccgcacgg tggcgcaggg caccaagaag gagggctgca ccatcctctt
1081 catggtgctc tacttcttcg gcatggccag ctccatctgg tgggtcattc tgtctctcac
1141 ttggttcctg gcggccggca tgaagtgggg ccacgaggcc atcgaggcca actcgcagta
1201 cttccacctg gccgcgtggg ccgtgcccgc cgtcaagacc atcactatcc tggccatggg
1261 ccaggtagac ggggacctgc tgagcgggt gtgctacgtt ggcctctcca gtgtggacgc
1321 gctgcgggc ttcgtgctgg cgcctctgtt cgtctacctc ttcataggca cgtccttctt
1381 gctggccggc ttcgtgtccc tcttccgtat ccgcaccatc atgaaacacg acggcaccaa
1441 gaccgagaag ctggagaagc tcatggtgcg catcggcgtc ttcagcgtgc tctacacagt
1501 gcccgccacc atcgtcctgg cctgctactt ctacgagcag gccttccgcg agcactggga
1561 gcgcacctgg ctcctgcaga cgtgcaagag ctatgccgtg ccctgcccgc ccggccactt
1621 cccgcccatg agcccgact tcaccgtctt catgatcaag tacctgatga ccatgatcgt
1681 cggcatcacc actggcttct ggatctggtc gggcaagacc ctgcagtcgt ggcgccgctt
1741 ctaccacaga cttagccaca gcagcaaggg ggagactgcg gtatgagccc cggcccctcc
1801 ccaccttcc caccccagcc ctcttgcaag aggagaggca cggtagggaa aagaactgct
1861 gggtggggc ctgtttctgt aactttctcc ccctctactg agaagtgacc tggaagtgag
1921 aagttctttg cagatttggg gcgaggggtg atttggaaaa gaagacctgg gtggaaagcg
1981 gtttggatga aagatttca ggcaaagact tgcaggaaga tgatgataac ggcgatgtga
2041 atcgtcaaag gtacgggcca gcttgtgcct aatagaaggt tgagaccagc agagactgct
2101 gtgagtttct cccggctccg aggctgaacg gggactgtga gcgatccccc tgctgcaggg
2161 cgagtggcct gtccagaccc ctgtgaggcc ccgggaaagg tacagccctg tctgcggtgg
2221 ctgctttgtt ggaagaggg agggcctcct gcggtgtgct tgtcaagcag tggtcaaacc
2281 ataatctctt ttcactgggg ccaaactgga gcccagatgg gttaatttcc agggtcagac
2341 attacggtct ctcctcccct gccccctccc gcctgttttt cctcccgtac tgctttcagg
2401 tcttgtaaaa taagcatttg gaagtcttgg gaggcctgcc tgctagaatc ctaatgtgag
2461 gatgcaaaag aaatgatgat aacatttga gataaggcca aggagacgtg gagtaggtat
2521 ttttgctact ttttcatttt ctggggaagg caggaggcag aaagacgggt gttttatttg
2581 gtctaatacc ctgaaaagaa gtgatgactt gttgcttttc aaaacaggaa tgcattttc
2641 cccttgtctt tgttgtaaga gacaaaagag gaaacaaaag tgtctccctg tggaaaggca
2701 taactgtgac gaaagcaact tttataggca aagcagcgca aatctgaggt ttcccgttgg
2761 ttgttaattt ggttgagata aacattcctt tttaaggaaa agtgaagagc agtgtgctgt
2821 cacacaccgt taagccagag gttctgactt cgctaaagga aatgtaagag gttttgttgt
2881 ctgttttaaa taaatttaat tcggaacaca tgatccaaca gactatgtta aaatattcag
2941 ggaaatctct cccttcattt actttttctt gctataagcc tatatttagg tttcttttct
3001 atttttttct cccatttgga tcctttgagg taaaaaaaca taatgtcttc agcctcataa
3061 taaaggaaag ttaattaaaa aaaaaaagca aagagccatt ttgtcctgtt ttcttggttc
3121 catcaatctg tttattaaac atcatccata tgctgaccct gtctctgtgt ggttgggttg
3181 ggaggcgatc agcagatacc atagtgaacg aagaggaagg tttgaaccat gggcccatc
3241 tttaaagaaa gtcattaaaa gaaggtaaac ttcaaagtga ttctggagtt ctttgaaatg
3301 tgctggaaga cttaaattta ttaatcttaa atcatgtact ttttttctgt aatagaactc
```

Figure 10 (cont.)

```
3361 ggattcttt  gcatgatggg  gtaaagctta  gcagagaatc  atgggagcta  acctttatcc
3421 cacctttgac  actaccctcc  aatcttgcaa  cactatcctg  tttctcagaa  cagttttaa
3481 atgccaatca  tagagggtac  tgtaaagtgt  acaagttact  ttatatatgt  aatgttcact
3541 tgagtggaac  tgcttttac  attaaagtta  aaatcgatct  tgtgtttctt  caaccttcaa
3601 aactatctca  tctgtcagat  ttttaaaact  ccaacacagg  ttttggcatc  ttttgtgctg
3661 tatcttttaa  gtgcatgtga  aatttgtaaa  atagagataa  gtacagtatg  tatattttgt
3721 aaatctccca  tttttgtaag  aaaatatata  ttgtatttat  acatttttac  tttggatttt
3781 tgttttgttg  gctttaaagg  tctacccccac  tttatcacat  gtacagatca  caaataaatt
3841 tttttaaata  c
```

SEQ ID NO:27
```
   1 ggggctcggg  acggccgggc  tgggagctgg  agcccacagc  gggaagcggc  cgccgcccgg
  61 gcctcgcagg  gctaggcgag  gcgaggggg  gcggggccgg  gcgctacggg  aaggggaggc
 121 cgcgcggacc  gggagccgca  ccgcgccagc  cgggctgcag  cggccgcgca  ccaaggctgc
 181 gatggggctg  gagacggaga  aggcggacgt  acagctcttc  atggacgacg  actcctacag
 241 ccaccacagc  ggcctcgagt  acgccgaccc  cgagaagttc  gcggactcgg  accaggaccg
 301 ggatccccac  cggctcaact  cgcatctcaa  gctgggcttc  gaggatgtga  tgcagagcc
 361 ggtgactacg  cactcctttg  acaaagtgtg  gatctgcagc  catgccctct  ttgaaatcag
 421 caaatacgta  atgtacaagt  tcctgacggt  gttcctggcc  attccctgg  ccttcattgc
 481 gggaattctc  tttgccaccc  tcagctgtct  gcacatctgg  attttaatgc  cttttgtaaa
 541 gacctgccta  atggttctgc  cttcagtgca  gacaatatgg  aagagtgtga  cagatgttat
 601 cattgctcca  ttgtgtacga  gcgtaggacg  atgcttctct  tctgtcagcc  tgcaactgag
 661 ccaggattga  atacttggac  cccaggtctg  gagattggga  tactgtaata  cttctttgtt
 721 attataacat  aaaagcacca  ctgttctgtt  catttcctag  ctgttctaat  taagaaaact
 781 attaagatga  gcaaccacat  ttagaaatgt  ttattgacag  gtcttttcaa  ataatgcttt
 841 tctaattaat  agccaaagat  ttcatatcta  actttgtaac  cagaattata  cagtaagttg
 901 acaccactta  gatttaaagg  cagacagttt  tgctttagta  caatagtata  cattttataa
 961 tgatgaactt  ataatgatta  agggacattt  ctataaaaat  actacaatag  ttttatgcac
1021 aacttcccat  taaaaatgag  attttcttatt  tgtttgtctg  ttttttactct  gggagtaata
1081 cttttaaat  taccttaca  tatatagtca  ctggcatact  gagaatatac  aatgatcctg
1141 gaaattgcag  taacaaaagc  acacaacgat  tatagtaact  ataagataca  ataaaacaaa
1201 taaatatgaa  agtagattca  tgaaaatgta  ttcctttaaa  atattgtttt  cctacaggcc
1261 tatttaacaa  gatgtttcat  tttactgtat  attttgtagt  taatataaat  gttgctctaa
1321 tcagattgct  taaaagcatt  tttattatat  ttatgttgtt  gaactaatat  atgaaataag
1381 taaatgtagc  tcccacaagg  taaacttcat  tggtaagatt  gcactgttct  gattatgtaa
1441 gcatttgtac  atcttctttg  gaaataaaag  ataaaa
```

SEQ ID NO:28
```
   1 gtttagaaca  gcctacagac  ccagtggcac  gagacgggcc  tctctcccaa  acatcttcca
  61 agccagatcc  tagtcagtgg  gaaagcccca  gcttcaaccc  ctttgggagc  cactctgttc
 121 tgcagaactc  cccacccctc  tcttctgagg  gctcctacca  ctttgaccca  gataactttg
 181 acgaatccat  ggatcccttt  aaaccaacta  cgaccttaac  aagcagtgac  ttttgttctc
 241 ccactggtaa  tcacgttaat  gaaatcttag  aatcacccaa  gaaggcaaag  tcgcgtttaa
 301 taacgactac  tgaacaagtg  aaatttctct  gttttctgtt  gagtggctgt  aaggtgaaga
 361 agcatgaaac  tcagtctctc  gccctggatg  catgttctcg  ggatgaaggg  gcagtgatct
 421 cccagatttc  agacatttct  aatagggatg  gccatgctac  tgatgaggag  aaactggcat
 481 ccacgtcatg  tggtcagaaa  tcagctggtg  ccgaggtgaa  aggtgagcca  gaggaagacc
 541 tggagtactt  tgaatgttcc  aatgttcctg  tgtctaccat  aaatcatgcg  ttttcatcct
 601 cagaagcagg  catagagaag  gagacgtgcc  agaagatgga  agaagacggg  tccactgtgc
 661 ttgggctgct  ggagtcctct  gcagagaagg  ccctgtgtc  ggtgtcctgt  ggaggtgaga
 721 gccccctgga  tgggatctgc  ctcagcgaat  cagacaagac  agccgtgctc  accttaataa
 781 gagaagagat  aattactaaa  gagattgaag  caatgaatg  gaagaagaaa  tacgaagaga
 841 cccggcaaga  agttttggag  atgaggaaaa  ttgtagctga  atatgaaaag  actattgctc
 901 aaatgattga  tgaacaaagg  acaagtatga  cctctcagaa  gagcttccag  caactgacca
```

Figure 10 (cont.)

```
 961 tggagaagga acaggccctg gctgaccrta actctgtgga aaggtccctt tctgatctct
1021 tcaggagata tgagaacctg aaaggtgttc tggaagggtt caagaagaat gaagaagcct
1081 tgaagaaatg tgctcaggat tacttagcca gagttaaaca agaggagcag cgataccagg
1141 ccctgaaaat ccacgcagaa gagaaactgg acaaagccaa tgaagagatt gctcaggttc
1201 gaacaaaagc aaaggctgag agtgcagctc tccatgctgg actccgcaaa gagcagatga
1261 aggtggagtc cctggaaagg gccctgcagc agaagaacca agaaattgaa gaactgacaa
1321 aaatctgtga tgagctgatt gcaaagctgg gaaagactga ctgagacact cccctgtta
1381 gctcaacaga tctgcatttg gctgcttctc ttgtgaccac aattatcttg ccttatccag
1441 gaataattgc ccctttgcag agaaaaaaaa aaacttaaaa aaagcacatg cctactgctg
1501 cctgtcccgc tttgctgcca atgcaacagc cctggaagaa accctagagg gttgcatagt
1561 ctagaaagga gtgtgacctg acagtgctgg agcctcctag tttcccccta tgaaggttcc
1621 cttaggctgc tgagtttggg tttgtgattt atctttagtt tgttttaaag tcatctttac
1681 tttcccaaat gtgttaaatt tgtaactcct ctttggggtc ttctccacca cctgtctgat
1741 ttttttgtga tctgtttaat ctttaattt tttagtatca gtggttttat ttaaggagac
1801 agtttggcct attgttactt ccaatttata atcaagaagg ggctctggat ccccttttaa
1861 attacacaca ctctcacaca catacatgta tgtttataga tgctgctgct cttttccctg
1921 aagcatagtc aagtaagaac tgctctacag aaggacatat ttccttggat gtgagaccct
1981 attttgaaat agagtcctga ctcagaacac caacttaaga atttggggga ttaaagatgt
2041 gaagaccaca gtcttgggtt ttcatatctg gagaagacta tttgccatga cgttttgttg
2101 ccctggtatt tggacactcc tcagctttaa tgggtgtggc ccctttaggg ttagtcctca
2161 gactaatgat agtgtctgct ttctgcatga acggcaatat gggactccct ccaagctagg
2221 gtttggcaag tctgccctag agtcatttac tctcctctgc ctccattgt taatacagaa
2281 tcaacattta gtcttcatta tctttttttt tttttttgag acagagtttc gatctatttt
2341 aagtatgtga agaaaatcta cttgtaaaag gctcagatct taattaaaag gtaattgtag
2401 cacattacca attataaggt gaagaaatgt ttttttccca agtgtgatgc attgttcttc
2461 agatgttgaa aagaaagcaa aaaatacctt ctaacttaag acagaatttt taacaaaatg
2521 agcagtaaaa gtcacatgaa ccactccaaa aatcagtgca ttttgcatat ttttaaacaa
2581 agacagcttg ttgaatactg agaagaggag tgcaaggaga aggtctgtac taacaaagcc
2641 aaattcctca agctcttact ggactcagtt cagagtggtg ggccattaac cccaacatgg
2701 aattttcca tataaatctc aatgaattcc ctttcatttg aataggcaaa cccaaatcca
2761 tgcaagtgtt ttaaagcact gtcctgtctt aatcttacat gctgaaagtc ttcatggtga
2821 tatgcactat attcagtata cgtatgtttt cctacttctc ttgtaaaact gttgcatgat
2881 ccaacttcag caatgaattg tgcctagtgg agaacctcta tagatcttaa aaaatgaatt
2941 attctttagc agtgtattac tcacatgggt gcaatcttta gccccaggga ggtcaataat
3001 gtcttttaaa gccagaagtc acatttacc aatatgcatt tatcataatt ggtgcttagg
3061 ctgtatattc aagcctgttg tcttaacatt ttgtataaaa aagaacaaca gaaattatct
3121 gtcatttgag aagtggcttg acaatcattt gagctttgaa agcagtcact gtggtgtaat
3181 atgaatgctg tcctagtggt catagtacca agggcacgtg tctccccttg gtataactga
3241 tttcctttt agtcctctac tgctaaataa gttaattttg catttgcag aaagaaacat
3301 tgattgctaa atcttttgc tgctgtgttt tggtgtttc atgtttactt gttttatatt
3361 gatctgtttt aagtatgaga ggcttatagt gccctccatt gtaaatccat agtcatcttt
3421 ttaagcttat tgtgtttaag aaagtagcta tgtgttaaac agaggtgatg gcagcccttc
3481 cctagcacac tggtggaaga gacccccttaa gaacctgacc ccagtgaatg aagctgatgc
3541 acagggagca ccaaaggacc ttcgttaagt gataattgtc ctggcctctc agccatgacc
3601 gttatgagga aatatccccc attcgaactt aacagatgcc tcctctccaa agagaattaa
3661 aatcgtagct tgtacagatc aagagaatat actgggcaga atgaagtatg tttgtttatt
3721 tttctttaaa aataaaggat tttggaactc tggagagtaa gaatatagta tagagtttgc
3781 ctcaacacat gtgagggcca ataacctgc tagctaggca gtaataaact ctgttacaga
3841 agagaaaaag gccgggcac agtggcttat tcctgtaatc ccaacactgt ggaaggccga
3901 ggcaggagga tcacttgagt ccaggagttt gaaacctacc taggcaacat ggtgaaacct
3961 tgtctctacc aaaataaaaa ttagctgggc atggtggcac gtgcctgtgg tcccagctac
4021 ttgggaggct gaggtgggag cctgggaggt caaggctgca gtgagccatg atcatgccac
4081 tgcactccat cctgggtgac agcaagatct tgtctc
```

Figure 10 (cont.)

SEQ ID NO:29

```
  1 cgagttcccc gaggtgtacg tgcccaccgt cttcgagaac tatgtggccg acattgaggt
 61 ggacggcaag caggtggagc tggcgctgtg ggacacggcg ggccaggagg actacgaccg
121 cctgcggccg ctctcctacc cggacaccga cgtcattctc atgtgcttct cggtggacag
181 cccggactcg ctggagaaca tccccgagaa gtgggtcccc gaggtgaagc acttctgtcc
241 caatgtgccc atcatcctgg tggccaacaa aaaagacctg cgcagcgacg agcatgtccg
301 cacagagctg gcccgcatga agcaggaacc cgtgcgcacg gatgacggcc gcgccatggc
361 cgtgcgcatc caagcctacg actacctcga gtgtctgcc aagaccaagg aaggcgtgcg
421 cgaggtcttc gagacggcca cgcgcgccgc gctgcagaag cgctacggct cccagaacgg
481 ctgcatcaac tgctgcaagg tgctatgagg gccgcgcccg tcgcgcctgc ccctgccggc
```

SEQ ID NO:30

```
   1 cggggagacc atggggcccc tctcagcccc ttcctgcaca cacctcatca cttggaaggg
  61 ggtcctgctc acagcatcac tttaaactt ctggaatccg cccaccactg ccgaagtcac
 121 gattgaagcc cagccaccca aagtttctga ggggaaggat gttcttctac ttgttcacaa
 181 tttgccccag aatcttcctg gctacttctg gtacaaaggg gaaatgacgg acctctacca
 241 ttacattata tcgtatatag ttgatggtaa aataattata tatgggcctg catacagtgg
 301 aagagaaaca gtatattcca acgcatccct gctgatccag aatgtcaccc ggaaggatgc
 361 aggaacctac accttacaca tcataaagcg aggtgatgag actagagaag aaattcgaca
 421 tttcaccttc accttatact atggtccaga cctcccaga atttacccttt cattcaccta
 481 ttacggttca ggagaaaacc tcgacttgtc ctgcttcacg aatctaacc caccggcaga
 541 gtattttgg acaattaatg ggaagtttca gcaatcagga caaaagctct tatccccca
 601 aattactaga aatcatagcg ggctctatgt ttgctctgtt cataactcag ccactggcaa
 661 ggaaatctcc aaatccatga cagtcaaagt ctctggtccc tgccatggag acctgacaga
 721 gtttcagtca tgactgcaac aactgagaca ctgagaaaaa gaacaggctg atacccttcat
 781 gaaattcaag acaaagaaga aaaaaactca atgttattgg actaaataat caaaaggata
 841 atgttttcat aattttttat tggaaaatgt gctgattctt tgaatgtttt attctccaga
 901 tttatgaact ttttttcttc agcaattggt aagtatact tttgtaaaca aaaattgaaa
 961 tatttgcttt tgctgtctat ctgaatgccc cagaattgtg aaactactca tgagtactca
1021 taggtttatg gtaataaagt tatttgcaca tgttccgtag ttt
```

SEQ ID NO:31

```
   1 gcaccaacca gcaccatgcc catgatactg gggtactggg acatccgcgg gctggcccac
  61 gccatccgcc tgctcctgga atacacagac tcaagctatg aggaaaagaa gtacacgatg
 121 ggggacgctc ctgattatga cagaagccag tggctgaatg aaaaattcaa gctgggcctg
 181 gactttccca atctgcccta cttgattgat ggggctcaca agatcaccca gagcaacgcc
 241 atcttgtgct acattgcccg caagcacaac ctgtgtgggg agacagaaga ggagaagatt
 301 cgtgtggaca ttttggagaa ccagaccatg gacaaccata tgcagctggg catgatctgc
 361 tacaatccag aatttgagaa actgaagcca aagtacttgg aggaactccc tgaaaagcta
 421 aagctctact cagagtttct ggggaagcgg ccatggtttg caggaaacaa gatcactttt
 481 gtagattttc tcgtctatga tgtccttgac ctccaccgta tatttgagcc caactgcttg
 541 gacgccttcc caaatctgaa ggacttcatc tcccgctttg agggcttgga gaagatctct
 601 gcctacatga agtccagccg cttcctccca agacctgtgt tctcaaagat ggctgtctgg
 661 ggcaacaagt agggccttga aggcaggagg tgggagtgag gagcccatac tcagcctgct
 721 gcccaggctg tgcagcgcag ctggactctg catcccagca cctgcctcct cgttccttc
 781 tcctgtttat tcccatcttt actcccaaga cttcattgtc cctcttcact cccctaaac
 841 ccctgtccca tgcaggccct tgaagcctc agctacccac tatccttcgt gaacatcccc
 901 tcccatcatt acccttcct gcactaaagc cagcctgacc ttccttcctg ttagtggttg
 961 tgtctgcttt aaagcctgcc tggccctcg cctgtggagc tcagcccga gctgtccccg
1021 tgttgcatga aggagcagca ttgactggtt tacaggccct gctcctgcag catggtcct
1081 gcctaggcct acctgatgga agtaaagcct caaccac
```

SEQ ID NO:32

```
  1 ttcaggaacc ggtttggtgc tggtgctgga ggcggctatg gctttggagg tggtgccggt
```

Figure 10 (cont.)

```
  61 agtggatttg gtttcggcgg tggagctggt ggtggctttg ggctcggtgg cggagctggc
 121 tttggaggtg gcttcggtgg ccctggcttt cctgtctgcc ctcctggagg tatccaagag
 181 gtcactgtca accagagtct cctgactccc ctcaacctgc aaatcgaccc cagcatccag
 241 agggtgagga ccgaggagcg cgagcagatc aagaccctca acaataagtt tgcctccttc
 301 atcgacaagg tgcggttcct ggagcagcag aacaaggttc tggacaccaa gtggaccctg
 361 ctgcaggagc agggcaccaa gactgtgagg cagaacctgg agccgttgtt cgagcagtac
 421 atcaacaacc tcaggaggca gctggacagc atcgtggggg aacggggccg cctggactca
 481 gagctgagaa acatgcagga cctggtggaa gacttcaaga acaagtatga ggatgaaatc
 541 aacaagcgta ccactgctga gaatgagttt gtgatgctga agaaggatgt agatgctgcc
 601 tacatgaaca aggtggagct ggaggccaag gttgatgcac tgatggatga gattaacttc
 661 atgaagatgt tctttgatgc ggagctgtcc cagatgcaga cgcatgtctc tgacacctca
 721 gtggtcctct ccatggacaa caaccgcaac ctggacctgg atagcatcat cgctgaggtc
 781 aaggcccagt atgaggagat tgccaaccgc agccggacag aagccgagtc ctggtatcag
 841 accaagtatg aggagctgca gcagacagct ggccggcatg gcgatgacct ccgcaacacc
 901 aagcatgaga tctctgagat gaaccggatg atccagaggc tgagagccga gattgacaat
 961 gtcaagaaac agtgcgccaa tctgcagaac gccattgcgg atgccgagca gcgtggggag
1021 ctggccctca aggatgccag gaacaagctg gccgagctgg aggaggccct gcagaaggcc
1081 aagcaggaca tggcccggct gctgcgtgag taccaggagc tcatgaacac caagctggcc
1141 ctggacgtgg agatcgccac ttaccgcaag ctgctggagg gcgaggaatg cagactcagt
1201 ggagaaggag ttggaccagt caacatctct gttgtcacaa gcagtgtttc ctctggatat
1261 ggcagtggca gtggctatgg cggtggcctc ggtggaggtc ttggcggcgg cctcggtgga
1321 ggtcttgccg gaggtagcag tggaagctac tactccagca gcagtggggg tgtcggccta
1381 ggtggtgggc tcagtgtggg gggctctggc ttcagtgcaa gcagtggccg agggctgggg
1441 gtgggctttg gcagtggcgg gggtagcagc tccagcgtca aatttgtctc caccacctcc
1501 tcctcccgga agagcttcaa gagctaagaa cctgctgcaa gtcactgcct tccaagtgca
1561 gcaacccagc ccatggagat tgcctcttct aggcagttgc tcaagccatg ttttatcctt
1621 ttctggagag tagtctagac caagccaatt gcagaaccac attctttggt tcccaggaga
1681 gccccattcc cagcccctgg tctcccgtgc cgcagttcta tattctgctt caaatcagcc
1741 ttcaggtttc ccacagcatg gcccctgctg acacgagaac ccaaagtttt cccaaatcta
1801 aatcatcaaa acagaatccc caccccaatc ccaaattttg ttttggttct aactacctcc
1861 agaatgtgt
```

SEQ ID NO:33
```
   1 agtgatcagg gccaaagcgg tcagtgagaa ggaagtggac tctggaaacg acatttatgg
  61 caaccctatc aagaggatcc agtatgagat caagcagata aagatgttca aagggcctga
 121 gaaggatata gagtttatct acacgccccc ctcctcggca gtgtgtgggg tctcgctgga
 181 cgttggagga aagaaggaat atctcattgc aggaaaggcc gaggggacg gcaagatgca
 241 catcaccctc tgtgacttca tcgtgccctg ggacaccctg agcaccacc agaagaagag
 301 cctgaaccac aggtaccaga tgggctgcga gtgcaagatc acgcgctgcc ccatgatccc
 361 gtgctacatc tcctcccgg acgagtgcct ctggatggac tgggtcacag agaagaacat
 421 caacgggcac caggccaagt tcttcgcctg catcaagaga agtgacggct cctgtgcgtg
 481 gtaccgcggc gcggcgcccc caagcagga gtttctcgac atcgaggacc ataagcagg
 541 cctccaacgc ccctgtggcc aactgcaaaa aaagcctcca agggtttcga ctggtccagc
 601 tctgacatcc cttcctggaa acagcatgaa taaaacactc atcccatggg tccaaattaa
 661 tatg
```

SEQ ID NO:34
```
   1 tgtcgccacc atggctccgc accgccccgc gcccgcgctg ctttgcgcgc tgtccctggc
  61 gctgtgcgcg ctgtcgctgc ccgtccgcgc ggccactgcg tcgcgggggg cgtcccaggc
 121 gggggcgccc caggggcggg tgcccgaggc gcggcccaac agcatggtgg tggaacaccc
 181 cgagttcctc aaggcaggga aggagcctgg cctgcagatc tggcgtgtgg agaagttcga
 241 tctggtgccc gtgccacca acctttatgg agacttcttc acgggcgacg cctacgtcat
 301 cctgaagaca gtgcagctga ggaacggaaa tctgcagtat gacctccact actggctggg
 361 caatgagtgc agccaggatg agagcggggc ggccgccatc tttaccgtgc agctggatga
```

Figure 10 (cont.)

```
 421 ctacctgaac ggccgggccg tgcagcaccg tgaggtccag ggcttcgagt cggccacctt
 481 cctaggctac ttcaagtctg gcctgaagta caagaaagga ggtgtggcat caggattcaa
 541 gcacgtggta cccaacgagg tggtggtgca gagactcttc caggtcaaag ggcggcgtgt
 601 ggtccgtgcc accgaggtac ctgtgtcctg ggagagcttc aacaatggcg actgcttcat
 661 cctggacctg ggcaacaaca tccaccagtg gtgtggttcc aacagcaatc ggtatgaaag
 721 actgaaggcc acacaggtgt ccaagggcat ccgggacaac gagcggagtg gccgggcccg
 781 agtgcacgtg tctgaggagg gcactgagcc cgaggcgatg ctccaggtgc tgggcccaa
 841 gccggctctg cctgcaggta ccgaggacac cgccaaggag gatgcggcca ccgcaagct
 901 ggccaagctc tacaaggtct ccaatggtgc agggaccatg tccgtctccc tcgtggctga
 961 tgagaacccc ttcgccagg gggcctgaa gtcagaggac tgcttcatcc tggaccacgg
1021 caaagatggg aaaatctttg tctgaaagg caagcaggca aacacggagg agaggaaggc
1081 tgccctcaaa acagcctctg acttcatcac caagatggac tacccaagc agactcaggt
1141 ctcggtcctt cctgagggcg gtgagaccc actgttcaag cagttcttca agaactggcg
1201 ggacccagac cagacagatg gcctgggctt gtcctacctt ccagccata tgccaacgt
1261 ggagcgggtg ccttcgacg ccgccaccct gcacacctcc actgccatgg ccgccagca
1321 cggcatggat gacgatggca caggccagaa acagatctgg agaatcgaag gttccaacaa
1381 ggtgccgtg gaccctgcca catatggaca gttctatgga ggcgacagct acatcattct
1441 gtacaactac cgccatggtg gccgccaggg gcagataatc tataactggc agggtgccca
1501 gtctacccag gatgaggtcg ctgcatctgc catcctgact gctcagctgg atgaggagct
1561 gggaggtacc cctgtccaga gccgtgtggt ccaaggcaag gagcccgccc acctcatgag
1621 cctgtttggt gggaagccca tgatcatcta caagggcggc acctcccgcg agggcgggca
1681 gacagcccct gccagcaccc gcctcttcca ggtccgcgcc aacagcgctg gagccacccg
1741 ggctgttgag gtattgccta aggctggtgc actgaactcc aacgatgcct ttgttctgaa
1801 aaccccctca gccgcctacc tgtgggtggg tacaggagcc agcgaggcag agaagacggg
1861 ggcccaggag ctgctcaggg tgctgcgggc ccaacctgtg caggtggcag aaggcagcga
1921 gccagatggc ttctgggagg ccctgggcgg gaaggctgcc taccgcacat ccccacggct
1981 gaaggacaag aagatggatg cccatcctcc tcgcctcttt gcctgctcca acaagattgg
2041 acgttttgtg atcgaagagg ttcctggtga gctcatgcag gaagacctgg caacggatga
2101 cgtcatgctt ctggacacct gggaccaggt ctttgtctgg gttggaaagg attctcaaga
2161 agaagaaaag acagaagcct tgacttctgc taagcggtac atcgagacgg acccagccaa
2221 tcgggatcgg cggacgccca tcaccgtggt gaagcaaggc tttgagcctc ctcctttgt
2281 gggctggttc cttggctggg atgatgatta ctggtctgtg gaccccttgg acagggccat
2341 ggctgagctg gctgcctgag gaggggcagg gcccacccat gtcaccggtc agtgccttt
2401 ggaactgtcc ttccctcaaa gaggccttag agcgagcaga gcagctctgc tatgagtgtg
2461 tgtgtgtgtg tgtgttgttt ctttttttt tttttacagt atccaaaaat agccctgcaa
2521 aaattcagag tccttgcaaa attgtctaaa atgtcagtgt ttgggaaatt aaatccaata
2581 aaaacatttt gaagtgtg
```

SEQ ID NO:35
gaagtaaaagatttttattgttctatagacacttctgaaaagagatctaattgagaaaat
atacaaagcatttaagagtttcatccccagagactgactgaaggcgttacagccctcctc
tccaaggctcagggctgagaacggttagcatatcgaatgatcagtaaaaacatgcaaaag
tgagaaggaaagggaaaaaggtgcattcccctaagctgaggggatggaatttcagaaca
gaggangcagggtggacaagtaccaaggtggctctccctttccctctgtgtnatctttca
aaaccanttccaagcntggatnaaagcaa SEQ ID NO:36
```
   1 caaagtctga gcccgctcc gctgatgcct gtctgcagaa tccgcaccaa ccagcaccat
  61 gcccatgact ctggggtact gggacatccg tggctggcc cacgccatcc gcttgctcct
 121 ggaatacaca gactcaagct atgtggaaaa gaagtacacg ctgggggacg ctcctgacta
 181 tgacagaagc cagtggctga tgaaaaatt caagctgggc ctggactttc ccaatctgcc
 241 ctacttgatt gatgggggctc acaagatcac ccagagcaat gccatcctgc gctacattgc
 301 ccgcaagcac aacctgtgtg gggagacaga agaggagaag attcgtgtgg acattttgga
 361 gaaccaggtt atggataacc acatggagct ggtcagactg tgctatgacc cagattttga
```

Figure 10 (cont.)

```
 421 gaaactgaag ccaaaatact tggaggaact ccctgaaaag ctaaagctct actcagagtt
 481 tctggggaag cggccatggt ttgcaggaga caagatcacc tttgtggatt tccttgccta
 541 tgatgtcctt gacatgaagc gtatatttga gcccaagtgc ttggacgcct tcctaaactt
 601 gaaggacttc atctcccgct ttgagggttt gaagaagatc tctgcctaca tgaagtccag
 661 ccaattcctc cgaggtcttt tgtttggaaa gtcagctaca tggaacagca aatagggccc
 721 agtgatgcca gaagatggga gggaggagcc aaccttgctg cctgcgaccc tggaggacag
 781 cctgactccc tggacctgcc ttcttccttt ttcttctctt ctactctctt ctcttcccca
 841 aggcctcatt ggcttccttt cttctaacat catccctccc cgcatcgagg ctctttaaag
 901 cttcagctcc ccactgtcct ccatcaaagt cccctccta acgtcttcct ttccctgcac
 961 taacgccaac ctgactgctt ttcctgtcag tgctttctc ttctttgaga agccagactg
1021 atctctgagc tccctagcac tgtcctcaaa gaccatctgt atgccctgct cccttgctg
1081 ggtccctacc ccagctccgt gtgatgccca gtaaagcctg aaccatgcct gccatgtctt
1141 gtcttattcc ctgaggctcc cttgactcag gactgtgctc gaattgtggg tggttttttg
1201 tcttctgttg tccacagcca gagcttagtg gatgggtgtg tgtgtgtgtg tgttgggggt
1261 ggtgatcagg caggttcata aatttccttg gtcatttctg ccctctagcc acatccctct
1321 gttcctcact gtggggatta ctacagaaag gtgctctgtg ccaagttcct cactcattcg
1381 cgctcctgta ggccgtctag aactggcatg gttcaaagag gggctaggc gatggggaag
1441 ggggctgagc agctcccagg cagactgcct tctttcaccc tgtcctgata gacttccctg
1501 atctagatat ccttcgtcat gacacttctc aataaaacgt atcccaccgt attgt
```

SEQ ID NO:37

```
   1 ggttgagaat gcttgcacca agcttgtcca ggcagctcag atgcttcagt cagacccta
  61 ctcagtgcct gctcgagatt atctaattga tgggtcaagg ggcatcctct ctggaacatc
 121 agacctgctc cttaccttcg atgaggctga ggtccgtaaa attattagag tttgcaaagg
 181 aattttggaa tatcttacag tggcagaggt ggtggagact atggaagatt tggtcactta
 241 cacaaagaat cttgggccag gaatgactaa gatggccaag atgattgacg agagacagca
 301 ggagctcact caccaggagc accgagtgat gttggtgaac tcgatgaaca ccgtgaaaga
 361 gttgctgcca gttctcattt cagctatgaa gatttttgta acaactaaaa actcaaaaaa
 421 ccaaggcata gaggaagctt taaaaaatcg caatttact gtagaaaaaa tgagtgctga
 481 aattaatgag ataattcgtg tgttacaact cacctcttgg gatgaagatg cctgggccag
 541 caaggacact gaagccatga agagagcatt ggcctccata gactccaaac tgaaccaggc
 601 caaaggttgg ctccgtgacc ctagtgcctc cccaggggat gctggtgagc aggccatcag
 661 acagatctta gatgaagctg gaaagttgg tgaactctgt gcaggcaaag aacgcaggga
 721 gattctggga acttgcaaaa tgctagggca gatgactgat caagtggctg acctccgtgc
 781 cagnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnaggctcg
1141 agccttggcc aaacaggtgg ccacggccct gcagaacctg cagaccaaaa ccaaccgggc
1201 tgtggccaac agcagaccgg ccaaagcagc tgtacacctt gagggcaaga ttgagcaagc
1261 acagcggtgg attgataatc ccacagtgga tgaccgtgga gtcggtcagg ctgccatccg
1321 ggggcttgtg gccgaaggc atcgtctggc taatgttatg atggggcctt atcggcaaga
1381 tcttctcgcc aagtgtgacc gagtggacca gctgacagcc cagctggctg acctggctgc
1441 cagaggggaa ggggagagtc ctcaggcacg agcacttgca tctcagctcc aagactcctt
1501 aaaggatcta aagctcgga tgcaggaggc catgactcag gaagtgtcag atgttttcag
1561 cgataccaca actcccatca gctgttggc agtggcagcc acggcgcctc ctgatgcgcc
1621 taacagggaa gaggtatttg atgagagggc agctaacttt gaaaaccatt caggaaagct
1681 tggtgctacg gccgagaagg cggctgcggt tggtactgct aataaatcaa cagtggaagg
1741 cattcaggcc tcagtgaaga cggcccgaga actcacaccc caggtggtct cggctgctcg
1801 tatcttactt aggaaccctg gaaatcaagc tgcttatgaa catttgaga ccatgaagaa
1861 ccagtggatc gataatgttg aaaaaatgac agggctggtg gacgaagcca ttgataccaa
```

Figure 10 (cont.)

```
1921 atctctgttg gatgcttcag aagaagcaat taaaaaagac ctggacaagt gcaaggtagc
1981 tatggccaac attcagcctc agatgctggt tgctggggca accagtattg ctcgtcgggc
2041 caaccggatc ctgctggtgg ctaagaggga ggtggagaat tccgaggatc ccaagttccg
2101 tgaggctgtg aaagctgcct ctgatgaatt gagcaaaacc atctccccga tggtgatgga
2161 tgcaaaagct gtggctggaa acatttccga ccctggactg caaaagagct tcctggactc
2221 aggatatcgg atcctgggag ctgtggccaa ggtcagagaa gccttccaac ctcaggagcc
2281 tgacttcccg ccgcctccac cagaccttga acaactccga ctaacagatg agcttgctcc
2341 tcccaaacca cctctgcctg aaggtgaggt ccctccacct aggcctccac caccagagga
2401 aaaggatgaa gagttccctg agcagaaggc cggggaggtg attaaccagc caatgatgat
2461 ggctgccaga cagctccatg atgaagctcg caaatggtcc agcaagggca atgacatcat
2521 tgcagcagcc aagcgcatgg ctctgctgat ggctgagatg tctcggctgg taagaggggg
2581 cagtggtacc aagcgggcac tcattcagtg tgccaaggac atcgccaagg cctcagatga
2641 ggtgactcgg ttggccaagg aggttgccaa gcagtgcaca gataaacgga ttagaaccaa
2701 cctcttacag gtatgtgagc gaatcccaac cataagcacc cagctcaaaa tcctgtccac
2761 agtgaaggcc accatgctgg gccggaccaa catcagtgat gaggagtctg agcaggccac
2821 agagatgctg gttcacaatg cccagaacct catgcagtct gtgaaggaga ctgtgcggga
2881 agctgaagct gcttcaatca aaattcgaac agatgctgga tttacactgc gctgggttag
2941 aaagactccc tggtaccagt aggcacctgg ctgagcctgg ctgcacaga aacctctact
3001 aaaaagaagg aaaatgatct gagtcccagg agctgcccag agttgctggg agctgaaaaa
3061 tcacatcctg gcctggcaca tcagaaagga atgggggcct cttcaaatta gaagacattt
3121 atactctttt ttcatggaca ctttgaaatg tgtttctgta taaagcctgt attctcaaac
3181 acagttacac ttgtgcaccc tctatcccaa taggcagact gggtttctag cccatggact
3241 tcacataagc tcagaatcca agtgaacact agccagacac tctgctctgc ccttgttccc
3301 taggggacac ttccctctgt ttctctttcc ttggctccca ttcactcttc cagaatccca
3361 agcccaggg cccaggcaaa tcagttacta agaagaaaat tgctgtgcct cccaaaattg
3421 ttttgagctt tccatgttgc tgccaaccat accttccttc cctggctgt gctacctggg
3481 tcctttcag aagtgagctt tgctgctaca ggggaaggtg gcctctgtgg agcccagca
3541 tatgggggcc tggattcatt tcctgccctt cctcagttta atccttctag tttcccacaa
3601 tataaaactg tacttcactg tcaggaagaa atcacagaat catatgattc tgcttttacc
3661 atgcccctga gcaatgtctg tgctagggaa acttcccgtc ccatatcctg cctcagcccg
3721 ccaaggtagc catcccatga acacactgtg tcctggtgct ctctgccact ggaagggcag
3781 agtagccagg gtgtggccct gccatcttcc cagcagggcc actcccggca ctccatgctt
3841 agtcactgcc tgcagaggtc tgtgctgagg cctatcatt cattcttagc tcttaattgt
3901 tcattttgag ctgaaatgct gcatttaat tttaaccaaa acatgtctcc tatcctggtt
3961 tttgtagcct tcctccacat ccttctaaa caagatttta aagacatgta ggtgtttgtt
4021 catctgtaac tctaaaagat ccttttaaa ttcagtccta agaaagagga gtgcttgtcc
4081 cctaagagtg tttaatggca aggcagccct gtctgaagga cacttcctgc ctaagggaga
4141 gtggtatttg cagactagaa ttctagtgct gctgaagatg aatcaatggg aaatactact
4201 cctgtaattc ctacctccct gcaaccaact acaaccaagc tctctgcatc tactcccaag
4261 tatggggttc aagagagtaa tgggtttcat atttcttatc accacagtaa gttcctacta
4321 ggcaaaatga gagggcagtg tttccttttt ggtacttatt actgctaagt atttcccagc
4381 acatgaaacc ttatttttc ccaagccag aaccagatga gtaaaggagt aagaaccttg
4441 cctgaacatc cttccttccc acccatcgct gtgtgttagt tccaacatc gaatgtgtac
4501 aacttaagtt ggtcctttac actcaggctt tcactatttc ctttataatg aggatgatta
4561 ttttcaaggc cctcagcata tttgtatagt tgcttgcctg atataaatgc aatattaatg
4621 cctttaaagt atgaatctat gccaaagatc acttgttgtt ttactaaaga aagattactt
4681 agaggaaata agaaaaatca tgtttgctct cccggttctt ccagtggttt gagacactgg
4741 tttacacttt atgccggatg tgcttttctc caatatcagt gctcgagaca cagtgaagca
4801 aattaaaaaa aa
```

SEQ ID NO:38

```
  1 atatccagcc tttgccgaat acatcctatc tgccacacat ccagcgtgag gtccctccag
 61 ctacaaggtg ggcaccatgg cggagaagtt tgactgccac tactgcaggg atccttgca
121 ggggaagaag tatgtgcaaa aggatggcca ccactgctgc ctgaaatgct ttgacaagtt
```

Figure 10 (cont.)

```
 181 ctgtgccaac acctgtgtgg aatgccgcaa gcccatcggt gcggactcca aggaggtgca
 241 ctataagaac cgcttctggc atgacacctg cttccgctgt gccaagtgcc ttcacccctt
 301 ggccaatgag acctttgtgg ccaaggacaa caagatcctg tgcaacaagt gcaccactcg
 361 ggaggactcc cccaagtgca agggtgctt caaggccatt gtggcaggag atcaaaacgt
 421 ggagtacaag gggaccgtct ggcacaaaga ctgcttcacc tgtagtaact gcaagcaagt
 481 catcgggact ggaagcttct tccctaaagg ggaggacttc tactgcgtga cttgccatga
 541 gaccaagttt gccaagcatt gcgtgaagtg caacaaggcc atcacatctg aggaatcac
 601 ttaccaggat cagccctggc atgccgattg ctttgtgtgt gttacctgct ctaagaagct
 661 ggctgggcag cgtttcaccg ctgtggagga ccagtattac tgcgtggatt gctacaagaa
 721 ctttgtggcc aagaagtgtg ctggatgcaa gaacccatc actgggaaaa ggactgtgtc
 781 aagagtgagc cacccagtct ctaaagctag gaagccccca gtgtgccacg gaaacgctt
 841 gcctctcacc ctgtttccca gcgccaacct ccggggcagg catccgggtg gagagaggac
 901 ttgtccctcg tgggtggtgg ttctttatag aaaaaatcga agcttagcag ctcctcgagg
 961 cccgggttg gtaaaggctc cagtgtggtg gcctatgaag acaatcctg gcacgactac
1021 tgcttccact gcaaaaaatg ctccgtgaat ctggccaaca agcgcttgt tttccaccag
1081 gagcaagtgt attgtcccga ctgtgccaaa aagctgtaaa ctgacagggg ctcctgtcct
1141 gtaaaatggc atttgaatct cgttctttgt gtccttactt tctgccctat accatcaata
1201 ggggaagagt ggtccttccc ttctttaaag ttctccttcc gtcttttctc ccattttaca
1261 gtattactca ataagggca cacagtgatc atattagcat ttagcaaaaa gcaaccctgc
1321 agcaaagtga atttctgtcc ggctgcaatt taaaaatgaa aacttaggta gattgactct
1381 tctgcatgtt tctcatagag cagaaaagtg ctaatcattt agccacttag tgatgtaagc
1441 aagaagcata ggagataaaa cccccactga gatgcctctc atgcctcagc tgggacccac
1501 cgtgtagaca cacgacatgc aagagttgca gcggctgctc caactcactg ctcaccctct
1561 tctgtgagca ggaaaagaac cctactgaca tgcatggttt aacttcctca tcagaactct
1621 gcccttcctt ctgttctttt gtgctttcaa ataactaaca cgaacttcca gaaaattaac
1681 atttgaactt agctgtaatt ctaaactgac ctttccccgt actaacgttt ggtttccccg
1741 tgtggcatgt tttctgagcg ttcctacttt aaagcatgga acatgcaggt gatttgggaa
1801 gtgtagaaag acctgagaaa acgagcctgt ttcagaggaa catcgtcaca acgaatactt
1861 ctggaagctt aacaaaacta accctgctgt ccttttatt gttttaatt aatattttg
1921 ttttaattga tagcaaaata gtttatgggt ttggaaactt gcatgaaaat attttagccc
1981 cctcagatgt tcctgcagtg ctgaaattca tcctacggaa gtaaccgcaa aactctag
```

SEQ ID NO:39

```
   1 tgccgcccta caccgtggtc tatttcccag ttcgagnnnn nnnnnnnnnn nnnnnnnnnn
  61 nnnnnnnnnn nnnnnnnngc tgctggcaga tcagggccag agctggaagg aggaggtggt
 121 gaccgtggag acgtggcagg agggctcact caaagcctcc tgcctatacg ggcagctccc
 181 caagttccag gacggagacc tcaccctgta ccagtccaat accatcctgc gtcacctggn
 241 nnnnnnnnnn nnnnnnnnnn nnnnnnnngg ctctatggga aggaccagca ggaggcagcc
 301 ctggtggaca tggtgaatga cggcgtggag gacctccgct gcaaatacat ctccctcatc
 361 tacaccaact atgaggcggg caaggatgac tatgtgaagg cactgccgg gcaactgaag
 421 ccttttgaga ccctgctgtc ccagaaccag ggaggcaaga ccttcattgt gggagaccag
 481 atctccttcg ctgactacaa cctgctggac ttgctgctga tccatgaggt cctagccct
 541 ggctgcctgg atgcgttccc cctgctctca gcatatgtgg ggcgcctcag tgcccggccc
 601 aagctcaagg ccttcctggc ctcccctgag tacgtgaacc tcccatcaa tggcaacggg
 661 aaacagtgag ggttgggggg actctgagcg g
```

SEQ ID NO:40

```
   1 cttttcacac tggccttaaa gaggatatat tagaagttga agtaggaagg gagccagaga
  61 ggccgatggc gcaaaggtac gacgatctac cccattacgg gggcatggat ggagtaggca
 121 tcccctccac gatgtatggg gacccgcatg cagccaggtc catgcagccg gtccaccacc
 181 tgaaccacgg gcctcctctg cactcgcatc agtacccgca cacagctcat accaacgcca
 241 tggcccccag catgggctcc tctgtcaatg acgctttaaa gagagataaa gatgccattt
 301 atggacaccc cctcttccct ctcttagcac tgatttttga gaaatgtgaa ttagctactt
```

Figure 10 (cont.)

```
 361 gtaccccccg cgagccgggg gtggcgggcg gggacgtctg ctcgtcagag tcattcaatg
 421 aagatatagc cgtgttcgcc aaacagattc gcgcagaaaa acctctattt tcttctaatc
 481 cagaactgga taacttgatg attcaagcca tacaagtatc aaggtttcat ctattggaat
 541 tagagaaggt acacgaatta tgtgacaatt tctgccaccg gtatattagc tgtttgaaag
 601 ggaaaatgcc tatcgatttg gtgatagacg atagagaagg aggatcaaaa tcagacagtg
 661 aagatataac aagatcagca aatctaactg accagccctc ttggaacaga gatcatgatg
 721 acacggcatc tactcgttca ggaggaaccc caggcccttc cagcggtggc cacacgtcac
 781 acagtgggga caacagcann nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnncacccstt
 961 acccttctga agaacagaaa aagcagttgg cacaagacac gggactcacc atccttcaag
1021 tgaacaattg gtttattaat gcccggagaa gaatagtgca gccatgata gaccagtcca
1081 accgagcagt aagtcaagga acaccttata atcctgatgg acagcccatg ggaggtttcg
1141 taatggacgg tcagcaacat atgggaatta gagcaccagg acctatgagt ggaatgggca
1201 tgaatatggg catggagggg cagtggcact acatgtaacc ttcatctagt taaccaatcg
1261 caaagcaagg gggaaggctg caaagtatgc caggggagta tgtagccgg ggtggtccaa
1321 tgggtgtgag tatgggacag ccaagttata cccaaccccca gatgcccccc catcctgctc
1381 agctgcgtca tgggccccc atgcatacgt acattcctgg acaccctcac cacccaacag
1441 tgatgatgca tggaggaccg ccccaccctg gaatgccaat gtcagcatca agccccacag
1501 ttcttaatac aggagaccca acaatgagtg gacaagtcat ggacattcat gctcagtagc
1561 ttaagggaat atgcattgtc tgcaatggtg actgattca aatcatgttt tttctgcaat
1621 gactgtggag ttccattctt ggcatctact ctggaccaag gagcatccct aattcttcat
1681 agggacctt aaaaagcagg aaataccaac tgaagtcaat ttggggggaca tgctaaataa
1741 ctatataaga cattaagaga acaaagagtg aaatattgta aatgctatta tactgttatc
1801 catattacgt tgtttcttat agatttttta aaaaaaatgt gaaatttttc cacactatgt
1861 gtgttgtttc catagctctt cacttcctcc agaagcctcc ttacattaaa aagccttaca
1921 gttatcctgc aagggacagg aaggtctgat ttgcaggatt tttagagcat taaaataact
1981 atcaggcaga agaatctttc ttctcgccta ggatttcagc catgcgcgcg ctctctctct
2041 ttctctctct tttcctctct ctccctcttt ctagcctggg gcttgaattt gcatgtctaa
2101 ttcatttact caccatattt gaattggcct gaacagatgt aaatcgggaa ggatgggaaa
2161 aactgcagtc atcaacaatg attaatcagc tgttgcaggc agtgtcttaa ggagactggt
2221 aggaggaggc atggaaacca aaaggccgtg tgtttagaag cctaattgtc acatcaagca
2281 tcattgtccc catgcaacaa ccaccacctt atacatcact tcctgttta agcagctcta
2341 aaacatagac tgaagattta ttttaatat gttgacttta tttctgagca aagcatcggt
2401 catgtgtgta tttttcata gtcccacctt ggagcattta tgtagacatt gtaaataaat
2461 tttgtgcaaa aaggactgga aaaatgaact gtattattgc aatttttttt t
```

SEQ ID NO:41

```
   1 ctcaataagc caaccatgtc tttcaaggat tacatccaag agaggagtga cccagtggag
  61 caaggcaaac cagttatacc tgcagctgtg ctggccggct tcacaggaag tggacctatt
 121 cagctgtggc agtttctcct ggagctgcta tcagacaaat cctgccagtc attcatcagc
 181 tggactggag acggatggga gtttaagctc gccgacccocg atgaggtggc ccgccggtgg
 241 ggaaagagga aaaataagcc caagatgaac tacgagaagc tgagccgggg cttacgctac
 301 tattacgaca gaacatcat ccacaagacg tgggggaagc gctacgtgta ccgcttcgtg
 361 tgcgacctcc agaacttgct gggttcacg cccgaggaac tgcacgccat cctgggcgtc
 421 cagcccgaca cggaggactg a
```

SEQ ID NO:42

```
   1 ggacgacaag gcgttcacca aggagctgga ccagtgggtc gagcagctga acgagtgtaa
  61 gcagctgaac gagaaccaag tgcggacgct gtgcgagaag gcaaaggaaa ttttaacaaa
 121 agaatcaaat gtgcaagagg ttcgttgccc tgttactgtc tgtggagatg tgcatggtca
 181 atttcatgat cttatgaac tctttagaat tggtggaaaa tcaccggata caaactactt
 241 attcatgggt gactatgtag acagaggata ttattcagtg gagactgtga ctcttcttgt
 301 agcattaaag gtgcgttatc cagaacgcat tacaatattg agaggaaatc acgaaagccg
```

Figure 10 (cont.)

```
 361 acaaattacc caagtatatg gcttttatga tgaatgtctg cgaaagtatg ggaatgccaa
 421 cgtttggaaa tattttacag atctctttga ttatcttcca cttacagctt tagtagatgg
 481 acagatattc tgcctccatg gtggcctctc tccatccata gacacactgg atcatataag
 541 agccctggat cgtttacagg aagttccaca tgagggccca atgtgtgatc tgttatggtc
 601 agatccagat gatcgtggtg gatggggtat ttcaccacgt ggtgctggct acacatttgg
 661 acaagacatt tctgaaacct ttaaccatgc caatggtctc acactggttt ctcgtgccca
 721 ccagcttgta atggagggat acaattggtg tcatgatcgg aatgtggtta ccatttcag
 781 tgcacccaat tactgttatc gttgtgggaa ccaggctgct atcatggaat tagatgacac
 841 tttaaaatat tccttccttc aatttgaccc agcgcctcgt cgtggtgagc ctcatgttac
 901 acggcgcacc ccagactact tcctataaat ttctcctggg aaacctgcct ttgtatgtgg
 961 aagtatacct ggcttttaa aatatatgta tttaaaaaca aaaagcaaca gtaatctatg
1021 tgtttctgta acaaattggg atctgtcttg gcattaaacc acatcatgga ccaaatgtgc
1081 catactaatg atgagcattt agcacaattt gagactgaaa tttagtacac tatgttctag
1141 gtcagtctaa cagtttgcct gctgtattta tagtaaccat tttcctttgg actgttcaag
1201 caaaaaggt aactaactgc ttcatctcct tttgcgctta tttggaaatt ttagttatag
1261 tgtttaactg gcatggatta atagagttgg agttttattt ttaagaaaaa ttcacaagct
1321 aacttccact aatccattat cctttatttt attgaaatgt ataattaact taactgaaga
1381 aaaggttctt cttgggagta tgttgtcata acatttaaag agatttccct tcatttaaac
1441 taaattactg ttttatgttg atctgcatat ttctgtatat ttgtcatgac agtgcttgca
1501 tcctatttgg tgtactcagc aaataaactt t
```

SEQ ID NO:43
```
   1 cctgtgagca ccacgtcaac ggctcccggc ccccatgcac gggggaggga gataccccca
  61 agtgtagcaa gatctgtgag cctggctaca gcccgaccta caaacaggac aagcactacg
 121 gatacaattc ctacagcgtc tccaatagcg agaaggacat catggccgag atctacaaaa
 181 acggccccgt ggagggagct ttctctgtgt attcggactt cctgctctac aagtcaggag
 241 tgtaccaaca cgtcaccgga gagatgatgg gtggccatgc catccgcatc ctgggctggg
 301 gagtggagaa tggcacaccc tactggctgg ttgccaactc ctggaacact gactggggtg
 361 acaatggctt ctttaaaata ctcagaggac aggatcactg tggaatcgaa tcagaagtgg
 421 tggctggaat tccacgcacc gatcagtact gggaaaagat ctaatctgcc gtgggcctgt
 481 cgtgccagtc ctggggcga gatggggta gaaatgcatt ttattcttta agttcacgta
 541 agatacaagt ttcagacagg gtctgaagga ctggattggc caaacatcag acctgtcttc
 601 caaggagacc aagtcctggc tacatcccag cctgtggtta cagtgcagac aggccatgtg
 661 agccaccgct gccagcacag agcgtccttc cccctgtaga ctagtgccgt agggagtacc
 721 tgttgcccca gctgactgtg gcccctccg tgatccatcc atctccaggg agcaagacag
 781 agaccagga atggaaagcg gagttcctaa caggatgaaa gttcccccat cagttcccc
 841 agtacctcca agcaagtagc tttccacatt tgtcacagaa atcagaggag agatggtgtt
 901 gggagccctt tggagaacgc cagtctccca ggcccctgc atctatcgag tttgcaatgt
 961 cacaacctct ctgatcttgt gctcagcatg attctttaat agaagtttta ttttttcgtg
1021 cactctgcta atcatgtggg tgagccagtg aacagcggg agacctgtgc tagttttaca
1081 gattgcctcc ttatgacgcg gctcaaaagg aaaccaagtg gtcaggagtt gtttctgacc
1141 cactgatctc tactaccaca aggagaatag tttaggagaa accagctttt actgttttg
1201 aaaaattaca gcttcaccct gtcaagttaa caaggaatgc ctgtgccaat aaaaggtttc
```

SEQ ID NO:44
```
   1 gtgtcccata gtgtttccaa acttggaaag ggcgggggag ggcgggagga tgcggagggc
  61 ggaggtatgc agacaacgag tcagagtttc cccttgaaag cctcaaaagt gtccacgtcc
 121 tcaaaaagaa tggaaccaat ttaagaagcc agcccgtgg ccacgtccct tcccccattc
 181 gctccctcct ctgcgccccc gcaggctcct cccagctgtg gctgcccggg ccccagccc
 241 cagccctccc attggtggag gcccttttgg aggcaccta ggccaggga aacttttgcc
 301 gtataaatag ggcagatccg ggctttatta ttttagcacc acggcagcag gaggtttcgg
 361 ctaagttgga ggtactggcc acgactgcat gcccgcgccc gcaggtgat acctccgccg
 421 gtgacccagg ggctctgcga cacaaggagt ctgcatgtct aagtgctaga catgctcagc
 481 tttgtggata cgcggacttt gttgctgctt gcagtaacct tatgcctagc aacatgccaa
```

Figure 10 (cont.)

```
 541 tctttacaag aggaaactgt aagaaagggc ccagccggag atagaggacc acgtggagaa
 601 aggggtccac caggccoccc aggcagagat ggtgaagatg gtcccacagg ccctcctggt
 661 ccacctggtc ctcctgccc ccctggtctc ggtgggaact ttgctgctca gtatgatgga
 721 aaaggagttg gacttggccc tggaccaatg ggcttaatgg gacctagagg cccacctggt
 781 gcagctggag ccccaggccc tcaaggtttc caaggacctg ctggtgagcc tggtgaacct
 841 ggtcaaactg gtcctgcagg tgctcgtggt ccagctggcc ctcctggcaa ggctggtgaa
 901 gatggtcacc ctggaaaacc cggacgacct ggtgagagag gagttgttgg accacagggt
 961 gctcgtggtt tccctggaac tcctggactt cctggcttca aaggcattag gggacacaat
1021 ggtctggatg gattgaaggg acagcccgt gctcctggtg tgaagggtga acctggtgcc
1081 cctggtgaaa atggaactcc aggtcaaaca ggagcccgtg ggcttcctgg tgagagga
1141 cgtgttggtg cccctggccc agctggtgcc cgtggcagtg atggaagtgt gggtcccgtg
1201 ggtcctgctn nnnnnnnnng gtctgctggc cctccaggct tcccaggtgc ccctggcccc
1261 aagggtgaaa ttggagctat tggtaacgct ggtcctgctg gtcccgccgg tccccgtggt
1321 gaagtgggtc ttccaggcct ctccggcccc gttgacctc ctggtaatcc tggagcaaac
1381 ggccttactg gtgccaaggg tgctgctggc cttccggcg ttgctggggc tcccggcctc
1441 cctggacccc gcggtattcc tggccctgtt ggtgctgccg gtgctactgg tgccagagga
1501 cttgttggtg agcctggtcc agctggctcc aaaggagaga gcggtaacaa gggtgagccc
1561 ggctctgctg ggccccaagg tcctcctggt cccagtggtg aagaaggaaa gagaggccct
1621 aatggggaag ctggatctgc cggccctcca ggacctcctg ggctgagagg tagtcctggt
1681 tctcgtggtc ttcctggagc tgatggcaga gctggcgtca tgggccctcc tggtagtcgt
1741 ggtgcaagtg gccctgctgg agtccgagga cctaatggag atgctggtcg ccctggggag
1801 cctggtctca tgggacccag aggtcttcct ggttcccctg gaaatatcgg ccccgctgga
1861 aaagaaggtc ctgtcggcct ccctggcatc gacggcaggc ctggcccaat tggccccgtt
1921 ggagcaagag gagagcctgg caacattgga ttccctggac ccaaaggccc cactggtgac
1981 cctggcaaaa acggtgataa aggtcatgct ggtcttgctg gtgctcgggg tgctccaggt
2041 cctgatggaa acaatggtgc tcagggacct cctggaccac agggtgttca aggtggaaaa
2101 ggtgaacagg gtcccgctgg tcctccaggc ttccagggtc tgcctggccc ctcaggtccc
2161 gctggtgaag ttggcaaacc aggagaaagg ggtctccatg gtgagtttgg tctccctggt
2221 cctgctggtc aagagggga acgcggtccc ccaggtgaga gtggtgctgc cggtcctact
2281 ggtcctattg gaagccgagg tccttctgga cccccagggc ctgatggaaa caagggtgaa
2341 cctggtgtgg ttggtgctgt gggcactgct ggtccatctg gtcctagtgg actcccagga
2401 gagagggtg ctgctggcat acctggaggc aagggagaaa agggtgaacc tggtctcaga
2461 ggtgaaattg gtaaccctgg cagagatggt gctcgtggtg ctcatggtgc tgtaggtgcc
2521 cctggtcctg ctggagccac aggtgaccgg ggcgaagctg gggctgctgg tcctgctggt
2581 cctgctggtc ctcggggaag ccctggtgaa cgtggcgagg tcggtcctgc tggccccaac
2641 ggatttgctg gtccggctgg tgctgctggt caaccgggtg ctaaaggaga aagaggaggc
2701 aaagggccta agggtgaaaa cggtgttgtt ggtccacag gccccgttgg agctgctggc
2761 ccagctggtc caaatggtcc ccccggtcct gctggaagtc gtggtgatgg aggccccct
2821 ggtatgactg gtttccctgg tgctgctgga cggactggtc cccaggacc ctctggtatt
2881 tctggccctc ctggtccccc tggtcctgct gggaaagaag ggcttcgtgg tcctcgtggt
2941 gaccaaggtc cagttggccg aactggagaa gtaggtgcag ttggtccccc tggcttcgct
3001 ggtgagaagg gtccctctgg agaggctggt actgctggac ctcctggcac tccaggtcct
3061 cagggtcttc ttggtgctcc tggtattctg ggtctccctg gctcgagagg tgaacgtggt
3121 ctacctggtg ttgctggtgc tgtgggtgaa cctggtcctc ttggcattgc cggcctcct
3181 ggggcccgtg gtcctcctgg tgctgtgggt agtcctggag tcaacggtgc tcctggtgaa
3241 gctggtcgtg atggcaaccc tgggaacgat ggtcccccag gtcgcgatgg tcaacccgga
3301 cacaagggag agcgcggtta ccctggcaat attggtcccg ttggtgctgc aggtgcacct
3361 ggtcctcatg gccccgtggg tcctgctggc aaacatggaa acgtggtga aactggtcct
3421 tctggtcctg ttggtcctgc tggtgctgtt ggcccaagag tcctagtgg cccacaaggc
3481 attcgtggcg ataagggaga gcccggtgaa aaggggccca aggtcttcc tggcttcaag
3541 ggacacaatg gattgcaagg tctgcctggt atcgctggtc accatggtga tcaaggtgct
3601 cctggctccg tgggtcctgc tggtcctagg ggccctgctg gtccttctgg ccctgctgga
3661 aaagatggtc gcactggaca tcctggtacg gttggacctg ctggcattcg aggccctcag
3721 ggtcaccaag gccctgctgg cccccctggt cccctggcc ctcctggacc tccaggtgta
```

Figure 10 (cont.)

```
3781 agcggtggtg gttatgactt tggttacgat ggagacttct acagggctga ccagcctcgc
3841 tcagcacctt ctctcagacc caaggactat gaagttgatg ctactctgaa gtctctcaac
3901 aaccagattg agacccttct tactcctgaa ggctctagaa agaacccagc tcgcacatgc
3961 cgtgacttga gactcagcca cccagagtgg agcagtggtt actactggat tgaccccaac
4021 caaggatgca ctatggaagc catcaaagta tactgtgatt tccctaccgg cgaaacctgt
4081 atccgggccc aacctgaaaa catcccagcc aagaactggt ataggagctc caaggacaag
4141 aaacacgtct ggctaggaga aactatcaat gctggcagcc agtttgaata taatgttgaa
4201 ggagtgactt ccaaggaaat ggctacccaa cttgccttca tgcgcctgct ggccaactat
4261 gcctctcaga acatcaccta ccactgcaag aacagcattg catacatgga tgaggagact
4321 ggcaacctga aaaaggctgt cattctacag ggctctaatg atgttgaact tgttgctgag
4381 ggcaacagca ggttcactta cactgttctt gtagatggct gctctaaaaa gacaaatgaa
4441 tggggaaaga caatcattga atacaaaaca aataagccat cacgcctgcc cttccttgat
4501 attgcacctt tggacatcgg tggtgctgac catgaattct tgtggacat tggcccagtc
4561 tgtttcaaat aaatgaactc aatctaaatt aaaaagaaa gaaatttgaa aaactttct
4621 ctttgccatt tcttcttctt ctttttaac tgaaagctga atccttccat ttcttctgca
4681 catctacttg cttaaattgt gggcaaaaga gaaaagaag gattgatcag agcattgtgc
4741 aatacagttt cattaactcc ttccccgct ccccaaaaa tttgaatttt tttttcaaca
4801 ctcttacacc tgttatggaa aatgtcaacc tttgtaagaa aaccaaaata aaaattgaaa
4861 aataaaaacc ataaacattt gcaccacttg tggcttttga atatcttcca cagagggaag
4921 tttaaaaccc aaacttccaa aggtttaaac tacctcaaaa cactttccca tgagtgtgat
4981 ccacattgtt aggtgctgac ctagacagag atgaactgag gtccttgttt tgttttgttc
5041 ataacacaaa ggtgctaatt aatagtattt cagatacttg aagaatgttg atggtgctag
5101 aagaatttga gaagaaatac tcctgtattg agttgtatcg tgtggtgtat tttttaaaaa
5161 atttgattta gcattcatat tttccatctt attcccaatt aaaagtatgc agattatttg
5221 cccaaagttg tcctcttctt cagattcagc atttgttctt tgccagtctc atttttcatct
5281 tcttccatgg ttccacagaa gctttgtttc tgggcaagc agaaaaatta aattgtacct
5341 attttgtata tgtgagatgt ttaaataaat tgtgaaaaaa atgaaataaa gcatgtttgg
5401 ttttccaaaa gaacatat
```

SEQ Id NO:45

```
   1 cagaccacag gaatacctaa tgccttttt ctcttcctgt ctttgtccct cacactacag
  61 caggcccctc ccttccctct tcaacctcat cctccctccc cacaggccca gagaaccagt
 121 tgggctttgt tctcctgcag gctatggttc atcatgcaaa tagctcctgt gtcagaaatg
 181 cttttggct tcaaataaca gaaaagctaa caccagcttt atcaataata atatcggtgg
 241 tttacttaag gtgtccagag atggtggaga acaggattgg tttcctcctc aatgtcaagg
 301 actcaaagac tctttctgtg gtagggccac atcctaaacc ctgtatcctg tgattattta
 361 cctgacaggg caaaagagat tttgcagatg caattaaggt taaggacctt gacgtgggaa
 421 gattgtgatt atttacctga cagggcaaaa gagatttgc agatgcaatt aaggttaagg
 481 accttgacgt gggaagatta ttctggatta tctaggtggg cgcaatttga tcacatgggt
 541 ccccagaagt ggagaacctt tccacctgt agaagccag agagctggca cctgagaagg
 601 acagaactgt cactgcagga tttgaagatg aaggggccca tgagccaagg aatgccagtg
 661 acctatagag gctaaaaaac agcaaggaaa tggactctcc ccagagcctc cagaggaatg
 721 cagccctgtt gatcacatga tcaccagatg gctgcccag agccaaatgt cgcttcctga
 781 gcaccatact caaaggcagg ggaagtggat ggagggcagg agctccattc ttgtttgcca
 841 ctctcctttt gtcaattggg aaaaaattcc agaaactctg ggagccctcc ccttacattt
 901 cctgggtcat ggggccagcc ctagctgctg gagggactga gaactgctgt tgagcagttt
 961 acctgacggc atctgccatg gcttggcagg aactctggct tgggagaga gcagcagcaa
1021 ggtattcaag caccacctcc accagcccc tccacattt cactcaggac tgagtaaagg
1081 agacactcag atgctactca gatgctggct tcagctaagt attttgcaaa gcctctcgtg
1141 ttcttacaag tttgtggcta tcatgacaaa atggagcagc tactatatc tacatataca
1201 actatggggg acctagtttt atctcattta ccacaatgtt ttcaatcatt ttttggatga
1261 cataatttt agcctcttct ctaaatgctt cctcaagctt tccttgcctt ccagccactg
1321 caaatgactt gcagtttccc ctacatggca cctgacccctt gtgcctcct ccctctgccc
1381 atggcccaga aagccctttc ctgtgccctc tggcttcctg ataaactcct atcatcttca
```

Figure 10 (cont.)

```
1441 agagccagtt cccatgccag ctctccccaa gtgctccact gaggcttccg taacacctct
1501 gttcccacat cgggttgact gtctttgttt tgtcattgct tgctctggct gtgtctccct
1561 cattagactg ggatgccttc aaggtaggga ccctatctgg gtcagcttgg cacccaaag
1621 cgtaccacag cacctgattc tgaggaggct ctcagtagat atctgttgag taaccagaat
1681 gtagggtggt cctgatggtt tctgacattg aatagaaaac agctccctat ttgatcttaa
1741 aataatcact ataacctgga catactgtac tagatgctgt ttttgtctga cttctactct
1801 gtcaatctct ttgcacctcc atttgttcat ctgtgaaatg aagaaaatgc tcatggagtt
1861 cagtgaagat taaatgaatg aatataggta gactgcctaa tctggcactt gccacgcagc
1921 tgacttcaat atagtagctc taatattatg gtccttgagg atcttactgt cttatggccc
1981 agaactgcat ttgattaaag aaggctcccc taaaaaaga gtcatacata ttccatttgt
2041 cctttcagaa ggccgtgaag catttacact ctttaagaca aattcccatc caaaaatagt
2101 taagatttct aaaatatttt gatgctgaaa gaggtgtgct tcagttgggt ggcaaatttg
2161 cttctatgga agattttaa tacaggttgt ttctatttta cttttctgg ctgaaaggat
2221 tttacattta ttcaaagtca aaagggaaaa gaaatccaag aactacagaa gagcagttga
2281 agtgatttat gcttgattc taaatgcaac ttatgtttat acataattta aaactcaaag
2341 aaagcatgct tatacaatca tgtgcaactt taaactttaa gaactctgga tgaatacatg
2401 gtggcaacag tccatgacac ctgaaaacat catttgtgga gtggcgtaga gttcagtgtt
2461 cgcagtcgca tattacaacc atgtttcaca cagccctgct cggtttgatt ttctccacgt
2521 ggttgataat tgtcttcagt tgctgctaag tgattttgca aatttc
```

SEQ ID NO:46

```
   1 gtccccgcgc cagagacgca gccgcgctcc caccaccac accaccgcg ccctcgttcg
  61 cctcttctcc gggagccagt ccgcgccacc gccgcgccc aggccatcgc caccctccgc
 121 agccatgtcc accaggtccg tgtcctcgtc ctcctaccgc aggatgttcg gcggcccggg
 181 caccgcgagc cggccgagct ccagccggag ctacgtgact acgtccaccc gcacctacag
 241 cctgggcagc gcgctgcgcc cagcaccag ccgcagcctc tacgcctcgt ccccgggcgg
 301 cgtgtatgcc acgcgctcct ctgccgtgcg cctgcggagc agcgtgcccg gggtgcggct
 361 cctgcaggac tggtggact tctcgctggc cgacgccatc aacaccgagt tcaagaacac
 421 ccgcaccaac gagaaggtgg agctgcagga gctgaatgac cgcttcgcca actacatcga
 481 caaggtgcgc ttcctggagc agcagaataa gatcctgctg gccgagctcg agcagctcaa
 541 gggccaaggc aagtcgcgcc tggggacct ctacgaggag gagatgcggg agctgcgccg
 601 gcaggtggac cagctaacca acgacaaagc ccgcgtcgag gtggagcgcg acaacctggc
 661 cgaggacatc atgcgcctcc gggagaaatt gcaggaggag atgcttcaga gagaggaagc
 721 cgaaaacacc ctgcaatctt tcagacagga tgttgacaat gcgtctctgg cacgtcttga
 781 ccttgaacgc aaagtggaat ctttgcaaga agagattgcc ttttgaaga aactccacga
 841 agaggaaatc caggagctgc aggctcagat tcaggaacag catgtccaaa tcgatgtgga
 901 tgtttccaag cctgacctca cggctgccct gcgtgacgta cgtcagcaat atgaaagtgt
 961 ggctgccaag aacctgcagg aggcagaaga atggtacaaa tccaagtttg ctgacctctc
1021 tgaggctgcc aaccggaaca atgacgccct gcgccaggca aagcaggagt ccactgagta
1081 ccggagacag gtgcagtccc tcacctgtga agtggatgcc cttaaaggaa ccaatgagtc
1141 cctggaacgc cagatgcgtg aaatggaaga gaactttgcc gttgaagctg ctaactacca
1201 agacactatt ggccgcctgc aggatgagat tcagaatatg aaggaggaaa tggctcgtca
1261 ccttcgtgaa taccaagacc tgctcaatgt taagatggcc cttgacattg agattgccac
1321 ctacaggaag ctgctggaag gcgaggagag caggatttct ctgcctcttc caaactttc
1381 ctccctgaac ctgagggaaa ctaatctgga ttcactccct ctggtgata cccactcaaa
1441 aaggacactt ctgattaaga cggttgaaac tagagatgga caggttatca acgaaacttc
1501 tcagcatcac gatgaccttg aataaaaatt gcacacactc agtgcagcaa tatattacca
1561 gcaagaataa aaagaaatc catatcttaa agaaacagct ttcaagtgcc tttctgcagt
1621 ttttcaggag cgcaagatag atttggaata ggaataagct ctagttctta acaaccgaca
1681 ctcctacaag atttagaaaa aagtttacaa cataatctag tttacagaaa aatcttgtgc
1741 tagaatactt tttaaaaggt atcttgaata ccattaaaac tgcttttttt tttccagcaa
1801 gtatccaacc aacttggttc tgcttcaata aatctttgga aaaactc
```

SEQ ID NO:47

Figure 10 (cont.)

```
   1 ggccagccga atccaagccg tgtgtactgc gtgctcagca ctgcccgaca gtcctagcta
  61 aacttcgcca actccgctgc ctttgccgcc accatgccca aaacgatcag tgtgcgtgtg
 121 accaccatgg atgcagagct ggagtttgcc atccagccca acaccaccgg gaagcagcta
 181 tttgaccagg tggtgaaaac tattggcttg agggaagttt ggttctttgg tctgcagtac
 241 caggacacta aaggtttctc cacctggctg aaactcaata agaaggtgac tgcccaggat
 301 gtgcggaagg aaagcccct gctctttaag ttccgtgcca agttctaccc tgaggatgtg
 361 tccgaggaat tgattcagga catcactcag cgcctgttct ttctgcaagt gaaagagggc
 421 attctcaatg atgatattta ctgcccgcct gagaccgctg tgctgctggc ctcgtatgct
 481 gtccagtcta agtatggcga cttcaataag gaagtgcata agtctggcta cctggccgga
 541 gacaagttgc tcccgcagag agtcctggaa cagcacaaac tcaacaagga ccagtgggag
 601 gagcggatcc aggtgtggca tgaggaacac cgtggcatgc tcaggagga tgctgtcctg
 661 gaatatctga agattgctca agatctggag atgtatggtg tgaactactt cagcatcaag
 721 aacaagaaag gctcagagct gtggctgggg gtggatgccc tgggtctcaa catctatgag
 781 cagaatgaca gactaactcc caagataggc ttccctgga gtgaaatcag gaacatctct
 841 ttcaatgata agaaatttgt catcaagccc attgacaaaa agccccgga cttcgtcttc
 901 tatgctcccc ggctgcggat taacaagcgg atcttggcct tgtgcatggg gaaccatgaa
 961 ctatacatgc gccgtcgcaa gcctgatacc attgaggtgc agcagatgaa ggcacaggcc
1021 cgggaggaga agcaccagaa gcagatggag cgtgctatgc tggaaaatga gaagaagaag
1081 cgtgaaatgg cagagaagga gaaagagaag attgaacggg agaaggagga gctgatggag
1141 aggctgaagc agatcgagga acagactaag aaggctcagc aagaactgga agaacagacc
1201 cgtagggctc tggaacttga gcaggaacgg aagcgtgccc agagcgaggc tgaaaagctg
1261 gccaaggagc gtcaagaagc tgaagaggcc aaggaggcct tgctgcaggc ctcccgggac
1321 cagaaaaaga ctcaggaaca gctggccttg gaaatggcag agctgacagc tcgaatctcc
1381 cagctggaga tggcccgaca gaagaaggag agtgaggctg tggagtggca gcagaaggcc
1441 cagatggtac aggaagactt ggagaagacc cgtgctgagc tgaagactgc catgagtaca
1501 cctcatgtgg cagagcctgc tgagaatgag caggatgagc aggatgagaa tggggcagag
1561 gctagtgctg acctacgggc tgatgctatg gccaaggacc gcagtgagga ggaacgtacc
1621 actgaggcag agaagaatga gcgtgtgcag aagcacctga aggccctcac ttcggagctg
1681 gccaatgcca gagatgagtc caagaagact gccaatgaca tgatccatgc tgagaacatg
1741 cgactgggcc gagacaaata caagaccctg cgccagatcc ggcagggcaa caccaagcag
1801 cgcattgacg aatttgagtc tatgtaatgg gcacccagcc tctagggacc cctcctccct
1861 ttttccttgt ccccacactc ctacacctaa ctcacctaac tcatactgtg ctggagccac
1921 taactagagc agccctggag tcatgccaag catttaatgt agccatggga ccaaacctag
1981 cccctagcc cccacccact tccctgggca aatgaatggc tcactatggt gccaatggaa
2041 cctcctttct cttctctgtt ccattgaatc tgtatggcta gaatatccta cttctccagc
2101 ctagaggtac tttccacttg attttgcaaa tgcccttaca cttactgttg tcctatggga
2161 gtcaagtgtg gagtaggttg gaagctagct cccctcctct ccctaccac tgtcttcttc
2221 agggtcctga gatttacacg gttggagtgt tatgcggtct agggaatgag acaggaccta
2281 ggatatcttc tccaggatgt caactgacct aaaatttgcc ctcccatccc gtttagagtt
2341 atttaggctt tgtaacgatt gggggataaa aagatgttca gtcattttg ttctacctc
2401 ccagatcgga tctgttgcaa actcagcctc aataagcctt gtcgttgact ttagggactc
2461 aatttctccc cagggtggat gggggaaatg gtgccttcaa gaccttcacc aaacatacta
2521 gaagggcatt ggccattcta ttgtggcaag gctgagtaga agatcctacc ccaattcctt
2581 gtaggagtat aggccggtct aaagtgagct ctatggcag atctacccct tacttattat
2641 tccagatctg cagtcacttc gtgggatctg cccctccctg cttcaatacc caaatcctct
2701 ccagctataa cagtagggat gagtacccaa aagctcagcc agcccatca ggactcttgt
2761 gaaaagagag gatatgttca cacctagcgt cagtattttc cctgctaggg gttttaggtc
2821 tcttcccctc tcagagctac ttgggccata gctcctgctc cacagccatc ccagccttgg
2881 catctagagc ttgatgccag taggctcaac tagggagtga gtgcaaaaag ctgagtatgg
2941 tgagagaagc ctgtgccctg atccaagttt actcaaccct ctcaggtgac caaaatcccc
3001 ttctcatcac tcccctccaa agaggtgact gggccctgcc tctgtttgac aaacctctaa
3061 cccaggtctt gacaccagct gttctgtccc ttggagctgt aaaccagaga gctgctgggg
3121 attctggcct agtcccttcc acaccccac cccttgctct caacccagga gcatccacct
3181 ccttctctgt ctcatgtgtg ctcttcttct ttctacagta ttatgtactc tactgatatc
```

Figure 10 (cont.)

```
3241 taaatattga tttctgcctt ccttgctaat gcaccattag aagatattag tcttggggca
3301 ggatgatttt ggcctcatta ctttaccacc cccacacctg gaaagcatat actatattac
3361 aaaatgacat tttgccaaaa ttattaatat aagaagcttt cagtattagt gatgtcatct
3421 gtcactatag gtcatacaat ccattcttaa agtacttgtt atttgttttt attattactg
3481 tttgtcttct ccccagggtt cagtcctcaa ggggccatcc tgtcccacca tgcagtgccc
3541 ctagcttaga gcctccctca attcccctg gccaccacc ccactctgt gcctgacctt
3601 gaggagtctt gtgtgcattg ctgtgaatta gctcacttgg tgatatgtcc tatattggct
3661 aaattgaaac ctggaattgt ggggcaatct attaatagct gccttaaagt cagtaactta
3721 cccttaggga ggctggggga aaaggttaga ttttgtattc aggggttttt tgtgtacttt
3781 ttgggttttt taaaaattgt ttttggaggg gtttatgctc aatccatgtt ctatttcagt
3841 gccaataaaa tttaggaaga cttc
```

SEQ ID NO:48

```
   1 ggtgtgcccg gagaggctga gcagcctgcg cctgagctgg tggaggtgga agtgggcagc
  61 acagcccttc tgaagtgcgg cctctcccag tcccaaggca acctcagcca tgtcgactgg
 121 ttttctgtcc acaaggagaa gcggacgctc atcttccgtg tgcgccaggg ccagggccag
 181 agcgaacctg gggagtacga gcagcggctc agcctccagg acagaggggc tactctggcc
 241 ctgactcaag tcacccccca agacgagcgc atcttcttgt gccagggcaa gcgccctcgg
 301 tcccaggagt accgcatcca gctccgcgtc tacaaagctc cggaggagcc aaacatccag
 361 gtcaaccccc tgggcatccc tgtgaacagt aaggagcctg aggaggtcgc tacctgtgta
 421 gggaggaacg ggtacccccat tcctcaagtc atctggtaca agaatggccg gcctctgaag
 481 gaggagaaga accgggtcca cattcagtcg tcccagactg tggagtcgag tggtttgtac
 541 accttgcaga gtattctgaa ggcacagctg gttaaagaag acaaagatgc ccagttttac
 601 tgtgagctca actaccggct gcccagtggg aaccacatga aggagtccag ggaagtcacc
 661 gtccctgttt tctaccgac agaaaaagtg tggctggaag tggagcccgt gggaatgctg
 721 aaggaagggg accgcgtgga aatcaggtgt ttggctgatg gcaaccctcc accacacttc
 781 agcatcagca gcagaaccc cagcaccagg gaggcagagg aagagacaac caacgacaac
 841 ggggtcctgg tgctggagcc tgcccggaag gaacacagtg ggcgctatga atgtcagggc
 901 ctggacttgg acaccatgat atcgctgctg agtgaaccac aggaactact ggtgaactat
 961 gtgtctgacg tccgagtgag tccgcagca cactgagaga caggaaggca gcagcctcac
1021 cctgacctgt gaggcagaga gtagccagga cctcgagttc cagtggctga gagaagagac
1081 aggccaggtg ctggaaaggg ggcctgtgct tcagttgcat gacctgaaac gggaggcagg
1141 aggcggctat cgctgcgtgg cgtctgtgcc cagcataccc ggcctgaacc gcacacagct
1201 ggtcaacgtg gccattttg gcccccttg gatggcattc aaggagagga aggtgtgggt
1261 gaaagagaat atggtgttga atctgtcttg tgaagcgtca gggcacccc ggcccaccat
1321 ctcctggaac gtcaacggca cggcaagtga acaagaccaa gatccacagc gagtcctgag
1381 caccctgaat gtcctcgtga ccccggagct gttggagaca ggtgttgaat gcacggcctc
1441 caacgacctg ggcaaaaaca ccagcatcct cttcctggag ctggtcaatt taaccaccct
1501 cacaccagac tccaacacaa ccactggcct cagcacttcc actgccagtc ctcataccag
1561 agccaacagc acctccacag agagaaagct gccggagccg gagagccggg gcgtggtcat
1621 cgtggctgtg attgtgtgca tcctggtcct ggcggtgctg ggcgctgtcc tctatttcct
1681 ctataagaag gcaagctgc cgtgcaggcg ctcagggaag caggagatca cgctgccccc
1741 gtctcgtaag agcgaacttg tagttgaagt taagtcagat aagctcccag aagagatggg
1801 cctcctgcag ggcagcagcg gtgacaagag ggctccggga gaccagggag agaaatacat
1861 cgatctgagg cattagcccc gaatcacttc agctcccttc cctgcctgga ccattcccag
1921 ctccctgctc actcttctct cagccaaagc ctccaaaggg actagagaga gcctcctgc
1981 tcccctcgcc tgcacacccc ctttcagagg gccactgggt taggacctga ggacctcact
2041 tggccctgca aggccgctt tcagggacc agtccaccac catctccacg ttgagtgaag
2101 ctcatcccaa gcaaggagcc ccagtctccc gagcgggtag gagagtttct tgtagaacgt
2161 gttttttctt tacacacatt atggctgtaa ataccctggct cctgccagca gctgagctgg
2221 gtagcctctc tgagctggga ttacaggtgt gagccactgc gcccagccaa
```

SEQ ID NO:49

```
   1 caaacttggt ggcaacttgc ctcccggtgc gggcgtctct cccccaccgt ctcaacatgc
```

Figure 10 (cont.)

```
 661  ggtctcaaag gagagaaagg agaccgggga cccaagggag aaaggggggat ggatggagcc
 721  agtattgtgg gaccccctgg gccgagaggg ccacctgggc acatcaaggt cttgtctaat
 781  tccttgatca atatcaccca tggattcatg aatttctcgg acattcctga gctggtgggg
 841  cctccggggc cggacgggtt gcctgggctg ccaggatttc cagggtccta gaggaccaaa
 901  aggtgacact ggtttacctg gctttccagg actaaaagga gaacagggcg agaagggaga
 961  gccgggtgcc atcctgacag aggacattcc tctggaaagg ctgatgggga aaaagggtga
1021  acctggaatg catggagccc caggaccaat ggggcccaaa ggaccaccag gacataaagg
1081  agaatttggc cttcccgggc gacctggtcg cccaggactg aatggcctca agggtaccaa
1141  aggagatcca ggggtcatta tgcagggccc acctggctta cctggccctc caggcccccc
1201  tgggccacct ggagctgtga ttaacatcaa aggagccatt ttcccaatac ccgtccgacc
1261  acactgcaaa atgccagttg atactgctca tcctgggagt ccagagctca tcacttttca
1321  cggtgttaaa ggagagaaag gatcctgggg tcttcctggc tcaaagggag aaaaaggcga
1381  ccagggagcc cagggaccac caggtcctcc acttgatcta gcttacctga gacactttct
1441  gaacaacttg aaggggggaga atggagacaa ggggttcaaa ggtgaaaaag gagaaaaagg
1501  agacattaat ggcagcttcc ttatgtctgg gcctccaggc ctgccggaa atccaggccc
1561  ggctggccaa aaaggggaga cagtcgttgg gccccaagga cccccaggtg ctcctggtct
1621  gcctgggcca cctggctttg gaagacctgg tgatcctggg ccaccggggc ccccggggcc
1681  accaggacct ccagctatcc tgggagcagc tgtggcccctt ccaggtcccc ctggccctcc
1741  aggacagcca gggcttcccg gatccagaaa cctggtcaca gcattcagca acatggatga
1801  catgctgcag aaagcgcatt tggttataga aggaacattc atctacctga gggacagcac
1861  tgagtttttc attcgtgtta gagatggctg gaaaaaatta cagctgggag aactgatccc
1921  cattcctgcc gacagccctc caccccctgc gctttccagc aacccacatc agcttctgcc
1981  tccaccaaac cctatttcaa gtgccaatta tgagaagcct gctctgcatt tggctgctct
2041  gaacatgcca ttttctgggg acattcgagc tgattttcag tgcttcaagc aggccagagc
2101  tgcaggactg ttgtccacct accgagca
```

SEQ ID NO:57

```
   1  tagaaattgt taattttaac aatccagagc aggccaacga ggctttgctc tcccgacccg
  61  aactaaaggt ccctcgctcc gtgcgctgct acgagcggtg tctcctgggg ctccaatgca
 121  gcgagctgtg cccgaggggt tcggaaggcg caagctgggc agcgacatgg ggaacgcgga
 181  gcgggctccg gggtctcgga gctttgggcc agtaccacg ctgctgctgc tcgccgcggc
 241  gctactggcc gtgtcggacg cactcgggcg cccctccgag gaggacgagg agctagtggt
 301  gccggagctg gagcgcgccc cgggacacgg gaccacgcgc ctccgcctgc acgcctttga
 361  ccagcagctg gatctggagc tgcggcccga cagcagcttt ttggcgcccg gcttcacgct
 421  ccagaacgtg gggcgcaaat ccgggtccga gacgccgctt ccggaaaccg acctggcgca
 481  ctgcttctac tccggcaccg tgaatggcga tcccagctcg gctgccgccc tcagcctctg
 541  cgagggcgtg cgcggcgcct tctacctgct gggggaggcg tatttcatcc agccgctgcc
 601  cgccgccagc gagcgcctcg ccaccgccgc cccaggggag aagccgccgg caccactaca
 661  gttccacctc ctgcggcgga atcggcaggg cgacgtcggc ggcacgtgcg gggtcgtgga
 721  cgacgagccc cggccgactg ggaaagcgga gaccgaagac gaggacgaag ggactgaggg
 781  cgaggacgaa ggggctcagt ggtcgccgca ggacccggca tgcaaggcg taggacagcc
 841  cacaggaact ggaagcataa gaaagaagcg atttgtgtcc agtcaccgct atgtggaaac
 901  catgcttgtg gcagaccagt cgatggcaga ttccacggc agtggtctaa agcattacct
 961  tctcacgttg ttttcggtgg cagccagatt gtacaaacac ccagcattc gtaattcagt
1021  tagcctggtg gtggtgaaga tcttggtcat ccacgatgaa cagaaggggc cggaagtgac
1081  ctccaatgct gccctcactc tgcggaactt ttgcaactgg cagaagcagc acaacccacc
1141  cagtgaccgg gatgcagagc actatgacac agcaattctt ttcaccagac aggacttgtg
1201  tgggtcccag acatgtgata ctcttgggat ggctgatgtt ggaactgtgt gtgatccgag
1261  cagaagctgc tccgtcatag aagatgatgg tttacaagct gccttcacca cagcccatga
1321  attaggccac gtgtttaaca tgccacatga tgatgcaaag cagtgtgcca gccttaatgg
1381  tgtgaaccag gattcccaca tgatggcgtc aatgctttcc aacctggacc acagccagcc
1441  ttggtctcct tgcagtgcct acatgattac atcatttctg gataatggtc atgggggaatg
1501  tttgatggac aagcctcaga atcccataca gctcccaggc gatctccctg gcacctcgta
1561  cgatgccaac cggcagtgcc agtttacatt tggggaggac tccaaacact gccccgatgc
```

Figure 10 (cont.)

```
1621 agccagcaca tgtagcacct tgtggtgtac cggcacctct ggtggggtgc tggtgtgtca
1681 aaccaaacac ttcccgtggg cggatggcac cagctgtgga gaagggaaat ggtgtatcaa
1741 cggcaagtgt gtgaacaaaa ccgacagaaa gcattttgat acgcctttc atggaagctg
1801 gggaatgtgg gggccttggg gagactgttc gagaacgtgc ggtggaggag tccagtacac
1861 gatgagggaa tgtgacaacc cagtcccaaa gaatggaggg aagtactgtg aaggcaaacg
1921 agtgcgctac agatcctgta accttgagga ctgtccagac aataatggaa aaacctttag
1981 agaggaacaa tgtgaagcac acaacgagtt ttcaaaagct tcctttggga gtgggcctgc
2041 ggtggaatgg attcccaagt acgctggcgt ctcaccaaag gacaggtgca agctcatctg
2101 ccaagccaaa ggcattggct acttcttcgt tttgcagccc aaggttgtag atggtactcc
2161 atgtagccca gattccacct ctgtctgtgt gcaaggacag tgtgtaaaag ctggttgtga
2221 tcgcatcata gactccaaaa agaagtttga taaatgtggt gtttgcgggg gaaatggatc
2281 tacttgtaaa aaaatatcag gatcagttac tagtgcaaaa cctggatatc atgatatcat
2341 cacaattcca actggagcca ccaacatcga agtgaaacag cggaaccaga ggggatccag
2401 gaacaatggc agctttcttg ccatcaaagc tgctgatggc acatatattc ttaatggtga
2461 ctacactttg tccaccttag agcaagacat tatgtacaaa ggtgttgtct tgaggtacag
2521 cggctcctct gcggcattgg aaagaattcg cagctttagc cctctcaaag agcccttgac
2581 catccaggtt cttactgtgg gcaatgccct tcgacctaaa attaaataca cctacttcgt
2641 aaagaagaag aaggaatctt tcaatgctat ccccactttt tcagcatggg tcattgaaga
2701 gtggggcgaa tgttctaagt catgtgaatt gggttggcag agaagactgg tagaatgccg
2761 agacattaat ggacagcctg cttccgagtg tgcaaaggaa gtgaagccag ccagcaccag
2821 accttgtgca gaccatccct gcccccagtg gcagctgggg gagtggtcat catgttctaa
2881 gacctgtggg aagggttaca aaaaaagaag cttgaagtgt ctgtcccatg atggagggt
2941 gttatctcat gagagctgtg atcctttaaa gaaacctaaa catttcatag acttttgcac
3001 aatggcagaa tgcagttaag tggtttaagt ggtgttagct ttgagggcaa ggcaaagtga
3061 ggaagggctg gtgcagggaa agcaagaagg ctggagggat ccagcgtatc ttgccagtaa
3121 ccagtgaggt gtatcagtaa ggtgggatta tgggggtaga tagaaaagga gttgaatcat
3181 cagagtaaac tgccagttgc aaatttgata ggatagttag tgaggattat taacctctga
3241 gcagtgatat agcataataa agccccgggc attattatta ttatttcttt tgttacatct
3301 attacaagtt tagaaaaaac aaagcaattg tcaaaaaaag ttagaactat tacaacccct
3361 gtttcctggt acttatcaaa tacttagtat catgggggtt gggaaatgaa aagtaggaga
3421 aaagtgagat tttactaaga cctgttttac tttacctcac taacaatggg gggagaaagg
3481 agtacaaata ggatctttga ccagcactgt ttatggctgc tatggtttca gagaatgttt
3541 atacattatt tctaccgaga attaaaactt cagattgttc aacatgagag aaaggctcag
3601 caacgtgaaa taacgcaaat ggcttcctct ttccttttt ggaccatctc agtctttatt
3661 tgtgtaattc atttttgagga aaaacaact ccatgtattt attcaagtgc attaaagtct
3721 acaatggaaa aaaagcagtg aagcattaga tgctggtaaa agctagagga gacacaatga
3781 gcttagtacc tccaacttcc ttctttcct accatgtaac cctgctttgg gaatatggat
3841 gtaaagaagt aacttgtgtc tcatgaaaat cagtacaatc acacaaggag gatgaaacgc
3901 cggaacaaaa atgaggtgtg tagaacaggg tcccacaggt ttggggacat tgagatcact
3961 tgtcttgtgg tggggaggct gctgaggggt agcaggtcca tctccagcag ctggtccaac
4021 agtcgtatcc tggtgaatgt ctgttcagct cttctgtgag aatatgattt tttccatatg
4081 tatatagtaa aatatgttac tataaattac atgtacttta taagtattgg tttgggtgtt
4141 ccttccaaga aggactatag ttagtaataa atgcctataa taacatattt attttatac
4201 atttatttct aatgaaaaaa acttttaaat tatatcgctt ttgtggaagt gcatataaaa
4261 tagagtattt atacaatata tgttactaga aataaaagaa cacttttgg
```

SEQ ID NO:58

```
  1 gggcccgggc gcgcgggagc gggagcggcc gggggagccg gagcgcacca tggaggcggc
 61 ggcaggcggc cgcggctgtt tccagccgca cccggggctg cagaagacgc tggagcagtt
121 ccacctgagc tccatgagct cgctgggcgg cccggccgct ttctcggcgc gctgggcgca
181 ggaggcctac aagaaggaga gcgccaagga ggcgggcgcg gccgcggtgc cggcgccggt
241 gcccgcagcc accgagccgc cgcccgtgct gcacctgccc gccatccagc cgccgccgcc
301 cgtgctgccc gggcccttct tcatgccgtc cgaccgctcc accgagcgct gcgagaccgt
361 actggaaggc gagaccatct cgtgcttcgt ggtgggaggc gagaagcgcc tgtgtctgcc
```

Figure 10 (cont.)

```
 421 gcagattctc aactcggtgc tgcgcgactt ctcgctgcag cagatcaacg cggtgtgcga
 481 cgagctccac atctactgct cgcgctgcac ggccgaccag ctggagatcc tcaaagtcat
 541 gggcatcctg cccttctcgg cgccctcgtg cgggctcatc accaagacgg acgccgagcg
 601 cctgtgcaac gcgctgctct acggcggcgc ctacccgccg ccctgcaaga aggagctggc
 661 cgccagcctg gcgctgggcc tggagctcag cgagcgcagc gtccgcgtgt accacgagtg
 721 cttcggcaag tgtaaggggc tgctggtgcc cgagctctac agcagcccga gcgccgcctg
 781 catccagtgc ctggactgcc gcctcatgta cccgccgcac aagttcgtgg tgcactcgca
 841 caaggccctg gagaaccgga cctgccactg gggcttcgac tcggccaact ggcgggccta
 901 catcctgctg agccaggatt acacgggcaa ggaggagcag gcgcgcctcg gccgctgcct
 961 ggacgacgtg aaggagaaat tcgactatgg caacaagtac aagcggcggg tgccccgggt
1021 ctcctctgag cctccggcct ccataagacc caaaacagat gacacctctt cccagtcccc
1081 cgcgccttcc gaaaaggaca agccgtccag ctggctgcgg accttggccg gctcttccaa
1141 taagagcctg ggctgtgttc accctcgcca gcgcctctct gctttccgac cctggtcccc
1201 cgcagtgtca gcgagtgaga aagagctctc cccacacctc ccggccctca tccgagacag
1261 cttctactcc tacaagagct tgagacagc cgtggcgccc aacgtggccc tcgcaccgcc
1321 ggcccagcag aaggttgtga gcagccctcc gtgtgccgcc gccgtctccc gggcccccga
1381 gcctctcgcc acttgcaccc agcctcggaa gcggaagctg actgtggaca ccccaggagc
1441 cccagagacg ctggcgcccg tggctgcccc agaggaggac aaggactcgg aggcggaggt
1501 ggaagttgaa agcagggagg aattcacctc ctccttgtcc tgctctctt ccccgtcctt
1561 tacctcatcc agctccgcca aggacctggg ctccccgggt gcgcgtgccc tgccctcggc
1621 cgtccctgat gctgcggccc ctgccgacgc cccagtgggg ctggaggcgg agctggagca
1681 cctgcggcag gcactggagg cggcctgga caccaaggaa gccaaagaga gttcctgca
1741 tgaggtggtc aagatgcgcg tgaagcagga ggagaagctc agcgcagccc tgcaggccaa
1801 gcgcagcctc caccaggagc tggagttcct acgcgtggcc aagaaggaga agctgcggga
1861 ggccacggag gccaagcgta acctgcggaa ggagatcgag cgtctccgcg ccgagaacga
1921 gaagaagatg aaagaggcca acgagtcacg gctgcgcctg aagcgggagc tggagcaggc
1981 gcggcaggcc cgggtgtgcg acaagggctg cgaggcgggc cgcctgcgcg ccaagtactc
2041 ggcccagatc gaagacctgc aggtgaagct gcagcacgcg gaggcggacc gggagcagct
2101 gcgggccgac ctgctgcggg agcgcgaggc ccgggagcac ctggagaagg tggtgaagga
2161 gctgcaggaa cagctgtggc cgcgggcccg ccccgaggct gcgggcagcg agggcgctgc
2221 ggagctggag ccgtagattc cgtgcctgcc gccgcagcgc cgccgacaac gcgggtgcag
2281 gggggcgcgg ctgggcggtg cagctccgcc cggctccgcc cctgcagccc acacagcaca
2341 acgtcttacc gtgcctatta ccaagcgagt gtttgtaacc atgtagtttt ggaacccact
2401 gcaaaatttt ctactggcca agttcaagtg agtaagccgc gtccccaac tacagctgga
2461 gacggggcca gctcggcggc ctgctggtcc tctgcttgct ggaacattct aacatttaca
2521 cttttgttat aagctattta aaaccagtaa ggagacttga aattcagaaa atcaacacat
2581 ttttaaatga ctaacttcta aaagcccaa cacatgacgc catctgaaga cccgcaacgg
2641 agtgggggtg gcggccgccc caccctcccc acccggggaa gccatcacag ctcatctgcc
2701 cgcggctgcg tgaggacagc aggggttttt cttcagagtc tattttttca gcgacaagga
2761 cccaggtctt cctgctgctg ccaggagag cagggacagt gccgcgtgcg agatgagctc
2821 gaacactgcc cgccttactg ccgcctaccc cgcccgccac gccgccgtcg atgccagcgc
2881 tgtccccacg ggtaccagga agtgcagagc cgcacaggag ctgcccgga gctgaggga
2941 cggtcttcgg ctcctctgca ccccgtgatt ctgcccacgc tcctccacca cgaggcactg
3001 acctgcgtcg ggtggtgacc gtggctggcg gtcacgccct cagcccctcc gggcacacgt
3061 gccgcctgac cgggcgaccc ttttcagttc ggcaaacgtc gctcccttca ttttgggact
3121 gaggctgcag cattggaaca aaagagcatt atttcaattt ttctttcttt ttttttgttc
3181 gttcatttaa acgtatattt agaactgcac tttgtccaca accttcctt ctctttctat
3241 tccccagtga actgaggttt ttaccgattt atagagcagt caaatccgaa gtgctcgagt
3301 gcttagaaac cccctctggt gcttggttga acaagggaat cacaagaaaa cgaaaatgca
3361 aaaactgaac ttcgggggtc gttctgtgcc ttccagcatc ttgtacagca aatcctgact
3421 cgtgtctttt tacccccaag atatctgtct tcagtagcga ctgaatctgc cactctcaga
3481 ataagttc
```

SEQ Id NO:59

Figure 10 (cont.)

```
   1 gccgccgccg ccatccgccg ccgcagccag cttccgccgc cgcaggaccg gcccctgccc
  61 cagcctccgc agccgcggcg cgtccacgcc cgcccgcgcc cagggcgagt cggggtcgcc
 121 gcctgcacgc ttctcagtgt tccccgcgcc ccgcatgtaa cccggccagg ccccccgcaac
 181 tgtgtccect gcagctccag ccccgggctg catcccccg cccgacacc agctctccag
 241 cctgctcgtc caggatggcc gcggccaagg ccgagatgca gctgatgtcc ccgctgcaga
 301 tctctgaccc gttcggatcc tttcctcact cgcccaccat ggacaactac cctaagctgg
 361 aggagatgat gctgctgagc aacgggctc cccagttcct cggcgccgcc ggggccccag
 421 agggcagcgg cagcaacagc agcagcagca gcagcggggg cggtggaggc ggcggggcg
 481 gcagcaacag cagcagcagc agcagcacct tcaaccctca ggcggacacg ggcgagcagc
 541 cctacgagca cctgaccgca gagtctttc ctgacatctc tctgaacaac gagaaggtgc
 601 tggtggagac cagttacccc agccaaacca ctcgactgcc ccccatcacc tatactggcc
 661 gcttttccct ggagcctgca cccaacagtg gcaacacctt gtggcccgag cccctcttca
 721 gcttggtcag tggcctagtg agcatgacca acccaccggc ctcctcgtcc tcagcaccat
 781 ctccagcggc ctcctccgcc tccgcctccc agagcccacc cctgagctgc gcagtgccat
 841 ccaacgacag cagtcccatt tactcagcgg cacccaccct ccccacgccg aacactgaca
 901 ttttccctga gccacaaagc caggccttcc cgggctcggc agggacagcg ctccagtacc
 961 cgcctcctgc ctaccctgcc gccaagggtg gcttccaggt tcccatgatc cccgactacc
1021 tgtttccaca gcagcagggg gatctgggcc tgggcacccc agaccagaag cccttccagg
1081 gcctggagag ccgcacccag cagccttcgc taaccctct gtctactatt aaggcctttg
1141 ccactcagtc gggctcccag gacctgaagg ccctcaatac cagctaccag tccagctca
1201 tcaaacccag ccgcatgcgc aagtaccca accggcccag caagacgccc ccccacgaac
1261 gcccttacgc ttgcccagtg gagtcctgtg atcgccgctt ctcccgctcc gacgagctca
1321 cccgccacat ccgcatccac acaggccaga agcccttcca gtgccgcatc tgcatgcgca
1381 acttcagccg cagcgaccac ctcaccaccc acatccgcac ccacacaggc gaaagccct
1441 tcgcctgcga catctgtgga agaaagtttg ccaggagcga tgaacgcaag aggcatacca
1501 agatccactt gcggcagaag gacaagaaag cagacaaaag tgttgtggcc tcttcggcca
1561 cctcctctct ctcttcctac ccgtccccgg ttgctacctc ttacccgtcc ccggttacta
1621 cctcttatcc atccccggcc accacctcat acccatcccc tgtgcccacc tccttctcct
1681 ctccggctc ctcgacctac ccatccctg tgcacagtgg cttcccctcc ccgtcggtgg
1741 ccaccacgta ctcctctgtt cccctgctt tcccggccca ggtcagcagc ttcccttcct
1801 cagctgtcac caactcctc agcgcctcca cagggctttc ggacatgaca gcaaccttt
1861 ctccaggac aattgaaatt tgctaaaggg aaaggggaaa gaaaggaaa agggagaaaa
1921 agaaacacaa gagacttaaa ggacaggagg aggagatggc cataggagag gagggttcct
1981 cttaggtcag atggaggttc tcagagccaa gtcctccctc tctactggag tggaaggtct
2041 attggccaac aatcctttct gcccacttcc ccttccccaa ttactattcc ctttgacttc
2101 agctgcctga aacagccatg tccaagttct tcacctctat ccaaagaact tgatttgcat
2161 ggatttggga taaatcattt cagtatcatc tccatcatat gcctgacccc ttgctccctt
2221 caatgctaga aaatcgagtt ggcaaaatgg ggtttgggcc cctcagagcc ctgcctgca
2281 cccttgtaca gtgtctgtgc catggatttc gtttttcttg gggtactctt gatgtgaaga
2341 taatttgcat attctattgt attatttgga gttaggtcct cacttggggg aaaaaaaaaa
2401 aagaaaagcc aagcaaacca atggtgatcc tctatttgt gatgatgctg tgacaataag
2461 tttgaacctt ttttttgaa acagcagtcc cagtattctc agagcatgtg tcagagtgtt
2521 gttccgttaa ccttttgta aatactgctt gaccgtactc tcacatgtgg caaaatatgg
2581 tttggttttt ctttttttt ttttgaaa gtgttttttc ttcgtccttt tggtttaaaa
2641 agtttcacgt cttggtgcct tttgtgat gcgccttgct gatggcttga catgtgcaat
2701 tgtgagggac atgctcacct ctagccttaa gggggcagg gagtgatgat ttggggagg
2761 ctttgggagc aaaataagga agagggctga gctgagcttc ggttctccag aatgtaagaa
2821 aacaaaatct aaaacaaaat ctgaactctc aaaagtctat ttttttaact gaaatgtaa
2881 atttataaat atattcagga gttggaatgt tgtagttacc tactgagtag gcggcgattt
2941 ttgtatgtta tgaacatgca gttcattatt ttgtggttct atttactt gtacttgtgt
3001 ttgcttaaac aaagtgactg tttggcttat aaacacattg aatgcgcttt attgcccatg
3061 ggatatgtgg tgtatatcct tccaaaaaat taaaacgaaa ataaagta
```

SEQ ID NO:60

Figure 10 (cont.)

```
   1 cattcataag actcagagct acggccacgg cagggacacg cggaaccaag acttggaaac
  61 ttgattgttg tggttcttct tggggttat gaaatttcat taatcttttt ttttccggg
 121 gagaaagttt ttggaaagat tcttccagat atttcttcat tttctttgg aggaccgact
 181 tactttttt ggtcttcttt attactcccc tccccccgtg ggacccgccg gacgcgtgga
 241 ggagaccgta gctgaagctg attctgtaca gcgggacagc gctttctgcc cctggggag
 301 caaccctcc ctcgccctg ggtcctacgg agcctgcact tcaagaggt acagcggcat
 361 cctgtggggg cctgggcacc gcaggaagac tgcacagaaa ctttgccatt gttggaacgg
 421 gacgttgctc cttccccgag cttccccgga cagcgtactt tgaggactcg ctcagctcac
 481 cggggactcc cacggctcac cccggacttg caccttactt ccccaacccg gccatagcct
 541 tggcttcccg gcgacctcag cgtggtcaca ggggccccc tgtgcccagg gaaatgtttc
 601 aggctttccc cggagactac gactccggct cccggtgcag ctcctcaccc tctgccagt
 661 ctcaatatct gtcttcggtg gactccttcg gcagtccacc caccgccgcg gcctcccagg
 721 agtgcgccgg tctcggggaa atgcccggtt ccttcgtgcc cacggtcacc gcgatcacaa
 781 ccagccagga cctccagtgg cttgtgcaac ccaccctcat ctcttccatg gcccagtccc
 841 aggggcagcc actggcctcc cagccccgg tgtcgaccc ctacgacatg ccgggaacca
 901 gctactccac accaggcatg agtggctaca gcagtggcgg agcgagtggc agtggtggc
 961 cttccaccag cggaactacc agtgggcctg ggcctgcccg cccagcccga gcccggccta
1021 ggagacccg agaggagacg ctcacccag aggaagagga gaagcgaagg gtgcgccggg
1081 aacgaaataa actagcagca gctaaatgca ggaaccggcg gagggagctg accgaccgac
1141 tccaggcgga gacagatcag ttggaggaag aaaaagcaga gctggagtcg gagatcgccg
1201 agctccaaaa ggagaaggaa cgtctggagt ttgtgctggt ggcccacaaa ccgggctgca
1261 agatccccta cgaagagggg cccgggccgg gcccgctggc ggaggtgaga gatttgccgg
1321 gctcagcacc ggctaaggaa gatggcttca gctggctgct gccgccccg ccaccaccgc
1381 ccctgccctt ccagaccagc caagacgcac ccccaacct gacggcttct ctctttacac
1441 acagtgaagt tcaagtcctc ggcgacccct tccccgttgt taacccttcg tacacttctt
1501 cgtttgtcct cacctgcccg gaggtctccg cgttcgccgg cgcccaacgc accagcggca
1561 gtgaccagcc ttccgatccc ctgaactcgc cctccctcct cgctcggtga actctttaga
1621 cacacaaaac aaacaaacac atggggaga gagacttgga agaggaggag gaggaggaga
1681 aggaggagag agagggaag agacaaagtg ggtgtgtggc ctccctggct cctccgtctg
1741 accctctgcg gccactgcgc cactgccatc ggacaggagg attccttgtg ttttgtcctg
1801 cctcttgttt ctgtgccccg gcgaggccgg agagctggtg actttgggga caggggtgg
1861 gaaggggatg gacaccccca gctgactgtt ggctctctga cgtcaaccca agctctgggg
1921 atgggtgggg aggggggcgg gtgacgccca ccttcgggca gtcctgtgtg aggatgaagg
1981 gacggggtg ggaggtaggc tgtggggtgg gctggagtcc tctccagaga ggctcaacaa
2041 ggaaaaatgc cactccctac ccaatgtctc ccacacccac ccttttttg gggtgcccag
2101 gttggtttcc cctgcactcc cgaccttagc ttattgatcc cacatttcca tggtgtgaga
2161 tcctctttac tctgggcaga agtgagcccc ccttaaagg gaattcgatg cccccctaga
2221 ataatctcat ccccccaccc gacttctttt gaaatgtgaa cgtccttcct tgactgtcta
2281 gccactccct cccagaaaaa ctggctctga ttggaatttc tggcctccta aggctcccca
2341 ccccgaaatc agccccagc cttgtttctg atgacagtgt tatcccaaga ccctgccccc
2401 tgccagccga ccctcctggc cttcctcgtt gggccgctct gatttcaggc agcaggggct
2461 gctgtgatgc cgtcctgctg gagtgattca tactgtgaaa tgagttggcc agattgtggg
2521 gtgcagctgg gtggggcagc acacctctgg ggggataatg tccccactcc cgaaagcctt
2581 tcctcggtct cccttccgtc catcccct cttcctcccc tcaacagtga gttagactca
2641 aggggtgac agaaccgaga aggggtgac agtcctccat ccacgtggcc tctctctctc
2701 tcctcaggac cctcagccct ggccttttc tttaaggtcc cccgaccaat ccccagccta
2761 ggacgccaac ttctcccacc ccttggcccc tcacatcctc tccaggaagg cagtgagggg
2821 ctgtgacatt tttccggaga agatttcaga gctgaggctt tggtaccccc aaaccccaa
2881 tatttttgga ctggcagact caaggggctg gaatctcatg attccatgcc cgagtccgcc
2941 catccctgac catggttttg gctctcccac cccgccgttc cctgcgcttc atctcatgag
3001 gatttcttta tgaggcaaat ttatatttt taatatcggg gggtggacca cgccgccctc
3061 catccgtgct gcatgaaaaa cattccacgt gccccttgtc gcgcgtctcc catcctgatc
3121 ccagacccat tccttagcta tttatccctt tcctggtttc cgaaaggcaa ttatatctat
3181 tatgtataag taaatatatt atatatggat gtgtgtgtgt gcgtgcgcgt gagtgtgtga
```

Figure 10 (cont.)

```
3241 gcgcttctgc agcctcggcc taggtcacgt tggccctcaa agcgagccgt tgaattggaa
3301 actgcttcta gaaactctgg ctcagcctgt ctcgggctga ccctttctg atcgtctcgg
3361 cccctctgat tgttcccgat ggtctctctc cctctgtctt ttctcctccg cctgtgtcca
3421 tctgaccgtt ttcacttgtc tcctttctga ctgtccctgc caatgctcca gctgtcgtct
3481 gactctgggt tcgttgggga catgagattt tattttttgt gagtgagact gagggatcgt
3541 agatttttac aatctgtatc tttgacaatt ctgggtgcga gtgtgagagt gtgagcaggg
3601 cttgctcctg ccaaccacaa ttcaatgaat ccccgacccc cctacccat gctgtacttg
3661 tggttctctt tttgtatttt gcatctgacc ccgggggct gggacagatt ggcaatgggc
3721 cgtcccctct cccttggtt ctgcactgtt gccaataaaa agctcttaaa aacgc
```

SEQ ID NO:61

```
   1 agcgagcttg cagcctcacc gacgagtctc aactaaaagg gactcccgga gctaggggtg
  61 gggactcggc ctcacacagt gagtgccggc tattggactt ttgtccagtg acagctgaga
 121 caacaaggac cacgggagga ggtgtaggag agaagcgccg cgaacagcga tcgcccagca
 181 ccaagtccgc ttccaggctt tcggtttctt tgcctccatc ttgggtgcgc cttccggcg
 241 tctaggggag cgaaggctga ggtggcagcg gcaggagagt ccggccgcga caggacgaac
 301 tcccccactg gaaaggattc tgaaagaaat gaagtcagcc ctcagaaatg aagttgactg
 361 cctgctggct ttctgttgac tggcccggag ctgtactgca agaccttgt gagcttccct
 421 agtctaagag taggatgtct gctgaagtca tccatcaggt tgaagaagca cttgatacag
 481 atgagaagga gatgctgctc tttttgtgcc gggatgttgc tatagatgtg gttccaccta
 541 atgtcaggga ccttctggat attttacggg aaagaggtaa gctgtctgtc ggggacttgg
 601 ctgaactgct ctacagagtg aggcgatttg acctgctcaa acgtatcttg aagatggaca
 661 gaaaagctgt ggagacccac ctgctcagga accctcacct tgtttcggac tatagagtgc
 721 tgatggcaga gattggtgag gatttggata aatctgatgt gtcctcatta atttttcctca
 781 tgaaggatta catgggccga ggcaagataa gcaaggagaa ggtttcttgg accttgtggt
 841 tgagttggag aaactaaatc tggttgcccc agatcaactg gatttattag aaaaatgcct
 901 aaagaacatc cacagaatag acctgaagac aaaaatccag aagtacaagc agtctgttca
 961 aggagcaggg acaagttaca ggaatgttct ccaagcagca atccaaaaga gtctcaagga
1021 tccttcaaat aacttcaggc tccataatgg gagaagtaaa gaacaaagac ttaaggaaca
1081 gcttggcgct caacaagaac cagtgaagaa atccattcag gaatcagaag ctttttttgcc
1141 tcagagcata cctgaagaga gatacaagat gaagagcaag cccctaggaa tctgcctgat
1201 aatcgattgc attggcaatg agacagagct tcttcgagac accttcactt ccctgggcta
1261 tgaagtccag aaattcttgc atctcagtat gcatggtata tcccagattc ttggccaatt
1321 tgcctgtatg cccgagcacc gagactacga cagctttgtg tgtgtcctgg tgagccgagg
1381 aggctcccag agtgtgtatg gtgtggatca gactcactca gggctccccc tgcatcacat
1441 caggaggatg ttcatgggag attcatgccc ttatctagca gggaagccaa agatgttttt
1501 tattcagaac tatgtggtgt cagagggcca gctggaggac agcagcctct tggaggtgga
1561 tgggccagcg atgaagaatg tggaattcaa ggctcagaag cgaggctgt gcacagttca
1621 ccgagaagct gacttcttct ggagcctgtg tactgcggac atgtccctgc tggagcagtc
1681 tcacagctca ccatccctgt acctgcagtg cctctcccag aaactgagac aagaaagaaa
1741 acgcccactc ctggatcttc acattgaact caatggctac atgtatgatt ggaacagcag
1801 agtttctgcc aaggagaaat attatgtctg gctgcagcac actctgagaa agaaacttat
1861 cctctcctac acataagaaa ccaaaaggct gggcgtagtg gctcacacct gtaatcccag
1921 cactttggga ggccaaggag ggcagatcac ttcaggtcag gagttcgaga ccagcctggc
1981 caacatggta aacgctgtcc ctagtaaaaa tacaaaaatt a
```

SEQ ID NO:62

```
   1 agagttgcac tgagtgtggc tgaagcagcg aggcgggagt ggaggtgcgc ggagtcaggc
  61 agacagacag acacagccag ccagccaggt cggcagtata gtccgaactg caaatcttat
 121 tttcttttca ccttctctct aactgcccag agctagcgcc tgtggctccc gggctggtgt
 181 ttcgggagtg tccagagagc ctggtctcca gccgcccccg ggaggagagc cctgctgccc
 241 aggcgctgtt gacagcggcg gaaagcagcg gtacccacgc gcccgccggg ggaagtcggc
 301 gagcggctgc agcagcaaag aacttcccg gctgggagga ccggagacaa gtggcagagt
 361 cccggagcca acttttgcaa gcctttcctg cgtcttaggc ttctccacgg cggtaaagac
```

Figure 10 (cont.)

```
 421 cagaaggcgg cggagagcca cgcaagagaa gaaggacgtg cgctcagctt cgctcgcacc
 481 ggttgttgaa cttgggcgag cgcgagccgc ggctgccggg cgcccctcc ccctagcagc
 541 ggaggagggg acaagtcgtc ggagtccggg cggccaagac ccgccgccgg ccggccactg
 601 cagggtccgc actgatccgc tccgcgggga gagccgctgc tctgggaagt gagttcgcct
 661 gcggactccg aggaaccgct gcgcacgaag agcgctcagt gagtgaccgc gacttttcaa
 721 agccgggtag cgcgcgcgag tcgacaagta agagtgcggg aggcatctta attaaccctg
 781 cgctccctgg agcgagctgg tgaggagggc gcagcgggga cgacagccag cgggtgcgtg
 841 cgctcttaga gaaactttcc ctgtcaaagg ctccggggg cgcgggtgtc ccccgcttgc
 901 cacagccctg ttgcggcccc gaaacttgtg cgcgcagccc aaactaacct cacgtgaagt
 961 gacggactgt tctatgactg caaagatgga aacgaccttc tatgacgatg ccctcaacgc
1021 ctcgttcctc ccgtccgaga gcggaccta tggctacagt aaccccaaga tcctgaaaca
1081 gagcatgacc ctgaacctgg ccgacccagt ggggagcctg aagccgcacc tccgcgccaa
1141 gaactcggac ctcctcacct cgcccgacgt ggggctgctc aagctggcgt cgcccgagct
1201 ggagcgcctg ataatccagt ccagcaacgg gcacatcacc accacgccga ccccacccca
1261 gttcctgtgc cccaagaacg tgacagatga gcaggagggc ttcgccgagg gcttcgtgcg
1321 cgccctggcc gaactgcaca gccagaacac gctgcccagc gtcacgtcgg cggcgcagcc
1381 ggtcaacggg gcaggcatgg tggctcccgc ggtagcctcg gtggcagggg gcagcggcag
1441 cggcggcttc agcgccagcc tgcacagcga gccgccggtc tacgcaaacc tcagcaactt
1501 caacccaggc gcgctgagca gcggcggcgg ggcgccctcc tacggcgcgg ccggcctggc
1561 cttttcccgcg caaccccagc agcagcagca gccgccgcac cacctgcccc agcagatgcc
1621 cgtgcagcac ccgcggctgc aggccctgaa ggaggagcct cagacagtgc ccgagatgcc
1681 cggcgagaca ccgccccctgt cccccatcga catggagtcc caggagcgga tcaaggcgga
1741 gaggaagcgc atgaggaacc gcatcgctgc ctccaagtgc cgaaaaagga agctggagag
1801 aatcgcccgg ctggaggaaa aagtgaaaac cttgaaagct cagaactcgg agctggcgtc
1861 cacggccaac atgctcaggg aacaggtggc acagcttaaa cagaaagtca tgaaccacgt
1921 taacagtggg tgccaactca tgctaacgca gcagttgcaa acatttgaa gagagaccgt
1981 cgggggctga ggggcaacga agaaaaaaaa taacacagag agacagactt gagaacttga
2041 caagttgcga cggagagaaa aaagaagtgt ccgagaacta aagccaaggg tatccaagtt
2101 ggactgggtt gcgtcctgac ggcgccccca gtgtgcacga gtgggaagga cttggcgcgc
2161 cctcccttgg cgtggagcca gggagcggcc gcctgcgggc tgccccgctt tgcggacggg
2221 ctgtccccgc gcgaacggaa cgttggactt ttcgttaaca ttgaccaaga actgcatgga
2281 cctaacattc gatctcattc agtattaaag ggggggagggg gaggggggtta caaactgcaa
2341 tagagactgt agattgcttc tgtagtactc cttaagaaca caaagcgggg ggagggttgg
2401 ggaggggcgg caggagggag gtttgtgaga gcgaggctga gcctacagat gaactctttc
2461 tggcctgcct tcgttaactg tgtatgtaca tatatatatt ttttaatttg atgaaagctg
2521 attactgtca ataaacagct tcatgccttt gtaagttatt tcttgtttgt ttgtttgggt
2581 atcctgccca gtgttgtttg taaataagag atttggagca ctctgagttt accatttgta
2641 ataaagtata taatttttt atgttttgtt tctgaaaatt ccagaaagga tatttaagaa
2701 aatacaataa actattggaa agtactcccc taacctcttt tctgcatcat ctgtagatac
2761 tagctatcta ggtggagttg aaagagttaa gaatgtcgat taaaatcact ctcagtgctt
2821 cttactatta agcagtaaaa actgttctct attagacttt agaaataaat gtacctgatg
2881 tacctgatgc tatggtcagg ttatactcct cctccccag ctatctatat ggaattgctt
2941 accaaaggat agtgcgatgt tcaggaggc tggaggaagg ggggttgcag tggagaggga
3001 cagcccactg agaagtcaaa catttcaaag tttggattgt atcaagtggc atgtgctgtg
3061 accatttata atgttagtag aaattttaca ataggtgctt attctcaaag caggaattgg
3121 tggcagattt tacaaaagat gtatccttcc aatttggaat cttctctttg acaattccta
3181 gataaaaaga tggcctttgc ttatgaatat ttataacagc attcttgtca caataaatgt
3241 attcaaatac caat
```

SEQ ID NO:63

```
   1 gtggagctac cgccaccgcc gccgccgatt ccggagccgg ggtagtcgcc gccgccgccg
  61 ccgctgcagc cactgcaggc accgctgccg ccgcctgagt agtgggctta ggaaggaaga
 121 ggtcatctcg ctcggagctt cgctcggaag ggtctttgtt ccctgcagcc ctcccacggg
 181 aatgacaatg gataaaagtg agctggtaca gaaagccaaa ctcgctgagc aggctgagcg
```

Figure 10 (cont.)

```
    241 atatgatgat atggctgcag ccatgaaggc agtcacagaa cagggcatg aactctccaa
    301 cgaagagaga aatctgctct ctgttgccta caagaatgtg gtaggcgccc gccgctcttc
    361 ctggcgtgtc atctccagca ttgagcagaa aacagagagg aatgagaaga agcagcagat
    421 gggcaaagag taccgtgaga agatagaggc agaactgcag gacatctgca atgatgttct
    481 ggagctgttg gacaaatatc ttattcccaa tgctacacaa ccagaaagta aggtgttcta
    541 cttgaaaatg aaaggagatt attttaggta tcttctgaa gtggcatctg gagacaacaa
    601 acaaaccact gtgtcgaact cccagcaggc ttaccaggaa gcatttgaaa ttagtaagaa
    661 agaaatgcag cctacacacc caattcgtct tggtctggca ctaaatttct cagtctttta
    721 ctatgagatt ctaaactctc ctgaaaaggc ctgtagcctg gcaaaaacgg catttgatga
    781 agcaattgct gaattggata cgctgaatga agagtcttat aaagacagca ctctgatcat
    841 gcagttactt agggacaatc tcactctgtg gacatcggaa aaccaggag acgaaggaga
    901 cgctggggag ggagagaact aatgtttctc gtgctttgtg atctgttcag tgtcactctg
    961 taccctcaac atatatccct tgtgcgat
```

SEQ ID NO:64
```
      1 gtgccgctcc ttggtggggg ctgttcatgg cggttccggg gtctccaaca ttttttccgg
     61 ctgtggtcct aaatctgtcc aaagcagagg cagtggagct tgaggttctt gctggtgtga
    121 aatgactgag tacaaactgg tggtggttgg agcaggtggt gttgggaaaa gcgcactgac
    181 aatccagcta atccagaacc actttgtaga tgaatatgat cccaccatag aggattctta
    241 cagaaaacaa gtggttatag atggtgaaac ctgtttgttg gacatactgg atacagctgg
    301 acaagaagag tacagtgcca tgagagacca atacatgagg acaggcgaag gcttcctctg
    361 tgtatttgcc atcaataata gcaagtcatt tgcggatatt aacctctaca gggagcagat
    421 taagcgagta aaagactcgg atgatgtacc tatggtgcta gtgggaaaca agtgtgattt
    481 gccaacaagg acagttgata caaacaagc ccacgaactg gccaagagtt acgggattcc
    541 attcattgaa acctcagcca agaccagaca gggtgttgaa gatgcttttt acacactggt
    601 aagagaaata cgccagtacc gaatgaaaaa actcaacagc agtgatgatg ggactcaggg
    661 ttgtatggga ttgccatgtg tggtgatgta acaagatact tttaaagttt tgtcagaaaa
    721 gagccacttt caagctgcac tgacaccctg gtcctgactt ccctggagga gaagtattcc
    781 tgttgctgtc ttcagtctca cagagaagct cctgctactt ccccagctct cagtagttta
    841 gtacaataat ctctatttga gaagttctca gaataactac ctcctcactt ggctgtctga
    901 ccagagaatg cacctcttgt tactccctgt tattttttctg ccctgggttc ttccacagca
    961 caaacacacc tctgccaccc caggttttttc atctgaaaag cagttcatgt ctgaaacaga
   1021 gaaccaaacc gcaaacgtga aattctattg aaaacagtgt cttgagctct aaagtagcaa
   1081 ctgctggtga ttttttttttt cttttttactg ttgaacttag aactatgcta atttttggag
   1141 aaatgtcata aattactgtt ttgccaagaa tatagttatt attgctgttt ggtttgttta
   1201 taatgttatc ggctctattc tctaaactgg catctgctct agattcataa atacaaaaat
   1261 gaatactgaa ttttgagtct atcctagtct tcacaacttt gacgtaatta aatccaactt
   1321 tcacagtgaa gtgcctttttt cctagaagtg gtttgtagac ttcctttata atatttcagt
   1381 ggaatagatg tctcaaaaat ccttatgcat gaaatgaatg tctgagatac gtctgtgact
   1441 tatctaccat tgaaggaaag ctatatctat ttgagagcag atgccatttt gtacatgtat
   1501 gaaattggtt ttccagaggc ctgttttggg gctttcccag gagaaagatg aaactgaaag
   1561 cacatgaata atttcactta ataatttta cctaatctcc acttttttca taggttacta
   1621 cctatacaat gtatgtaatt tgtttcccct agcttactga taaacctaat attcaatgaa
   1681 cttccatttg tattcaaatt tgtgtcatac cagaaagctc tacatttgca gatgttcaaa
   1741 tattgtaaaa ctttggtgca ttgttattta atagctgtga tcagtgattt tcaaacctca
   1801 aatatagtat attaacaaat tacattttca ct
```

SEQ ID NO:65
```
      1 atgaaggtga taagcttatt catttttggtg ggatttatag gagagttcca aagttttttca
     61 agtgcctcct ctccagtcaa ctgccagtgg gacttctatg cccttggtc agaatgcaat
    121 ggctgtacca agactcagac tcgcaggcgg tcagttgctg tgtatgggca gtatggaggc
    181 cagccttgtg tggaaatgc ttttgaaaca cagtcctgtg aacctacaag aggatgtcca
    241 acagaggagg gatgtggaga gcgttcagg tgcttttcag gtcagtgcat cagcaaatca
    301 ttggtttgca atggggattc tgactgtgat gaagacagtg ctgatgaaga cagatgtgag
```

Figure 10 (cont.)

```
 361 gactcagaaa ggagaccttc ctgtgatatc gataaacctc ctcctaacat agaacttact
 421 ggaaatggtt acaatgaact cactggccag tttaggaaca gagtcatcaa taccaaaagt
 481 tttggtggtc aatgtagaaa ggtgtttagt ggggatggaa aagatttcta caggctgagt
 541 ggaaatgtcc tgtcctatac attccaggtg aaaataaata atgatcttaa ttatgaattt
 601 tacaatagta cttggtctta tgtaaaacat acgtcgacag aacacacatc atctagtcgg
 661 aagcgctcct tttttagatc ttcatcatct tcttcacgca gttatacttc acataccaat
 721 gaaatccata aaggaaagag ttaccaactg ctggttgttg agaacactgt tgaagtggct
 781 cagttcatta ataacaatcc agaattttta caacttgctg agccattctg gaaggagctt
 841 tcccacctcc cctctctgta tgactacagt gcctaccgaa gattaatcga ccagtacggg
 901 acacattatc tgcaatctgg gtcgttagga ggagaataca gagttctatt ttatgtggac
 961 tcagaaaaat taaaacaaaa tgatttttaat tcagtcgaag aaaagaaatg taaatcctca
1021 ggttggcatt ttgtcgttaa atttttcaagt catggatgca aggaactgga aaacgcttta
1081 aaagctgctt caggaaccca gaacaatgta ttgcgaggag aaccgttcat cagaggggga
1141 ggtgcaggct tcatatctgg ccttagttac ctagagctgg acaatcctgc tggaaacaaa
1201 aggcgatatt ctgcctggc  agaatctgtg actaatcttc ctcaagtcat aaaacaaaag
1261 ctgacacctt tatatgagct ggtaaaggaa gtaccttgtg cctctgtgaa aaaactatac
1321 ctgaaatggg ctcttgaaga gtatctggat gaatttgacc cctgtcattg ccggccttgt
1381 caaaatggtg gtttggctac tgttgagggg acccattgtc tgtgccattg caaaccgtac
1441 acatttggtg cggcgtgtga gcaaggagtc ctcgtaggga atcaagcagg aggggttgat
1501 ggaggttgga gttgctggtc ctcttggagc ccctgtgtcc aagggaagaa aacaagaagc
1561 cgtgaatgca ataacccacc tcccagtggg ggtgggagat cctgcgttgg agaaacgaca
1621 gaaagcacac aatgcgaaga tgaggagctg gagcacttga ggttgcttga accacattgc
1681 tttcctttgt ctttggttcc aacagaattc tgtccatcac ctcctgcctt gaaagatgga
1741 tttgttcaag atgaaggtcc aatgtttcct gtggggaaaa atgtagtgta cacttgcaat
1801 gaaggatact ctcttattgg aaacccagtg gccagatgtg agaagattt  acggtggctt
1861 gttggggaaa tgcattgtca gaaaattgcc tgtgttctac ctgtactgat ggatggcata
1921 cagagtcacc cccaaaaacc tttctacaca gttggtgaga aggtgactgt ttcctgttca
1981 ggtggcatgt ccttagaagg tccttcagca tttctctgtg gctccagcct taagtggagt
2041 cctgagatga agaatgcccg ctgtgtacaa aaagaaaatc cgttaacaca ggcagtgcct
2101 aaatgtcagc gctgggagaa actgcagaat tcaagatgtg tttgtaaaat gccctacgaa
2161 tgtggaccct ccttggatgt atgtgctcaa gatgagagaa gcaaaaggat actgcctctg
2221 acagtttgca agatgcatgt tctccactgt cagggtagaa attacaccct tactggtagg
2281 gacagctgta ctctgcctgc ctcagctgag aaagcttgtg gtgcctgccc actgtgggga
2341 aaatgtgatg ctgagagcag caaatgtgtc tgccgagaag catcggagtg cgaggaagaa
2401 gggtttagca tttgtgtgga agtgaacggc aaggagcaga cgatgtctga gtgtgaggcg
2461 ggcgctctga gatgcagagg gcagagcatc tctgtcacca gcataaggcc ttgtgctgcg
2521 gaaacccagt aggctcctgg aggccatggt cagcttgctt ggaatccagc aggcagctgg
2581 ggctgagtga aacatctgc  acaactgggc actggacagc ttttccttct tctccagtgt
2641 ctaccttcct cctcaactcc cagccatctg tataaacaca atcctttgtt ctcccaaatc
2701 tgaatcgaat tactcttttg cctccttttt aatgtcagta aggatatgag cctttgcaca
2761 ggctggctgc gtgttcttga aataggtgtt accttctctg ggccttggtt ttttaaaatc
2821 tgtaaaatta gaggattgca ctagagaaac ttgaatgctc cattcaggcc tatcatttta
2881 ttaagtatga ttgacacagc ccatgggcca gaacacactc tacaaaatga ctaggataac
2941 agaaagaacg tgatctcctg attagagagg gtggttttcc tcaatggaac caaatataaa
3001 gaggacttga acaaaaatga cagatacaaa ctatttctat cctgagtagt aatctcacac
3061 ttcatcctat agagtcaacc accacagata ggaattcctt attcttttt  taatttttt
3121 aagacagagt ctcacttgt  tgcccaggct ggagcgcagt ggggtgatct catctccctg
3181 caacctccgc ctcctgggtt gaagcgattc ttgtgcctca gcttcccaag cagctgggat
3241 tacaggtgcc cgccaccacg cccagctaat ttttgcattt tagtagaga tggggtttcac
3301 catgttggcc atgctcgtct ccaactcctg acctcaggta atccgtctgc cttggcctcc
3361 caaatgctgg gattacagac atgaaccacc acgcctggct ggaatactta ctcttgtcgg
3421 gagattgaac cactaaaatg ttagagcaga attcattatg ctgtggtcac aggggtgtct
3481 tgtctgagaa caaatacaat tcagtcttct ctttggggtt ttagtatgtg tcaaacatag
3541 gactggaagt ttgcccctgt tcttttttct tttgaaagaa catcagttca tgcctgaggc
```

Figure 10 (cont.)

```
3601 atgagtgact gtgcatttga gatagttttc cctattctgt ggatacagtc ccagagtttt
3661 cagggagtac acaggtagat tagtttgaag cattgacctt ttatttattc cttatttctc
3721 tttcatcaaa acaaaacagc agctgtggga ggagaaatga gagggcttaa atgaaattta
3781 aaataagcta tattatacaa atactatctc tgtattgttc tgaccctggt aaatatattt
3841 caaaacttca gatgacaagg attagaacac tcattaagat gctattcttc
```

SEQ ID NO:66
```
  1 ctaacccaga aacatccaat tctcaaactg aagctcgcac tctcgcctcc agcatgaaag
 61 tctctgccgc ccttctgtgc ctgctgctca tagcagccac cttcattccc caagggctcg
121 ctcagccaga tgcaatcaat gccccagtca cctgctgtta taacttcacc aataggaaga
181 tctcagtgca gaggctcgcg agctatagaa gaatcaccag cagcaagtgt cccaaagaag
241 ctgtgatctt caagaccatt gtggccaagg agatctgtgc tgacccccaag cagaagtggg
301 ttcaggattc catggaccac ctggacaagc aaacccaaac tccgaagact gaacactca
361 ctccacaacc caagaatctg cagctaactt attttcccct agctttcccc agacaccctg
421 ttttatttta ttataatgaa ttttgtttgt tgatgtgaaa cattatgcct taagtaatgt
481 taattcttat ttaagttatt gatgttttaa gtttatcttt catggtacta gtgttttta
541 gatacagaga cttggggaaa ttgcttttcc tcttgaacca cagttctacc cctgggatgt
601 tttgagggtc tttgcaagaa tcattaatac aaagaatttt ttttaacatt ccaatgcatt
661 gctaaaatat tattgtggaa atgaatattt tgtaactatt acaccaaata aatatattc
721 tgtac
```

SEQ ID NO:67
```
   1 ttcaatgttg atgtgaaaaa ttcaatgact ttcagcggcc cggtggaaga catgtttgga
  61 tatactgttc aacaatatga aaatgaagaa ggaaaatggg tgcttattgg ttctccgtta
 121 gttggccaac ccaaaaacag aactggagat gtctataagt gtccagttgg gagaggtgaa
 181 tcattacctt gcgtaaagtt ggatctacca gttaatacat caattcccaa tgtcacagaa
 241 gtaaaggaga acatgacatt tggatcaact ttagtcacca acccaaatgg aggatttctg
 301 gcttgtgggc ccttatatgc ctatagatgt ggacatttgc attacacaac tggaatctgt
 361 tctgacgtca gcccacatt tcaagtcgtg aattccattg ccctgtaca agaatgcagc
 421 actcaactgg acatagtcat agtgctggat ggttccaaca gtatttaccc atgggacagt
 481 gttacagctt ttttaaatga ccttcttgaa agaatggata ttggtcctaa acagacacag
 541 gttggaattg tacagtatgg agaaaacgtg acccatgagt tcaacctcaa taagtattct
 601 tccaccgaag aggtacttgt tgcagcaaag aaaatagtcc agagaggtgg ccgccagact
 661 atgacagctc ttggaataga cacagcaaga aaggaggcat tcacgaaagc ccggggtgcc
 721 cgaagaggag ttaaaaaagt catggttatt gtgacagatg gagagtctca tgacaatcat
 781 cgactgaaga aggtcatcca agactgtgaa gatgaaaaca ttcaacggtt ttccatagct
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnctt catatgaaat ggaaatgtct cagactggct tcagtgctca ttattcacag
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnngttac actgtaaact ctgctactgc ttcttctgga
1261 gatgtgctct atattgctgg acagcctcgg tacaatcata caggccaggt cattatctac
1321 aggatggaag atggaaacat caaaattctc cagacgctca gtggagaaca gattggttcc
1381 tactttggca gtattttaac aacaactgac attgacaagg attctaatac tgacattctt
1441 ctagtcggag cccctatgta catgggaaca gagaaggagg agcaaggaaa agtgtatgtg
1501 tatgctctca atcagacaag gtttgaatat caaatgagcc tggaacctat taagcagacg
1561 tgctgttcat ctcggcagca caattcatgc acaacagaaa acaaaaatga gccatgcggg
1621 gctcgttttg gaactgcaat tgctgctgta aaagacctca atcttgatgg atttaatgac
1681 atcgtgatag gagctccgct ggagatgatc acggggagc tgtgtacatt tatcatggaa
1741 gtggcaagac tataaggaaa gagtatgcac aacgtattcc atcaggtggg gatggtaaga
1801 cactgaaatt ttttggccag tctatccacg gagaaatgga tttaaatggt gacggtctga
1861 cagatgtgac tattgggggc cttgtggtg ctgccctctt ctggtcccga gatgtggccg
```

Figure 10 (cont.)

```
  61 ttaggggtcc gggccccggg ctgctgctgc tggccgtcct gtgcctgggg acagcggtgc
 121 cctccacggg agcctcgaag agcaagaggc aggctcagca aatggttcag ccccagtccc
 181 cggtggctgt cagtcaaagc aagcccggtt gttatgacaa tggaaaacac tatcagataa
 241 atcaacagtg ggagcggacc tacctaggca atgcgttggt ttgtacttgt tatggaggaa
 301 gccgaggttt taactgcgag agtaaacctg aagctgaaga gacttgcttt gacaagtaca
 361 ctgggaacac ttaccgagtg ggtgacactt atgagcgtcc taaagactcc atgatctggg
 421 actgtacctg catcgggct gggcgaggga gaataagctg taccatcgca aaccgctgcc
 481 atgaaggggg tcagtcctac aagattggtg acacctggag gagaccacat gagactggtg
 541 gttacatgtt agagtgtgtg tgtcttggta atggaaaagg agaatggacc tgcaagccca
 601 tagctgagaa gtgttttgat catgctgctg ggacttccta tgtggtcgga gaaacgtggg
 661 agaagcccta ccaaggctgg atgatggtag attgtacttg cctgggagaa ggcagcggac
 721 gcatcacttg cacttctaga aatagatgca acgatcagga cacaaggaca tcctatagaa
 781 ttggagacac ctggagcaag aaggataatc gaggaaacct gctccagtgc atctgcacag
 841 gcaacggccg aggagagtgg aagtgtgaga ggcacacctc tgtgcagacc acatcgagcg
 901 gatctggccc cttcaccgat gttcgtgcag ctgtttacca accgcagcct caccccagc
 961 ctcctcccta tggccactgt gtcacagaca gtggtgtggt ctactctgtg gggatgcagt
1021 ggctgaagac acaaggaaat aagcaaatgc tttgcacgtg cctgggcaac ggagtcagct
1081 gccaagagac agctgtaacc cagacttacg gtggcaactc aaatggagag ccatgtgtct
1141 taccattcac ctacaatggc aggacgtgca gcacaacttc gaattatgag caggaccaga
1201 aatactcttt ctgcacagac cacactgttt tggttcagac tcgaggagga aattccaatg
1261 gtgccttgtg ccacttcccc ttcctataca acaaccacaa ttacactgat tgcacttctg
1321 agggcagaag agacaacatg aagtggtgtg ggaccacaca gaactatgat gccgaccaga
1381 agtttgggtt ctgccccatg gctgcccacg aggaaatctg cacaaccaat gaagggggtca
1441 tgtaccgcat tggagatcag tgggataagc agcatgacat gggtcacatg atgaggtgca
1501 cgtgtgttgg gaatggtcgt ggggaatgga catgcattgc ctactcgcag cttcgagatc
1561 agtgcattgt tgatgacatc acttacaatg tgaacgacac attccacaag cgtcatgaag
1621 aggggcacat gctgaactgt acatgcttcg gtcagggtcg gggcaggtgg aagtgtgatc
1681 ccgtcgacca atgccaggat tcagagactg ggacgtttta tcaaattgga gattcatggg
1741 agaagtatgt gcatggtgtc agataccagt gctactgcta tggccgtggc attgggagt
1801 ggcattgcca acctttacag acctatccaa gctcaagtgg tcctgtcgaa gtatttatca
1861 ctgagactcc gagtcagccc aactccacc ccatccagtg gaatgcacca cagccatctc
1921 acatttccaa gtacattctc aggtggagac ctgtgagtat cccacccaga aaccttggat
1981 actgagtctc ctaatcttat caattctgat ggtttctttt tttcccagct tttgagccaa
2041 caactctgat taactattcc tatagcattt actatatttg tttagtgaac aaacaatatg
2101 tggtcaatta aattgacttg tagactg
```

SEQ ID NO:50

```
   1 accccccgcac ccagctccgc aggaccggcg ggcgcgcgcg ggctctggag gccacgggca
  61 tgatgcttcg ggtcctggtg ggggctgtcc tccctgccat gctactggct gccccaccac
 121 ccatcaacaa gctggcactg ttcccagata agagtgcctg gtgcgaagcc aagaacatca
 181 cccagatcgt gggccacagc ggctgtgagg ccaagtccat ccagaacagg gcgtgcctag
 241 gacagtgctt cagctacagc gtccccaaca ccttcccaca gtccacagag tccctggttc
 301 actgtgactc ctgcatgcca gcccagtcca tgtgggagat tgtgacgctg gagtgcccgg
 361 gccacgagga ggtgccagg gtggacaagc tggtggagaa gatcctgcac tgtagctgcc
 421 aggcctgcgg caaggagcct agtcacgagg gctgagcgt ctatgtgcag ggcgaggacg
 481 ggccgggatc ccagcccggc acccaccctc accccatcc caccccat cctggcgggc
 541 agaccctga gcccgaggac cccctgggg cccccacac agaggaagag gggctgagg
 601 actgaggccc cccaactct tcctccctc tcatccccct gtggaatgtt gggtctcact
 661 ctctggggaa gtcaggggag aagctgaagc ccccctttgg cactggatgg acttggcttc
 721 agactcggac ttgaatgctg cccggttgcc atggagatct gaaggggcgg ggttagagcc
 781 aagctgcaca atttaatata ttcaagagtg ggggaggaa gcagaggtct tcaggctct
 841 tttttgggg ggggtggtct cttcctgtct ggcttctaga gatgtgcctg tgggagggg
 901 aggaagttgg ctgagccatt gagtgctggg ggaggccatc caagatggca tgaatcgggc
 961 taaggtccct gggggtgcag atggtactgc tgaggtcccg ggcttagtgt gagcatcttg
```

Figure 10 (cont.)

```
1021 ccagcctcag gcttgaggga gggctgggct agaaagacca ctggcagaaa caggaggctc
1081 cggcccacag gtttccccaa ggcctctcac cccacttccc atctccaggg aagcgtcgcc
1141 ccagtggcac tgaagtggcc ctccctcagc ggaggggttt gggagtcagg cctgggcagg
1201 accctgctga ctcgtggcgc gggagctggg agccaggctc tccgggcctt tctctggctt
1261 ccttggcttg cctggtgggg gaaggggagg aggggaagaa ggaaagggaa gagtcttcca
1321 aggccagaag gaggggggaca accccccaag accatccctg aagacgagca tcccctcct
1381 ctccctgtta gaaatgttag tgcccgcac tgtgcccaa gttctaggcc cccagaaag
1441 ctgccagagc cggccgcctt ctcccctctc ccagggatgc tctttgtaaa tatcggatgg
1501 gtgtgggagt gaggggttac ctccctcgcc caaggttcc agaggcccta ggcgggatgg
1561 gctcgctgaa cctcgaggaa ctccaggacg aggaggacat gggacttgcg tggacagtca
1621 gggttcactt gggctctctc tagctcccca attctgcctg cctcctccct cccagctgca
1681 ctttaacect agaaggtggg gacctggggg gagggacagg gcaggcgggc ccatgaagaa
1741 agccctcgt tgcccagcac tgtctgcgtc tgctcttctg tgcccagggt ggctgccagc
1801 ccactgcctc ctgcctgggg tggcctggcc ctcctggctg ttgcgacgcg ggcttctgga
1861 gcttgtcacc attggacagt ctccctgatg gaccctcagt cttctcatga ataaattc
```

SEQ ID NO:51
```
   1 atccgtcccg gataagaccc gctgtctggc cctgagtagg gtgtgacctc cgcagccgca
  61 gaggaggagc gcagcccggc ctcgaagaac ttctgcttgg gtggctgaac tctgatcttg
 121 acctagagtc atggccatgg caaccaaagg aggtactgtc aaagctgctt caggattcaa
 181 tgccatggaa gatgcccaga ccctgaggaa ggccatgaaa gggctcggca ccgatgaaga
 241 cgccattatt agcgtccttg cctaccgcaa caccgcccag cgccaggaga tcaggacagc
 301 ctacaagagc accatcggca gggacttgat agacgacctg aagtcagaac tgagtggcaa
 361 cttcgagcag gtgattgtgg ggatgatgac gcccacggtg ctgtatgacg tgcaagagct
 421 gcgaagggcc atgaagggag ccggcactga tgagggctgc ctaattgaga tcctggcctc
 481 ccggaccct gaggagatcc ggcgcataag ccaaacctac cagcagcaat atggacggag
 541 ccttgaagat gacattcgct ctgacacatc gttcatgttc cagcgagtgc tggtgtctct
 601 gtcagctggt gggagggatg aaggaaatta tctggacgat gctctcgtga gacaggatgc
 661 ccaggacctg tatgaggctg gagagaagaa atgggggaca gatgaggtga aatttctaac
 721 tgttctctgt tcccggaacc gaaatcacct gttgcatgct ttgatgaata caaaaggata
 781 tcacagaagg atattgaaca gagtattaaa tctgaaacat ctggtagctt tgaagatgct
 841 ctgctggcta tagtaaagtg catgaggaac aaatctgcat attttgctga aaagctctat
 901 aaatcgatga agggcttggg caccgatgat aacaccctca tcagagtgat ggtttctcga
 961 gcagaaattg acatgttgga tatccgggca cacttcaaga gactctatgg aaagtctctg
1021 tactcgttca tcaagggtga cacatctgga gactacagga aagtactgct tgttctctgt
1081 ggaggagatg attaaaataa aaatcccaga aggacaggag gattctcaac actttgaatt
1141 ttttaacttt catttttcta cactgctatt atcattatct cagaatgctt atttccaatt
1201 aaaacgccta cagctgcctc ct
```

SEQ ID NO:52
```
   1 tggggcagcc gcgcccgcgg tgttttccgc ccggcgctgg cggctgctgc gcccgcggct
  61 ccccagtgcc ccgagtgccc cgcgggcccc gcgagcggga gtgggaccca gccctaggc
 121 agaacccagg cgccgcgccc gggacgcccg cggagagagc cactccgcc cacgtcccat
 181 ttcgccctc gcgtccggag tcctcgtggc cagatctaac catgagctac cctggctatc
 241 ccccgccccc aggtggctac ccaccagctg caccaggtgg tgtccctgg ggaggtgctg
 301 cctaccctcc tccgcccagc atgcccccca tcgggctgga taacgtggcc acctatgcgg
 361 ggcagttcaa ccaggactat ctctcgggaa tggcggccaa catgtctggg acatttggag
 421 gagccaacat gcccaacctg taccctgggg cccctggggc tggctaccca ccagtgcccc
 481 ctggcggctt tgggcagccc cctctgccc agcagcctgt tcctccctat gggatgtatc
 541 caccccagg aggaaaccca ccctccagga tgcctcata tccgccatac ccaggggccc
 601 ctgtgccggg ccagcccatg ccaccccccg gacagcagcc cccagggccc tacctgggc
 661 agccaccagt gacctaccct ggtcagcctc cagtgccact ccctgggcag cagcagccag
 721 tgccgagcta cccaggatac ccggggtctg ggactgtcac cccgctgtg ccccaaccc
 781 agtttggaag ccgaggcacc atcactgatg ctcccggctt tgacccctg cgagatgccg
```

Figure 10 (cont.)

```
 841 aggtcctgcg gaaggccatg aaaggcttcg ggacggatga gcaggccatc attgactgcc
 901 tggggagtcg ctccaacaag cagcggcagc agatcctact ttccttcaag acggcttacg
 961 gcaaggattt gatcaaagat ctgaaatctg aactgtcagg aaactttgag aagacaatct
1021 tggctctgat gaagaccccca gtcctctttg acatttatga gataaaggaa gccatcaagg
1081 gggttggcac tgatgaagcc tgcctgattg agatcctcgc ttcccgcagc aatgagcaca
1141 tccgagaatt aaacagagcc tacaaagcag aattcaaaaa gaccctggaa gaggccattc
1201 gaagcgacac atcagggcac ttccagcggc tcctcatctc tctctctcag ggaaaccgtg
1261 atgaaagcac aaacgtggac atgtcactcg cccagagaga tgcccaggag ctgtatgcgg
1321 ccggggagaa ccgcctggga acagacgagt ccaagttcaa tgcggttctg tgctcccgga
1381 gccgggccca cctggtagca gttttcaatg agtaccagag aatgacaggc cgggacattg
1441 agaagagcat ctgccgggag atgtccgggg acctggagga gggcatgctg gccgtggtga
1501 aatgtctcaa gaataccccca gccttctttg cggagaggct caacaaggcc atgaggggcg
1561 caggaacaaa ggaccggacc ctgattcgca tcatggtgtc tcgcagcgag accgacctcc
1621 tggacatcag atcagagtat aagcggatgt acggcaagtc gctgtaccac gacatctcgg
1681 gagatacttc aggggattac cggaagattc tgctgaagat ctgtggtggc aatgactgaa
1741 cagtgactgg tggctcactt ctgcccacct gccggcaaca ccagtgccag gaaaaggcca
1801 aaagaatgtc tgtttctaac aaatccacaa atagccccga gattcaccgt cctagagctt
1861 aggcctgtct tccacccctc ctgaccgta tagtgtgcca caggacctgg gtcggtctag
1921 aactctctca ggatgccttt tctacccccat ccctcacagc ctcttgctgc taaaatagat
1981 gtttcatttt tctgactcat gcaatcattc ccctttgcct gtggctaaga cttggcttca
2041 tttcgtcatg taattgtata ttttatttg gaggcatatt ttcttttctt acagtcattg
2101 ccagacagag gcatacaagt ctgtttgctg catacacatt tctggtgagg gcgactgggt
2161 gggtgaagca ccgtgtcctc gctgaggaga gaaagggagg cgtgcctgag aaggtagcct
2221 gtgcatctgg tgagtgtgtc acgagctttg ttactgccaa actcactcct ttttagaaaa
2281 aacaaaaaaa aagggccaga aagtcattcc ttccatcttc cttcagaaa ccacgagaac
2341 aaagccagtt ccctgtcagt gacagggctt cttgtaattt gtggtatgtg ccttaaacct
2401 gaatgtctgt agccaaaact tgtttccaca ttaagagtca gccagctctg aatggtctg
2461 gaaatgtc
```

SEQ ID NO:53

```
   1 tagacgcacc ctctgaagat ggtgactccc tcctgagaag ctggacccct tggtaaaaga
  61 caaggccttc tccaagaaga atatgaaagt gttactcaga cttatttgtt tcatagctct
 121 actgatttct tctctggagg ctgataaatg caaggaacgt gaagaaaaaa taatttagt
 181 gtcatctgca aatgaaattg atgttcgtcc ctgtcctctt aacccaaatg aacacaaagg
 241 cactataact tggtataaag atgacagcaa gacacctgta tctacagaac aagcctccag
 301 gattcatcaa cacaaagaga aactttggtt tgttcctgct aaggtggagg attcaggaca
 361 ttactattgc gtggtaagaa attcatctta ctgcctcaga attaaaataa gtgcaaaatt
 421 tgtggagaat gagcctaact tatgttataa tgcacaagcc atatttaagc agaaactacc
 481 cgttgcagga gacggaggac ttgtgtgccc ttatatggag ttttttaaaa atgaaaataa
 541 tgagttacct aaattacagt ggtataagga ttgcaaacct ctacttcttg acaatataca
 601 ctttagtgga gtcaaagata ggctcatcgt gatgaatgtg gctgaaaagc atagagggaa
 661 ctatacttgt catgcatcct acacatactt gggcaagcaa tatcctatta cccgggtaat
 721 agaatttatt actctagagg aaaacaaacc cacaaggcct gtgattgtga gcccagctaa
 781 tgagacaatg gaagtagact gggatccca gatacaattg atctgtaatg tcaccggcca
 841 gttgagtgac attgcttact ggaagtggaa tgggtcagta attgatgaag atgacccagt
 901 gctagggaaa gactattaca gtgtggaaaa tcctgcaaac aaaagaagga gtaccctcat
 961 cacagtgctt aatatatcgg aaattgaaag tagattttat aaacatccat ttacctgttt
1021 tgccaagaat acacatggta tagatcagc atatatccag ttaatatatc cagtcactaa
1081 tttccagaag cacatgattg gtatatgtgt cacgttgaca gtcataattg tgtgttctgt
1141 tttcatctat aaaatcttca gattgacat tgtctttgg tacagggatt cctgctatga
1201 ttttctccca ataaagctt cagatggaaa gacctatgac gcatatatac tgtatccaaa
1261 gactgttggg gaagggtcta cctctgactg tgatattttt gtgtttaaag tcttgcctga
1321 ggtcttggaa aaacagtgtg gatataagct gttcattat ggaagggatg actacgttgg
```

Figure 10 (cont.)

```
1381 ggaagacatt gttgaggtca ttaatgaaaa cgtaaagaaa agcagaagac tgattatcat
1441 tttagtcaga gaaacatcag gcttcagctg gctgggtggt tcatctgaag agcaaatagc
1501 catgtataat gctcttgttc aggatggaat taaagttgtc ctgcttgagc tggagaaaat
1561 ccaagactat gagaaaatgc cagaatcgat taaattcatt aagcagaaac atggggctat
1621 ccgctggtca ggggacttta cacagggacc acagtctgca aagacaaggt tctggaagaa
1681 tgtcaggtac cacatgccag tccagcgacg gtcaccttca tctaaacacc agttactgtc
1741 accagccact aaggagaaac tgcaagaga ggctcacgtg cctctcgggt agcatggaga
1801 agttgccaag agttctttag gtgcctcctg tcttatggcg ttgcaggcca ggttatgcct
1861 catgctgact tgcagagttc atggaatgta actatatcat cctttatccc tgaggtcacc
1921 tggaatcaga ttattaaggg aataagccat gacgtcaata gcagcccagg cacttcaga
1981 gtagagggct tgggaagatc ttttaaaaag gcagtaggcc cggtgtggtg gctcacgcct
2041 ataatcccag cactttggga ggctgaagtg ggtggatcac cagaggtcag gagttcgaga
2101 ccagcccagc caacatggca aaacccatc tctactaaaa atacaaaaat gagctaggca
2161 tggtggcaca cgcctgtaat cccagctaca cctgaggctg aggcaggaga attgcttgaa
2221 ccggggagac ggaggttgca gtgagccgag tttgggccac tgcactctag cctggcaaca
2281 gagcaagact ccgtctcaaa aaagggcaa taaatgccct ctctgaatgt ttgaactgcc
2341 aagaaaaggc atggagacag cgaactagaa gaaagggcaa gaaggaaata gccaccgtct
2401 acagatggct tagttaagtc atccacagcc caagggcggg gctatgcctt gtctggggac
2461 cctgtagagt cactgaccct ggagcggctc tcctgagagg tgctgcaggc aaagtgagac
2521 tgacacctca ctgaggaagg gagacatatt cttggagaac tttccatctg cttgtatttt
2581 ccatacacat ccccagccag aagttagtgt ccgaagaccg aatttattt tacagagctt
2641 gaaaactcac ttcaatgaac aaagggattc tccaggattc caaagttttg aagtcatctt
2701 agctttccac aggagggaga gaacttaaaa aagcaacagt agcagggaat tgatccactt
2761 cttaatgctt tcctccctgg catgaccatc ctgtcctttg ttattatcct gcattttacg
2821 tctttggagg aacagctccc tagtggcttc ctccgtctgc aatgtccctt gcacagccca
2881 cacatgaacc atccttccca tgatgccgct cttctgtcat cccgctcctg ctgaaacacc
2941 tcccaggggc tccacctgtt caggagctga agccatgct ttcccaccag catgtcactc
3001 ccagaccacc tccctgccct gtcctccagc ttcccctcgc tgtcctgctg tgtgaattcc
3061 caggttggcc tggtggccat gtcgcctgcc cccagcactc ctctgtctct gctcttgcct
3121 gcaccccttcc tcctcctttg cctaggaggc cttctcgcat tttctctagc tgatcagaat
3181 tttaccaaaa ttcagaacat cctccaattc cacagtctct gggagacttt ccctaagagg
3241 cgacttcctc tccagccttc tctctctggt caggcccact gcagagatgg tggtgagcac
3301 atctgggagg ctggtctccc tccagctgga attgctgctc tctgagggag aggctgtggt
3361 ggctgtctct gtccctcact gccttccagg agcaatttgc acatgtaaca tagatttatg
3421 taatgcttta tgtttaaaaa cattccccaa ttatcttatt taattttgc aattattcta
3481 attttatata tagagaaagt gacctatttt ttaaaaaaat cacactctaa gttctattga
3541 acctaggact tgagcctcca tttctggctt ctagtctggt gttctgagta cttgatttca
3601 ggtcaataac ggtcccccct cactccacac tggcacgttt gtgagaagaa atgacatttt
3661 gctaggaagt gaccgagtct aggaatgctt ttattcaaga caccaaattc caaacttcta
3721 aatgttggaa ttttcaaaaa ttgtgtttag atttatgaa aaactcttct actttcatct
3781 attcttttccc tagaggcaaa catttcttaa aatgtttcat tttcattaaa aatgaaagcc
3841 aaatttatat gccaccgatt gcaggacaca agcacagttt taagagttgt atgaacatgg
3901 agaggacttt tggtttttat atttctcgta tttaatatgg gtgaacacca actttattt
3961 ggaataataa tttcctcct aaacaaaaac acattgagtt taagtctctg actcttgcct
4021 ttccacctgc tttctcctgg gcccgctttg cctgcttgaa ggaacagtgc tgttctggag
4081 ctgctgttcc aacagacagg gcctagcttt catttgacac acagactaca gccagaagcc
4141 catggagcag ggatgtcacg tcttgaaaag cctattagat gttttacaaa tttaattttg
4201 cagattattt tagtctgtca tccagaaaat gtgtcagcat gcatagtgct aagaaagcaa
4261 gccaatttgg aaacttaggt tagtgacaaa attggccaga gagtggggt gatgatgacc
4321 aagaattaca agtagaatgg cagctggaat ttaaggaggg acaagaatca atggataagc
4381 gtgggtggag gaagatccaa acagaaaagt gcaagttat tccccatctt ccaagggttg
4441 aattctggag gaagaagaca cattcctagt tccccgtgaa cttcctttga cttattgtcc
4501 ccactaaaac aaaacaaaaa acttttaatg ccttccacat taattagatt ttcttgcagt
4561 tttttatgg cattttttta aagatgccct aagtgttgaa gaagagtttg caaatgcaac
```

Figure 10 (cont.)

```
    4621 aaaatattta attaccggtt gttaaaactg gtttagcaca atttatattt tccctctctt
    4681 gcctttctta tttgcaataa aaggtattga gccatttttt aaatgacatt tttgataaat
    4741 tatgtttgta ctagttgatg aaggagtttt ttttaacctg tttatataat tttgcagcag
    4801 aagccaaatt ttttgtatat taaagcacca aattcatgta cagcatgcat cacggatcaa
    4861 tagactgtac ttattttcca ataaaatttt caaacttttgt actgtta
```

SEQ ID NO:54
```
      1 ccctgcactc tcgctctcct gccccacccc gaggtaaagg gggcgactaa gagaagatgg
     61 tgttgctcac cgcggtcctc ctgctgctgg ccgcctatgc ggggccggcc cagagcctgg
    121 gctccttcgt gcactgcgag ccctgcgacg agaaagccct ctccatgtgc cccccagcc
    181 ccctgggctg cgagctggtc aaggagccgg gctgcggctg ctgcatgacc tgcgccctgg
    241 ccgaggggca gtcgtgcggc gtctacaccg agcgctgcgc ccaggggctg cgctgcctcc
    301 cccggcagga cgaggagaag ccgctgcacg ccctgctgca cggccgcggg gtttgcctca
    361 acgaaaagag ctaccgcgag caagtcaaga tcgagagaga ctcccgtgag cacgaggagc
    421 ccaccacctc tgagatggcc gaggagacct actcccccaa gatcttccgg cccaaacaca
    481 cccgcatctc cgagctgaag gctgaagcag tgaagaagga ccgcagaaag aagctgaccc
    541 agtccaagtt tgtcggggga gccgagaaca ctgcccaccc ccggatcatc tctgcacctg
    601 agatgagaca ggagtctgag cagggcccct gccgcagaca catggaggct tccctgcagg
    661 agctcaaagc cagcccacgc atggtgcccc gtgctgtgta cctgcccaat tgtgaccgca
    721 aaggattcta caagagaaag cagtgcaaac cttcccgtgg ccgcaaacgt ggcatctgct
    781 ggtgcgtgga caagtacggg atgaagctgc caggcatgga gtacgttgac ggggactttc
    841 agtgccacac cttcgacagc agcaacgttg agtgatgcgt ccccccccaa cctttccctc
    901 accccctccc accccagcc ccgactccag ccagcgcctc cctccacccc aggacgccac
    961 tcatttcatc tcatttaagg gaaaaatata tatctatcta tttg
```

SEQ ID NO:55
```
      1 cgcagcgggt cctctctatc tagctccagc ctctcgcctg cgccccactc cccgcgtccc
     61 gcgtcctagc cgaccatggc cgggccctg cgcgccccgc tgctcctgct ggccatcctg
    121 gccgtggccc tggccgtgag ccccgcggcc ggctccagtc ccggcaagcc gccgcgccta
    181 gtgggaggcc ccatggacgc cagcgtggag gaggagggtg tgcggcgtgc actggacttt
    241 gccgtcggcg agtacaacaa agccagcaac gacatgtacc acagccgcgc gctgcaggtg
    301 gtgcgcgccc gcaagcagat cgtagctggg gtgaactact tcttggacgt ggagctgggc
    361 cgaaccacgt gtaccaagac ccagcccaac ttggacaact gcccttcca tgaccagcca
    421 catctgaaaa ggaaagcatt ctgctctttc cagatctacg ctgtgccttg gcagggcaca
    481 atgaccttgt cgaaatccac ctgtcaggac gcctaggggt ctgtaccggg ctggcctgtg
    541 cctatcacct cttatgcaca cctcccaccc cctgtattcc caccctgga ctggtggccc
    601 ctgccttggg gaaggtctcc ccatgtgcct gcaccaggag acagacagag aaggcagcag
    661 gcggcctttg ttgctcagca aggggctctg ccctccctcc ttccttcttg cttctcatag
    721 ccccggtgtg cggtgcatac accccacct cctgcaataa aatagtagca tc
```

SEQ ID NO:56
```
      1 gaaagatgga tcactccagc tcaaagagaa catgtgggaa tgaaaggaca ggctgggccc
     61 aaaggagaaa agggtgatgc tggggaggag cttcctggcc ctcctgaacc ttctgggcct
    121 gttggaccca cggcaggagc agaagcagag ggctctggcc taggctgggg ctcggacgtc
    181 ggctctggct ctggtgacct ggtgggcagt gagcagctgc tgagaggtcc tccaggaccc
    241 ccagggccac ctggcttacc tgggattcca ggaaaaccag gaactgatgt tttcatggga
    301 cccccctggat ctcctggaga ggatggacct gctggtgaac ctgggccccc gggccctgag
    361 ggacagcctg gagttgatgg agccaccggc cttccgggga tgaaagggga gagggagca
    421 agagggccta atggctcagt tggtgaaaag ggtgaccctg gcaacagagg cttacctgga
    481 cccccgggga aaagggaca agctggccct cctggggtca tgggaccccc agggcctcct
    541 ggaccccctg ggccccagg cctggatgc acaatgggac ttggattcga ggataccgaa
    601 ggctctggaa gcacccagct attgaatgaa cccaaactct ccagaccaac ggctgcaatt
```

Figure 10 (cont.)

```
1921 tagttaaagt gaccatgaat tttgagccaa ataaagtgaa tattcaaaag aaaaactgcc
1981 atatggaggg aaaggaaaca gtatgcataa atgctacagt gtgttttgat gtgaaattaa
2041 agtctaaaga agacacgatt tatgaagctg atttgcagta ccgtgtcacc ctagattcac
2101 taagacaaat atcacgaagt tttttctctg gaactcaaga gagaaaggtt caaaggaaca
2161 tcacagttcg aaaatcagaa tgcactaagc actccttcta catgttgaca agcatgactt
2221 tcaggactct gtgagaataa cgttggactt taatcttacc gatccagaaa atgggcctgt
2281 tcttgatgat tctctaccaa actcagtaca tgaatatatt ccctttgcca aagattgtgg
2341 aaataaggaa aaatgtatct cagacctcag cctgcatgtc gccaccactg aaaaggacct
2401 gctgattgtc cgatcccaga atgataagtt caacgttagc ctcacagtca aaaatacaaa
2461 ggacagtgcc tataacacca ggacaatagt gcattattct ccaaatctag tttttttcagg
2521 aattgaggct atccaaaaag acagttgtga atctaatcat aatatcacat gtaaagttgg
2581 atatcccttc ctgagaagag gagagatggt aactttcaaa atattgtttc agtttaacac
2641 atcctatctc atggaaaatg tgaccattta tttaagtgca acaagtgaca gcgaagaacc
2701 tcctgaaacc ctttctgata atgtagtaaa catttctatc ccggtaaaat atgaagttgg
2761 actacagttt tacagctctg caagtgaata ccacatttca attgctgcca atgagacagt
2821 ccctgaagtt attaattcta ctgaggacat tggaaatgaa attaatatct tctacttgat
2881 tagaaaaagt ggatcttttc caatgccaga gcttaagctg tcaatttcat tccccaatat
2941 gacatcaaat ggttaccctg tgctgtaccc aactggattg tcatcttctg agaatgcaaa
3001 ctgcagaccc catatctttg aggatccttt cagtatcaac tctggaaaga aaatgactac
3061 atcaactgac catctcaaac gaggcacaat tctggactgc aatacatgta aatttgctac
3121 catcacatgt aatctcactt cttctgacat cagccaagtc aatgtttcgc ttatcttgtg
3181 gaaaccaact tttataaaat catatttttc cagcttaaat cttactataa ggggagaact
3241 tcggagtgaa aatgcatctc tggttttaag tagcagcaat caaaaaagag agcttgctat
3301 tcaaatatcc aaagatgggc taccgggcag agtgccatta tgggtcatcc tgctgagtgc
3361 ttttgccgga ttgttgctgt taatgctgct cattttagca ctgtggaaga ttggattctt
3421 caaaagacca ctgaaaaaga aatggagaa a.
```

SEQ ID NO:68

```
   1 gtatcactca gaatctggca gccagttccg tcctgacaga gttcacagca tatattggtg
  61 gattcttgtc catagtgcat ctgctttaag aattaacgaa agcagtgtca agacagtaag
 121 gattcaaacc atttgccaaa aatgagtcta agtgcattta ctctcttcct ggcattgatt
 181 ggtggtacca gtggccagta ctatgattat gatttttccc tatcaattta tgggcaatca
 241 tcaccaaact gtgcaccaga atgtaactgc cctgaaagct acccaagtgc catgtactgt
 301 gatgagctga aattgaaaag tgtaccaatg gtgcctcctg aatcaagta tctttacctt
 361 aggaataacc agattgacca tattgatgaa aaggcctttg agaatgtaac tgatctgcag
 421 tggctcattc tagatcacaa ccttctagaa aactccaaga taaagggag agttttctct
 481 aaattgaaac aactgaagaa gctgcatata aaccacaaca cctgacaga gtctgtgggc
 541 ccacttccca aatctctgga ggatctgcag cttactcata acaagatcac aaagctgggc
 601 tctttttgaag gattggtaaa cctgacctc atccatctcc agcacaatcg gctgaaagag
 661 gatgctgttt cagctgcttt taaaggtctt aaatcactcg aataccttga cttgagcttc
 721 aatcagatag ccagactgcc ttctggtctc cctgtctctc ttctaactct ctacttagac
 781 aacaataaga tcagcaacat ccctgatgag tatttcaagc gttttaatgc attgcagtat
 841 ctgcgtttat ctcacaacga actggctgat agtggaatac ctggaaattc tttcaatgtg
 901 tcatccctgg ttgagctgga tctgtcctat aacaagctta aaaacatacc aactgtcaat
 961 gaaaaccttg aaaactatta cctggaggtc aatcaacttg agaagtttga cataaagagc
1021 ttctgcaaga tcctggggcc attatcctac tccaagatca gcatttgcg tttggatggc
1081 aatcgcatct cagaaaccag tcttccaccg gatatgtatg aatgtctacg tgttgctaac
1141 gaagtcactc ttaattaata tctgtatcct ggaacaatat tttatggtta tgtttttctg
1201 tgtgtcagtt ttcatagtat ccatatttta ttactgttta ttacttccat gaatttaaaa
1261 atctgaggga aatgttttgt aaacatttat tttttttaaa gaaaagatga aaggcaggcc
1321 tatttcatca caagaacaca cacatataca cgaatagaca tcaaactcaa tgctttattt
1381 gtaaatttag tgtttttttta tttctactgt caaatgatgt gcaaaacctt ttactggttg
1441 catggaaatc agccaagttt tataatcctt aaatcttaat gttcctcaaa gcttggatta
1501 aatacatatg gatgttactc tcttgcacca aattatcttg atacattcaa atttgtctgg
```

Figure 10 (cont.)

```
1561 ttaaaaaata ggtggtagat attgaggcca agaatattgc aaaatacatg aagcttcatg
1621 cacttaaaga agtattttta gaataagaat ttgcatactt acctagtgaa acttttctag
1681 aattatttt cactctaagt catgtatgtt tctctttgat tatttgcatg ttatgtttaa
1741 taagctacta gcaaaataaa acatagcaaa tg
```

SEQ ID NO:69
```
   1 tggacagagg agcagtaaca atccccactc tccaattgtg gaagagttcc aagtcccata
  61 caacaaactc caggtgatct ttaagtcaga cttttccaat gaagagcgtt ttacggggtt
 121 tgctgcatac tatgttgcca cagacataaa tgaatgcaca gatttgtag atgtcccttg
 181 tagccacttc tgcaacaatt tcattggtgg ttacttctgc tcctgcccc cggaatattt
 241 cctccatgat gacatgaaga attgcggagt taattgcagt ggggatgtat tcactgcact
 301 gattggggag attgcaagtc ccaattatcc caaaccatat ccagagaact caaggtgtga
 361 ataccagatc cggttggaga aagggttcca agtggtggtg accttgcgga gagaagattt
 421 tgatgtggaa gcagctgact cagcgggaaa ctgccttgac agtttagttt ttgttgcagg
 481 agatcggcaa tttggtcctt actgtggtca tggattccct gggcctctaa atattgaaac
 541 caagagtaat gctcttgata tcatcttcca aactgatcta acagggcaaa aaaagggctg
 601 gaaacttcgc tatcatggag atccaatgcc ctgccctaag gaagacactc ccaattctgt
 661 ttgggagcct gcgaaggcaa aatatgtctt tagagatgtg gtgcagataa cctgtctgga
 721 tgggtttgaa gttgtggagg gacgtgttgg tgcaacatct ttctattcga cttgtcaaag
 781 caatggaaag tggagtaatt ccaaactgaa atgtcaacct gtggactgtg gcattcctga
 841 atccattgag aatggtaaag ttgaagaccc agagagcact ttgtttggtt ctgtcatccg
 901 ctacacttgt gaggagccat attactacat ggaaaatgga ggaggtgggg agtatcactg
 961 tgctggtaac gggagctggg tgaatgaggt gctgggcccg gagctgccga aatgtgttcc
1021 aggtctgtgg agtccccaga gaacccttg aagaaaaaca gaggataatt ggaggatccg
1081 atgcagatat taaaaacttc ccctggcaag tcttctttga caacccatgg gctggtggag
1141 cgctcattaa tgagtactgg gtgctgacgg ctgctcatgt tgtggaggga aacagggagc
1201 caacaatgta tgttgggtcc acctcagtgc agacctcacg gctggcaaaa tccaagatgc
1261 tcactcctga gcatgtgttt attcatccgg gatggaagct gctggaagtc ccagaaggac
1321 gaaccaattt tgataatgac attgcactgg tgcggctgaa agacccagtg aaaatgggac
1381 ccacgtctc tccatctgc ctaccaggca cctcttccga ctacaacctc atggatgggg
1441 acctgggact gatctcaggc tggggccgaa cagagaagag agatcgtgct gttcgcctca
1501 aggcggcaag gttacctgta gctcctttaa gaaaatgcaa agaagtgaaa gtggagaaac
1561 ccacagcaga tgcagaggcc tatgtttca ctcctaacat gatctgtgct ggaggagaga
1621 agggcatgga tagctgtaaa ggggacagtg gtgggccctt tgctgtacag gatcccaatg
1681 acaagaccaa attctacgca gctggcctgg tgtcctgggg gccccagtgt gggacctatg
1741 ggctctacac acgggtaaag aactatgttg actggataat gaagactatg caggaaaata
1801 gcacccccg tgaggactaa tccagataca tcccaccagc ctctccaagg gtggtgacca
1861 atgcattacc ttctgttcct tatgatattc tcattatttc atcatgactg aaagaagaca
1921 cgagcgaatg atttaaatag aacttgattg ttgagacgcc ttgctagagg tagagtttga
1981 tcatagaatt gtgctggtca tacatttgtg gtctgactcc tggggtcct ttcccggag
2041 tacctattgt agataacact atgggtgggg cactcctttc ttgcactatt ccacagggat
2101 accttaattc tttgtttcct ctttacctgt tcaaaattcc atttacttga tcattctcag
2161 tatccactgt ctatgtacaa taaggatgt ttataagc
```

SEQ ID NO:70
```
   1 aaactctgat ctggggagga accaggacta catagatcaa ggcagttttc ttctttgaga
  61 aactatccca gatatcatca tagagtcttc tgctcttcct caactaccaa agaaaaacat
 121 cagcgaagca gcaggccatg caccccccaa aaactccatc tggggctctt catagaaaaa
 181 ggaaaatggc agcctggccc ttctccaggc tgtggaaagt ctctgatcca attctcttcc
 241 aaatgacctt gatcgctgct ctgttgcctg ctgttcttgg caattgtggt cctccaccca
 301 ctttatcatt tgctgccccg atggatatta cgttgactga gacacgcttc aaaactggaa
 361 ctactctgaa atacacctgc tccctggct acgtcagatc ccattcaact cagacgctta
 421 cctgtaattc tgatggcgaa tgggtgtata acaccttctg tatctacaaa cgatgcagac
 481 acccaggaga gttacgtaat gggcaagtag agattaagac agatttatct tttggatcac
```

Figure 10 (cont.)

```
 541 aaatagaatt cagctgttca gaaggatttt tcttaattgg ctcaaccact agtcgttgtg
 601 aagtccaaga tagaggagtt ggctggagtc atcctctccc acaatgtgaa attgtcaagt
 661 gtaagcctcc tccagacatc aggaatggaa ggcacagcgg tgaagaaaat ttctacgcat
 721 acggcttttc tgtcacctac agctgtgacc cccgcttctc actcttgggc catgcctcca
 781 tttcttgcac tgtggagaat gaaacaatag gtgtttggag accaagccct cctacctgtg
 841 aaaaaatcac ctgtcgcaag ccagatgttt cacatgggga aatggtctct ggatttggac
 901 ccatctataa ttacaaagac actattgtgt ttaagtgcca aaaaggtttt gttctcagag
 961 gcagcagtgt aattcattgt gatgctgata gcaaatggaa tccttctcct cctgcttgtg
1021 agcccaatag ttgtattaat ttaccagaca ttccacatgc ttcctgggaa acatatccta
1081 ggccgacaaa agaggatgtg tatgttgttg ggactgtgtt aaggtaccgc tgtcatcctg
1141 gctacaaacc cactacagat gagcctacga ctgtgatttg tcagaaaaat ttgagatgga
1201 ccccatacca aggatgtgag gcgttatgtt gccctgaacc aaagctaaat aatggtgaaa
1261 tcactcaaca caggaaaagt cgtcctgcca atcactgtgt ttatttctat ggagatgaga
1321 tttcattttc atgtcatgag accagtaggt tttcagctat atgccaagga gatggcacgt
1381 ggagtccccg aacaccatca tgtggagaca tttgcaattt tcctcctaaa attgcccatg
1441 ggcattataa acaatctagt tcatacagct ttttcaaaga agagattata tatgaatgtg
1501 ataaaggcta cattctggtc ggacaggcga aactctcctg cagttattca cactggtcag
1561 ctccagcccc tcaatgtaaa gctctgtgtc ggaaaccaga attagtgaat ggaaggttgt
1621 ctgtggataa ggatcagtat gttgagcctg aaaatgtcac catccaatgt gattctggct
1681 atggtgtggt tggtccccaa agtatcactt gctctgggaa cagaacctgg tacccagagg
1741 tgcccaagtg tgagtgggag accccccgaag gctgtgaaca agtgctcaca ggcaaaagac
1801 tcatgcagtg tctcccaaac ccagaggatg tgaaaatggc cctggaggta tataagctgt
1861 ctctggaaat tgaacaactg gaactacaga gagacagcgc aagacaatcc actttggata
1921 aagaactata attttttctca aaagaaggag gaaaaggtgt cttgctggct tgcctcttgc
1981 aattcaatac agatcagttt agcaaatcta ctgtcaattt ggcagtgata ttcatcataa
2041 taaatatcta gaaatgataa tttgctaaag tttagtgctt tgagattgtg aaattattaa
2101 tcatcctctg tgtggctcat gttttgctt ttcaacacac aaagcacaaa tttttttcg
2161 attaaaaatg tatgtat
```

SEQ Id NO:71
```
  1 gccctgctgg ccctgctggt gctcccnnnn nnnnnnnnnn nnnnnnnnnn nnnggtcctc
 61 aaggcccacg tggtgacaaa ggtgaaacag gtgaacgtgg agctgctggc atcaaaggac
121 atcgaggatt ccctggtaat ccaggtgccc caggttctcc agggccctgc tggtcagcag
181 ggtgcaatcg gcagtccagg acctgcaggc cccagaggac ctgttggacc cagtggacct
241 cctggcaaag atggaaccag tggacatcca ggtcccattg gaccaccagg gcctcgaggt
301 aacagaggtg aaagaggatc tgagggctcc ccaggccacc cagggcaacc aggccctcct
361 ggacctcctg gtgcccctgg tccttgc
```

SEQ Id NO:72
```
  1 gggcgcgggg agagggcgcg ggagcggctc gcgcggcagg taccatgcgg acgcgcgagc
 61 ccggcgaggg ccccggcagg cccggtcccr gctcggggc gcgctgagac ggcgggtgag
121 ctccacgaga gcgccgtcgc cacttcgggc caactttgcg attcccgaca gttaagcaat
181 ggggagacat ttggctttgc tcctgcttct gctccttctc ttccaacatt ttggagacag
241 tgatggcagc caacgacttg aacagactcc tctgcagttt acacacctcg agtacaacgt
301 caccgtgcag gagaactctg cagctaagac ttatgtgggg catcctgtca agatgggtgt
361 ttacattaca catccagcgt gggaagtaag gtacaaaatt gtttccggag acagtgaaaa
421 cctgttcaaa gctgaagagt acattctcgg agactttgc tttctaagaa taaggaccaa
481 aggaggaaat acagctattc ttaatagaga agtgaaggat cactacacat tgatagtgaa
541 agcacttgaa aaaaatacta atgtggaggc gcgaacaaag gtcagggtgc aggtgctgga
601 tacaaatgac ttgagaccgt tattctcacc cacctcatac agcgtttctt tacctgaaaa
661 cacagctata aggaccagta tcgcaagagt cagcgccacg gatcagaca taggaaccaa
721 cggggaattt tactacagtt ttaaagatcg aacagatatg tttgctattc acccaaccag
781 tggtgtgata tgttaactg gtagacttga ttacctagag accaagctct atgagatgga
841 aatcctcgct gcggaccgtg gcatgaagtt gtatgggagc agtggcatca gcagcatggc
```

Figure 10 (cont.)

```
 901 caagctaacg gtgcacatcg aacaggccaa tgaatgtgct ccggtgataa cagcagtgac
 961 attgtcacca tcagaactgg acagggaccc agcatatgca attgtgacag tggatgactg
1021 cgatcagggt gccaatggtg acatagcatc tttaagcatc gtggcaggtg accttctcca
1081 gcagtttaga acagtgaggt cctttccagg gagtaaggag tataaagtca aagccatcgg
1141 tggcattgat tgggacagtc atcctttcgg ctacaatctc acactacagg ctaaagataa
1201 aggaactccg ccccagttct cttctgttaa agtcattcac gtgacttctc cacagttcaa
1261 agccgggcca gtcaagtttg aaaaggatgt ttacagagca gaaataagtg aatttgctcc
1321 tcccaacaca cctgtggtca tggtaaaggc cattcctgct tattcccatt tgaggtatgt
1381 ttttaaaagt acacctggaa aagctaaatt cagtttaaat tacaacactg gtctcatttc
1441 tattttagaa ccagttaaaa gacagcaggc agcccatttt gaacttgaag taacaacaag
1501 tgacagaaaa gcgtccacca aggtcttggt gaaagtctta ggtgcaaata gcaatccccc
1561 tgaatttacc cagacagcgt acaaagctgc ttttgatgag aacgtgccca ttggtactac
1621 tgtcatgagc ctgagtgccg tagaccctga tgagggtgag aacgggtacg tgacatacag
1681 tatcgcaaat ttaaatcatg tgccgtttgc gattgaccat ttcactggtg ccgtgagtac
1741 gtcagaaaac ctggactacg aactgatgcc tcgggtttat actctgagga ttcgtgcatc
1801 agactggggc ttgccgtacc gccgggaagt cgaagtcctt gctacaatta ctctcaataa
1861 cttgaatgac aacacacctt tgtttgagaa aataaattgt gaagggacaa ttcccagaga
1921 tctaggcgtg ggagagcaaa taaccactgt ttctgctatt gatgcagatg aacttcagtt
1981 ggtacagtat cagattgaag ctggaaatga actggatttc tttagtttaa accccaactc
2041 gggggtattg tcattaaagc gatcgctaat ggatggctta ggtgcaaagg tgtctttcac
2101 agtctgagaa tcacagctac agatggagaa aatttttgcca caccattata tatcaacata
2161 acagtggctg ccagtcacaa gctggtaaac ttgcagtgtg aagagactgg tgttgccaaa
2221 atgctggcag agaagctcct gcaggcaaat aaattacaca accagggaga ggtggaggat
2281 attttcttcg attctcactc tgtcaatgct cacataccgc agtttagaag cactcttccg
2341 actggtattc aggtaaagga aaaccagcct gtgggttcca gtgtaatttt catgaactcc
2401 actgaccttg acactggctt caatggaaaa ctggtctatg ctgtttctgg aggaaatgag
2461 gatagttgct tcatgattga tatggaaaca ggaatgctga aaattttatc tcctcttgac
2521 cgtgaaacaa cagacaaata caccctgaat attaccgtct atgaccttgg gataccccag
2581 aaggctgcgt ggcgtcttct acatgtcgtg gttgtcgatg ccaatgataa tccacccgag
2641 tttttacagg agagctattt tgtggaagtg agtgaagaca aggaggtaca tagtgaaatc
2701 atccaggttg aagccacaga taaagacctg ggcccaacg gacacgtgac gtactcaatt
2761 gttacagaca cagacacatt ttcaattgac agcgtgacgg tgttgttaa catcgcacgc
2821 cctctggatc gagagctgca gcatgagcac tccttaaaga ttgaggccag ggaccaagcc
2881 agagaagagc ctcagctgtt ctccactgtc gttgtgaaag tatcactaga agatgttaat
2941 gacaacccac ctacatttat tccacctaat tatcgtgtga aagtccgaga ggatcttcca
3001 gaaggaaccg tcatcatgtg gttagaagcc cacgatcctg atttaggtca gtctggtcag
3061 gtcagcacac agccttctgg accacggaga aggaaacttc gatgtggata aactcagtgg
3121 agcagttagg atcgtccagc agttggactt tgagaagaag caagtgtata atctcactgt
3181 gagggccaaa gacaagggaa agccagtttc tctgtcttct acttgctatg ttgaagttga
3241 ggtggttgat gtgaatgaga acctgcaccc acccgtgttt tccagctttg tggaaaaggg
3301 gacagtgaaa gaagatgcac ctgttggttc attggtaatg acggtgtcgg ctcatgatga
3361 ggacgccaga agagatgggg agatccgata ctccattaga gatggctctg gcgttggtgt
3421 tttcaaaata ggtgaagaga caggtgtcat agagacgtca gatcgactgg accgtgaatc
3481 gacctcccat tattggctaa cagtctttgc aaccgatcag ggtgtcgtgc ctctttcatc
3541 gttcatagag atctacatag aggttgagga tgtcaatgac aatgcaccac agacatcaga
3601 gcctgtttat tacccagaaa tcatggaaaa ttctcctaaa gatgtatctg tggtccagat
3661 cgaggcattt gatccagatt cgagctctaa tgacaagctc atgtacaaaa ttacaagtgg
3721 aaatccacaa ggattctttt caatacatcc taaaacaggt ctcatcacaa ctacgtcaag
3781 gaagctagac cgagaacagc aagatgaaca catattagag gttactgtga cagacaatgg
3841 tagtccccccc aaatcaacca ttgcaagagt cattgtgaaa atccttgatg aaaatgacaa
3901 caaacctcag tttctgcaaa agttctacaa aatcagactc cctgagcggg aaaagccaga
3961 ccgagaaaga aatgccagac gggagccgct ctatcgcgtc atagccaccg acaaggatga
4021 gggcccccaat gcagaaatct cctacagcat cgaagacggg aatgagcatg gcaaattttt
4081 catcgaaccg aaaactggag tggtttcgtc caagaggttt tcagcagctg gagaatatga
```

Figure 10 (cont.)

```
4141 tattctttca attaaggcag ttgacaatgg tcgccctcaa aagtcatcaa ccaccagact
4201 ccatattgaa tggatctcca agcccaaacc gtccctggag cccatttcat ttgaagaatc
4261 atttttacc tttactgtga tggaaagtga ccccgttgct cacatgattg gagtaatatc
4321 tgtggagcct cctggcatac cctttggtt tgacatcact ggtggcaact acgacagtca
4381 cttcgatgtg gacaagggaa ctggaaccat cattgttgcc aaacctcttg atgcagaaca
4441 gaagtcaaac tacaacctca cagtcgaggc tacagatgga accaccacta tcctcactca
4501 ggtattcatc aaagtaatag acacaaatga ccatcgtcct cagtttcta catcaaagta
4561 tgaagttgtt attcctgaag atacagcgcc agaaacagaa attttgcaaa tcagtgctgt
4621 ggatcaggat gagaaaaaca aactaatcta cactctgcag agcagtagag atccactgag
4681 tctcaagaaa tttcgtcttg atcctgcaac cggctctctc tatacttctg agaaactgga
4741 tcatgaagct gttcaccagc acaccctcac ggtcatggta cgagatcaag atgtgcctgt
4801 aaaacgcaac tttgcaagga ttgtggtcaa tgtcagcgac acgaatgacc acgcccgtg
4861 gttcaccgct tcctcctaca aagggcgggt ttatgaatcg gcagccgttg gctcagttgt
4921 gttgcaggtg acggctctgg acaaggacaa agggaaaaat gctgaagtgc tgtactcgat
4981 cgagtcagnn nnnnnnngaa atattggaaa ttcttttatg attgatcctg tcttgggctc
5041 tattaaaact gccaagaat tagatcgaag taaccaagcg gagtatgatt taatggtaaa
5101 agctacagat aagggcagtc caccaatgag tgaaataact tctgtgcgta tctttgtcac
5161 aattgctgac aacgcctctc cgaagtttac atcaaaagaa tattctgttg aacttagtga
5221 aactgtcagc attgggagtt tcgttgggat ggttacagcc catagtcaat catcagtggt
5281 gtatgaaata aaagatggaa ataccaggtga tgctttgat attaatccac attctggaac
5341 tatcatcact cagaaagccc tggactttga aactttgccc atttacacat tgataataca
5401 aggaactaac atggctggtt tgtccactaa tacaacggtt ctagttcact tgcaggatga
5461 gaatgacaac gcgccagttt ttatgcaggc agaatataca ggactcatta gtgaatcagc
5521 ctcaattaac agcgtggtcc taacagacag gaatgtccca ctggtgattc gagcagctga
5581 tgctgataaa gactcaaatg ctttgcttgt atatcacatt gttgaaccat ctgtacacac
5641 atattttgct attgattcta gcactggtgc tattcataca gtactaagtc tggactatga
5701 agaaacaagt atttttcact ttaccgtcca agtgcatgac atgggaaccc cacgttatt
5761 tgctgagtat gcagcgaatg taacagtaca tgtaattgac attaatgact gccccctgt
5821 gtttgccaag ccattatatg aagcatctct tttgttacca acatacaaag gagtaaagt
5881 catcacagta aatgctacag atgctgattc aagtgcattc tcacagttga tttactccat
5941 caccgaaggc aacatcgggg agaagttttc tatggactac aagactggtg ctctcactgt
6001 ccaaaacaca actcagttaa gaagccgcta cgagctaacc gttagagctt ccgatggcag
6061 atttgccggc cttacctctg tcaaaattaa tgtgaaagaa agcaaagaaa gtcacctaaa
6121 gtttacccag gatgtctact ctgcggtagt gaaagagaat tccaccgagg ccgaaacatt
6181 agctgtcatt actgctattg ggaatccaat caatgagcct ttgttttatc acatcctcaa
6241 cccagatcgc agatttaaaa taagccgcac ttcaggagtt ctgtcaacca ctggcacgcc
6301 cttcgatcgt gagcagcagg aggcgtttga tgtggttgta gaagtgacag aggaacataa
6361 gccttctgca gtggcccacg ttgtcgtgaa ggtcattgta gaagaccaaa atgataatgc
6421 gccggtgttt gtcaaccttc cctactacgc cgttgttaaa gtggacactg aggtgggcca
6481 tgtcattcgc tatgtcactg ctgtagacag agacagtggc agaaacgggg aagtgcatta
6541 ctacctcaag gaacatcatg aacactttca aattggaccc ttgggtgaaa tttcactgaa
6601 aaagcaattt gagcttgaca ccttaaataa agaatatctt gttacagtgg ttgcaaaaga
6661 tggagggaac ccggccttt cagcggaagt tatcgttccg atcactgtca tgaataaagc
6721 catgcctgtg tttgaaaaac ctttctacag tgcagagatt gcagagagca tccaggtgca
6781 cagccctgtg gtccacgtgc aggctaacag cccggaaggc tgaaagtgt tctacagcat
6841 cacagacgga gacccttca gccagttcac tattaacttc aatactggag ttatcaatgt
6901 catagctcct ctggactttg aggcccaccc ggcatataag ctgagcatac gcgcaactga
6961 ctccttgacg ggcgctcatg ctgaagtatt tgtggacatc atagtagacg acatcaatga
7021 taaccctcct gtgtttgctc agcagtctta tgcggtgacc ctgtctgagg catctgtaat
7081 tggaacgtct gttgttcaag ttagagccac cgattctgat tcagaaccaa atagaggaat
7141 ctcataccag atgtttggga atcacagcaa gagtcatgat catttcatg tagacagcag
7201 cactggcctc atctcactac tcagaaccct ggattacgag cagtccggc agcacacgat
7261 ttttgtgagg gcagttgatg gtggtatgcc cacgctgagc agtgatgtga ttgtcacggt
7321 ggacgttacc gacctcaatg ataatccacc actctttgaa caacagattt atgaagccag
```

Figure 10 (cont.)

```
 7381 aattagcgag cacgcccctc atgggcattt cgtgacctgt gtaaaagcct atgatgcaga
 7441 cagttcagac atagacaagt tgcagtattc cattctgtct ggcaatgatc ataaacattt
 7501 tgtcattgac agtgcaacag ggattatcac cctctcaaac ctgcaccggc acgccctgaa
 7561 gccattttac agtcttaacc tgtcagtgtc tgatggagtt tttagaagtt ccacccaggt
 7621 tcatgtaact gtaattggag gcaatttgca cagtcctgct ttccttcaga acgaatatga
 7681 agtggaacta gctgaaaacg ctccoctaca taccctggtg atggaggtga aaactacgga
 7741 tggggattct ggtatttatg gtcacgttac ttaccatatt gtaaatgact ttgccaaaga
 7801 cagattttac ataaatgaga gaggacagat atttactttg gaaaacttg atcgagaaac
 7861 cccggcggag aaagtgatct cagtccgttt aatggctaag gatgctggag gaaaagttgc
 7921 tttctgcacc gtgaatgtca tccttacaga tgacaatgac aatgcaccac aatttcgagc
 7981 aaccaaatac gaagtgaata tcgggtccag tgctgctaaa gggacttcag tcgttaaagt
 8041 tcttgcaagt gatgccgatg agggctccaa tgccgacatc acctatgcca ttgaagcaga
 8101 ctctgaaagt gtaaagaga atttggaaat taacaaactg tccggcgtaa tcactacaaa
 8161 ggagagcctc attggcttgg aaaatgaatt cttcactttc tttgttagag ctgtggataa
 8221 tgggtctcca tcaaaagaat ctgttgttct tgtctatgtt aaaatccttc caccggaaat
 8281 gcagcttcca aaattttcag aaccttccta tacctttaca gtgtcagagg acgtgcctat
 8341 tggaacagag atagatctca tccgagcaga acatagtggg actgttcttt acagcctggt
 8401 caaagggaat actccagaaa gcaataggga tgagtccttt gtgattgaca gacagagcgg
 8461 gagactgaag ttggagaaga gtcttgatca tgagacaact aagtggtatc agttttccat
 8521 actggccagg tgcactcaag atgaccatga gatggtggct tctgtagatg ttagtatcca
 8581 agtgaaagat gcaaatgaca acagcccggt ctttgaatct agtccatatg aggcattcat
 8641 tgttgaaaac ctgccagggg gaagtagagt aattcagatc agggcatctg atgctgactc
 8701 aggaaccaac ggccaagtta tgtatagcct ggatcagtca caaagtgtgg aagtcattga
 8761 atcctttgcc attaacatgg aaacaggctg gattacaact ttaaaggaac ttgaccatga
 8821 aaagagagac aattaccaga ttaaagtggt tgcatcagat catggtgaaa agatccagct
 8881 atcctccaca gccattgtgg atgttaccgt caccgatgtc aacgatagtc caccacgatt
 8941 cacggccgag atctataaag ggactgtgag tgaggatgac ccccaaggtg gggtgattgc
 9001 catcttaagt accacggatg ctgattctga agagatcaac agacaagtta catatttcat
 9061 aacaggaggg gatcctttag gacagtttgc cgttgaaact atacagaatg aatggaaggt
 9121 atatgtgaag aaacctctag acagggaaaa aagggacaat taccttctta ctatcacggc
 9181 aactgatggc accttctcat caaaagcgat agttgaagtg aaagttctgg atgcaaatga
 9241 caacagtcca gtttgtgaaa agactttata ttcagacact attcctgaag acgtccttcc
 9301 tggaaaattg atcatgcaga tctctgctac agacgcagac atccgctcta acgctgaaat
 9361 tacttacacg ttattgggtt caggtgcaga aaaattcaaa ctaaatccag acacaggtga
 9421 actgaaaacg tcaaccccc ttgatcgtga ggagcaagct gtttatcatc ttctcgtcag
 9481 ggccacagat ggaggaggaa gattctgcca agccagtatt gtgctcacgc tagaagatgt
 9541 gaacgataac gcccccgaat tctctgccga tccttatgcc atcaccgtgt ttgaaaacac
 9601 agagccggga acgctgctga caagagtgca ggccacagat gccgacgcag gattaaatcg
 9661 gaagatttta tactcactga ttgactctgc tgatgggcag ttctccatta acgaattatc
 9721 tggaattatt cagttagaaa accctttgga cagagaactc caggcagtat acaccctctc
 9781 tttgaaagct gtggatcaag gcttgccaag gaggctgact gccactggca ctgtgattgt
 9841 atcagttctt gacataaatg caaccccccc tgtgtttgag taccgtgaat atggtgccac
 9901 cgtgtctgag gacattcttg tggaactgaa agttcttcaa gtgtatgcag caagtcggga
 9961 tattgaagca aatgcagaaa tcacctactc aataataagt ggaaatgaac atgggaaatt
10021 cagcatagat tctaaaacag nnnnnnnnnn nnnnnnnnnn nnnnnnnnnn nnnnnnnnnn
10081 nnnnnnnnnn nnnnnnnnnn nnnnnnnnnn nnnnnnnnnn nnnnnnnnnn nnnnnnnnnn
10141 nnnnnnnnnn nnnnnnnnnn nnnnnnnnnn nnnnnnnnnn nnnnnnnnnn nnnnnnnnnn
10201 nnnnnnnnnn nnnnnnnnnn nnnnnnnnnn nnnnnnnnnn nnnnnnnnnn nnnnnnnnnn
10261 nnnnnnnnnn nnnnnnnnnn nnnnnnnnnn nnnnnnnnnn nnnnnnnnnn nnnnnnnnnn
10321 nnnnnnnnnn nnnnnnnnnn nnnnnnnnnn nnnnnnnnnn nnnnnnnnnn nnnnnnnnnn
10381 nnnnnnnnnn nnnnnnnnnn nnnnnnnnnn nnnnnnnnnn nnnnnnnnnn nnnnnnnnnn
10441 nnnnnnnnnn nnnnnnnnnn nnnnnnnnnn nnnnnnnnnn nnnnnnnnnn nnnnnnnnnn
10501 nnnnnnnnnn nnnnnnnnnn nnnnnnnnnn nnnnnnngaa aataagccag tgggcttcag
10561 cgtgctgcag ctggtagtaa cagatgagga ttcttcccat aacggtccac ccttcttctt
```

Figure 10 (cont.)

```
10621 tactattgta actggaaatg atgagaaggc ttttgaagtt aacccgcaag gagtcctcct
10681 gacatcatct gccatcaaga ggaaggagaa agatcattac ttactgcagg tgaaggtggc
10741 agataatgga aagcctcagt tgtcatcttt gacatacatt gacattaggg taattgagga
10801 gagcatctat ccgcctgcga ttttgcccct ggagattttc atcacctctt ctggagaaga
10861 atactcaggt ggcgtcattg ggaagatcca tgccacagac caggacgtgt atgatactct
10921 aacctacagt ctcgaccctc agatggacaa cctgttctct gtttccagca caggggcaa
10981 gctgatagca cacaaaaagc tagacatagg gcaatacctt ctcaatgtca gcgtaacaga
11041 tgggaagttc acgacggtgg ccgacatcac agtgcatatc agacaagtca cacaggagat
11101 gttgaaccac accatcgcga tccgctttgc caacctcact ccggaagaat tcgttggtga
11161 ctactggcgc aacttccagc gagctttacg gaacatcctg ggtgtgagga ggaacgacat
11221 acagattgtt agtttgcagt cctctgaacc tcacccacat ctggacgtct tacttttgt
11281 agagaaacca ggtagtgctc agatctcaac aaaacaactt ctgcacaaga ttaactcttc
11341 cgtgactgac attgaggaaa tcattggagt taggatactg aatgtattcc agaaactctg
11401 cgcgggactg gactgcccct ggaagttctg cgatgaaaag gtgtctgtgg atgaaagtgt
11461 gatgtcaaca cacagcacag ccagactgag ttttgtgact ccccgccacc acagggcagc
11521 ggtgtgtctc tgcaaagagg gaaggtgccc acctgtccac catggctgtg aagatgatcc
11581 gtgccctgag ggatccgaat gtgtgtctga tccctgggag gagaaacaca cctgtgtctg
11641 tcccagcggc aggtttggtc agtgcccagg gagttcatct atgacactga ctggaaacag
11701 ctacgtgaaa taccgtctga cggaaatgaa aaacaaatta gagatgaaac tgaccatgag
11761 gctcagaaca tattccacgc atgcggttgt catgtatgct cgaggaactg actatagcat
11821 cttggagatt catcatggaa ggtgcagtca annnnnnnn nnnnnnnn nnnnnnnn
11881 nnnnnnnnn nnncattcag gtcaatgatg ggcagtggca cgcagtggcc ctggaagtga
11941 atggaaacta tgctcgcttg gttctagacc aagttcatac tgcatcgggc acagcccag
12001 ggactctgaa aaccctgaac ctggataact atgtgttttt tggtggccac atccgtcagc
12061 agggaacaag gcatggaaga agtcctcaag ttggtaatgg tttcagggggt tgtatggact
12121 ccatttattt gaatgggcag gagctccctt taaacagcaa accagaagc tatgcacaca
12181 tcgaagagtc ggtggatgta tctccaggct gcttcctgac ggccacggaa gactgcgcca
12241 gcaaccctg ccagaatgga ggcgtttgca atccgtcacc tgctggaggt tattactgca
12301 aatgcagtgc cttgtacata gggacccact gtgagataag cgtcaatccg tgttcctcca
12361 agccatgcct ctatggggc acgtgtgttg tcgacaacgg aggctttgtt tgccagtgta
12421 gaggattata tactggtcag aggtgtcagc ttagtccata ctgcaaagat gaaccctgta
12481 agaatgcgg aacatgcttt gacagtttgg atggcgccgt ttgtcagtgt gattcgggtt
12541 ttaggggaga aaggtgtcag agtgatatcg acgagtgctc tggaaaccct tgcctgcacg
12601 gggccctctg tgagaacacg cacggctcct atcactgcaa ctgcagccac gagtacaggg
12661 gacgtcactg cgaggatgct gcgcccaacc agtatgtgtc cacgccgtgg aacattgggt
12721 tggcggaagg aattggaatc gttgtgtttg ttgcagggat attttactg gtggtggtgt
12781 ttgttctctg ccgtaagatg attagtcgga aaaagaagca tcaggctgaa cctaaagaca
12841 agcacctggg acccgctacg gctttcttgc aaagaccgta ttttgattcc aagctaaata
12901 agaacatta ctcagacata ccaccccagg tgcctgtccg gcctatttcc tacacccga
12961 gtattccaag tgactcaaga aacaatctgg accgaaattc cttcgaagga tctgctatcc
13021 cagagcatcc cgaattcagc acttttaacc ccgagtctgt gcacgggcac cgaaaagcag
13081 tggcggtctg cagcgtggcg ccaaacctgc ctcccccacc cccttcaaac tcccttctg
13141 acagcgactc catccagaag cctagctggg acttttgacta tgacacaaaa gtggtggatc
13201 ttgatccctg tctttccaag aagcctctag aggaaaagcc ttcccagcca tacagtgccc
13261 gggaaagcct gtctgaagtg cagtctctga gtccttcca gtccgaatcg tgcgatgaca
13321 atgggtatca ctgggataca tcagattgga tgccaagcgt tcctctgccg gacatacaag
13381 agttccccaa ctatgaggtg attgatgagc agacacccct gtactcagca gatccaaacg
13441 ccatcgatac ggactattac cctggaggct acgacatcga aagtgatttt cctccacccc
13501 cagaagactt ccccgcagct gatgagctac caccgttacc gcccgaattc agcaatcagt
13561 ttgaatccat ccaccctcct agagacatgc ctgccgcggg tagcttgggt tcttcatcaa
13621 gaaaccggca gaggttcaac ttgaatcagt atttgcccaa ttttatccc ctcgatatgt
13681 ctgaacctca aacaaaaggc actggtgaga atagtacttg tagagaaccc atgccctt
13741 acccgccagg gtatcaaaga cacttcgagg cgccgctgt cgagagcatg ccatgtctg
13801 tgtacgcctc caccgcctcc tgctctgacg tgtcagcctg ctgcgaagtg gagtccgagg
```

Figure 10 (cont.)

```
13861 tcatgatgag tgactatgag agcggggacg acggccactt cgaagaggtg acgatcccgc
13921 ccctggattc ccagcagcac acggaagtct gactctcaac tcccccaaa gtgcctgact
13981 ttagtgaacc tagaggtgat gtgagtaatc cgcgctgttc tttgcagcag tgcttccaag
14041 ctttttttgg tgagccgaat gggcatggct gcgctggatc ctgcgcctct ggacgtgcta
14101 gccatttcca gtgtcccaac tactgtcatc gtgaggtttt catcggctgt gccatttccc
14161 aacgtctttt gggatttaca tctgtctgtg ttaaaataat caaacgaaaa atcagtcctg
14221 tgttgtcagc atgattcatg tatttatata gatttgatta ttttaatttt cctgtctctt
14281 tttttgtaa attttatgta cagatttgat ttttcatagt tttaactaga tttccaagat
14341 attttgtgca tttgtttcaa ctgaattttg gtggtgtcag tgccattatc tagcaccctg
14401 atttttttt ttttactata accagggttt cattctgtct ttttccactg aagtgtgaca
14461 ttttgttagt acatttcagt gtagtcattc atttctagct gtacatagga tgaaggagag
14521 atcagataca tgaacatgtc ttacatgggt tgctgtattt agaattataa acatttttca
14581 ttattggaaa gtgtaacggg gaccttctgc atacctgttt agaaccaaaa ccaccatgac
14641 acagttttta tagtgtctgt atatttgtga tgcaatggtc ttgtaaaggt ttttaatgaa
14701 aactaccatt agccagtctt cttactgac aataaattat taataaaat
```

SEQ Id NO:73

```
   1 gattttaggt gatgggcaag tcagaaagtc agatggatat aactgatatc aacactccaa
  61 agccaaagaa gaaacagcga tggactccac tggagatcag cctctcggtc cttgtcctgc
 121 tcctcaccat catagctgtg acaatgatcg cactctatgc aacctacgat gatggtattt
 181 gcaagtcatc agactgcata aaatcagctg ctcgactgat ccaaaacatg gatgccacca
 241 ctgagccttg tacagacttt ttcaaatatg cttgcggagg ctggttgaaa cgtaatgtca
 301 ttcccgagac cagctcccgt tacggcaact ttgacatttt aagagatgaa ctagaagtcg
 361 ttttgaaaga tgtccttcaa gaacccaaaa ctgaagatat agtagcagtg cagaaagcaa
 421 aagcattgta caggtcttgt ataaatgaat ctgctattga tagcagaggt ggagaacctc
 481 tactcaaact gttaccagac atatatgggt ggccagtagc aacagaaaac tgggagcaaa
 541 aatatggtgc ttcttggaca gctgaaaaag ctattgcaca actgaattct aaatatggga
 601 aaaaagtcct tattaatttg tttgttggca ctgatgataa gaattctgtg aatcatgtaa
 661 ttcatattga ccaacctcga cttggcctcc cttctagaga ttactatgaa tgcactggaa
 721 tctataaaga ggcttgtaca gcatatgtgg attttatgat ttctgtggcc agattgattc
 781 gtcaggaaga aagattgccc atcgatgaaa accagcttgc tttggaaatg aataaagtta
 841 tggaattgga aaaagaaatt gccaatgcta cggctaaacc tgaagatcga aatgatccaa
 901 tgcttctgta taacaagatg acattggccc agatccaaaa taacttttca ctagagatca
 961 atgggaagcc attcagctgg ttgaatttca caaatgaaat catgtcaact gtgaatatta
1021 gtattacaaa tgaggaagat gtggttgttt atgctccaga atatttaacc aaacttaagc
1081 ccattcttac caaatattct gccagagatc ttcaaaattt aatgtcctgg agattcataa
1141 tggatcttgt aagcagcctc agccgaacct acaaggagtc cagaaatgct ttccgcaagg
1201 cccttttatgg tacaacctca gaaacagcaa cttggagacg ttgtgcaaac tatgtcaatg
1261 ggaatatgga aaatgctgtg gggaggcttt atgtggaagc agcatttgct ggagagagta
1321 aacatgtggt cgaggatttg attgcacaga tccgagaagt ttttattcag actttagatg
1381 acctcacttg gatggatgcc gagacaaaaa agagagctga agaaaaggcc ttagcaatta
1441 aagaaaggat cggctatcct gatgacattg tttcaaatga taacaaactg aataatgagt
1501 acctcgagtt gaactacaaa gaagatgaat acttcgagaa cataattcaa aatttgaaat
1561 tcagccaaag taaacaactg aagaagctcc gagaaaaggt ggacaaagat gagtggataa
1621 gtggagcagc tgtagtcaat gcatttact cttcaggaag aaatcagata gtcttcccag
1681 ccggcattct gcagccccc ttctttagtg cccagcagtc caatccattg aactatgggg
1741 gcatcggcat ggtcatagga cacgaaatca cccatggctt cgatgacaat ggcagaaact
1801 ttaacaaaga tggagacctc gttgactggt ggactcaaca gtctgcaagt aactttaagg
1861 agcaatccca gtgcatggtg tatcagtatg gaaacttttc ctgggacctg gcaggtggac
1921 agcaccttaa tggaattaat acactgggag aaaacattgc tgataatgga ggtcttggtc
1981 aagcatacag agcctatcag aattatatta aaagaatgg cgaagaaaaa ttacttcctg
2041 gacttgacct aaatcacaaa caactatttt tcttgaactt tgcacaggtg tggtgtggaa
2101 cctataggcc agagtatgcg gttaactcca ttaaaacaga tgtgcacagt ccaggcaatt
2161 tcaggattat tgggactttg cagaactctg cagagttttc agaagccttt cactgccgca
```

Figure 10 (cont.)

```
2221 agaattcata catgaatcca gaaaagaagt gccgggtttg gtgatcttca aaagaagcat
2281 tgcagcccett ggctagactt gccaacacca cagaaatggg gaattctcta atcgaaagaa
2341 aatgggccct aggggtcact gtactgactt gagggtgatt aacagagagg gcaccatcac
2401 aatacagata acattaggtt gtcctagaaa gggtgtggag ggaggaaggg ggtctaaggt
2461 ctatcaagtc aatcatttct cactgtgtac ataatgctta atttctaaag ataatattac
2521 tgtttatttc tgtttctcat atggtctacc agtttgctga tgtccctaga aaacaatgca
2581 aaacctttga ggtagaccag gatttctaat caaaagggaa aagaagatgt tgaagaatac
2641 agttaggcac cagaagaaca gtaggtgaca ctatagttta aaacacattg cctaactact
2701 agtttttact tttatttgca acatttacag tccttcaaaa tccttccaaa gaattcttat
2761 acacattggg gccttggagc ttacatagtt ttaaactcat ttttgccata catcagttat
2821 tcattctgtg atcatttatt ttaagcactc ttaaagcaaa aaatgaatgt ctaaaattgt
2881 tttttgttgt acctgcttg actgatgctg agattcttca ggcttcctgc aattttctaa
2941 gcaatttctt gctctatctc tcaaaacttg gtattttca gagatttata taaatgtaaa
3001 aataataatt tttatattta attattaact acatttatga gtaactatta ttataggtaa
3061 tcaatgaata ttgaagtttc agcttaaaat aaacagttgt gaaccaagat ctataaagcg
3121 atatacagat gaaaatttga gactatttaa acttataaat catattgatg aaaagattta
3181 agcacaaact ttagggtaaa aattgccatt ggacagttgt ctagagatat atatacttgt
3241 ggttttcaaa ttggactttc aaaattaaat ctgtccctga gagtgtctct gataaaaggg
3301 caaatctgca cctatgtagc tctgcatctc ctgtcttttc aggtttgtca tcagatggaa
3361 atattttgat aataaattga aattgtgaac tcattgctcc ctaagactgt gacaactgtc
3421 taactttaga agtgcatttc tgaatagaaa tgggaggcct ctgatggacc ttctagaatt
3481 ataagtcaca aagagttctg gaaaagaact gtttactgct tgataggaat tcatcttttg
3541 aggcttctgt tcctctcttt tcctgttgta ttgactattt tcgttcatta cttgattaag
3601 attttacaaa agaggagcac ttccaaaatt cttatttttc ctaacaaaag atgaaagcag
3661 ggaatttcta tctaaatgat gagtattagt tccctgtctc ttgaaaaatg cccatttgcc
3721 tttaaaaaaa aaagttacag aaatactata acatatgtac ataaattgca taagcataa
3781 gtatacagtt caataaactt aactttaact gaacaatggc cctgtagcca gcacctgtaa
3841 gaaacagagc agtaccagcg ctctaaaagc acctccttgt cactttatta ctcccagaac
3901 aacaactatc ctgacttcta atatcattca ctagctttgc ctggttttgt cttttatgca
3961 gatagaatca atcagtatgt attctttgt gcctggcttc tttctctcag ccttacattt
4021 gtgagattcc tctgtattgt gctgattgtg gatcttttca ttctcattgc agaataatgt
4081 tctattgtgg gacttattac aatttgttca tcctattgtt gatgggcact tgagaacttt
4141 ccatttggc gctattacaa atagtgcaac tatgaatgta ctgcatgtta ccatcttact
4201 tgagccttta atggacttat ttcttcaaat ccttccaaaa attattataa gcattgaaat
4261 tatagtttca agccaactgt ggatacccett acccttttcct cctttatcac aaccaccgtt
4321 acaagtatac ttatatttcc ctaaaataca tttaaaactt acctaagtga catttgtagt
4381 tggagtaata ggagcttcca gctctaataa aacagctgtc tctaacttat tttatttcca
4441 tcatgtcaga gcaggtgaag agccagaagt gaagagtgac tagtacaaat tataaaaagc
4501 cactagactc ttcactgtta gctttttaaa acattaggct cccatcccta tggaggaaca
4561 actctccagt gcctggatcc cctctgtcta caaatataag attttctggg cctaaaggat
4621 agatcaaagt caaaaatagc aatgcctccc tatccctcac acatccagac atcatgaatt
4681 ttacatggta ctcttgttga gttctgtaga gccttctgat gtctctaaag cactaccgat
4741 tctttggagt tgtcacatca gataagacat atctctaatt ccatccataa atccagttct
4801 actatggctg agttctggtc aaagaaagaa agtttagaag ctgagacaca aagggttggg
4861 agctgatgaa actcacaaat gatggtagga agaagctctc gacaatacccc gttggcaagg
4921 agtctgcctc catgctgcag tgttcgagtg gattgtaggt gcaagatgga aaggattgta
4981 ggtgcaagct gtccagagaa aagagtcctt gttccagccc tattctgcca ctcctgacag
5041 ggtgaccttg ggtatttgca atattccttt gggcctctgc ttctctcacc taaaaaaaga
5101 gaattagatt atattggtgg ttctcagcaa gagaaggagt atgtgtccaa tgctgccttc
5161 ccatgaatct gtctcccagt tatgaatcag tgggcaggat aaactgaaaa ctcccattta
5221 cgtgtctgaa tcgagtgaga caaaatttta gtccaaataa caagtaccaa agtttatca
5281 agtttgggtc tgtgctgctg ttactgttaa ccatttaagt ggggcaaaac cttgctaatt
5341 ttctcaaaag catttatcat tcttgttgcc acagctggag ctctcaaact aaaagacatt
5401 tgttattttg gaaagaagaa agactctatt ctcaaagttt cctaatcaga aattttatc
```

Figure 10 (cont.)

```
5461 agtttccagt ctcaaaaata caaaataaaa acaaacgttt ttaatact
```

SEQ ID NO:74
```
   1 atgtccaatc agggaagtaa gtacgtcaat aaggaaattc aaaatgctgt caacggggtg
  61 aaacagataa agactctcat agaaaaaaca aacgaagagc gcaagacact gctcagcaac
 121 ctagaagaag ccaagaagaa gaaagaggat gccctaaatg agaccaggga atcagagaca
 181 aagctgaagg agctcccagg agtgtgcaat gagaccatga tggccctctg ggaagagtgt
 241 aagccctgcc tgaaacagac ctgcatgaag ttctacgcac gcgtctgcag aagtggctca
 301 ggcctggttg gccgccagct tgaggagttc ctgaaccaga gctcgccctt ctacttctgg
 361 atgaatggtg accgcatcga ctccctgctg gagaacgacc ggcagcagac gcacatgctg
 421 gatgtcatgc aggaccactt cagccgcgcg tccagcatca tagacgagct cttccaggac
 481 aggttcttca cccgggagcc ccaggatacc taccactacc tgcccttcag cctgccccac
 541 cggaggcctc acttcttctt tcccaagtcc cgcatcgtcc gcagcttgat gcccttctct
 601 ccgtacgagc ccctgaactt ccacgccatg ttccagccct tccttgagat gatacacgag
 661 gctcagcagg ccatggacat ccacttccat agcccggcct tccagcaccc gccaacagaa
 721 ttcatacgag aaggcgacga tgaccggact gtgtgccggg agatccgcca caactccacg
 781 ggctgcctgc ggatgaagga ccagtgtgac aagtgccggg agatcttgtc tgtggactgt
 841 tccaccaaca accccctccca ggctaagctg cggcgggagc tcgacgaatc cctccaggtc
 901 gctgagaggt tgaccaggaa atacaacgag ctgctaaagt cctaccagtg aagatgctc
 961 aacacctcct ccttgctgga gcagctgaac gagcagttta actgggtgtc ccggctggca
1021 aacctcacgc aaggcgaaga ccagtactat ctgcgggtca ccacggtggc ttcccacact
1081 tctgactcgg acgttccttc cggtgtcact gaggtggtcg tgaagctctt tgactctgat
1141 cccatcactg tgacggtccc tgtagaagtc tccaggaaga accctaaatt tatggagacc
1201 gtggcggaga aagcgctgca ggaataccgc aaaaagcacc gggaggagtg agatgtggat
1261 gttgcttttg cacctacggg ggcatctgag tccagctccc ccaagatga gctgcagccc
1321 cccagagaga gctctgcacg tcaccaagta accaggcccc agcctccagg cccccaactc
1381 cgcccagcct ctccccgctc tggatcctgc actctaacac tcgactctgc tgctcatggg
1441 aagaacagaa ttgctcctgc atgcaactaa ttcaataaaa ctgtcttgtg agctg
```

SEQ ID NO:75
```
   1 gaaggaaaaa gagcaacaga tccagggagc attcacctgc cctgtctcca aacagccttg
  61 tgcctcacct accccaacc tcccagaggg agcagctatt taaggggagc aggagtgcag
 121 aacaaacaag acggcctggg gatacaactc tggagtcctc tgagagagcc accaaggagg
 181 agcaggggag cgacggccgg ggcagaagtt gagaccaccc agcagaggag ctaggccagt
 241 ccatctgcat ttgtcaccca agaactctta ccatgaagac cctcctactg ttggcagtga
 301 tcatgatctt tggcctactg caggcccatg ggaatttggt gaatttccac agaatgatca
 361 agttgacgac aggaaaggaa gccgcactca gttatggctt ctacggctgc cactgtggcg
 421 tgggtggcag aggatccccc aaggatgcaa cggatcgctg ctgtgtcact catgactgtt
 481 gctacaaacg tctggagaaa cgtggatgtg gcaccaaatt tctgagctac aagtttagca
 541 actcggggag cagaatcacc tgtgcaaaac aggactcctg cagaagtcaa ctgtgtgagt
 601 gtgataaggc tgctgccacc tgttttgcta gaaacaagac gacctacaat aaaaagtacc
 661 agtactattc caataaacac tgcagaggga caccctcg ttgctgagtc ccctcttcc
 721 tggaaacctt ccacccagtg ctgaatttcc ctctctcata ccctccctcc ctaccctaac
 781 caagttcctt ggccatgcag aaagcatccc tcacccatcc tagaggcag gcaggagccc
 841 ttctataccc acccagaatg agacatccag cagatttcca gccttctact gctctcctcc
 901 acctcaactc cgtgcttaac caaagaagct gtactccggg gggtctcttc tgaataaagc
 961 aattagc
```

SEQ ID NO:76
```
   1 gctccatcaa gtatgatggt gaaggatgaa tatgtgcatg actttgaggg acagccatcg
  61 ttgtccactg aaggacattc aattcaaacc atccagcatc caccaagtaa tcgtgcatcg
 121 acagagacat acagcacccc agctctgtta gccccatctg agtctaatgc taccagcact
```

Figure 10 (cont.)

```
 181 gccaactttc ccaacattcc tgtggcttcc acaagtcagc ctgccagtat actgggggc
 241 agccatagtg aaggactgtt gcagatagca tcagggcctc agccaggaca gcagcagaat
 301 ggatttactg gtcagccagc tacttaccat cataacagca ctaccacctg gactggaagt
 361 aggactgcac catacacacc taatttgcct caccaccaaa acggccatct tcagcaccac
 421 ccgcctatgc cgccccatcc cggacattac tggcctgttc acaatgagct tgcattccag
 481 cctcccattt ccaatcatcc tgctcctgag tattggtgtt ccattgctta ctttgaaatg
 541 gatgttcagg taggagagac atttaaggtt ccttcaagct gccctattgt tactgttgat
 601 ggatacgtgg acccttctgg aggagatcgc ttttgtttgg gtcaactctc caatgtccac
 661 aggacagaag ccattgagag agcaaggttg cacataggca aaggtgtgca gttggaatgt
 721 aaaggtgaag gtgatgtttg ggtcaggtgc cttagtgacc acgcggtctt tgtacagagt
 781 tactacttag acagagaagc tgggcgtgca cctggagatg ctgttcataa gatctaccca
 841 agtgcatata taaaggtctt tgatttgcgt cagtgtcatc gacagatgca gcagcaggcg
 901 gctactgcac aagctgcagc agctgcccag gcagcagccg tggcaggaaa catccctggc
 961 ccaggatcag taggtggaat agctccagct atcagtctgt cagctgctgc tggaattggt
1021 gttgatgacc ttcgtcgctt atgcatactc aggatgagtt ttgtgaaagg ctggggaccg
1081 gattacccaa gacagagcat caaagaaaca ccttgctgga ttgaaattca cttacaccgg
1141 gccctccagc tcctagacga agtacttcat accatgccga ttgcagaccc acaaccttta
1201 gactgaggtc ttttaccgtt ggggccctta accttatcag gatggtggac tacaaaatac
1261 aatcctgttt ataatctgaa gatatatttc actttgttc tgcttatct tttcataaag
1321 ggttgaaaat gtgtttgctg ccttgctcct agcagacaga aactggatta aaacaatttt
1381 ttttttcctc ttcagaactt gtcaggcatg gctcagagct tgaagattag gagaaacaca
1441 ttcttattaa ttcttcacct gttatgtatg aaggaatcat tccagtgcta gaaaatttag
1501 ccctttaaaa cgtcttagag ccttttatct gcagaacatc gatatgtata tcattctaca
1561 gaataatcca gtattgctga ttttaaaggc agagaagttc tcaaagttaa ttcacctatg
1621 ttattttgtg tacaagttgt tattgttgaa catacttcaa aaataatgtg ccatgtgggt
1681 gagttaattt taccaagagt aactttactc tgtgtttaaa aagtaagtta ataatgtatt
1741 gtaatctttc atccaaaata ttttttgcaa gttatattag tgaagatggt ttcaattcag
1801 attgtcttgc aacttcagtt ttatttttgc caaggcaaaa aactcttaat ctgtgtgtat
1861 attgagaatc ccttaaaatt accagacaaa aaaatttaaa attacgtttg ttattcctag
1921 tggatgactg ttgatgaagt atacttttcc cctgttaaac agtagttgta ttcttctgta
1981 tttctaggca caaggttggt tgctaagaag cctataagag gaatttcttt tccttcattc
2041 atagggaaag gttttgtatt ttttaaaaca ctaaaagcag cgtcactcta cctaatgtct
2101 cactgttctg caaaggtggc aatgcttaaa ctaaataatg aataaactga atatttgga
2161 aactgctaaa ttctatgtta aatactgtgc agaataatgg aaacattaca gttcataata
2221 ggtagtttgg atatttttgt acttgatttg atgtgacttt ttttggtata atgtttaaat
2281 catgtatgtt atgatattgt ttaaaattca gttttgtat cttggggcaa gactgcaaac
2341 ttttttatat cttttggtta ttctaagccc tttgccatca atgatcatat caattggcag
2401 tgactttgta tagagaattt aagtagaaaa gttgcagatg tattgactgt accacagaca
2461 caatatgtat gcttttacc tagctggtag cataaataaa actgaatctc aacat
```

SEQ ID NO:77
```
   1 gcaggcccgt tggaagtggt tgtgacaacc ccagcaatgt ggagaagcct ggggcttgcc
  61 ctggctctct gtctcctccc atcgggagga acagagagcc aggaccaaag ctccttatgt
 121 aagcaacccc cagcctggag cataagagat caagatccaa tgctaaactc caatggttca
 181 gtgactgtgg ttgctcttct tcaagccagc tgatacctgt gcatactgca ggcatctaaa
 241 ttagaagacc tgcgagtaaa actgaagaaa gaaggatatt ctaatatttc ttatattgtt
 301 gttaatcatc aaggaatctc ttctcgatta aaatacacac atcttaagaa taaggtttca
 361 gagcatattc ctgttcatca acaagaagaa aaccaaacag atgtctggac tctttaaat
 421 ggaagcaaag atgacttcct catatatgat agatgtggcc gtcttgtata tcatcttggt
 481 ttgccttttt ccttcctaac tttcccatat gtagaagaag ccattaagat tgcttactgt
 541 gaaaagaaat gtggaaactg ctctctcacg actctcaaag atgaagactt tgtaaacgt
 601 gtatctttgg ctactgtgga taaacagtt gaaactccat cgcctcatta ccatcatgag
 661 catcatcaca atcatggaca tcagcacctt ggcagcagtg agctttcaga gaatcagcaa
 721 ccaggagcac caaatgctcc tactcatcct gctcctccag gccttcatca ccaccataag
```

Figure 10 (cont.)

```
 781 cacaagggtc agcataggca gggtcaccca gagaaccgag atatgccagc aagtgaagat
 841 ttacaagatt tacaaaagaa gctctgtcga aagagatgta taaatcaatt actctgtaaa
 901 ttgcccacag attcagagtt ggctcctagg agctgatgct gccattgtcg acatctgata
 961 tttgaaaaaa cagggtctgc aatcacctga cagtgtaaag aaaacctccc atctttatgt
1021 agctgacagg gacttcgggc agaggagaac ataactgaat cttgtcagtg acgtttgcct
1081 ccagctgcct gacaaataag tcagcagctt atacccacag aagccagtgc cagttgacgc
1141 tgaaagaatc aggcaaaaaa gtgagaatga ccttcaaact aaatatttaa aataggacat
1201 actccccaat ttagtctaga cacaatttca tttccagcat ttttataaac taccaaatta
1261 gtgaaccaaa aatagaaatt agatttgtgc aaacatggag aaatctactg aattggcttc
1321 cagattttaa attttatgtc atagaaatat tgactcaaac catatttttt atgatggagc
1381 aactgaaagg tgattgcagc ttttggttaa tatgtcttt tttttctttt tccagtgttc
1441 tatttgcttt aatgagaata gaaacgtaaa ctatgaccta ggggtttctg ttggataatt
1501 agcagtttag aatggaggaa gaacaacaaa gacatgcttt ccattttttt ctttacttat
1561 ctctcaaaac aatattactt tgtctttca atcttctact tttaactaat aaaataagtg
1621 gatttgtat tttaagatcc agaaatactt aacacgtgaa tatttgcta aaaaagcata
1681 tataactatt ttaaatatcc atttatcttt tgtatatcta agactcatcc tgattttac
1741 tatcacacat gaataaagcc tttgtatctt tctttctcta atgttgtatc atactcttct
1801 aaaacttgag tggctgtctt aaaagatata aggggaaaga taatattgtc tgtctctata
1861 ttgcttagta agtatttcca tagtcaatga tggtttaata ggtaaaccaa accctataaa
1921 cctgacctcc tttatggtta atactattaa gcaagaatgc agtacagaat tggatacagt
1981 acggatttgt ccaaataaat tcaataaaaa ccttaaa
```

SEQ ID NO:78
```
   1 caaccacttg acaacctggt tagaagatgc ccgccagcat tccaattcca acatggtcat
  61 tatgcttatt ggaaataaaa gtgatttaga atctagaaga gaagtaaaaa aagaagaagg
 121 tgaagctttt gcacgagaac atggactcat cttcatggaa acgtctgcta agactgcttc
 181 caatgtagaa gaggcattta ttaatacagc aaaagaaatt tatgaaaaaa ttcaagaagg
 241 agtctttgac attaataatg aggcaaatgg cattaaaatt ggccctcagc atgctgctac
 301 caatgcaaca catgcaggca atcaggaggg acagcaggct ggggcggct gctgttgagt
 361 ctgttttac tgtctagctg cccaacgggg cctactcact tattcttca cccctctcc
 421 tcctgctcag ctgagacatg aaactatttg aaatggcttt atgtcacaga agactttaat
 481 ccgtcaaatt cttgtataac tttgaataaa tggttaatgt tcacttaaaa gacagatttt
 541 ggagattgta ttcatatcta tttgcatttg atttctaggt caattgatgt gattatttt
 601 gttaaatgtt gtcttgtgcc cttaactacg aactgaattg tattaaacac tacaaagtca
 661 tcttgagtat tttaaatcgg tttgtgtagt taggtttccc aacatctgtg gttacctaat
 721 gtttaatatt atagaactgt cctcagaaac tttgtcaatt ttcacggcta taaggaaaca
 781 gaaggactct tttaattctg tatttatcat ttactttctg tatatatagt ttaataacct
 841 gcttgggtgt aatttgccaa gcttgaattc tttaatgcat ttgcataaat tctatactgt
 901 ttagagctta aagctacaga agcattgtta ggaattgctt ggacactgaa ttttaaactt
 961 tttgacattg ttaacaagca tgttcatctt ttcttgtcac tagtccaaga aaaatatgct
1021 taatgtatat tacaaaggct ttgtatatgt taacctgttt taatgccaaa agtttgcttt
1081 gtccacaatt tccttaagac ctcttcagaa agggatttgt ttgccttaat gaatactgtt
1141 gggaaaaaac acagtataat gagtgaaaag ggcagaagca agaaatttct acatcttagc
1201 gactccaaga agaatgagta tccacattta gatggcacat tatgaggact ttaatctttc
1261 cttaaacaca ataatgtttt ctttttttctt ttattcacat gatttctaag tatatttttc
1321 atgcaggaca gtttttcaac cttgatgtac agtgactgtg taaaatttt ctttcagtgg
1381 caacctctat aatctttaaa atatggtgag catcttgtct gttttgaagg ggatatgaca
1441 ataaatctat cagatggaaa atcctgtt
```

SEQ ID NO:79
```
   1 cctgggtctg acgcggccct gttcgagggg gcctctcttg tttatttatt tattttccgt
  61 gggtgcctcc gagtgtgcgc gcgctctcgc tacccggcgg ggaggggtg ggggagggc
 121 ccgggaaaag ggggagttgg agccggggtc gaaacgccgc gtgacttgta ggtgagagaa
```

Figure 10 (cont.)

```
 181 cgccgagccg tcgccgcagc ctccgccgcc gagaagccct tgttcccgct gctgggaagg
 241 agagtctgtg ccgacaagat ggcggacggg gagctgaacg tggacagcct catcacccgg
 301 ctgctggagg tacgaggatg tcgtccagga aagattgtgc agatgactga agcagaagtt
 361 cgaggcttat gtatcaagtc tcgggagatc tttctcagcc agcctattct tttggaattg
 421 gaagcaccgc tgaaaatttg tggagatatt catggacaat atacagattt actgagatta
 481 tttgaatatg gaggtttccc accagaagcc aactatcttt tcttaggaga ttatgtggac
 541 agaggaaagc agtctttgga aaccattgt ttgctattgg cttataaaat caaatatcca
 601 gagaacttct ttctcttaag aggaaaccat gagtgtgcta gcatcaatcg catttatgga
 661 ttctatgatg aatgcaaacg aagatttaat attaaattgt ggaagacctt cactgattgt
 721 tttaactgtc tgcctatagc agccattgtg gatgagaaga tcttctgttg tcatggagga
 781 ttgtcaccag acctgcaatc tatggagcag attcggagaa ttatgagacc tactgatgtc
 841 cctgatacag gtttgctctg tgatttgcta tggtctgatc cagataagga tgtgcaaggc
 901 tggggagaaa atgatcgtgg tgtttccttt acttttggag ctgatgtagt cagtaaattt
 961 ctgaatcgtc atgatttaga tttgatttgt cgagctcatc aggtggtgga agatggatat
1021 gaatttttg ctaaacgaca gttggtaacc ttattttcag ccccaaatta ctgtggcgag
1081 tttgataatg ctggtggaat gatgagtgtg gatgaaactt tgatgtgttc atttcagata
1141 ttgaaaccat ctgaaaagaa agctaaatac cagtatggtg gactgaattc tggacgtcct
1201 gtcactccac ctcgaacagc taatccgccg aagaaaaggt gaagaaagga ttctgtaaa
1261 gaaaccatca gatttgttaa ggacatactt cataatatat aagtgtgcac tgtaaaacca
1321 tccagccatt tgacacccct tatgatgtca cacctttaac ttaaggagac gggtaaagga
1381 tcttaaattt tttctaata gaaagatgtg ctacactgta ttgtaataag tatactctgt
1441 tatagtcaac aaagttaaat ccaaattcaa aattatccat taaagttaca tcttcatgta
1501 tcacaatttt taaagttgaa aagcatccca gttaaactag atgtgatagt taaaccagat
1561 gaaagcatga tgatccatct gtgtaatgtg gttttagtgt tgcttggttg tttaattatt
1621 ttgagcttgt tttgttttg tttgttttca ctagaataat ggcaaatact tctaattttt
1681 ttccctaaac attttaaaa gtgaaatatg ggaagagctt tacagacatt caccaactat
1741 tattttccct tgtttatcta cttagatatc tgtttaatct tactaagaaa actttcgcct
1801 cattacatta aaaggaatt ttagagattg attgtttaa aaaaaatac gcacattgtc
1861 caatccagtg atttaatca tacagtttga ctgggcaaac tttacagctg atagtgaata
1921 ttttgcttta tacaggaatt gacactgatt tggatttgtg cactctaatt tttaacttat
1981 tgatgctcta ttgtgcagta gcatttcatt taagataagg ctcatatagt attacccaac
2041 tagttggtaa tgtgattatg tggtaccttg gctttaggtt ttcattcgca cggaacacct
2101 tttggcatgc ttaacttcct ggtaacacct tcacctgcat tggttttctt tttcttttt
2161 cttttctttt tttttttttt ttttttttga gttgttgttt gttttagat ccacagtaca
2221 tgagaatcct ttttttgacaa gccttgaaa gctgacactg tctcttttc ctccctctat
2281 acgaaggatg tatttaaatg aatgctggtc agtgggacat tttgtcaact atgggtattg
2341 ggtgcttaac tgtctaatat tgccatgtga atgttgtata cgattgtaag gcttatgtca
2401 ctaaagattt ttattctgat ttttcataa tcaaggtca tatgatactg tatagacaag
2461 ctttgtagtg aagtatagta gcaataattt ctgtacctga tcaagtttat tgcagccttt
2521 cttttcctat ttctttttt taagggttag tattaacaaa tggcaatgag tagaaaagtt
2581 aacatgaaga ttttagaagg agagaactta caggacacag atttgtgatt ctttgactgt
2641 gacactattg gatgtgattc taaaagcttt tattgagcat tgtcaaattt gtaagcttca
2701 tagggatgga catcatatct ataatgccct tctatatgtg ctaccataga tgtgacattt
2761 ttgaccttaa tatcgtcttt gaaaatgtta aattgagaaa cctgttaact tacatttat
2821 gaattggcac attgtattac ttactgcaag agatatttca ttttcagcac agtgcaaaag
2881 ttctttaaaa tgcatatgtc tttttttcta attccgtttt gttttaaagc acattttaaa
2941 tgtagttttc tcatttagta aaagttgtct aattgatatg aagcctgact gattttttt
3001 ttccttacag tgagacattt aagcacacat tttattcaca tagatactat gtccttgaca
3061 tattgaaatg attctttct gaaagtattc atgatctgca tatgatgtat taggttaggt
3121 cacaaaggtt ttatctgagg tgatttaaat aacttcctga ttggagtgtg taagctgagc
3181 gatttctaat aaaattttag ttgtacactt ttagtagtca cagtgaagca ggtctagaaa
3241 ataagccttt ggcagggaaa aagggcaatg ttgattaatc tcagtattaa accacattaa
3301 tctgtatccc attgtctggc ttttgtaaat tcatccaggt caagactaag tatgttggtt
3361 aataggaatc cttttttttt tttaaagact aaatgtgaaa aaataatcac tacttaagct
```

Figure 10 (cont.)

```
3421 aattaatatt ggtcattaaa tttaaaggat ggaaatttat catgtttaaa aattattcaa
3481 gcactcttaa aaccacttaa acagcctcca gtcataaaaa tgtgttcttt acaaatattt
3541 gcttggcaac acgacttgaa ataaataaaa ctttgtttct taggagaaaa
```

SEQ ID NO:80
```
   1 gcaacctgcc ccattatccc tggctgcgaa acaaccatcg agatttccaa agggcgaaca
  61 gggctgggcc tgagcatcgt tgggggttca gacacgctgc tgggtgccat tattatccat
 121 gaagtttatg aagaaggagc agcatgtaaa gatggaagac tctgggctgg agatcagatc
 181 ttagaggtga atggaattga cttgagaaag gccacacatg atgaagcaat caatgtcctg
 241 agacagacgc cacagagagt gcgcctgaca ctctacagag atgaggcccc atacaaagag
 301 gaggaagtgt gtgacaccct cactattgag ctgcagaaga agccgggaaa aggcctagga
 361 ttaagtattg ttggtaaaag aaacgatact ggagtatttg tgtcagacat tgtcaaagga
 421 ggaattgcag atgccgatgg aagactgatg cagggagacc agatattaat ggtgaatggg
 481 gaagacgttc gtaatgccac ccaagaagcg gttgccgctt tgctaaagtg ttccctaggc
 541 acagtaacct tggaagttgg aagaatcaaa gctggtccat tccattcaga gaggaggcca
 601 tctcaaagca gccaggtgag tgaaggcagc ctgtcatctt tcacttttcc actctctgga
 661 tccagtacat ctgagtcact ggaaagtagc tcaaagaaga atgcattggc atctgaaata
 721 cagggattaa gaacagtcga aatgaaaaag ggccctactg actcactggg aatcagcatt
 781 gctggaggag taggcagccc acttggtgat gtgcctatat ttattgcaat gatgcaccca
 841 actggagttg cagcacagac ccaaaaactc agagttgggg ataggattgt caccatctgt
 901 ggcacatcca ctgagggcat gactcacacc caagcagtta acctactgaa aaatgcatct
 961 ggctccattg aaatgcaggt ggttgctgga ggagacgtga gtgtggtcac aggtcatcag
1021 caggagcctg caagttccag tctttctttc actgggctga cgtcaagcag tatatttcag
1081 gatgatttag gacctcctca atgtaagtct attacactag agcgaggacc agatggctta
1141 ggcttcagta tagttggagg atatggcagc cctcatggag acttacccat ttatgttaaa
1201 acagtgtttg caaagggagc agcctctgaa gacggacgtc tgaaaagggg cgatcagatc
1261 attgctgtca atggcagag tctagaagga gtcacccatg aagaagctgt tgccatcctt
1321 aaacggacaa aaggcactgt cactttgatg gttctctctt gaattggctg ccagaattga
1381 accaacccaa ccctagctc acctcctact gtaaagagaa tgcactggtc ctgacaattt
1441 ttatgctgtg ttcagccggg tcttcaaaac tgtagggggg aaataacact taagtttctt
1501 tttctcatct agaaatgctt tccttactga caacctaaca tcatttttct tttcttcttg
1561 cattttgtga acttaaagag aaggaatatt tgtgtaggtg aatctcgttt ttatttgtgg
1621 agatatctaa tgttttgtag tcacatgggc aagaattatt acatgctaag ctggttagta
1681 taaagaaaga taattctaaa gctaaccaaa gaaaatggct tcagtaaatt aggatgaaaa
1741 atgaaaatat
```

SEQ ID NO:81
```
   1 ggagcgcaat ggcgtccaac cccgaacggg gggagattct gctcacggaa ctgcagggggg
  61 attcccgaag tcttccgttt tctgagaatg tgagtgctgt tcaaaaatta gacttttcag
 121 atacaatggt gcagcagaaa ttggatgata tcaaggatcg aattaagaga gaaataagga
 181 aagaactgaa aatcaaagaa ggagctgaaa atctgaggaa agtcacaaca gataaaaaaa
 241 gtttggctta tgtagacaac attttgaaaa aatcaaataa aaaattagaa gaactacatc
 301 acaagctgca ggaattaaat gcacatattg ttgtatcaga tccagaagat attacagatt
 361 gcccaaggac tccagatact ccaaataatg accctcgttg ttctactagc aacaatagat
 421 tgaaggcctt acaaaaacaa ttggatatag aacttaaagt aaaacaaggt gcagagaata
 481 tgatacagat gtattcaaat ggatcttcaa aggatcggaa actccatggt acagctcagc
 541 aactgctcca ggacagcaag acaaaaatag aagtcatacg aatgcagatt cttcaggcag
 601 tccagactaa tgaattggct tttgataatg caaaacctgt gataagtcct cttgaacttc
 661 ggatggaaga attaaggcat catttttagga tagagtttgc agtagcagaa ggtgcaaaga
 721 atgtaatgaa attacttggc tcaggaaaag taacagacag aaaagcactt tcagaagctc
 781 aagcaagatt taatgaatca agtcagaagt tggacctttt aaagtattca ttagagcaaa
 841 gattaaacga agtccccaag aatcatccca aaagcaggat tattattgaa gaactttcac
 901 ttgttgctgc atcaccaaca ctaagtccac gtcaaagtat gatatctacg caaaatcaat
 961 atagtacact atccaaacca gcagcactaa caggtacttt ggaagttcgt cttatgggct
```

Figure 10 (cont.)

```
1021 gccaagatat cctagagaat gtccctggac ggtcaaaagc aacatcagtt gcactgcctg
1081 gttggagtcc aagtgaaacc agatcatctt tcatgagcag aacgagtaaa agtaaaagcg
1141 gaagtagtcg aaatcttcta aaaaccgatg acttgtccaa tgatgtctgt gctgttttga
1201 agctcgataa tactgtggtt ggccaaacta gctggaaacc catttccaat cagtcatggg
1261 accagaagtt tacactggaa ctggacaggt cacgtgaact ggaaatttca gtttattggc
1321 gtgattggcg gtctctgtgt gctgtaaaat ttctgaggtt agaagatttt ttagacaacc
1381 aacggcatgg catgtgtctc tatttggaac cacagggtac tttatttgca gaggttacct
1441 tttttaatcc agttattgaa agaagaccaa aacttcaaag acaaaagaaa attttttcaa
1501 agcaacaagg caaaacattt ctcagagctc tcaaatgaa tattaatatt gccacttggg
1561 gaaggctagt aagaagagct attcctacag taaatcattc tggcaccttc agccctcaag
1621 ctcctgtgcc tactacagtg ccagtggttg atgtacgcat ccctcaacta gcacctccag
1681 ctagtgattc tacagtaacc aaattggact ttgatcttga gcctgaacct cctccagccc
1741 caccacgagc ttcttctctt ggagaaatag atgaatcttc tgaattaaga gttttggata
1801 taccaggaca ggattcagag actgttttg atattcagaa tgacagaaat agtatacttc
1861 caaaatctca atctgaatac aagcctgata ctcctcagtc aggcctagaa tatagtggta
1921 ttcaagaact tgaggacaga agatctcagc aaaggtttca gtttaatcta caagatttca
1981 ggtgttgtgc tgtcttggga agaggacatt ttggaaaggt gcttttagct gaatatataaaa
2041 acacaaatga gatgtttgct ataaaagcct taagaaagg agatattgtg gctcgagatg
2101 aagtagacag cctgatgtgt gaaaaagaa tttttgaaac tgtgaatagt gtaaggcatc
2161 ccttttttggt gaaccttttt gcatgtttcc aaaccaaaga gcatgtttgc tttgtaatgg
2221 aatatgctgc cggtggggac ctaatgatgc acattcatac tgatgtcttt tctgaaccaa
2281 gagctgtatt ttatgctgct tgtgtagttc ttgggttgca gtatttacat gaacacaaaa
2341 ttgtttatag agatttgaaa ttggataact tattgctaga tacagagggc tttgtgaaaa
2401 ttgctgattt tggtcttgc aaagaaggaa tgggatatgg agatagaaca agcacatttt
2461 gtggcactcc tgaattctt gccccagaag tattaacaga aacttcttat acaagggctg
2521 tagattggtg gggccttggc gtgcttatat atgaaatgct tgttggtgag tctcccttc
2581 ctggtgatga tgaagaggaa gtttttgaca gtattgtaaa tgatgaagta aggtatccaa
2641 ggttcttatc tacagaagcc atttctataa tgagaaggct gttaagaaga aatcctgaac
2701 ggcgccttgg ggctagcgag aaagatgcag aggatgtaaa aaagcaccca tttttccggc
2761 taattgattg gagcgctctg atggacaaaa aagtaaagcc accatttata cctaccataa
2821 gaggacgaga agatgttagt aatttttgatg atgaatttac ctcagaagca cctattctga
2881 ctccacctcg agaaccaagg atactttcgg aagaggagca ggaaatgttc agagattttg
2941 actacattgc tgattggtgt taagttgcta gacactgcga aaccaagctg actcacaaga
3001 agacctctta aaaatagcaa cccttcattt gctctctgtg ccaccaatag cttctgagtt
3061 ttttgttgtt gttgttttta ttgaaacacg tgaagatttg tttaaaagta ccattctaat
3121 acttcttcaa aagtggctcc tcattgtact tcagcgtaaa tatgagcact ggaaacagtt
3181 tcatggagtt taagttgagt gaacatcggc catgaaaatc catcacgaat acttttggat
3241 caatagtcta tttt
```

SEQ ID NO:82

```
   1 atgaaattca agttacatgt gaattctgcc aggcaataca aggacctgtg gaatatgagt
  61 gatgacaaac ccttttctatg tactgcgcct ggatgtggcc agagtgaagt caccctgctg
 121 agaaatgaag tggcacagct gaaacagctt cttctggctc ataaagattg ccctgtaacc
 181 gccatgcaga agaaatctgg ctatcatact gctgataaag atgatagttc agaagacatt
 241 tcagtgccga gtagtccaca tacagaagct atacagcata gttcggtcag cacatccaat
 301 ggagtcagtt caacctccaa ggcagaagct gtagccactt cagtcctcac ccagatggcg
 361 gaccagagta cagagcctgc tctttcacag atcgttatgg ctccttcctc ccagtcacag
 421 ccctcaggaa gttgattaaa aacctgcagt acaacagttt tagatactca ttagtgactt
 481 caaagggaaa tcaaggaaag accagtttc
```

SEQ ID NO:83

```
   1 gaattctgga agttcattga agagtctgaa attagggact tatttcaaat ttggacatgg
  61 ctagtcgagg cgcaacaaga cccaacggcc caaatactgg aaataaaata tgccagttca
 121 aactagtact tctgggagag tccgctgttg gcaaatcaag cctagtgctt cgttttgtga
```

Figure 10 (cont.)

```
    181 aaggccaatt tcatgaattt caagagagta ccattggggc tgcttttcta acccaaactg
    241 tatgtcttga tgacactaca gtaaagtttg aaatctggga tacagctggt caagaaggat
    301 accatagcct agcaccaatg tactacagag gagcacaagc agccatagtt gtatatgata
    361 tcacaaatga ggagtccttt gcaagagcaa aaaattgggt taaagaactt cagaggcaag
    421 caagtcctaa cattgtaata gctttatcgg gaaacaaggc cgacctagca aataaaagag
    481 cagtagattt ccaggaagca cagtcctatg cagatgacaa tagtttatta ttcatggaga
    541 catccgctaa aacatcaatg aatgtaaatg aaatattcat ggcaatagct aaaaaattgc
    601 caaagaatga accacaaaat ccaggagcaa attctgccag aggaggagga gtagacctta
    661 ccgaacccac acaaccaacc aggaatcagt gttgtagtaa ctaaacctct agtttgaac
```

SEQ Id NO:84
```
      1 gacgctctgg gccgccacct ccgcggaccc tgagcgcaag agccaagccg ccagcgctgc
     61 gatgtgggcc acgctgccgc tgctctgcgc cggggcctgg ctcctgggag tcccgtctg
    121 cggtgccgcc gaactgtgcg tgaactcctt agagaagttt cacttcaagt catggatgtc
    181 taagcaccgt aagacctaca gtacggagga gtaccaccac aggctgcaga cgtttgccag
    241 caactggagg aagataaacg cccacaacaa tgggaaccac acatttaaaa tggcactgaa
    301 ccaattttca gacatgagct ttgctgaaat aaaacacaag tatctctggt cagagcctca
    361 gaattgctca gccaccaaaa gtaactacct tcgaggtact ggtccctacc caccttccgt
    421 ggactggcgg aaaaaaggaa attttgtctc acctgtgaaa atcagggtg cctgcggcag
    481 ttgctggact ttctccacca ctggggccct ggagtctgcg atcgccatcg caaccggaaa
    541 gatgctgtcc ttggcggaac agcagctggt ggactgcgcc caggacttca ataatcacgg
    601 ctgccaaggg ggtctcccca gccaggcttt cgagtatatc ctgtacaaca aggggatcat
    661 gggtgaagac acctaccct accagggcaa ggatggttat tgcaagttcc aacctggaaa
    721 ggccatcggc tttgtcaagg atgtagccaa catcacaatc tatgacgagg aagcgatggt
    781 ggaggctgtg gccctctaca ccctgtgag ctttgccttt gaggtgactc aggacttcat
    841 gatgtataga accggcatct actccagtac ttcctgccat aaaactccag ataaagtaaa
    901 ccatgcagta ctggctgttg ggtatggaga aaaaaatggg atcccttact ggatcgtgaa
    961 aaactcttgg ggtccccagt ggggaatgaa cggtacttc ctcatcgagc gcggaaagaa
   1021 catgtgtggc ctggctgcct gcgcctccta cccatccct ctggtgtgag ccgtggcagc
   1081 cgcagcgcag actggcggag aaggagagga acgggcagcc tgggcctggg tggaaatcct
   1141 gccctggagg aagttgtggg gagatccact gggaccccca acattctgcc ctcacctctg
   1201 tgcccagcct ggaaacctac agacaaggag gagttccacc atgagctcac ccgtgtctat
   1261 gacgcaaaga tcaccagcca tgtgccttag tgtccttctt aacagactca aaccacatgg
   1321 accacgaata ttcttttctgt ccagaagggc tactttccac atatagagct ccagggactg
   1381 tcttttctgt attcgctgtt caataaacat tgagtgagca cctccccaga tgg
```

SEQ ID NO:85
```
      1 ggtcggggcc cgcggccgct cgcgcctctc gatgggcagc tcgcacttgc tcaacaaggg
     61 cctgccgctt ggcgtccgac ctccgatcat gaacgggccc ctgcaccgc ggccctggt
    121 ggcattgctg gatggccggg actgcacagt ggagatgccc atcctgaagg acgtggccac
    181 tgtggccttc tgcgacgcgc agtccacgca ggagatccat gagaaggtcc tgaacgaggc
    241 tgtggggccc tgatgtacc acaccatcac tctcaccagg gaggacctgg agaagttcaa
    301 agccctccgc atcatcgtcc ggattggcag tggttttgac aacatcgaca tcaagtcggc
    361 cggggattta ggcattgccg tctgcaacgt gcccgcggcg tctgtggagg agacggccga
    421 ctcgacgctg tgccacatcc tgaacctgta ccggcgggcc acctggctgc accaggcgct
    481 gcgggagggc acacgagtcc agagcgtcga gcagatccgc gaggtggcgt ccggcgctgc
    541 caggatccgc ggggagacct tggcatcat cggacttgtc gcgtggggca ggcagtggcg
    601 ctgcgggcca aggccttcgg cttcaacgtg ctcttctacg accttactt gtcggatggc
    661 gtggagcggg cgctggggct gcagcgtgtc agcaccctgc aggacctgct cttccacagc
    721 gactgcgtga ccctgcactg cggcctcaac gagcacaacc accacctcat caacgacttc
    781 accgtcaagc agatgagaca aggggccttc ctggtgaaca gcccggggg tggcctggtg
    841 gatgagaagg cgctggccca ggccctgaag gagggccgga tccgcggcgc ggccctggat
    901 gtgcacgagt cggaaccctt cagctttagc cagggccctc tgaaggatgc acccaacctc
    961 atctgcaccc ccatgctgc atggtacagc gagcaggcat ccatcgagat gcgagaggag
```

Figure 10 (cont.)

```
1021 gcggcacggg agatccgcag agccatcaca ggccggatcc cagacagcct gaagaactgt
1081 gtcaacaagg accatctgac agccgccacc cactgggcca gcatggaccc cgccgtcgtg
1141 caccctgagc tcaatggggc tgcctatagg taccctccgg gcgtggtggg cgtggccccc
1201 actggcatcc cagctgctgt ggaaggtatc gtcccagcg ccatgtccct gtcccacggc
1261 ctgcccctg tggcccaccc gccccacgcc ccttctcctg gccaaacgt caagcccgag
1321 gcggatagag accacgccag tgaccagttg tagcccggga ggagctctcc agcctggcg
1381 cctgggcaga gggcccggaa accctcggac cagagtgtgt ggaggaggca tctgtgtggt
1441 ggccctggca ctgcagagac tggtccgggc tgtcaggagg cgggaggggg cagcgctggg
1501 cctcgtgtcg cttgtcgtcg tccgtcctgt gggcgctctg ccctgtgtcc ttcgcgttcc
1561 tcgttaagca gaagaagtca gtagttattc tcccatgaac gttcttgtct gtgtacagtt
1621 tttagaacat tacaaaggat ctgtttgctt agctgtcaac aaaaagaaaa cctgaaggag
1681 catttggaag tcaatttgag gttttttttt ttgttttttt ttttttgta tgttggaacg
1741 tgccccagaa tgaggcagtt ggcaaacttc tcaggacaat gaatccttcc cgttttcctt
1801 tttatgccac acagtgcatt gttttttcta cctgcttgtc ttattttag aataatttag
1861 aaaaacaaaa caaaggctgt ttttcctaat tttggcatga accccccctt gttccaaatg
1921 aagacggcat cacgaagcag ctccaaaagg aaaagcttgg gcggtgccca gcgtgcccgc
1981 tgcccatcga cgtctgtcct ggggacgtgg agggtggcag cgtccccgcc tgcaccagtg
2041 ccgtcctgct gatgtggtag gctagcaata ttttggttaa aatcatgttt gtg
```

SEQ ID NO:86
```
   1 cgcgcggcca ggccctctta gccctctgcc gtttgggggg cacgggtgaa cctgccgccc
  61 cactcccacc ccgccccgcc ccgcccgtac agccaaatcg gaagggacga gcctgccctt
 121 tgaaagggtt tttttttcttg ctcctgcgga gggcgcccca gccatggccc tcaggagctc
 181 cctagacccc gcagggactg ccctccatcc cggccgccgg ggcccgccct ctgcatcccg
 241 cgggcagcct gtgtgaagcg gcctcccgca gccccggcc cctccccat ggaggaggag
 301 gagggggcgg tggccaagga gtggggcacg accccgcgg ggcccgtctg gaccgcggtg
 361 ttcgactacg aggcggcggg cgacgaggag ctgaccctgc ggagggggcga tcgcgtccag
 421 gtgctttccc aagactgtgc ggtgtccggc gacgagggct ggtggaccgg gcagctcccc
 481 agcggccgcg tgggcgtctt ccccagcaac tacgtggccc ccggcgcccc cgctgcaccc
 541 gcgggcctcc agctgcccca ggagatcccc ttccacgagc tgcagctaga ggagatcatc
 601 ggtgtggggg gctttggcaa ggtctatcgg gccctgtggc gtggcgagga ggtggcagtc
 661 aaggccgccc ggctggaccc tgagaaggac ccggcagtga cagcggagca ggtgtgccag
 721 gaagcccggc tctttggagc cctgcagcac cccaacataa ttgccttag gggcgcctgc
 781 ctcaacccccc cacacctctg cctagtgatg gagtatgccc ggggtggtgc actgagcagg
 841 gtgctggcag gtcgccgggt gccacctcac gtgctggtca actgggctgt gcaggtggcc
 901 cgggcatga actacctaca caatgatgcc cctgtgccca tcatccaccg ggacctcaag
 961 tccatcaaca tcctgatcct ggaggccatc gagaaccaca acctcgcaga cacggtgctc
1021 aagatcacgg acttcggcct cgcccgcgag tggcacagaa ccaccaagat gagcgctgcg
1081 gggacctacg cctggatggc gccggaggtt atccgtctct ccctcttctc caaaagcagt
1141 gatgtctgga gcttcggggt gctgctgtgg gagctgctga cggggaggt cccctaccgt
1201 gagatcgacg ccttggccgt ggcgtatggc gtggctatga ataagctgac gctgcccatt
1261 ccctccacgt gccccgagcc ctttgcccgc ctcctggagg aatgctggga cccagacccc
1321 cacgggcggc cagatttcgg tagcatcttg aagcggcttg aagtcatcga acagtcagcc
1381 ctgttccaga tgccactgga gtccttccac tcgctgcagg aagactggaa gctggagatt
1441 cagcacatgt ttgatgacct tcggaccaag gagaaggagc ttcggagccg tgaggaggag
1501 ctgctgcggg cggcacagga gcagcgcttc caggaggagc agctgcgcg cgggagcag
1561 gagctggcag aacgtgagat ggacatcgtg aacgggagc tgcacctgct catgtgccag
1621 ctgagccagg agaagcccg gtccgcaag cgcaagggca acttcaagcg cagccgcctg
1681 ctcaagctgc gggaaggcgg cagccacatc agcctgccct ctggctttga gcataagatc
1741 acagtccagg cctctccaac tctggataag cggaaaggat ccgatggggc cagcccccct
1801 gcaagcccca gcatcatccc ccggctgagg gccattcgcc tgactcccgt ggactgtggt
1861 ggcagcagca gtggcagcag cagtggagga agtgggacat ggagccgcgg tgggccccca
1921 aagaaggaag aactggtcgg gggcaagaag aagggacgaa cgtgggggcc cagctccacc
1981 ctgcagaagg agcgggtggg aggagaggag aggctgaagg ggctggggga aggaagcaaa
```

Figure 10 (cont.)

```
2041 cagtggtcat caagtgcccc caacctgggc aagtccccca aacacacacc cagtcgccgc
2101 tggcttcgcc agcctcaatg agatggagga gttcgcggag gcagaggatg gaggcagcag
2161 cgtgccccct tcccctact cgacccgtc ctacctctca gtgccactgc ctgccgagcc
2221 ctccccgggg gcgcgggcgc cgtgggagcc gacgccgtcc gcgcccccg ctcggtgggg
2281 acacggcgcc cggcggcgct gcgacctggc gctgctaggc tgcgccacgc tgctgggggc
2341 tgtgggcctg ggcgccgacg tggccgaggc gcgcgcggcc gacggtgagg agcagcggcg
2401 ctggctcgac ggcctcttct ttccccgcgc cggccgcttc ccgcggggcc tcagcccacc
2461 cgcgcgtccc cacggccgcc gcgaagacgt gggcccggc ctgggcctgg cgccctcggc
2521 caccctcgtg tcgctgtcgt ccgtgtccga ctgcaactcc acgcgttcac tgctgcgctc
2581 tgacagtgac gaggccgcac cggccgcgcc ctcccacca ccctcccgc ccgcgcccac
2641 acccacgccc tcgcccagca ccaaccccct ggtggacctg gagctggaga gcttcaagaa
2701 ggacccccgc cagtcgctca cgcccaccca cgtcacggct gcatgcgctg tgagccgcgg
2761 gcaccggcgg acgccatcgg atggggcgct ggggcagcgg gggccgcccg agcccgcggg
2821 ccatggccct ggcctcgtg accttctgga cttccccgc ctgccgacc ccaggccct
2881 gttcccagcc cgccgccggc ccctgagtt cccaggccgc ccaccaccc tgacctttgc
2941 cccgagacct cggccggctg ccagtcgccc ccgcttggac ccctggaaac tggtctcctt
3001 cggccggaca ctcaccatct cgcctcccag caggccagac actccggaga gccctgggcc
3061 cccagcgtg cagcccacac tgctggacat ggacatggag gggcagaacc aagacagcac
3121 agtgccctg tgcggggccc acggctccca ctaaggcctg cccaccaccg cccgcctggg
3181 cagccatgaa tgtagcgccc caggccctgc cccagcccgc catgccacaa ggtggggag
3241 gccctgggca ggatgttcac tctatttatt ggggaaggag ggagggggg gacacttaac
3301 ttattccttt gtacccagg gggtggagcc ctgtgcccac cctgcactgg ggggagggtg
3361 ggcagggata ctcagggaca gggcatcatg ggggatttgg cacaaaatgg agcattaaag
3421 gtaacccctg ccccc
```

SEQ ID NO:87

```
   1 gggcccgccc ctggtcacag ccagactgac tcagtttccc tgggaggtcc cgctcgagcc
  61 cgtccttccc ctccctctgc ccgccccag ccctcgcccc accctcggcg cccgcacatc
 121 tgcctgctca gctccagacg gcgcccggac ccccgggcgc gggatccagc caggtgggag
 181 ccccgcagat gaggtctctg aaggtgtgcc tgaaccagtg ccagcctgcc ctgtctgcag
 241 catcggcctg atggggtggt gactgatccc tcagggctcc ggagccatgt ggcccaacgg
 301 cagttccctg gggcctgtt tccggcccac aaacattacc ctggaggaga gacggctgat
 361 cgcctcgccc tggttcgccg cctccttctg cgtggtgggc ctggcctca acctgctggc
 421 cctgagcgtg ctggcgggcg cgcggcaggg gggttcgcac acgcgctcct ccttcctcac
 481 cttcctctgc ggcctcgtcc tcaccgactt cctggggctg ctggtgaccg gtaccatcgt
 541 ggtgtcccag cacgccgcgc tcttcgagtg gcacgccgtg gaccctggct gccgtctctg
 601 tcgcttcatg ggcgtcgtca tgatcttctt cggcctgtcc ccgctgctgc tgggggccgc
 661 catggcctca gagcgctacc tgggtatcac ccggcccttc tcgcgcccgg cggtcgcctc
 721 gcagcgccgc gcctgggcca ccgtggggct ggtgtgggcg gccgcgctgg cgctgggcct
 781 gctgcccctg ctgggcgtgg gtcgctacac cgtgcaatac ccggggtcct ggtgcttcct
 841 gacgctgggc gccgagtccg gggacgtggc cttcgggctg ctcttctcca tgctgggcgg
 901 cctctcggtc gggctgtcct tcctgctgaa cacggtcagc gtggccaccc tgtgccacgt
 961 ctaccacggg caggaggcgg cccagcagcg tccccgggac tccgaggtgg agatgatggc
1021 tcagctcctg gggatcatgg tggtggccag cgtgtgttgg ctgcccttc tggtcttcat
1081 cgcccagaca gtgctgcgaa accgcctgc catgagcccc gcgggcagc tgtcccgcac
1141 cacggagaag gagctgctca tctacttgcg cgtggccacc tggaaccaga tcctggaccc
1201 ctgggtgtat atcctgttcc gccgcgccgt gctccggcgt ctccagcctc gcctcagcac
1261 ccggccagg tgctgtccc tccagcccca gtcacgcag cgctcgggcc tgcagtagga
1321 agtggacaga gcgcccctcc cgcgccttc cgcggagccc ttggccccct ggacagccca
1381 tctgcctgtt ctgaggattc aggggctggg ggtgctggat ggacagtggg catcagcagc
1441 agggttttgg gttgacccca atccaacccg ggaccccca actcctccct gatccttta
1501 ccaagcactc tcccttcctc ggccctttt tccatccag agctcccacc ccttctctgc
1561 gtccctccca accccaggaa gggcatgcag acattggaag agggtcttgc attgctattt
1621 tttttcttag acggagtctt gctctgtccc ccaggctgga gtgcagtggc gcaatctcag
```

Figure 10 (cont.)

```
1681 ctcactgcaa cctccacctc ccgggttcaa gcgattctcc tgcctcagcc tcctgagtag
1741 ctgggactat aggcgcgcgc caccacgccc ggctaatttt tgtatttta gtagagacgg
1801 ggtttcaccg tgttggccag gctggtcttg aactcctgac ctcaggtgat tcaccagcct
1861 cagcctccca aagtgctggg atcacaggca tgaaccacca cacctggcca ttttttttt
1921 ttttttaga cggagtctca ctctgtggcc cagcctggag tacagtggca cgatctcggc
1981 tcactgcaac ctccgcctcc cgggttcaag cgattctcgt gcctcagcct cccgagcagc
2041 tgggattaca ggcgtaagcc actgcgccg gccttgcatg ctctttgacc ctgaatttga
2101 cctacttgct ggggtacagt tgcttccttt tgaacctcca acagggaagg ctctgtccag
2161 aaaggattga atgtgaacgg gggcacccccc ttttcttgcc aaaatatatc tctgcctttg
2221 gttttat
```

SEQ ID NO:88

```
   1 cccggacatg gccgccaaca tgtacagggt cggagactac gtctactttg agaactcctc
  61 cagcaaccca tacctgatcc ggagaatcga ggagctcaac aagacggcca atgggaacgt
 121 ggaggccaaa gtggtgtgct tctaccggag gcgggacatc tccagcaccc tcatcgccct
 181 ggccgacaag cacgcaaccc tgtcagtctg ctataaggcc ggaccggggg cggacaacgg
 241 cgaggaaggg gaaatagaag aggaaatgga gaatccggaa atggtggacc tgcccgagaa
 301 actaaagcac cagctgcggc atcgggagct gttcctctcc cggcagctgg agtctctgcc
 361 cgccacgcac atcaggggca agtgcagcgt cacccctgctc aacgagaccg agtcgctcaa
 421 gtcctacctg gagcgggagg atttcttctt ctattctcta gtctacgacc cacagcagaa
 481 gaccctgctg gcagataaag gagagattcg agtaggaaac cggtaccagg cagacatcac
 541 cgacttgtta aaagaaggcg aggaggatgg ccgagaccag tccaggttgg agacccaggt
 601 gtgggaggcg cacaacccac tcacagacaa gcagatcgac cagttcctgg tggtggcccg
 661 ctctgtgggc accttcgcac gggccctgga ctgcagcagc tccgtccgac agcccagcct
 721 gcacatgagc gccgcagctg cctcccgaga catcaccctg ttccacgcca tggatactct
 781 ccacaagaac atctacgaca tctccaaggc catctcggcg ctggtgccgc agggcgggcc
 841 cgtgctctgc agggacgaga tggaggagtg gtctgcatca gaggccaacc ttttcgagga
 901 agccctggaa aaatatggga aggatttcac ggacattcag caagattttc tcccgtggaa
 961 gtcgctgacc agcatcattg agtactacta catgtggaag accaccgaca gatacgtgca
1021 gcagaaacgc ttgaaagcag ctgaagctga gagcaagtta aagcaagttt atattcccaa
1081 ctataacaag ccaaatccga accaaatcag cgtcaacaac gtcaaggccg gtgtggtgaa
1141 cggcacgggg gcgccgggcc agagccctgg ggctggccgg gcctgcgaga gctgttacac
1201 cacacagtct taccagtggt attcttgggg tccccctaac atgcagtgtc gtctctgcgc
1261 atcttgttgg acatattgga agaaatatgg tggcttgaaa atgccaaccc ggttagatgg
1321 agagaggcca ggaccaaacc gcagtaacat gagtccccac ggcctccag cccggagcag
1381 cgggagcccc aagtttgcca tgaagaccag gcaggctttc tatctgcaca cgacgaagct
1441 gacgcggatc gcccggcgcc tgtgccgtga gatcctgcgc ccgtggcacg ctgcgcggaa
1501 cccctacctg cccatcaaca gcgcggccat caaggccgag tgcacggcgc ggctgcccga
1561 agcctcccag agcccgctgg tgctgaagca ggcggtacgc aagccgctgg aagccgtgct
1621 tcggtatctt gagacccacc ccgcccccc caagcctgac ccgtgaaaa gcgtgtccag
1681 cgtgctcagc agcctgacgc ccgccaaggt ggcccccgtc atcaacaacg gctcccccac
1741 catcctgggc aagcgcagct acgagcagca caacggggtg gacggcaaca tgaagaagcg
1801 cctcttgatg cccagtaggg gtctggcaaa ccacggacag accaggcaca tgggaccaag
1861 ccggaacctc ctgctcaacg ggaagtccta ccccaccaaa gtgcgcctga tccgggggggg
1921 ctccctgccc ccagtcaagc ggcggcggat gaactggatc gacgccccgg gtgacgtgtt
1981 ctacatgccc aaagaggaga ccaggaagat ccgcaagctg ctctcatcct cggaaaccaa
2041 gcgtgctgcc cgccggccct acaagccat cgccctgcgc cagagccagg ccctgccgcc
2101 gcggccaccg ccacctgcgc ccgtcaacga cgagcccatc gtcatcgagg actaggggcc
2161 gccccacct gcggccgccc cccgcccctc gcccgcccac acggcccctt ccagccagc
2221 ccgccgcccg cccctcagtt tggtagtgcc ccacctcccg ccctcacctg aagagaaacg
2281 cgctccttgg cggacactgg gggaggagag gaagaagcgc ggctaactta ttccgagaat
2341 gccgaggagt tgtcgttttt agctttgtgt ttacttttg gctggagcgg agatgagggg
2401 ccaccccgtg ccctgtgct gcggggcctt ttgccggag gccgggccct aaggttttgt
2461 tgtgttctgt tgaaggtgcc attttaaatt ttattttat tactttttt gtagatgaac
```

Figure 10 (cont.)

```
2521 ttgagctctg taacttacac ctggaatgtt aggatcgtgc ggccgcggcc ggccgagctg
2581 cctggcgggg ttggcccttg tcttttcaag taattttcat attaaacaaa aacaaagaaa
2641 aaaaatctta taaaaaggaa aa
```

SEQ ID NO:89
```
  1 atgagagagt acaaagtggt ggtgctgggc tcgggcggcg tgggcaagtc cgcgctcacc
 61 gtgcagttcg tgacgggctc cttcatcgag aagtacgacc cgaccatcga agactttac
121 cgcaaggaga ttgaggtgga ctcgtcgccg tcggtgctgg agatcctgga tacggcgggc
181 accgagcagt tcgcgtccat gcgggacctg tacatcaaga acggccaggg cttcatcctg
241 gtctacagcc tcgtcaacca gcagagcttc caggacatca gcccatgcg ggaccagatc
301 atccgcgtga agcggtacga gcgcgtgccc atgatcctgg tgggcaacaa ggtggacctg
361 gagggtgagc gcgaggtctc gtacggggag ggcaaggccc tggctgagga gtggagctgc
421 cccttcatgg agacgtcggc caaaaacaaa gcctcggtag acgagctatt tgccgagatc
481 gtgcggcaga tgaactacgc ggcgcagtcc aacggcgatg agggctgctg ctcggcctgc
541 gtgatcctct ga
```

SEQ ID NO:90
```
  1 gagctgcggg cgctgctgct gtggggccgc cgcctgcggc ctttgctgcg ggcgccggcg
 61 ctggcggccg tgccgggagg aaaaccaatt ctgtgtcctc ggaggaccac agcccagttg
121 ggccccaggc gaaacccagc ctggagcttg caggcaggac gactgttcag cacgcagacc
181 gccgaggaca aggaggaacc cctgcactcg attatcagca gcacagagag cgtgcagggt
241 tccacttcca aacatgagtt ccaggccgag acaaagaagc ttttggacat tgttgcccgg
301 tccctgtact cagaaaaaga ggtgtttata cgggagctga tctccaatgc cagcgatgcc
361 ttggaaaaac tgcgtcacaa actggtgtct gacggccaag cactgccaga aatggagatt
421 cacttgcaga ccaatgccga gaaggcacc atcaccatcc aggatactgg tatcgggatg
481 acacaggaag agctggtgtc caacctgggg acgattgcca gatcggggtc aaaggccttc
541 ctggatgctc tgcagaacca ggctgaggcc agcagcaaga tcatcggcca gtttggagtg
601 ggtttctact cagctttcat ggtggctgac agagtggagg tctattcccg ctcggcagcc
661 ccggggagcc tgggttacca gtggctttca gatggttctg gagtgtttga aatcgccgaa
721 gcttcgggag ttagaaccgg gacaaaaatc atcatccacc tgaaatccga ctgcaaggag
781 ttttccagcg aggcccgggt gcgagatgtg gtaacgaagt acagcaactt cgtcagcttc
841 cccttgtact tgaatggaag gcggatgaac accttgcagg ccatctggat gatggacccc
901 aaggatgtcc gtgagtggca acatgaggag ttctaccgct acgtcgcgca ggctcacgac
961 aagccccgct acaccctgca ctataagacg gacgcaccgc tcaacatccg cagcatcttc
1021 tacgtgcccg acatgaaacc gtccatgttt gatgtgagcc gggagctggg ctccagcgtt
1081 gcactgtaca gccgcaaagt cctcatccag accaaggcca cggacatcct gcccaagtgg
1141 ctgcgcttca tccgaggtgt ggtggacagt gaggacattc ccctgaacct cagccgggag
1201 ctgctgcagg agagcgcact catcaggaaa ctccgggacg ttttacagca gaggctgatc
1261 aaattcttca ttgaccagag taaaaaagat gctgagaagt atgcaaagtt ttttgaagat
1321 tacggcctgt tcatgcggga gggcattgtg accgccaccg agcaggaggt caaggaggac
1381 atagcaaagc tgctgcgcta cgagtcctcg gcgctgccct ccgggcagct aaccagcctc
1441 tcagaatacg ccagccgcat gcgggccggc acccgcaaca tctactacct gtgcgccccc
1501 aaccgtcacc tggcagagca ctcaccctac tatgaggcca tgaagaagaa agacacagag
1561 gttctcttct gctttgagca gtttgatgag ctcaccctgc tgcaccttcg tgagtttgac
1621 aagaagaagc tgatctctgt ggagacggac atagtcgtgg atcactacaa ggaggagaag
1681 tttgaggaca ggtccccagc cgccgagtgc ctatcagaga aggagacgga ggagctcatg
1741 gcctggatga gaaatgtgct ggggtcgcgt gtcaccaacg tgaaggtgac cctccgactg
1801 gacacccacc ctgccatggt caccgtgctg gagatggggg ctgccgcca ttcctgcgc
1861 atgcagcagc tggccaagac ccaggaggag cgcgcacagc tcctgcagcc cacgctggag
1921 atcaacccca ggcacgcgct catcaagaag ctgaatcagc tgcgcgcaag cgagcctggc
1981 ctggctcagc tgctggtgga tcagatatac gagaacgcca tgattgctgc tggacttgtt
2041 gacgaccta gggccatggt gggccgcttg aatgagctgc ttgtcaaggc cctggagcga
2101 cactgacagc caggggggcca gaaggactga caccacagat gacagcccca cctccttgag
```

Figure 10 (cont.)

```
    2161 ctttatttac ctaaatttaa aggtatttct taacccga
```

SEQ ID NO:91
```
       1 agtgatgtcc ttgcattgcc cattttaag caagaagagt cgagtttgcc tcctgataat
      61 gagaataaaa tcctgccttt tcaatatgtg ctttgtgctg ctacctctcc agcagtgaaa
     121 ctccatgatg aaaccctaac gtatctcaat caaggacagt cttatgaaat tcgaatgcta
     181 gacaatagga aacttggaga acttccagaa attaatggca aattggtgaa gagtatattc
     241 cgtgtggtgt tccatgacag aaggcttcag tacactgagc atcagcagct agagggctgg
     301 aggtggaacc gacctggaga cagaattctt gacatagata tcccgatgtc tgtgggtata
     361 atcgatccta gggctaatcc aactcaacta aatacagtgg agttcctgtg ggaccctgca
     421 aagaggacat ctgtgtttat tcaggtgcac tgtattagca cagagttcac tatgaggaaa
     481 catggtggag aaaaggggt gccattccga gtacaaatag ataccttcaa ggagaatgaa
     541 aacggggaat atactgagca cttacactcg gccagctgcc agatcaaagt tttcaagcca
     601 aaggtgcaga cagaaagcaa aaaacggata gggaaaaaat ggagaaacga acacctcatg
     661 aaaaggagaa atatcagcct tcctatgaga caaccatact cacagagtgt tctccatggc
     721 ccgagatcac gtatgtcaat aactccccat cacctggctt caacagttcc catagcagtt
     781 tttctcttgg ggaaggaaat ggttcaccaa accaccagcc agagccaccc cctccagtca
     841 cagataacct cttaccaaca accacacctc aggaagctca gcagtggttg catcgaaatc
     901 gttttctac attcacaagg ctttttcacaa acttctcagg ggcagattta ttgaaattaa
     961 ctagagatga tgtgatccaa atctgtggcc ctgcagatgg aatcagactt tttaatgcat
    1021 taaaaggccg gatggtgcgt ccaaggttaa ccatttatgt ttgtcaggaa tcactgcagt
    1081 tgagggagca gcaacaacag cagcagcaac agcagcagaa gcatgaggat ggagactcaa
    1141 atggtacttt cttcgtttac catgctatct atctagaaga actaacagct gttgaattga
    1201 cagaaaaaat tgctcagctt ttcagcattt cccttgcca gatcagccag atttacaagc
    1261 aggggccaac aggaattcat gtgctcatca gtgatgagat gatacagaac tttcaggaag
    1321 aagcatgttt tattctggac acaatgaaag cagaaaccaa tgatagctat catatcatac
    1381 tgaagtagga gtgcggcgtt tcgtgcccag tggctgctcc ttccttcacc tctgaaaacg
    1441 gccctcttga aggggatat gaatggagat ttgaaggtct gcaagaacct gactcgtctg
    1501 actgtgtgtg gaggagtcca ggccatggag gcagaatcct ggccctctgt gttggcccaa
    1561 gctcttgtgg tacacacaga ttactgccca atatgcagtt ctgcagctgt tttagttaaa
    1621 tttctggacc ttgttgttgt taaatatcag tagaaactct acataattta gagtgtatgt
    1681 agggcataat gatgatggga attgtgtgat gtttaacagg aagatcttaa attttgtgat
    1741 atggagccct gtaattttt tcttatataa aaatgggtat ctatattcat
```

SEQ ID NO:92
```
       1 aggtctgttc cgcatgaaac tcctgctggg gaaggacttc cctgcctccc cacccaaggg
      61 ctacttcctg accaagatct tccacccgaa cttgggcgcc aatggcgaga tgtgcgtcaa
     121 cgtgctcaag agggactgga cggctgagct gggcatccga cacgtactgc tgaccatcaa
     181 gtgcctgctg atccaccta accccgagtc tgcactcaac gaggaggcgg gccgcctgct
     241 cttggagaac tacgaggagt atgcggctcg ggcccgtctg ctcacagaga tccacggggg
     301 cgccggcggg cccagcggca gggccaaagc cgggcgggcc ctggccagtg gcactgcagc
     361 ttcctccacc gactctgggg ccccagggg cttgggaggg gctgagggtc ccatggccaa
     421 gaagcatgct ggcgagcgcg ataagaagct ggcggccaag aaaaagacgg acaagaagcg
     481 ggcgctacgg cggctgtagt gggctctctt cctccttcca ccgtgaccc aacctctcct
     541 gtccctccc tccaactctg tctctaagtt atttaaatta tggctgggt cggggagggt
     601 acaggggca ctgagacctg gatttgtttt tttaaataaa gttggaaaag ca
```

SEQ ID NO:93
```
       1 gtcgtgttct ccgagttcct gtctctctgc caacgccgcc cggatggctt cccaaaaccg
      61 cgacccagcc gccactagcg tcgccgccgc ccgtaaagga gctgagccga gcggggcgc
     121 cgccggggt ccggtgggca aaaggctaca gcaggagctg atgaccctca tgatgtctgg
     181 cgataaaggg atttctgcct tccctgaatc agacaaccct tcaaatggg tagggaccat
     241 ccatggagca gctggaacag tatatgaaga cctgaggtat aagctctcgc tagagttccc
```

Figure 10 (cont.)

```
    301 cagtggctac ccttacaatg cgcccacagt gaagttcctc acgccctgct atcacccaa
    361 cgtggacacc cagggtaaca tatgcctgga catcctgaag gaaaagtggt ctgccctgta
    421 tgatgtcagg accattctgc tctccatcca gagccttcta ggagaaccca acattgatag
    481 tcccttgaac acacatgctg ccgagctctg gaaaaacccc acagctttta agaagtacct
    541 gcaagaaacc tactcaaagc aggtcaccag ccaggagccc tgacccaggc tgcccagcct
    601 gtccttgtgt cgtcttttta atttttcctt agatggtctg tcctttttgt gatttctgta
    661 taggactctt tatcttgagc tgtggtattt ttgttttgtt tttgtctttt aaattaagcc
    721 tcggttgagc ccttgtatat taaataaatg cattttgtc cttttttaga c
```

SEQ ID NO:94
```
      1 ctccagcagc acccgagagg gtcaggagaa aagcggagga agctgggtag gccctgaggg
     61 gcctcggtaa gccatcatga ccacccggca agccacgaag gatcccctcc tccggggtgt
    121 atctcctacc cctagcaaga ttccggtacg ctctcagaaa cgcacgcctt tccccactgt
    181 tacatcgtgc gccgtggacc aggagaacca agatccaagg agatgggtgc agaaaccacc
    241 gctcaatatt caacgccccc tcgttgattc agcaggcccc aggccgaaag ccaggcacca
    301 ggcagagaca tcacaaagat tggtggggat cagtcagcct cggaaccct tggaagagct
    361 caggcctagc cctaggggtc aaaatgtggg gcctgggccc cctgcccaga cagaggctcc
    421 agggaccata gagtttgtgg ctgaccctgc agccctggcc accatcctgt caggtgaggg
    481 tgtgaagagc tgtcacctgg ggcgccagcc tagtctggct aaaagagtac tggttcgagg
    541 aagtcaggga ggcaccaccc agagggtcca gggtgttcgg gcctctgcat atttggcccc
    601 cagaaccccc acccaccgac tggaccctgc cagggcttcc tgcttctcta ggctggaggg
    661 accaggacct cgaggccgga cattgtgtcc ccagaggcta caggctctga tttcaccttc
    721 aggaccttcc tttcacccct ccactcgccc cagtttccag gagctaagaa gggagacagc
    781 tggcagcagc cggacttcag tgagccaggc ctcaggattg ctcctggaga ccccagtcca
    841 gcctgctttc tctcttccta aaggagaacg cgaggttgtc actcactcag atgaaggagg
    901 tgtggcctct cttggtctgg cccagcgagt accattaaga gaaaaccgag aaatgtcaca
    961 taccagggac agccatgact cccacctgat gccctcccct gcccctgtgg cccagcccctt
   1021 gcctggccat gtggtgccat gtccatcacc ctttggacgg gctcagcgtg taccctcccc
   1081 aggccctcca actctgacct catattcagt gttgcggcgt ctaccgttc aacctaaaac
   1141 ccggttcaca cccatgccat caaccccag agttcagcag gcccagtggc tcgtggtgt
   1201 ctccctcag tcctgctctg aagatcctgc cctgccctgg gagcaggttg ccgtccggtt
   1261 gtttgaccag gagagttgta taaggtcact ggagggttct gggaaaccac cggtggccac
   1321 tccttctgga ccccactcta acagaacccc cagcctccag gaggtgaaga ttcaacgcat
   1381 cggtatcctg caacagctgt tgagacagga agtagagggg ctggtagggg gccagtgtgt
   1441 ccctcttaat ggaggctctt ctctggatat ggttgaactt cagcccctgc tgactgagat
   1501 ttctagaact ctgaatgcca cagagcataa ctctgggact tcccaccttc ctggactgtt
   1561 aaaacactca gggctgccaa agccctgtct tccagaggag tgcggggaac cacagccctg
   1621 ccctccggca gagcctgggc cccagaggc cttctgtagg agtgagcctg agataccaga
   1681 gccctccctc caggaacagc ttgaagtacc agagccctac cctccagcag aacccaggcc
   1741 cctagagtcc tgctgtagga gtgagcctga ataccggag tcctctcgcc aggaacagct
   1801 tgaggtacct gagccctgcc ctccagcaga acccaggccc ctagagtcct actgtaggat
   1861 tgagcctgag ataccggagt cctctcgcca ggaacagctt gaggtacctg agccctgccc
   1921 tccagcagaa cccgggcccc ttcagcccag cacccagggg cagtctggac ccccagggcc
   1981 ctgccctagg gtagagctgg ggcatcaga gccctgcacc ctgaacata gaagtctaga
   2041 gtccagtcta ccacctgct gcagtcagtg ggctccagca accaccagcc tgatcttctc
   2101 ttcccaacac ccgctttgtg ccagcccccc tatctgctca ctccagtctt tgagaccccc
   2161 agcaggccag gcaggcctca gcaatctggc ccctcgaacc ctagccctga gggagcgcct
   2221 caaatcgtgt ttaaccgcca tccactgctt ccacgaggct cgtctggacg atgagtgtgc
   2281 cttttacacc agccgagccc ctccctcagg ccccacccgg gtctgcacca acctgtggc
   2341 tacattactc gaatggcagg atgccctgtg tttcattcca gttggttctg ctgcccccca
   2401 gggctctcca tgatgagaca accactcctg ccctgccgta cttcttcctt ttagccctta
   2461 tttattgtcg gtctgcccat gggactggga gccgcccact tttgtcctca ataaagtttc
   2521 taaagta
```

Figure 10 (cont.)

SEQ ID NO:95

```
   1 agaataatca tgggccagac tgggaagaaa tctgagaagg gaccagtttg ttggcggaag
  61 cgtgtaaaat cagagtacat gcgactgaga cagctcaaga ggttcagacg agctgatgaa
 121 gtaaaggtat gtttagttcc aatcgtcaga aaattttgga aagaacggaa atcttaaacc
 181 aagaatggaa acagcgaagg atacagcctg tgcacatcct gacttctgtg agctcattgc
 241 gcgggactag ggagtgttcg gtgaccagtg acttggattt tccaacacaa gtcatcccat
 301 taaagactct gaatgcagtt gcttcagtac ccataatgta ttcttggtct ccctacagc
 361 agaattttat ggtggaagat gaaactgtta tacataacat tccttatatg ggagatgaag
 421 ttttagatca ggatggtact ttcattgaag aactaataaa aaattatgat gggaaagtac
 481 acggggatag agaatgtggg tttataaatg atgaaatttt tgtggagttg gtgaatgccc
 541 ttggtcaata taatgatgat gacgatgatg atgatggaga cgatcctgaa gaaagagaag
 601 aaaagcagaa agatctggag gatcaccgag atgataaaga aagccgccca cctcggaaat.
 661 ttccttctga taaaattttt gaagccattt cctcaatgtt tccagataag ggcacagcag
 721 aagaactaaa ggaaaaatat aaagaactca ccgaacagca gctcccaggc gcacttcctc
 781 ctgaatgtac ccccaacata gatggaccaa atgctaaatc tgttcagaga gagcaaagct
 841 tacactcctt tcatacgctt ttctgtaggc gatgttttaa atatgactgc ttcctacatc
 901 cttttcatgc aacacccaac acttataagc ggaagaacac agaaacagct ctagacaaca
 961 aaccttgtgg accacagtgt taccagcatt tggagggagc aaaggagttt gctgctgctc
1021 tcaccgctga gcggataaag accccaccaa aacgtccagg aggccgcaga agaggacggc
1081 ttcccaataa cagtagcagg cccagcaccc ccaccattaa tgtgctggaa tcaaaggata
1141 cagacagtga tagggaagca gggactgaaa cgggggggaga gaacaatgat aaagaagaag
1201 aagagaagaa agatgaaact tcgagctcct ctgaagcaaa ttctcggtgt caaacaccaa
1261 taaagatgaa gccaaatatt gaacctcctg agaatgtgga gtggagtggt gctgaagcct
1321 caatgtttag agtcctcatt ggcacttact atgacaattt ctgtgccatt gctaggttaa
1381 ttgggaccaa aacatgtaga caggtgtatg agtttagagt caaagaatct agcatcatag
1441 ctccagctcc cgctgaggat gtggatactc ctccaaggaa aaagaagagg aaacaccggt
1501 tgtgggctgc acactgcaga aagatacagc tgaaaaagga cggctcctct aaccatgttt
1561 acaactatca accctgtgat catccacggc agccttgtga cagttcgtgc ccttgtgtga
1621 tagcacaaaa ttttttgtgaa aagtttttgtc aatgtagttc agagtgtcaa aaccgctttc
1681 cgggatgccg ctgcaaagca cagtgcaaca ccaagcagtg cccgtgctac ctggctgtcc
1741 gagagtgtga ccctgacctc tgtcttactt gtggagccgc tgaccattgg gacagtaaaa
1801 atgtgtcctg caagaactgc agtattcagc ggggctccaa aaagcatcta ttgctggcac
1861 catctgacgt ggcaggctgg gggattttta tcaaagatcc tgtgcagaaa aatgaattca
1921 tctcagaata ctgtggagag attatttctc aagatgaagc tgacagaaga gggaaagtgt
1981 atgataaata catgtgcagc tttctgttca acttgaacaa tgatttttgtg gtggatgcaa
2041 cccgcaaggg taacaaaatt cgttttgcaa atcattcggt aaatccaaac tgctatgcaa
2101 aagttatgat ggttaacggt gatcacagga taggtatttt tgccaagaga gccatccaga
2161 ctggcgaaga gctgttttt gattacagat acagccaggc tgatgccctg aagtatgtcg
2221 gcatcgaaag agaaatggaa atcccttgac atctgctacc tcctccccc tcctctgaaa
2281 cagctgcctt agcttcagga acctcgagta ctgtgggcaa tttagaaaaa gaacatgcag
2341 tttgaaattc tgaatttgca aagtactgta agaataattt atagtaatga gtttaaaaat
2401 caacttttta ttgccttctc accagctgca aagtgttttg taccagtgaa ttttttgcaat
2461 aatgcagtat ggtacatttt tcaactttga ataaagaata cttgaacttg tc
```

SEQ ID NO: 96

```
   1 caggtctgag gcgaagctag gtgagccgtg ggaagaaaag agggagcagc tagggcgcgg
  61 gtctccctcc tcccggagtt tggaacggct gaagttcacc ttccagcccc tagcgcgtt
 121 cgcgccgcta ggcctggctt ctgaggcggt tgcggtgctc ggtcgccgcc taagcggggc
 181 agggtgcgaa caggggcttc gggccacgct tctcttggcg acaggatttt gctgtgaagt
 241 ccgtccggga aacggaggaa aaaagagtt gcgggaggct gtctgctaat aacggttctt
 301 gatacatatt tgccagactt caagatttca gaaaaggggt gaaagagaag attgcaactt
 361 tgagtcagac ctgtaggcct gatagactga ttaaaccaca gaaggtgacc tgctgagaaa
 421 agtggtacaa atactgggaa aaacctgctc ttctgcgtta agtgggagac aatgtcacaa
 481 gttaaaagct cttattccta tgatgccccc tcggatttca tcaattttc atccttggat
```

Figure 10 (cont.)

```
 541 gatgaaggag atactcaaaa catagattca tggtttgagg agaaggccaa tttggagaat
 601 aagttactgg ggaagaatgg aactggaggg cttttcagg gcaaaactcc tttgagaaag
 661 gctaatcttc agcaagctat tgtcacacct ttgaaaccag ttgacaacac ttactacaaa
 721 gaggcagaaa aagaaaatct tgtggaacaa tccattccgt caaatgcttg ttcttccctg
 781 gaagttgagg cagccatatc aagaaaaact ccagcccagc ctcagagaag atctcttagg
 841 ctttctgctc agaaggattt ggaacagaaa gaaagcatc atgtaaaaat gaaagccaag
 901 agatgtgcca ctcctgtaat catcgatgaa attctaccct ctaagaaaat gaaagtttct
 961 aacaacaaaa agaagccaga ggaagaaggc agtgctcatc aagatactgc tgaaaacaat
1021 gcatcttccc cagagaaagc caagggtaga catactgtgc cttgtatgcc acctgcaaag
1081 cagaagtttc taaaaagtac tgaggagcaa gagctggaga agagtatgaa aatgcagcaa
1141 gaggtggtgg agatgcggaa aagaatgaa gaattcaaga aacttgctct ggctggaata
1201 gggcaacctg tgaagaaatc agtgagccag gtcaccaaat cagttgactt ccacttccgc
1261 acagatgagc gaatcaaaca acatcctaag aaccaggagg aatataagga agtgaacttt
1321 acatctgaac tacgaaagca tccttcatct cctgcccgag tgactaaggg atgtaccatt
1381 gttaagcctt tcaacctgtc ccaaggaaag aaaagaacat ttgatgaaac agtttctaca
1441 tatgtgcccc ttgcacagca agttgaagac ttccataaac gaaccctaa cagatatcat
1501 ttgaggagca agaaggatga tattaacctg ttaccctcca aatcttctgt gaccaagatt
1561 tgcagagacc cacagactcc tgtactgcaa accaaacacc gtgcacgggc tgtgacctgc
1621 aaaagtacag cagagctgga ggctgaggag ctcagaaat tgcaacaata caaattcaaa
1681 gcacgtgaac ttgatccag aatacttgaa ggtgggccca tcttgccaa gaaaccacct
1741 gtgaaaccac ccaccgagcc tattggcttt gatttggaaa ttgagaaaag aatccaggag
1801 cgagaatcaa agaagaaaac agaggatgaa cactttgaat ttcattccag accttgccct
1861 actaagattt tggaagatgt tgtgggtgtt cctgaaaaga aggtacttcc aatcaccgtc
1921 cccaagtcac cagcctttgc attgaagaac agaattcgaa tgcccaccaa agaagatgag
1981 gaagaggacg aaccggtagt gataaaagct caacctgtgc cacattatgg ggtgccttt
2041 aagcccccaaa tccagagcc aagaactgtg gaaatatgcc ctttctcgtt tgattctcga
2101 gacaaagaac gtcagttaca gaaggagaag aaaataaaag aactgcagaa agggggggtg
2161 cccaagttca aggcacttcc cttgcctcat tttgacacca ttaacctgcc agagaagaag
2221 gtaaagaatg tgacccagat tgaacctttc tgcttggaga ctgacagaag aggtgctctg
2281 aaggcacaga cttggaagca ccagctggaa gaagaactga gacagcagaa agaagcagct
2341 tgtttcaagg ctcgtccaaa caccgtcatc tctcaggagc cctttgttcc caagaaagag
2401 aagaaatcag ttgctgaggg cctttctggt tctctagttc aggaaccttt tcagctggct
2461 actgagaaga gagccaaaga gcggcaggag ctggagaaga gaatggctga ggtagaagcc
2521 cagaaagccc agcagttgga ggaggccaga ctacaggagg aagagcagaa aaaagaggag
2581 ctggccaggc tacggagaga actggtgcat aaggcaaatc caatacgcaa gtaccagggt
2641 ctggagataa agtcaagtga ccagcctctg actgtgcctg tatctcccaa attctccact
2701 cgattccact gctaaactca gctgtgagct gcggataccg cccggcaatg ggacctgctc
2761 ttaacctcaa acctaggacc gtcttgcttt gtcattgggc atggagagaa cccatttctc
2821 cagactttta cctacccgtg cctgagaaag catacttgac aactgtggac tccagttttg
2881 ttgagaattg ttttcttaca ttactaaggc taataatgag atgtaactca tgaatgtctc
2941 gattagactc catgtagtta cttcctttaa accatcagcc ggcttttat atgggtcttc
3001 actctgacta gaatttagtc tctgtgtcag cacagtgtaa tctctattgc tattgcccct
3061 tacgactctc accctctccc cactttttt aaaattta accagaaaat aaagatagtt
3121 aaatcctaag atagagatta agtcatggtt taaatgagga acaatcagta aatcagattc
3181 tgtcctcttc tctgcatacc gtgaatttat agttaaggat cccttttgctg tgagggtaga
3241 aaacctcacc aactgcacca gtgaggaaga agactgcgtg gattcatggg gagcctcaca
3301 gcagccacgc agcaggctct gggtggggct gccgttaagg cacagttctt tccttactgg
3361 tgctgataac aacagggaac cgtgcagtgt gcattttaag acc
```

SEQ ID NO:97

```
   1 cttcaacccg cgccggcggc gactgcagtt cctgcgagcg aggagcgcgg gacctgctga
  61 cacgctgacg ccttcgagcg cggccgggg cccggagcgg ccggagcagc ccgggtcctg
 121 accccggccc ggctcccgct ccgggctctg ccggcgggcg ggcgagcgcg gcgcggtccg
 181 ggccgggggg atgtctcggc ggacgcgctg cgaggatctg gatgagctgc actaccagga
```

Figure 10 (cont.)

```
 241 cacagattca gatgtgccgg agcagaggga tagcaagtgc aaggtcaaat ggacccatga
 301 ggaggacgag cagctgaggg ccctggtgag gcagtttgga cagcaggact ggaagttcct
 361 ggccagccac ttccctaacc gcactgacca gcaatgccag tacaggtggc tgagagtttt
 421 gaatccagac cttgtcaagg ggccatggac caaagaggaa gaccaaaaag tcatcgagct
 481 ggttaagaag tatggcacaa agcagtggac actgattgcc aagcacctga agggccggct
 541 ggggaagcag tgccgtgaac gctggcacaa ccacctcaac cctgaggtga agaagtcttg
 601 ctggaccgag gaggaggacc gcatcatctg cgaggcccac aaggtgctgg gcaaccgctg
 661 ggccgagatc gccaagatgt tgccagggag gacagacaat gctgtgaaga atcactggaa
 721 ctctaccatc aaaaggaagg tggacacagg aggcttcttg agcgagtcca aagactgcaa
 781 gcccccagtg tacttgctgc tggagctcga ggacaaggac ggcctccaga gtgcccagcc
 841 cacggaaggc cagggaagtc ttctgaccaa ctggccctcc gtccctccta ccataaagga
 901 ggaggaaaac agtgaggagg aacttgcagc agccaccaca tcgaaggaac aggagcccat
 961 cggtacagat ctggacgcag tgcgaacacc agagcccttg gaggaattcc cgaagcgtga
1021 ggaccaggaa ggctccccac cagaaacgag cctgccttac aagtgggtgg tggaggcagc
1081 taacctcctc atccctgctg tgggttctag cctctctgaa gccctggact tgatcgagtc
1141 ggaccctgat gcttggtgtg acctgagtaa atttgacctc cctgaggaac catctgcaga
1201 ggacagtatc aacaacagcc tagtgcagct gcaagcgtca catcagcagc aagtcctgcc
1261 accccgccag ccttccgccc tggtgcccag tgtgaccgag taccgcctgg atggccacac
1321 catctcagac ctgagccgga gcagccgggg cgagctgatc cccatctccc cagcactga
1381 agtcggggc tctggcattg gcacaccgcc ctctgtgctc aagcggcaga ggaagaggcg
1441 tgtggctctg tcccctgtca ctgagaatag caccagtctg tccttcctgg attcctgtaa
1501 cagcctcacg cccaagagca cacctgttaa gaccctgccc ttctcgccct cccagtttct
1561 gaacttctgg aacaaacagg acacattgga gctggagagc cctcgctga catccacccc
1621 agtgtgcagc cagaaggtgg tggtcaccac accactgcac cgggacaaga caccctgca
1681 ccagaaacat gctgcgtttg taaccccaga tcagaagtac tccatggaca acactcccca
1741 cacgccaacc ccgttcaaga acgccctgga gaagtacgga cccctgaagc cctgccaca
1801 gaccccgcac ctggaggagg acttgaagga ggtgctgcgt tctgaggctg gcatcgaact
1861 catcatcgag gacgacatca ggcccgagaa gcagaagagg aagcctgggc tgcggcggag
1921 ccccatcaag aaagtccgga agtctctggc tcttgacatt gtggatgagg atgtgaagct
1981 gatgatgtcc acactgccca gtctctatc cttgccgaca actgcccctt caaactcttc
2041 cagcctcacc ctgtcaggta tcaaagaaga caacagcttg ctcaaccagg gcttcttgca
2101 ggccaagccc gagaaggcag cagtggccca gaagcccga agccacttca cgacacctgc
2161 ccctatgtcc agtgcctgga agacggtggc ctgcgggggg accagggacc agcttttcat
2221 gcaggagaaa gcccggcagc tcctgggccg cctgaagccc agccacacat ctcggaccct
2281 catcttgtcc tgaggtgttg agggtgtcac gagcccattc tcatgtttac aggggttgtg
2341 ggggcagagg gggtctgtga atctgagagt cattcaggtg acctcctgca gggagccttc
2401 tgccaccagc ccctccccag actctcaggt ggaggcaaca gggccatgtg ctgccctgtt
2461 gccgagccca gctgtgggcg ctcctggtg ctaacaacaa agttccactt ccaggtctgc
2521 ctggttccct ccccaaggcc acagggagct ccgtcagctt ctcccaagcc cacgtcaggc
2581 ctggcctcat ctcagaccct gcttaggatg ggggatgtgg ccaggggtgc tcctgtgctc
2641 accctctctt ggtgcatttt tttggaagaa taaaattgcc tctctctt
```

SEQ ID NO:98

```
   1 atgaggttga cgctactttg ttgcacctgg agggaagaac gtatgggaga ggaaggaagc
  61 gagttgcccg tgtgtgcaag ctgcggccag aggatctatg atggccagta cctccaggcc
 121 ctgaacgcgg actggcacgc agactgcttc aggtgttgtg actgcagtgc ctccctgtcg
 181 caccagtact atgagaagga tgggcagctc ttctgcaaga aggactactg gcccgctat
 241 ggcgagtcct gccatgggtg ctctgagcaa atcaccaagg gactggtat ggtggctggg
 301 gagctgaagt accaccccga gtgtttcatc tgcctcacgt gtgggacctt tatcggtgac
 361 ggggacacct acacgctggt ggagcactcc aagctgtact gcgggcactg ctactaccag
 421 actgtggtga ccccgtcat cgagcagatc ctgctgact cccctggctc ccacctgcc
 481 cacaccgtca cctggtgtc catcccagcc tcatctcatg gcaagcgtgg actttcagtc
 541 tccattgacc ccccgcacgg cccaccgggc tgtggcaccg agcactcaca cacgtccgc
 601 gtccagggag tggatccggg ctgcatgagc ccagatgtga agaattccat ccacgtcgga
```

Figure 10 (cont.)

```
 661 gaccggatct tggaaatcaa tggcacgccc atccgaaatg tgccctgga cgagattgac
 721 ctgctgattc aggaaaccag ccgcctgctc cagctgaccc tcgagcatga ccctcacgat
 781 acactgggcc acgggctggg gcctgagacc agcccctga gctctccggc ttatactccc
 841 agcggggagg cgggcagctc tgcccggcag aaacctgtct tcgcaaggac ctgggtcgct
 901 ctgagtccct ccgcgtagtc tgccggccac accgcatctt ccggccgtcg gacctcatcc
 961 acggggaggt gctgggcaag ggctgcttcg gccaggctat caaggtgaca caccgtgaga
1021 caggtgaggt gatggtgatg aaggagctga tccggttcga cgaggagacc cagaggacgt
1081 tcctcaagga ggtgaaggtc atgcgatgcc tggaacaccc caacgtgctc aagttcatcg
1141 gggtgctcta caaggacaag aggctcaact tcatcactga gtacatcaag ggcggcacgc
1201 tccggggcat catcaagagc atggacagcc agtacccatg gagccagaga gtgagctttg
1261 ccaaggacat cgcatcaggg atggcctacc tccactccat gaacatcatc caccgagacc
1321 tcaactccca caactgcctg gtccgcgaga caagaatgt ggtggtgct gacttcgggc
1381 tggcgcgtct catggtggac gagaagactc agcctgaggg cctgcggagc ctcaagaagc
1441 cagaccgcaa gaagcgctac accgtggtgg gcaaccccta ctggatggca cctgagatga
1501 tcaacggccg cagctatgat gagaaggtgg atgtgttctc ctttgggatc gtcctgtgcg
1561 agatcatcgg gcgggtgaac gcagaccctg actacctgcc ccgcaccatg gactttggcc
1621 tcaacgtgcg aggattcctg gaccgctact gccccccaaa ctgcccccg agcttcttcc
1681 ccatcaccgt gcgctgttgc gatctggacc ccgagaagag gccatccttt gtgaagctgg
1741 aacactggct ggagaccctc cgcatgcacc tggccggcca cctgccactg ggcccacagc
1801 tggagcagct ggacagaggt ttctgggaga cctaccggcg cggcgagagc ggactgcctg
1861 cccaccctga ggtccccgac tga
```

SEQ ID NO:99

```
   1 atgcctggct tcgactacaa gttcctggag aagcccaagc gacggctgct gtgcccactg
  61 tgcgggaagc ccatgcgcga gcctgtgcag gtttccacct gcggccaccg tttctgcgat
 121 acctgcctgc aggagttcct cagtgaagga gtcttcaagt gccctgagga ccagcttcct
 181 ctggactatg ccaagatcta cccagacccg gagctggaag tacaagtatt gggcctgcct
 241 atccgctgca tccacagtga ggagggctgc cgctggagtg ggccactacg tcatctacag
 301 ggccacctga atacctgcag cttcaatgtc attccctgcc ctaatcgctg ccccatgaag
 361 ctgagccgcc gtgatctacc tgcacacttg cagcatgact gccccaagcg gcgcctcaag
 421 tgcgagtttt gtggctgtga cttcagtggg gaggcctatg aggtggatga gagttctctg
 481 ggctttggtt atcccaagtt catctcccac caggacattc gaaagcgaaa ctatgtgcgg
 541 gatgatgcag tcttcatccg tgctgctgtt gaactgcccc ggaagatcct cagctga
```

SEQ ID NO:104

```
   1 ttgcaggctg ctgggctggg gctaagggct gctcagtttc cttcagcggg gcactgggaa
  61 gcgccatggc actgcagggc atctcggtcg tggagctgtc cggcctggcc ccggggccgt
 121 tctgtgctat ggtcctggct gacttcgggg cgcgtgtggt acgcgtggac cggcccggct
 181 cccgctacga cgtgagccgc ttgggccggg gcaagcgctc gctagtgctg gacctgaagc
 241 agccgcgggg agccgccgtg ctgcggcgtc tgtgcaagcg gtcggatgtg ctgctggagc
 301 ccttccgccg cggtgtcatg gagaaactcc agctgggccc agagattctg cagcgggaaa
 361 atccaaggct tatttatgcc aggctgagtg gatttggcca gtcaggaagc ttctgccggt
 421 tagctggcca cgatatcaac tatttggctt tgtcaggtgt tctctcaaaa attggcagaa
 481 gtggtgagaa tccgtatgcc ccgctgaatc tcctggctga ctttgctggt ggtggcctta
 541 tgtgtgcact gggcattata atggctcttt ttgaccgcac acgcactggc aagggtcagg
 601 tcattgatgc aaatatggtg gaaggaacag catatttaag ttctttttctg tggaaaactc
 661 agaaatcgag tctgtgggaa gcacctcgag gacagaacat gttggatggt ggagcacctt
 721 tctatacgac ttacaggaca gcagatgggg aattcatggc tgttggagca atagaacccc
 781 agttctacga gctgctgatc aaaggacttg gactaaagtc tgatgaactt cccaatcaga
 841 tgagcatgga tgattggcca gaaatgaaga agaagtttgc agatgtattt gcaaagaaga
 901 cgaaggcaga gtggtgtcaa atctttgacg gcacagatgc ctgtgtgact ccggttctga
 961 cttttgagga ggttgttcat catgatcaca caaggaacg gggctcgttt atcaccagtg
1021 aggagcagga cgtgagcccc cgccctgcac ctctgctgtt aaacacccca gccatccctt
1081 ctttcaaaag ggatcctttc ataggagaac acactgagga gatacttgaa gaatttggat
```

Figure 10 (cont.)

```
1141 tcagccgcga agagatttat cagcttaact cagataaaat cattgaaagt aataaggtaa
1201 aagctagtct ctaacttcca ggcccacggc tcaagtgaat ttgaatactg catttacagt
1261 gtagagtaac acataacatt gtatgcatgg aaacatggag gaacagtatt acagtgtcct
1321 accactctaa tcaagaaaag aattacagac tctgattcta cagtgatgat tgaattctaa
1381 aaatggttat cattagggct tttgatttat aaaactttgg gtacttatac taaattatgg
1441 tagttattct gccttccagt ttgcttgata tatttgttga tattaagatt cttgacttat
1501 attttgaatg ggttctagtg aaaaaggaat gatatattct tgaagacatc gatatacatt
1561 tatttacact cttgattcta caatgtagaa aatgaggaaa tgccacaaat tgtatggtga
1621 taaaagtcac gtgaaacaga gtgattggtt gcatccaggc cttttgtctt ggtgttcatg
1681 atctccctct aagcacattc caaactttag caacagttat cacactttgt aatttgcaaa
1741 gaaaagtttc acctgtattg aatcagaatg ccttcaactg aaaaaaacat atccaaaata
1801 atgaggaaat gtgttggctc actacgtaga gtccagaggg acagtcagtt ttagggttgc
1861 ctgtatccag taactcgggg cctgtttccc cgtgggtctc tgggctgtca gctttccttt
1921 ctccatgtgt ttgatttctc ctcaggctgg tagcaagttc tggatcttat acccaacaca
1981 cagcaacatc cagaaataaa gatct
```

SEQ ID NO:114

```
   1 cggaggcgct gggcgcacgg cgcggagccg gccggagctc gaggccggcg gcggcgggag
  61 agcgaccegg gcggcctcgt agcggggccc cggatcccg agtggcggcc ggagcctcga
 121 aaagagattc tcagcgctga ttttgagatg atgggcttgg gaaacgggcg tcgcagcatg
 181 aagtcgccgc ccctcgtgct ggccgccctg gtggcctgca tcatcgtctt gggcttcaac
 241 tactggattg cgagctcccg gagcgtggac ctccagacac ggatcatgga gctggaaggc
 301 agggtccgca gggcggctgc agagagaggc gccgtggagc tgaagaagaa cgagttccag
 361 ggagagctgg agaagcagcg ggagcagctt gacaaaatcc agtccagcca caacttccag
 421 ctggagagcg tcaacaagct gtaccaggac gaaaaggcgg ttttggtgaa taacatcacc
 481 acaggtgaga ggctcatccg agtgctgcaa gaccagttaa agaccctgca gaggaattac
 541 ggcaggctgc agcaggatgt cctccagttt cagaagaacc agaccaacct ggagaggaag
 601 ttctcctacg acctgagcca gtgcatcaat cagatgaagg aggtgaagga acagtgtgag
 661 gagcgaatag aagaggtcac caaaaagggg aatgaagctg tagcttccag agacctgagt
 721 gaaaacaacg accagagaca gcagctccaa gccctcagtg agcctcagcc caggctgcag
 781 gcagcaggcc tgccacacac agaggtgcca caagggaagg gaaacgtgct tggtaacagc
 841 aagtcccaga caccagcccc cagttccgaa gtggttttgg attcaaagag acaagttgag
 901 aaagaggaaa ccaatgagat ccaggtggtg aatgaggagc ctcagaggga caggctgccg
 961 caggagccag gccgggagca ggtggtggaa gacagacctg taggtggaag aggcttcggg
1021 ggagccggag aactgggcca gaccccacag gtgcaggctg ccctgtcagt gagccaggaa
1081 aatccagaga tggagggccc tgagcgagac cagcttgtca tccccgacgg acaggaggag
1141 gagcaggaag ctgccgggga agggagaaac cagcagaaac tgagaggaga agatgactac
1201 aacatggatg aaaatgaagc agaatctgag acagacaagc aagcagccct ggcagggaat
1261 gacagaaaca tagatgtttt taatgttgaa gatcagaaaa gagacaccat aaatttactt
1321 gatcagcgtg aaaagcggaa tcatacactc tgaattgaac tggaatcaca tatttcacaa
1381 cagggccgaa gagatgacta taaaatgttc atgagggact gaatactgaa aactgtgaaa
1441 tgtactaaat aaaatgtaca tctgaagatg attattgtga aatttagta tgcactttgt
1501 gtaggaaaaa atggaatggt cttttaaaca gcttttgggg gggtactttg gaagtgtcta
1561 ataaggtgtc acaattttg gtagtaggta tttcgtgaga agttcaacac caaaactgga
1621 acatagttct ccttcaagtg ttggcgacag cggggcttcc tgattctgga atataacttt
1681 gtgtaaatta acagccacct atagaagagt ccatctgctg tgaaggagag acagagaact
1741 ctgggttccg tcgtcctgtc cacgtgctgt accaagtgct ggtgccagcc tgttacctgt
1801 tctcactgaa aagtctggct aatgctcact tgtagtcact tctgattctg acaatcaatc
1861 aatcaatggc ctagagcact gactgttaac acaaacgtca ctagcaaagt agcaacagct
1921 ttaagtctaa atacaaagct gttctgtgtg agaatttttt aaaaggctac ttgtataata
1981 acccttgtca ttttaatgt acaaaacgct attaagtggc ttagaatttg aacatttgtg
2041 gtctttattt actttgcttc gtgtgtgggc aaagcaacat cttccctaaa tatatattac
2101 caagaaaagc aagaagcaga ttaggttttt gacaaaacaa acaggccaaa aggggggctga
2161 cctggagcag agcatggtga gaggcaaggc atgagagggc aagtttgttg tggacagatc
```

Figure 10 (cont.)

```
2221 tgtgcctact ttattactgg agtaaaagaa aacaaagttc attgatgtcg aaggatatat
2281 acagtgttag aaattaggac tgtttagaaa aacaggaata caatggttgt ttttatcata
2341 gtgtacacat ttagcttgtg gtaaatgact cacaaaactg attttaaaat caagttaatg
2401 tgaattttga aaattactac ttaatcctaa ttcacaataa caatggcatt aaggtttgac
2461 ttgagttggt tcttagtatt atttatggta aataggctct taccacttgc aaataactgg
2521 ccacatcatt aatgactgac ttcccagtaa ggctctctaa ggggtaagta ggaggatcca
2581 caggatttga gatgctaagg ccccagagat cgtttgatcc aaccctctta ttttcagagg
2641 ggaaaatggg gcctagaagt tacagagcat ctagctggtg cgctggcacc cctggcctca
2701 cacagactcc cgagtagctg ggactacagg cacacagtca ctgaagcagg ccctgtttgc
2761 aattcacgtt gccacctcca acttaaacat tcttcatatg tgatgtcctt agtcactaag
2821 gttaaacttt cccacccaga aaaggcaact tagataaaat cttagagtac tttcatactc
2881 ttctaagtcc tcttccagcc tcactttgag tcctccttgg ggttgatagg aatttctct
2941 tgctttctca ataaagtctc tattcatctc atgtttaatt tgtacgcata gaattgctga
3001 gaaataaaat gttctgttca acttaaaaaa aaaaaaaaaa aa
```

SEQ ID NO:115

```
   1 cgggcgatgc cgcgctgcgg gggggccgca cagccgccgc caccgccacc gccgcgggt
  61 ggggtgggag gggcgggaac gcgcgccgcc gcctccaggg tgggcgcctt tcgccgtgga
 121 cgccgaccgt ccgggacgag ggtttcatca ccttaaatgg ttttgaacca atgaaggtgt
 181 attcccttaa aaagacggac agccatcgt gtgaactata gagtttgtgg acagatttat
 241 attgggttca tagtggcgtc atgcacgcag actcctgcaa gttccctaa gttcttagag
 301 gactgctttg ccttttgatc tgagagttgc aaagttccat aaagaatggc ccttgtggat
 361 aagcacaaag tcaagagaca gcgattggac agaatttgtg aaggtatccg ccccagatc
 421 atgaacggcc ccctgcaccc ccgccccctg gtggcgctgc tggacggccg cgactgcact
 481 gtggagatgc ccatcctgaa ggacctggcc actgtggcct tctgtgacgc gcagtcgacg
 541 caggaaatcc acgagaaggt tctaaacgaa gccgtgggcg ccatgatgta ccacaccatc
 601 accctcacca gggaggacct ggagaagttc aaggccctga gagtgatcgt gcggataggc
 661 agtggctatg caacgtggaa catcaaggct gccggcgagc tcggaattgc cgtgtgcaac
 721 atccgtctg cagccgtgga agagacagcg gactctacca tctgccacat cctcaacctg
 781 taccggagga acacgtggct gtaccaggca ctgcgggaag gcacgcgggt tcagagcgtg
 841 gagcagatcc gcgaggtggc ctcgggagcg gcccgcatcc gtggggagac gctgggcctc
 901 attggctttg gtcgcacggg gcaggcggtt gcagttcgag ccaaggcctt tggattcagc
 961 gtcatatttt atgaccccta cttgcaggat gggatcgagc ggtccctggg cgtgcagagg
1021 gtctacaccc tgcaggattt gctgtatcag agcgactgcg tctccttgca ctgcaatctc
1081 aacgaacata accaccacct catcaatgac tttaccataa agcagatgag gcagggagca
1141 ttccttgtga acgcagcccg tggcggcctg gtggacgaga aagccttagc acaagccctc
1201 aaggagggca ggatacgagg ggcagccctc gacgtgcatg agtcagagcc cttcagcttt
1261 gctcagggtc cgttgaaaga tgccccgaat ctcatctgca ctcctcacac tgcctggtac
1321 agtgagcagg cgtcactgga gatgagggag gcagctgcca ccgagatccg ccgagccatc
1381 acaggtcgca tcccagaaag cttaagaaat tgtgtgaaca aggaattctt tgtcacatca
1441 gcgccttggt cagtaataga ccagcaagca attcatcctg agctcaatgg tgccacatac
1501 agatatccgc caggcatcgt gggtgtggct ccaggaggac ttcctgcagc catggaaggg
1561 atcatccctg gaggcatccc agtgactcac aacctcccga cagtggcaca tccttcccaa
1621 gcgccctctc ccaaccagcc cacaaaacac ggggacaatc gagagcaccc caacgagcaa
1681 tagcagagaa tgccagaagg taatcactca gatacacttg gaccaagag acagtgaaaa
1741 atagatgaac taagagaaaa agaatcggat ggtctttgta actgattctg gacatatgca
1801 tcattgatgt tgcagtgttg aaactacaag agctagaaaa ctgaagatgt cgtctgctta
1861 cggaagcgct gaaagactag gatgtgattt attaacgacc aacttctgtt attgtgtgtt
1921 aagtttttca tctgtgcatc aaatcacaaa agaataaaat agagcttttt cctttatcag
1981 tcccttgggc acagcaggtc ctgaacaccc tgctctacaa tgttgcatca agagttcaaa
2041 caacaaaata aaaatatata gaggaaatc cccatcctgt gacttgagtc ccttaagtct
2101 acaggggctg gtgacctctt tttgctaata ggaaaatcac attactacaa aatggggaga
```

Figure 10 (cont.)

```
2161 aaactgtttg cctgtggtag acacctgcac gcataggatt gaagacagta caggctgctg
2221 tacagagaag cgcctctcac atctgaactg catactgagc gggcaagtcg gttgtaagtt
2281 cagtaaaacc ctctgatgat gcaaaaaaaa aaaaaagta ttaagtttca caagctgttt
2341 gtactcaaat atattttctc agtttcag
```

SEQ ID NO:116

```
   1 catttgggga cgctctcagc tctcggcgca cggcccagct tccttcaaaa tgtctactgt
  61 tcacgaaatc ctgtgcaagc tcagcttgga gggtgatcac tctacacccc caagtgcata
 121 tgggtctgtc aaagcctata ctaactttga tgctgagcgg gatgctttga acattgaaac
 181 agccatcaag accaaaggtg tggatgaggt caccattgtc aacatttga ccaaccgcag
 241 caatgcacag agacaggata ttgccttcgc ctaccagaga aggaccaaaa aggaacttgc
 301 atcagcactg aagtcagcct tatctggcca cctggagacg gtgatttgg gcctattgaa
 361 gacacctgct cagtatgacg cttctgagct aaaagcttcc atgaagggc tgggaaccga
 421 cgaggactct ctcattgaga tcatctgctc cagaaccaac caggagctgc aggaaattaa
 481 cagagtctac aaggaaatgt acaagactga tctggagaag gacattattt cggacacatc
 541 tggtgacttc cgcaagctga tggttgccct ggcaaagggt agaagagcag aggatggctc
 601 tgtcattgat tatgaactga ttgaccaaga tgctcgggat ctctatgacg ctggagtgaa
 661 gaggaaagga actgatgttc ccaagtggat cagcatcatg accgagcgga gcgtgcccca
 721 cctccagaaa gtatttgata ggtacaagag ttacagccct tatgacatgt tggaaagcat
 781 caggaaagag gttaaggag acctggaaaa tgctttcctg aacctggttc agtgcattca
 841 gaacaagccc ctgtatttg ctgatcggct gtatgactcc atgaagggca aggggacgcg
 901 agataaggtc ctgatcagaa tcatggtctc ccgcagtgaa gtggacatgt tgaaaattag
 961 gtctgaattc aagagaaagt acggcaagtc cctgtactat tatatccagc aagacactaa
1021 gggcgactac cagaaagcgc tgctgtacct gtgtggtgga gatgactgaa gcccgacacg
1081 gcctgagcgt ccagaaatgg tgctcaccat gcttccagct aacaggtcta gaaaaccagc
1141 ttgcgaataa cagtccccgt ggccatccct gtgagggtga cgttagcatt accccaacc
1201 tcattttagt tgcctaagca ttgcctggcc ttcctgtcta gtctctcctg taagccaaag
1261 aaatgaacat tccaaggagt tggaagtgaa gtctatgatg tgaaacactt tgcctcctgt
1321 gtactgtgtc ataaacagat gaataaactg aatttgtact tt
```

SEQ ID NO:117

```
   1 gccccaggtg cgcttcccct agagagggat tttccggtct cgtgggcaga ggaacaacca
  61 ggaacttggg ctcagtctcc accccacagt ggggcggatc cgtcccggat aagacccgct
 121 gtctggccct gagtagggtg tgacctccgc agccgcagag gaggagcgca gcccggcctc
 181 gaagaacttc tgcttgggtg gctgaactct gatcttgacc tagagtcatg gccatggcaa
 241 ccaaaggagg tactgtcaaa gctgcttcag gattcaatgc catggaagat gcccagaccc
 301 tgaggaaggc catgaaaggg ctcggcaccg atgaagacgc cattattagc gtccttgcct
 361 accgcaacac cgcccagcgc caggagatca ggacagccta caagagcacc atcggcaggg
 421 acttgataga cgacctgaag tcagaactga gtggcaactt cgagcaggtg attgtgggga
 481 tgatgacgcc cacggtgctg tatgacgtgc aagagctgcg aagggccatg aagggagccg
 541 gcactgatga gggctgccta attgagatcc tggcctcccg gacccctgag gagatccggc
 601 gcataagcca aacctaccag cagcaatatg gacggagcct tgaagatgac attcgctctg
 661 acacatcgtt catgttccag cgagtgctgg tgtctctgtc agctggtggg agggatgaag
 721 gaaattatct ggacgatgct ctcgtgagac aggatgccca ggacctgtat gaggctggag
 781 agaagaaatg ggggacagat gaggtgaaat ttctaactgt tctctgttcc cggaaccgaa
 841 atcacctgtt gcatgtgttt gatgaataca aaaggatatc acagaaggat attgaacaga
 901 gtattaaatc tgaaacatct ggtagctttg aagatgctct gctggctata gtaaagtgca
 961 tgaggaacaa atctgcatat tttgctgaaa agctctataa atcgatgaag ggcttgggca
1021 ccgatgataa caccctcatc agagtgatgg tttctcgagc agaaattgac atgttggata
1081 tccgggcaca cttcaagaga ctctatggaa agtctctgta ctcgttcatc aagggtgaca
1141 catctggaga ctacaggaaa gtactgcttg ttctctgtgg aggagatgat taaaataaaa
```

Figure 10 (cont.)

```
1201 atcccagaag gacaggagga ttctcaacac tttgaatttt tttaacttca tttttctaca
1261 ctgctattat cattatctca gaatgcttat ttccaattaa aacgcctaca gctgcctcct
1321 agaatataga ctgtctgtat tattattcac ctataattag tcattatgat gctttaaagc
1381 tgtacttgca tttcaaagct tataagatat aaatggagat tttaaagtag aaataaatat
1441 gtattccatg ttttaaaag attactttct actttgtgtt tcacagacat tgaatatatt
1501 aaattattcc atatttctt ttcagtgaaa aattttttaa atggaagact gttctaaaat
1561 cacttttttc cctaatccaa ttttagagt ggctagtagt ttcttcattt gaaattgtaa
1621 gcatccggtc agtaagaatg cccatccagt tttctatatt tcatagtcaa agccttgaaa
1681 gcatctacaa atctcttttt ttaggttttg tccatagcat cagttgatcc ttactaagtt
1741 tttcatggga gacttccttc atcacatctt atgttgaaat cactttctgt agtcaaagta
1801 taccaaaacc aatttatctg aactaaattc taaagtatgg ttatacaaac catatacatc
1861 tggttaccaa acataaatgc tgaacattcc atattattat agttaatgtc ttaatccagc
1921 ttgcaagtga atggaaaaaa aaataagctt caaactaggt attctgggaa tgatgtaatg
1981 ctctgaattt agtatgatat aaagaaaact tttttgtgct aaaaatactt tttaaaatca
2041 attttgttga ttgtagtaat ttctatttgc actgtgcctt tcaactccag aaacattctg
2101 aagatgtact tggatttaat taaaaagttc actttgt
```

SEQ ID NO:118

```
   1 gctgctgcgc ccgcggctcc ccagtgcccc gagtgccccg cgggccccgc gagcgggagt
  61 gggacccagc cctaggcaga acccaggcgc cgcgcccggg acgcccgcgg agagagccac
 121 tcccgcccac gtcccatttc gccccccgcg tccggagtcc ccgtggccag atctaaccat
 181 gagctaccct ggctatcccc cgccccagg tggctaccca ccagctgcac caggtggtgg
 241 tccctgggga ggtgctgcct accctcctcc gcccagcatg cccccatcg ggctggataa
 301 cgtggccacc tatgcggggc agttcaacca ggactatctc tgggaatgg cggccaacat
 361 gtctgggaca tttggaggag ccaacatgcc caacctgtac cctggggccc ctgggctgg
 421 ctacccacca gtgccccctg gcggctttgg gcagccccc tctgcccagc agcctgttcc
 481 tccctatggg atgtatccac cccaggagg aaacccaccc tccaggatgc cctcatatcc
 541 gccataccca ggggcccctg tgccgggcca gcccatgcca ccccccggac agcagccccc
 601 aggggcctac cctgggcagc caccagtgac ctaccctgt cagcctccag tgccactccc
 661 tgggcagcag cagccagtgc cgagctaccc aggatacccg gggtctggga ctgtcacccc
 721 cgctgtgccc caacccagt ttggaagccg aggcaccatc actgatgctc ccggctttga
 781 cccctgcga gatgccgagg tcctgcggaa ggccatgaaa ggcttcggga cggatgagca
 841 ggccatcatt gactgcctgg ggagtcgctc caacaagcag cggcagcaga tcctactttc
 901 cttcaagacg gcttacggca aggatttgat caaagatctg aaatctgaac tgtcaggaaa
 961 ctttgagaag acaatcttgg ctctgatgaa gacccagtc ctcttgaca tttatgagat
1021 aaaggaagcc atcaagggg ttggcactga tgaagcctgc ctgattgaga tcctcgcttc
1081 ccgcagcaat gagcacatcc gagaattaaa cagagcctac aaagcagaat caaaaagac
1141 cctggaagag gccattcgaa gcgacacatc agggcacttc cagcggctcc tcatctctct
1201 ctctcaggga aaccgtgatg aaagcacaaa cgtggacatg tcactcgccc agagagatgc
1261 ccaggagctg tatgcggccg gggagaaccg cctgggaaca gacgagtcca gttcaatgc
1321 ggttctgtgc tcccggagcc gggcccacct ggtagcagtt tcaatgagt accagagaat
1381 gacaggccgg gacattgaga agagcatctg ccgggagatg tccggggacc tggaggaggg
1441 catgctggcc gtggtgaaat gtctcaagaa tacccagcc ttctttgcgg agaggctcaa
1501 caaggccatg aggggggcag aacaaaggga ccggaccctg attcgcatca tggtgtctcg
1561 cagcgagacc gacctcctgg acatcagatc agagtataag cggatgtacg gcaagtcgct
1621 gtaccacgac atctcgggag atacttcagg ggattaccgg aagattctgc tgaagatctg
1681 tggtggcaat gactgaacag tgactggtgg ctcacttctg cccacctgcc ggcaacacca
1741 gtgccaggaa aaggccaaaa gaatgtctgt ttctaacaaa tccacaaata gccccgagat
1801 tcaccgtcct agagcttagg cctgtcttcc acccctcctg accgtatag tgtgccacag
1861 gacctgggtc ggtctagaac tctctcagga tgccttttct accccatccc tcacagcctc
1921 ttgctgctaa aatagatgtt tcatttttct gaaaaaaa
```

SEQ ID NO:119

Figure 10 (cont.)

```
   1 ggctcatgct cgggagcgtg gttgagcggc tggcgcggtt gtcctggagc aggggcgcag
  61 gaattctgat gtgaaactaa cagtctgtga gccctggaac ctccactcag agaagatgaa
 121 ggatatcgac ataggaaaag agtatatcat ccccagtcct gggtatagaa gtgtgaggga
 181 gagaaccagc acttctggga cgcacagaga ccgtgaagat tccaagttca ggagaactcg
 241 accgttggaa tgccaagatg ccttggaaac agcagcccga gccgagggcc tctctcttga
 301 tgcctccatg cattctcagc tcagaatcct ggatgaggag catcccaagg gaaagtacca
 361 tcatggcttg agtgctctga agcccatccg gactacttcc aaacaccagc acccagtgga
 421 caatgctggg cttttttcct gtatgacttt ttcgtggctt tcttctctgg cccgtgtggc
 481 ccacaagaag ggggagctct caatggaaga cgtgtggtct ctgtccaagc acgagtcttc
 541 tgacgtgaac tgcagaagac tagagagact gtggcaagaa gagctgaatg aagttgggcc
 601 agacgctgct tccctgcgaa gggttgtgtg gatcttctgc cgcaccagcc tcatcctgtc
 661 catcgtgtgc ctgatgatca cgcagctggc tggcttcagt ggaccagcct tcatggtgaa
 721 acacctcttg gagtataccc aggcaacaga gtctaacctg cagtacagct tgttgttagt
 781 gctgggcctc ctcctgacgg aaatcgtgcg gtcttggtcg cttgcactga cttgggcatt
 841 gaattaccga accggtgtcc gcttgcgggg ggccatccta accatggcat ttaagaagat
 901 ccttaagtta aagaacatta aagagaaatc cctgggtgag ctcatcaaca tttgctccaa
 961 cgatgggcag agaatgtttg aggcagcagc cgttggcagc ctgctggctg gaggaccgt
1021 tgttgccatc ttaggcatga tttataatgt aattattctg ggaccaacag gcttcctggg
1081 atcagctgtt tttatcctct tttacccagc aatgatgttt gcatcacggc tcacagcata
1141 tttcaggaga aaatgcgtgg ccgccacgga tgaacgtgtc cagaagatga atgaagttct
1201 tacttacatt aaatttatca aaatgtatgc ctgggtcaaa gcattttctc agagtgttca
1261 aaaaatccgc gaggaggagc gtcggatatt ggaaaaagct gggtacttcc agagcatcac
1321 tgtgggtgtg gctcccattg tggtggtgat tgccagcgtg gtgaccttct ctgttcatat
1381 gaccctgggc ttcgatctga cagcagcaca ggctttcaca gtggtgacag tcttcaattc
1441 catgacttt gctttgaaag taacaccgtt ttcagtaaag tccctctcag aagcctcagt
1501 ggctgttgac agatttaaga gtttgtttct aatggaagag gttcacatga taaagaacaa
1561 accagccagt cctcacatca agatagagat gaaaaatgcc accttggcat gggactcctc
1621 ccactccagt atccagaact cgcccaagct gacccccaaa atgaaaaaag acaagagggc
1681 ttccaggggc aagaaagaga aggtgaggca gctgcagcgc actgagcatc aggcggtgct
1741 ggcagagcag aaaggccacc tcctcctgga cagtgacgag cggcccagtc ccgaagagga
1801 agaaggcaag cacatccacc tgggccacct gcgcttacag aggacactgc acagcatcga
1861 tctggagatc caagagggta aactggttgg aatctgtggc agtgtgggaa gtggaaaaac
1921 ctctctcatt tcagccattt taggccagat gacgcttcta gagggcagca ttgcaatcag
1981 tggaaccttc gcttatgtgg cccagcaggc ctggatcctc aatgctactc tgagagacaa
2041 catcctgttt gggaaggaat atgatgaaga aagatacaac tctgtgctga acagctgctg
2101 cctgaggcct gacctggcca ttcttcccag cagcgacctg acggagattg gagagcgagg
2161 agccaacctg agcggtgggc agcgccagag gatcagcctt gcccgggcct tgtatagtga
2221 caggagcatc tacatcctgg acgacccct cagtgcctta gatgccatg tgggcaacca
2281 catcttcaat agtgctatcc ggaaacatct caagtccaag acagttctgt ttgttaccca
2341 ccagttacag tacctggttg actgtgatga agtgatcttc atgaaagagg ctgtattac
2401 ggaaagaggc acccatgagg aactgatgaa tttaaatggt gactatgcta cccatttaa
2461 taacctgttg ctgggagaga caccgccagt tgagatcaat tcaaaaaagg aaaccagtgg
2521 ttcacagaag aagtcacaag acaagggtcc taaaacagga tcagtaaaga aggaaaaagc
2581 agtaaagcca gaggaagggc agcttgtgca gctggaagag aaagggcagg gttcagtgcc
2641 ctggtcagta tatggtgtct acatccaggc tgctgggggc cccttggcat tcctggttat
2701 tatggccctt ttcatgctga atgtaggcag caccgcctc agcacctggt ggttgagtta
2761 ctggatcaag caaggaagcg ggaacaccac tgtgactcga ggaacgaga cctcggtgag
2821 tgacagcatg aaggacaatc ctcatatgca gtactatgcc agcatctacg ccctctccat
2881 ggcagtcatg ctgatcctga aagccattcg aggagttgtc tttgtcaagg gcacgctgcg
2941 agcttcctcc cggctgcatg acgagctttt ccgaaggatc ttcgaagcc ctatgaagtt
3001 ttttgacacg accccacag ggaggattct caacaggttt tccaaagaca tggatgaagt
3061 tgacgtgcgg ctgccgttcc aggccgagat gttcatccag aacgttatcc tggtgttctt
3121 ctgtgtggga atgatcgcag gagtcttccc gtggttcctt gtggcagtgg ggccccttgt
```

Figure 10 (cont.)

```
3181 catcctctttt tcagtcctgc acattgtctc cagggtcctg attcgggagc tgaagcgtct
3241 ggacaatatc acgcagtcac ctttcctctc ccacatcacg tccagcatac agggccttgc
3301 caccatccac gcctacaata aagggcagga gtttctgcac agataccagg agctgctgga
3361 tgacaaccaa gctccttttt ttttgtttac gtgtgcgatg cggtggctgg ctgtgcggct
3421 ggacctcatc agcatcgccc tcatcaccac cacggggctg atgatcgttc ttatgcacgg
3481 gcagattccc ccagcctatg cgggtctcgc catctcttat gctgtccagt taacggggct
3541 gttccagttt acggtcagac tggcatctga gacagaagct cgattcacct cggtggagag
3601 gatcaatcac tacattaaga ctctgtcctt ggaagcacct gccagaatta agaacaaggc
3661 tccctcccct gactggcccc aggagggaga ggtgaccttt gagaacgcag agatgaggta
3721 ccgagaaaac ctccctctcg tcctaaagaa agtatccttc acgatcaaac ctaaagagaa
3781 gattggcatt gtgggcgga caggatcagg gaagtcctcg ctggggatgg ccctcttccg
3841 tctggtggag ttatctggag gctgcatcaa gattgatgga gtgagaatca gtgatattgg
3901 ccttgccgac ctccgaagca aactctctat cattcctcaa gagccggtgc tgttcagtgg
3961 cactgtcaga tcaaatttgg acccccttcaa ccagtacact gaagaccaga tttgggatgc
4021 cctggagagg acacacatga aagaatgtat tgctcagcta cctctgaaac ttgaatctga
4081 agtgatggag aatggggata acttctcagt gggggaacgg cagctcttgt gcatagctag
4141 agccctgctc cgccactgta agattctgat tttagatgaa gccacagctg ccatggacac
4201 agagacagac ttattgattc aagagaccat ccgagaagca tttgcagact gtaccatgct
4261 gaccattgcc catcgcctgc acacggttct aggctccgat aggattatgg tgctggccca
4321 gggacaggtg gtggagtttg acacccatc ggtccttctg tccaacgaca gttcccgatt
4381 ctatgccatg tttgctgctg cagagaacaa ggtcgctgtc aagggctgac tcctccctgt
4441 tgacgaagtc tcttttcttt agcatttgc cattcctgc ctggggcggg cccctcatcg
4501 cgtcctccta ccgaaacctt gcctttctcg attttatctt tcgcacagca gttccggatt
4561 ggcttgtgtg tttcactttt agggagagtc atattttgat tattgtattt attccatatt
4621 catgtaaaca aaatttagtt tttgttctta attgcactct aaaaggttca gggaaccgtt
4681 attataattg tatcagaggc ctataatgaa gctttatacg tgtagctata tctatatata
4741 attctgtaca tagcctatat ttacagtgaa aatgtaagct gtttattta tattaaaata
4801 agcactgtgc taataacagt gcatattcct ttctatcatt tttgtacagt ttgctgtact
4861 agagatctgg ttttgctatt agactgtagg aagagtagca tttcattctt ctctagctgg
4921 tggtttcacg gtgccaggtt ttctgggtgt ccaaaggaag acgtgtggca atagtgggcc
4981 ctccgacagc cccctctgcc gcctcccac ggccgctcca ggggtggctg gagacgggtg
5041 ggcggctgga gaccatgcag agcgccgtga gttctcaggg ctcctgcctt ctgtcctggt
5101 gtcacttact gtttctgtca ggagagcagc ggggcgaagc ccaggcccct tttcactccc
5161 tccatcaaga atggggatca cagagacatt cctccgagcc ggggagtttc tttcctgcct
5221 tcttcttttt gctgttgttt ctaaacaaga atcagtctat ccacagagag tcccactgcc
5281 tcaggttcct atggctggcc actgcacaga gctctccagc tccaagacct gttggttcca
5341 agccctggag ccaactgctg cttttgaggg tggcactttt tcatttgcct attcccacac
5401 ctccacagtt cagtggcagg gctcaggatt tcgtgggtct gtttccttt ctcaccgcag
5461 tcgtcgcaca gtctctctct ctctctcccc tcaaagtctg aactttaag cagctcttgc
5521 taatcagtgt ctcacactgg cgtagaagtt tttgtactgt aaagagacct acctcaggtt
5581 gctggttgct gtgtggtttg gtgtgttccc gcaaacccc tttgtgctgt ggggctggta
5641 gctcaggtgg gcgtggtcac tgctgtcatc aattgaatgg tcagcgttgc atgtcgtgac
5701 caactagaca ttctgtcgcc ttagcatgtt tgctgaacac cttgtggaag caaaaatctg
5761 aaaatgtgaa taaaattatt ttggattttg t
```

SEQ ID NO:120

```
  1 aaacttcccg cacgcgttac aggagccagg tcggtataag cgccacgcct cgccgccgt
 61 caagctgtcc acatccctgg cctcagcccg ccacatcacc ctgacctgct tacgcccaga
121 tttttcttcaa tcacatctga ataaatcact tgaagaaagc ttatagcttc attgcaccat
181 gtgtggcatt tgggcgctgt ttggcagtga tgattgcctt tctgttcagt gtctgagtgc
241 tatgaagatt gcacacagag gtccagatgc attccgtttt gagaatgtca atggatacac
301 caactgctgc tttggattc accggttggc ggtagttgac ccgctgtttg gaatgcagcc
361 aattcgagtg aagaaatatc cgtattgtgt gctctgttac aatggtgaaa tctacaacca
421 taagaagat caacagcatt ttgaatttga ataccagacc aaagtggatg gtgagataat
```

Figure 10 (cont.)

```
 481 ccttcatctt tatgacaaag gaggaattga gcaaacaatt tgtatgttgg atggtgtgtt
 541 tgcatttgtt ttactggata ctgccaataa gaaagtgttc ctgggtagag atacatatgg
 601 agtcagacct ttgtttaaag caatgacaga agatggattt ttggctgtat gttcagaagc
 661 taaaggtctt gttacattga agcactccgc gactcccttt ttaaaagtgg agccttttct
 721 tcctggacac tatgaagttt tggatttaaa gccaaatggc aaagttgcat ccgtggaaat
 781 ggttaaatat catcactgtc gggatgtacc cctgcacgcc ctctatgaca atgtggagaa
 841 actcttttcca ggttttgaga tagaaactgt gaagaacaac ctcaggatcc tttttaataa
 901 tgctgtaaag aaacgtttga tgacagacag aaggattggc tgcctttat caggggcttg
 961 ggactccagc ttggttgctg ccactctgtt gaagcagctg aagaagccc aagtacagta
1021 tcctctccag acatttgcaa ttggcatgga agacagcccc gatttactgg ctgctagaaa
1081 ggtggcagat catattggaa gtgaacatta tgaagtcctt tttaactctg aggaaggcat
1141 tcaggctctg gatgaagtca tatttccctt ggaaacttat gacattacaa cagttcgtgc
1201 ttcagtaggt atgtatttaa tttccaagta tattcggaag aacacagata gcgtggtgat
1261 cctctctgga gaaggatcag atgaacttac gcagggttac atatattttc acaaggctcc
1321 ttctcctgaa aaagccgagg aggagagtga gaggcttctg agggaactct atttgtttga
1381 tgttctccgc gcagatcgaa ctactgctgc ccatggtctt gaactgagag tcccatttct
1441 agatcatcga ttttttttcct attacttgtc tctgccacca gaaatgagaa ttccaaagaa
1501 tgggatagaa aaacatctcc tgagagagac gtttgaggat tccaatctga tacccaaaga
1561 gattctctgg cgaccaaaag aagccttcag tgatggaata acttcagtta agaattcctg
1621 gtttaagatt ttacaggaat acgttgaaca tcaggttgat gatgcaatga tggcaaatgc
1681 agcccagaaa tttcccttca atactcctaa aaccaaagaa ggatattact accgtcaagt
1741 ctttgaacgc cattaccag gccgggctga ctggctgagc cattactgga tgcccaagtg
1801 gatcaatgcc actgacccttt ctgcccgcac gctgacccac tacaagtcag ctgtcaaagc
1861 ttaggtggtc tttatgctgt aatgtgaaag caaatatttc ttcgtgttgg atgggactg
1921 tgggtagata ggggaacaat gagagtcaac tcaggctaac ttgggtttga aaaaaataaa
1981 attcctaaat tt
```

SEQ ID NO:121

```
   1 aggttcaagt ggagctctcc taaccgacgc gcgtctgtgg agaagcggct tggtcggggg
  61 tggtctcgtg gggtcctgcc tgtttagtcg ctttcagggt tcttgagccc cttcacgacc
 121 gtcaccatgg aagtgtcacc attgcagcct gtaaatgaaa atatgcaagt caacaaaata
 181 aagaaaaatg aagatgctaa gaaaagactg tctgttgaaa gaatctatca aaagaaaaca
 241 caattggaac atattttgct ccgcccagac acctacattg gtctgtgga attagtgacc
 301 cagcaaatgt gggtttacga tgaagatgtt ggcattaact atagggaagt cacttttgtt
 361 cctggtttgt acaaaatctt tgatgagatt ctagttaatg ctgcggacaa caaacaaagg
 421 gacccaaaaa tgtcttgtat tagagtcaca attgatccgg aaaacaattt aattagtata
 481 tggaataatg gaaaaggtat tcctgttgtt gaacacaaag ttgaaaagat gtatgtccca
 541 gctctcatat ttggacagct cctaacttct agtaactatg atgatgatga aagaaagtg
 601 acaggtggtc gaaatggcta tggagccaaa ttgtgtaaca tattcagtac caaatttact
 661 gtggaaacag ccagtagaga atacaagaaa atgttcaaac agacatggat ggataatatg
 721 ggaagagctg gtgagatgga actcaagccc ttcaatggag aagattatac atgtatcacc
 781 tttcagcctg atttgtctaa gtttaaaatg caaagcctgg acaaagatat tgttgcacta
 841 atggtcagaa gagcatatga tattgctgga tccaccaaag atgtcaaagt ctttcttaat
 901 ggaaataaac tgccagtaaa aggatttcgt agttatgtgg acatgtattt gaaggacaag
 961 ttggatgaaa ctggtaactc cttgaaagta atacatgaac aagtaaacca caggtgggaa
1021 gtgtgtttaa ctatgagtga aaaaggcttt cagcaaatta gctttgtcaa cagcattgct
1081 acatccaagg gtggcagaca tgttgattat gtagctgatc agattgtgac taaacttgtt
1141 gatgttgtga agaagaagaa caagggtggt gttgcagtaa agcacatca ggtgaaaaat
1201 cacatgtgga tttttgtaaa tgccttaatt gaaaacccaa cctttgactc tcagacaaaa
1261 gaaacatga ctttacaacc caagagcttt ggatcaacat gccaattgag tgaaaaattt
1321 atcaaagctg ccattggctg tggtattgta gaaagcatac taaactgggt gaagtttaag
1381 gcccaagtcc agttaaacaa gaagtgttca gctgtaaaac ataatagaat caagggaatt
```

Figure 10 (cont.)

```
1441 cccaaactcg atgatgccaa tgatgcaggg ggccgaaact ccactgagtg tacgcttatc
1501 ctgactgagg gagattcagc caaaactttg gctgtttcag gccttggtgt ggttgggaga
1561 gacaaatatg gggttttccc tcttagagga aaaatactca atgttcgaga agcttctcat
1621 aagcagatca tggaaaatgc tgagattaac aatatcatca agattgtggg tcttcagtac
1681 aagaaaaact atgaagatga agattcattg aagacgcttc gttatgggaa gataatgatt
1741 atgacagatc aggaccaaga tggttcccac atcaaaggct tgctgattaa ttttatccat
1801 cacaactggc cctctcttct gcgacatcgt tttctggagg aatttatcac tcccattgta
1861 aaggtatcta aaaacaagca agaaatggca ttttacagcc ttcctgaatt tgaagagtgg
1921 aagagttcta ctccaaatca taaaaaatgg aaagtcaaat attacaaagg tttgggcacc
1981 agcacatcaa aggaagctaa agaatacttt gcagatatga aaagacatcg tatccagttc
2041 aaatattctg gtcctgaaga tgatgctgct atcagcctgg cctttagcaa aaaacagata
2101 gatgatcgaa aggaatggtt aactaatttc atggaggata gaagacaacg aaagttactt
2161 gggcttcctg aggattactt gtatggacaa actaccacat atctgacata taatgacttc
2221 atcaacaagg aacttatctt gttctcaaat tctgataacg agagatctat cccttctatg
2281 gtggatggtt tgaaaccagg tcagagaaag gttttgttta cttgcttcaa acggaatgac
2341 aagcgagaag taaaggttgc ccaattagct ggatcagtgg ctgaaatgtc ttcttatcat
2401 catggtgaga tgtcactaat gatgaccatt atcaatttgg ctcagaattt tgtgggtagc
2461 aataatctaa acctcttgca gcccattggt cagtttggta ccaggctaca tggtggcaag
2521 gattctgcta gtccacgata catctttaca atgctcagct ctttggctcg attgttattt
2581 ccaccaaaag atgatcacac gttgaagttt tatatgatg acaaccagcg tgttgagcct
2641 gaatggtaca ttcctattat tcccatggtg ctgataaatg gtgctgaagg aatcggtact
2701 gggtggtcct gcaaaatccc caactttgat gtgcgtgaaa ttgtaaataa catcaggcgt
2761 ttgatggatg gagaagaacc tttgccaatg cttccaagtt acaagaactt caagggtact
2821 attgaagaac tggctccaaa tcaatatgtg attagtggtg aagtagctat tcttaattct
2881 acaaccattg aaatctcaga gcttcccgtc agaacatgga cccagacata caaagaacaa
2941 gttctagaac ccatgttgaa tggcaccgag aagacacctc ctctcataac agactatagg
3001 gaataccata cagataccac tgtgaaattt gttgtgaaga tgactgaaga aaaactggca
3061 gaggcagaga gagttggact acacaaagtc ttcaaactcc aaactagtct cacatgcaac
3121 tctatggtgc ttttgacca cgtaggctgt taaagaaat atgacacggt gttggatatt
3181 ctaagagact tttttgaact cagacttaaa tattatggat taagaaaaga atggctccta
3241 ggaatgcttg gtgctgaatc tgctaaactg aataatcagg ctcgctttat cttagagaaa
3301 atagatggca aaataatcat tgaaaataag cctaagaaag aattaattaa agttctgatt
3361 cagaggggat atgattcgga tcctgtgaag gcctggaaag aagcccagca aaaggttcca
3421 gatgaagaag aaaatgaaga gagtgacaac gaaaaggaaa ctgaaaagag tgactccgta
3481 acagattctg gaccaacctt caactatctt cttgatatgc ccctttggta tttaaccaag
3541 gaaaagaaag atgaactctg caggctaaga aatgaaaaag aacaagagct ggacacatta
3601 aaaagaaaga gtccatcaga tttgtggaaa gaagcttgg ctacatttat tgaagaattg
3661 gaggctgttg aagccaagga aaaacaagat gaacaagtcg gacttcctgg aaagggggg
3721 aaggccaagg ggaaaaaaac acaaatggct gaagttttgc cttctccgcg tggtcaaaga
3781 gtcattccac gaataaccat agaaatgaaa gcagaggcag aaaagaaaaa taaaaagaaa
3841 attaagaatg aaaatactga aggaagccct caagaagatg gtgtggaact agaaggccta
3901 aaacaaagat tagaaaagaa acagaaaaga gaaccaggta caaagacaaa gaaacaaact
3961 acattggcat ttaagccaat caaaaaagga aagaagagaa atccctggtc tgattcagaa
4021 tcagatagga gcagtgacga aagtaatttt gatgtccctc cacgagaaac agagccacgg
4081 agagcagcaa caaaaacaaa attcacaatg gatttggatt cagatgaaga tttctcagat
4141 tttgatgaaa aaactgatga tgaagatttt gtccatcag atgctagtcc acctaagacc
4201 aaaacttccc caaaacttag taacaaagaa ctgaaaccac agaaaagtgt cgtgtcagac
4261 cttgaagctg atgatgttaa gggcagtgta ccactgtctt caagccctcc tgctacacat
4321 ttcccagatg aaactgaaat tacaaaccca gttcctaaaa agaatgtgac agtgaagaag
4381 acagcagcaa aaagtcagtc ttccacctcc actaccggtg ccaaaaaag gctgcccca
4441 aaaggaacta aagggatcc agctttgaat tctggtgtct ctcaaaagcc tgatcctgcc
4501 aaaaccaaga atcgccgcaa aaggaagcca tccacttctg atgattctga ctctaatttt
4561 gagaaaattg tttcgaaagc agtcacaagc aagaaatcca aggggagag tgatgacttc
4621 catatggact tgactcagc tgtggctcct cgggcaaaat ctgtacgggc aaagaaacct
```

Figure 10 (cont.)

```
4681 ataaagtacc tggaagagtc agatgaagat gatctgtttt aaaatgtgag gcgattattt
4741 taagtaatta tcttaccaag cccaagactg gttttaaagt tacctgaagc tcttaacttc
4801 ctcccctctg aatttagttt ggggaaggtg tttttagtac aagacatcaa agtgaagtaa
4861 agcccaagtg ttctttagct ttttataata ctgtctaaat agtgaccatc tcatgggcat
4921 tgttttcttc tctgctttgt ctgtgtttg agtctgcttt cttttgtctt taaaacctga
4981 tttttaagtt cttctgaact gtagaaatag ctatctgatc acttcagcgt aaagcagtgt
5041 gtttattaac catccactaa gctaaaacta gagcagtttg atttaaaagt gtcactcttc
5101 ctcctttct actttcagta gatatgagat agagcataat tatctgtttt atcttagttt
5161 tatacataat ttaccatcag atagaacttt atggttctag tacagatact ctactacact
5221 cagcctctta tgtgccaagt tttctttaa gcaatgagaa attgctcatg ttcttcatct
5281 tctcaaatca tcagaggcca aagaaaaaca ctttggctgt gtctataact tgacacagtc
5341 aatagaatga agaaaattag agtagttatg tgattatttc agctcttgac ctgtcccctc
5401 tggctgcctc tgagtctgaa tctcccaaag agagaaacca atttctaaga ggactggatt
5461 gcagaagact cggggacaac atttgatcca agatcttaaa tgttatattg ataaccatgc
5521 tcagcaatga gctattagat tcatttggg aaatctccat aatttcaatt tgtaaacttt
5581 gttaagacct gtctacattg ttatatgtgt gtgacttgag taatgttatc aacgttttg
5641 taaatattta ctatgttttt ctattagcta aattccaaca attttgtact ttaataaa
```

SEQ ID NO:122

```
   1 gcgccatgga gcagtggcgg cagtgcggcc gctggctcat cgattgcaag gtcctgccgc
  61 ccaaccacg ggtggtgtgg ccctcggccg tggtcttcga cctggcgcag gcgctgcgcg
 121 acggggtcct tctgtgccag ctgctgcaca acctctcccc cggctccatc gacctcaagg
 181 acatcaactt ccggccgcag atgtccagt ttctgtgttt gaagaacata cgcaccttcc
 241 tgaaagtctg ccacgataaa tttggattaa ggaacagcga gctgtttgac ccctttgacc
 301 tcttcgatgt gcgagacttt ggaaaggtca tctccgcggt gtcgaggctc tccctgcaca
 361 gcatcgcgca gaacaaaggg atcaggcctt ttccctcaga ggagaccaca gagaatgacg
 421 atgacgtcta ccgcagcctg gaggagctgg ccgacgagca tgacctgggg gaggacatct
 481 acgactgcgt cccgtgtgag gatggagggg acgacatcta cgaggacatc atcaaggtgg
 541 aggtgcagca gcccatgatt agatacatgc agaaaatggg catgactgaa gatgacaaga
 601 ggaactgctg cctgctggag atccaggaga ccgaggccaa gtactaccgc accctggagg
 661 acattgagaa gaactacatg agcccctgc ggctggtgct gagcccggcg gacatggcag
 721 ctgtcttcat taacctggag gacctgatca aggtgcatca cagcttcctg agggccatcg
 781 acgtgtccgt gatggtgggg ggcagcacgc tggccaaggt cttcctcgat ttcaaggaaa
 841 ggcttctgat ctacggggag tactgcagcc acatggagca cgcccagaac acactgaacc
 901 agctcctggc cagccgggag gacttcaggc agaaagtcga ggagtgcaca ctgaaggtcc
 961 aggatggaaa atttaagctg caagacctgc tggtggtccc catgcagagg gtgctcaaat
1021 accacctgct cttgaaggag cttctgagcc attctgcgga acggcctgag aggcagcagc
1081 tcaaagaagc actggaagcc atgcaggact ggcgatgta catcaatgaa gttaaacggg
1141 acaaggagac cttgaggaaa atcagcgaat tcagagttc tatagaaaat ttgcaagtga
1201 aactggagga atttggaaga ccaaagattg acggggaact gaaagtccgg tccatagtca
1261 accacaccaa gcaggacagg tacttgttcc tgtttgacaa ggtggtcatc gtctgcaagc
1321 ggaagggcta cagctacgag ctcaaggaga tcatcgagct gctgttccac aagatgaccg
1381 acgacccat gaacaacaag gacgtcaaga agtctcacgg gaaaatgtgg tcctacggct
1441 tctacctaat tcaccttcaa ggaaagcagg gcttccagtt tttctgcaaa acagaagata
1501 tgaagaggaa gtggatggag cagtttgaga tggccatgtc aaacatcaag ccagacaaag
1561 ccaatgccaa ccaccacagt ttccagatgt acgtttga caagaccacc aactgcaaag
1621 cctgcaaaat gttcctcagg ggcaccttct accagggata catgtgtacc aagtgtggcg
1681 tcggggcaca caaggagtgc ctggaagtga tacctccctg caagttcact tctcctgcag
1741 atctggacgc ctccggagcg ggaccaggtc ccaagatggt ggccatgcag aattaccatg
1801 gcaacccagc ccctcccggg aagcctgtgc tgaccttcca gacgggcgac gtgcttgagc
1861 tgctgagggg cgaccctgag tctccgtggt ggagggtcg tctggtacaa accaggaagt
1921 cagggtattt ccccagctca tctgtgaagc cctgccctgt ggatggaagg ccgcccatca
1981 gccggccgcc atcccgggag atcgactaca ctgcatacccc ctggtttgca ggtaacatgg
2041 agaggcagca gacggacaac ctgctcaagt cccacgccag cgggacctac ctgatcaggg
```

Figure 10 (cont.)

```
2101 agcggcctgc cgaggctgag cgctttgcaa taagcatcaa gttcaatgat gaggtgaagc
2161 acatcaaggt ggtggagaag gacaactgga tccacatcac agaggccaag aaattcgaca
2221 gcctcctgga gttggtggag tactaccagt gccactcact gaaggagagc ttcaagcagc
2281 tggacaccac actcaagtac ccctacaagt cccgggaacg ttcggcctcc agggcctcca
2341 gccggtcccc agcttcctgt gcttcctaca actttctttt tctcagtcct cagggcctca
2401 gctttgcttc tcagggcccc tccgctccct tctggtcagt gttcacgccc cgcgtcatcg
2461 gcacagctgt ggccaggtat aactttgccg cccgagatat gagggagctt tcgctgcggg
2521 agggtgacgt ggtgaggatc tacagccgca tcggcggaga ccagggctgg tggaagggcg
2581 agaccaacgg acggattggc tggtttcctt caacgtacgt agaagaggag ggcatccagt
2641 gacggcagga acgtggacaa gactcgcaga ttttcttggg agagtcactc cagccctgaa
2701 gtctgtctct agctcctctg tgactcagag gggaaatacc aacctcccag tct
```

FIGURE 20
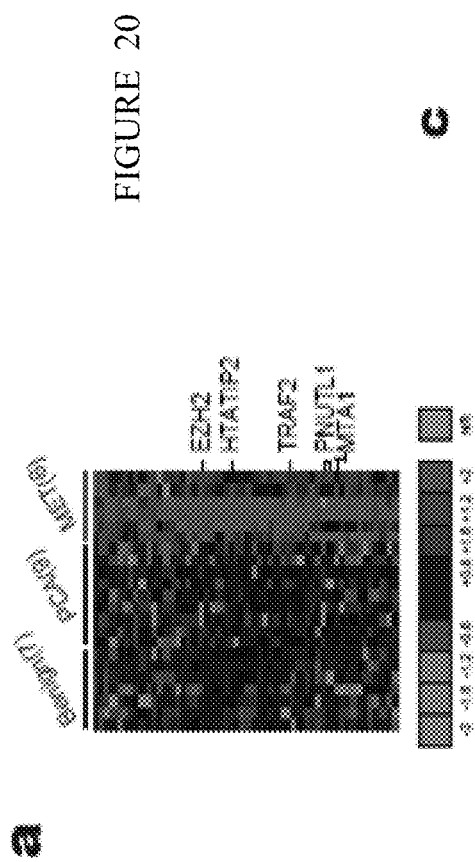
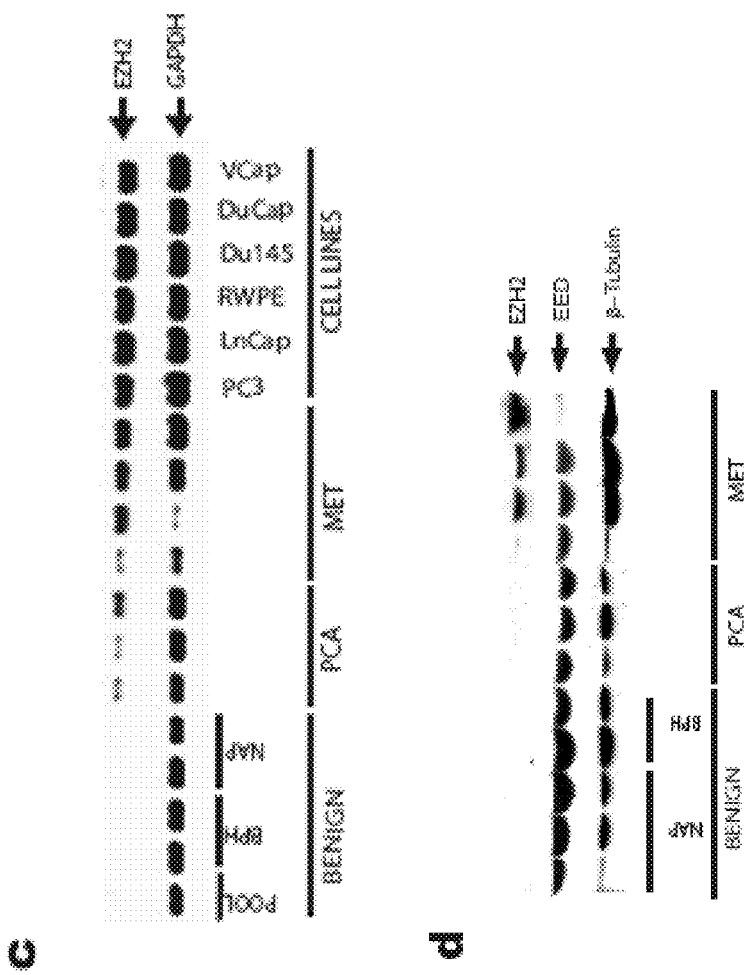

FIGURE 22A - C
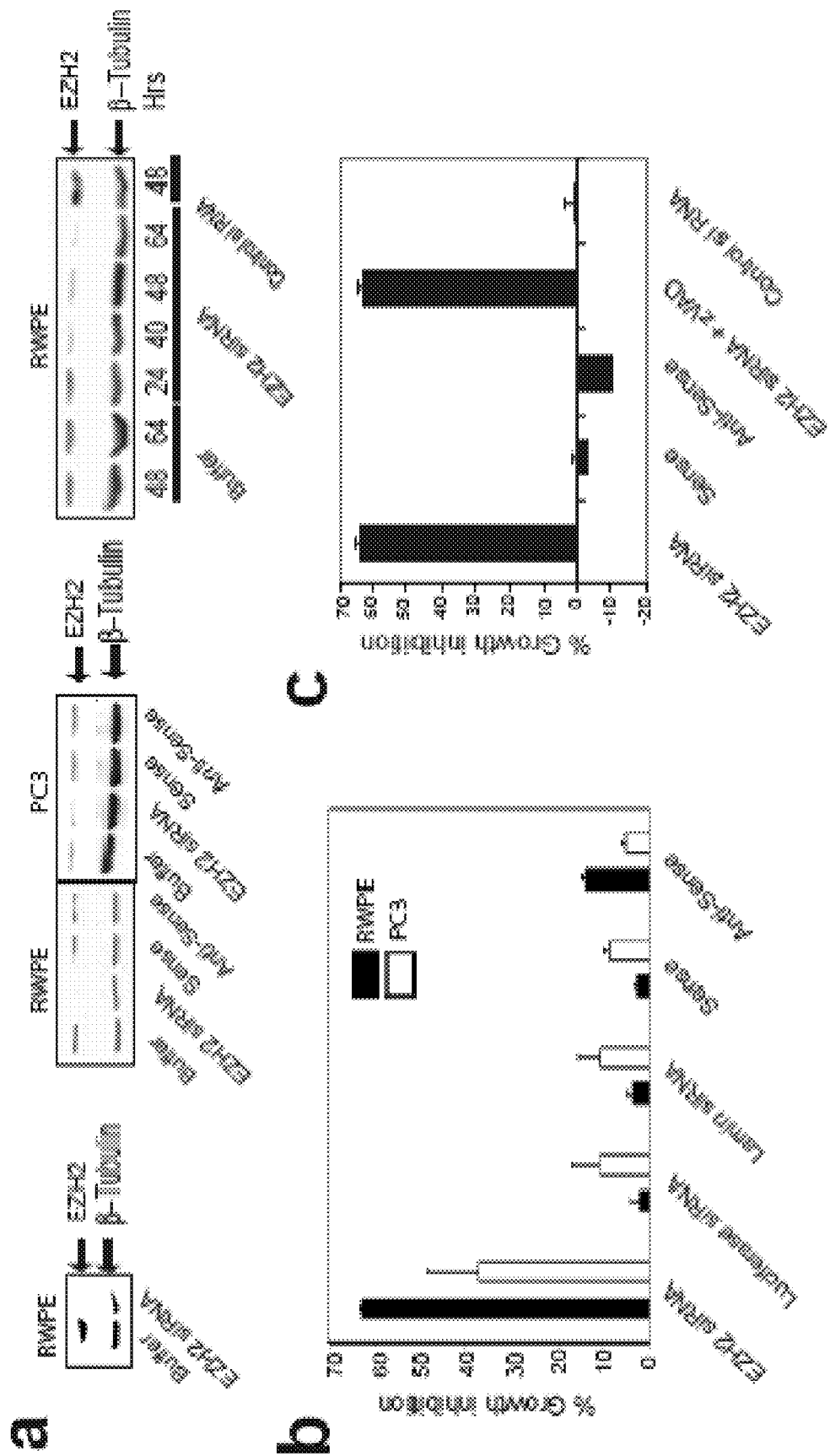

Immunoblot Analysis for AMACR in Prostate Cancer and Normal Sera

IMMUNOBLOT ANALYSIS
OF URINE SAMPLES FOR AMACR

U1-U10 : FEMALES WITH BLADDER CANCER
U11-U20 : MALES WITH BLADDER CANCER
AND INC PROSTATE

Figure 31
a
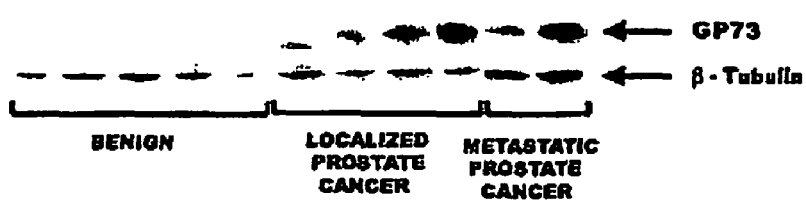
b
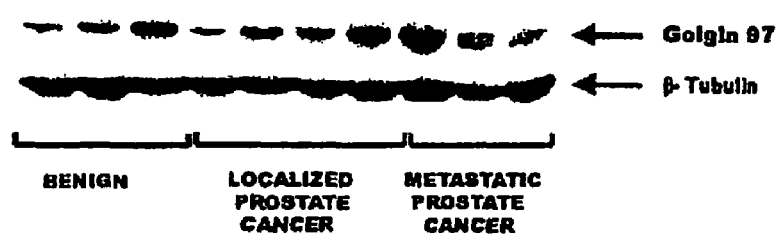

Figure 32
a) 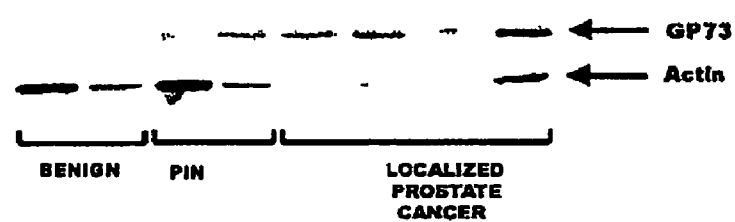
b) 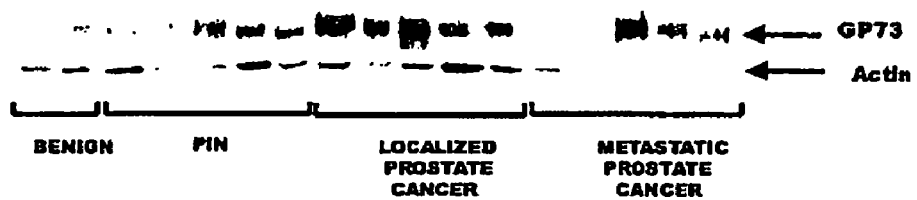

EXPRESSION PROFILE OF PROSTATE CANCER

This application is a continuation in part of copending application Ser. No. 11/343,797, filed Jan. 31, 2006, which is a divisional of application Ser. No. 10/210,120, filed Aug. 1, 2002, now U.S. Pat. No. 7,229,774, which claims priority to U.S. Provisional Application Ser. No. 60/309,581 filed Aug. 2, 2001 and U.S. Provisional Application Ser. No. 60/334,468 filed Nov. 15, 2001, each of which is herein incorporated by reference in its entirety.

This invention was made with government support under Grant No. 5 P50 CA69568 awarded by the National Institutes of Health. The Government has certain rights in the invention.

FIELD OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al, Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166:402 [2001]). Thus, development of additional serum and tissue biomarkers to supplement PSA screening is needed.

SUMMARY OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

In some embodiments, the present invention provides a method of screening compounds, comprising contacting a prostate cell sample with a test compound (e.g., a drug, an siRNA or an antisense RNA); and detecting a change in EZH2 expression in the prostate cell sample in the presence of the test compound relative to the absence of the test compound. In some embodiments, the detecting comprises detecting EZH2 mRNA. In other embodiments, the detecting comprises detecting EZH2 polypeptide. In some embodiments, the cell is in vitro. In other embodiments, the cell is in vivo (e.g., in a non human animal). In some embodiments, the non-human animal comprises an exogenous EZH2 gene (e.g., overexpresses the exogenous EZH2 gene). In some embodiments, the animal exhibits symptoms of prostate cancer and the test compound reduces or eliminates the symptoms. In some embodiments, the detecting comprises detecting only a change in EZH2 expression. In some embodiments, detecting comprises the use of an EZH2 specific detection reagent.

In other embodiments, the present invention provides a method of screening compounds, comprising: contacting a prostate cell sample with a test compound; and detecting a change in at least one activity of EZH2 in the prostate cell sample in the presence of the test compound relative to the absence of the test compound.

In still further embodiments, the present invention provides a non-human animal (e.g., a mouse) comprising an exogenous EZH2 gene. In some embodiments, the transgenic animal overexpresses the EZH2 gene. In some embodiments, the transgenic animal exhibits symptoms of prostate cancer.

The present invention additionally provides a method, comprising: contacting a transgenic animal expressing an exogenous EZH2 gene with a test compound; and detecting a change in at least one activity of EZH2 or level of expression of EZH2 in the presence of the test compound relative to the absence of the test compound.

In yet other embodiments, the present invention provides a method of inhibiting the growth of cells, comprising: contacting a cell that expresses EZH2 with a reagent for inhibiting EZH2 expression in the cell, wherein the reagent is an antisense oligonucleotide under conditions such that the expression of EZH2 in the cell is inhibited. In some embodiments, the cell is a prostate cancer cell. In some embodiments, the contacting further results in a decrease in proliferation of the cell. In some embodiments, the method further comprises the step of, prior to the contacting step, measuring the level of expression of EZH2 in the cell. In some embodiments, the method comprises the step of selecting the reagent based on the level of expression of EZH2 in the cell.

In yet further embodiments, the present invention provides a method of inhibiting the growth of cells, comprising: contacting a cell that expresses EZH2 with a reagent for inhibiting EZH2 expression in the cell, wherein the reagent is drug under conditions such that the expression of EZH2 in the cell is inhibited.

In additional embodiments, the present invention provides a method of inhibiting the growth of cells, comprising: contacting a cell that expresses EZH2 with a reagent for inhibiting EZH2 expression in the cell, wherein the reagent is an siRNA under conditions such that the expression of EZH2 in the cell is inhibited.

DESCRIPTION OF THE FIGURES

FIG. 1 shows a gene expression profile of prostate cancer samples.

FIG. 3 shows the expression of hepsin in prostate cancer samples as determined by Northern blot analysis and immunohistochemistry.

FIG. 4 shows the expression of pim-1 in prostate cancer samples as determined by Northern blot analysis and immunohistochemistry.

FIG. 9 describes exemplary accession numbers and sequence ID Numbers for exemplary genes of the present invention.

FIG. 10 provides exemplary sequences of some genes of the present invention.

FIG. 19A shows AMACR protein expression in localized hormone naive PCA. FIG. 19B shows strong AMACR expression in a naive lymph node metastasis. Error bars represent the 95% CI of the mean expression of the primary naive prostate cancer and corresponding lymph node metastases.

FIG. 17A shows PCA demonstrating strong hormonal effect due to anti-androgen treatment. FIG. 17B shows Western Blot analysis representing the baseline AMACR expression in different prostate cell lines (Left) and Western Blot analysis of LNCaP cells for AMACR and PSA expression after treatment with an androgen or an anti-androgen for 24 h and 48 hours (right).

FIG. 20 describes the identification and validation of EZH2 over-expression in metastatic prostate cancer. FIG. 20a shows a cluster diagram depicting genes that molecularly distinguish metastatic prostate cancer (MET) from clinically localized prostate cancer (PCA). FIG. 20b shows a DNA microarray analysis of prostate cancer that reveals upregulation of EZH2 in metastatic prostate cancer. FIG. 20c shows RT-PCR analysis of the EZH2 transcript in prostate tissue and cell lines. FIG. 20d shows increased expression of EZH2 protein in prostate cancer.

FIG. 21a shows tissue microarray analysis of EZH2 expression. The mean EZH2 protein expression for the indicated prostate tissues is summarized using error bars with 95% confidence intervals. FIG. 21b shows a Kaplan-Meier analysis demonstrating that patients with clinically localized prostate cancers that have high EZH2 expression (Moderate/Strong staining) have a greater risk for prostate cancer recurrence after prostatectomy (log rank test, p=0.03).

FIG. 22 shows the role of EZH2 in prostate cell proliferation. FIG. 22a shows an immunoblot analysis of RNA interference using siRNA duplexes targeting the EZH2 sequence in prostate cells. FIG. 22b shows that RNA interference of EZH2 decreases cell proliferation as assessed by cell counting assay. FIG. 22c shows that RNA interference of EZH2 inhibits cell proliferation as assessed by WST assay.

FIG. 23a shows a schematic diagram of EZH2 constructs used in transfection/transcriptome analysis. ER, modified ligand binding domain of estrogen receptor. H-1 and H-2, homology domains 1 and 2 which share similarity between EZH2 and E(z). CYS, cysteine-rich domain. SET, SET domain. TAG, myc-epitope tag. NLS, nuclear localization signal. FIG. 23b shows confirmation of expression of EZH2 constructs used in a. An anti-myc antibody was used. FIG. 23d shows SAM analysis of gene expression profiles of EZH2 transfected cells compared against EZH2 .SET transfected cells. FIG. 23e shows a model for potential functional interactions of EZH2 as elucidated by transcriptome analysis and placed in the context of previously reported interactions. +, induction. –, repression.

FIG. 29a shows an immunoblot analysis of the humoral response to AMACR. FIG. 29b shows a control experiment where the humoral response was blocked.

FIG. 30a shows the level of GP73 in individual samples after microarray analysis. FIG. 30b shows the result of GP73 transcripts determined by DNA microarray analysis from 76 prostate samples grouped according to sample type and averaged.

FIG. 31 shows that GP73 protein is upregulated in prostate cancer. FIG. 31a shows Western blot analysis of GP73 protein in prostate cancer. FIG. 31b shows an immunoblot analysis of the Golgi resident protein Golgin 97.

FIG. 32 shows immunoblot analysis of normal and prostate cancer epithelial cells.

GENERAL DESCRIPTION

Figure 1A:
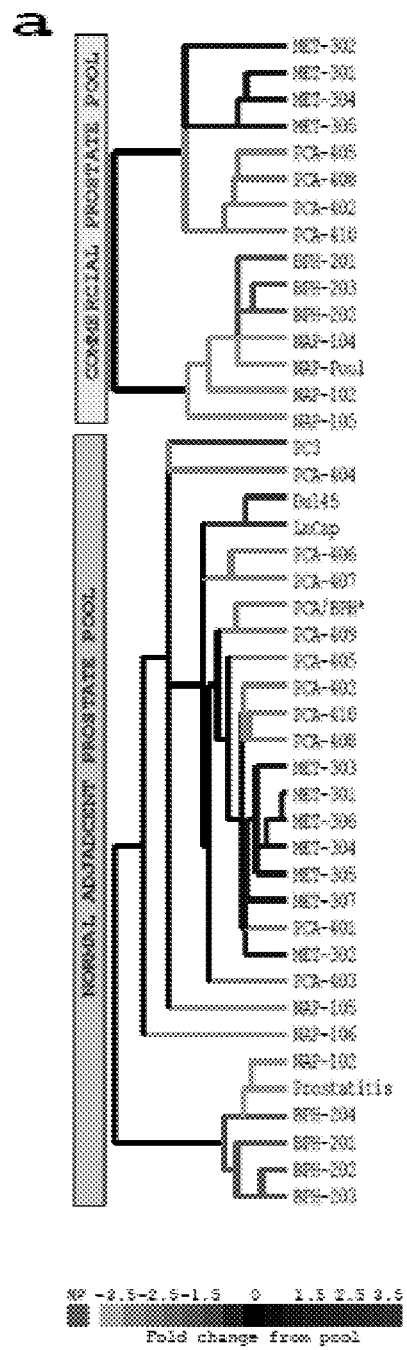
FIG. 1a shows a dendrogram describing the relatedness of the samples.

Exploring the molecular circuitry that differentiates indolent PCA from aggressive PCA has the potential to lead to the discovery of prognostic markers and novel therapeutic targets. Insight into the mechanisms of prostate carcinogenesis is also gleaned by such a global molecular approach. Similar to breast cancer (Lopez-Otin and Diamandis, Endor. Rev., 19:365 [1998]), PCA develops in a complex milieu of genetic and environmental factors in which steroid hormone signaling plays a central role. The primary precursor lesion of PCA, high-grade prostatic intraepithelial neoplasia (HG-PIN), has several characteristics similar to other early invasive carcinomas (i.e., chromosomal abnormalities and cytologic features). Loss of specific chromosomal regions (e.g., 8p21, 10q, 13q, 17p) along with losses and mutations of tumor suppressor genes such as Nkx3.1, PTEN, Rb, and p53 have been implicated in the initiation and progression of prostate cancer (Abate-Shen and Shen, supra). With the emergence of global profiling strategies, a systematic analysis of genes involved in PCA is now possible. DNA microarray technology is revolutionizing the way fundamental biological questions are addressed in the post-genomic era. Rather than the traditional approach of focusing on one gene at a time, genomic-scale methodologies allow for a global perspective to be achieved. The power of this approach lies in its ability to comparatively analyze genome-wide patterns of mRNA expression (Brown and Botstein, Nat. Gent., 21:33 [1999]). Obtaining large-scale gene expression profiles of tumors allows for the identification of subsets of genes that function as prognostic disease markers or biologic predictors of therapeutic response (Emmert-Buck et al., Am. J. Pathol., 156:1109 [2000]). Golub et al. used DNA arrays in the molecular classification of acute leukemias (Golub et al., Science 286:531 [1999], demonstrating the feasibility of using microarrays for identifying new cancer classes (class discovery) and for assigning tumors to known classes (class prediction). Using a similar approach, Alizadeh et al showed that diffuse large B-cell lymphoma could be dissected into two prognostic categories by gene expression profiling (Alizadeh et al., Nature 403:503 [2000]). They provided evidence that lymphomas possessing a gene expression signature characteristic of germinal center B cells had a more favorable prognosis than those expressing genes characteristic of activated peripheral B-cells. Similar large-scale classifications of breast cancer and melanoma have been undertaken, and as with the other studies, molecular classification was the primary focus (Alizadeh et al., supra).

Accordingly, the present invention provides an analysis of gene expression profiles in benign and malignant prostate tissue. Three candidate genes, AMACR, hepsin and pim-1, identified by DNA microarray analysis of PCA, were characterized at the protein level using PCA tissue microarrays. Analysis of the differential gene expression profiles of normal and neoplastic prostate has led to the identification of a select set of genes that define a molecular signature for PCA. The expression profiling experiments of the present invention demonstrate a role for multiple, collaborative gene expression alterations which ultimately manifest as the neoplastic phenotype. By making direct comparative hybridizations of normal and neoplastic tissues, genes that molecularly distinguish benign tissue from malignant are identified.

α-Methylacyl-CoA Racemase (AMACR) is an enzyme that plays an important role in bile acid biosynthesis and β-oxidation of branched-chain fatty acids (Ferdinandusse et al., J. Lipid Res., 41:1890 [2000]; Kotti et al., J. Biol. Chem., 275:20887 [2000]). Mutations of the AMACR gene have been shown to cause adult-onset sensory motor neuropathy (Ferdinandusse et al., Nat. Genet., 24:188 [2000]). In diagnostically challenging prostate biopsy cases, pathologists often employ the basal cell markers 34βE12 or p63, which stain the basal cell layer of benign glands that is not present in malignant glands. Thus, in many biopsy specimens, the pathologist must rely on absence of staining to make the final diagnosis of prostate cancer. Experiments conducted during the development of the present invention identified AMACR as a marker expressed in cancerous biopsy tissue. Thus, the clinical utility of AMACR in prostate needle biopsies is large. For example, at the University of Michigan Medical Center, approximately 400 prostate needle biopsies are performed per year and approximately 20% require the use of a basal-cell specific marker to evaluate difficult lesions, characterized by a small amount of atypical glands. Accordingly, it is contemplated that in combination with basal cell specific markers, such as 34βE12 or p63, screening for AMACR expression by the methods of the present invention results in fewer cases diagnosed as "atypical without a definitive diagnosis."

Identification of the over-expression of AMACR in prostate cancer has clinical utility beyond diagnostic uses. Experiments conducted during the development of the present invention revealed that the only non-cancerous tissue to expresses significant levels of AMACR protein is the human liver. The present invention is not limited to a particular mechanism. Indeed, an understanding of the mechanism in not necessary to practice the present invention. Nonetheless, it is contemplated that AMACR activity is required for prostate cancer growth and by virtue of its specificity serves as a therapeutic target.

Additional experiments conducted during the course of development of the present invention investigated AMACR expression in different groups of prostate cancer, including the aspect of neo-adjuvant hormonal withdrawal in localized disease. AMACR expression was found to be hormone independent in cell culture experiments. PSA, a gene known to be regulated by androgens, demonstrated hormone related alterations in expression under the same conditions. The present invention is not limited to a particular mechanism. Indeed, an understanding of the mechanism is not necessary to practice the present invention. Nonetheless, it is contemplated that these findings provide evidence that AMACR is not regulated by the androgen pathway. It is further contemplated that the decreased AMACR expression in hormone refractory tissue allows the use of AMACR as a biomarker for hormone resistance. It is also contemplated that, given the fact that hormone treatment in the mean of hormonal withdrawal did not affect AMACR expression in the cell culture, that some other mechanism than the androgen pathway is responsible for AMACR downregulation in the integrity of cancer tissue.

The present invention is not limited to a particular mechanism. Indeed, an understanding of the mechanism is not necessary to practice the present invention. Nonetheless, it is contemplated that, alternatively, AMACR is over expressed in the development of cancer, perhaps playing an important role in providing energy for the neoplastic cells. However, as the tumors become de-differentiated, they no longer require these sources of energy. It is contemplated that poorly differentiated tumors may take over other pathways to accomplish this same activity of branched fatty acid oxidation. There is no association with the proliferative rate of the tumor cells and AMACR expression.

AMACR expression was also examined in other cancers. Examination of other tumors demonstrated that colon cancer has the highest AMACR expression. As colorectal cancers are not known to be hormonally regulated, the fact that de-differentiation and decreased AMACR expression were correlated in PCA further supports the hypothesis that de-differentiation leads to decreased AMACR expression in the hormone refractory metastatic PCA. Hormone treatment is also a front line therapy in metastatic prostate cancer but is known to loose efficacy, selecting out hormone insensitive clones. The present invention is not limited to a particular mechanism. Indeed, an understanding of the mechanism is not necessary to practice the present invention. Nonetheless, it is contemplated that this phenomenon explains the observation that strong hormone treatment effect is consistent with decreased AMACR expression due to selection of potentially more de-differentiated cells.

The AMACR gene product is an enzyme, which plays an important role in bile acid biosynthesis and beta-oxidation of branched-chain fatty acids (Kotti et al., J. Biol. Chem. 275: 20887 [2000]; Ferdinandusse et al., J Lipid Res 42:137 [2001]). AMACR over expression occurs in tumors with a high percentage of lipids such as PCA and colorectal cancer. The relationship between fatty acid consumption and cancer is a controversial subject in the development of PCA and colorectal cancer (Moyad, Curr Opin Urol 11:457 [2001]; Willett, Oncologist 5:393 [2000]). An essential role for AMACR in the oxidation of bile acid intermediates has been demonstrated. AMACR encodes an enzyme which catalyzes the racemization of alpha-methyl branched carboxylic coenzyme A thioesters and is localized in peroxisomes and mitochondria (Schmitz et al., Eur J Biochem 231:815 [1995]). The present invention is not limited to a particular mechanism. Indeed, an understanding of the mechanism is not necessary to practice the present invention. Nonetheless, it is contemplated that, as AMACR is involved in the metabolism of lipids, that this leads to alterations in the oxidant balance of a cell. It is further contemplated that these changes are associated with DNA damage, malignant transformation, and other parameters of cell disturbance.

Additional experiments conducted during the course of development of the present invention demonstrated that AMACR mRNA and protein product are over expressed in a number of adenocarcinomas, including colorectal, prostate, breast, and ovarian and melanoma. Adenocarcinoma from the colorectum and prostate demonstrated consistent AMACR over expression (92% and 83% of tumor, respectively). Thus, AMACR is of use in the diagnosis of colonic neoplasia. For example, in some embodiments of the present invention, AMACR is used in the diagnosis of dysplasia. Specifically, in the setting of inflammatory bowel disease (IBD), where the identification of dysplasia may be diagnostically challenging, one evaluates putative lesions for their AMACR protein expression intensity. In some embodiments, this is performed in conjunction with the analysis of the adenomatous polyposis coli gene, since mutations in this gene are also believed to occur early in the development of colorectal neoplasia (Kinzler and Vogelstein, Cell 87:159 [1996]; Tsao and Shibata, Am J Pathol 145: 531 [1994]).

Colonic adenomas (Kinzler and Vogelstein, supra; Tsao and Shibata, supra) and high-grade PIN (McNeal and Bostwick, Hum Pathol 17:64 [1986]; McNeal et al., Lancet 1:60 [1986]) are well know precursors of invasive colonic and prostate cancer, respectively. Experiments conducted during the course of development of the present invention demonstrated that AMACR is over expressed in colorectal adenomas (75%) and high-grade PIN (64%). Further supporting AMACR expression in early neoplastic lesions was the presence of focal AMACR expression in some atrophic prostate lesions. Some atrophic lesions (i.e., proliferative inflammatory atrophy and postatrophic hyperplasia) have recently been recognized as proliferative in nature with molecular alterations suggestive of early neoplastic changes (De Marzo et al., Am J Pathol 155:1985 [1999]; Shah et al, Am J Pathol 158:1767 [2001]). Some morphologically benign prostate glands were also observed to have focal moderate AMACR staining. The present invention is not limited to a particular mechanism. Indeed, an understanding of the mechanism is not necessary to practice the present invention. Nonetheless, it is contemplated that AMACR may have a role in the early steps of cancer development.

Several cancers that are associated with AMACR over expression, including colorectal, prostate and breast cancer, have been linked to high-fat diet. The exact mechanism how high-fat diet contributes to tumorigenesis in these organ systems is unknown, but emerging evidence suggest that peroxisome proliferator activated receptor (PPAR) mediated pathway plays a critical role (Debril et al., J. Mol. Med. 79:30 [2001]). Diet fatty acids have been shown to function as peroxisome proliferators and bind to and activate PPARs (Zomer et al., J. Lipid Res. 41:1801 [2000]), a family of nuclear receptor transcriptional factors. Activation of PPAR mediated pathways in turn control cell proliferation and differentiation. In addition, it can also alter the cellular oxidant balance (Yeldandi et al., Mutat. Res. 448:159 [2000]). The present invention is not limited to a particular mechanism. Indeed, an understanding of the mechanism is not necessary to practice the present invention. Nonetheless, it is contemplated that these effects act in concert to contribute to the tumorigenesis of several cancers. This hypothesis is supported by the findings that peroxisome proliferators, when given to mice, enhance the development colon adenomatous polyps in mice (Saez et al., Nat. Med. 4:1058 [1998]). In addition, PPARs are expressed in several prostate cancer cell lines and their ligands, and peroxisome proliferators, when added to culture, affect the growth of these cell lines (Shappell et al., Cancer Res. 61:497 [2001]; Mueller et al., PNAS 97:10990 [2000]). A phase II clinical trial also showed that troglitazone, a PPARγ activator, could stabilize PSA level in patients with prostate cancer (Kubota et al., Cancer Res. 58:3344 [1998]; Hisatake et al., Cancer Res. 60:5494 [2000]).

AMACR is an involved in the β-oxidation of pristanic acid (Ferdinandusse et al., J. Lipid. Res. 41:1890 [2000]). Pristanic acid can function as a PPAR α activator and promote cell growth (Zomer et al., J. Lipid Res. 41:1801 [2000]). The present invention is not limited to a particular mechanism. Indeed, an understanding of the mechanism is not necessary to practice the present invention. Nonetheless, it is contemplated that hyperfunctioning of β-oxidation pathway leads to exhaustion of reducing molecules and alters the cellular oxidant status (Yeldandi et al., Mutat. Res. 448:159 [2000]).

The present invention further provides methods of targeting AMACR as a therapeutic target in cancer treatment. Over expressed in high percentage of colorectal, prostate, breast and melanoma, but not in adjacent normal tissues, AMACR is targeted using antibody or enzyme inhibitors. Toxicity is expected not to be a major concern because individuals with congenital absence of this enzyme have no or insignificant clinical manifestations (Clayton et al., Biochem. Soc. Trans. 29:298 [2001]).

Experiments conducted during the course of development of the present invention further demonstrated that AMACR is present in the serum of prostate cancer patients. In addition, a humoral response to AMACR was identified based on the presence of antibodies to AMACR in the serum of prostate cancer patients.

Annexins are a group of structurally related calcium-binding proteins, which have a domain that binds to phospholipids and an amino terminal domain that determines specificity (Smith et al., Trends. Genet. 10:241 [1994]; Mailliard et al., J Biol. Chem. 271:719 [1996]). The annexins are involved in regulation of membrane trafficking, cellular adhesion and possible tumorigenesis. Experiments conducted during the course of development of the present invention used cDNA microarrays to study the expression patterns of multiple annexin family members in a wide range of prostate tissue samples in order to determine their role in PCA progression. Meta-analysis of gene expression data was employed to help further validate the cDNA expression array findings. Finally, high-density tissue microarrays were used to assess annexin protein expression levels by immunohistochemistry.

Eight annexins were evaluated for their mRNA expression levels in benign prostatic tissue, localized hormone naïve PCA and metastatic hormone refractory PCA samples. Five annexins (1,2,4,7,and 11) demonstrated a progressive down regulation at the transcript level going from benign prostatic tissue to localized PCA to hormone refractory PCA. In order to validate the cDNA expression array finding of these 5 annexin family members, a meta-analysis was performed, which confirmed that when looking across 4 studies where at least two studies reported results, annexin 1,2,4, and 6 were significantly down regulated in localized PCA samples when compared to benign prostatic tissue. Therefore the meta-analysis confirmed results on annexin 1, 2, and 4. In these examples, summary statistics across all datasets found these annexins to be significantly down regulated at the cDNA level. However, not all of the 4 studies had significant down-regulation. Annexin 4, for example, was significantly down regulated in two of four studies but the resultant summary statistic, which also takes into account the number of samples evaluated, was statistically significant. Annexins 7,8, and 13 were not found to be significantly under expressed. As demonstrated in FIG. 1, annexin 7 does decrease significantly when comparing localized PCA and metastatic PCA.

The protein expression levels of all above five annexins tested were statistically significantly decreased in hormone refractory PCA samples when compared to either localized PCA or benign prostate tissue. Four of 5 annexins also demonstrated a decrease in protein expression in clinically localized PCA as compared to benign prostate tissue. However, in none of these cases was the protein expression found to be significantly decreased. This second validation method at the protein level confirmed the cDNA expression array data for annexin 1,2,4, 7, and 11.

Based on gene expression array data described herein, localized PCA cells down regulate their mRNA levels of annexins but maintained the corresponding protein expression levels. The present invention is not limited to a particular mechanism. Indeed, an understanding of the mechanism is not necessary to practice the present invention. Nonetheless, it is contemplated that post-translational alteration may compensate for decrease mRNA, producing enough protein to maintain levels seen with benign samples. Since annexins play an important role in maintaining cellular adhesion, once the cells eventually lose this ability, tumor progression may occur. Therefore, as one might anticipate, annexin expression levels decreased significantly in the advanced hormone refractory PCA samples. This was confirmed at the protein level by significant decreases as demonstrated by immunohistochemistry.

A sequential down-regulation of annexins in both transcriptional and translational levels in metastatic PCA samples was observed. Annexin I, also called lipocortin, has been described as a phospholipase A2 inhibitor, and served as a substrate of epidermal growth factor receptor (Pepinsky et al., Nature 321:81 [1986]; Wallner et al., Nature 320:77 [1986]). The significant reduction of protein level has been shown in esophageal and prostate tumor cells (Paweletz et al., Cancer Res. 60:6293 [2000]). Annexin 2, also called p36, appears an efficient substrate of protein kinase C and Src pp60 (Hubaishy et al., Biochemistry 34:14527 [1995]). Annexin 4, called endonexin, regulates Cl-flux by mediating calmodulin kinase II (CaMKII) activity (Chan et al., J. Biol. Chem. 269: 32464 [1994]). Annexin 7, synexin, is involved in Duchenne's muscular dystrophy (Selbert et al. Exp. Cell. Res. 222:199 [1996]). Its gene is located on human chromosome 10q21, and its protein expression was decreased in hormone refractory tumor cells. In conclusion, the results of experiments conducted during the course of development of the present invention suggest that down regulation of several annexin family members may play a role in the development of the lethal PCA phenotype.

Additional experiments conducted during the course of development of the present invention identified additional markers that exhibited altered (e.g., increased or decreased) expression in prostate cancer. Additional markers include, but are not limited to, EZH2, Annexins 1, 2, 4, 7, and 11, CTBP 1 and 2, GP73, ABCC5 (MDR5), ASNS, TOP2A, and Vav2. In particular, EZH2 was identified as a marker that was overexpressed in prostate cancer, and in particular, in metastatic prostate cancer. EZH2 was further identified as being correlated with clinical failure (e.g., increased PSA levels). In addition, siRNA inhibition of EZH2 resulted in a decrease in cell proliferation of a prostate cancer cell line.

The present invention thus identifies markers and targets for diagnostic and therapeutic agents in a variety of cancers.

Definitions

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described in illustrative Examples 1-15 below.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression (e.g., hepsin, pim-1, EZH2, or AMACR) in said prostate cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-15 below.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "prostate cancer expression profile map" refers to a presentation of expression levels of genes in a particular type of prostate tissue (e.g., primary, metastatic, and pre-cancerous prostate tissues). The map may be presented as a graphical representation (e.g., on paper or on a computer screen), a physical representation (e.g., a gel or array) or a digital representation stored in computer memory. Each map corresponds to a particular type of prostate tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "prostate specific antigen failure" refers to the development of high prostate specific antigen levels in a patient following prostate cancer therapy (e.g., surgery). See Examples 3 and 4 for examples of how prostate specific antigen failure is determined. As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "basal cell marker" refers to a marker (e.g., an antibody) that binds to proteins present in the basal cell layer of benign prostate glands. Exemplary basal cell markers include, but are not limited to, 34βE12 and p63 (See e.g., O'Malley et al., Virchows Arch. Pathol. Anat. Histopathol., 417:191 [1990]; Wojno et al., Am. J. Surg. Pathol., 19:251 [1995]; Googe et al., Am. J. Clin. Pathol., 107:219 [1997]; Parsons et al., Urology 58:619; and Signoretti et al., Am. J. Pathol., 157:1769 [2000]).

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnostics, including but not limited to, cancer markers. In particular, the present invention provides gene expression profiles associated with prostate cancers. Accordingly, the present invention provides method of characterizing prostate tissues, kits for the detection of markers, as well as drug screening and therapeutic applications.

I. Markers for Prostate Cancer

The present invention provides markers whose expression is specifically altered in cancerous prostate tissues. Such markers find use in the diagnosis and characterization of prostate cancer.

A. Identification of Markers

Experiments conducted during the development of the present invention resulted in the identification of genes whose expression level was altered (e.g., increased or decreased) in PCA. The methods utilized glass slide cDNA microarrays that included approximately 5000 known, named genes, 4400 ESTs, and 500 control elements, as well as normal and cancerous prostate tissue. Differentially expressed genes were divided into functional clusters. The expression of relevant genes was confirmed using Western blot analysis. Protein expression in prostate tissues was measured for several genes of interest.

The methods of the present invention (See e.g., Example 2) were used to identify clusters of genes that were up or down regulated in PCA, benign prostate tissue, pre-cancerous tissue, and normal prostate. From these clusters, two genes, hepsin and pim-1 were identified as genes that were of particular relevance. Immunohistochemistry (See e.g., Example 4) was used to characterize the presence of hepsin and pim-1 proteins in prostate tissue. Hepsin was found to stain strongly in pre-cancerous tissue (HG-PIN). In addition, hepsin was found to stain less strongly in PCA tissues of men found to have an increased risk of metastasis as measured by PSA failure (increased PSA following surgery), thus confirming the diagnostic utility of hepsin. In addition, deceased expression of pim-1 in PCA tissue was also found to be associated with increased risk of PSA failure. Accordingly, in some embodiments, the present invention provides methods of detecting and characterizing prostate tissues.

The methods of the present invention identified a further gene, alpha-methyl-CoA racemase (AMACR), that was found to be expressed in PCA, but not benign prostate tissue (See e.g., Example 5). AMACR was found to be present in the serum and urine of prostate or bladder cancer patients. In addition, a humoral response to AMACR was identified. In still further embodiments, the methods of the present invention were used to characterize the EZH2 gene. EZH2 was found to be up-regulated in metastatic prostate cancer. The inhibition of EZH2 expression in prostate cells inhibited cell proliferation in vitro, as well as inducing transcriptional repression of a variety of genes. The methods of the present invention further identified CtBP1 and CTBP2, as well as that GP73 as being over-expressed in metastatic prostate cancer relative to localized prostate cancer and benign tissue.

In still further embodiments, the methods of the present invention identified annexins 1, 2, 4, 7 and 11 as being significantly decreased in hormone refractory PCA when compared to localized hormone naïve Pca. Tissue microarray analysis revealed a significant decrease in protein expression for annexins 1, 2, 4, 7 and 11 in hormone refractory PCA as compared to localized Pca. No significant differences were detected between the clinically localized PCA and non-cancerous prostate tissues.

B. Detection of Markers

In some embodiments, the present invention provides methods for detection of expression of cancer markers (e.g., prostate cancer markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In preferred embodiments, the presence of a cancer marker is used to provide a prognosis to a subject. For example, the detection of hepsin or pim-1 in prostate tissues is indicative of a cancer that is likely to metastasize and the expression of hepsin is indicative of a pre-cancerous tissue that is likely to become cancerous. In addition, the expression of AMACR is indicative of cancerous tissue. The information provided is also used to direct the course of treatment. For example, if a subject is found to have a marker indicative of a highly metastasizing tumor, additional therapies (e.g., hormonal or radiation therapies) can be started at a earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer may be utilized, including but not limited to, those described in the illustrative examples below (e.g., FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. Additional markers are also contemplated to be within the scope of the present invention. Any suitable method may be utilized to identify and characterize cancer markers suitable for use in the methods of the present invention, including but not limited to, those described in illustrative Examples 1-15 below. For example, in some embodiments, markers identified as being up or down-regulated in PCA using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. For example, a panel may include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of cancers of various stages or prognoses (e.g., likelihood of future metastasis). Such maps can be used for comparison with patient samples. In some embodiments comparisons are made using the method described in Example 2. However, the present invention is not limited to the method described in Example 2. Any suitable method may be utilized, including but not limited to, by computer comparison of digitized data. The comparison data is used to provide diagnoses and/or prognoses to patients.

1. Detection of RNA

In some preferred embodiments, detection of prostate cancer markers (e.g., including but not limited to, those disclosed herein) is detected by measuring the expression of corresponding mRNA in a tissue sample (e.g., prostate tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers is detected by measuring the expression of the corresponding protein or polypeptide. Protein expression may be detected by any suitable method. In some embodiments, proteins are detected by the immunohistochemistry method of Example 4. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis or PSA failure) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

4. Kits

In yet other embodiments, the present invention provides kits for the detection and characterization of prostate cancer. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In vivo Imaging

In some embodiments, in vivo imaging techniques are used to visualize the expression of cancer markers in an animal (e.g., a human or non-human mammal). For example, in some embodiments, cancer marker mRNA or protein is labeled using an labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers described herein (e.g., hepsin, pim-1, AMACR, EZH2, CTBP). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers identified using the methods of the present invention (e.g., including but not limited to, hepsin, pim-1, AMACR, EZH2, and CTBP). For example, in some embodiments, the present invention provides methods of screening for compound that alter (e.g., increase or decrease) the expression of cancer marker genes. In some embodiments, candidate compounds are antisense agents (e.g., oligonucleotides) directed against cancer markers. See Section IV below for a discussion of antisense therapy. In other embodiments, candidate compounds are antibodies that specifically bind to a cancer marker of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer markers activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic (e.g., androgen independent) prostate cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein or biologically active portion thereof is evaluated. Preferred biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BlAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anticancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. App 1 699:499-525 [1997]). Further, fluorescence energy transfer may also be conveniently utilized, as described herein, to detect binding without further purification of the complex from solution.

The assay can include contacting the cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., prostate cancer). In some embodiments, therapies target cancer markers (e.g., including but not limited to, hepsin, pim-1, AMACR, EZH2, and CTBP).

A. Antisense Therapies

In some embodiments, the present invention targets the expression of cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O(CH$_2$)$_2$ON(CH$_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_3$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of cancer markers of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. patent application Ser. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a cancer marker of the present invention (e.g., hepsin, pim-1, EZH2, Annexin, CTBP, GP73, and AMACR). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., hepsin, pim-1, EZH2, Annexin, CTBP, GP73, and AMACR), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., hepsin, pim-1, EZH2, Annexin, CTBP, GP73, and AMACR). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al, EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

EXAMPLE 1

Preparation of Total RNA and Reference Pools

The prostate surgical specimens were obtained from The University of Michigan Specialized Research Program in Prostate Cancer (S.P.O.R.E.) Tumor Bank with Institutional Review Board approval. Tumors samples were derived from patients with clinically localized and advanced hormone refractory prostate cancer. Table 1 shows the samples used in the present studies. All patients were operated on between 1993 and 1998 for clinically localized prostate cancer as determined by preoperative PSA, digital-rectal examination, and prostate needle biopsy. In addition, a subset of patients received bone and CAT scans to evaluate the possibility of metastatic spread. All patients received radical prostatectomy as a monotherapy (i.e., no hormonal or radiation therapy). The advanced prostate tumors were collected from a series of 12 rapid autopsies performed at the University of Michigan on men who died of hormone refractory prostate cancer. In brief, the majority of these patients had either widely metastatic prostate cancer which was treated with hormonal therapy followed by chemotherapy, or patients who presented with clinically localized disease which progressed and were then treated with both hormonal and chemotherapy. The majority of cases had multiple metastatic lesions to numerous sites. All autopsies were performed within 4-6 hours after death. The clinical and pathologic findings of these cases have recently been reported (Rubin et al., Clin. Cancer Res., 6:1038 [2000]). All samples used for the tissue microarray study were fixed in 10% formalin.

Tissues were homogenized using a polytron homogenizer (Brinkman Instruments) in Trizol (Gibco BRL) and the total RNA was isolated according to the standard Trizol protocol. The total RNA obtained was further subjected to an additional round of phenol chloroform extraction, precipitated and resuspended in RNAse free water. Total RNA was quantitated by spectrophotmetric (260/280 nm) absorbance and integrity judged by denaturing-formaldehyde agarose gel electrophoresis. Total RNA from four normal tissues was combined in equal concentrations to obtain the reference pool. The human prostate total RNA used in the commercial reference pool was obtained from Clontech, Inc.

TABLE 1

Prostate Samples

| ID | PSA level | Tissue | Gleason Score |
|---|---|---|---|
| BPH-201 | 6.2 | Prostate | NA |
| BPH-202 | 3.9 | Prostate | NA |
| BPH-203 | 3.9 | Prostate | NA |
| BPH-204 | 4.6 | Prostate | NA |
| BPH-205 | 4.6 | Prostate | NA |
| BPH-206 | 4.6 | Prostate | NA |
| BPH-207 | 4.8 | Prostate | NA |
| BPH-208 | 13.6 | Prostate | NA |
| BPH-209 | 9.8 | Prostate | NA |
| BPH-210 | 4.6 | Prostate | NA |
| BPH-211 | 2.6 | Prostate | NA |
| BPH-212 | 7.1 | Prostate | NA |
| BPH-214 | | Prostate | NA |
| BPH-215 | 5.4 | Prostate | NA |
| Prostatitis | 9.8 | Prostate | NA |
| NAP-101 | 4.6 | Prostate | NA |
| NAP-102 | 9.8 | Prostate | NA |
| NAP-104 | 7 | Prostate | NA |
| NAP-105 | 0.09 | Prostate | NA |
| NAP-107 | 4.7 | Prostate | NA |
| PCA-401 | 5.2 | Prostate | 4 + 4 |
| PCA-402 | 22 | Prostate | 4 + 3 |
| PCA-403 | 4.7 | Prostate | 3 + 3 |
| PCA-404 | 8.5 | Prostate | 3 + 3 |
| PCA-405 | 4.6 | Prostate | 3 + 3 |
| PCA-406 | 7.8 | Prostate | 3 + 3 |
| PCA-407 | 7.8 | Prostate | 3 + 3 |
| PCA-408 | 5.4 | Prostate | 3 + 3 |
| PCA-409 | 7 | Prostate | 3 + 3 |
| PCA-410 | 44.6 | Prostate | 4 + 4 |
| PCA-414 | | Prostate | 3 + 4 |
| PCA-416 | 24.1 | Prostate | 4 + 4 |
| PCA-417 | 12.4 | Prostate | 4 + 4 |
| PCA-420 | | Prostate | 3 + 3 |
| PCA-421 | 13.6 | Prostate | 3 + 4 |
| MET-301 | | Lung | NA |
| MET-302 | | Liver | NA |
| MET-303 | | Liver | NA |
| MET-304 | | Stomach | NA |
| MET-305 | | Adrenal | NA |
| MET-306 | | Prostate | NA |
| MET-307 | | Lymph Node | NA |
| MET-308 | | Lymph Node | NA |
| MET-309 | | Lymph Node | NA |
| MET-310 | | Liver | NA |
| MET-311 | | Soft tissue | NA |
| MET-312 | | Liver | NA |
| MET-313 | | Soft tissue | NA |
| MET-314 | | Soft tissue | NA |
| MET-315 | | Soft tissue | NA |
| MET-316 | | Soft tissue | NA |
| MET-317 | | Liver | NA |
| MET-318 | | bone | NA |
| MET-319 | | bone | NA |
| MET-320 | | bone | NA |

Samples employed in the study. Designating PSA level in ng/mL, Organ sources and Gleason scores. Normal adjacent prostate (NAP), Benign prostatic hyperplasia (BPH), Localized prostate cancer (PCA) and Hormone refractory metastatic prostate cancer (MET).
NA refers to "not applicable".

EXAMPLE 2

Microarray Analysis

This example describes the use of microarray analysis to identify genes that demonstrate an altered level of expression in cancerous or benign prostate tissues.

A. Experimental Methods

Microarray analysis of gene expression was conducted essentially as described by the Brown and Derisi Labs (available at the Internet site www.microarrays.org). The sequence-verified cDNA clones on the human cDNA microarray are available from the web site of Research Genetics. Based on the latest Unigene build, the 10K human cDNA microarray used covers approximately 5520 known, named genes and 4464 ESTs. All chips have various control elements that include human, rat, and yeast genomic DNAs, SSC, yeast genes and "housekeeping genes," among others. In addition, 500 cancer- and apoptosis-related cDNAs from Research Genetics were used to serve as independent controls for clone tracking and function as duplicates for quality control. Three metastatic prostate cancer cell lines: DU-145, LnCAP, and PC3 were also profiled for gene expression.

Fluorescently labeled (Cy5) cDNA was prepared from total RNA from each experimental sample. The two reference samples used in this study were labeled using a second distinguishable fluorescent dye (Cy3) and included a pool of normal adjacent prostate tissue (NAP) from four patients (distinct from those used in the experimental samples) and a commercial pool of normal prostate tissues (CP). In addition to minimizing patient-to-patient variation, comparisons against pools of normal prostate tissue facilitate the discovery of genes that molecularly distinguish prostate neoplasms. The two reference pools are different in that one is comprised of normal adjacent prostate tissue, which may be influenced by paracrine effects mediated by PCA, and furthermore is exposed to the same environmental and genetic factors as the adjacent PCA. By contrast, the CP pool is derived from 19 individuals with no known prostate pathology and also represents a renewable commercially available reference resource.

Purified PCR products, generated using the clone inserts as template, were spotted onto poly-L-lysine coated microscope slides using an Omnigrid robotic arrayer (GeneMachines, CA) equipped with quill-type pins (Majer Scientific, AZ). One full print run generated approximately 100 DNA microarrays. Protocols for printing and post-processing of arrays are well known in the art.

B. Data Analysis

Primary analysis was done using the Genepix software package. Images of scanned microarrays were gridded and linked to a gene print list. Initially, data was viewed as a scatter plot of Cy3 versus Cy5 intensities. Cy3 to Cy5 ratios were determined for the individual genes along with various other quality control parameters (e.g., intensity over local background). The Genepix software analysis package flags spots as absent based on spot characteristics (refer to the web site of Axon Instruments, Inc.). Bad spots or areas of the array with obvious defects were manually flagged. Spots with small diameters (<50 microns) and spots with low signal strengths <350 fluorescence intensity units over local background in the more intense channel were discarded. Flagged spots were not included in subsequent analyses. Data were scaled such that the average median ratio value for all spots was normalized to 1.0 per array.

These files were then imported into a Microsoft Access database. The data for the required experiments were extracted from the database in a single table format with each row representing an array element, each column a hybridization and each cell the observed normalized median of ratios for the array element of the appropriate hybridization. Prior to clustering, the normalized median of ratio values of the genes were log base 2 transformed and filtered for presence across arrays and selected for expression levels and patterns depending on the experimental set as stated. Average linkage hierarchial clustering of an uncentered Pearson correlation similarity matrix was applied using the program Cluster (Eisen et al., PNAS 95:14863 [1998]), and the results were analyzed and figures generated with the program TreeView. TreeView and Cluster are available from Michael Eisen's lab at the Lawrence Berkeley National Lab.

C. Results

Over forty 10K human cDNA microarrays were used to assess gene expression in four clinical states of prostate-derived tissues in relation to two distinct reference pools of normal specimens. FIG. 1 provides an overview of the variation in gene expression across the different tissue specimens analyzed. A hierarchical clustering algorithm was employed to group genes and experimental samples based on similarities of gene expression patterns over all the genes and samples tested, respectively.

1. Expression Dendrograms

Relationships between the experimental samples are summarized as dendrograms (FIG. 1a), in which the pattern and length of the branches reflect the relatedness of the samples. FIG. 1a shows dendrograms that reveal the variation in gene expression pattern between experimental samples with the two references employed. Individual samples in each group are indicated by the branches of the same color whereby METs are in dark blue, localized PCAs in orange, NAPs in light blue, BPHs in gray, and cell lines in pink. Asterisk (*) indicates a sample that was initially documented as BPH, but was later confirmed to have 5% cancer tissue. The details of metastatic samples used in this study are as follows: MET 301, from Lung; MET 302 and 303 from liver; MET 304, from stomach; MET 305 from adrenal gland; MET 306 from prostate; and MET 307 was from lymph node. Hierarchical clustering of the data identified distinct patterns of gene expression between the various groups analyzed. Each row represents a single gene with 1520 genes depicted in b, and 1006 genes depicted in c. The results represent the ratio of hybridization of fluorescent cDNA probes prepared from each experimental mRNA to the respective reference pools. These ratios are a measure of relative gene expression in each experimental sample and are depicted according to the color scale at the bottom left. Red and green colors in the matrix represent genes that are up- and down-regulated, respectively, relative to the reference pool employed. Black lines in the matrix represent transcript levels that are unchanged, while gray lines signify technically inadequate or missing data (NP, not present). Color saturation reflects the magnitude of the ratio relative to the median for each set of samples.

Figure 1B:
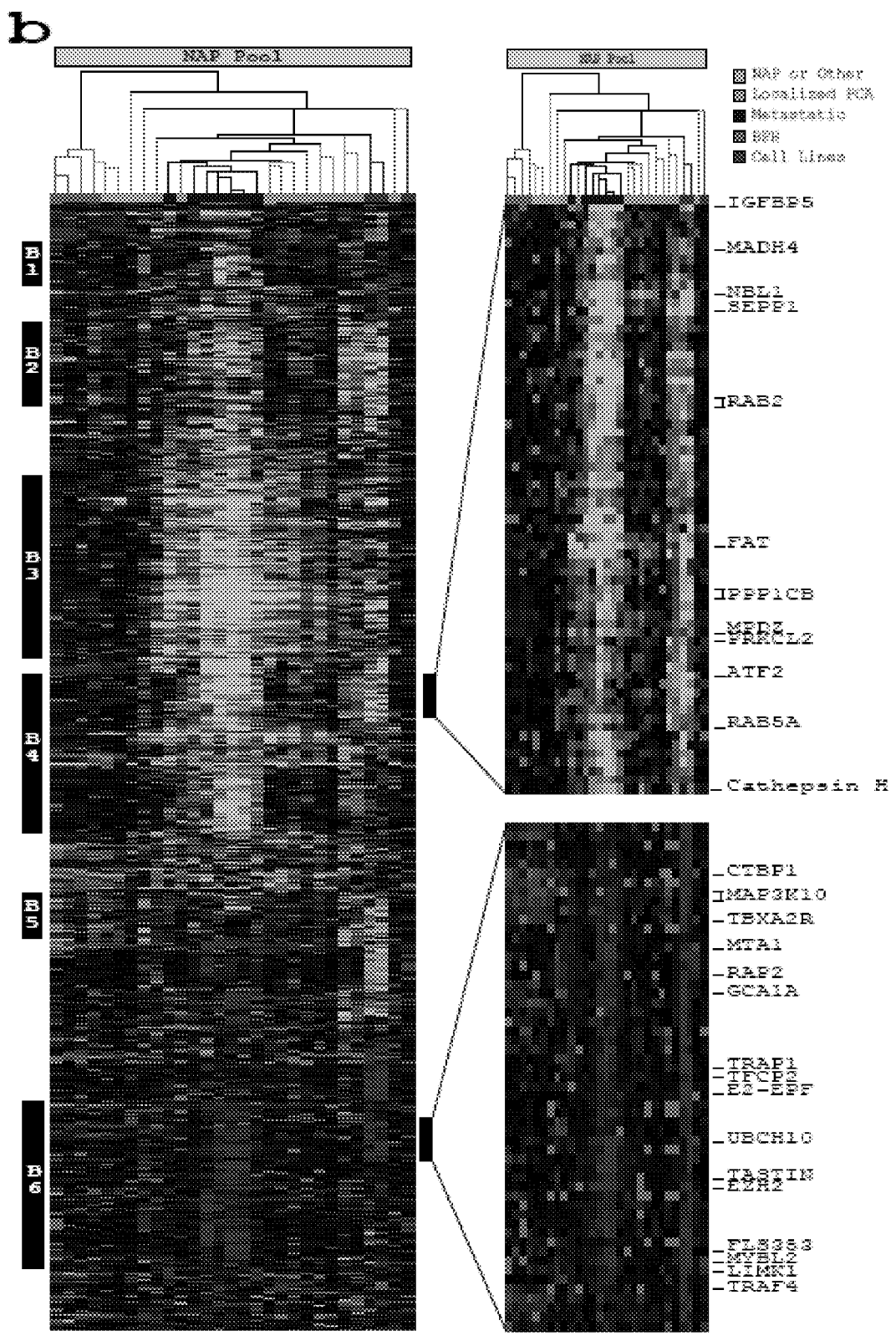
FIG. 1b shows a cluster diagram of the samples groups compared against normal adjacent prostate pool as a reference.

FIG. 1b shows a cluster diagram of the various sample groups compared against normal adjacent prostate pool as reference. Prior to hierarchical average-linkage clustering, the data was filtered for at least a 2-fold change in expression ratio and ratio measurements present in 50% of the samples. By this method, 1520 genes were selected from the NAP reference data set. Indicated by vertical bars on the left (b1 to b6) of FIG. 1b are regions identified with characteristic gene expression signatures. Clusters b1 and b5 show genes up-regulated in localized PCA but not in metastatic PCA. Clusters b2 and b4 highlight genes down-regulated in metastatic PCA and the cell lines DU145 and LnCAP. Cluster b3 identifies genes down-regulated in both localized PCA and metastatic PCA. Cluster b6 highlights genes that are primarily up-regulated in metastatic PCA alone. Portions of Clusters b4 and b6 are shown enlarged with selected genes shown using Human genome organization (HUGO) gene nomenclature.

Figure 1C:
FIGS. 1c shows a cluster diagram of the samples groups compared against commercial prostate pool reference.

FIG. 1c shows a cluster diagram of the various sample groups compared against the commercial prostate pool reference. Prior to hierarchical average-linkage clustering, the data was filtered for at least a 3-fold change in expression ratio and ratio measurements present in 75% of the samples resulting in a total of 1006 genes. Regions with distinct patterns (c1-c6) are indicated by vertical bars to the right of FIG. 1c. Cluster c1 depicts genes down-regulated in both localized PCA and metastatic PCA. Cluster c2 represents genes down-regulated only in metastatic PCA. Cluster c3 shows genes that are highly represented in the commercial pool. Cluster c4 highlights genes that are up-regulated in localized PCA and in metastatic PCA. Cluster c5 represent genes with a low representation in the commercial pool. Cluster c6, represents genes that are down-regulated in metastatic PCA but are up-regulated in all other samples used.

Benign conditions of the prostate such as BPH and NAP cluster separately from malignant PCA cell lines or tissues, regardless of the reference pool used. Within the PCA cluster, it is also evident that metastatic PCA and clinically localized PCA formed distinct subgroups. Similarly, in the "benign" grouping, BPH tended to distinguish itself from NAP. Interestingly, one of the "BPH" samples initially clustered with the localized PCA group. Upon further histopathologic review, however, it was discovered that this sample contained a small focus of neoplastic tissue (~5%), thus accounting for its initial misclassification (now designated PCA+BPH in FIG. 1a).

Eisen matrix formats (Eisen et al, supra) of the variation in gene expression are also presented (FIG. 1b and 1c). With a global perspective of the data, it is apparent that metastatic PCA dominates the analysis and has the greatest variation in gene expression of the samples tested. Bars on the left or right of each matrix represent clusters of coordinately expressed genes highlighting interrelationships between specimens. For example, Clusters b3 and c1 represent genes down-regulated in both localized and metastatic PCA (FIGS. 1b and 1c). By contrast, Clusters b6 and b4 highlight genes that are specifically up- and down-regulated in metastatic PCA, respectively (FIG. 1b). IGFBP-5, DAN1, FAT tumor suppressor and RAB5A are examples of genes that are down-regulated specifically in metastatic PCA and also have a proposed role in oncogenesis ("magnified" regions, FIG. 1b). Similarly, cancer-related genes that are up-regulated in metastatic PCA include MTA-1 (metastasis-associated 1), MYBL2, and FLS353 (preferentially expressed in colorectal cancer). Many genes in this "met-specific" cluster are shared by both the metastatic PCA tissue and the two PCA cell lines DU145 and LnCAP.

Additional prostate tissue specimens were profiled against a commercial prostate reference pool (CPP). A total of 53 prostate specimens were profiled against the commercial pool. They include 4 normal adjacent prostate tissue (NAP), 14 benign prostatic hyperplasia (BPH), 1 prostatitis, 14 localized prostate cancer (PCA) and 20 hormone refractory metastatic PCA (MET). Prior to hierarchial average-linkage clustering, the data was filtered for at least 3-fold change in Cy5/Cy3 ratios and measurements present in 75% of the samples. By this method 1325 genes were selected. The data expands on FIG. 1c with an additional 40 samples, which include all from FIG. 1b, and also includes 28 additional prostate specimens.

2. Focused Clusters

Figure 6:
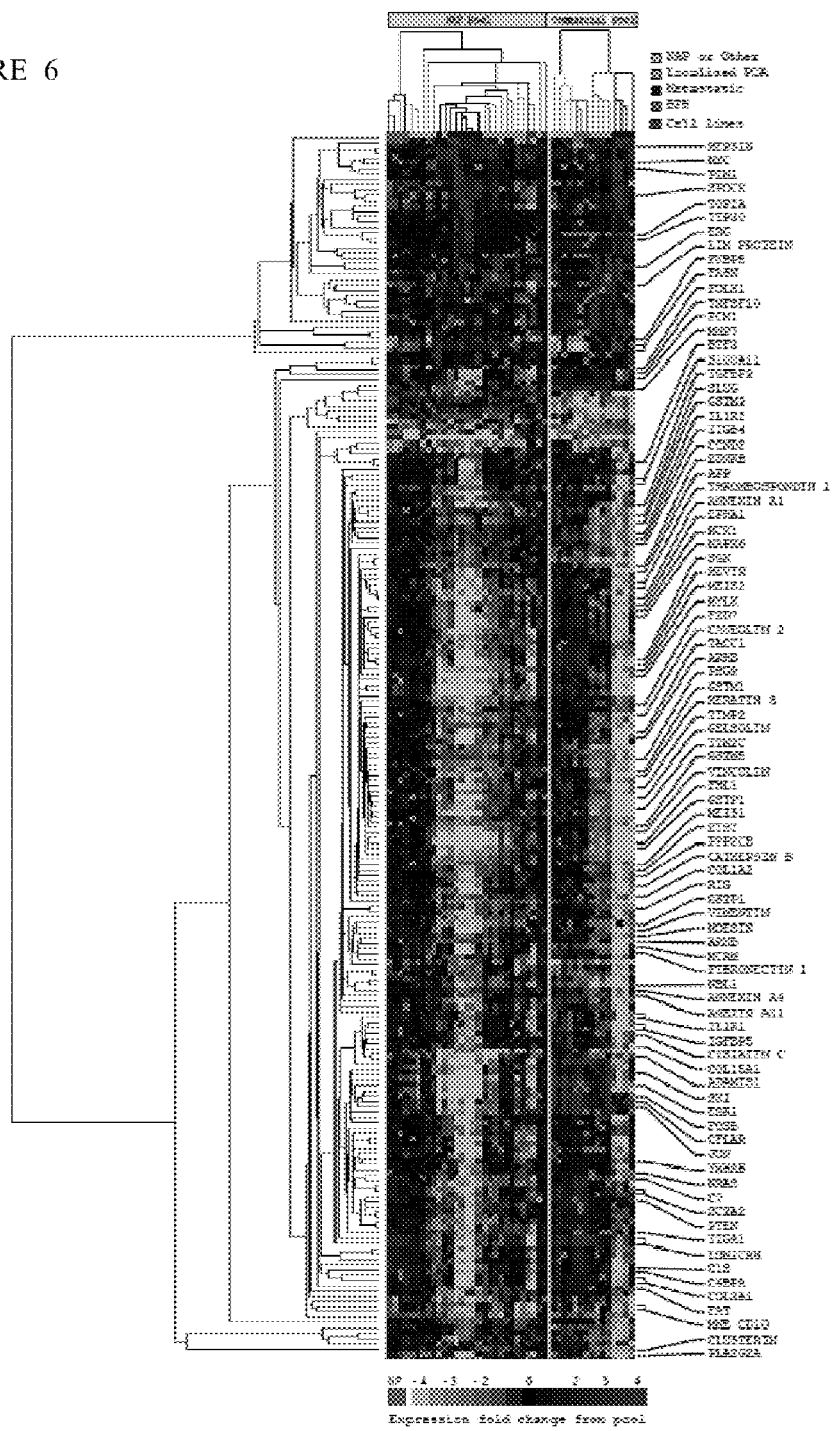
FIG. 6 shows a focused cluster of prostate cancer related genes.

Data was next assessed by examining functional groups of known, named genes. Cancer-related functional clusters were arbitrarily defined including cell growth/cell death, cell adhesion, anti-protease/protease, free radical scavengers, inflammation/immunity, phosphatase/kinase, transcription, and miscellaneous (FIGS. 2 and 6).

Figure 7A:
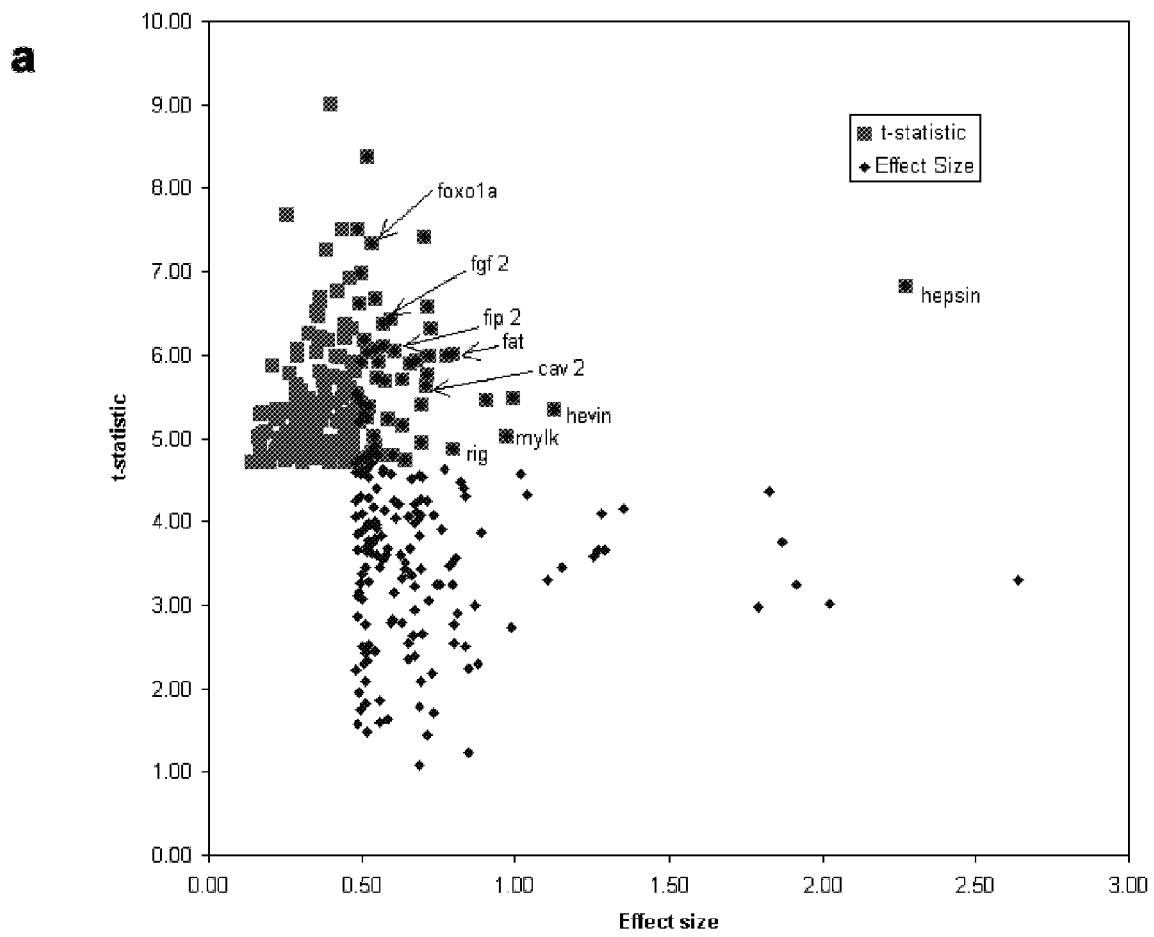
FIG. 7 shows data for gene selection based on computed t-statistics for the NAP and CP pools.
Figure 7B:
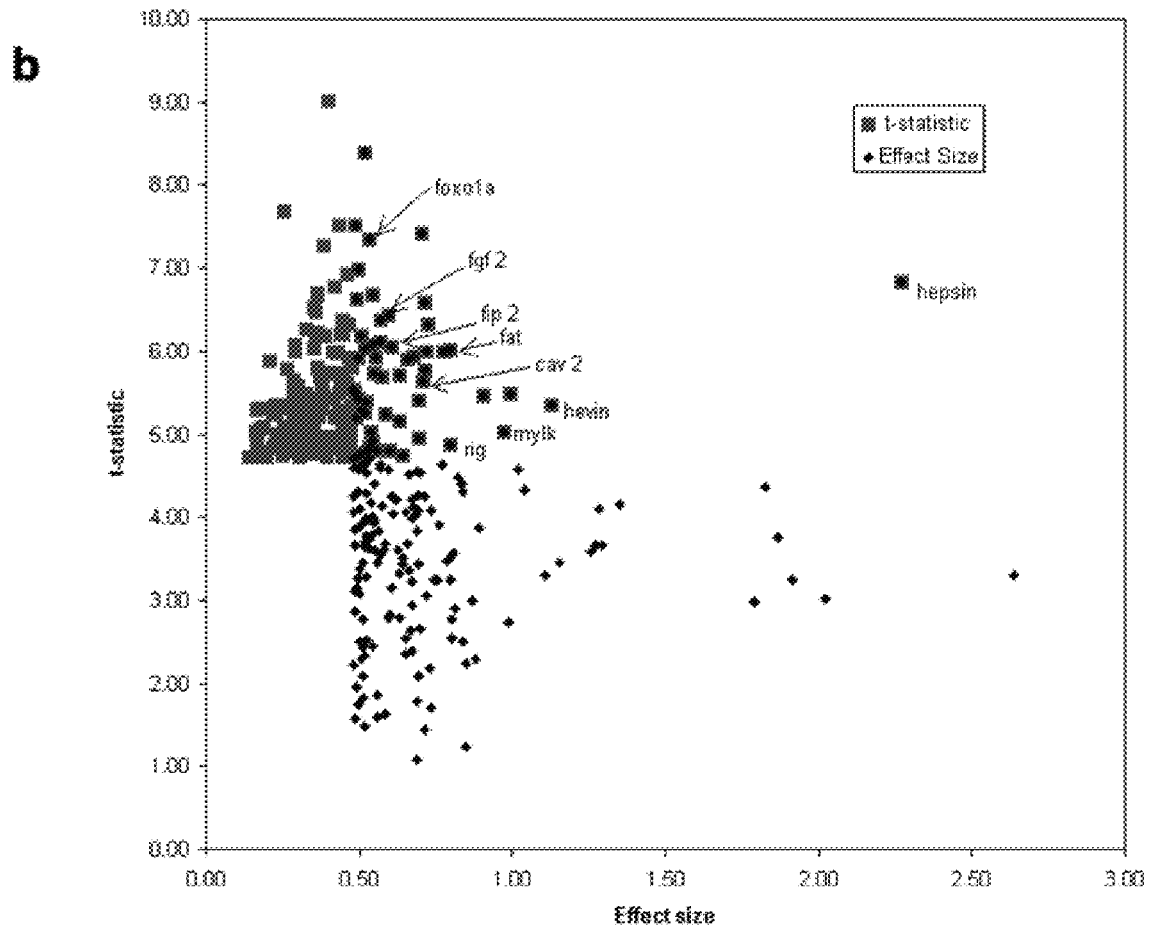

One of several available methods of gene selection was used to create a more limited set of genes for future exploration. In one method, t-statistics (based on MET/PCA vs. benign) were computed for each gene. The cell line samples were excluded from the analysis. Also, genes and ESTs that had data missing from 20% of samples were excluded from analysis. The t-statistics were ranked in two ways. First, they were ranked by absolute magnitude, which takes into account the inter-sample variability in expression ratios. Second, they were ranked by the magnitude of the numerator of the test statistic, which is based on the biological difference in expression ratios and designated as "effect size" (for MET/PCA vs. benign). A scatterplot of the genes with the 200 largest effect sizes and 200 largest t-statistics was then plotted (See FIG. 7). FIG. 7 shows gene selection based on computed t-statistics for each gene. Two groups were used in the analysis: PCA/MET and benign (NAP/BPH). FIG. 7a shows analysis of NAP pool data. FIG. 7b shows analysis of CP pool data. Selected genes are named and 200 genes for each data set are shown. Gene selection based on each method is shown. Selected gene names or symbols (as specified by Human genome organization (HUGO) gene nomenclature) are shown.

Genes that made both lists were also looked at separately in order to identify potential candidate genes. Implementing this methodology on both reference pool data sets (NAP and CP) yielded genes that included hepsin, pim-1, IM/ENIGMA, TIMP2, hevin, rig, and thrombospondin-1, among others. Several genes identified using gene selection methods are described in more detail in the context of "functional" clusters described in FIG. 2.

Figure 2A:
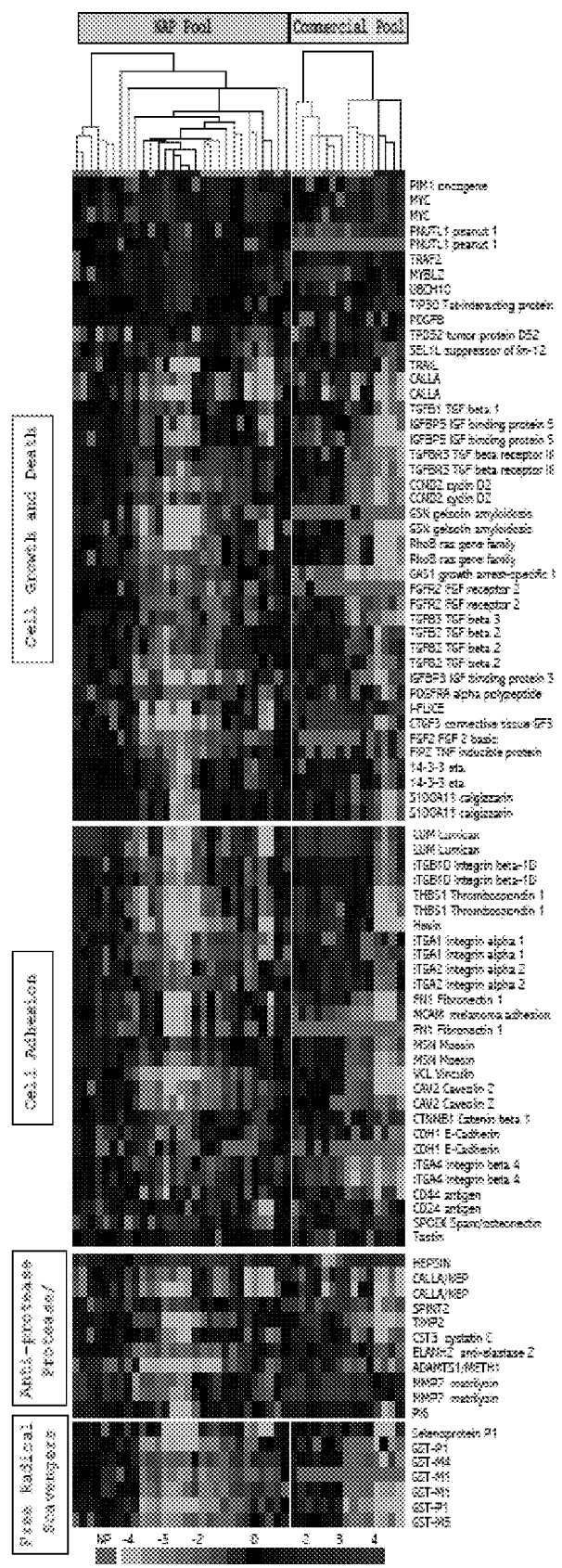
FIG. 2 shows functional clusters of genes differentially expressed in prostate cancer.
Figure 2B:
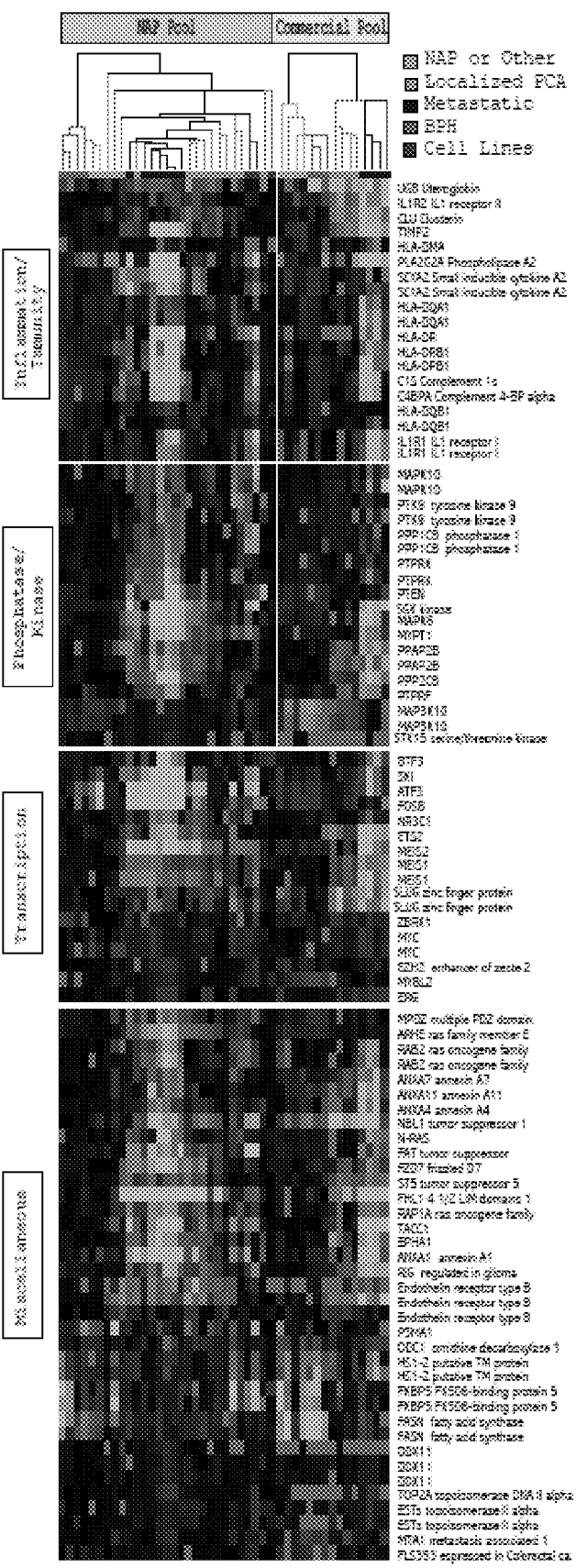

FIG. 2 shows the differential expression of functional clusters of select genes in prostate cancer. Gene names or symbols (as specified by Human genome organization (HUGO) gene nomenclature) are shown. The same convention for representing changes in transcript levels was used as in FIG. 1. The sample order from FIG. 1 was preserved for clarity.

Figure 8:
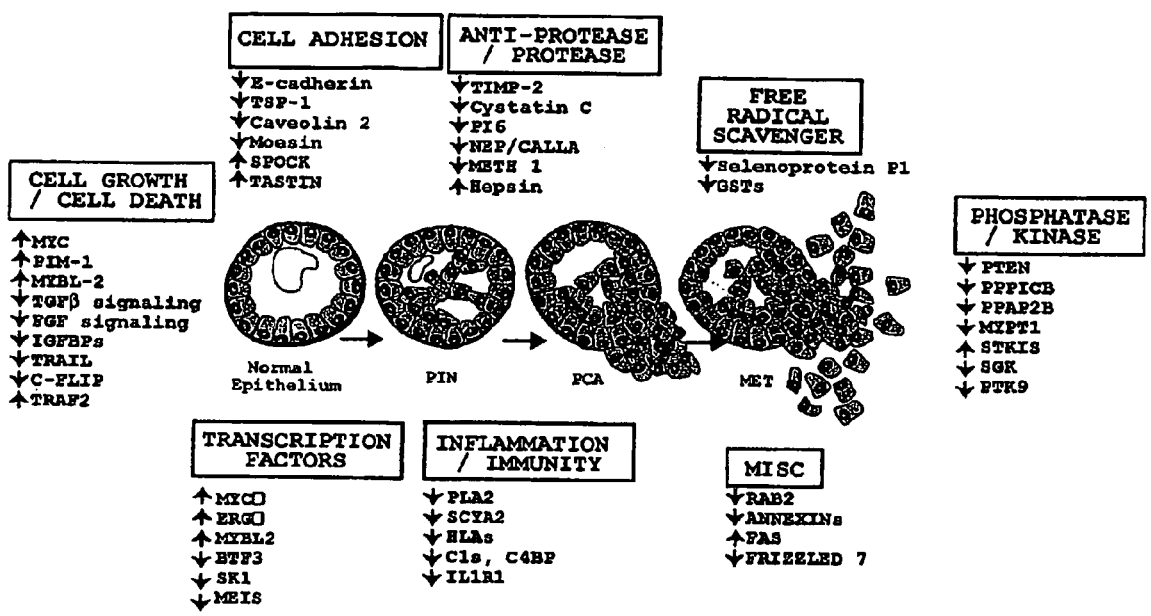
FIG. 8 shows an overview of genes differentially expressed in prostate cancer.

FIG. 8 shows a focused cluster of PCA-related genes. The same convention for representing changes in transcript levels was used as in FIG. 1. This cluster of 231 genes was generated by selecting for a 3.5-fold variation in at least 2 of any class, and ratio measurements present in 75% of the samples. Classes included: PCA vs. NAP, MET vs. NAP, PCA vs. CP and MET vs. CP.

The reliability of the hierarchical clustering results was assessed using three separate methods: that of Calinski and Harabasz (1974), Hartigan (1975) and Krzanowski and Lai (1985). The number of "stable" clusters estimated by all these methods is two. In the CP pool data set, that would elicit a valid benign cluster (NAP and BPH) and a malignant cluster (PCA and MET).

Many of the genes identified in these "focused" clusters have been implicated directly or indirectly as cancer biomarkers or mediators of carcinogenesis. Several have been shown to be dysregulated in PCA. For example, the tumor suppressor gene PTEN was down-regulated, while the proto-oncogene myc was up-regulated in the microarray analysis of PCA (FIG. 2) (Abate-Shen and Shen, supra). Likewise, decreased expression of E-cadherin and increased expression of fatty acid synthase, both of which have been shown to be dysregulated in PCA were observed (Tomita et al., Cancer Res., 60:3650 [2000] and Shurbaji et al., Hum. Pathol., 27:917 [1996]). In addition to uncharacterized expressed sequence tags (ESTs), there are numerous genes that were identified by the screen but not previously known to be associated with PCA. It is contemplated that they find use as cancer markers.

Exemplary nucleic acid sequences for some of the genes identified in focused clusters are shown in FIGS. 9 and 10. The present invention is not limited to the particular nucleic acid sequences described in FIGS. 9 and 10. One skilled in the art recognizes that additional variants, homologs, and mutants of the described sequences find use in the practice of the present invention.

3. Comparison Between NAP and CP pools

Figure 5:
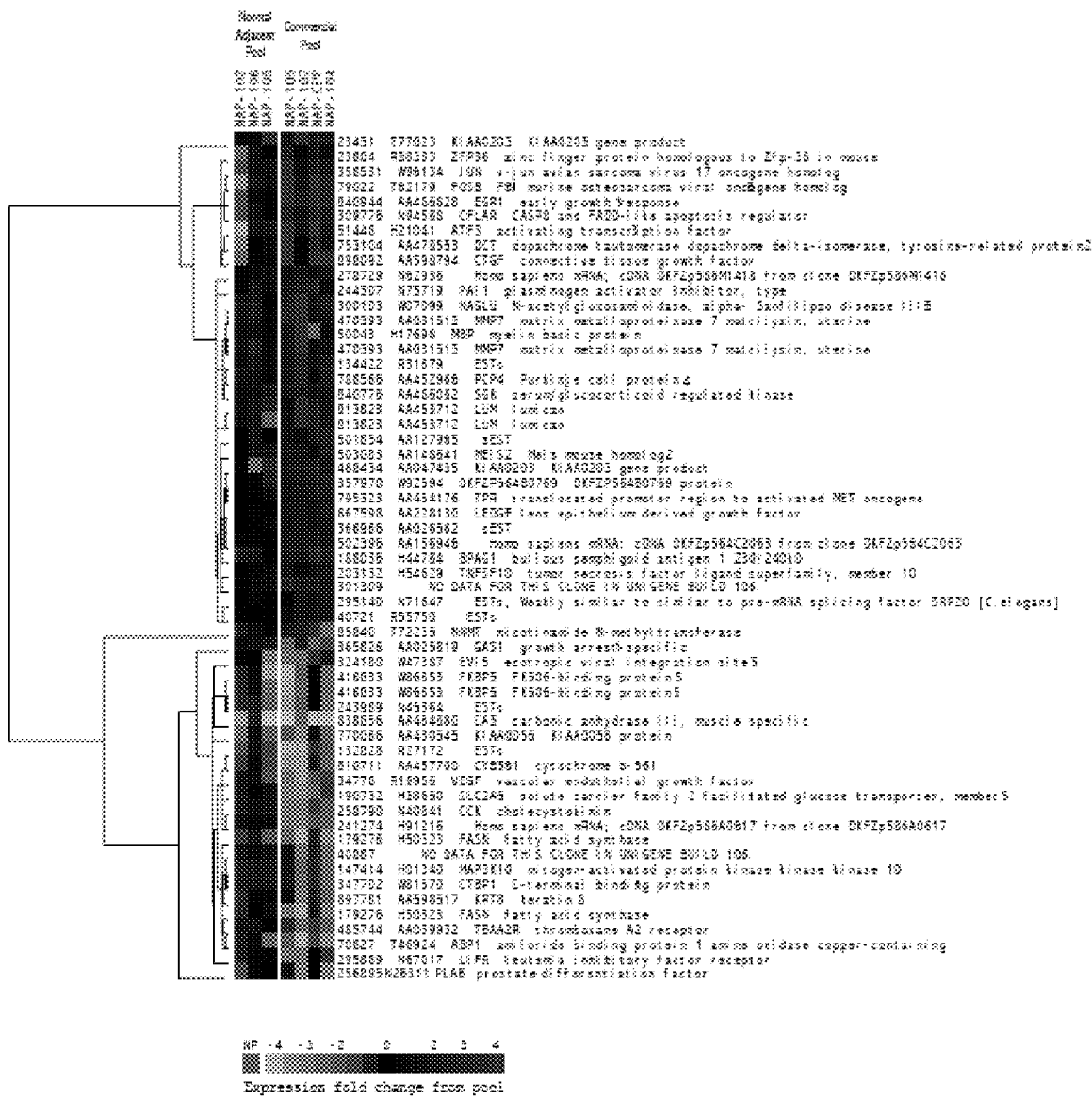
FIG. 5 shows a comparison of gene expression profiles for normal adjacent prostate tissue and normal prostate tissue reference.

A direct comparison between the NAP and CP pool was also made and notable gene expression differences were readily apparent. FIG. 5 shows a comparison between the NAP and CP pools. The same convention for representing changes in transcript levels was used as in FIG. 1. The cluster was obtained by selecting for genes with at least a 2.5-fold variation in any two of the samples of each class, namely the normal tissues versus the NAP pool and normal tissue versus the CP pool at a 50% filter. Of the genes analyzed 59 were selected with this criteria. Genes that were found to be up-regulated in the NAP pool in comparison with CP pool included connective tissue growth factor, EGR-1 (Early Growth Response 1), matrilysin (MMP7), CFLAR/I-FLICE (caspase 8 and FADD-like apoptosis regulator), lumican, serum glucocorticoid regulated kinase, lens epithelium derived growth factor, PAI1 (plasminogen activator inhibitor type I), JUN and FOS B, among others. Vascular endothelial growth factor (VEGF), growth arrest specific (GAS1), cholecystokinin (CCK), amiloride binding protein (ABP1) were among the down-regulated genes in the normal adjacent prostate pool when compared to the commercial pool. The present invention is not limited to a particular mechanism. Indeed, an understanding of the mechanism is not necessary to practice the present invention. Nonetheless, it is contemplated that the gene expression differences between normal prostate adjacent to PCA (NAP) and normal prostate tissue from individuals without prostate pathology (CP) may be attributable to a "field effect" induced by PCA itself.

EXAMPLE 3

Northern Blot Analysis

Thirty micrograms of total RNA was resolved by denaturing formaldehyde agarose gel and transferred onto Hybond membrane (Amersham) by a capillary transfer set up. Hybridizations were performed by the method described by Church and Gilbert, 1984. Signal was visualized and quantitated by phosphorimager. For relative fold estimation, the ratio between the signals obtained from hepsin and GAPDH probes was calculated.

Figure 3A:
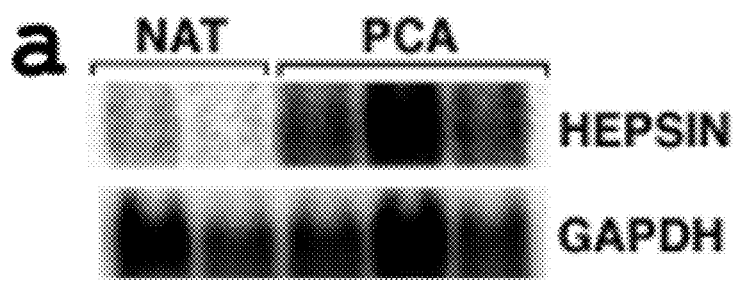
FIG. 3a shows Northern blot analysis of human hepsin (top) and normalization with GAPDH (bottom). NAT indicates normal adjacent prostate tissue and PCA indicates prostate cancer.

Selected genes identified by microarray analysis were corroborated by Northern analysis. For example, hevin, 4½ LIM domain protein and gelsolin were shown to be 3.2-, 3.2- and 1.9-fold down-regulated, respectively by microarray and 8.8-, 4.5-, and 3.5-fold down-regulated by Northern analysis. Similarly, hepsin was 4.3-fold up-regulated by microarray and 11.3-fold up-regulated by Northern analysis (FIG. 3a). As hepsin is a cell-surface serine protease with transcript expression precisely restricted to localized and metastatic PCA, its expression was examined in more detail at the protein level (See Example 4 below).

EXAMPLE 4

Tissue Analysis

This example describes the analysis of protein expression in normal and cancerous prostate tissues.

A. Tissue Microarray Construction.

Kononen et al have described a method for evaluating tumor tissues in large numbers on a single glass slide (Kononen et al., Nat. Med., 4:844 [1998]). These high-density tissue microarrays allow for analysis of up to 1,000 tissue samples on a single slide. These slides can be evaluated by routine light microscopy on hematoxylin and eosin (H&E) prepared and immunohistochemically stained slides. Thus, candidate cancer biomarkers, identified by gene expression methodologies, can be evaluated at the protein level over a large number of clinically stratified tumor specimens.

Prostate tissues used in microarray analysis included 4 BPH, 8 NAP, 1 commercial pool of normal prostate tissue (from 19 individuals), 1 prostatitis, 11 localized PCA, and 7 metastatic PCA specimens. High-density tissue microarrays (TMA) were assembled using a manual tissue puncher/array (Beecher Instruments, Silver Springs, Md.) as previously described (Kononen et al., Nat. Med., 4:844 [1998]; Perrone et al., J. Natl. Cancer Inst., 92:937 [2000]). The instrument consists of thin-walled stainless steel needles with an inner diameter of approximately 600 µm and stylet used to transfer and empty the needle contents. The assembly is held in an X-Y position guide that is manually adjusted by digital micrometers. Small biopsies are retrieved from selected regions of donor tissue and are precisely arrayed in a new paraffin block. Tissue cores were 0.6 mm in diameter and ranged in length from 1.0 mm to 3.0 mm depending on the depth of tissue in the donor block. Multiple replicate core samples of normal, HGPIN, and PCA were acquired from each tissue block of each case. Cores were inserted into a 45×20×12 mm recipient bock and spaced at a distance of 0.8 mm apart. Prostate tumor grading was performed using the system described by Gleason (Gleason, Cancer Chemother Rep., 50:125 [1966]). Pathologic stages for the radical prostatectomies were determined using the TNM staging system (Schroder et al., Prostate Suppl., 4:129 [1992]). Surgical margins were assessed separately and are not included in tumor staging.

B. Immunohistochemistry

TMA sections were cut at five-micron thick intervals for immunohistochemistry. Initial sections were stained for hematoxylin and eosin to verify histology. TMA slides prepared from formalin-fixed paraffin embedded tissue were heated for 0.5-1 hours at 60° centigrade. All slides were placed in 10 millimolar citrate buffer (pH 6.0) and microwaved for 5 minutes. Standard biotin-avidin complex immunohistochemistry was performed. The affinity purified polyclonal Rabbit antibody against hHepsin was used at a 1:40 dilution (original concentration 0.2 mg/ml) for this study. Immunostaining intensity was scored by a dedicated genitourinary pathologist as absent, weak, moderate, or strong. Scoring was performed using a telepathology system in a blinded fashion without knowledge of overall Gleason score (e.g., tumor grade), tumor size, or clinical outcome (Perrone et al., supra). A total of 738 tissue samples from benign (n=205), high-grade PIN (n=38), localized prostate cancer (n=335) and hormone refractory prostate cancer (n=160) were examined.

Similarly, pim-1 was analyzed using two TMA blocks from a total of 810 PCA samples from 135 patients. Six PCA samples were evaluated from each case and a median score was calculated. In addition, a small number of samples with benign prostatic tissues (e.g., benign epithelium and atrophy) and HG-PIN were examined. Immunohistochemistry was performed as above, using a rabbit polyclonal antibody against the N-terminus of pim-1 (Santa Cruz Biotechnology) at a 1:100 dilution. Pim-1 demonstrated cytoplasmic staining and was graded as either negative, weak, moderate, or strong. All samples were reviewed blinded with respect to all related pathology and clinical data.

C. Statistical Methods

A nonparametric ANOVA test (Mann-Whitney [two categories]) was employed to evaluate whether the prostate samples expressed hepsin and pim-1 at different levels based on various parameters (tissue type, Gleason score, and tumor size). Kaplan-Meier analysis was used to estimate the cumulative percentage of PSA free progression ("survival"). The log-rank test was employed to assess the differences in disease free progression hepsin immunostaining. Cox proportional-hazard regression was used for multivariate analysis. Commercial software from SPSS (Chicago, Ill.) was used for this study.

D. Results

1. Hepsin

Figure 3B:
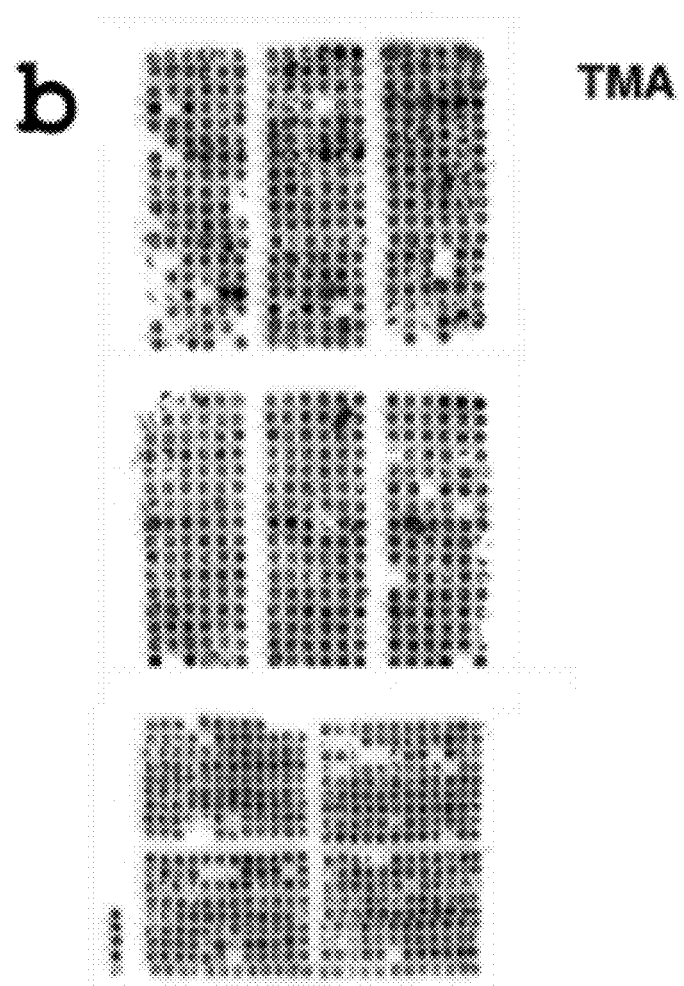
FIG. 3b shows tissue microarrays used for hepsin analysis.

Microarrays used in this study are shown in FIG. 3b. Over 700 benign and malignant prostate tissues were immunohistochemically profiled on tissue microarrays (FIG. 3c-e) using an affinity-purified hepsin-peptide antibody (Tsuji et al., J. Biol. Chem., 266:16948 [1991]). FIG. 3 shows the overexpression of Hepsin, a transmembrane serine protease, in prostate cancer. FIG. 3a shows a Northern blot analysis of human hepsin (top) and normalization with GAPDH (bottom). NAT indicates normal adjacent prostate tissue and PCA indicates prostate cancer. FIG. 3b shows tissue microarrays used for hepsin analysis. Staining was done with hemotoxylin and eosin to verify histology.

Figure 3C:
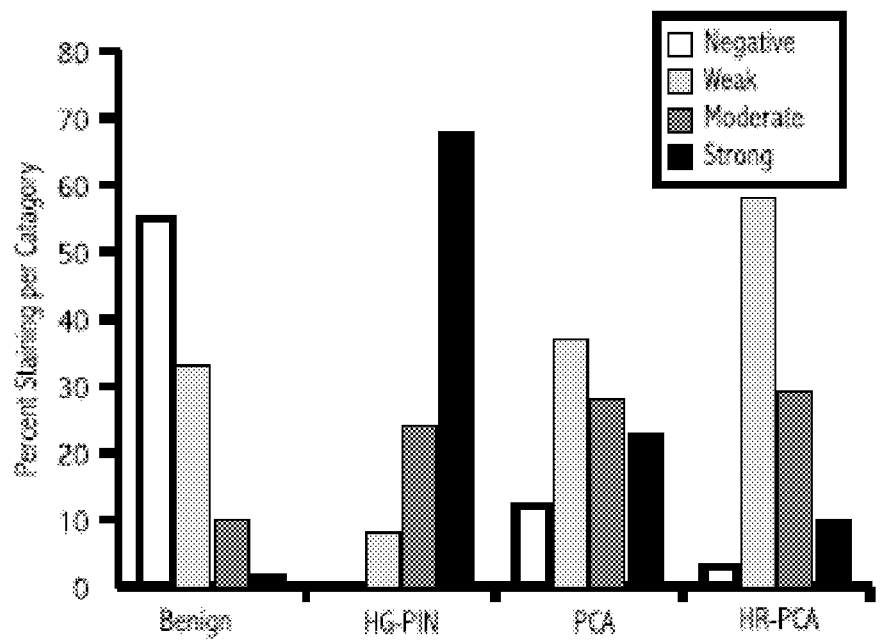
FIG. 3c shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET).
Figure 3D:
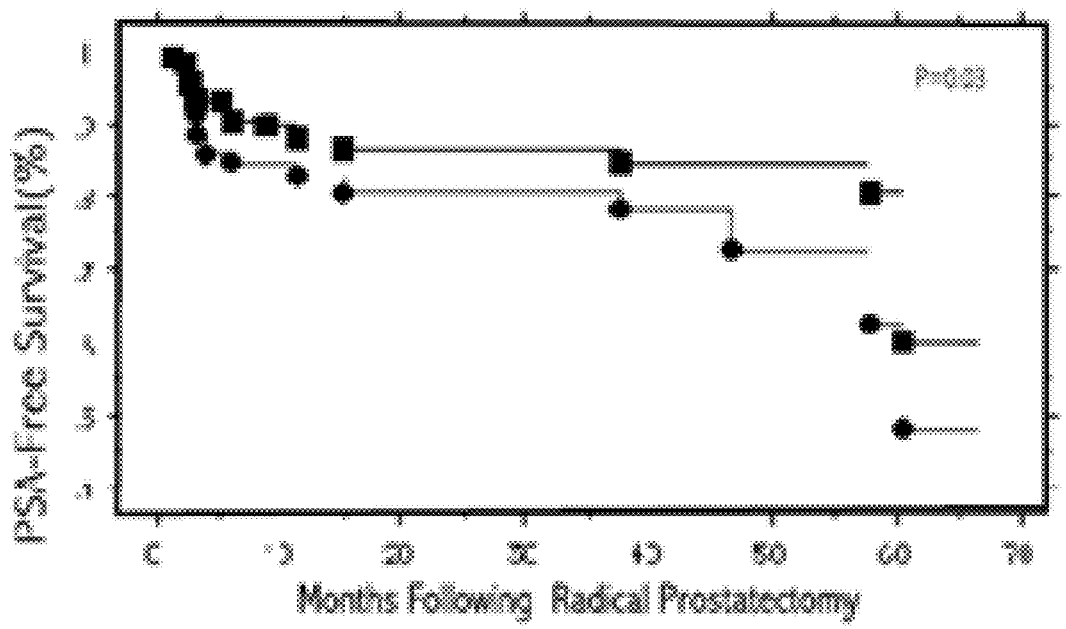
FIG. 3d shows Kaplan Meier Analysis.

Immunohistochemical stains demonstrated absent or weak staining of benign prostate (c1), strong staining in localized prostate cancer (c2-6), and strong staining in a high-grade prostate tumor (magnification 100× was used for all images, samples measure 0.6 mm in diameter). Benign prostate glands demonstrate weak expression in the secretory, luminal cells and strong basal cell staining. In areas where prostate cancer and benign prostate glands are seen, significant hepsin staining differences are observed. Infiltrating prostate cancers (d3-4) demonstrate strong hepsin protein expression. Magnification for all images was 400×. FIG. 3c shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). Relative strength of hepsin staining was qualitatively assessed and categorized. Percentage of hepsin staining per category is shown on the y-axis. FIG. 3d shows Kaplan Meier Analysis. PSA-free survival was stratified by level of hepsin protein expression into two categories absent/low expression (circles) versus moderate/strong expression (squares).

Internal controls showed that liver tissue, as previously described, stained strongly for hepsin. Overall, hepsin exhibited predominantly membrane staining and was preferentially expressed in neoplastic prostate over benign prostate (Mann-Whitney test, p<0.0001). Importantly, the precursor lesion of PCA, HG-PIN, had the strongest expression of hepsin, and almost never had absent staining (Mann-Whitney, p<0.0001). Most cases of low or absent hepsin staining were seen in benign prostate specimens. In addition, hormone refractory metastatic cancers were intermediate in staining intensity between localized prostate tumors and benign prostate.

Men who develop elevated PSA levels following radical prostatectomy are at a high risk to develop distant metastases and die due to prostate cancer (Pound et al., JAMA, 281:1591 [1999]. Therefore, to assess the usefulness of hepsin as a potential PCA biomarker, PSA failure was defined as a PSA elevation of greater than 0.2 ng/ml following radical prostatectomy. Analysis was performed on 334 localized prostate cancer samples treating each as an independent sample. PSA elevation following radical prostatectomy was significantly associated with absent and low hepsin immunostaining with a 28% (46/119 samples) PSA failure rate, in contrast to 17% (28/141 samples) PSA failure rate for tumors with moderate to strong hepsin expression (FIG. 3d, Log Rank test P=0.03). Multivariate analysis was performed to examine if these results were independent of Gleason score, a well-established histologic grading system for PCA (Gleason, Hum. Pathol., 23:273 [1992]). Based on the results from fitting a Cox proportional hazards model, there is an association of weak or absent hepsin protein expression in PCA with increased risk of PSA elevation following prostatectomy, similar to high Gleason score (corresponding risk ratios were 2.9 (p=0.0004) and 1.65 (p=0.037), respectively). Weak or absent hepsin expression was also associated with large prostate cancers; the median tumor dimension for prostate tumors with moderate to strong expression was 1.3 cm but 1.5 cm for tumors with absent or weak staining (Mann-Whitney Rank test, P=0.043). Taken together, hepsin protein expression in PCA correlated inversely with measures of patient prognosis.

Hepsin is a 51 kDa transmembrane protein with highest expression in the liver, and like PSA, is a serine protease (Kurachi et al., Methods Enzymol., 244:100 [1994]). The protease domain of hepsin has access to the extracellular space and can potentially activate other proteases or degrade components of extracellular matrix. The function of hepsin is poorly understood. It has been proposed to have a role in controlling cell growth (Torres-Rosado et al., PNAS, 90:7181 [1993], cell morphology, and activating the extrinsic coagulation pathway on the cell surface, leading to thrombin formation (Kazama et al, J. Biol. Chem., 270:66 [1995]). Additionally, hepsin mRNA levels have been shown to be elevated in ovarian carcinomas (Tanimoto et al., Cancer Res., 57:2884 [1997]). The present invention is not limited to a particular mechanism. Indeed, an understanding of the mechanism is not necessary to practice the present invention. Nonetheless, it is contemplated that the high expression of hepsin in HG-PIN, and not benign prostate, suggests that hepsin plays a role in the establishment of PIN or in the transition from HG-PIN to carcinoma. Subsequent decreases in hepsin expression seen in large localized cancers and hormone-refractory cancers suggest a decreased requirement of this protease in later stages of PCA. Alternatively, patients with advanced PCA often develop disseminated intravascular coagulation (DIC) (Riddell et al., J. Nucl. Med., 37:401 [1996]) whereby hepsin may play an important role.

2. pim-1

Tumorigenic growth of the prostate depends on the evasion of normal homeostatic control mechanisms, where cell proliferation exceeds cell death (Bruckheimer and Kyprianou, Cell Tissue Res., 301: 153 [2000]). While it is well known that the oncogene myc is overexpressed in many PCAs (Buttyan et al., prostate 11:327-37 [1987]; Abate-Shen and Shen, supra), the present invention demonstrates that the proto-oncogene pim-1 kinase is similarly up-regulated (cell growth/cell death cluster, FIG. 2). Previous studies suggest that the cooperative interaction between pim-1 and myc may induce lymphoid cell transformation by promoting cell cycle progression and blocking apoptosis (Shirogane, et al., Immunity 11:709 [1999]). The present analysis supports a similar co-transcriptional regulation (or gene amplification) of pim-1 and myc possibly mediating a synergistic oncogenic effect in PCA.

Figure 4A:
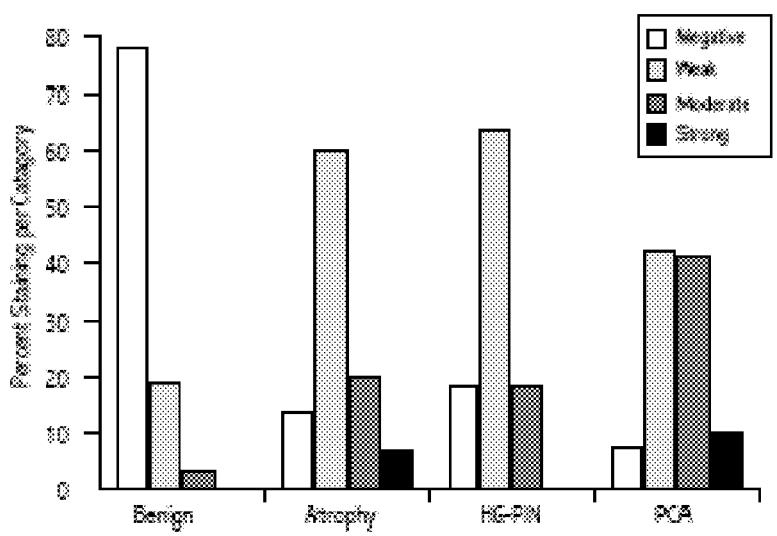
FIG. 4a shows a histogram of pim-1 protein expression by tissue type as assessed from 810 tissue microarray elements. High-grade intraepithelial neoplasia (HG-PIN). Localized prostate cancer (PCA).
Figure 4B:
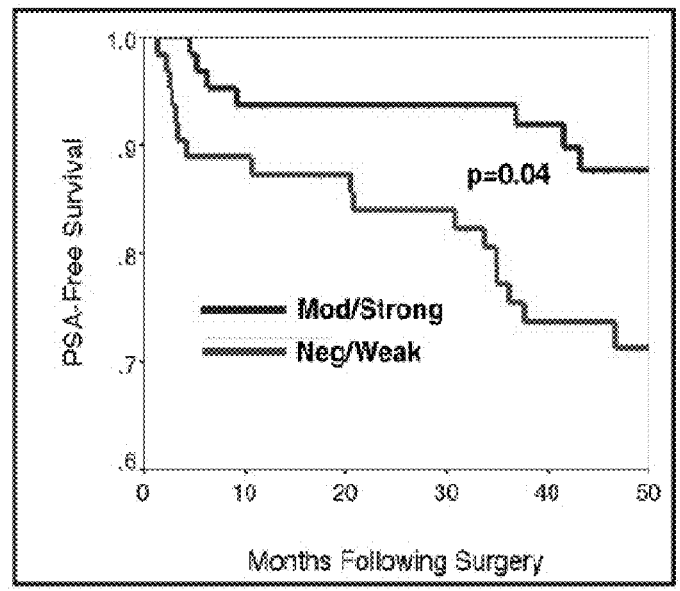
FIG. 4b shows a Kaplan-Meier analysis. The tope line represents patients with strong Pim-1 staining. The bottom line represents patients with absent/weak Pim-1 expression.

Pim-1 kinase protein expression in PCA was also explored using high-density TMAs. FIG. 4 shows the overexpression of pim-1 in prostate cancer. Immunohistochemical stains demonstrated absent or weak staining of benign prostate, and strong cytoplasmic staining in localized prostate cancer. Benign prostate glands demonstrated absent or weak expression in the secretory, luminal cells. Infiltrating prostate cancers demonstrated strong pim-1 protein expression. Magnification for all images 1000×. FIG. 4a shows a histogram of pim-1 protein expression by tissue type as assessed from 810 tissue microarray elements. High-grade intraepithelial neoplasia (HG-PIN). Localized prostate cancer (PCA). Relative strength of pim-1 staining is represented in the included legend. The percentage of pim-1 staining per category shown on y-axis. FIG. 4b shows Kaplan-Meier analysis demonstrating that patients with PCA that have negative to weak pim-1 expression (bottom line) are at a greater risk of developing PSA-failure following prostatectomy (log rank p=0.04). PSA-free survival was stratified by level of pim-1 protein expression into two categories absent/weak expression (bottom line) versus moderate/strong expression (top line).

Pim-1 protein was found to be markedly overexpressed in PCA (FIG. 4). Negative to weak pim-1 protein expression was observed in the majority of benign prostatic epithelial (97%), prostatic atrophy (73%), and high-grade PIN (82%) samples (FIG. 4a). In contrast, moderate to strong pim-1 expression was observed in approximately half of the PCA samples (51%) (FIG. 4a). Kaplan-Meier analysis for PSA-free survival demonstrated positive extraprostatic extension, seminal vesicle invasion, Gleason score greater than 7 and decreased pim-1 expression to be associated with a higher cumulative rate of PSA failure (FIG. 4b). By univariate Cox models, it was found that Pim-1 expression is a strong predictor of PSA recurrence (hazard ratio (HR)=2.1 (95% CI 1.2-3.8, p=0.01)).

Among the variables examined, significant predictors of PSA recurrence were Gleason score (HR=1.8 (95% CI 1.1-3.0), p=0.03), Gleason pattern 4/5 PCA (HR=3.9(95% CI 1.8-8.3), p<0.001), extraprostatic extension status (HR=2.6 (95% CI 1.6-4.2), p<0.0001), surgical margin status (HR=2.6 (95% CI 1.2-5.6), p=0.01), seminal vesicle status (HR=3.5 (95% CI 2.0-6.2), p<0.0001), the natural log of pre-operative PSA level (HR=2.5 (95% CI 1.6-3.8), p<0.001), HR=2.4, p<0.001), and maximum tumor dimension (HR=2.7 (95% CI 1.6-4.7), p<0.0001). Presence of Gleason pattern 4/5 PCA (HR=3.8 (95% CI 1.4-10.0), p<0.01), Ln(PSA) (HR=2.1 (95% CI 1.1-3.9), p=0.02), and decreased pim-1 protein expression (HR=4.5 (95% CI 1.6-15.2), p=0.01) were both found to be significant predictors of PSA recurrence by a multivariate Cox model. Thus, even more so than hepsin, decreased expression of pim-1 kinase in PCA correlated significantly with measures of poor patient outcome.

Pim-1 kinase is a proto-oncogene that is regulated by cytokine receptors (Matikainen et al, Blood 93:1980 [1999]). It was first described as a common site of proviral integration in murine retrovirus-induced T cell lymphomas (Cuypers et al., Cell 37:141 [1984]), and was previously thought to be involved exclusively in hematopoietic malignancies (Breuer et al., Nature 340:61 [1989]). Co-transcriptional regulation of pim-1 and myc was observed in the experiments described herein (FIG. 2 cell growth/cell death cluster). Chronic overexpression of myc in the ventral prostate of transgenic mice induced epithelial abnormalities similar to low-grade PIN, but progression to adenocarcinoma in this model was never observed (Zhang et al., Prostate 43:278 [2000]). The present invention is not limited to any one mechanism. Indeed, an understanding of the mechanism is not necessary to practice the present invention. Nonetheless, it is contemplated that pim-1 overexpression may potentiate myc-induced prostate carcinogenesis.

FIG. 8 provides a schematic overview of representative genes differentially expressed in PCA identified by DNA microarray analysis. Genes are grouped functionally and arrows represent up- or down-regulation in metastatic hormone-refractory PCA (MET) and/or localized PCA (PCA) relative to normal prostate epithelium. See FIG. 2 for gene expression levels.

EXAMPLE 5

AMACR Expression Analysis

The Example describes the analysis of the gene expression data described in Examples 1-4 above to identify AMACR as being consistently over-expressed in prostate cancer.

A. Tissue Samples

In order to examine the widest range of prostate cancer specimens, clinical samples were taken from the radical prostatectomy series at the University of Michigan and from the Rapid Autopsy Program. Both programs are part of the University of Michigan Prostate Cancer Specialized Program of Research Excellence (S.P.O.R.E.) Tissue Core.

Prostatectomy cases for the tissue microarray (TMA) outcomes array were selected from a cohort of 632 patients, who underwent radical retropubic prostatectomy at the University of Michigan as a monotherapy (i.e., no hormonal or radiation therapy) for clinically localized prostate cancer between the years of 1994 and 1998. Clinical and pathology data for all patients was acquired with approval from the Institutional Review Board at the University of Michigan. Detailed clinical, pathology, and TMA data is maintained on a secure relational database (Manley et al., Am. J. Pathol., 159:837 [2001]).

Processing of the prostate specimens began within approximately 15-20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol., 164:1583 [2000]). Briefly, alternate sections of the prostate gland were submitted for histologic review. The remaining sections were frozen and stored in the SPORE Tissue Core. These samples were collected only from patients who had signed an IRB-approved informed consent. The samples were snap-frozen in OCT embedding media at −80° C. and stored in a holding area until the pathology report was finalized. These frozen samples were not available to researchers until adequate diagnosis and staging had been performed. The samples used for cDNA expression array analysis and RT-PCR were all evaluated by the study pathologists. All samples were grossly trimmed such that greater than 95% of the sample represented the desired lesion (e.g., prostate cancer, BPH, or benign prostate). Samples with prostate cancer were also assigned a Gleason score based on the sample used for molecular analysis.

In order to study hormone refractory prostate cancer, a Rapid Autopsy Protocol was used, which represents a valuable source of metastatic prostate tumors. Modeled after protocols developed at the University of Washington (Seattle, Wash.) and Johns Hopkins University (Baltimore, Md.), this program allows men with advanced prostate cancer to consent to an autopsy immediately after death. To date, 23 complete autopsies have been performed with a median time of 2 hours from death to autopsy. This procedure has previously been described in detail (Rubin et al., Clin. Cancer Res., 6:1038 [2000]). In brief, patients diagnosed with hormone refractory prostate cancer were asked to take part in a posthumous tissue donor program. The objectives and procedures for tissue donation were explained to the patient. Having agreed to participate in this IRB-approved tumor donor program, permission for autopsy is obtained before the death, with consent provided by the patient, or by next of kin. Hormone refractory primary and metastatic prostate cancer samples were collected using liquid nitrogen. Mirrored samples from the same lesion were placed in 10% buffered formalin. The fixed samples were embedded in paraffin and used for the development of TMAs. As with the prostatectomy samples, the study pathologist reviewed the glass slides, circled areas of viable prostate cancer, while avoiding areas of necrosis, and used these slides as a template for TMA construction.

B. Pathology and Evaluation

Pro states were inked before the assessment of surgical margins. Surgical margins from the apex and base were cut perpendicular to the prostatic urethral axis. The seminal vesicles were cut perpendicular to their entry into the prostate gland and submitted as the seminal vesicle margin. The prostates for this study were all partially embedded, taking alternate full sections from the apex, mid, and base. Detailed prostatectomy pathology reports included the presence or absence of surgical margin involvement by tumor (surgical margin status), the presence of extrapro static extension, and seminal vesicle invasion. Tumors were staged using the TNM system, which includes extraprostatic extension and seminal vesicle invasion but does not take into account surgical margin status (Bostwick et al., Simin. Urol. Oncol., 17:222 [1999]). Tumors were graded using the Gleason grading system (Gleason, Cancer Chemother. Rep., 50:125 [1966]; Gleason, The Veterans Administration Cooperative Urological Research Group. Histologic Grading and Clinical Staging of Prostate Carcinoma. In: Tannenbaum M, editor. Urologic Pathology: The Prostate. Philadelphia: Lea & Febiger; 1977. p. 171-98).

As preparation for the construction of the TMAs, all glass slides were re-reviewed to identify areas of benign prostate, pro static atrophy, high-grade pro static intraepithelial neoplasia, and prostate cancer. To optimize the transfer of these designated tissues to the arrays, area of tumor involvement was encircled on the glass slide template as tightly around each lesion as possible. Areas with infiltrating tumor adjacent to benign glands were avoided.

C. RT-PCR

Total RNA integrity was judged by denaturing-formaldehyde agarose gel electrophoresis. cDNA was prepared using 1 μg of total RNA isolated from prostate tissue specimens. Primers used to amplify specific gene products were: AMACR sense, 5' CGTATGCCCCGCTGAATCTCGTG-3' (SEQ ID NO:100); AMACR antisense, 5'-TGGCCAAT-CATCCGTGCTCATCTG-3' (SEQ ID NO:101); GAPDH sense, 5'-CGGAGTCAACGGATTTGGTCGTAT-3' (SEQ ID NO:102); and GAPDH antisense, 5'-AGCCTTCTC-CATGGTGGTGAAGAC-3' (SEQ ID NO:103). PCR conditions for AMACR and GAPDH comprised 94° C. for 5 min, 28 cycles of 95° C. for 1 min, 60° C. for 1 min (annealing), and 72° C. for 1 min, and a final elongation step of 72° C. for 7 min. PCR reactions used a volume of 50 μl, with 1 unit of Taq DNA polymerase (Gibco BRL). Amplification products (5 μl) were separated by 2% agarose gel electrophoresis and visualized by ultraviolet light.

D. Immunoblot Analysis

Representative prostate tissue specimens were used for Western blot analysis. Tissues were homogenized in NP-40 lysis buffer containing 50 mmol/L Tris-HCl, pH 7.4, 1% Nonidet P-40 (Sigma, St. Louis. Mo.) and complete proteinase inhibitor cocktail (Roche, Ind., USA). Fifteen μg of protein extracts were mixed with SDS sample buffer and electrophoresed onto a 10% SDS-polyacrylamide gel under reducing conditions. The separated proteins were transferred onto nitrocellulose membranes (Amersham Pharmacia Biotech, Piscataway, N.J.). The membrane was incubated for 1 hour in blocking buffer (Tris-buffered saline with 0.1% Tween (TBS-T) and 5% nonfat dry milk). The AMACR antibody (Obtained from Dr. R Wanders, University of Amsterdam) was applied at 1:10,000 diluted in blocking buffer overnight at 4° C. After washing three times with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.) and autoradiography.

For 13-tubulin western blots, the AMACR antibody probed membrane was stripped with Western Re-Probe buffer (Geno-tech, St. Louis, Mo.) and blocked in Tris-buffered saline with 0.1% Tween (TBS-T) with 5% nonfat dry milk and incubated with rabbit anti 13-tubulin antibodies (Santa Cruz Biotechnologies, Santa Cruz, Calif.) at 1:500 for two hours. The western blot was then processed as described above.

E. Immunohistochemistry

Standard indirect immunohistochemistry (IHC) was performed to evaluate AMACR protein expression using a polyclonal anti-AMACR antibody. Protein expression was scored as negative (score=1), weak (score 2), moderate (3) and strong (4). In order to evaluate whether AMACR protein expression was associated with prostate cancer proliferation, a subset of samples were evaluated using the monoclonal mouse IgG Mib-1 antibody for Ki-67 (1:150 dilution, Coulter-Immunotech, Miami, Fla.). Microwave pretreatment (30 minutes at 100 C in Tris EDTA Buffer) for antigen retrieval was performed using 3,3' diaminobenzidine tetrahydrochloride as a chromogen. Lymph node tissue with known high Ki-67 positivity was used as a control.

F. Tissue Microarray Construction, Digital Image Capture, and Analysis

Five TMAs were used for this study. Three contained tissue from the prostatectomy series and two contained hormone refractory prostate cancer from the Rapid Autopsy Program. The TMAs were assembled using the manual tissue arrayer (Beecher Instruments, Silver Spring, Md.) as previously described (Kononen et al., Nat. Med., 4:844 [1998]; Perrone et al., J. Natl. Cancer Inst., 92:937 [2000]). Tissue cores from the circled areas (as described above) were targeted for transfer to the recipient array blocks. Five replicate tissue cores were sampled from each of the selected tissue types. The 0.6 mm diameter TMA cores were each spaced at 0.8 mm from core-center to core-center. After construction, 4 μm sections were cut and H&E staining was performed on the initial slide to verify the histology.

TMA H&E images were acquired using the BLISS Imaging System (Bacus Labs, Lombard, Ill.). AMACR protein expression was evaluated in a blinded manner. All images were scored for AMACR protein expression intensity. In addition, all TMA samples were assigned a diagnosis (i.e., benign, atrophy, high-grade prostatic intraepithelial neoplasia, and prostate cancer). This is recommended because the targeted tissues may not be what is actually transferred. Therefore, verification was performed at each step. TMA slides were evaluated for proliferation index using a CAS200 Cell Analysis System (Bacus Labs). Selected areas were evaluated under the 40X objective. Measurements were recorded as the percentage of total nuclear area that was positively stained. All positive nuclear staining, regardless of the intensity, was measured. Sites for analysis were selected to minimize the presence of stromal and basal cells; only tumor epithelium was evaluated. Specimens were evaluated for Ki-67 expression as previously described (Perrone et al, J. Natl. Cancer Inst. 92:937 [2000]). Each measurement was based on approximately 50-100 epithelial nuclei. Due to the fixed size of TMA samples, 5 repeat non-overlapping measurement was the maximum attainable.

G. Analysis of Prostate Needle Biopsies

In order to evaluate the usefulness of AMACR expression in diagnostic 18 gauge needle biopsies, 100 consecutive biopsies with prostate cancer or atypia that required further work-up were tested for AMACR expression. All cases were immunostained using two basal cell specific markers (34βE12 and p63) and AMACR. Cases were evaluated for cancer sensitivity and specificity. Twenty-six of these cases were seen in consultation with a pathologist and were considered diagnostically difficult, requiring expert review and additional characterization.

H. Results

Figure 11:
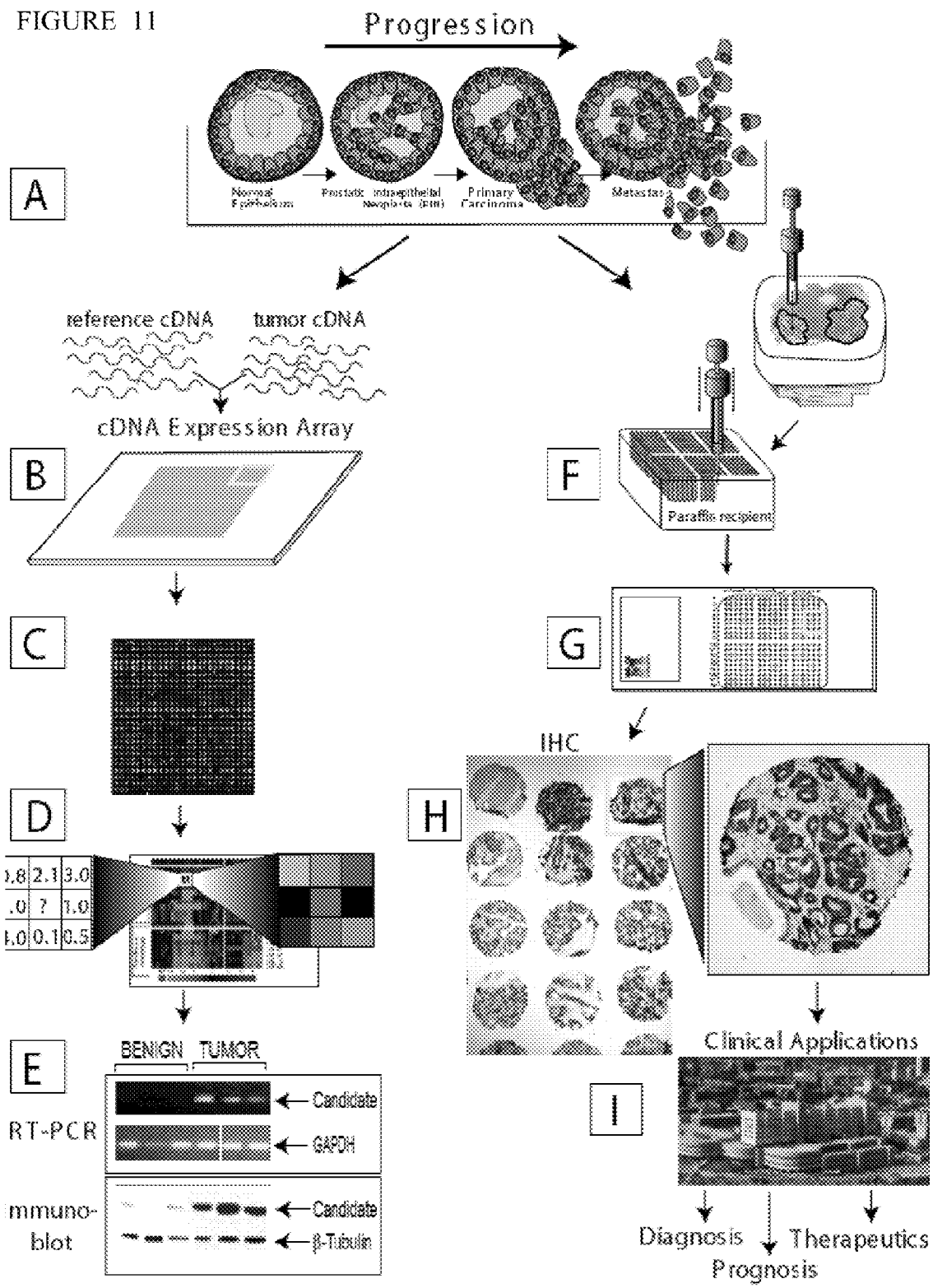
FIG. 11 an overview of the discovery and characterization of AMACR in prostate cancer utilized in some embodiments of the present invention.

FIG. 11 shows a schematic of the DNA and tissue microarray paradigm that lead to the discovery and characterization of AMACR in prostate cancer. A) Prostate cancer progression as adapted from Abate-Shen and Shen, (Genes Dev., 14:2410 [2000]). Distinct molecular changes occur at each stage of prostate cancer progression that can be studied using DNA microarray or "chip" technology. B) cDNA generated from tumor (prostate cancer) and reference (benign prostate tissue) samples is labeled with distinguishable fluorescent dyes and interrogated with a DNA microarray that can monitor thousands of genes in one experiment. C) After hybridization, the DNA microarray is analyzed using a scanner and fluorescence ratios determined for each gene (in this case prostate cancer/benign tissue). D) The ratios are deposited into a computer database and subsequently analyzed using various statistical algorithms. One exemplary method of surveying the data (Eisen et al, PNAS 95:14863 [1998]) assigns color intensity to the ratios of gene expression. In this case, shades of red represent genes that are up-regulated in prostate cancer (e.g., a ratio of 4.0) and shades of green represent genes that a down-regulated (e.g., ratio of 0.1). Genes that are unchanged between tumor and benign tissues are represented by a black color and missing elements by a gray color. E) Genes that are identified by DNA microarray can then be validated at the transcript level (e.g., Northern blot, RT-PCR) or at the protein level (e.g., immunoblot). F) Construction of prostate cancer tissue microarrays facilitates the study of hundreds of patients (rather than hundreds of genes). G) Each tissue microarray slide contains hundreds of clinically stratified prostate cancer specimens linked to clinical and pathology databases (not shown). H) Tissue microarray slides can then be analyzed using various molecular or biochemical methods (in this case immunohistochemistry). I) Both DNA and tissue microarray data have clinical applications. Examples include, but are not limited to: 1. using gene expression profiles to predict patient prognosis, 2. identification of clinical markers and 3. development of novel therapeutic targets.

Figure 12:
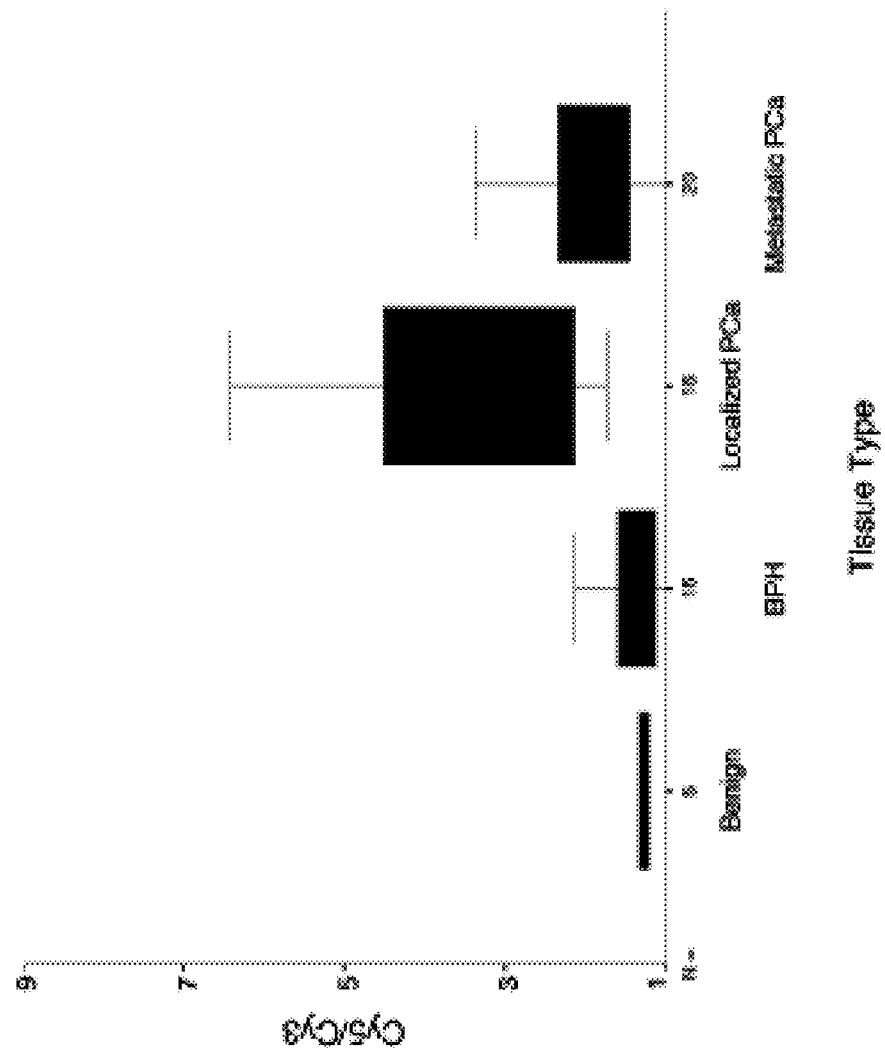
FIG. 12 describes a DNA microanalysis of AMACR expression in prostate cancer.

FIG. 12 summarizes AMACR transcript levels as determined by DNA microarray analysis over 57 prostate cancer specimens. Samples (Dhanasekaran et al., Nature 412: 822 [2001]) were grouped according to tissue type and averaged.

The experimental sample was labeled in the Cy5 channel while the reference sample (pool of benign prostate tissue) was labeled in the Cy3 channel. The box-plot demonstrates the range of AMACR expression within each group. Tissues were grouped into the following classes benign (normal adjacent prostate tissue), benign prostatic hyperplasia (BPH), clinically localized prostate cancer, and metastatic prostate cancer. In relation to benign prostate tissues, localized prostate cancer and metastatic prostate cancer were 3.1 (Mann-Whitney test, p<0.0001)and 1.67 (Mann-Whitney test, p<0.004) fold up-regulated, respectively (represented as Cy5/Cy3 ratios).

Figure 13:
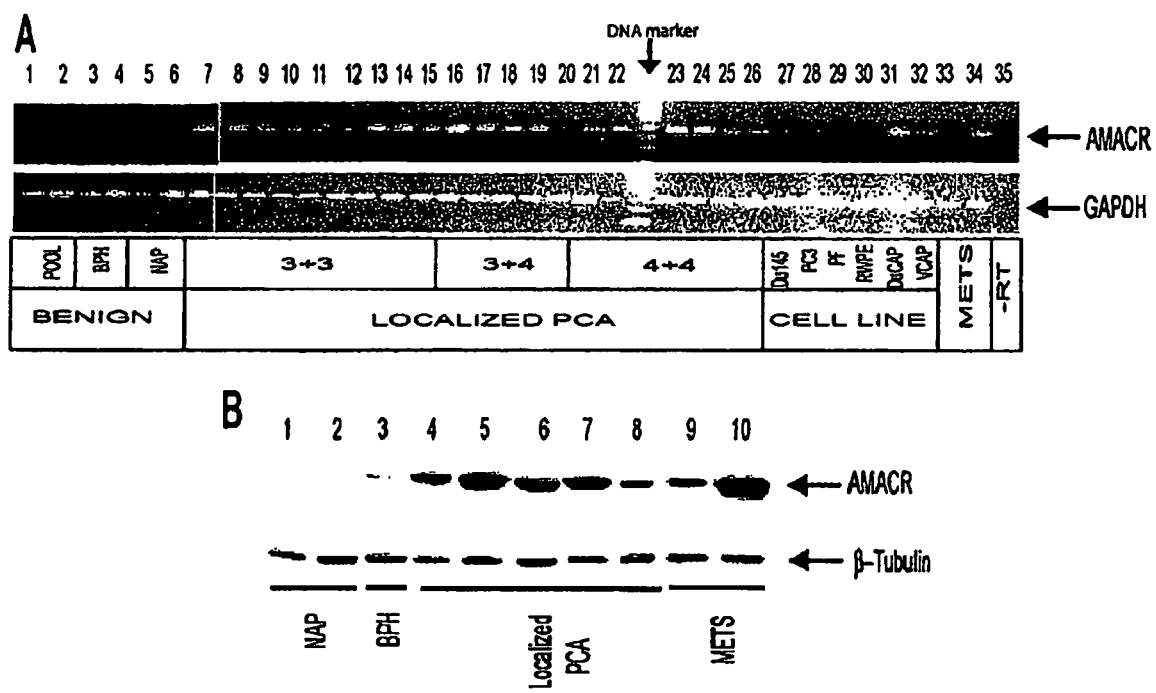
FIG. 13 describes an analysis of AMACR transcript and protein levels in prostate cancer.

DNA microarray results of AMACR mRNA levels were validated using an independent experimental methodology. AMACR-specific primers were generated and RT-PCR performed on the various RNA samples from 28 prostate tissue specimens and 6 prostate cell lines (FIG. 13A). GAPDH served as the loading control. Pool, refers to RNA from normal prostate tissues obtained from a commercial source. NAP, normal adjacent prostate tissue from a patient who has prostate cancer. 3+3, 3+4, 4+4, refers to the major and minor Gleason patterns of the clinically localized prostate cancer (PCA) examined. MET, metastatic prostate cancer. Various prostate cell lines are also examined. RT-PCR without enzyme served as a negative control. An RT-PCR product was clearly observed in the 20 localized prostate cancer samples but not in the benign samples examined. Metastatic prostate cancer and prostate cell lines displayed varying levels of AMACR transcript as compared to localized prostate cancer.

In order to gauge AMACR protein levels, immunoblot analysis was performed on selected prostate tissue extracts (FIG. 13B). β-tubulin served as a control for sample loading. Similar to AMACR transcript, over-expression of AMACR protein was observed in malignant prostate tissue relative to benign prostate tissue.

In order to validate protein expression of AMACR in situ, a separate cohort of prostate samples from those used in the cDNA expression array analysis was used. These prostate samples were taken from the University of Michigan Prostate SPORE Tissue Core and were assembled onto high-density tissue microarrays (schematically illustrated in FIG. 11F-H). Moderate to strong AMACR protein expression was seen in clinically localized prostate cancer samples with predominately cytoplasmic localization. A large contrast in levels of AMACR in malignant epithelia relative to adjacent benign epithelia was seen. Prostatic intraepithelial neoplasia (PIN) and some atrophic lesions, which are thought to be potentially pre-cancerous lesions (Putzi et al., Urology 56:828 [2000]; Shah et al., Am. J. Pathol., 158:1767 [2001]), demonstrated cytoplasmic staining of AMACR. High-grade prostate cancer also demonstrated strong cytoplasmic staining. However, no association was identified with AMACR staining intensity and Gleason (tumor) score. Many of the metastatic prostate cancer samples demonstrated only weak AMACR expression. The metastatic samples showed uniform PSA immunostaining, confirming the immunogenicity of these autopsy samples.

Figure 14:
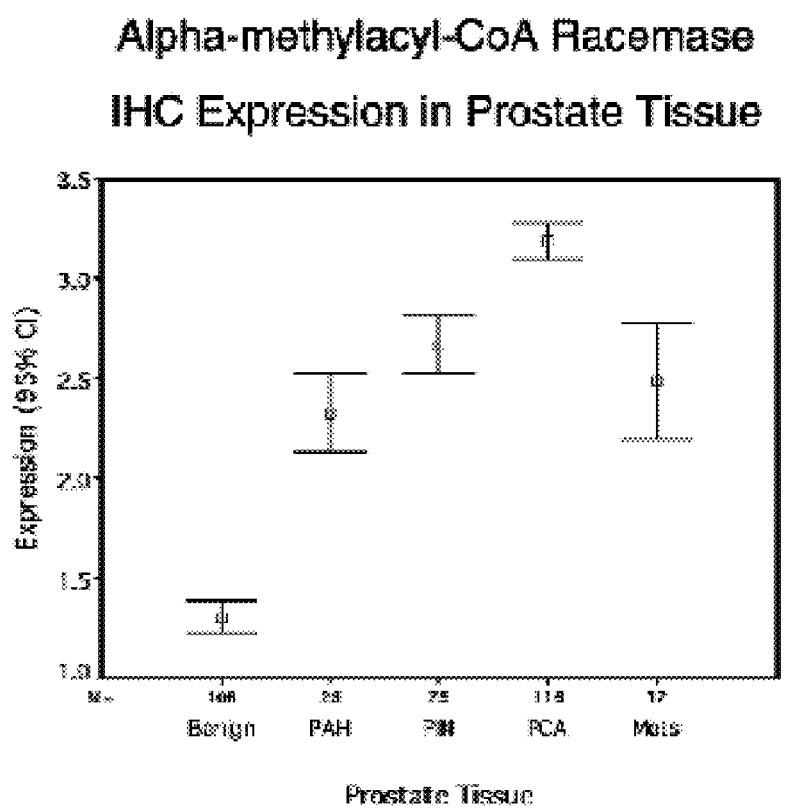
FIG. 14 describes an analysis of AMACR protein expression using prostate cancer tissue microarrays.

In order to assess AMACR protein expression over hundreds of prostate specimens, the tissue microarray data was quantitated. Benign prostate, atrophic prostate, PIN, localized prostate cancer, and metastatic prostate cancer demonstrated mean AMACR protein staining intensity of 1.0 (SE 0), 2.0 (SE 0.1), 2.5 (SE 0.1), 3.0 (SE 0), and 2.5 (SE 0.1), respectively (ANOVA p-value<0.0001). This data is graphically summarized using error bars representing the 95% confidence interval for each tissue category (FIG. 14).

The correlation of AMACR levels with tumor proliferation was next investigated using Ki-67 (Perrone et al., supra). There was no significant association between AMACR expression and Ki-67 expression with a correlation coefficient of 0.13 (p-value=0.22). In addition, no significant associations were identified between AMACR protein expression and pathology parameters such as radical prostatectomy, Gleason score, tumor stage, tumor size (cm), or surgical margin status. AMACR protein levels were next evaluated for association with PSA recurrence following surgery in 120 prostatectomy cases with a median follow-up time of 3 years. No statistically significant association was identified. AMACR demonstrated uniform moderate to strong expression in clinically localized prostate cancer with a high sensitivity for tumor and an equally high specificity. In addition, a preliminary survey of normal tissues including ovary, liver, lymph nodes, spleen, testis, stomach, thyroid, colon, pancreas, cerebrum, and striated muscle revealed significant AMACR protein expression in only normal liver.

The large difference in AMACR protein levels between normal secretory epithelial cells and malignant cells provides a clinical use for testing AMACR expression in prostate needle biopsy specimens. In diagnostically challenging cases, pathologists often employ the basal cell markers 34βE12 (O'Malley et al., Virchows Arch A Patho. Anat. Histopathol., 417:191 [1990]; Wojno et al., Am. J. Surg. Pathol., 19:251 [1995]; Googe et al, Am. J. Clin. Pathol., 107:219 [1997] or p63 (Parson et al., Urology 58:619 [2001]; Signoretti et al., Am. J. Pathol., 157:1769 [2000]), which stain the basal cell layer of benign glands. This second basal cell layer is absent in malignant glands. In many equivocal biopsy specimens, the surgical pathologist must rely on absence of staining to make the final diagnosis of prostate cancer. The clinical utility of AMACR immunostaining on 94 prostate needle biopsies was evaluated. The results are shown in Table 2. The sensitivity and specificity were calculated as 97% and 100%, respectively. These results included 26 cases where the final diagnosis required the use of a basal cell specific immunohistochemical marker (i.e., 34βE12 or p63).

This example demonstrated that AMACR is associated with PCA and that AMACR expression in prostate biopsies is useful for the diagnosis of cancer in inconclusive biopsy samples.

TABLE 2

Clinical utility of Assessing AMACR Protein in Prostate Needle Biopsies (n = 94)

| Sensitivity (TP/(TP + FN)) | Specificity (TN/(TN + FP)) | Positive Predictive Value (TP/(TP + FP)) | Negative Predictive Value (TN/(TN + FN)) |
|---|---|---|---|
| 97% ((68/(2 + 68)) | 100% ((24/(24 + 0)) | 100% ((68/(68 + 0)) | 92% ((24/24 + 2)) |

EXAMPLE 6

Hormone Regulation of AMACR

This example describes studies that indicate that AMACR expression is hormone independent.

A. Sample Collection, cDNA Array and TMA Construction and Evaluation

Clinical samples were taken from the radical prostatectomy series and from the Rapid Autopsy Program at the University of Michigan. Both are part of the University of Michigan Prostate Cancer Specialized Program of Research Excellence (S.P.O.R.E.). Primary PCA of metastatic cases as well as lymph node metastases were contributed in collaboration from the University of Ulm, Germany. Detailed clinical and expression analysis as well as TMA data was acquired and maintained on a secure relational database according to the Institutional Review Board protocol of both institutions. Tissue procurement for expression analysis on the RNA level is described in the above examples. For the development of TMA, samples were embedded in paraffin. The study pathologist reviewed slides of all cases and circled areas of interest. These slides were used as a template for construction of the six TMAs used in this study. All TMAs were assembled using a manual tissue arrayer (Beecher Instruments, Silver Spring, Md.). At least three tissue cores were sampled from each donor block. Histologic diagnosis of the tissue cores was verified by standard haematoxylin and eosin (H&E) staining of the initial TMA slide. Standard biotin-avidin complex immunohistochemistry (IHC) was performed using a polyclonal anti-AMACR antibody (Ronald Wanders, University of Amsterdam). Digital images were acquired using the BLISS Imaging System (Bacus Lab, Lombard, Ill.). Staining intensity was scored as negative (score=1), weak (score 2), moderate (3) and strong (4). For exploration of the treatment effect by the means of hormonal withdrawal before radical prostatectomy, standard slides were used for regular H&E staining and consecutive sections for detection of AMACR expression. In order to test AMACR expression in poorly differentiated colon cancers, cases were used from a cohort of well-described colon tumors. In addition to well-differentiated colon cancers, a recently described subset of poorly differentiated colon carcinomas with a distinctive histopathological appearance, termed large cell minimally differentiated carcinomas, was used. These poorly differentiated colon carcinomas had a high frequency of the microsatellite instability phenotype.

B. Cell Culture and Immunoblot Analysis

Prostate cell lines (RWPE-1, LNCaP, PC3 and DU145) were obtained from the American Tissue Culture Collection. Cells were maintained in RPMI-1640 with 8% decomplemented fetal bovine serum, 0.1% glutamine and 0.1% penicillin and streptomycin (BioWhittaker, Walkersville, Md.). Cells were grown to 75% confluence and then treated for 24 and 48 with the antiandrogen bicalutamide (CASODEX, Zeneca Pharmaceuticals, Plankstadt, Germany) at a final concentration of 20 µM or with methyltrienolone (synthetic androgen (R1881); NEN, Life Science Products, Boston, Mass.) at a final concentration of 1 nM. Cells were harvested and lysed in NP-40 lysis buffer containing 50 mmol/L Tris-HCl, pH 7.4, 1% Nonidet P-40 (Sigma, St. Louis, Mo.) and complete proteinase inhibitor cocktail (Roche, Ind., USA). 15 µg of protein extracts were mixed with SDS sample buffer and electrophoresed onto a 10% SDS-polyacrylamide gel under reducing conditions. After transferring, the membranes (Amersham Pharmacia Biotech, Piscataway, N.J.) were incubated for 1 hour in blocking buffer (Tris-buffered saline with 0.1% Tween and 5% nonfatdry milk). The AMACR antibody was applied at 1:10.000 diluted blocking buffer overnight at 4° C. After three washes with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.). For β-tubulin blots, membranes were stripped with Western Re-Probe buffer (Geno-tech, St. Louis, Mo.) and blocked in Tris-buffered saline with 0.1% Tween with 5% nonfat dry milk and incubated with rabbit anti β-tubulin antibodies (Santa Cruz Biotechnologies, Santa Cruz, Calif.) at 1:500 for two hours. For PSA expression the membranes were reprobed in the described manner with PSA antibody (rabbit polyclonal; DAKO Corporation, Carpinteria, Calif.) at 1:1000 dilution and further processed.

C. Statistical Analysis

Primary analysis of the cDNA expression data was done with the Genepix software. Cluster analysis with the program Cluster and generation of figures with TreeView was performed as described above. AMACR protein expression was statistically evaluated using the mean score result for each prostate tissue type (i.e., benign prostate, naive localized or advanced prostate cancer, hormone treated and hormone refractory prostate cancer). To test for significant differences in AMACR protein expression between all tissue types, a one-way ANOVA test was performed. To determine differences between all pairs, a post-hoc analysis using the Scheffé method was applied as described above. For comparison of naive primaries to their corresponding lymph node metastases with respect to AMACR protein expression, a non parametric analysis (Mann Whitney test) was performed. To compare AMACR expression intensity to the scored hormonal effect of the pretreated localized prostate cancer cases the Mantel-Haenszel Chi-Square test was applied. AMACR expression scores are presented in a graphical format using error-bars with 95% confidence intervals. P-values<0.05 were considered statistically significant.

D. Results

Figure 15:
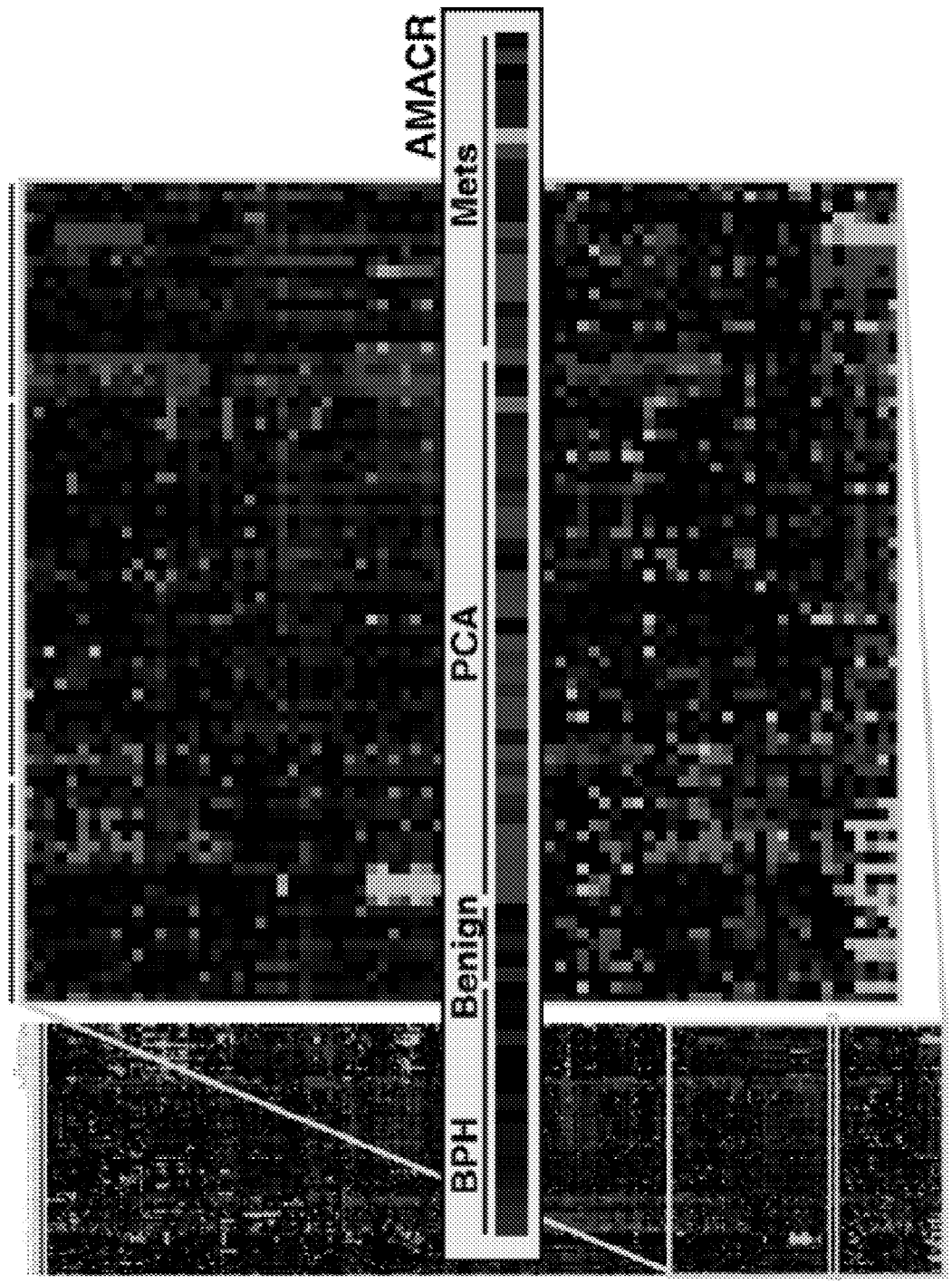
FIG. 15 shows relative gene expression of AMACR in several samples.

Hierarchical clustering of 76 prostate tissues including benign, BPH, localized PCA and metastatic PCA and filtering for only those genes with a 1.5 fold expression difference or greater, clustered the samples into histologically distinct groups as described above. As demonstrated by a TreeView presentation of this data (FIG. 15), AMACR was one of several genes that demonstrated over expression at the cDNA level of PCA samples with respect to benign pooled prostate tissue. The highest level of over expression by cDNA analysis was in the clinically localized PCA cases.

Figure 16A:
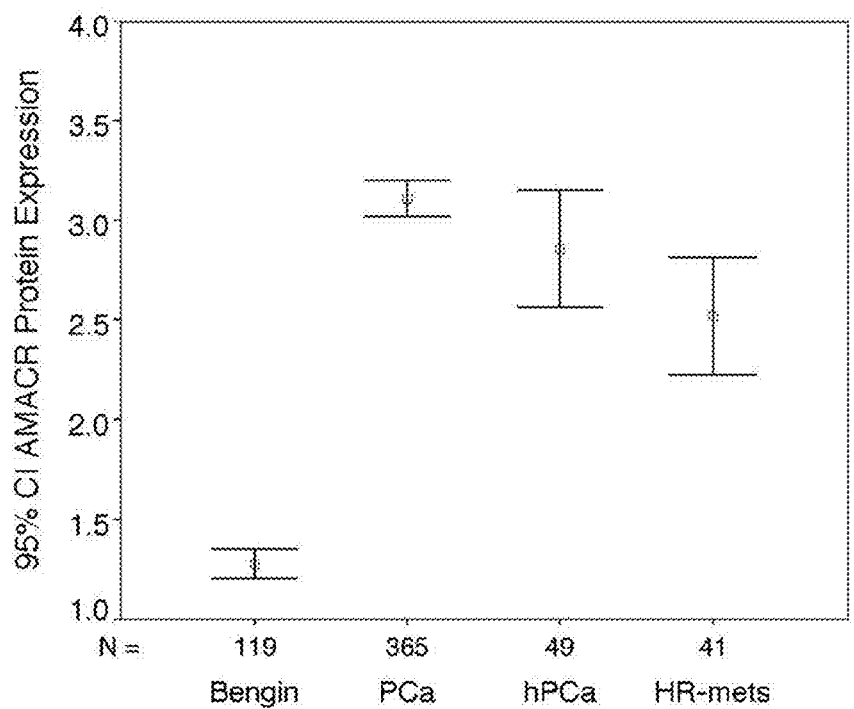
FIG. 16 shows AMACR protein expression PCA.
Figure 16B:
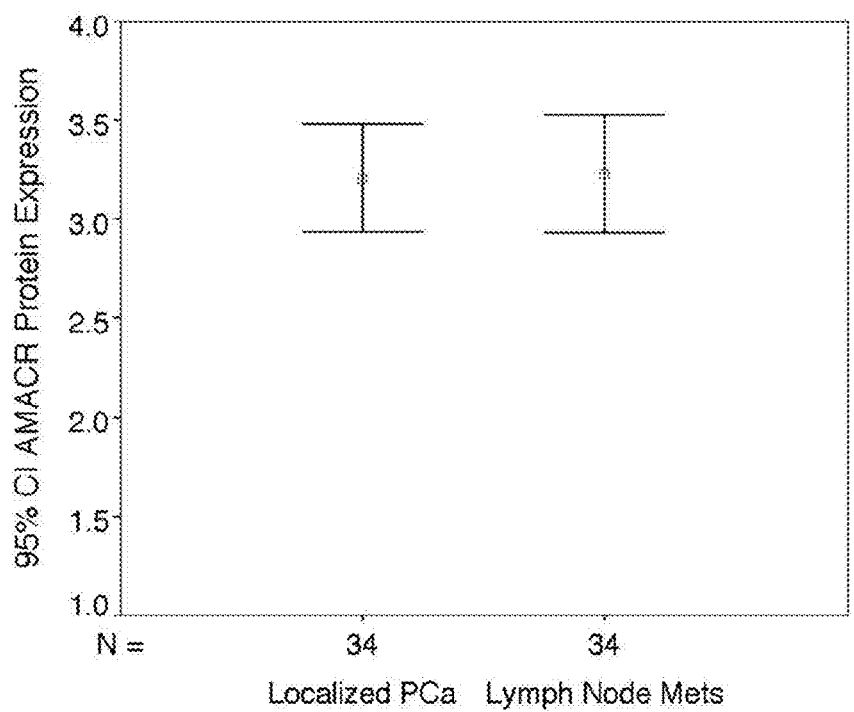

In order to further investigate the role of AMACR protein expression in samples with variable differentiation and exposure to anti-androgen treatment, several TMAs with a wide range of PCA were constructed: a total of 119 benign prostate samples, 365 primary hormone naive PCA samples, 37 naive prostate cancer lymph node metastases, and 41 hormone refractory metastatic PCA samples were evaluated. An additional 49 hormone treated primary prostate cancers (including 22 on standard slides) were examined for histologic changes associated with anti-androgen treatment and AMACR protein expression. The mean AMACR protein expression levels for each tissue category is presented in FIG. 16. Benign prostate, naive primary prostate cancer, hormone treated primary cancer, and hormone refractory metastatic tissue had a mean staining intensity of 1.28 (Standard Error SE 0.038, 95% Confidence Intervals CI 1.20-1.35), 3.11(SE 0.046, CI 3.02-3.20), 2.86 (SE 0.15, CI 2.56-3.15) and 2.52 (SE 0.15, CI 2.22-2.28), respectively). One-way ANOVA analysis revealed a p-value of <0.0001. To specifically examine the difference between different tissue types, a post-hoc pair-wise comparison was performed. Clinically localized PCA demonstrated a significantly stronger AMACR protein expression as compared to benign prostate tissue (post-hoc analysis using Scheffé method, mean difference=1.83, p<0.0001, CI 1.53-2.13). A significant decrease in AMACR protein expression was observed in the metastatic hormone refractory PCA samples with respect to clinically localized PCA (0.59, p=0.002, CI 0.15-1.03). Hormone treated primaries had a mean AMACR expression of 2.86, which was between the expression levels of naive primaries (3.11) and hormone refractory cases (2.52) (post-hoc analysis using Scheffé method, p=0.51, CI −0.66-0.16 and p=0.56, CI −0.23-0.91). There was no significant difference in AMACR expression in the 37 naive primary prostate samples and lymph node metastases derived from the same patient (Mann Whitney test, p=0.8). In other words, matched primaries and lymph node metastases showed similar AMACR expression pattern.

Figure 17:
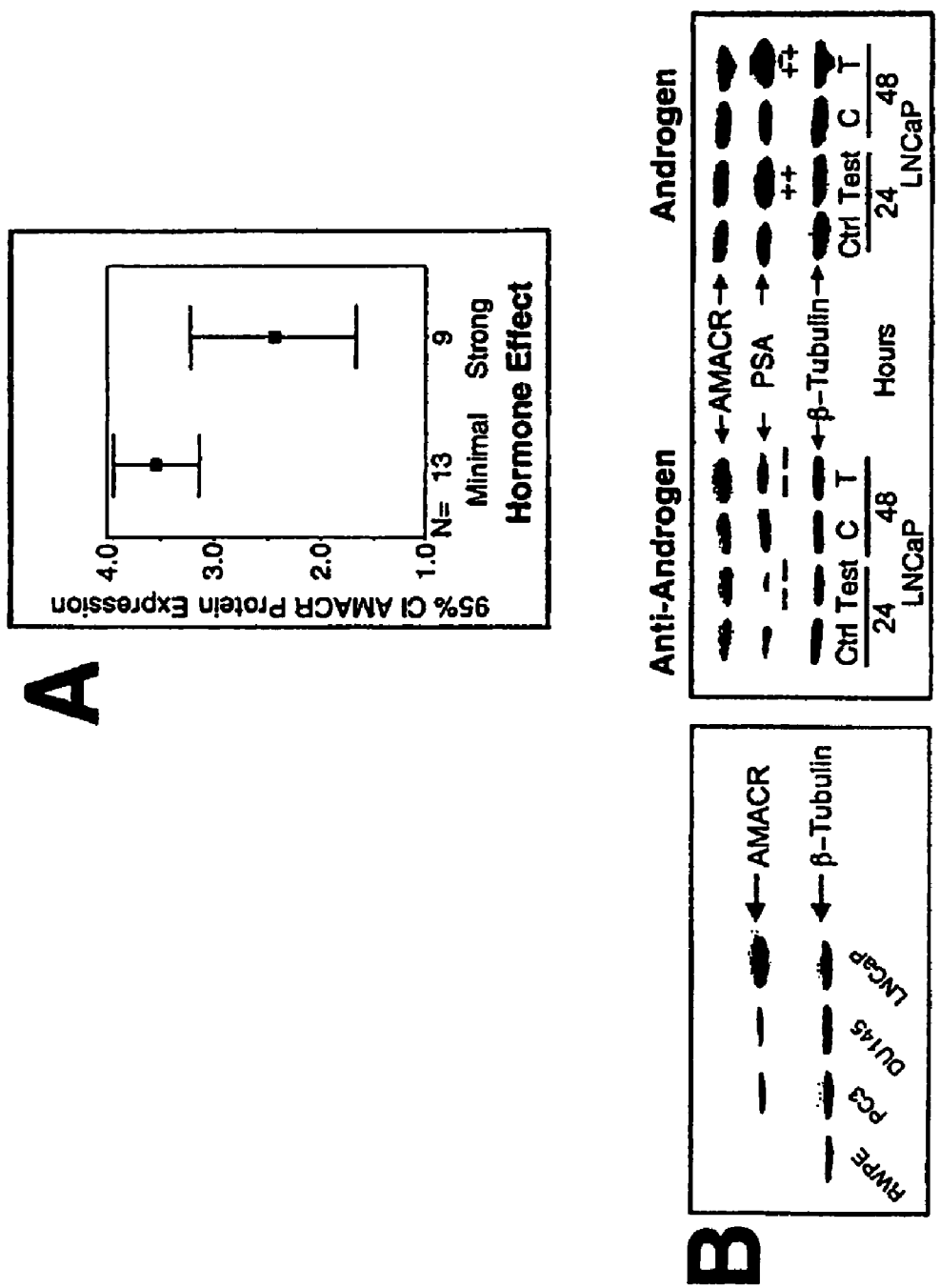
FIG. 17 shows the hormonal effect on AMACR expression.

A subset of 22 PCA cases in which the patients received variable amount and types of anti-androgen treatment prior to surgery was examined. These cases were evaluated blindly with respect to treatment protocol for histological evidence of hormone treatment (H&E slide) and AMACR protein expression. The hormonal effect visible on the H&E slides was classified from 1 to 4 with 1 representing "no effect" and 4 showing a "very strong effect". 13 cases demonstrated either no or moderate hormonal effect, and 9 cases had a very strong hormonal effect. Statistical analysis revealed a significant difference between these two groups with respect to AMACR expression intensity (FIG. 17, Mantel-Haenszel Chi-Square, p=0.009). FIG. 17 presents an example of a PCA case treated prior to surgery with anti-androgens that has a strong hormonal effect appreciated on H&E and decreased AMACR protein expression (FIG. 17A). In this dataset there was neither a correlation between treatment duration nor treatment type (monotherapy or complete hormonal withdrawal for hormone deprivation) and AMACR expression.

For further exploration of the hormonal effect on AMACR expression, primary cell culture experiments and Western blot analysis were performed. As demonstrated in FIG. 17 Panel B, LNCaP cells, derived from a metastatic lesion but considered hormone responsive, showed a higher baseline AMACR expression as compared to PC3 and DU-145 cells, which are both hormone independent cell lines derived from metastatic lesions. A benign cell line, RWPE-1 (Bello et al., Carcinogenesis 18:1215 [1997]), showed near absent AMACR expression, which is consistent with the in situ protein expression data. To simulate an anti-androgen treatment, the hormone responsive cell line LNCaP was treated with bicalutamide in a final concentration of 20 µM for a time period of 24 and 48 hours. AMACR expression in cell lysates of LNCaP cells did not change at either time point when exposed to anti-androgen therapy. Under the same conditions, PSA, a gene known to be regulated by the androgen receptor, showed decreased protein expression. In addition, when LNCaP cells were exposed to a synthetic androgen R1881, no increase in AMACR expression was observed (FIG. 17, Panel B). Therefore, these cell culture experiments provide evidence that AMACR expression is not regulated by the androgen pathway.

The present invention is not limited to a particular mechanism. Indeed, an understanding of the mechanism is not necessary to practice the present invention. Nonetheless, it is contemplated that another explanation for these observations was that AMACR over expression occurred in PCA, but as these tumors became poorly differentiated, as in the hormone refractory PCA, AMACR expression was down regulated either directly or indirectly due to the process of de-differentiation. To elucidate this potential correlation colon cancer samples were examined for AMACR expression (See Example 7). AMACR protein expression is also observed in some other tumor types, with the highest overall expression in colorectal cancers. Colorectal cancers are not known to be regulated by androgens and were therefore used as a control to test this hypothesis. Four well differentiated and seven anaplastic colon cancer samples were chosen. The poorly differentiated tumors have distinct molecular alterations distinguishing them from the common well to moderately differentiated colorectal tumors (Hinoi et al., Am. J. Pathol. 159:2239 [2001]). Strong AMACR protein expression in a moderately differentiated colon cancer was observed. This tumor still forms well defined glandular structures. The surrounding benign colonic tissue does not express AMACR. The anaplastic colon cancers demonstrated weak AMACR protein expression. Primarily data revealed positive AMACR expression in 4/4 well differentiated cases but only 4/7 anaplastic colonic cancers. Three of the anaplastic colon cancers had weak to moderate expression. Metastatic hormone refractory PCA demonstrated weak AMACR protein expression in tissue microarrays.

EXAMPLE 7

AMACR Expression in a Variety of Cancers

A. Analysis of Online EST and SAGE Database

The National Cancer Institute Cancer Genome Anatomy Project (CGAP) has several gene expression databases available online for comparing gene expression across multiple samples (See the Internet Web site of the National Cancer Institute). Both EST and SAGE databases offer Virtual Northern blots, which allow users to visualize and compare the expression level of a particular gene among multiple samples. The SAGE database includes over 5 million tags from 112 libraries of multiple benign and malignant tissues.

B. Selection of Study Cases

A total of 96 cases of cancers from different sites were selected for construction of a multi-tumor tissue microarray. The tissue microarray was constructed to perform a wide survey of multiple common tumor types. A minimum of three tissue cores (0.6 mm in diameter) was taken for each case. Tumors surveyed included colorectal adenocarcinoma (n=15 cases), renal cell carcinoma (6), prostatic adenocarcinoma (6), urothelial carcinoma (4), cervical squamous cell carcinoma (6), lung non-small cell carcinoma (4), lymphoma (15), melanoma (9) and several other cancer types. Normal adjacent tissue was taken when available. The prostate tissue microarray was constructed from selected patients who underwent radical prostatectomies as monotherapy for clinically localized prostate cancer. This tissue microarray contained a spectrum of prostatic tissue including prostatic atrophy, high-grade prostatic intraepithelial neoplasia (PIN), and clinically localized prostate cancer. In addition, standard slides were used to confirm results for colon cancer. Twenty-four cases of colorectal adenocarcinoma (16 well to moderately differentiated carcinoma and 8 large cell minimally differentiated carcinoma) and 8 endoscopically derived colorectal adenomas were selected for immunostaining for AMACR. For breast carcinoma, a TMA of 52 cases of invasive ductal carcinoma was used. Specimens were collected and analyzed in accordance with the Institutional Review Board guidelines.

C. Immunohistochemistry

Standard avidin-biotin complex immunohistochemistry was used. Pre-treatment was performed by steaming the slides for 10 minutes in sodium citrate buffer in a microwave oven. The slides were then incubated sequentially with primary antibody (1:2000 dilution, polyclonal rabbit anti-AMACR antibody), biotinylated secondary antibody, avidin-biotin complex and chromogenic substrate 3,3'-diaminobenzidine. Slides were evaluated for adequacy using a standard bright field microscope. Digital images were then acquired using the BLISS Imaging System (Bacus Lab, Lombard, Ill.) and evaluated by two pathologists. Protein expression was scored as negative, weak stain (faint cytoplasmic stain or granular apical staining), moderate (diffuse granular cytoplasmic stain) and strong (diffuse intense cytoplasmic stain). Only moderate and strong staining was considered as positive staining.

D. Laser Capture Microdissection

Sections of 2 radical prostatectomy samples were frozen in OCT in accordance with an Institutional Review Board protocol. Frozen sections (5 μm thick) were fixed in 70% alcohol for 10 minutes and then stained in hemotoxylin and eosin. Prostate cancer and benign prostate glands were dissected on a μCUT laser capture microdissector (MMI GmbH, Heidelberg, Germany). Approximately 6000 cells were harvested. Total RNA was isolated using Qiagen micro-isolation kit (Qiagen, San Diego, Calif.). Reverse transcription was performed using both oligo dT and random hexamer primers. Primers used to amplify specific gene products were: AMACR sense, 5'-CGTATGCCCCGCTGAATCTCGTG-3' (SEQ ID NO:123); AMACR antisense, 5'-TGGCCAAT-CATCCGTGCTCATCTG-3' (SEQ ID NO:105); GAPDH sense, 5'AGCCTTCTCCATGGTGGTGAAGAC-3' (SEQ ID NO:106); and GAPDH antisense, 5'-AGCCTTCTCCATG-GTGGTGAAGAC-3' (SEQ ID NO:107). PCR conditions for AMACR and GAPDH were: heat denaturation at 94° C. for 5 min, cycles of 94° C. for 1 min, 60° C. for 1 min, and 72° C. for 1 min (32 cycles for GAPDH, 40 cycles for AMACR), and a final extension step at 72° C. for 5 min. PCR products were then separated on 2% agarose gel and visualized by UV illumination.

E. Results

Using the Virtual Northern tool from the online CGAP program, AMACR expression was surveyed in two databases, EST and SAGE libraries. AMACR was found to be expressed in a wide range of tissues, including central and peripheral nervous system, colon, kidney, breast, pancreas, prostate and blood. Compared to their normal counterparts, a number of cancers have elevated AMACR expression, including tumors arising in bone marrow, breast, colon, genitourinary system, lung, lymph node, nervous system, pancreas, prostate, soft tissue and uterus.

Figure 18:
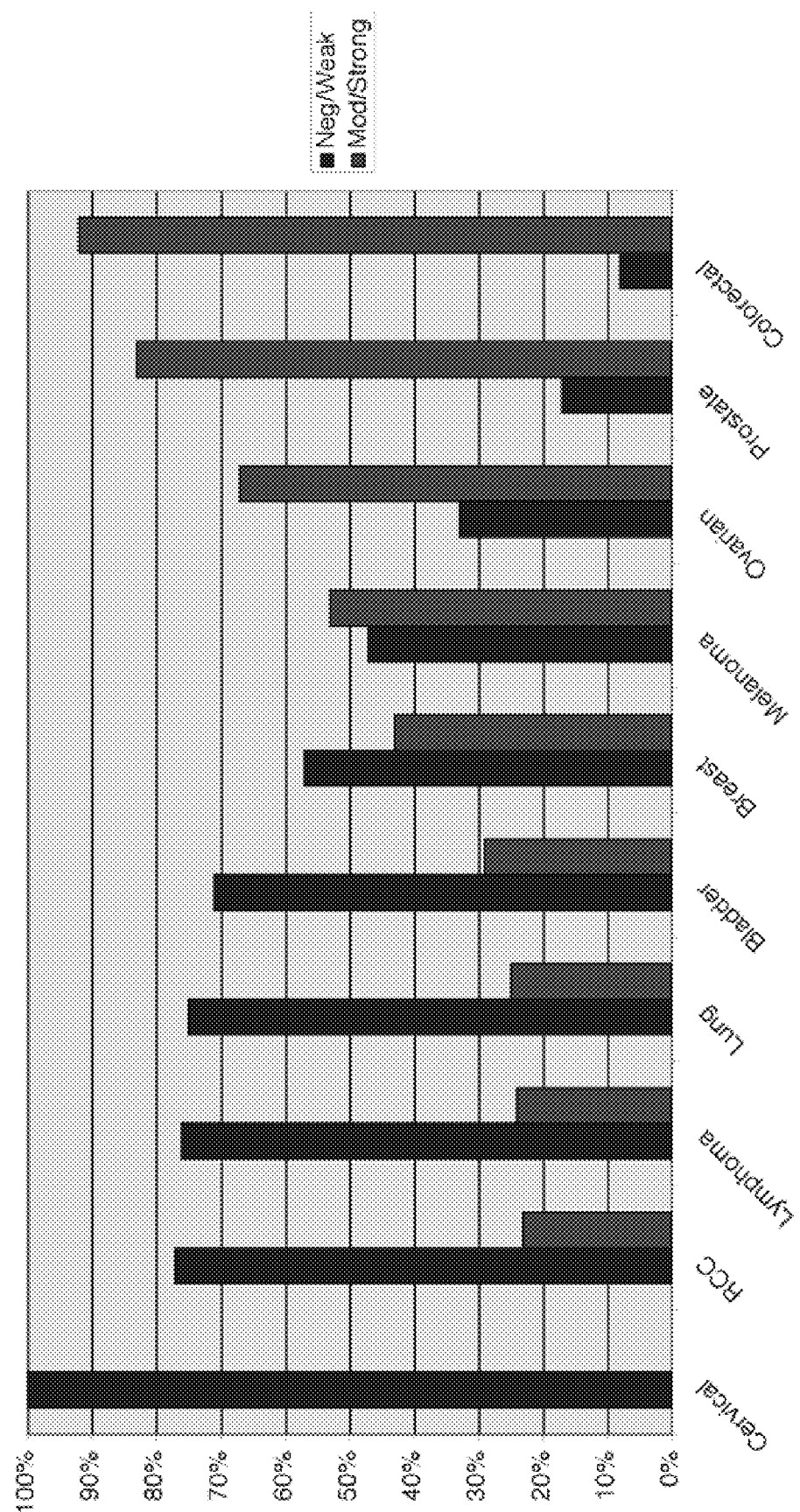
FIG. 18 shows AMACR over-expression in multiple tumors. AMACR protein expression was evaluated by immunohistochemistry on a multi-tumor and a breast cancer tissue microarray. Percentage of cases with positive staining (moderate and strong staining intensity) is summarized on the Y-axis. The left bar represents negative or weak staining and the right bar represents moderate or strong staining.

To confirm the gene expression data, AMACR immunohistochemistry was performed on a multi-tumor tissue array that included some of the most common cancers from multiple sites. AMACR protein level was increased in many cancers, including colorectal, prostate, ovarian, lung cancers, lymphoma and melanoma (FIG. 18). In particular, AMACR over-expression was observed in 92% and 83% of colorectal and prostate cancer, respectively. Using a breast cancer tissue microarray, it was found that AMACR over-expression was present in 44% of invasive ductal carcinomas. AMACR over expression was not observed in female cervical squamous cell carcinoma (6 cases).

Figure 19:
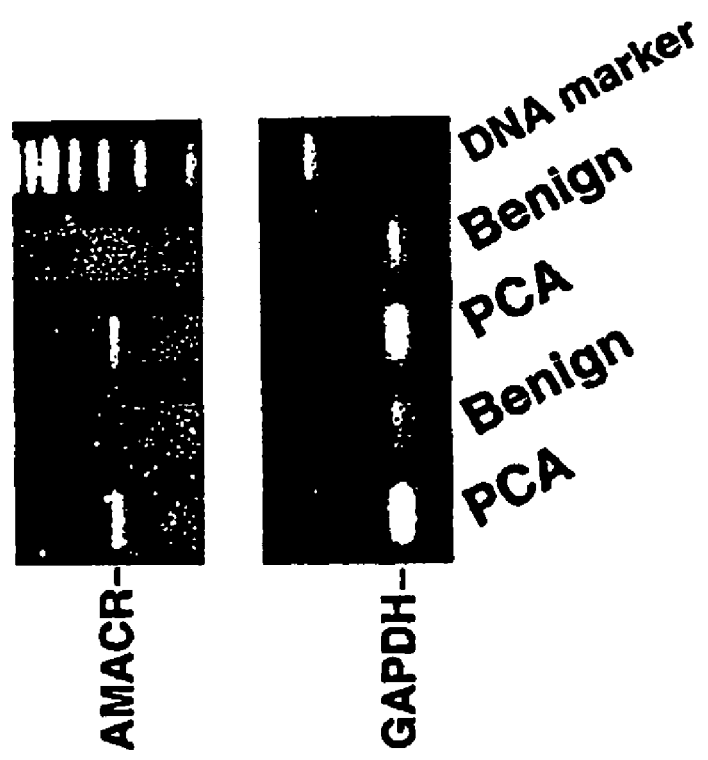
FIG. 19 shows the results of laser capture microdissection (LCM) and RT-PCR amplification of AMACR in prostate cancer. LCM was used to isolate pure prostate cancer and benign glands and AMACR gene expression was characterized by RT-PCR in 2 radical prostatectomies. A constitutively expressed gene, GAPDH, was used as quantitative control of input mRNA. AMACR expression is barely detectable in benign glands, and is elevated in prostate cancer.

To further characterize AMACR expression in a spectrum of proliferative prostate lesions, a prostate tissue microarray, which included prostate cancer, high grade PIN and atrophic glands, was utilized. Positive AMACR staining (moderate and strong staining) was observed in 83% and 64% of clinically localized prostate cancer and high-grade PIN, respectively. Focal AMACR expression was observed in 36% of the atrophic lesions and in rare morphologically benign glands. To confirm that AMACR protein over-expression was the result of increased gene transcription, laser capture microdissection was used to isolate cancerous and benign prostatic glands. RT-PCR was performed to assess the AMACR mRNA expression. Benign glands had very low baseline expression (FIG. 19). In contrast, prostate cancer had much higher mRNA level, confirming that increased AMACR gene transcription leads to elevated protein over expression in prostate cancer.

AMACR expression was studied in 24 colorectal adenocarcinomas, including 16 well to moderately differentiated, and 8 poorly differentiated large cell adenocarcinomas. Overall, 83% (20/24) demonstrated positive AMACR protein expression. All (16/16, 100%) cases of well to moderately differentiated carcinoma had positive staining, compared to 64% (5/8) of poorly differentiated carcinoma. AMACR expression was examined in 8 colorectal adenoma biopsies obtained by colonoscopy. Moderate staining was present in 6 (75%) cases. Compared with well-differentiated adenocarcinomas, adenomas usually showed more focal (10-60% of cells) and less intense staining.

EXAMPLE 8

Characterization of EZH2 Expression in Prostate Cancer

A. SAM Analysis

SAM analysis was performed by comparing gene expression profiles of 7 metastatic prostate cancer samples against 10 clinically localized prostate cancer samples. Data was normalized per array by multiplication by a factor to adjust the aggregate ratio of medians to one, then log base 2 transformed and median centered. This normalized data was divided into two groups for comparison using a two-class, unpaired t-test. Critical values for the analysis include: Iterations=500, Random Number Seed 1234567, a fold change cutoff of 1.5 and a delta cutoff of 0.985, resulting in a final largest median False Discovery Rate of 0.898% for the 535 genes selected as significant (55 relatively up and 480 relatively down regulated between MET and PCA). These 535 genes were analyzed using Cluster (Eisen et al., PNAS 95:14863 [1998]) implementing average linkage hierarchical clustering of genes. The output was visualized by Treeview (Eisen et al., [1998], supra).

B. RT-PCR

Reverse transcription and PCR amplification were performed with 1 μg total RNA isolated from the indicated prostate tissues and cell lines. Human EZH2 forward (5'-GCCAGACTGGGAAGAAATCTG-3' (SEQ ID NO:108)), reverse (5'-TGTGCTGGAAAATCCAAGTCA-3' (SEQ ID NO:109)) and GAPDH sense (5'-CGGAGTCAACG-GATTTGGTCGTAT-3' (SEQ ID NO:110)), antisense 5'-AGCCTTCTCCATGGTGGTGAAGAC-3' (SEQ ID NO:111)) primers were used. The amplified DNA was resolved on agarose gels and visualized with ethidium bromide.

C. Immunoblot Analysis

Prostate tissue extracts were separated by SDS-PAGE and blotted onto nitrocellulose membranes. Anti-EZH2 (Sewalt et al., Mol. Cell. Biol. 18:3586 [1998]), anti-EED (Sewalt et al., supra), and polyclonal anti-tubulin (Santa Cruz biotechnology) antibodies were used at 1:1000 dilution for immunoblot analysis. The primary antibodies were detected using horseradish peroxidase-conjugated secondary antibodies and visualized by enhanced chemiluminescence as described by the manufacturer (Amersham-Pharmacia).

D. Tissue Microarray Analysis

Clinically stratified prostate cancer tissue microarrays used in this study have been described previously (See above examples). Tissues utilized were from the radical prostatectomy series at the University of Michigan and from the Rapid Autopsy Program, which are both part of University of Michigan Prostate Cancer Specialized Program of Research Excellence (S.P.O.R.E.) Tissue Core. Institutional Review Board approval was obtained to procure and analyze the tissues used in this study.

EZH-2 protein expression was evaluated on a wide range of prostate tissue to determine the intensity and extent in situ. Immunohistochemistry was performed on three tissue microarrays (TMA) containing samples of benign prostate, prostatic atrophy, high-grade prostatic intraepithelial neoplasia (PIN), clinically localized prostate cancer (PCA), and metastatic hormone refractory prostate cancer (HR-METSs). Standard biotin-avidin complex immunohistochemistry (IHC) was performed to evaluate EZH2 protein expression using a polyclonal anti-EZH2 antibody. Protein expression was scored as negative (score=1), weak (score 2), moderate (3) and strong (4).

Approximately 700 TMA samples (0.6 mm diameter) were evaluated for this study (3-4 tissue cores per case). The TMAs were assembled using a manual tissue arrayer (Beecher Instruments, Silver Spring, Md.) as previously described (See above examples). Four replicate tissue cores were sampled from each of the selected tissue types. After construction, 4 μm sections were cut and hematoxylin and eosin staining was performed on the initial slide to verify the histologic diagnosis. TMA hematoxylin and eosin images were acquired using the BLISS Imaging System (Bacus Lab, Lombard, Ill.). EZH2 protein expression was evaluated in a blinded manner by the study pathologist using a validated web-based tool (Manley et al., Am. J. Pathol. 159:837 [2001]; Bova et al, Hum. Pathol. 32:417 [2001]) and the median value of all measurements from a single patient were used for subsequent analysis.

E. Clinical Outcomes Analysis

To assess individual variables for risk of recurrence, Kaplan-Meier survival analysis was performed and a univariate Cox proportional hazards model was generated. PSA-recurrence was defined as 0.2 ng/ml following radical prostatectomy. Covariates included Gleason sum, preoperative PSA, maximum tumor dimension, tumor stage, and surgical margin status. To assess the influence of several variables simultaneously including EZH2 protein expression, a final multivariate Cox proportional hazards model of statistically significant covariates was generated. Statistical significance in univariate and multivariate Cox models were determined by Wald's test. A p-value <0.05 was considered statistically significant.

F. EZH2 Constructs

Myc-tagged EZH2-pCMV was used. The Myc-EZH2 fragment was released with BamHI/XhoI double digest and was sub-cloned into the mammalian expression vector pcDNA3 (Invitrogen). An EZH2-ER in-frame fusion expression construct was generated by replacing the FADD fragment released by Kpn I/Not I double digest of the FADD-ER construct (originally derived from Myc-ER (Littlewood et al., Nuc. Acids. Res. 23:1686 [1995]) with the PCR amplified human EZH2 devoid of its stop codon. The EZH2 .SET mutant DNA was amplified using the primers 5'GGGGTAC-CATGGGCGGCCGCGAACAAAAGTTGATT 3' (SEQ ID NO:112) and 5'GGGGAATTCTCATGCCAGCAATAGAT-GCTTTTT3' (SEQ ID NO:113) and subsequently sub-cloned into pcDNA3 utilizing the in built KpnI/EcoRI sites. Expression of these constructs was verified by immunoblot analysis of the expressed proteins using either anti-Myc HRP (Roche, Inc) or anti-EZH2 antibodies.

G. RNA interference 21-nucleotide sense and antisense RNA oligonucleotides were chemically synthesized (Dharmacon Research Inc.) and annealed to form duplexes. The siRNA employed in the study were targeted to the region corresponding from 85 to 106 of the reported human EZH2 (NM004456). Control siRNA duplexes targeted luciferase, lamin and AMACR (NM014324). The human transformed prostate cell line RWPE (Webber et al., Carcinogenesis 18:1225 [1997]) and PC3 were plated at $2\times10^5$ cells per well in a 12 well plate (for immunoblot analysis, cell counts, and fluorescence activated cell sorting (FACS) analysis) and $1.5\times10^4$ cell per well in a 96 well plate (for WST-1 proliferation assays). Twelve hours after plating, the cells were transfected with 60 picomoles of siRNA duplex, sense or antisense oligonucleotides (targeting EZH2) using oligofectamine (Invitrogen). A second identical transfection was performed 24 hours later. Forty-eight hours after the first transfection, the cells were lysed for immunoblot analysis and trypsinized for cell number estimation or FACS analysis. Cell viability was assessed 60 hours after the initial transfection.

H. Cell Proliferation Assays

Cell proliferation was determined with the colorimetric assay of cell viability, based on the cleavage of tetrazolium salt WST-1 by mitochondrial dehydrogenases as per manufacturers instructions (Roche, Inc.). The absorbance of the formazan dye formed, which directly correlates with the number of metabolically active cells in the culture, was measured at 450 nm (Bio-Tek instruments), an hour after the addition of the reagent. Cell counts were estimated by trypsinizing cells and analysis by coulter cell counter.

I. Flow Cytometric Analysis

Trypsinized cells were washed with phosphate buffered saline (PBS) and cell number was determined by using a coulter cell counter. For FACS analysis, the washed cells were fixed in 70% ethanol overnight. Before staining with propidium iodide, the cells were washed again with PBS and analyzed by flow cytometry (Becton Dickinson).

J. Microarray Analysis of EZH2 Transfected Cells

Initial testing of this transient transfection/transcriptome analysis system demonstrated that transient overexpression of TNFR1 (p55), a receptor for tumor necrosis factor, induced similar expression profiles as was observed with incubation of cells with TNF (Kumar-Smith et al., J. Biol. Chem. 24:24 [2001]). Other molecules have been similarly tested with this approach. Cells were transfected with different EZH2 constructs and transfection efficiency was monitored by beta-galactosidase assay and was approximately 30-50%. EZH2 . SET mutant expressing samples were compared to EZH2 expressing samples using the SAM analysis package (Tusher et al., PNAS 98:5116 [2001]). Data was pre-processed by multiplication by a normalization factor to adjust the aggregate ratio of medians to one, log base 2 transformed and median centered each array, individually. This pre-processed data was divided into 2 groups for comparison using a two-class, unpaired t-test. Critical values for the analysis include: iterations=5000, (720 at convergence) random Number Seed 1234567, a fold change of 1.5 and a delta cutoff of 0.45205, resulting in a final largest median False Discovery Rate of 0.45% for the 161 genes selected as significant. These 161 genes were supplemented by the values for EZH2 and then analyzed using Cluster implementing average linkage hierarchical clustering of genes. The output was visualized in Treeview. Selected genes identified as being repressed by EZH2 (e.g., EPC and cdc27) were re-sequenced to confirm identity.

The molecular identity of a cell is determined by the genes it expresses (and represses). Embryogenesis and cell differentiation intimately depend upon keeping certain genes "on" and other genes "of". When the transcriptional "memory" of a cell is perturbed this can lead to severe developmental defects (Jacobs et al., Semin. Cell Dev. Biol. 10:227 [1999]; Francis et al., Nat. Rev. Mol. Cell. Biol. 2:409 [2001]). Lack of differentiation, or anaplasia, is a hallmark of cancer, which results from normal cells "forgetting" their cellular identity. Thus, it is not surprising that dysregulation of the transcriptional maintenance system can lead to malignancy (Francis et al., supra; Jabobs et al., Nature 397:164 [1999]; Beuchle et al., Development 128:993 [2001]).

Studies in *Drosophila melanogaster* have been instrumental in the understanding of the proteins involved in transcriptional maintenance (Beuchle et al., [[2001], supra; Strutt et al., Mol. Cell. Biol. 17:6773 [1997]; Tie et al., Development 128:275 [2001]). Two groups of proteins have been implicated in the maintenance of homeotic gene expression and include polycomb (PcG) and trithorax (trxG) group proteins (Mahmoudi et al., Oncogene 20:3055 [2001]; Lajeunesse et al., Development 122:2189 [1996]). PcG proteins act in large complexes and are thought to repress gene expression, while trxG proteins are operationally defined as antagonists of PcG proteins and thus activate gene expression (Francis et al., Nat. Rev. Mol. Cell. Biol. 2:409 [2001]; Mahmoudi et al., supra). There are at least twenty PcG and trxG proteins in *Drosophila*, and many have mammalian counterparts. In human malignancies, PcG and trxG proteins have primarily been found to be dysregulated in cells of hematopoietic origin (Yu et al, Nature 378:505 [1995]; Raaphorst et al., Am. J. Pathol., 157:709 [2000]; van Lohuizzen et al., Cell 65:737 [1991]. EZH2 is the human homolog of the *Drosophila* protein Enhancer of Zeste (E(z)) ((Laible et al., Embo. J. 16:3219 [1997]), for which genetic data defines as a PcG protein with additional trxG properties (LaJeunesse et al, supra). E(z) and EZH2 share homology in four regions including domain I, domain II, a cysteine-rich amino acid stretch, and a C-terminal SET domain (Laible et al, supra). The SET domain is a highly conserved domain found in chromatin-associated regulators of gene expression often modulating cell growth pathways (Jenuwein et al., Cell. Mol. Life Sci. 54:80 [1998]). EZH2 is thought to function in a PcG protein complex made up of EED, YY1 and HDAC2 (Satijn et al., Biochim. Biophys. Acta. 1447:1 [1999]). Disruption of the EZH2 gene in mice causes embryonic lethality suggesting a crucial role in development (O'Carroll et al., Mol. Cell. Biol. 21:4330 [2001]).

In previous studies (See e.g., Example 1), the gene at the top of the "list" of genes significantly up-regulated in metastatic prostate cancer was EZH2, which had a d-score (Tusher et al. PNAS 98:5116 [2001]) of 4.58 and a gene-specific FDR of 0.0012 (also called a "q-value" which is analogous to p-values, but adapted to multiple inference scenarios. FIG. 20a displays the 55 up-regulated genes identified by this approach. FIG. 20b summarizes the gene expression of EZH2 in 74 prostate tissue specimens analyzed on DNA microarrays made up of 10 K elements. The EZH2 transcript was significantly increased in metastatic prostate cancer with respect to clinically localized prostate cancer (Mann-Whitney test, p=0.001) and benign prostate (p=0.0001).

As independent experimental validation of DNA microarray results, RT-PCR was performed on 18 prostate samples and cell lines. As expected, EZH2 mRNA transcript levels were elevated in malignant prostate samples relative to benign (FIG. 20c). To determine whether EZH2 is up-regulated at the protein level in metastatic prostate cancer, tissue extracts were examined by immunoblotting. In the samples examined by immunoblot analysis, EZH2 protein was markedly elevated in metastatic prostate cancer relative to localized prostate cancer or benign prostate (FIG. 20d).

Figure 21:
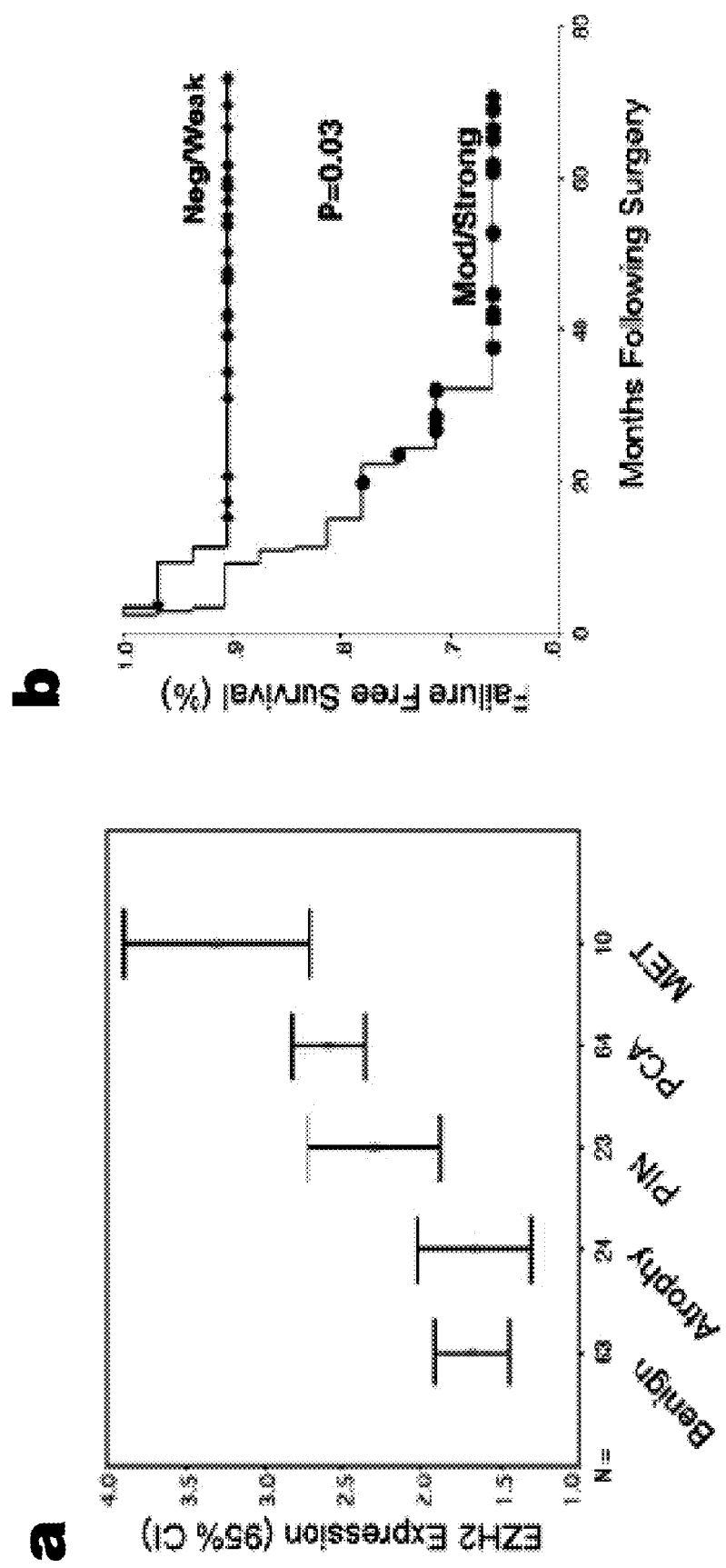
FIG. 21 shows that EZH2 protein levels correlate with the lethal progression and aggressiveness of prostate cancer.

Importantly, EED, a PcG protein that forms a complex with EZH2 (vanLohuizen et al, supra; Sewalt et al, supra), along with an un-related protein, β-tubulin, did not exhibit similar protein dysregulation. EZH2 protein expression was evaluated on a wide range of prostate tissues (over 700 tissue microarray elements) to determine the intensity and extent of expression in situ (FIG. 21a,b). When highly expressed, EZH2 expression was primarily observed in the nucleus as suggested previously (Raaphorst et al., supra). The staining intensity was increased from benign, prostatic atrophy, prostatic intraepithelial neoplasia (PIN), to clinically localized prostate cancer with median staining intensity of 1.7 (standard error [SE], 0.1; 95% confidence interval [CI], 1.5-1.9), 1.7 (SE, 0.2; 95% CI, 1.3-2.0), 2.3 (SE, 0.2.; 95% CI, 1.9-2.7), and 2.6 (SE, 0.1; 95% CI, 2.4-2.8), respectively (FIG. 24b). The strongest EZH2 protein expression was observed in hormone-refractory metastatic prostate cancer with a median staining intensity of 3.3 (SE, 0.3; 95% CI, 2.7-3.9). There was a statistically significant difference in EZH2 staining intensity between benign prostate tissue and localized prostate cancer (ANOVA post-hoc analysis mean difference 0.9, p<0.0001). Although metastatic prostate cancer had a higher mean expression level than localized prostate cancer, the difference did not reach statistical significance (ANOVA post-hoc analysis mean difference 0.7, p=0.3). These findings suggest that as prostate neoplasia progresses there was a trend towards increased EZH2 protein expression, mimicking that seen by DNA expression array analysis. The present invention is not limited to a particular mechanism. Indeed, an understanding of the mechanism is not necessary to practice the present invention. Nonetheless, it is contemplated that this observation suggests that EZH2 levels may indicate how aggressive an individual's prostate cancer is given that the highest level of expression was observed in hormone-refractory, metastatic prostate cancer. Therefore, to test this hypothesis, the utility of EZH2 protein levels to predict clinical outcome in men treated with surgery for clinically localized prostate cancer was examined.

Two hundred and twenty-five (225) specimens from sixty-four patients (3-4 replicate samples per patient) with clinical follow up were interrogated on a single tissue microarray. These men had a median age of 61 years (range 43-76 years) and a 7.3 ng/ml median pre-operative serum prostate specific antigen (PSA) (range 0.8-21.0 ng/ml). Pathologic examination of their prostatectomy specimens indicated that 77% had organ-confined disease (pT2 stage) and 72% had negative surgical margins. The patient demographics and tumor stages were representative of the over 1500 radical prostatectomy patients. In order to test the utility of EZH2 as a potential tissue biomarker for prostate cancer, the clinical outcome of these 64 cases was examined, taking into account clinical and pathological parameters. Clinical failure was defined as either a 0.2 ng/ml PSA elevation or disease recurrence following prostatectomy (e.g., development of metastatic disease). By Kaplan-Meier analysis (FIG. 21c), EZH2 staining intensity of 3 and greater was significantly associated with clinical failure in 31% (10/32) of patients in contrast to 9% (3/32) of patients with an EZH2 protein levels below 3 (log rank p=0.03). There was no significant correlation between EZH2 levels and Gleason score (<7 versus=7), tumor stage (pT2 versus pT3), or surgical margin status (negative versus positive). There was a significant (p=0.048) albeit weak (Pearson coefficient=0.33) correlation between EZH2 protein levels and proliferation index in situ as assessed by Ki-67 labeling index. Multivariable Cox-Hazards regression analysis revealed that EZH2 protein expression (=3 versus<3) was the best predictor of clinical outcome with a recurrence ratio of 4.6 (95% CI 1.2-17.1, p=0.02), which was significantly better than surgical margin status, maximum tumor dimension, Gleason score, and pre-operative PSA. Thus, monitoring EZH2 protein levels in prostate specimens may provide additional prognostic information not discernible with current clinical and pathology parameters alone.

To shed light into the functional role of EZH2 in prostate cancer progression, EZH2 expression in transformed prostate cells in vitro was disrupted using RNA interference. T. Tuschl and colleagues recently reported that duplexes of 21-nucleotide RNA (siRNAs) mediate RNA interference in cultured mammalian cells in a gene-specific fashion (Elbashir et al., Nature 411:494 [2001]). RNA interference has been used effectively in insect cell lines to "knock-down" the expression of specific proteins, owing to sequence-specific, double stranded-RNA mediated RNA degradation (Hammond et al, Nature 404:293 [2000]). siRNAs are potent mediators of gene silencing, several orders of magnitude more potent than conventional antisense or ribozyme approaches (Macejak et al., Hepatology 31:769 [2000]). Thus, a 21-nucleotide stretch of the EZH2 molecule was targeted using criteria provided by Elbashir et al. (supra), and RNA oligonucleotides were synthesized commercially. After the RNA oligos were annealed to form siRNA duplexes, they were tested on the transformed androgen-responsive prostate cell line RWPE (Webber et al., Carcinogenesis 18:1225 [1997]; Bello et al, Carcinogenesis 18:1215 [1997]) as well as the metastatic prostate cancer cell line PC3. Forty-eight hours after transfection with siRNA duplexes, the levels of endogenous EZH2 protein were quntitated. When EZH2 protein was specifically down-regulated in prostate cell lines, the levels of the un-related control protein, β-tubulin, remained unchanged (FIG. 22a). The sense or anti-sense oligonucleotides comprising the EZH2 duplex, as well as un-related siRNA duplexes, did not affect EZH2 protein levels (FIG. 22a, middle and right panels), verifying the specificity of the siRNA approach in both prostate cell lines.

The phenotype of EZH2 "knock-down" prostate cells was next examined. By phase contrast microscopy, it was observed that siRNA directed against EZH2 markedly inhibited cell number/confluency relative to buffer control. Cell counts taken 48 hrs after transfection with siRNA showed a 62% inhibition of RWPE cell growth mediated by the EZH2 siRNA duplex, which is in contrast to the corresponding sense and anti-sense EZH2 oligonucleotides or control duplexes (targeting luciferase and lamin) which exhibited minimal inhibition (FIG. 22b). The prostate cancer cell line, PC3, demonstrated a similar growth inhibition mediated by EZH2 siRNA, suggesting that the findings are not a peculiarity of the RWPE cell line (FIG. 22b). Using a commercially available cell proliferation reagent WST-1, which measures mitochondrial dehydrogenase activity, a decrease in cell proliferation mediated by the EZH2 siRNA duplex, but not by un-related duplexes, was observed (FIG. 22c). In the time frame considered (48 hrs), RNA interference of EZH2 did not induce apoptosis as assessed by propidium iodide staining of nuclei or PARP cleavage. Consistent with this, the broad-spectrum caspase inhibitor, z-VAD-fmk, failed to attenuate EZH2 siRNA induced inhibition of cell proliferation (FIG. 22c).

Thus, activation of the apoptosis pathway does not account for the decreases in cell number observed by RNA interference of EZH2.

Figure 22D:
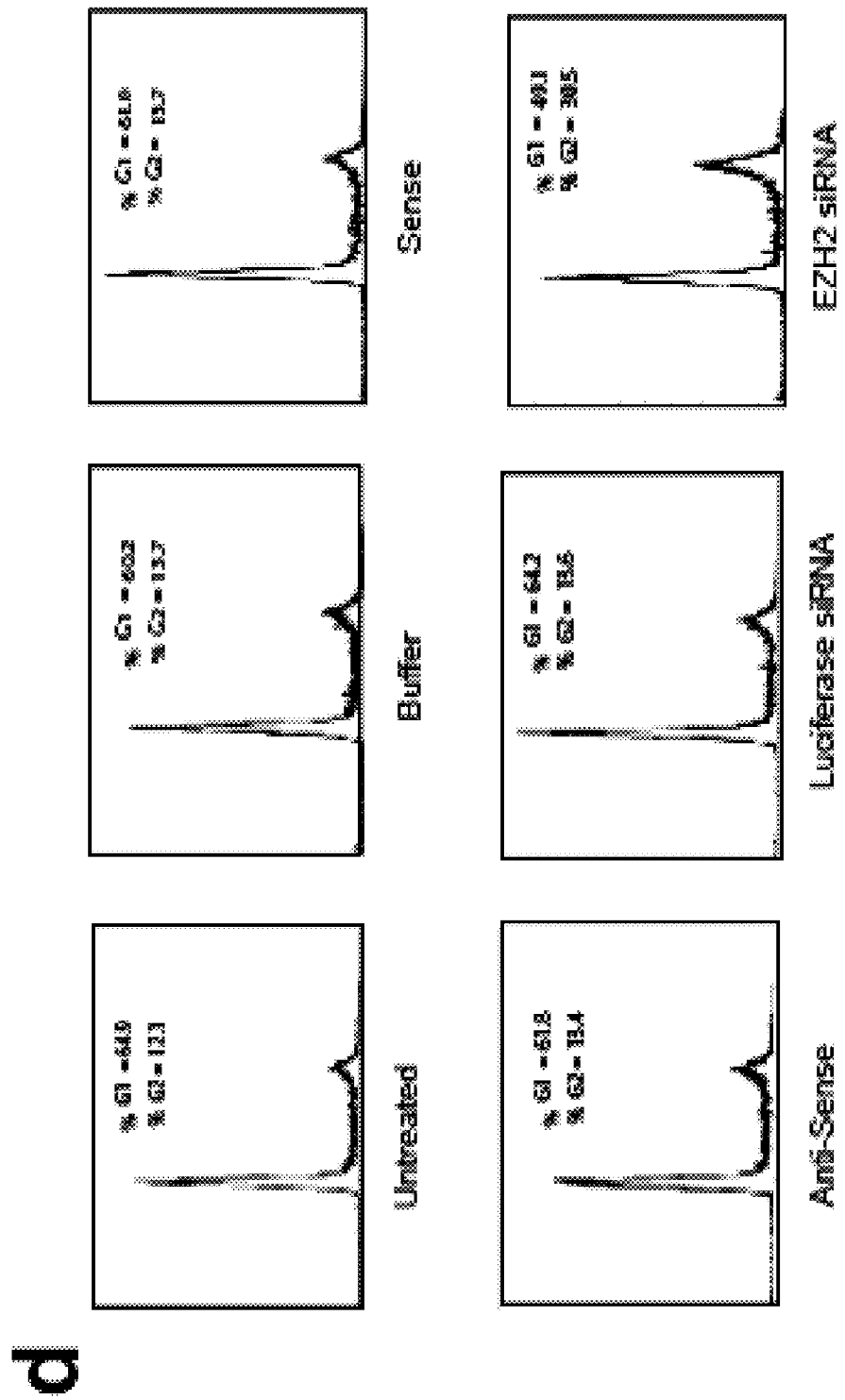
FIG. 22d shows that RNA interference of EZH2 induces G2/M arrest of prostate cells.

Various PcG Group proteins have been suggested to play a role in cell cycle progression (Jacobs et al., Nature 397:164 [1999]; Visser et al., Br. J. Hematol. 112:950 [2001]; Borck et al. Curr. Opin. Genet. Dev. 11:175 [2001]). Flow cytometric analysis of EZH2 siRNA-treated prostate cells demonstrated cell cycle arrest in the G2/M phase (FIG. 22d). Un-related control siRNA duplexes failed to induce a similar cell cycle dysregulation. Few apoptotic cells (sub-G1 cells) were present in any of the experimental samples tested as assessed by flow cytometry (FIG. 22d). The present invention is not limited to a particular mechanism. Indeed, an understanding of the mechanism is not necessary to practice the present invention. Nonetheless, it is contemplated that these observations suggest that EZH2 plays a role in prostate cell proliferation by mitigating the G2/M transition.

To further understand the functional role of EZH2 in prostate cells, an epitope-tagged version of wild-type EZH2 and a deletion mutant of EZH2 missing the conserved SET domain in the eukaryotic expression vector pcDNA3 were generated (FIG. 23a). An "inducible"-version of EZH2 was also generated by creating a fusion protein with a modified murine estrogen receptor (ER) (FIG. 26a) (Littlewood et al., Nuc. Acid. Res. 23:1686 [1995]; Juin et al., Genes Dev. 13:1367 [1999]). EZH2-ER fusion was expressed in cells (FIG. 26b) and is inactivated, presumably by sequestration/binding to hsp90 and other proteins (Littlewood et al., supra). Upon treatment of cells with 4-hydroxytamoxifen, hsp90 dissociates from the ER fusion and liberates its activity. Expression of the epitope-tagged EZH2 constructs was confirmed by transfection in 293 (FIG. 23b), RWPE and in other mammalian cell lines.

PcG proteins have been proposed to mediate their functions by repression of target genes (Laible et al., supra; Jacobs et al, Semin Cell Dev. Biol. 10:227 [1999]). To begin to test this hypothesis, RWPE prostate cells were transiently transfected with wild-type EZH2 and global gene expression alterations were monitored using DNA microarrays. While RNA from the experimental (transfected) cell line was labeled with one fluorescent dye, the paired reference sample was labeled with a second distinguishable fluorescent dye. By making direct comparisons between "gene"-transfected cell lines and control vector-transfected cell lines the molecular differences between the samples were observed. When EZH2 was overexpressed in RWPE cells or SUM149 breast carcinoma cells, there was a consistent repression of a cohort of genes (FIG. 23c, d). This exclusive repression of genes was unique compared to other molecules tested in this system including c-myc and TNFR1, among others. When compared to vector-transfected cells the only gene that was significantly up-regulated in EZH2-transfected cells was EZH2 itself (FIG. 23c).

EZH2-mediated transcriptional repression was dependent on an intact SET domain (FIG. 23c), as deletion of this domain did not produce a repressive phenotype and in some cases "de-repressed" genes. EZH2 has been shown to interact with histone deacetylase 2 (HDAC2) via the EED protein (van der Vlag et al., Nat. Genet. 23:474 [1999]). In the experiments described above, EZH2-mediated gene silencing was dependent on HDAC activity, as the commonly used HDAC inhibitor, trichostatin A (TSA) completely abrogated the effects of EZH2 (FIG. 23c). Thus, EZH2 function requires both an intact SET domain as well as endogenous HDAC activity.

To identify genes that are significantly repressed by EZH2, wild-type EZH2-transfected cells were compared with EZH2.SET-transfected cells. Using this approach, 163 genes were consistently repressed while no genes were activated at an FDR of 0.0045 (FIG. 23d). Examination of the significant gene list identified the PcG group protein EPC, which is the human homolog of the *drosophila* protein Enhancer of Polycomb (E(Pc)) as being consistently repressed by EZH2 (FIG. 23c). Of the *Drosophila* PcG proteins, E(Pc) and E(z) are related in that they both act as suppressors of variegation (Su(var)) (Sinclair et al., Genetics 148:211 [1998]) and are the only PcG proteins to have yeast homologs, emphasizing the evolutionary conservation of this PcG pair. In addition to EPC, a host of other transcriptional regulators/activators were transcriptionally silenced by EZH2 including MDNA, RNF5, RNF15, ZNF42, ZNF262, ZNFN1A1, RBM5, SPIB, and FOXF2, among others (FIG. 23c). MDNA, also known as myeloid cell nuclear differentiation antigen, mediates transcriptional repression by interacting with the transcription factor YY1, which is a PcG homolog of *Drosophila* Pho and shown to be part of the EZH2/EED complex of proteins (Satijin et al., Mol. Cell. Biol. 21:1360 [2001]).

Figure 23:
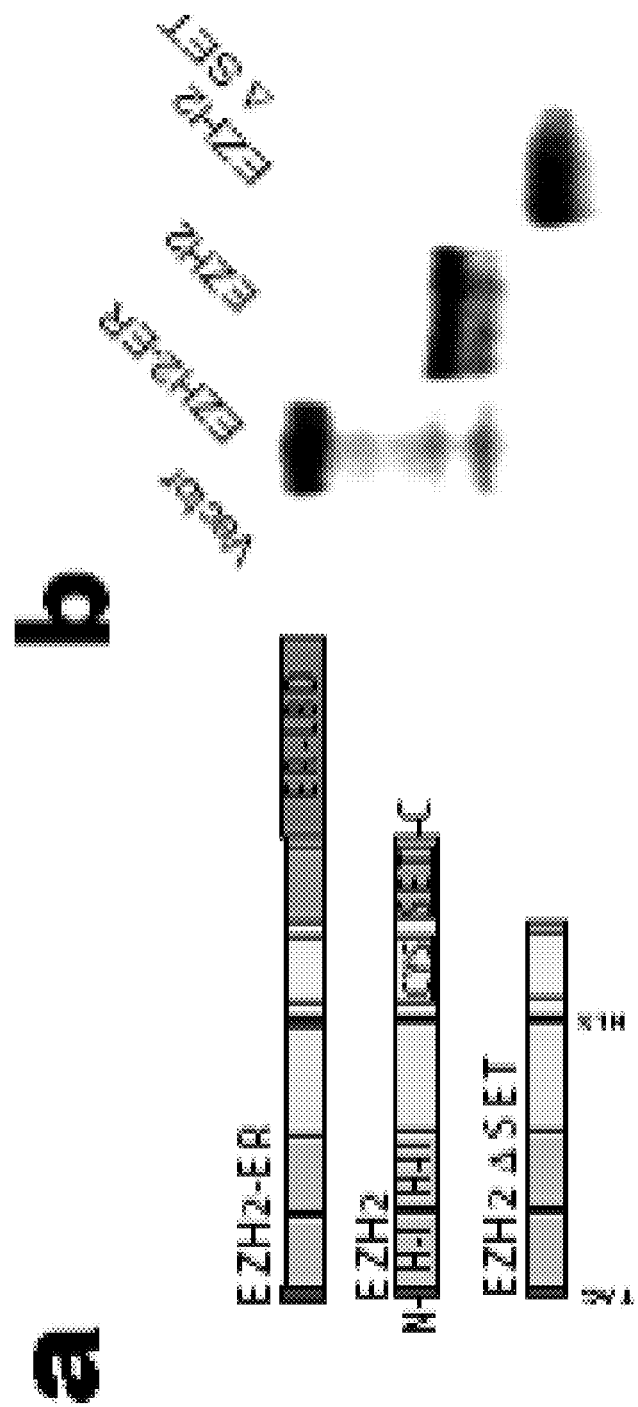
FIG. 23 shows that EZH2 functions as a transcriptional repressor in prostate cells.
Figure 23C:
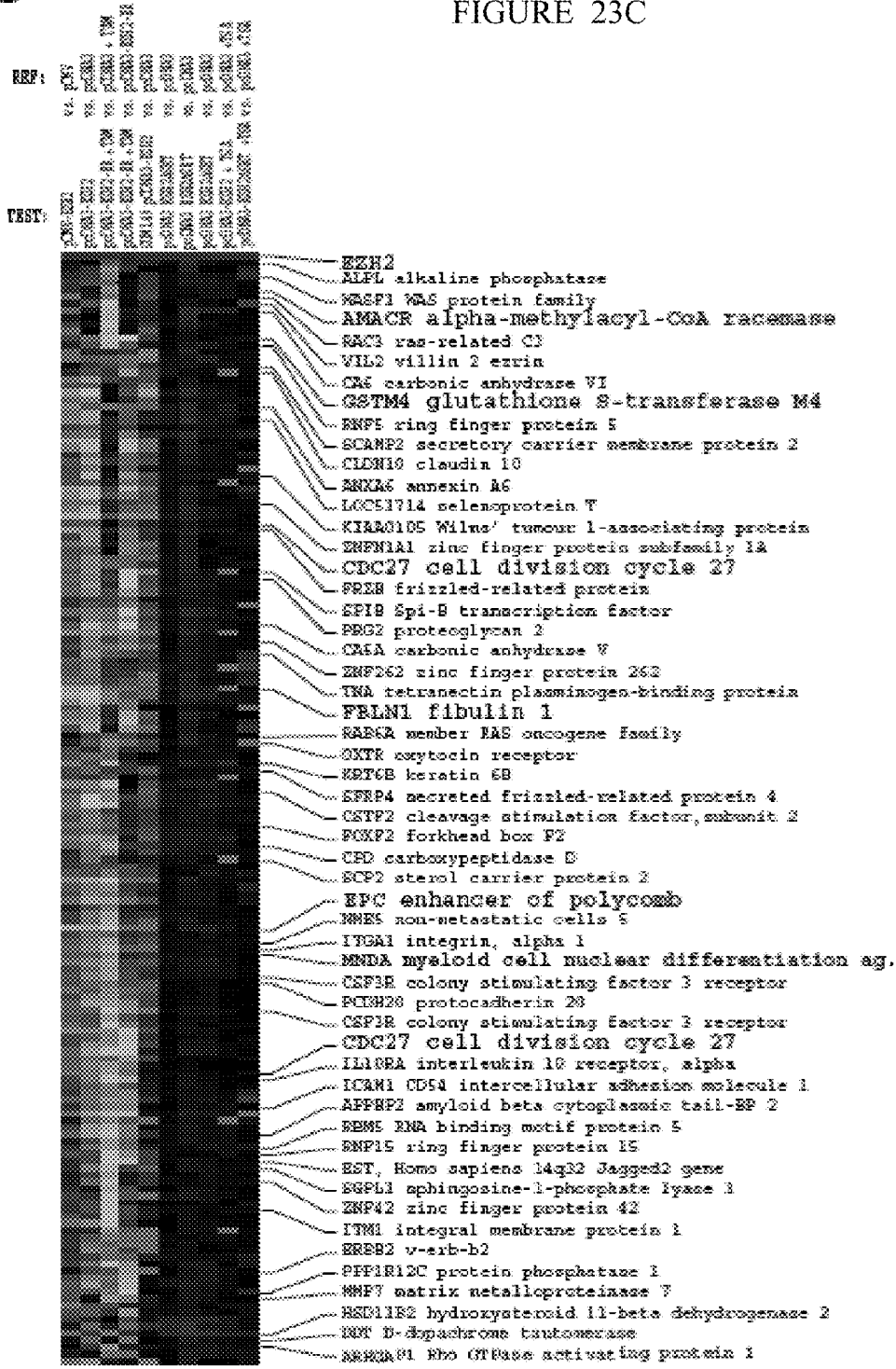
FIG. 23c shows a cluster diagram of genes that are significantly repressed by EZH2 overexpression.

In addition to transcriptional repression in prostate cells, the results also support a role for EZH2 in regulating cell growth (FIG. 23). Transcriptional repression of cdc27 (two independent Unigene clones) was also observed. Cdc27 is part of the anaphase-promoting complex (APC) which mediates ubiquitination of cyclin B1, resulting in cyclinB/cdk complex degradation (Jorgensen et al., Mol. Cell. Biol. 18:468 [1998]). Another family of proteins that was repressed when EZH2 was targeted was the solute carriers. At least 5 distinct members were shown to be repressed (i.e., SSLC34A2, SLC25A16, SLC25A6, SLC16A2, and SLC4A3).

EXAMPLE 9

Expression of AMACR in Serum and Urine

Figure 24:
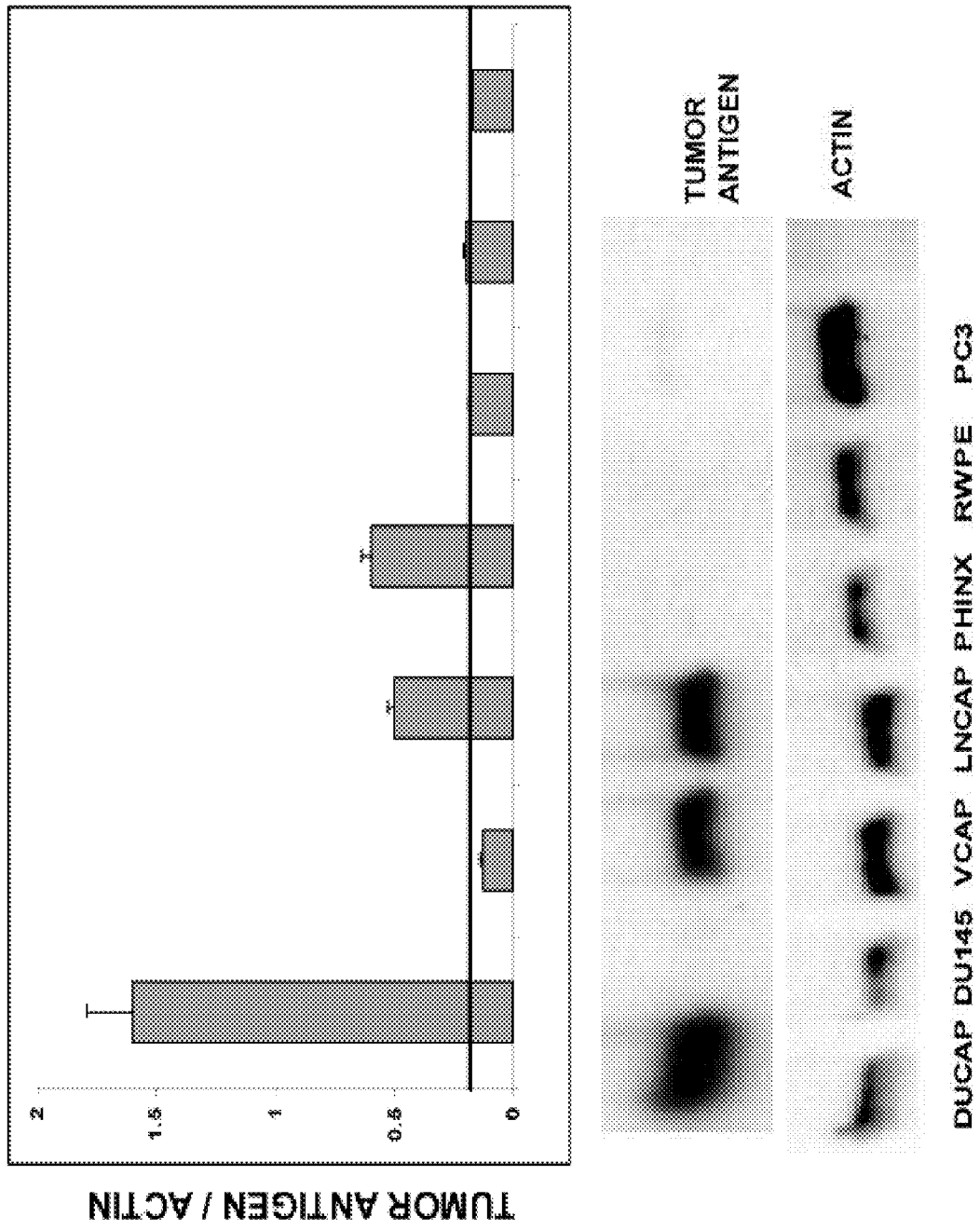
FIG. 24 shows the detection of AMACR in PCA cell lines.

This example describes the expression of AMACR in serum and urine. AMACR was detected by standard immunoblotting and by protein microarray using a polyclonal rabbit anti-AMACR antibody. The results are shown in FIGS. 24-27. FIG. 24 shows the detection of AMACR protein in PCA cell lines by quantitation of microarray data. DUCAP, DU145, and VCAP are prostate cancer cell lines. RWPE is a benign prostate cell line. PHINX is a human embryonic kidney cell line.

Figure 25:
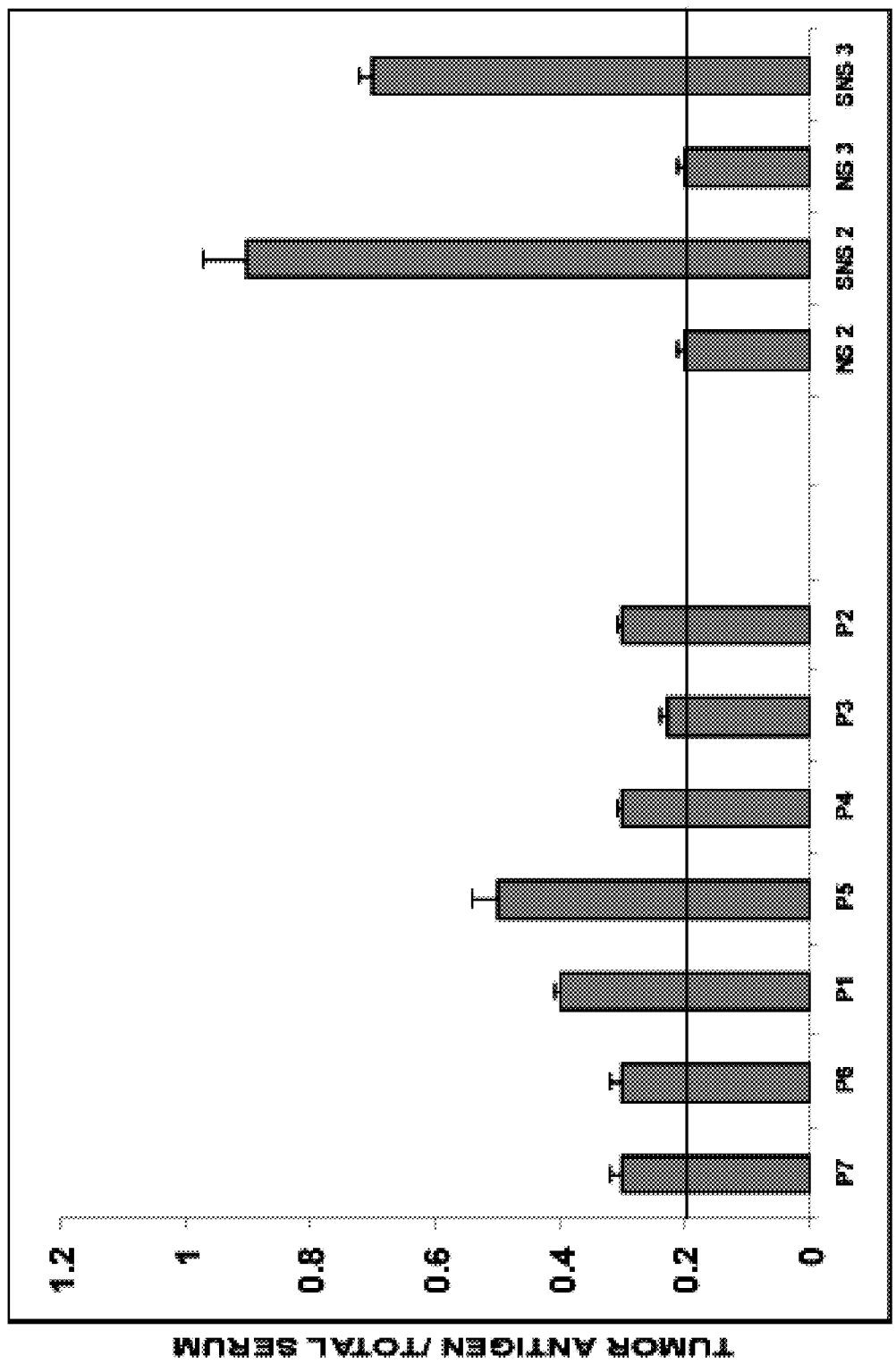
FIG. 25 shows the detection of AMACR protein in serum by quantitation of microarray data.
Figure 26:
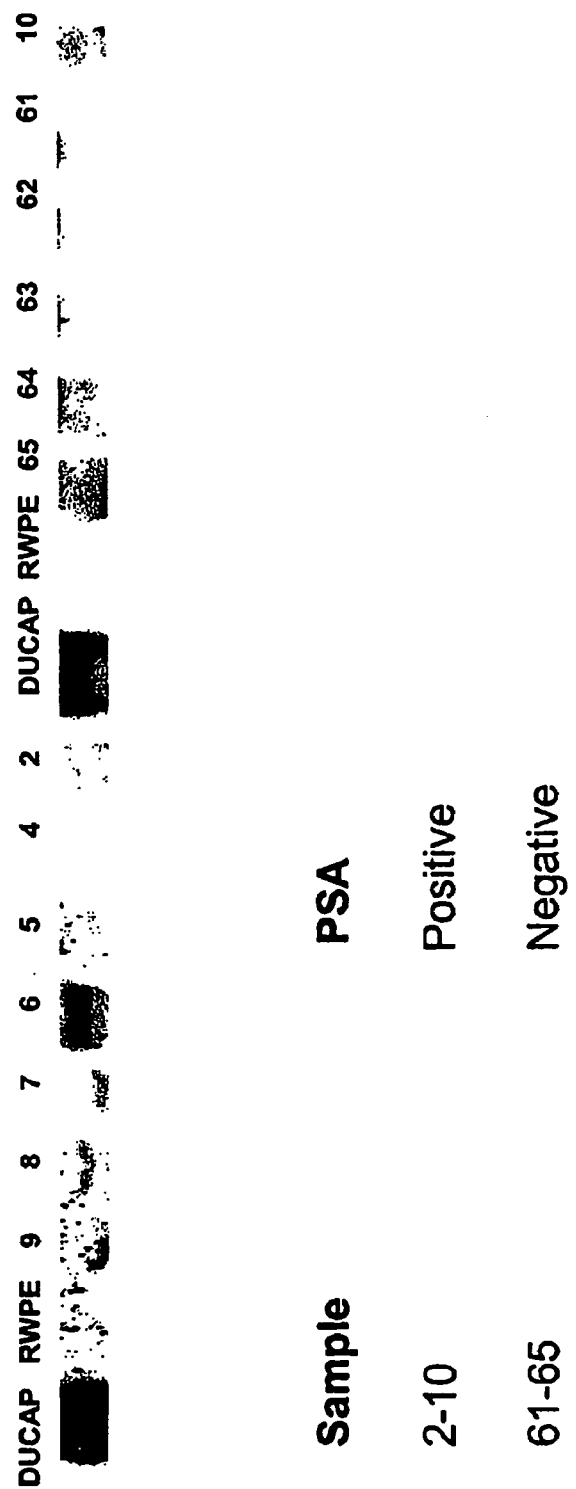
FIG. 26 shows an immunoblot analysis of serum from patients with either negative or positive PSA antigen.
Figure 27:
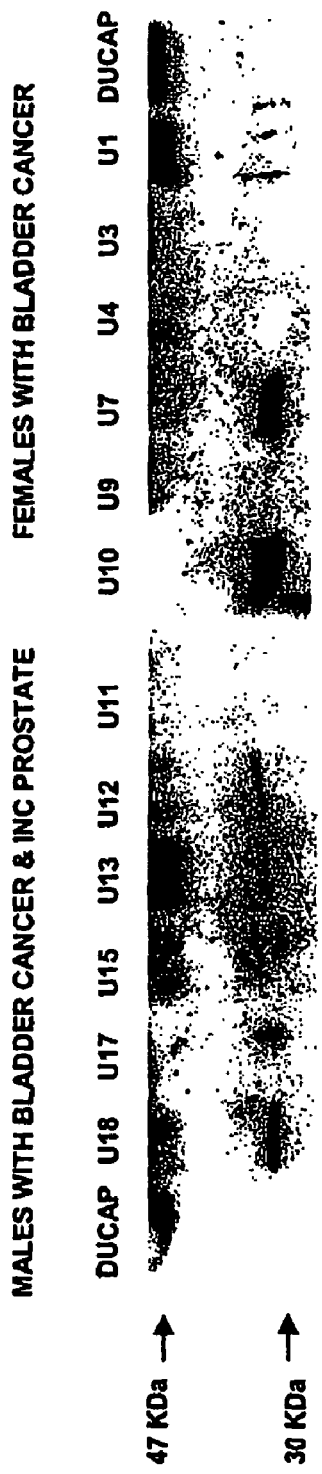
FIG. 27 shows an immunoblot analysis of the presence of AMACR in urine samples from patients with bladder cancer (females) or bladder cancer and increased PSA (males).

FIG. 25 shows the detection of AMACR protein in serum by quantitation of microarray data. P1-P7 represent serum from patients with prostate cancer. NS2 and NS3 represent serum from patients that do not have PCA. SNS2 and SNS3 represent serum from patients that do not have PCA that has been spiked with AMACR protein. FIG. 26 shows an immunoblot analysis of serum from patients with either negative or positive PSA antigen. FIG. 27 shows an immunoblot analysis of the presence of AMACR in urine samples from patients with bladder cancer (females) or bladder cancer and incidental prostate cancer (males). The results demonstrate that AMACR can be detected in the serum and urine of patients with bladder cancer or bladder cancer and prostate cancer.

EXAMPLE 10

AMACR as a Tumor Antigen

Figure 28:
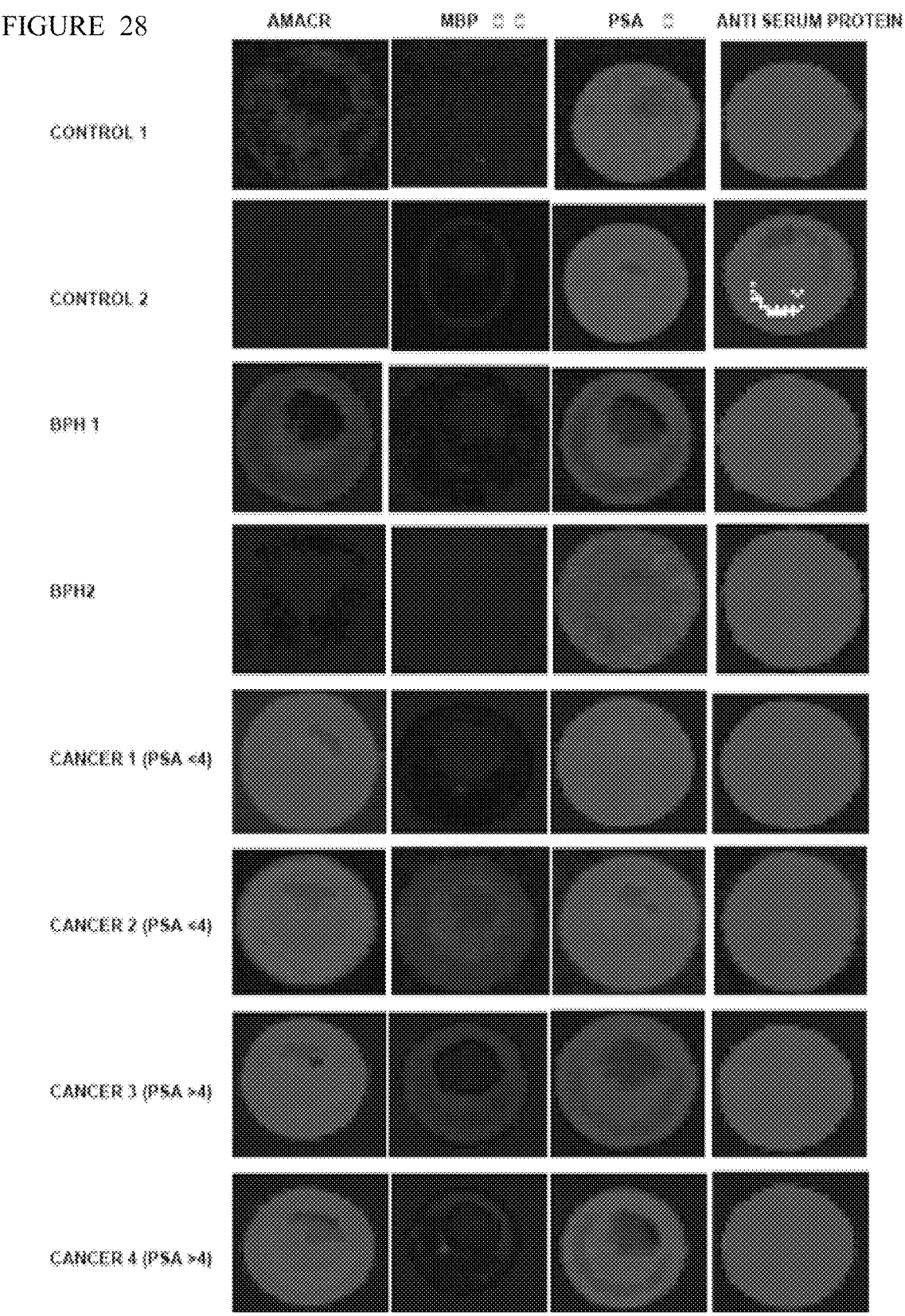
FIG. 28 shows representative data of a humoral response by protein microarray analysis.

This example describes the presence of an immune response against AMACR in serum. FIG. 28 shows representative data of a humoral response by protein microarray analysis. Tumor antigens including AMACR, PSA, CEA, HSPs were spotted onto nitrocellulose coated slides. The slides were incubated with sera from different patients to detect a humoral response. The microarray was then washed. A Cy5 labeled goat anti-human IgG was used to detect the humoral response. The slide was then scanned using a microarray scanner (Axon). After data normalization, intensity of spots reflects the presence, absence or strength of humoral response to specific tumor antigen. A specific humoral response to AMACR was detected in cancer patients but not in controls. Cancer refers to sera from prostate cancer patients. BPH refers to sera from patients with benign prostate hyperplasia.

Figure 29:
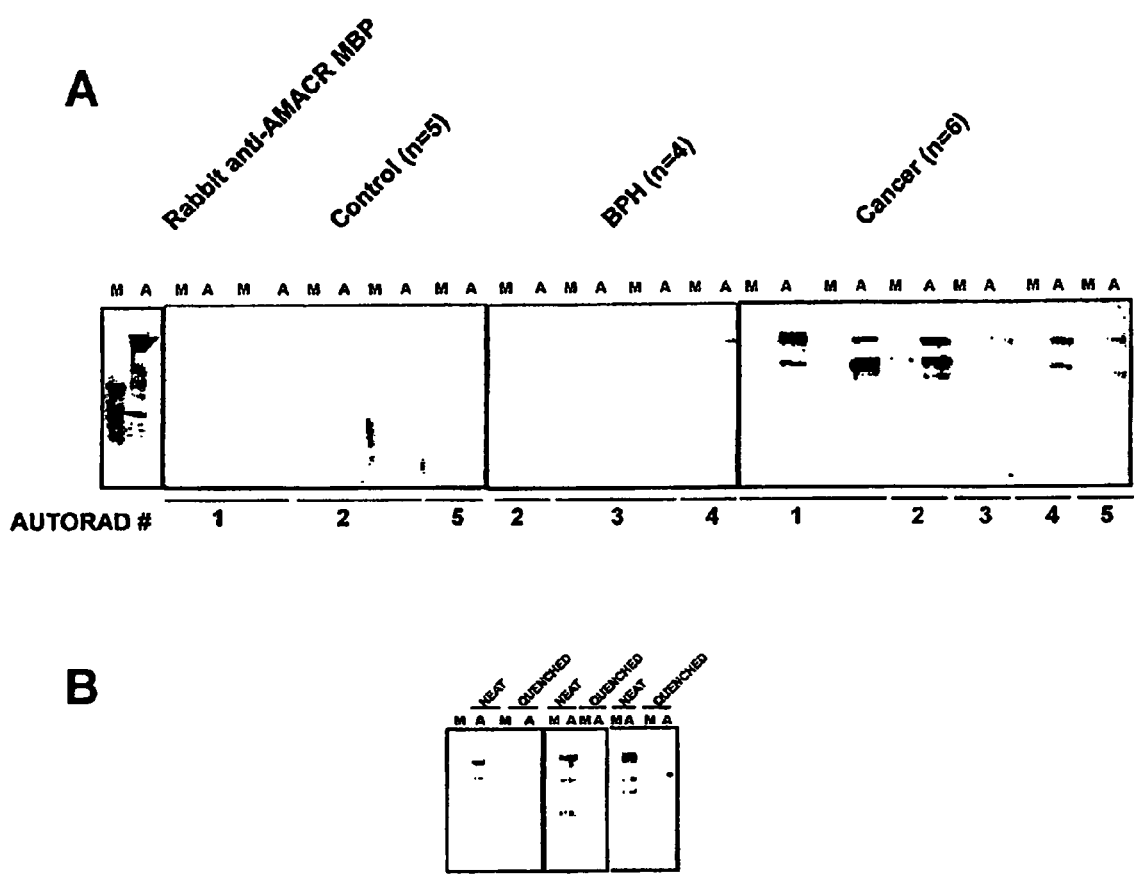
FIG. 29 shows immunoblot analysis of the humoral response of AMACR.

FIG. 29 shows immunoblot analysis of the humoral response to AMACR. FIG. 29A shows an SDS-PAGE gel containing recombinant MBP (control protein=M) and recombinant AMACR-MBP (A) that was run and transferred to nitrocellulose paper. Each strip blot was then incubated with human sera. A humoral response to the AMACR was detected using an HRP-conjugated anti-human antibody. Only AMACR and fragments of AMACR were detected in sera from prostate cancer patients and not in controls. FIG. 29B shows a control experiment whereby the humoral response is blocked with recombinant AMACR (quenched) and thus shows the specificity of the response.

This example demonstrates that AMACR functions as a tumor antigen in human serum of prostate cancer patients. A specific immune response was generated to AMACR in the serum of PCA patients, but not in controls.

EXAMPLE 11

Expression of GP73 in Prostate Cancer

This example describes the association of GP73 with prostate cancer.

A. Methods

Microarray analysis, RT-PCR, Western blotting, and immunohistochemistry were performed as described in the above examples.

B. Results

Figure 30:
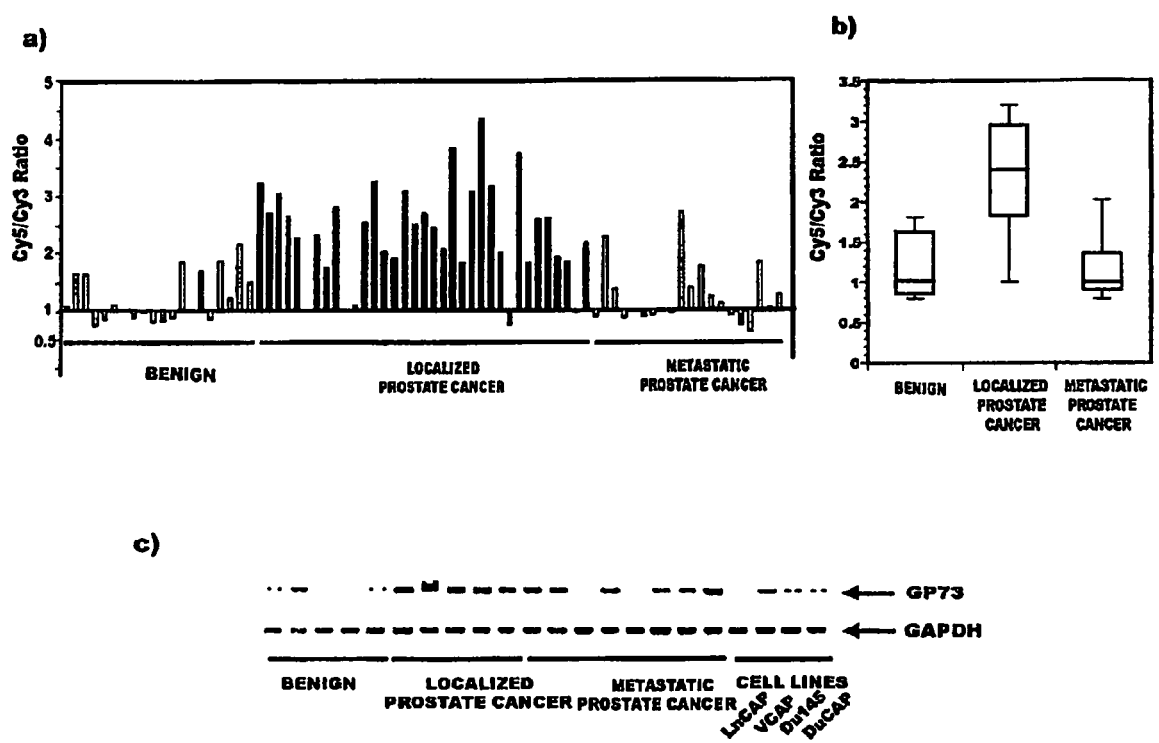
FIG. 30 shows GP73 Transcript levels in prostate cancer.

FIG. 30 shows GP73 Transcript levels in prostate cancer. FIG. 30a shows the level of GP73 in individual samples after microarray analysis. The graph shows the values of Cy5 versus Cy3 ratio wherein the prostate cancer tissue sample RNA were labeled with Cy5 fluorescent dye, while the reference sample (pool of benign tissue RNA) sample was labeled with Cy3 fluorescent dye. A total of 76 individual experiments from different prostate tissue are plotted and they are classified as benign, prostate cancer and metastatic cancer types. FIG. 30b shows the result of GP73 transcripts determined by DNA microarray analysis from 76 prostate samples grouped according to sample type and averaged. The experimental samples were labeled with Cy5 fluorescent dye, whereas the reference sample (pool of benign tissue sample) was labeled with Cy3 fluorescent dye. The box plot demonstrates the range of GP73 expression within each group. The middle horizontal bar indicates median values; the upper and lower limits of the boxes, interquartile ranges; and the error bars, 95% confidence intervals. FIG. 30c demonstrates that GP73 transcript levels are elevated in prostate cancer. RT-PCR was used to detect GP73 transcript levels in RNA preparations from prostate tissue extracts. GAPDH served as the loading control.

FIG. 31 shows that GP73 protein is upregulated in prostate cancer. FIG. 31a shows Western blot analysis of GP73 protein in prostate cancer. Total tissue proteins from benign, cancer and metastatic tissues (10 μg) were analyzed using anti-GP73 antiserum. β-Tubulin serves as control for sample loading. FIG. 31b shows an immunoblot analysis of the Golgi resident protein Golgin 97. The Golgin 97 protein levels were analyzed in the prostate tissue sample to indicate the level of Golgi structure in normal and cancerous prostate tissue. β-Tubulin serves as control for sample loading.

Tissue microarray analysis of GP73 protein in normal and cancerous prostate tissue was also performed. GP73 protein expression was analyzed by standard biotin-avidin immunohistochemical analysis using a polyclonal mouse antibody to GP73. Protein expression was evaluated on a wide range of prostate tissue using high-density tissue microarrays. High levels of staining were observed in prostate cancer tissue. Some normal epithelial cells did not stain for GP73 in a sub region of prostate cancer tissue.

FIG. 32 shows immunoblot analysis of normal and prostate cancer epithelial cells. The epithelial cells were isolated from normal prostate tissue and cancer tissue to specifically isolate the protein from epithelial cell for GP73 immunoblot analysis. For this purpose, laser capture microdissected samples were used. Actin western serves as control.

EXAMPLE 12

Lethal Markers and Targets

This example describes the identification of lethal markers. The markers serve as potential therapeutic targets. Markers were identified by correlating the number of samples with clinical parameters and gene expression. Specifically, the present study identified markers that have an expression profile similar to EZH2, which serves as a prototypic lethal biomarker of prostate cancer. These genes were identified by a scoring system that takes into account whether localized prostate cancer has recurred or not recurred. In addition, genes that have highly correlated expression with EZH2 were identified that may serve as markers to supplement EZH2.

| mean | dev | Total High | 16 bph_count | 13 pca_count | 16 pcau_count | 6 pcar_count | 20 met_count | score | UNIQID | NAME |
|---|---|---|---|---|---|---|---|---|---|---|
| −0.024 | 0.3725 | 0.7206 | 0 | 4 | 5 | 6 | 16 | 18 | 5814 | NULL ESTs Hs.30237 |
| −0.306 | 0.1707 | 0.0351 | 0 | 0 | 3 | 3 | 14 | 17 | 2506 | HN1 |
| −0.348 | 0.2394 | 0.1312 | 0 | 2 | 1 | 4 | 14 | 16 | 5112 | CSF2 |
| 0.0623 | 0.1578 | 0.3779 | 0 | 1 | 2 | 3 | 13 | 15 | 6053 | ASNS |
| −0.246 | 0.1689 | 0.0921 | 0 | 2 | 0 | 2 | 15 | 15 | 1520 | NULL ESTs Hs.16304 |
| −0.212 | 0.1386 | 0.0648 | 0 | 2 | 0 | 2 | 15 | 15 | 8273 | PRC1 |
| −0.352 | 0.1458 | −0.06 | 0 | 3 | 7 | 3 | 14 | 14 | 34 | GPAA1 |
| −0.292 | 0.2538 | 0.2153 | 0 | 0 | 1 | 3 | 10 | 13 | 5239 | KIAA1691 |
| −0.141 | 0.1572 | 0.1729 | 0 | 2 | 5 | 3 | 12 | 13 | 8562 | NULL Human clone 23614 |
| −0.21 | 0.1083 | 0.0067 | 0 | 4 | 4 | 2 | 15 | 13 | 3351 | FLJ11715 hypothetical protein |
| −0.22 | 0.1846 | 0.1495 | 0 | 5 | 4 | 5 | 13 | 13 | 2715 | NULL ESTs |
| −0.638 | 0.2696 | −0.099 | 1 | 5 | 4 | 3 | 15 | 13 | 9556 | FLJ12443 hypothetical protein |
| −0.142 | 0.1396 | 0.1371 | 0 | 0 | 2 | 2 | 10 | 12 | 1158 | TGFBI |
| −0.124 | 0.1606 | 0.1967 | 0 | 1 | 1 | 3 | 10 | 12 | 5292 | NULL ESTs |
| −0.444 | 0.2474 | 0.0504 | 0 | 1 | 2 | 2 | 11 | 12 | 3689 | NUF2R hypothetical protein |
| −0.205 | 0.2362 | 0.2674 | 0 | 2 | 1 | 2 | 12 | 12 | 1219 | ABCC5 |
| −0.09 | 0.2214 | 0.3526 | 0 | 4 | 2 | 4 | 12 | 12 | 1360 | MEN1 |
| −0.241 | 0.1541 | 0.0673 | 0 | 5 | 3 | 2 | 15 | 12 | 8476 | SARM and HEAT/Armadillo motif |
| −0.874 | 0.3367 | −0.201 | 0 | 1 | 4 | 2 | 10 | 11 | 3747 | H2BFB |
| −0.196 | 0.254 | 0.3122 | 0 | 2 | 1 | 3 | 10 | 11 | 4941 | VAV2 |
| −0.166 | 0.1486 | 0.1307 | 0 | 2 | 4 | 2 | 11 | 11 | 8636 | NULL ESTs Hs.23268 |
| 0.0255 | 0.1542 | 0.3338 | 0 | 3 | 3 | 3 | 11 | 11 | 280 | TOP2A |
| −0.226 | 0.2536 | 0.2812 | 0 | 4 | 3 | 4 | 11 | 11 | 2156 | EZH2 |
| −0.031 | 0.1826 | 0.3346 | 0 | 4 | 4 | 2 | 13 | 11 | 1979 | NULL ESTs Hs.268921 |
| −0.48 | 0.2967 | 0.1131 | 0 | 2 | 0 | 2 | 10 | 10 | 906 | MGC5627 hypothetical protein |
| −0.243 | 0.1421 | 0.0411 | 0 | 2 | 8 | 2 | 10 | 10 | 3728 | NULL ESTs |
| −0.133 | 0.1806 | 0.2279 | 0 | 2 | 2 | 2 | 10 | 10 | 8759 | RAB24 |
| −0.192 | 0.1782 | 0.1645 | 0 | 3 | 2 | 2 | 11 | 10 | 2029 | FLJ12876 hypothetical protein |
| −0.617 | 0 | −0.617 | 0 | 3 | 2 | 2 | 10 | 9 | 3928 | DGKD |
| 0.1079 | 0.1132 | 0.3343 | 0 | 3 | 2 | 2 | 10 | 9 | 5372 | ODF2 |
| −0.288 | 0.1221 | −0.043 | 0 | 4 | 3 | 3 | 10 | 9 | 7193 | KIAA0602 |
| −0.167 | 0.2278 | 0.2883 | 0 | 4 | 2 | 2 | 11 | 9 | 8535 | EHM2 |
| −0.95 | 0.3504 | −0.249 | 0 | 4 | 2 | 2 | 11 | 9 | 9824 | SLC19A1 |
| −0.314 | 0.187 | 0.06 | 1 | 4 | 2 | 2 | 11 | 9 | 9447 | LIG1 |
| 0.1366 | 0.1883 | 0.5132 | 1 | 4 | 3 | 2 | 10 | 8 | 327 | NULL ESTs |
| −0.586 | 0.2952 | 0.0044 | 0 | 5 | 2 | 2 | 11 | 8 | 1269 | DGKZ | mean: mean expression in BPH
Dev: standard deviation in BPH
High: 2 SD's above the mean (threshold)
Bph: # of BPH samples > thresh
PCA: # of PCA samples > thresh (>1 yr no recur)
Pcau: # of PCA samples > thresh (<1 yr followup)
Pcar: # of PCA samples > thresh (recur)
Met: # of metastatic samples > thresh
Score: = met + pcar − pca
Total: # of samples in category Exemplary lethal markers identified using the above methods include ABCC5 (MDR5). This multi-drug resistance gene actively pumps cyclic nucleotides and other small molecules out of cells. An unrelated study found that this enzyme is potently Inhibited by phosphodiesterase inhibitors, including sildenafil (viagra). The present invention is not limited to a particular mechanism. Indeed, an understanding of the mechanism is not required to practice the present invention. Nonetheless, it is contemplated that sildenafil may be useful in the treatment of aggressive PCA.

Another lethal marker identified is asparagine synthetase (ASNS). Current therapeutics for the inhibition of ASNS include asparaginase, an enzyme that destroys asparagine in the body. It has been shown that cancers expressing the synthetase are resistant. Analogs are being developed to inhibit the synthetase.

Top2A (topoisomerase 2) and the Vav2 Oncogene were also identified using the methods of the present invention. Vav2 is required for cell spreading, but is dependent on src. The present invention is not limited to a particular mechanism. Indeed, an understanding of the mechanism is not required to practice the present invention. Nonetheless, it is contemplated src inhibitors can stop vav2 mediated cell spreading This example describes the identification of cancer markers overexpressed in prostate cancers. The present invention is not limited to a particular mechanism. Indeed, an understanding of the mechanism is not necessary to practice the present invention. Nonetheless, it is contemplated that therapeutic compounds that inhibit these lethal markers are useful in the treatment of prostate cancer.

EXAMPLE 13

Characterization of Annexin Expression in Prostate Cancer

This Example describes the expression of Annexins in prostate cancer.

A. Materials and Methods

Prostate Sample Collection

Prostate tissues were taken from the radical prostatectomy series and the rapid autopsy program available through the University of Michigan Prostate Cancer Specialized Program of Research Excellence (S.P.O.R.E.) Tissue Core. This program is approved by Institutional Review Board at the University of Michigan.

Hormone naïve, clinically localized PCA samples used for this study were taken from a cohort of men who underwent radical retropubic prostatectomy as a monotherapy (i.e., no hormonal or radiation therapy) for clinically localized PCA between the years 1994 and 1998. Processing of the prostatic tissues started within 20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol. 164:1583 [2000]). The snap frozen samples used for cDNA expression array analysis were all evaluated by one of the study pathologists. All samples were grossly trimmed to ensure greater than 95% of the sample represented the desired lesion.

Hormone refractory PCA samples were collected from the rapid autopsy program (Rubin et al., [2000], supra). Snap frozen samples were used for cDNA expression array analysis. Mirrored samples from the same lesion were placed in 10% buffered formalin. The fixed samples are embedded in paraffin. As with the prostatectomy samples, the study pathologist reviewed the glass slides, circled areas of viable prostate cancer, avoiding areas of necrosis, and used these slides as a template for tissue microarray construction. In this study, twenty (20) hormone refractory metastatic PCAs were extracted from 15 rapid autopsy cases performed from 1997 to 2000. The patients' ages ranged from 53 to 84 and time from diagnosis to death ranged from 21 to 193 months. All 15 patients died with widely metastatic PCA after extensive treatment, which included antiandrogens and chemotherapy.

Prostatectomy samples were evaluated for the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Semin. Urol. Oncol. 17:222 [1999]). Tumors were graded using the Gleason grading system (Gleason, [1966], supra).

Immunohistochemistry

After paraffin removal and hydration, the tissue microarray slides were immersed in 10 mM citrate buffer placed in a pressure cooker chamber and microwaved for 10 minutes for optimal antigen retrieval. Immunostaining was performed using a Dako autostainer (DAKO, Carpinteria, Calif.). The primary antibody was incubated for 45 minutes at room temperature and a secondary biotin-labeled antibody for 30 minutes. Streptavidin-LSA amplification method (DAKO K0679) was carried out for 30 minutes followed by peroxidase/diaminobenzidine substrate/Chromagen. The slides were counterstained with hematoxylin. Polyclonal antibodies directed against the N-terminus of annexin 1 (dilution 1:50), annexin 2 (dilution 1:100), annexin 4 (dilution 1:100), annexin 7 (dilution 1:500), and annexin 11 (dilution 1:100) were obtained from a signal source (Santa Cruz Biotechnology, Santa Cruz, Calif.). Protein expression as determined by two pathologists immunohistochemistry was scored as negative (score=1), weak (score 2), moderate (3) or strong (4), using the system described above.

Tissue Microarray Construction, Digital Image Capture, and Analysis

Tissue microarrays were constructed as previously described to evaluate protein expression in a wide range of samples ranging from benign prostate tissue taken from the prostatectomy samples to hormone refractory PCA. Three tissue microarrays were used for this study consisting of benign prostate, localized PCAs, and hormone refractory PCA. The tissue microarrays were assembled using the manual tissue arrayer (Beecher Instruments, Silver Spring, Md.) as previously described (Kononen et al., [1998], supra; Perrone et al., [2000], supra). Tissue cores from the circled areas of interest were targeted for transfer to the recipient array blocks. The 0.6 mm diameter tissue microarray cores were each spaced at 0.8 mm from core-center to core-center. Tissue microarray images were acquired using the BLISS Imaging System (Bacus Lab, Lombard, Ill.).

Statistical Analyses

To investigate the statistical significance associated with the differential expression of annexins across 4 independent gene expression studies, standard methods (Hedges et al., Statistical Methods for Meta-analysis meta-analysis. Orlando, Academic Press 1985, pp xxii, 369) were used to combine the results. For each of the studies, a t-statistic was computed (with the two groups being benign tissue compared against localized prostate cancer) and the associated p-values were transformed using a negative logarithmic transformation. These numbers were then doubled and added together to arrive at a summary measure of differential gene expression across the three studies. To assess the statistical significance associated with this summary measure, a permutation-based approach was adopted (Hedges et al., supra). Namely, the tissue types were permutated within studies, and the summary measure was computed for the permutated data. A p-value was computed using the permutation distribution of the summary measure. The issue then arises of whether or not the t-statistics from the three studies are comparable.

Annexin protein expression was statistically evaluated using the mean score results from each tissue microarray sample for each prostate tissue type (i.e., benign, localized PCA, and hormone refractory PCA). To determine differences between all pairs (e.g., localized prostate cancer versus benign), an ANOVA with a post-hoc analysis was performed using the Scheffé method (Scheffae et al., supra). The mean expression scores for all examined cases were presented in a graphical format by using error-bars with 95% confidence intervals.

B. Results

Figure 33:
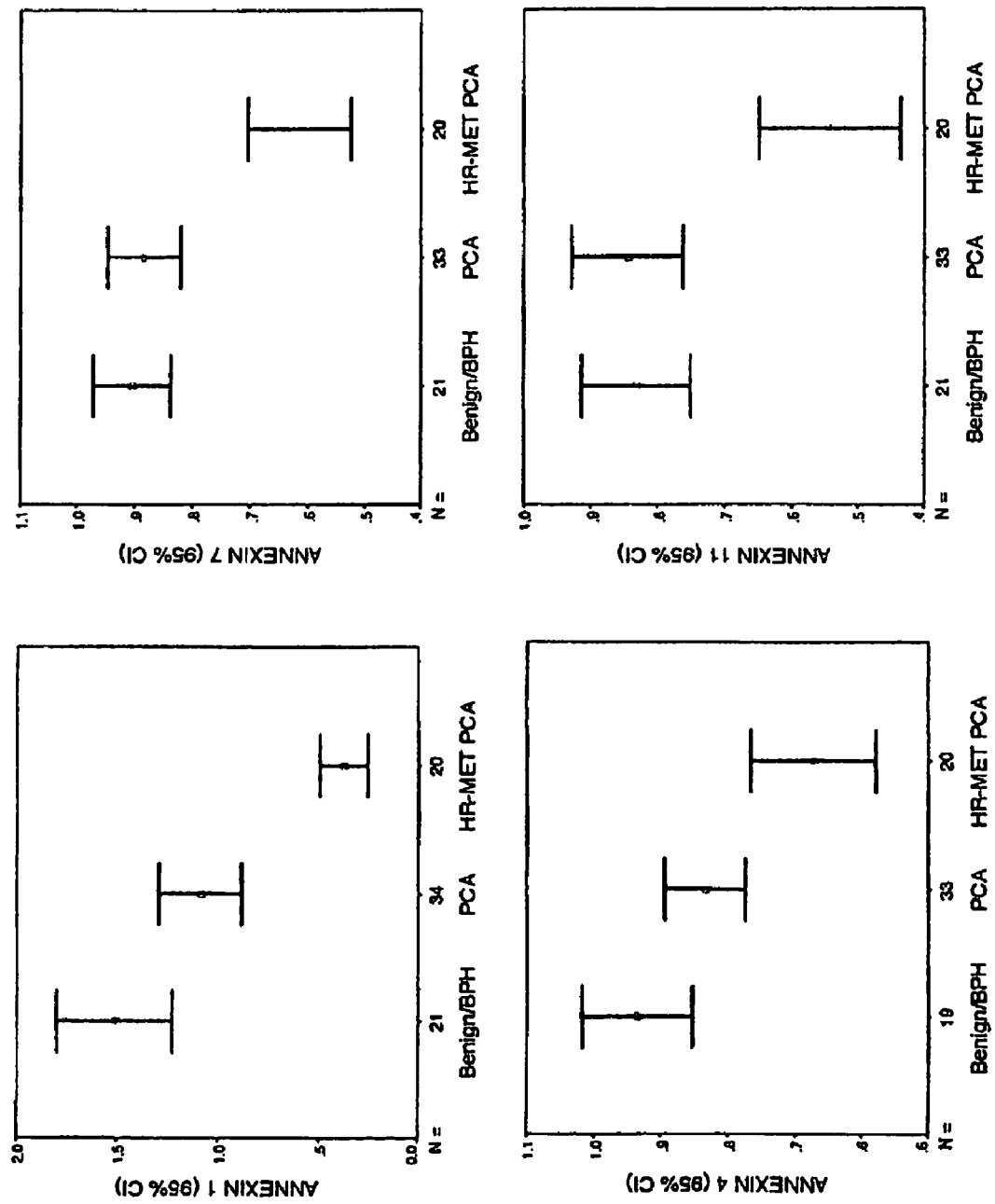
FIG. 33 shows the cDNA expression of select annexin gene family members.

Expression array analysis revealed a significant dysregulation of annexin family members with PCA progression. The cDNA expression of annexins 1, 2, 4, 7 and 11 were significantly decreased in the hormone refractory PCA samples as compared to localized hormone sensitive PCA samples with 2.2, 1.5, 1.3, 1.4 and 1.8 fold decrease, respectively (all p-values<0.01) (Table 3 and FIG. 33). Annexins 1 and 4 showed significant decreases of mRNA expression in localized PCA samples as compared to the benign samples. There were no significant differences between localized hormone naive PCA and the benign samples for annexin 2, 7, and 11. No cDNA dysregulation between the tested prostate samples and annexins 8 and 13 was observed. Annexin 6 demonstrated a slight decrease in cDNA expression between localized PCA and benign samples, which was not statistically significant (Table 3).

Figure 34:
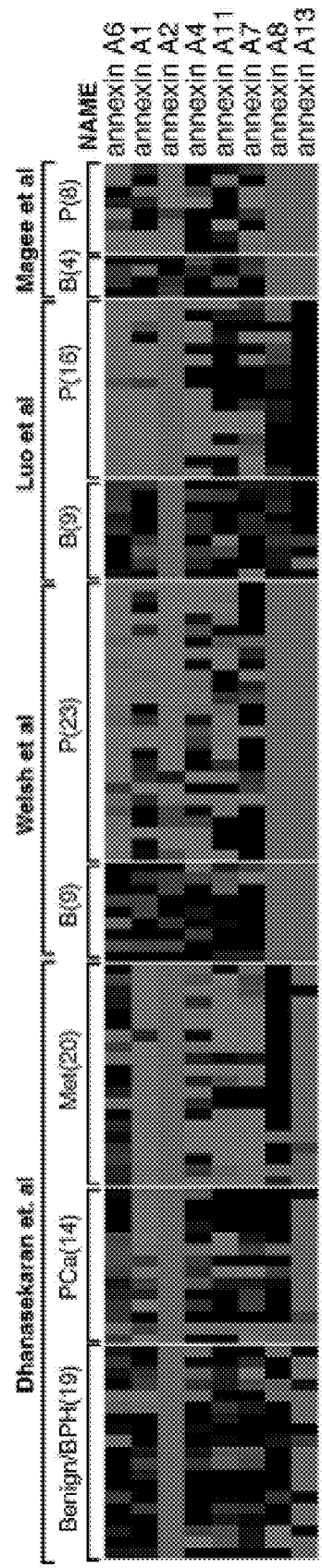
FIG. 34 shows a heat map representation of annexin family gene expression across four prostate cancer profiling studies. Over and under expression at the transcript level are represented by shades of red and green, respectively. Gray shading indicates that insufficient data was available. Each square represents an individual tissue sample.

In order to cross validate the cDNA expression results for these annexin family members, a meta-analysis of gene expression was performed. Annexin family members cDNA expression results were evaluated using a series of data sets (Welsh et al., Cancer Res. 61:5974 [2001]; Luo et al., Cancer Res. 61:4683 [2001]; Magee et al., Cancer Res. 61:5692 [2001]). The analysis evaluated annexins for each of the individual studies as well as performing a summary statistic, taking into account the significance of the gene expression across the 4 studies. The meta-analysis compared differences between clinically localized PCA and benign prostate tissue as not all of the studies had hormone refractory metastatic PCA. The meta-analysis (Table 4 and FIG. 34) demonstrated that annexins 1, 2, 4, and 6 were significantly down regulated across independent studies. Annexin 6 was down regulated to a significant level in 4 of 4 studies. Annexin 1 demonstrated down regulation in 3 of 4 studies. Annexins 2 and 4 were down regulated in 2 studies and overall considered to be significantly under expressed by the meta-analysis. Annexin 7 was not found to be significantly under expressed in any of the 4 studies at the transcript level.

Immunohistochemistry was performed to confirm these results at the protein level (Table 5). By immunohistochemistry, a significant decrease in protein expression for annexins 1, 2, 4, 7 and 11 in hormone refractory PCA samples as compared to localized PCA samples was identified with 2.5 (3.8 vs. 1.5 median expression), 2.4 (4 vs. 1.7 median expression), 3.6 (4 vs. 1.1 median expression) and 3.3 (4 vs. 1.2 median expression) fold decreases, respectively (Kruskal Wallis test, all p-values p<0.05). No statistically significant differences were seen between benign and localized PCA samples in any of the annexins tested.

TABLE 3

Gene Expression of Select Annexins.

| Annexin | Benign | | BPH[1] | | Loc-PCA[2] | | Met-PCA[3] | | Ratio PCA/Met | p Value* |
|---|---|---|---|---|---|---|---|---|---|---|
| | Count | Median | Count | Median | Count | Median | Count | Median | | |
| 1 | 5 | 1.56 | 16 | 1.35 | 16 | 0.69 | 20 | 0.31 | 2.23 | <0.001 |
| 2 | 5 | 0.79 | 16 | 0.69 | 16 | 0.74 | 20 | 0.49 | 1.51 | 0.009 |
| 4 | 5 | 0.91 | 16 | 0.97 | 16 | 0.9 | 20 | 0.69 | 1.30 | 0.001 |
| 6 | 5 | 1.2 | 16 | 1.29 | 16 | 1.05 | 20 | 1.15 | 0.91 | 0.377 |
| 7 | 5 | 0.8 | 16 | 0.88 | 16 | 0.88 | 20 | 0.62 | 1.42 | <0.001 |
| 8 | 5 | 1.14 | 16 | 1.06 | 16 | 0.99 | 20 | 1.19 | 0.83 | 0.156 |
| 11 | 5 | 0.99 | 16 | 0.76 | 16 | 0.94 | 20 | 0.52 | 1.81 | <0.001 |
| 13 | 5 | 1.08 | 16 | 1.35 | 16 | 1.03 | 20 | 0.94 | 1.10 | 0.393 |

*Kruskal Wallis Test.
[1]BPH, benign prostatic hyperplasia.
[2]Loc-PCA, localized prostate cancer.
[3]Met-PCA, metastatic hormone refractory prostatic cancer.
Ratio PCA/Met, ratio of expression of localized PCA over hormone refractory PCA.

TABLE 4

Meta-Analysis of cDNA Prostate Gene Expression Studies for Annexin Family Members

| Annexin | Present study | Welsh et al. | Luo et al. | Magee et al. | Summary p-Value |
|---|---|---|---|---|---|
| 6 | 0.024 | 0.0001 | 0.0001 | 0.026 | 0.0001 |
| 1 | 0.0001 | 0.031 | 0.0007 | 0.23 | 0.0001 |
| 2 | NA | 0.0001 | NA | 0.002 | 0.0001 |
| 11 | NA | 0.010 | NA | 0.6 | 0.17 |
| 7 | 0.25 | 0.48 | 0.38 | 0.088 | 0.20 |
| 4 | 0.33 | 0.023 | 0.0093 | 0.58 | 0.011 |
| 13 | 0.177 | NA | 1.00 | NA | 0.48 |
| 8 | 0.79 | NA | 0.104 | NA | 0.29 |

TABLE 5

Tissue Microarray Protein Expression for Annexins by Tissue Type

| Annexin | Benign | | Loc-PCA[2] | | Met-PCA[3] | | PCA/MET | p-value* |
|---|---|---|---|---|---|---|---|---|
| | Count | Median | Count | Median | Count | Median | | |
| 1 | 37 | 2.59 | 360 | 2.45 | 162 | 1.46 | 1.68 | <0.001 |
| 2 | 57 | 3.95 | 82 | 3.62 | 214 | 1.47 | 2.46 | <0.001 |
| 4 | 23 | 3.65 | 357 | 3.96 | 141 | 1.57 | 2.52 | <0.001 |
| 7 | 26 | 3.77 | 350 | 3.97 | 126 | 1.32 | 3.01 | <0.001 |
| 11 | 23 | 4.00 | 360 | 3.99 | 163 | 1.30 | 3.01 | <0.001 |

*Kruskal Wallis Test.
1, BPH, benign prostatic hyperplasia.
[2]Loc-PCA, localized prostate cancer.
[3]Met-PCA, metastatic hormone refractory prostatic cancer.

EXAMPLE 14

Association of CtBP with Prostate Cancer

This example describes the expression of C-terminal binding proteins 1 and 2 (CtBP1 and CtBP2) in prostate cancer. Microarray analysis, Western Blots, immunohistochemistry, and statistical analysis were performed as described in the above examples.

Figure 35:
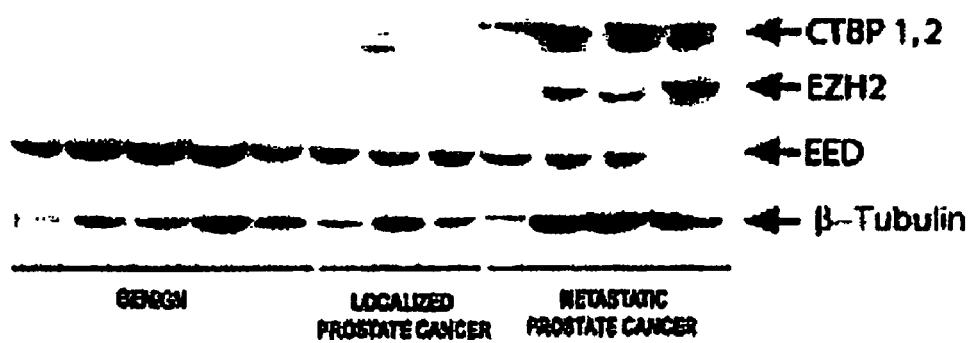
FIG. 35 shows the expression of CtBP proteins in PCA specimens.
Figure 38:
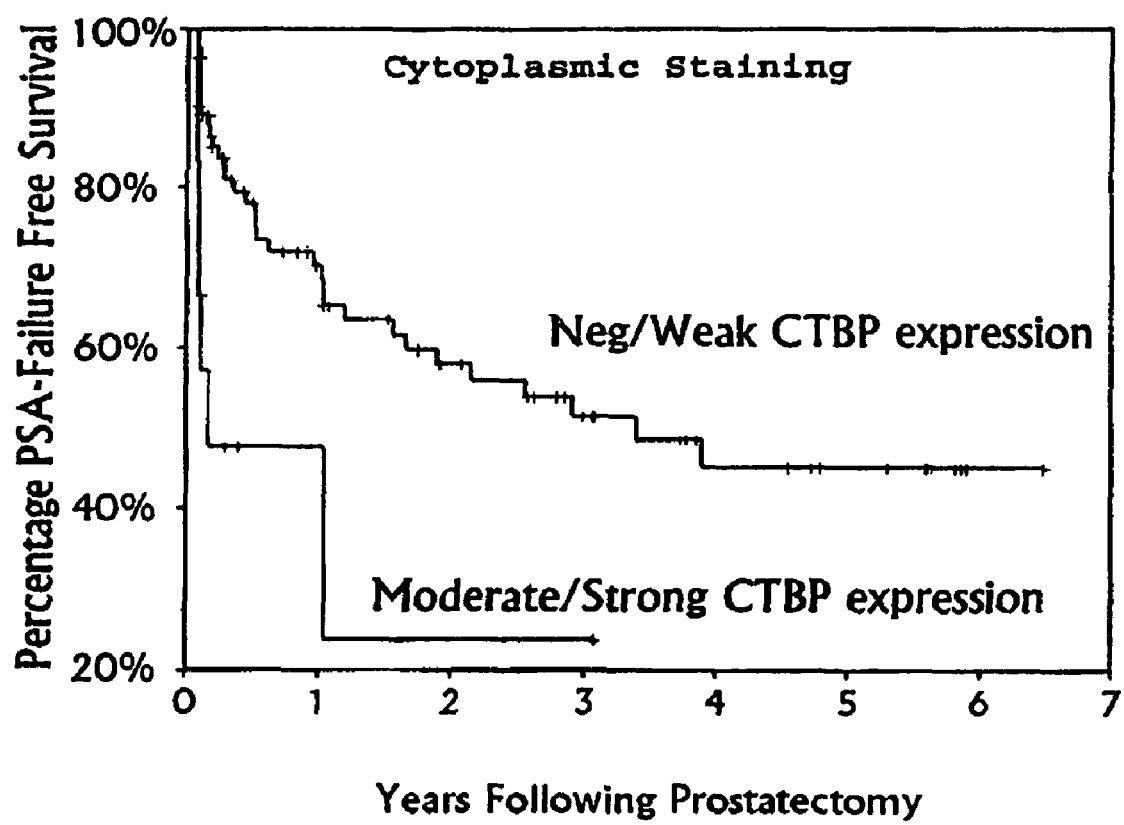
FIG. 38 shows a Kaplan-Meier Analysis of prostate cancer tissue microarray data.

The CtBP transcript was found to be up-regulated in metastatic prostate cancer (FIG. 38). Tissue extracts were used to validate this finding at the protein level using an antibody that recognizes CtBP1 and CtBP2 (Sewalt et al., Mol. Cell. Biol. 19:777 [1999]. The results are shown in FIG. 35. FIG. 35 shows the Expression of CtBP proteins in PCA specimens. Extracts from selected prostate specimens were assessed for expression of CtBP and PcG proteins by immunoblot analysis. Protein level was equalized in each extract before loading and blots were stained with Ponceau S to confirm equal loading. β-tubulin was used as a control protein.

Both CtBPs were over-expressed in metastatic prostate cancer relative to localized prostate cancer and benign tissue. EZH2 protein was also elevated in metastatic prostate cancer relative to localized prostate cancer or benign prostate (FIG. 35). EED, a PcG protein that forms a complex with EZH2, along with an un-related protein, β-tubulin, did not exhibit similar protein dysregulation. Thus, both transcriptional repressors (CtBP and EZH2) are mis-expressed in metastatic prostate cancer.

To determine in situ expression of CtBP, immunohistochemistry of prostate tissue sections were performed using prostate tissue microarrays. Benign prostatic epithelia exhibited exclusively nuclear staining consistent with CtBP's role as a transcriptional repressor. Both clinically localized and metastatic prostate cancer exhibited nuclear staining as well. Most of the metastatic prostate cancer cases and a fraction of the localized prostate cancer cases exhibited distinct cytoplasmic staining of CtBP.

Figure 36:
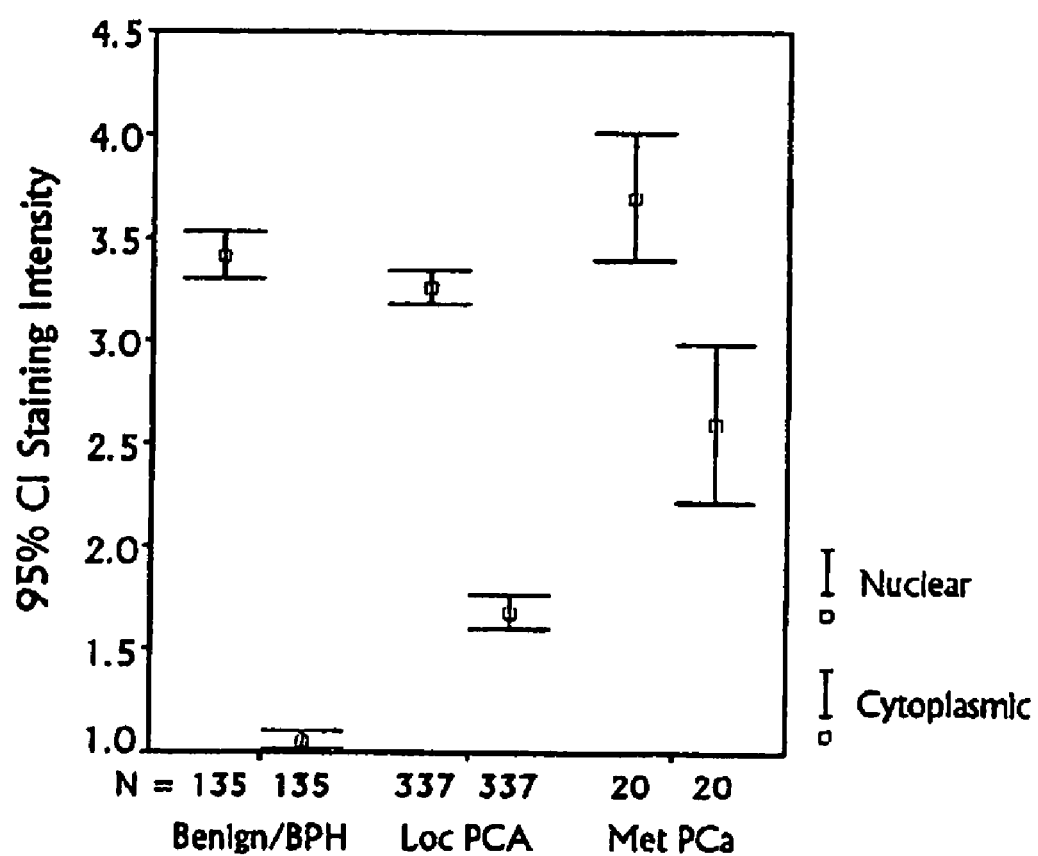
FIG. 36 shows tissue microarray analysis of CtBP in prostate cancer that suggests mis-localization during prostate cancer progression.
Figure 37:
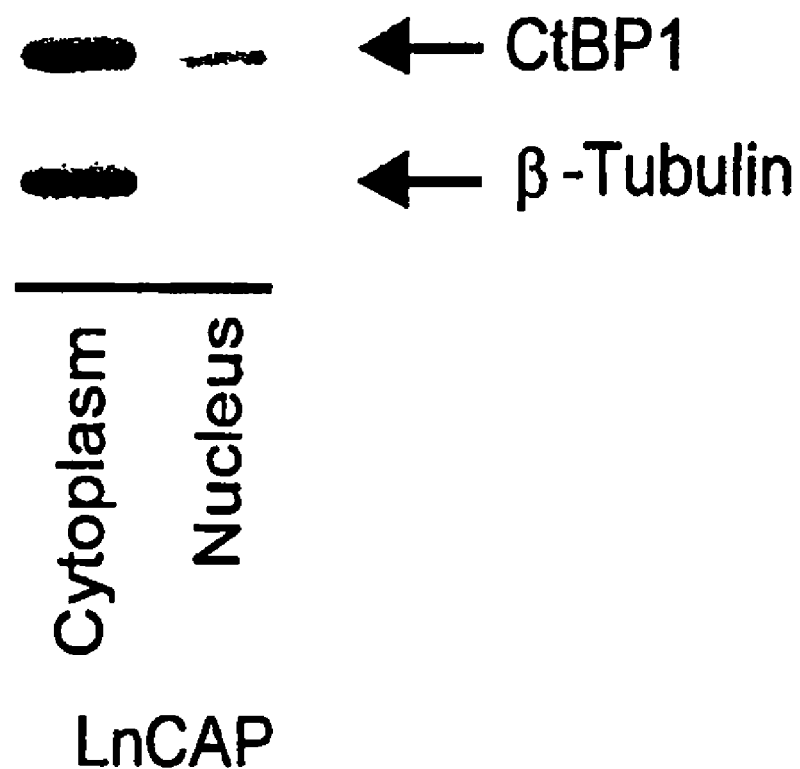
FIG. 37 shows the sub-cellular fractionation of LNCaP cells.

FIG. 36 shows tissue microarray analysis of CtBP in prostate cancer that suggests mis-localization during prostate cancer progression. The mean CtBP protein expression for the indicated prostate tissues and sub-cellular compartment is summarized using error bars with 95% confidence intervals. FIG. 37 shows the sub-cellular fractionation of LNCaP cells. The results show an increased level of CtBP 1 in the cytoplasm relative to the nucleus. CtBP2 is weakly expressed in the cell lines and is not easily apparent. β-tubulin, which is not expressed in the nucleus, is provided as a control. FIG. 38 shows a Kaplan-Meier Analysis of prostate cancer tissue microarray data. The results demonstrate that the presence of cytoplasmic CtBP may be associated with a poorer clinical outcome. The median follow up time for all patients was 1 year (range 2 month to 6.5 years). Over this follow up time, 38% of the patients developed a recurrence or PSA elevation greater than 0.2 ng/ml. Prostate tumors from 97 patients demonstrated near uniform nuclear protein expression for CTBP. Cytoplasmic expression was variable with 85 of 97 cases (88%) demonstrating weak cytoplasmic staining and 12 (12%) with moderate to strong CTBP expression. There was a significant association with increased CTBP cytoplasmic staining intensity and PSA recurrence or presence of recurrent disease following prostatectomy with a relative risk of 1.7 (Cox regression analysis p=0.034). The data presented demonstrates a Kaplan-Meier Analysis of outcome stratified by negative/weak cytoplasmic CTBP staining and moderate/strong staining. CTBP cytoplasmic expression predicted recurrence even when Gleason score was taken into account in a multivariable model, suggesting that CTBP is a prognostic predictor of poor outcome [Gleason relative risk 1.4 (p=0.005) and cCTBP rr 1.6 (p=0.042)].

CtBP has been shown to bind nitric oxide synthase (NOS), which is thought to shift the localization of CtBP from the nuclear compartment to the cytoplasmic compartment (Riefler et al., J. Biol. Chem. 276:48262 [2001]). Weigert and colleagues have proposed a cytoplasmic role for CtBP in the induction of Golgi membrane fission (Weigart et al., Nature 402:429 [1999]). To further support the preliminary immunohistochemical findings, LNCaP (metastatic) prostate cancer cells were fractionated and it was found that CtBP levels were higher in the cytosol relative to the nucleus (FIG. 38).

EXAMPLE 15

Methods of Characterizing Cancer Markers

This example describes exemplary methods for the characterization of new cancer markers of the present invention. These methods, in combination with the methods described in the above examples, are used to characterized new cancer markers and identify new diagnostic and therapeutic targets.

A. Determination of Quantitative mRNA Transcript Levels of Cancer Markers in Prostate Cancer Specimens In some embodiments, markers revealed to be over or under expressed in cancer microarrays (See e.g., Example 1 for a description of microarrays) are quantitated using real-time PCR (Wurmbach et al., J. Biol. Chem. 276:47195 [2001]).

In preferred embodiments, cDNA from over 100 prostate samples for archived cDNA samples and associated clinical data are available (See Example 1). The level of expression in the microarray is compared to those obtained by real-time PCR. To identify genes with dysregulation of expression, real-time PCR analysis of cDNA generated from laser-capture microdissected prostate cancer epithelia and benign epithelia is performed.

B. Detection of Mis-localized Transcripts

In some embodiments, in order to determine if a cancer marker normally present in the nucleus of a cell (e.g., a transcriptional repressor) is mis-localized to the cytoplasm (or other mis-locations) in cancer, the expression of the marker is examined in tissue extracts from preferably at least 20 benign prostate samples, 20 prostate cancer specimens, and 20 metastatic prostate specimens. Expression of the marker in benign prostate cell lines (RWPE), primary prostatic epithelial cells (Clonetics, Inc.) and a panel of prostate cancer cells including LNCaP, DU145, PC3, DUCaP, and VCaP cells is also examined. Once overall expression of prostate cell lines and tissues is established, the cellular localization of the marker is determined by 2 methods. In the first method, the cell and tissue extracts are fractionated into a nuclear fraction and a cytosolic fraction (NE-PER, Pierce-Endogen; Orth et al., J. Biol. Chem. 271:16443 [1996]). Quantitated protein is then analyzed by immunoblotting. Relative levels of cytosolic and nuclear cancer marker are determined by densitometry. To verify clean fractionation, antibodies to β-tubulin and PCNA (or lamin A) are used to assess cytosolic and nuclear fractions, respectively.

In the second method, cells are immunostained with antibodies to the cancer marker followed by detection using anti-rabbit FITC secondary antibody. Confocal microscopy (U of M Anatomy and Cell Biology Core Facility) is used to examine in situ localization of the cancer markers.

In some embodiments, mis-localization is further investigated by sequencing the gene in cells containing the mis-located transcript (e.g., metastatic cases) for mutations.

C. Correlation of Cancer Markers with Clinical Outcome

In some preferred embodiments, the association of expression or mis-localization of a cancer marker with clinical outcome is investigated. The ratio of total cancer marker to β-tubulin by immunoblot analysis of prostate cancer tissue extracts is first determined and associated with clinical outcome parameters. For markers suspected of being mis-localized in cancer (e.g., CtBP), the ratio of cytoplasmic marker to nuclear marker is next determined by immunoblot analysis of prostate cancer tissue extracts and associated with clinical outcome parameters. For example, it is contemplated that a high cytoplasmic/nuclear cancer marker ratio may portend a poor clinical outcome. In some embodiments (e.g., where a cancer marker is suspected of being mis-localized), immuno-histochemistry of prostate cancer tissue microarrays is used to determine whether the presence of cytoplasmic marker correlates with poor clinical outcome. Tissue microarrays are prepared and performed as described in the above examples.

Briefly, high-density tissue microarrays (TMA) are constructed as previously described (Perrone et al, supra; Kononen et al., supra). Immunostaining intensity is scored by a genitourinary pathologist as absent, weak, moderate, or strong (or alternatively analyzed separately as for cytoplasmic and nuclear staining). Scoring is performed using a telepathology system in a blinded fashion without knowledge of overall Gleason score (e.g., tumor grade), tumor size, or clinical outcome (Perrone et al., supra). Tumor samples are derived from patients with clinically localized, advanced hormone refractory prostate cancer and naive metastatic PCA. Cases of clinically localized prostate cancer are identified from the University of Michigan Prostate S.P.O.R.E. Tumor Bank. All patients were operated on between 1993 and 1998 for clinically localized prostate cancer as determined by preoperative PSA, digital-rectal examination, and prostate needle biopsy. All tissues used are collected with institutional review board approval. The advanced prostate tumors are collected from a series of 23 rapid autopsies performed at the University of Michigan on men who died of hormone refractory prostate cancer. The clinical and pathologic findings of these cases have been reported (Rubin et al., [2000], supra).

Statistical analysis of the array data is used to correlate the cancer marker protein measurements on the TMA with clinical outcomes, such as time to PSA recurrence and survival time. This analysis involves survival analysis methods for correlating the measurements with these censored response times. Kaplan-Meier curves are plotted for descriptive purposes. Univariate analyses is performed using the Cox model associating the biomarker with the survival time. In addition, multivariate Cox regression analysis is performed to test whether the biomarker adds any prognostic information over and above that available from known prognostic markers (i.e., Gleason score, tumor stage, margin status, PSA level before surgery).

D. RNA Interference

In some embodiments, RNA interference of cancer markers is used to investigate the role of the cancer marker in cell culture and well as for application as a therapeutic cancer treatment (See e.g., Example 8 for an example of RNA interference). 21-nucleotide RNAs (siACE-RNAi) are synthesized through a commercial vendor (Dharmacon Research, Inc.). RNA interference has been used in mammalian cells (Elbashir et al., Nature 411:494 [2001]). Several siRNA duplexes and controls are designed for each marker. The design of the siRNA duplexes uses criteria provided by Elbashir et al. (Elbashir et al., supra) and Dharmacon Research which include: starting approximately 75 bases downstream of the start codon, locating an adenine-adenine dimer, maintaining G/C content around 50%, and performing a BLAST-search against EST databases to ensure that only one gene is targeted. Multiple (e.g., two) siRNA duplexes are designed for each molecule of interest since whether the siRNA duplex is functional is a relatively empirical process. In addition, it is contemplated that using two siRNA duplexes may provide a combined "knock-down" effect. As a control, a "scrambled" siRNA, in which the order of nucleotides is randomized, is designed for each molecule of interest. Oligonucleotides are purchased deprotected and desalted. Upon arrival, the oligonucleotides are annealed to form a duplex using the manufacturer's provided protocol.

To test the efficacy of each siRNA duplex, prostate cell lines (RWPE, DU145, LnCAP, and PC3) are transfected with the OLIGOFECTAMINE reagent as described (Elbashir et al., supra). The cells are assayed for gene silencing 48 hrs post-transfection by immunoblotting with respective antibodies. A number of controls are included: buffer controls, sense siRNA oligo alone, anti-sense siRNA oligo alone, scrambled siRNA duplex, and siRNA duplexes directed against unrelated proteins. If significant silencing is not appreciated after single transfection, sequential transfection is performed and inhibition is monitored at later time points (i.e., 8 days later) as suggested by others (Breiling et al., Nature. 412: 51 [2001]). This may be necessary with proteins that have a long half-life.

In addition to the transient expression of siRNAs, a method for stable expression of siRNAs in mammalian cells is used (Brummelkamp et al., Science 296:550 [2002]). Prostate cancer cell lines are generated that express siRNA targeting cancer markers using the pSUPER system. Scrambled siRNA is used as a control. The cell lines facilitate downstream characterization of cancer markers that may be cumbersome using duplexes transiently. If inhibition of a specific cancer marker is found to be toxic to cells, the pSUPER cassette containing siRNA to the marker is cloned into an inducible vector system (e.g., Tet on/off).

E. Generation of Mutants.

To study the function of cancer markers of the present invention, mutants of cancer markers are generated in eukaryotic expression vectors. myc-epitope tagged versions of cancer marker mutants are generated in both pcDNA3 and pcDNA3-ER (a modified estrogen receptor ligand binding domain). In the case of the ER constructs, the vectors produce an in-frame fusion protein with modified ER, thus generating a post-transcriptionally inducible vector (Littlewood et al., Nucleic Acids Res. 23: 686 [1995]). The ER-ligand domain is mutated and fails to bind endogenous estrogen, yet can be activated by 4-hydroxytamoxifen (Littlewood et al., supra). The ER-fusion proteins are inactivated in the absence of ligand presumably due to binding of proteins such as hsp90. In the presence of exogenously added 4-hydroxytamoxifen, ER-fusions become liberated. By using an inducible vector system, cell lines expressing a "toxic" or growth inhibitory version of a cancer marker can still be isolated.

Various N-terminal and C-terminal deletion mutants are generated that encompass function domains of the cancer marker (e.g., the PXDLS, dehydrogenase, and PDZ binding domains of CtBP; Chinnadurai, Mol Cell. 9: 213 [2002]). It is contemplated that some of the mutant versions of the cancer markers of the present invention act as dominant negative inhibitors of endogenous cancer marker function. Expression of epitope-tagged cancer markers and mutants is assessed by transient transfection of human embryonic kidney cells (using FUGENE) and subsequent Western blotting.

F. Establishing Stable Cell Lines Expressing Cancer Markers And Mutants

In some embodiments, cell lines stably expressing cancer markers of the present invention are generated for use in downstream analysis. FUGENE is used to transiently transfect prostate cell lines (RWPE, DU145, LnCAP, and PC3) with cancer markers and fusions or mutants using the above mentioned vectors and appropriate G418 selection. Prostate cell lines with varied expression levels of endogenous cancer marker protein are used. Both individual clones and pooled populations are derived and expression of cancer markers and mutants assessed by immunoblotting for the epitope tag. By also using an inducible system, clones expressing toxic versions of cancer markers or mutants can be isolated.

G. Cell Proliferation and Apoptosis Studies

In some embodiments, the role of cancer marker expression in prostate cell proliferation is investigated using a multi-faceted approach that includes 1. RNA interference, 2. transient transfection of cancer markers and potential dominant negative mutants, and 3. comparing stable transfectants of cancer markers and mutants. The following predictions are tested using these methods: 1. whether inhibition of cancer markers will block cell growth and 2. whether overexpression of cancer markers will enhance cell proliferation.

Cell proliferation is assessed by cell counting (Coulter counter) over a time course in culture by using the WST-1 reagent (Roche, Inc.), which is a non-radioactive alternative to [$^3$H]-thymidine incorporation and analogous to the MTT assay. The rate of incorporation of the DNA labeling dye bromodeoxyuridine (BrdU) will also be measured as described previously (Jacobs et al., Nature. 397:164 [1999]). Potential cell cycle arrest induced by siRNA or dominant negative inhibitors of is determined by conventional flow cytometric methods. By using stable cell lines that "activate" cancer markers and mutants in a 4-hydroxytamoxifen-dependent fashion, cell proliferation and cell cycle alterations are monitored in a highly controlled in vitro system. To confirm that overexpression or inhibition of cancer markers does not activate the apoptosis pathway, several assays are used including propidium iodide staining of nuclei, TUNEL assay and caspase activation.

If a cancer marker is found to be a regulator of cell proliferation in prostate cells, studies are designed to address how components of cell cycle machinery are modulated by the cancer marker. Thus, in order to study cancer marker mediated effects on the cell cycle machinery of prostate cells, cancer marker functions are modulated with the above mentioned tools (i.e., siRNA, dominant negative inhibition, etc.) and the expression levels (transcript and protein) of cyclins (cyclin D1,E,A), cyclins-dependent kinases (cdk2, cdk4, cdk6) and cyclin-dependent kinase inhibitors (p21 CIP1, p27KIP1, p45SKP2, p16INK4) are monitored.

H. Cell Adhesion and Invasion Assays

If a cancer marker is suspected of altering cell adhesion (e.g., the transcriptional repression of an epithelial gene program such as E-cadherin), the methods described above are used to investigate whether over-expression of the cancer marker causes increased or decreased cell adhesion. Adhesion to extracellular matrix components, human bone marrow endothelium (HBME) as well as to human umbilical vein endothelial cells (HUVEC) is tested. Cancer markers are further tested for their ability to modulate invasion of PCA.

Known methods are used in these studies (Cooper et al., Clin. Cancer Res. 6:4839 [2000]). Briefly, snap-apart 96-well tissue culture plates are coated with crude bone and kidney matrices. Plates are incubated overnight at room temperature under sterile conditions and stored at 4° C. until needed. Assay plates are also coated with extracellular matrix components (e.g., human collagen I, human fibronectin, mouse laminin I) and human transferrin at various concentrations according to the manufacturer's instruction (Collaborative Biomedical Products, Bedford, Mass.). Endothelial cells (HBME or HUVEC) are seeded onto bone matrices or plastic substrata at a concentration of 900 cells/µl and grown to confluence. Tumor cells are removed from the flask by a 15-20 minute treatment with 0.5 mM EDTA in Hank's balanced salt solution. Once the EDTA solution is removed, the cells are resuspended in adhesion medium (e.g., minimum essential medium (MEM) with 1% bovine serum albumin (BSA) supplemented with 10 uCi$^{51}$ Cr sodium salt (NEN, Boston, Mass.)) for 1 hour at 37° C. Cells are then washed three times in isotope free media and 1×10$^5$ radio-labeled tumor cells are resuspended in adhesion media and layered upon a confluent layer of endothelial cells for 30 min at 37° C. In addition, radiolabeled tumor cells are applied to crude bone matrices. Again, plates are washed three times in phosphate buffered saline and adhesion is determined by counting individual wells on a gamma counter. Cell adhesion is reported relative to the adhesion of controls (PC-3 cells on plastic), which are set to 100.

Cell invasion assays are performed using a classic Boyden chamber assay. Both strategies to inhibit and overexpress cancer markers are evaluated. Previous reports have correlated increased cell migration in a Boyden Chamber system with increased invasive properties in vivo (Klemke et al., J Cell Biol. 140:61 [1998]. Commercially available 24-well invasion chambers are used (e.g., BD biosciences, Chemicon International).

I. Transcriptional Suppression in Prostate Cancer Cells

In some embodiments, the effect of cancer markers on gene silencing in prostate cells is assessed. Gene silencing is assayed in several ways. First, gene expression alterations induced by transient transfection of cancer markers and mutants in prostate cell lines (RWPE, DU145, LnCAP, and PC3) is assayed using FUGENE. Twelve to 48 hours after transfection, cells are harvested and a portion is processed to confirm expression of the transfectants by immunoblotting. Using vector-transfected cells as a reference sample, total RNA from transfected cells is then assessed on 20K cDNA microarrays.

In addition to transient transfections, stable cell lines overexpressing cancer markers and cancer marker mutants are generated. Patterns of gene expression from cancer marker and cancer marker mutant expressing cell lines are compared to vector-matched controls in order to identify a gene or group genes that is repressed by a given cancer marker. The present invention is not limited to a particular mechanism. Indeed, and understanding of the mechanism is not necessary to practice the present invention. Nonetheless, it is contemplated that genes identified as repressed by a given cancer marker will be increased (de-repressed) upon knock-down of the cancer marker (e.g., by siRNA inhibition).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of screening compounds, comprising:
   a) contacting a prostate cell sample with a test compound; and
   b) detecting a change in Enhancer of Zeste Homolog 2 (EZH2) expression in said prostate cell sample in the presence of said test compound relative to the absence of said test compound.

2. The method of claim 1, wherein said detecting comprises detecting EZH2 mRNA.

3. The method of claim 1, wherein said detecting comprises detecting EZH2 polypeptide.

4. The method of claim 1, wherein said cell is in vitro.

5. The method of claim 1, wherein said cell is in vivo.

6. The method of claim 1, wherein said test compound comprises an antisense compound.

7. The method of claim 1, wherein said test compound comprises a drug.

8. The method of claim 1, wherein said test compound comprises an siRNA.

9. The method of claim 1, wherein said detecting comprises the use of an EZH2 specific detection reagent.

* * * * *

SEQUENCE LISTING

```
<160> NUMBER OF SEQ ID NOS: 123

<210> SEQ ID NO 1
<211> LENGTH: 1783
<212> TYPE: DNA
<213> ORGANISM: Homo sapiens

<400> SEQUENCE: 1
tcgagcccgc tttccaggga ccctacctga gggcccacag gtgaggcagc ctggcctagc      60
aggccccacg ccaccgcctc tgcctccagg ccgcccgctg ctgcggggcc accatgctcc     120
tgcccaggcc tggagactga cccgacccccg gcactacctc gaggctccgc ccccacctgc     180
tggaccccag ggtcccaccc tggcccagga ggtcagccag ggaatcatta acaagaggca     240
gtgacatggc gcagaaggag ggtggccgga ctgtgccatg ctgctccaga cccaaggtgg     300
cagctctcac tgcggggacc ctgctacttc tgacagccat cggggcggca tcctgggcca     360
ttgtggctgt tctcctcagg agtgaccagg agccgctgta cccagtgcag gtcagctctg     420
cggacgctcg gctcatggtc tttgacaaga cggaagggac gtggcggctg ctgtgctcct     480
cgcgctccaa cgccagggta gccggactca gctgcgagga gatgggcttc ctcagggcac     540
tgacccactc cgagctggac gtgcgaacgg cgggcgccaa tggcacgtcg ggcttcttct     600
gtgtggacga ggggaggctg ccccacaccc agaggctgct ggaggtcatc tccgtgtgtg     660
attgccccag aggccgtttc ttggccgcca tctgccaaga ctgtggccgc aggaagctgc     720
ccgtggaccg catcgtggga ggcgggaca ccagcttggg ccggtggccg tggcaagtca     780
gccttcgcta tgatggagca cacctctgtg ggggatccct gctctccggg gactgggtgc     840
tgacagccgc ccactgcttc ccggagcgga accgggtcct gtcccgatgg cgagtgtttg     900
ccggtgccgt ggcccaggcc tctccccacg gtctgcagct gggggtgcag gctgtggtct     960 accacgggg ctatcttccc tttcgggacc ccaacagcga ggagaacagc aacgatattg    1020
ccctggtcca cctctccagt ccctgcccc tcacagaata catccagcct gtgtgcctcc    1080
cagctgccgg ccaggccctg gtggatggca agatctgtac cgtgacgggc tgggcaaca    1140 cgcagtacta tggccaacag gccggggtac tccaggaggc tcgagtcccc ataatcagca    1200
atgatgtctg caatggcgct gacttctatg gaaaccagat caagcccaag atgttctgtg    1260
```

| | |
|---|---:|
| ctggctaccc cgagggtggc attgatgcct gccagggcga cagcggtggt cccttttgtgt | 1320 |
| gtgaggacag catctctcgg acgccacgtt ggcggctgtg tggcattgtg agttggggca | 1380 |
| ctggctgtgc cctggcccag aagccaggcg tctacaccaa agtcagtgac ttccgggagt | 1440 |
| ggatcttcca ggccataaag actcactccg aagccagcgg catggtgacc cagctctgac | 1500 |
| cggtggcttc tcgctgcgca gcctccaggg cccgaggtga tcccggtggt gggatccacg | 1560 |
| ctgggccgag gatgggacgt ttttcttctt gggcccggtc cacaggtcca aggacaccct | 1620 |
| ccctccaggg tcctctcttc cacagtggcg ggcccactca gccccgagac cacccaacct | 1680 |
| caccctcctg accccccatgt aaatattgtt ctgctgtctg ggactcctgt ctaggtgccc | 1740 |
| ctgatgatgg gatgctcttt aaataataaa gatggttttg att | 1783 |

<210> SEQ ID NO 2
<211> LENGTH: 2623
<212> TYPE: DNA
<213> ORGANISM: Homo sapiens

<400> SEQUENCE: 2

| | |
|---|---:|
| gaggaggccc gagaggagtc ggtggcagcg gcggcggcgg gaccggcagc agcagcagca | 60 |
| gcagcagcag caaccactag cctcctgccc cgcggcgttg cgacgagccc cacgagccgc | 120 |
| tcaccccgcc gttctcagcg ctgcccgacc ccgctggcgc gcctcccgcc gcagtcccgg | 180 |
| cagcgcctca gttgtcctcc gactcgcccc cggccttcgc gcagcgcagc acagccgcac | 240 |
| gcaccgcagc acagcacagc acagcccagg catagcttcg gcacagcccc ggctccggct | 300 |
| cctgcggcag ctcctctggc acgtccctgc gccgacattc tggaggttgg atgctcttgt | 360 |
| ccaaaatcaa ctcgcttgcc cacctgcgcg ccgcgcccctg caacgacctg cacgccacca | 420 |
| agctggcgcc cggcaaggag aaggagcccc tggagtcgca gtaccaggtg ggcccgctac | 480 |
| tgggcagcgg cggcttcggc tcggtctact caggcatccg cgtctccgac aacttgccgg | 540 |
| tggccatcaa acacgtggag aaggaccgga tttccgactg gggagagctg cctaatggca | 600 |
| ctcgagtgcc catggaagtg gtcctgctga agaaggtgag ctcgggtttc tccggcgtca | 660 |
| ttaggctcct ggactggttc gagaggcccg acagtttcgt cctgatcctg gagaggcccg | 720 |
| agccggtgca agatctcttc gacttcatca cggaaagggg agccctgcaa gaggagctgg | 780 |
| cccgcagctt cttctggcag gtgctggagg ccgtgcggca ctgccacaac tgcggggtgc | 840 |
| tacaccgcga catcaaggac gaaaacatcc ttatcgacct caatcgcggc gagctcaagc | 900 |
| tcatcgactt cgggtcgggg gcgctgctca aggacaccgt ctacacggac ttcgatggga | 960 |
| cccgagtgta tagccctcca gagtggatcc gctaccatcg ctaccatggc aggtcggcgg | 1020 |
| cagtctggtc cctggggatc ctgctgtatg atatggtgtg tggagatatt cctttcgagc | 1080 |
| atgacgaaga gatcatcagg ggccaggttt tcttcaggca gagggtctct tcagaatgtc | 1140 |
| agcatctcat tagatggtgc ttggccctga gaccatcaga taggccaacc ttcgaagaaa | 1200 |
| tccagaacca tccatggatg caagatgttc tcctgcccca ggaaactgct gagatccacc | 1260 |
| tccacagcct gtcgccgggg cccagcaaat agcagccttt ctggcaggtc ctccctctc | 1320 |
| ttgtcagatg cccgagggag gggaagcttc tgtctccagc ttcccgagta ccagtgacac | 1380 |
| gtctcgccaa gcaggacagt gcttgataca ggaacaacat ttacaactca ttccagatcc | 1440 |
| caggcccctg gaggctgcct cccaacagtg gggaagagtg actctccagg ggtcctaggc | 1500 |
| ctcaactcct cccatagata ctctcttctt ctcataggtg tccagcattg ctggactctg | 1560 |

-continued

| | |
|---|---|
| aaatatcccg ggggtgsggg gtggggtgg gcagaaccct gccaatgaa ctctttcttc | 1620 |
| atcatgagtt ctgctgaatg ccgcgatggg tcaggtaggg gggaaacagg ttgggatggg | 1680 |
| ataggactag cacattttaa gtccctgtca cctcttccga ctctttctga gtgccttctg | 1740 |
| tggggactcc ggctgtgctg ggagaaatac ttgaacttgc ctcttttacc tgctgcttct | 1800 |
| ccaaaaatct gcctgggttt tgttccctat ttttctctcc tgtcctccct cacccctcc | 1860 |
| ttcatatgaa aggtgccatg gaagaggcta cagggccaaa cgctgagcca cctgcccttt | 1920 |
| tttctgcctc ctttagtaaa actccgagtg aactggtctt ccttttggt ttttacttaa | 1980 |
| ctgtttcaaa gccaagacct cacacacaca aaaaatgca caaccaagc aatcaacaga | 2040 |
| aaagctgtaa atgtgtgtac agttggcatg gtagtataca aaaagattgt agtggatcta | 2100 |
| atttttaaga aattttgcct ttaagttatt ttacctgttt ttgtttcttg ttttgaaaga | 2160 |
| tgcgcattct aacctggagg tcaatgttat gtatttattt atttatttat ttggttccct | 2220 |
| tcctattcca agcttccata gctgctgccc tagttttctt tcctcctttc ctcctctgac | 2280 |
| ttggggacct tttggggag ggctgcgacg cttgctctgt tgtggggtg acgggactca | 2340 |
| ggcgggacag tgctgcagct ccctggcttc tgtggggccc ctcacctact tacccaggtg | 2400 |
| ggtcccggct ctgtgggtga tgggaggggc cattgctgac tgtgtatata ggataattat | 2460 |
| gaaacacagt tctggatggt gtgccttcca gatcctctct ggggctgtgt tttgagcagc | 2520 |
| aggtagcctg ctggttttat ctgagtgaaa tactgtacag gggaataaaa gagatcttat | 2580 |
| ttttttttta tacttgcgtt tggaataaaa acctttggc ttt | 2623 |

<210> SEQ ID NO 3
<211> LENGTH: 2226
<212> TYPE: DNA
<213> ORGANISM: Homo sapiens

<400> SEQUENCE: 3

| | |
|---|---|
| gaacaatgaa gaaagcccca cagccactgt tgctgagcag ggagaggata ttacctccaa | 60 |
| aaaagacagg ggagtattaa agattgtcaa aagagtgggg aatggtgagg aaacgccgat | 120 |
| gattggagac aaagtttatg tccattacaa aggaaaattg tcaaatggaa agaagtttga | 180 |
| ttccagtcat gatagaaatg aaccatttgt ctttagtctt ggcaaaggcc aagtcatcaa | 240 |
| ggcatgggac attggggtgg ctaccatgaa gaaaggagag atatgccatt tactgtgcaa | 300 |
| accagaatat gcatatggct cggctggcag tctccctaaa attccctcga atgcaactct | 360 |
| ctttttttgag attgagctcc ttgatttcaa aggagaggat ttatttgaag atggaggcat | 420 |
| tatccggaga accaaacgga aaggagaggg atattcaaat ccaaacgaag gagcaacagt | 480 |
| agaaatccac ctggaaggcc gctgtggtgg aaggatgttt gactgcagag atgtggcatt | 540 |
| cactgtgggc gaaggagaag accacgacat tccaattgga attgacaaag ctctggagaa | 600 |
| aatgcagcgg gaagaacaat gtatttata tcttggacca agatatggtt ttggagaggc | 660 |
| agggaagcct aaatttggca ttgaacctaa tgctgagctt atatatgaag ttacacttaa | 720 |
| gagcttcgaa aaggccaaag aatcctggga gatggatacc aaagaaaaat tggagcaggc | 780 |
| tgccattgtc aaagagaagg gaaccgtata cttcaaggga ggcaaataca tgcaggcggt | 840 |
| gattcagtat gggaagatag tgtcctggtt agagatggaa tatggtttat cagaaaagga | 900 |
| atcgaaagct tctgaatcat ttctcccttgc tgcctttctg aacctggcca tgtgctacct | 960 |
| gaagcttaga gaatacacca aagctgttga atgctgtgac aaggcccttg gactggacag | 1020 |
| tgccaatgag aaaggcttgt ataggagggg tgaagcccag ctgctcatga cgagtttga | 1080 |

-continued

| | |
|---|---|
| gtcagccaag ggtgactttg agaaagtgct ggaagtaaac ccccagaata aggctgcaag | 1140 |
| actgcagatc tccatgtgcc agaaaaaggc caaggagcac aacgagcggg accgcaggat | 1200 |
| atacgccaac atgttcaaga gtttgcaga gcaggatgcc aaggaagagg ccaataaagc | 1260 |
| aatgggcaag aagacttcag aagggggtcac taatgaaaaa ggaacagaca gtcaagcaat | 1320 |
| ggaagaagag aaacctgagg gccacgtatg acgccacgcc aaggagggaa gagtcccagt | 1380 |
| gaactcggcc cctcctcaat gggctttccc ccaactcagg acagaacagt gtttaatgta | 1440 |
| aagtttgtta tagtctatgt gattctggaa gcaaatggca aaaccagtag cttcccaaaa | 1500 |
| acagcccccc tgctgctgcc cggagggttc actgaggggt ggcacgggac cactccaggt | 1560 |
| ggaacaaaca gaaatgactg tggtgtggag ggagtgagcc agcagcttaa gtccagctca | 1620 |
| tttcagtttc tatcaacctt caagtatcca attcagggtc cctggagatc atcctaacaa | 1680 |
| tgtggggctg ttaggtttta cctttgaact ttcatagcac tgcagaaacc tttaaaaaaa | 1740 |
| aaatgcttca tgaatttctc ctttcctaca gttgggtagg gtaggggaag gaggataagc | 1800 |
| ttttgttttt taaatgactg aagtgctata aatgtagtct gttgcatttt taaccaacag | 1860 |
| aacccacagt agaggggtct catgtctccc cagttccaca gcagtgtcac agacgtgaaa | 1920 |
| gccagaacct cagaggccac ttgcttgctg acttagcctc ctcccaaagt ccccctcctc | 1980 |
| agccagcctc cttgtgagag tggctttcta ccacacacag cctgtccctg ggggagtaat | 2040 |
| tctgtcattc ctaaaacacc cttcagcaat gataatgagc agatgagagt ttctggatta | 2100 |
| gcttttccta ttttcgatga agttctgaga tactgaaatg tgaaagagc aatcagaatt | 2160 |
| gtgcttttc tcccctcctc tattccttt agggaataat attcaataca cagtacttcc | 2220 |
| tcccag | 2226 |

<210> SEQ ID NO 4
<211> LENGTH: 7515
<212> TYPE: DNA
<213> ORGANISM: Homo sapiens

<400> SEQUENCE: 4

| | |
|---|---|
| atggaggagg tggtgattgc cggcatgttc gggaagctgc cagagtcgga gaacttgcag | 60 |
| gagttctggg acaacctcat cggcggtgtg acatggtca cggacgatga ccgtcgctgg | 120 |
| aaggctgggc tctacggcct gccccggcgg tccggcaagc tgaaggacct gtctaggttt | 180 |
| gatgcctcct tcttcggagt ccaccccaag caggcacaca cgatggaccc tcagctgcgg | 240 |
| ctgctgctgg aagctaccta tgaagccatc gtggacggag gcatcaaccc agattcactc | 300 |
| cgaggaacac acactggcgt ctgggtgggc gtgagcggct ctgagacctc ggaggccctg | 360 |
| agccgagacc ccgagacact cgtgggctac agcatggtgg gctgccagcg agcgatgatg | 420 |
| gccaaccggc tctccttctt cttcgacttc agagggccca gcatcgcact ggacacagcc | 480 |
| tgctcctcca gcctgatggc cctgcagaac gcctaccagg ccatccacag cgggcagtgc | 540 |
| cctgccgcca tcgtgggggg catcaacgtc ctgctgaagc ccaacaccte cgtgcagttc | 600 |
| ttgaggctgg ggatgctcag ccccgagggc acctgcaagg ccttcgacac agcggggaat | 660 |
| gggtactgcc gctcggaggg tgtggtggct gtcctgctga ccaagaagtc cctggcccgg | 720 |
| aaggtctaca ccaccatcct gaacaaaggc accaatacag atggcttcaa ggagcaaggc | 780 |
| gtgaccttcc ctcaggatat ccaggagcag cctatccgct cgttgtacca gtcgccggga | 840 |
| gtggcccctg agtcatttga atacatcgaa gcccacggac caggcaccaa ggtgggcgac | 900 |

```
ccccaggagc gtaatggcat cacccgagcc ctgtgcgcca cccgccagga gccgctgctc    960
atcggctcca ccaagtccaa catggggcac ccggagccag cctcgggct cgacgccctg   1020
gccaaggtgc tgctgtccct ggagcacggg ctctgggccc caacctgca cttccatagc   1080
cccaaccctg agatcccagc gctgttggat gggcggctgc aggtggtgga ccagcccctg   1140
cccgtccgtg gcggcaacgt gggcatcaac tcctttggct cgggggctc caacatgcac   1200
atcatcctga ggcccaacac gcagtccgcc cccgcacccg cccacatgc caccctgccc   1260
cgtctgctgc gggccagcgg acgcacccct gaggccgtgc agaagctgct ggagcagggc   1320
ctccggcaca gccagggcct ggcttttcctg agcatgctga cgacatcgc ggctgtcccc   1380
gccaccgcca tgcccttccg tggctacgct gtgctgggtg gtgagacgcg gtggcccaga   1440
gtgcagcagg tgcccgctgg cgagcgcccg ctctggttca tctgctctgg gatgggcaca   1500
cagtggcgtg gaatggggct gagccttatg cgcctggacc gcttccgaga ttccatccta   1560
cgctccgatg aggctgtgaa ccgattcggc ctgaaggtgt cacagctgct gctgagcaca   1620
gacgagagca cctttgatga catcgtccat tcgtttgtga gcctgactgc catccagata   1680
ggcctcatag acctgctgag ctgcatggga cctgaggcag atggcatcgt cggccactcc   1740
ctgggggagt ggctgtcggt acgcgacggc tgcctgtccc aggaggaggc cgtcctcgct   1800
gcctactgga ggggacagtg catcaaagaa gccccacttc cgccggcgc catggcagcc   1860
gtgggcttgt cctgggagga gtgtaaacag cgctgccccc ctgcggtggt gcccgcctgc   1920
cacaactcca aggacacagt caccatctcg ggacctcagg ccccggtgtt tgagttcgtg   1980
gagcagctga ggaaggaggg tgtgtttgcc aaggaggtgc ggaccggcgg tatggccttc   2040
cactcctact tcatggaggc catcgcaccc ccactgctgc aggagctcaa gaaggtgatc   2100
cgggagccga agccacgttc agcccgctgg ctcagcacct ctatcccga ggcccagtgg   2160
cacagcagcc tggcacgcac gtcttccgcc gagtacaatg tcaacaacct ggtgagccct   2220
gtgctgttcc aggaggccct gtggcacgtg cctgagcacg cggtggtgct ggagatcgcc   2280
ccgacccgt gccctcaggc tgtcctgaag cgggtccgta agccgagctg caccatcatc   2340
ccccgtatga agaaggatca cagggacaac ctggagttct cctggccgg catcggcagg   2400
ctgcacctct caggcatcga cgccaacccc aatgccttgt tcccacctgt ggagtcccca   2460
gctccccgag gaactcccct catctcccca ctcatcaagt gggaccacag cctggcctgg   2520
gacgcgccgg ccgccgagga cttccccaac ggttcaggtt cccctcagc caccatctac   2580
acatgcacac caagctccga gtctcctgac cgctacctgg tggaccacac catcgacggt   2640
cgcgtcctct tccccgccac tggctacctg agcatagtgt ggaagacgct ggcccgcgcc   2700
tgggctgggt ccgagcagct gcctgtggtg tttgaggatg tggtgcagca ccaggccacc   2760
atcctgccca agactgggac agtgtccttg gaggtacggc tcctggaggc caccggtgcc   2820
ttcgaggtgt cagagaacgg caacctggta gtgagtggga aggtgtacca gtgggatgac   2880
cctgacccca ggctcttcga ccacccggaa agtccccacc ccaattcccc acggagtccc   2940
ctcttcctgg cccaggcaga agtttacaag gagctgcgtc tgcgtggcta cgactacggc   3000
cctcatttcc agggcatcct ggaggccagc ctggaaggtg actcggggag gctgctgtgg   3060
aaggataact gggtgagctt catggacacc atgctgcaga tgtccatcct gggctcggcc   3120
aagcacggcc tgtacctacc cacccgtgtc accgccatcc acatcgaccc tgccacccac   3180
aggcagaagc tgtacacact gcaggacaag gcccaagtgg ctgacgtggt ggtgagcagg   3240
tggccgaggg tcacagtggc gggaggcgtc cacatctccg ggctccacac tgagtcggcc   3300
```

```
ccgcggcggc acgaggagca gcaggtgccc atcctggaga agttttgctt cactccccac   3360
acggaggagg ggtgcctgtc tgagcacgct gccctcgagg aggagctgca actgtgcaag   3420
gggctggtcg aggcactcga gaccaaggtg acccagcagg gctgaagat ggtggtgccg    3480
gactggacgg ggcccagatc ccccgggac ccctcacagc aggaactgcc ccggctgttg    3540
tcggctgcct gcaggcttca gctcaacggg aacctgcagc tggagctggc gcaggtgctg   3600
gcccaggaga ggcccaagct gccagaggac cctctgctca gcggcctcct ggactccccg   3660
gcactcaagg cctgcctgga cactgccgtg gagaacatgc ccagcctgaa gatgaaggtg   3720
gtggaggtgc tggccggcca cggtcacctg tattcccgca tcccaggcct gctcagcccc   3780
catcccctgc tgcagctgag ctacacggcc accgaccgcc accccaggc cctggaggct    3840
gcccaggccg agctgcagca gcgacgtt gcccagggcc agtgggatcc cgcagaccct    3900
gcccccagcg ccctgggcag cgcggacctc ctggtgtgca actgtgctgt ggctgccctc   3960
ggggacccgg cctcagctct cagcaacatg gtggctgccc tgagagaagg gggctttctg   4020
ctcctgcaca cactgctccg ggggcaccct cgggacatcg tggccttcct cacctccact   4080
gagccgcagt atggccaggg catcctgagc caggacgcgt gggagagcct cttctccagg   4140
gtgtcgctgc gcctggtggg cctgaagaag tccttctacg cgccacgct cttcctgtgc    4200
cgccggccca ccccgcagga cagccccatc ttcctgccgg tggacgatac cagcttccgc   4260
tgggtggagt ctctgaaggg catcctggct gacgaagact cttcccggcc tgtgtggctg   4320
aaggccatca actgtgccac ctcgggcgtg gtgggcttgg tgaactgtct ccgccgagag   4380
cccggcggaa ccgtccggtg tgtgctgctc tccaacctca gcagcacctc ccacgtcccg   4440
gaggtggacc cgggctccgc agaactgcag aaggtgttgc agggagacct ggtgatgaac   4500
gtctaccgcg acggggcctg gggggttttc cgccacttcc tgctggagga caagcctgag   4560
gagccgacgc acatgccctt tgtgagcacc ctcacccggg ggaccctgtc ctccatccgc   4620
tgggtctgct cctcgctgcg ccatgcccag cccacctgcc ctggcgccca gctctgcacg   4680
gtctactacg cctccctcaa cttccgcgac atcatgctgg ccactggcaa gctgtccct    4740
gatgccatcc cagggaagtg gacctcccag gacagcctgc taggtatgga gttctcgggc   4800
cgagacgcca gcgcaagcg tgtgatggga ctggtgcctg ccaagggcct ggccacctct   4860
gtcctgctgt caccggactt cctctgggat gtgccttcca actggacgct ggaggaggcg   4920
gcctcggtgc ctgtcgtcta cagcacggcc tactacgcgc tggtggtgcg tgggcgggtg   4980
cgccccgggg agacgctgct catccactcg ggctcgggcg gcgtgggcca ggccgccatc   5040
gccatcgccc tcagtctggg ctgccgcgtc ttcaccaccg tggggtcggc tgagaagcgg   5100
gcgtacctcc aggccaggtt ccccagctc gacagcacca gcttcgccaa ctccgggac    5160
acatccttcg agcagcatgt gctgtggcac acgggcggga agggcgttga cctggtcttg   5220
aactccttgg cggaagagaa gctgcaggcc agcgtgaggt gcttcggtac gcacggtcgc   5280
ttcctggaaa ttggcaaatt cgaccttct cagaaccacc cgctcggcat ggctatcttc    5340
ctgaagaacg tgacattcca cgggtccta ctggatgcgt tcttcaacga gagcagtgct    5400
gactggcggg aggtgtgggc gcttgtcgag gccgccatcc gggatgggt ggtacgcgcc    5460
ctcaagtgca cggtgttcca tggggcccag gtggaggacg ccttccgcta catggcccaa   5520
gggaagcaca ttggcaaagt cgtcgtgcag gtgcttgcgg aggagccggc agtgctgaag   5580
gggccaaac ccaagctgat gtcggccatc tccaagacct tctgcccggc ccacaagagc   5640
```

```
tacatcatcg ctggtggtct gggtggcttc ggcctggagt tggcgcagtg gctgatacag    5700
cgtggggtgc agaagctcgt gttgacttct cgctccggga tccggacagg ctaccaggcc    5760
aagcaggtcc gccggtggag gcgccagggg ctacaggtgc aggtgtccac cagcaacatc    5820
agctcactgg aggggggccg gggcctcatt gccgaggcgg cgcagcttgg gcccgtgggg    5880
ggcgtcttca acctgccgt ggtcttgaga gatggcttgc tggagaacca gaccccagag    5940
ttcttccagg acgtctgcaa gcccaagtac agcggcaccc tgaacctgga cagggtgacc    6000
cgagaggcgt gccctgagct ggactacttt gtggtcttct cctctgtgag ctgcgggcgt    6060
ggcaatgcgg gacagagcaa ctacggcttt gccaattccg ccatggagcg tatctgtgag    6120
aaacgccggc acgaaggcct cccaggcctg gccgtgcagt ggggcgccat cggcaccgtg    6180
ggcattttgg tggagacgat gagcaccaac gacacgatcg tcagtggcac gctgcccacg    6240
cgcattggcg tccttggcct ggaggtgctg gacctcttcc tgaaccagcc ccacatggtc    6300
ctgagcagct ttgtgctggc tgagaaggct gcggcctata gggacaggga cagccagcgg    6360
gacctggtgg aggccgtggc acacatcctg ggcatccgcg acttggctgc tgtcaacctg    6420
ggcggctcac tggcggacct gggcctggac tcgctcatga gcgcgccggt gcgccagacg    6480
ctggagcgtg agctcaacct ggtgctgtcc gtgcgcgagg tgcggcaact cacgctccgg    6540
aaactgcagg agctgtcctc aaaggcggat gaagccagcg agctggcatg ccccacgccc    6600
aaggaggatg gtctggccca gcagcagact cagctgaacc tgcgctccct gctggtgaaa    6660
ccggagggcc ccaccctgat gcggctcaac tccgtgcaga gctcggagcg gccccctgttc    6720 ctggtgcacc caatcgaggc taccaccgtg ttccacagcc tcggtcccgg tctcagcatc    6780
cccacctatg gcctgcagtg caccccggct gcgcccccttg acagcatcca cagcctggct    6840
gcctactaca tcgactgcat caggcaggtg cagcccgagg gccctaccg cgtggccggc    6900 tactcctacg gggcctgcgt ggcctttgaa atgtgctccc agctgcaggc ccagcagagc    6960 ccagcccca cccacaacag cctcttcctg ttcgacggct cgcccaccta cgtactggcc    7020
tacacccaga gctaccgggc aaagctgacc ccaggctgta aggctgaggc tgagacggag    7080
gccatatgct tcttcgtgca gcagttcacg gacatggagc acaacagggt gctggaggcg    7140
ctgctgccgc tgaagggcct agaggagcgt gtggcagccg ccgtggacct gatcatcaag    7200
agccaccagg gcctggaccg ccaggagctg agctttgcgg cccggtcctt ctactacagg    7260
ctgcgtgccg ctgaccagta tacacccaag gccaagtaca gtggcaacgt gatgctactg    7320
cgggccaaga cgggtggccg ctacggcgag gacctgggcg cggactacaa cctctcccag    7380
gtatgcgacg ggaaagtatc cgtccatatc atcgagggtg accaccgcac gctgctggag    7440
ggcagcggcc tggagtccat catcagcatc atccacagct ccctggctga gccacgtgtg    7500
agtcgggagg gctag    7515
```

<210> SEQ ID NO 5
<211> LENGTH: 2653
<212> TYPE: DNA
<213> ORGANISM: Homo sapiens

<400> SEQUENCE: 5

```
ctcaaaaggg gccggatttc cttctcctgg aggcagatgt tgcctctctc tctcgctcgg      60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
```

-continued

```
gccggctctg ctcgcgccga gatgtggaat ctccttcacg aaaccgactc ggctgtggcc      300
accgcgcgcc gcccgcgctg gctgtgcgct ggggcgctgg tgctggcggg tggcttcttt      360
ctcctcggct tcctcttcgg gtggtttata aaatcctcca atgaagctac taacattact      420
ccaaagcata atatgaaagc attttggat gaattgaaag ctgagaacat caagaagttc       480
ttatataatt ttacacagat accacattta gcaggaacag aacaaaactt tcagcttgca      540
aagcaaattc aatcccagtg gaaagaattt ggcctggatt ctgttgagct agcacattat      600
gatgtcctgt tgtcctaccc aaataagact catcccaact acatctcaat aattaatgaa      660
gatggaaatg agattttcaa cacatcatta tttgaaccac ctcctccagg atatgaaaat      720
gtttcggata ttgtaccacc tttcagtgct ttctctcctc aaggaatgcc agagggcgat      780
ctagtgtatg ttaactatgc acgaactgaa gacttcttta aattggaacg ggacatgaaa      840
atcaattgct ctgggaaaat tgtaattgcc agatatggga agttttcag aggaaataag       900 gttaaaaatg cccagctggc aggggccaaa ggagtcattc tctactccga ccctgctgac      960
tactttgctc ctggggtgaa gtcctatcca gatggttgga atcttcctgg aggtggtgtc     1020
cagcgtggaa atatcctaaa tctgaatggt gcaggagacc ctctcacacc aggttaccca     1080
gcaaatgaat atgcttatag gcgtggaatt gcagaggctg ttggtcttcc aagtattcct     1140
gttcatccaa ttggatacta tgatgcacag aagctcctag aaaaaatggg tggctcagca     1200
ccaccagata gcagctggag aggaagtctc aaagtgccct acaatgttgg acctggcttt     1260
actgaaaact tttctacaca aaaagtcaag atgcacatcc actctaccaa tgaagtgaca     1320
agaatttaca atgtgatagg tactctcaga ggagcagtgg aaccagacag atatgtcatt     1380
ctgggaggtc accgggactc atgggtgttt ggtggtattg accctcagag tggagcagct     1440
gttgttcatg aaattgtgag gagctttgga acactgaaaa aggaagggtg gagacctaga     1500
agaacaattt tgtttgcaag ctgggatgca gaagaatttg gtcttcttgg ttctactgag     1560
tgggcagagg agaattcaag actccttcaa gagcgtggcg tggcttatat taatgctgac     1620
tcatctatag aaggaaacta cactctgaga gttgattgta caccgctgat gtacagcttg     1680
gtacacaacc taacaaaaga gctgaaaagc cctgatgaag gctttgaagg caaatctctt     1740
tatgaaagtt ggactaaaaa aagtccttcc ccagagttca gtggcatgcc caggataagc     1800
aaattgggat ctggaaatga ttttgaggtg ttcttccaac gacttggaat tgcttcaggc     1860
agagcacggt atactaaaaa ttgggaaaca aacaaattca gcggctatcc actgtatcac     1920
agtgtctatg aaacatatga gttggtggaa aagttttatg atccaatgtt taaatatcac     1980
ctcactgtgg cccaggttcg aggagggatg tgtttgagc tagccaattc catagtgctc     2040
ccttttgatt gtcgagatta tgctgtagtt ttaagaaagt atgctgacaa aatctacagt     2100
atttctatga acatccaca ggaaatgaag acatacagtg tatcatttga ttcacttttt     2160
tctgcagtaa agaattttac agaaattgct tccaagttca gtgagagact ccaggacttt     2220
gacaaaagca acccaatagt attaagaatg atgaatgatc aactcatgtt tctggaaaga     2280
gcatttattg atccattagg gttaccagac aggcctttt ataggcatgt catctatgct      2340
ccaagcagcc acaacaagta tgcaggggag tcattcccag gaatttatga tgctctgttt     2400
gatattgaaa gcaaagtgga cccttccaag gcctggggag aagtgaagag acagatttat     2460
gttgcagcct tcacagtgca ggcagctgca gagactttga gtgaagtagc ctaagaggat     2520
tctttagaga atccgtattg aatttgtgtg gtatgtcact cagaaagaat cgtaatgggt     2580
```

-continued

| | |
|---|---|
| atattgataa attttaaaat tggtatattt gaaataaagt tgaatattat atataaaaaa | 2640 |
| aaaaaaaaaa aaa | 2653 |

<210> SEQ ID NO 6
<211> LENGTH: 1750
<212> TYPE: DNA
<213> ORGANISM: Homo sapiens

<400> SEQUENCE: 6

| | |
|---|---|
| cctcactgac tataaaagaa tagagaagga agggcttcag tgaccggctg cctggctgac | 60 |
| ttacagcagt cagactctga caggatcatg gctatgatgg aggtccaggg gggacccagc | 120 |
| ctgggacaga cctgcgtgct gatcgtgatc ttcacagtgc tcctgcagtc tctctgtgtg | 180 |
| gctgtaactt acgtgtactt taccaacgag ctgaagcaga tgcaggacaa gtactccaaa | 240 |
| agtggcattg cttgtttctt aaaagaagat gacagttatt gggaccccaa tgacgaagag | 300 |
| agtatgaaca gccctgctg gcaagtcaag tggcaactcc gtcagctcgt tagaaagatg | 360 |
| attttgagaa cctctgagga aaccatttct acagttcaag aaaagcaaca aaatatttct | 420 |
| cccctagtga gagaaagagg tcctcagaga gtagcagctc acataactgg gaccagagga | 480 |
| agaagcaaca cattgtcttc tccaaactcc aagaatgaaa aggctctggg ccgcaaaata | 540 |
| aactcctggg aatcatcaag gagtgggcat tcattcctga gcaacttgca cttgaggaat | 600 |
| ggtgaactgg tcatccatga aaagggtttt actacatct attcccaaac atactttcga | 660 |
| tttcaggagg aaataaaaga aaacacaaag aacgacaaac aaatggtcca atatatttac | 720 |
| aaatacacaa gttatcctga ccctatattg ttgatgaaaa gtgctagaaa tagttgttgg | 780 |
| tctaaagatg cagaatatgg actctattcc atctatcaag ggggaatatt tgagcttaag | 840 |
| gaaaatgaca gaatttttgt ttctgtaaca aatgagcact tgatagacat ggaccatgaa | 900 |
| gccagttttt ttggggcctt tttagttggc taactgacct ggaaagaaaa agcaataacc | 960 |
| tcaaagtgac tattcagttt tcaggatgat acactatgaa gatgtttcaa aaaatctgac | 1020 |
| caaaacaaac aaacagaaaa cagaaaacaa aaaaacctct atgcaatctg agtagagcag | 1080 |
| ccacaaccaa aaaattctac aacacacact gttctgaaag tgactcactt atcccaagag | 1140 |
| aatgaaattg ctgaaagatc tttcaggact ctacctcata tcagtttgct agcagaaatc | 1200 |
| tagaagactg tcagcttcca aacattaatg caatggttaa catcttctgt ctttataatc | 1260 |
| tactccttgt aaagactgta gaagaaagag caacaatcca tctctcaagt agtgtatcac | 1320 |
| agtagtagcc tccaggtttc cttaagggac aacatcctta agtcaaaaga gagaagaggc | 1380 |
| accactaaaa gatcgcagtt tgcctggtgc agtggctcac acctgtaatc ccaacatttt | 1440 |
| gggaacccaa ggtgggtaga tcacgagatc aagagatcaa gaccatagtg accaacatag | 1500 |
| tgaaacccca tctctactga aagtacaaaa attagctggg tgtgttggca catgcctgta | 1560 |
| gtcccagcta cttgagaggc tgaggcaaga gaattgtttg aacccgggag gcagaggttg | 1620 |
| cagtgtggtg agatcatgcc actacactcc agcctggcga cagagcgaga cttggtttca | 1680 |
| aaaaaaaaaa aaaaaaaaac ttcagtaagt acgtgttatt tttttcaata aaattctatt | 1740 |
| acagtatgtc | 1750 |

<210> SEQ ID NO 7
<211> LENGTH: 6597
<212> TYPE: DNA
<213> ORGANISM: Homo sapiens

<400> SEQUENCE: 7

-continued

```
ggtcacatga ctccagtcta gctcgcattg cggctcccgc ccgggcgagt tctcgccccc      60
gcgcggccgt tgccgaggag acggcgcatg tcccgccgcg cgttgccccc tctgcagtac     120
ccccgcccct cttctcccac cacaatgaga tcctaagatg gcggtggctg cggcggttgg     180
cgctgcgtag ctgaggtcga aaaggcggcc actggggccg aggcagccag gaaacgtgtg     240
ggcctctctg ctgcggtctc cgagggccga ccgctgccgg cggcgggtcg tggggggctga    300
ctgtcgctct gcctttgaca ggagaggctg cttcttgtag aggaaacagc tttgaagtgt     360
ggagcgggaa aggagcagtt tctgagctgc aaaaactagt ttctaaacag agagttaatt    420
gttaaatcca gtatggccac aggaggaggt ccctttgaag atggcatgaa tgatcaggat    480
ttaccaaact ggagtaatga gaatgttgat gacaggctca acaatatgga ttggggtgcc    540
caacagaaga aagcaaatag atcatcagaa aagaataaga aaaagtttgg tgtagaaagt    600
gataaaagag taaccaatga tatttctccg gagtcgtcac caggagttgg aaggcgaaga    660
acaaagactc cacatacgtt cccacacagt agatacatga gtcagatgtc tgtcccagag    720
caggcagaat tagagaaact gaaacagcgg ataaacttca gtgatttaga tcagagaagc    780
attggaagtg attcccaagg tagagcaaca gctgctaaca caaacgtca gcttagtgaa     840
aaccgaaagc ccttcaactt tttgcctatg cagattaata ctaacaagag caaagatgca    900
tctacaagtc ccccaaacag agaaacgatt ggatcagcac agtgtaaaga gttgtttgct    960
tctgctttaa gtaatgacct cttgcaaaac tgtcaggtgt ctgaagaaga tgggagggga   1020
gaacctgcaa tggagagcag ccagattgta agcaggcttg ttcaaattcg cgattatatt   1080
actaaagcta gttccatgcg ggaagatctt gtagagaaaa atgagagatc tgctaatgtt   1140
gagcgcctta ctcatctaat agatcacctt aaagaacaag agaagtcata tatgaaattt   1200
cttaaaaaaa tccttgccag agatcctcag caggagccta tggaagagat agaaaatttg   1260
aagaaacaac atgatttatt aaaagaatg ttacaacagc aggagcaact aagagctcta   1320
cagggacggc aggctgcact tctagctctg caacataaag cagagcaagc tattgcagtg   1380
atggatgatt ctgttgttgc agaaactgca ggtagcttat ctggcgtcag tatcacatct   1440
gaactaaatg aagaattgaa tgacttaatt cagcgttttc ataatcagct tcgtgattct   1500
cagcctccag ctgttccaga caatagaaga caggcagaaa gtctttcatt aactagggag   1560
gtttcccaga gcaggaaacc atcagcttca gaacgtttac ctgatgagaa agtcgaactt   1620
tttagcaaaa tgagagtgct acaggaaaag aaacaaaaaa tggacaaatt gcttggagaa   1680
cttcatacac ttcgagatca gcatcttaac aattcatcat cctctccaca aaggagtgtc   1740
gatcagagaa gtacttcagc tccctctgct tctgtaggct tggcaccggt tgtcaatgga   1800
gaatccaata gcctcacatc atctgttcct tatcctactg cttctctagt atctcagaat   1860
gagagtgaaa acgaaggcca cctcaatcca tctgaaaaac tccagaagtt aaatgaagtt   1920
cgaaagagat tgaatgagct aagagaatta gttcattatt atgaacaaac gtcagacatg   1980
atgacagatg ctgtgaatga aacaggaaa gatgaagaaa ctgaagagtc agaatatgat   2040
tctgagcatg aaaattccga gcctgttact aacattcgaa atccacaagt agcttccact   2100
tggaatgaag taaatagtca tagtaatgca cagtgtgttt ctaataatag atgggcga    2160
acagttaatt ctaattgtga aattaacaac agatctgctg ccaacataag ggctctaaac   2220
gtgcctcctt ctttagattg tcgatataat agagaagggg aacaggagat tcatgttgca   2280
caaggtgaag atgatgagga ggaggaggaa gaagcagaag aggagggagt cagtggagct   2340
```

```
tcattatcta gtcacaggag cagtctggtt gatgagcatc cagaagatgc tgaatttgaa    2400
cagaagatca accgacttat ggctgcaaaa cagaaactta gacagttaca agatcttgtt    2460
gctatggtac aggatgatga tgcagctcaa ggagttatct ctgccagtgc atcaaatttg    2520
gatgatttct acccagcaga agaagacacc aagcaaaatt caaataacac tagaggaaat    2580
gccaataaaa cacagaaaga tactggagta atgaaaagg caagagagaa attttatgag     2640
gctaaactac agcagcaaca gagagagcta aaacaattgc aggaagaaag aaagaaactg    2700
attgacattc aggagaaaat tcaagcattg caaacggcat gccctgactt acagctgtca    2760
gctgctagtg tgggtaactg tcccaccaaa aaatatatgc cagctgttac ttcaaccccA    2820
actgttaatc aacacgagac cagtacaagc aaatctgttt ttgagcctga agattcttca    2880
atagtagata atgagttgtg gtcagaaatg agaagacatg aaatgttgag ggaggagctg    2940
cgacagagaa gaaagcagct tgaagctctg atggctgaac atcagaggag gcaaggtcta    3000
gctgaaactg catctccagt ggctgtgtca ttgagaagtg atggatctga gaacctatgt    3060
actcctcagc aaagtagaac agaaaaaacg atggcaactt ggggagggtc tacccagtgt    3120
gcactagatg aagaaggaga tgaagacggt tacctttctg aaggaattgt tcggacagat    3180
gaagaggagg aagaagagca agatgccagt tccaatgata acttttctgt gtgtccttct    3240
racagtgtga atcataactc ctacaatgga aaggaaacta aaaataggtg gaagaacaat    3300
tgcccttttt cggcagatga aaattatcgt cctttagcca agacaaggca acagaatatc    3360
agcatgcaac ggcaagaaaa ccttcgttgg gtgtcagagc tctcttacgt agaagagaaa    3420
gaacaatggc aagaacaaat caatcagcta agaaacagc ttgattttag tgtcagtatt     3480
tgtcagactt tgatgcaaga ccagcagact ctatcttgtc tgctacaaac tcttctcacg    3540
ggtccttaca gtgttatgcc cagcaatgtt gcatctcctc aagtacactt cataatgcac    3600
cagttgaacc agtgctatac tcagctaaca tggcaacaga ataatgttca gaggttgaaa    3660
caaatgctaa atgaacttat gcgccagcaa aatcagcatc cagaaaaacc tggaggcaag    3720
gaaagaggca gtagtgcatc gcaccctcct tctcccagtt tattttgtcc tttcagctTT    3780
ccaacacagc ctgtaaatct cttcaatata cctggattta ctaacttttc atcatttgca    3840
ccaggtatga atttcagccc ttatttcct tctaattttg gagattttc tcagaatatc      3900 tctacaccca gtgaacagca gcaacccta gcccagaatt cttcaggaaa aacagaatat    3960
atggcttttc caaaaccttt tgaaagcagt tcctctattg gagcagagaa accaaggaat    4020
aaaaaactgc ctgaagagga ggtggaaagc agtaggacac catggttata tgaacaagaa    4080
ggtgaagtag agaaaccatt tatcaagact ggattttcag tgtctgtaga aaaatctaca    4140
agtagtaacc gcaaaaatca attagataca aacggaagaa gacgccagtt tgatgaagaa    4200
tcactggaaa gctttagcag tatgcctgat ccagtagatc caacaacagt gactaaaaca    4260
ttcaagacaa gaaaagcgtc tgcacaggcc agcctggcat ctaaagataa aactcccaag    4320
tcaaaaagta agaagaggaa ttctactcag ctgaaaagca gagttaaaaa catcaggtat    4380
gaaagtgcca gtatgtctag cacatgtgaa ccttgcaaaa gtaggaacag acattcagcc    4440
cagactgaag agcctgttca agcaaaagta ttcagcagaa agaatcatga gcaactggaa    4500
aaaataataa atgtaatag gtctacgaaa atatcttcag aaactgggag tgattttcc     4560 atgtttgaag ctttgcgaga tactattat tctgaagtag ctacattaat ttctcaaaat    4620
gaatctcgtc cacattttct tattgaactc ttccatgagc tgcagctact aaacacagac    4680
tacttgagac agagggcttt atatgcattg caggacatag tatccagaca tatttctgag    4740
```

| | |
|---|---|
| agccatgaaa aaggagaaaa tgtaaagtca gtaaactctg gtacttggat agcatcaaac | 4800 |
| tcagaactta ctcctagtga gagccttgct actactgatg atgaaacttt tgagaagaac | 4860 |
| tttgaaagag aaacccataa aataagtgag caaaatgatg ctgataatgc tagtgtcctg | 4920 |
| tctgtatcat caaattttga gccttttgca acagatgatc taggtaacac cgtgattcac | 4980 |
| ttagatcaag cattagccag aatgagagaa tatgagcgta tgaagactga ggctgaaagt | 5040 |
| aactcaaata tgagatgcat ctgcaggatt attgaggatg gagatggtgc tggtgcaggt | 5100 |
| actacagtta ataatttaga agaaactccc gttattgaaa atcgtagttc acaacaacct | 5160 |
| gtaagtgaag tttctaccat cccatgtcct agaattgata ctcagcagct ggaccggcaa | 5220 |
| attaaagcaa ttatgaaaga agtcattcct tttttgaagg agcacatgga tgaagtatgc | 5280 |
| tcctcgcagc ttctaacttc agtaaggcgc atggttttga cccttaccca gcaaaatgat | 5340 |
| gagagcaaag agtttgtaaa gttctttcat aaacaacttg gaagtatatt acaggattca | 5400 |
| ctggcaaaat ttgctggcag aaaactgaaa gactgtggag aagatcttct tgtagagata | 5460 |
| tctgaagtgt tgttcaatga attggctttc tttaagctta tgcaagattt ggataataat | 5520 |
| agtataactg ttaaacagag atgcaaaagg aaaatagaag caactggagt gatacaatct | 5580 |
| tgtgccaaag agctaaaagg attcttgaag atcatggctc acctgctgga gagattgatg | 5640 |
| atgaagacaa agacaaggat gaaactgaaa cagttaagca gactcaaaca tctgaggtgt | 5700 |
| atgatggtcc caaaaatgta agatctgata tttctgatca agaggaagat gaagaaagtg | 5760 |
| aaggatgtcc agtgtctatt aatttgtcta agctgaaac tcaggcttta actaattatg | 5820 |
| gaagtggaga agatgaaaat gaggatgaag aaatggaaga atttgaagaa ggccctgtgg | 5880 |
| atgtccagac ttccctccag gctaacactg aagctactga agaaaatgaa catgatgaac | 5940 |
| aggtcctaca acgtgacttt aaaaagacag cagaaagcaa aaatgtccca ttggaacgag | 6000 |
| aagccactag taaaaatgac caaaataact gtcctgtgaa accctgttac ctcaatatct | 6060 |
| tggaagatga gcaacctttaa atagtgctg cccataagga gtcacctcct actgttgatt | 6120 |
| caactcaaca gcctaaccct tgccgttac gtttacctga atggaaccc ttagtgccta | 6180 |
| gagtcaaaga agttaaatct gctcaggaaa ctcctgaaag ctctctggct ggaagtcctg | 6240 |
| atactgaatc tccagtgtta gtgaatgact atgaagcaga atctggtaat ataagtcaaa | 6300 |
| agtctgatga agaagatttt gtaaaagttg aagatttacc actgaaactg acaatatatt | 6360 |
| cagaggcaga tctaagaaag aaaatggtag aagaagaaca gaaaaaccat ttatctggtg | 6420 |
| aaatatgtga aatgcagacc gaagaattag ctggaaattc tgagacacta aaagaacctg | 6480 |
| aaacggtggg agcccagagt atatgagatg tcttcagagg ctcatctaac tctgtcctta | 6540 |
| catactcaat gcatatatga aaacaatact aaataaacat ctgatctgta taaaaat | 6597 |

<210> SEQ ID NO 8
<211> LENGTH: 479
<212> TYPE: DNA
<213> ORGANISM: Homo sapiens

<400> SEQUENCE: 8

| | |
|---|---|
| ctccaaaggc aaaatctcc agccctacag agactgagcg gtgcatcgag tccctgattg | 60 |
| ctgtcttcca gaagtatgct ggaaaggatg gttataacta cactctctcc aagacagagt | 120 |
| tcgtaagctt catgaataca gaactagctg ccttcacaaa gaaccagaag gaccctggtg | 180 |
| tccttgaccg catgatgaag aaactggaca ccaacagtga tggtcagcta gatttctcag | 240 |

```
aatttcttaa tctgattggt ggcctagcta tggcttgcca tgactccttc ctcaaggctg    300
tcccttccca gaagcggacc tgaggacccc ttggccctgg ccttcaaacc cacccccttt    360
ccttccagcc tttctgtcat catctccaca gcccacccat ccctgagca cactaaccac     420 ctcatgcagg ccccacctgc caatagtaat aaagcaatgt cacttttta aaacatgaa     479

<210> SEQ ID NO 9
<211> LENGTH: 2465
<212> TYPE: DNA
<213> ORGANISM: Homo sapiens

<400> SEQUENCE: 9
gccgcttcct gcctggattc cacagcttcg cgccgtgtac tgtcgcccca tccctgcgcg     60
cccagcctgc caagcagcgt gccccggttg caggcgtcat gcagcgggcg cgacccacgc    120
tctgggccgc tgcgctgact ctgctggtgc tgctccgcgg gccgccggtg gcgcgggctg    180
gcgcgagctc ggcgggcttg gtcccgtgg tgcgctgcga gccgtgcgac gcgcgtgcac     240
tggcccagtg cgcgcctccg cccgccgtgt gcgcggagct ggtgcgcgag ccgggctgcg    300
gctgctgcct gacgtgcgca ctgagcgagg ccagccgtg cggcatctac accgagcgct     360
gtggctccgg ccttcgctgc cagccgtcgc ccgacgaggc gcgaccgctg caggcgctgc    420
tggacggccg cgggctctgc gtcaacgcta gtgccgtcag ccgcctgcgc gcctacctgc    480
tgccagcgcc gccagctcca ggaaatgcta gtgagtcgga ggaagaccgc agcgccggca    540
gtgtggagag cccgtccgtc tccagcacgc accgggtgtc tgatcccaag ttccaccccc    600
tccattcaaa gataatcatc atcaagaaag gcatgctaa agacagccag cgctacaaag    660
ttgactacga gtctcagagc acagatacc agaacttctc ctccgagtcc aagcgggaga    720
cagaatatgg tccctgccgt agagaaatgg aagacacact gaatcacctg aagttcctca    780
atgtgctgag tccagggggt gtacacattc caactgtga caagaaggga ttttataaga    840
aaaagcagtg tcgcccttcc aaaggcagga agcggggctt ctgctggtgt gtggataagt    900
atgggcagcc tctcccaggc tacaccacca aggggaagga ggacgtgcac tgctacagca    960
tgcagagcaa gtagacgcct gccgcaaggt taatgtggag ctcaaatatg ccttattttg   1020
cacaaaagac tgccaaggac atgaccagca gctggctaca gcctcgattt atatttctgt   1080
ttgtggtgaa ctgatttttt ttaaaccaaa gtttagaaag aggttttga aatgcctatg    1140 gtttctttga atggtaaact tgagcatctt ttcactttcc agtagtcagc aaagagcagt   1200
ttgaattttc ttgtcgcttc ctatcaaaat attcagagac tcgagcacag cacccagact   1260
tcatgcgccc gtggaatgct caccacatgt tggtcgaagc ggccgaccac tgactttgtg   1320
acttaggcgg ctgtgttgcc tatgtagaga acacgcttca cccccactcc ccgtacagtg   1380
cgcacaggct ttatcgagaa taggaaaacc tttaaacccc ggtcatccgg acatcccaac   1440
gcatgctcct ggagctcaca gccttctgtg gtgtcatttc tgaaacaagg gcgtggatcc   1500
ctcaaccaag aagaatgttt atgtcttcaa gtgacctgta ctgcttgggg actattggag   1560
aaaataaggt ggagtcctac ttgtttaaaa aatatgtatc taagaatgtt ctagggcact   1620
ctgggaacct ataaaggcag gtatttcggg ccctcctctt caggaatctt cctgaagaca   1680
tggcccagtc gaaggcccag gatggctttt gctgcgccc cgtggggtag gagggacaga   1740
gagacaggga gagtcagcct ccacattcag aggcatcaca agtaatggca caattcttcg   1800
gatgactgca gaaaatagtg ttttgtagtt caacaactca agacgaagct tatttctgag   1860
gataagctct ttaaaggcaa agctttattt tcatctctca tcttttgtcc tccttagcac   1920
```

```
aatgtaaaaa agaatagtaa tatcagaaca ggaaggagga atggcttgct ggggagccca    1980
tccaggacac tgggagcaca tagagattca cccatgtttg ttgaacttag agtcattctc    2040
atgcttttct ttataattca cacatatatg cagagaagat atgttcttgt taacattgta    2100
tacaacatag ccccaaatat agtaagatct atactagata atcctagatg aaatgttaga    2160
gatgctattt gatacaactg tggccatgac tgaggaaagg agctcacgcc cagagactgg    2220
gctgctctcc cggaggccaa acccaagaag gtctggcaaa gtcaggctca gggagactct    2280
gccctgctgc agacctcggt gtggacacac gctgcataga gctctccttg aaaacagagg    2340
ggtctcaaga cattctgcct acctattagc ttttctttat ttttttaact ttttggggg    2400 aaaagtattt ttgagaagtt tgtcttgcaa tgtatttata aatagtaaat aaagttttta    2460
ccatt                                                                2465
```

<210> SEQ ID NO 10
<211> LENGTH: 807
<212> TYPE: DNA
<213> ORGANISM: Homo sapiens

<400> SEQUENCE: 10

```
atgccgcgct ccttcctggt caagaagcat ttcaacgcct ccaaaaagcc aaactacagc      60
gaactggaca cacatacagt gattatttcc ccgtatctct atgagagtta ctccatgcct     120
gtcataccac aaccagagat cctcagctca ggagcataca gccccatcac tgtgtggact     180
accgctgctc cattccacgc ccagctaccc aatggcctct ctcctctttc cggatactcc     240
tcatctttgg ggcgagtgag tccccctcct ccatctgaca cctcctccaa ggaccacagt     300
ggctcagaaa gccccattag tgatgaagag gaaagactac agtccaagct ttcagacccc     360
catgccattg aagctgaaaa gtttcagtgc aatttatgca ataagaccta ttcaactttt     420
tctgggctgg ccaaacataa gcagctgcac tgcgatgccc agtctagaaa atctttcagc     480
tgtaaatact gtgacaagga atatgtgagc ctgggcgccc tgaagatgca tattcggacc     540
cacacattac cttgtgtttg caagatctgc ggcaaggcgt tttccagacc ctggttgctt     600
caaggacaca ttagaactca cacgggggag aagcctttt cttgccctca ctgcaacaga     660
gcatttgcag acaggtcaaa tctgagggct catctgcaga cccattctga tgtaaagaaa     720
taccagtgca aaaactgctc caaaaccttc tccagaatgt ctctcctgca caaacatgag     780
gaatctggct gctgtgtagc acactga                                        807
```

<210> SEQ ID NO 11
<211> LENGTH: 1266
<212> TYPE: DNA
<213> ORGANISM: Homo sapiens

<400> SEQUENCE: 11

```
ctcggaagcc cgtcaccatg tcgtgcgagt cgtctatggt tctcgggtac tgggatattc      60
gtgggctggc gcacgccatc cgcctgctcc tggagttcac ggatacctct tatgaggaga    120
aacggtacac gtgcggggaa gctcctgact atgatcgaag ccaatggctg gatgtgaaat    180
tcaagctaga cctggacttt cctaatctgc cctacctcct ggatgggaag aacaagatca    240
cccagagcaa tgccatcttg cgctacatcg ctcgcaagca acacatgtgt ggtgagactg    300
aagaagaaaa gattcgagtg gacatcatag agaaccaagt aatggatttc cgcacacaac    360
tgataaggct ctgttacagc tctgaccacg aaaaactgaa gcctcagtac ttggaagagc    420
```

```
tacctggaca actgaaacaa ttctccatgt ttctgtggaa attctcatgg tttgccgggg      480
aaaagctcac ctttgtggat tttctcacct atgatatctt ggatcagaac cgtatatttg      540
accccaagtg cctggatgag ttcccaaacc tgaaggcttt catgtgccgt tttgaggctt      600
tggagaaaat cgctgcctac ttacagtctg atcagttctg caagatgccc atcaacaaca      660
agatggccca gtggggcaac aagcctgtat gctgagcagg aggcagactt gcagagcttg      720
ttttgtttca tcctgtccgt aagggggtcag cgctcttgct ttgctctttt caatgaatag      780
cacttatgtt actggtgtcc agctgagttt ctcttgggta taaaggctaa aagggaaaaa      840
ggatatgtgg agaatcatca agatatgaat tgaatcgctg cgatactgtg gcatttccct      900
actccccaac tgagttcaag ggctgtaggt tcatgcccaa gccctgagag tgggtactag      960
aaaaaacgag attgcacagt tggagagagc aggtgtgtta atggactgg agtccctgtg     1020 aagactgggt gaggataaca caagtaaaac tgtggtactg atggacttaa ccggagttcg     1080
gaaaccgtcc tgtgtacaca tgggagttta gtgtgataaa ggcagtattt cagactggtg     1140
ggctagccaa tagagttggc aattgcttat tgaaactcat taaaaataat agagccccac     1200
ttgacactat tcactaaaat taatctggaa tttaaggccc aacattaaac acaaagctgt     1260
attgat                                                                 1266

<210> SEQ ID NO 12
<211> LENGTH: 1308
<212> TYPE: DNA
<213> ORGANISM: Homo sapiens

<400> SEQUENCE: 12
gccacgtgct gctgggtctc agtcctccac ttccgtgtc ctctggaagt tgtcaggagc       60
aatgttgcgc ttgtacgtgt tggtaatggg agtttctgcc ttcacccttc agcctgcggc      120
acacacaggg gctgccagaa gctgccggtt tcgtgggagg cattacaagc gggagttcag      180
gctggaaggg gagcctgtag ccctgaggtg ccccaggtg ccctactggt tgtgggcctc      240
tgtcagcccc cgcatcaacc tgacatggca taaaaatgac tctgctagga cggtcccagg      300
agaagaagag acacggatgt gggcccagga cggtgctctg tggcttctgc cagccttgca      360
ggaggactct ggcacctacg tctgcactac tagaaatgct tcttactgtg acaaaatgtc      420
cattgagctc agagtttttg agaatacaga tgctttcctg ccgttcatct catacccgca      480
aattttaacc ttgtcaacct ctggggtatt agtatgccct gacctgagtg aattcacccg      540
tgacaaaact gacgtgaaga ttcaatggta caaggattct cttcttttgg ataaagacaa      600
tgagaaattt ctaagtgtga gggggaccac tcacttactc gtacacgatg tggccctgga      660
agatgctggc tattaccgct gtgtcctgac atttgcccat gaaggccagc aatacaacat      720
cactaggagt attgagctac gcatcaagaa aaaaaaagaa gagaccattc ctgtgatcat      780
tccccccctc aagaccatat cagcttctct ggggtcaaga ctgacaatcc cgtgtaaggt      840
gtttctggga accggcacac ccttaaccac catgctgtgg tggacggcca atgacaccca      900
catagagagc gcctacccgg gaggccgcgt gaccgagggg ccacgccagg aatattcaga      960
aaataatgag aactacattg aagtgccatt gattttttgat cctgtcacaa gagaggattt     1020
gcacatggat tttaaatgtg ttgtccataa taccctgagt tttcagacac tacgcaccac     1080
agtcaaggaa gcctcctcca cgttctcctg gggcattgtg ctggccccac tttcactggc     1140
cttcttggtt ttgggggaa tatggatgca cagacggtgc aaaacacgaa ctggaaaagc     1200
agatggtctg actgtgctat ggcctcatca tcaagacttt caatcctatc ccaagtgaaa     1260
```
taaatggaat gaaataattc aaacacaaaa aaaaaaaaaa aaaaaaaa                    1308

<210> SEQ ID NO 13
<211> LENGTH: 5994
<212> TYPE: DNA
<213> ORGANISM: Homo sapiens

<400> SEQUENCE: 13
gcgctgcccg cctcgtcccc accccccaac cccccgcgcc cgccctcgga cagtccctgc      60
tcgcccgcgc gctgcagccc catctcctag cggcagccca ggcgcggagg gagcgagtcc     120
gccccgaggt aggtccagga cgggcgcaca gcagcagccg aggctggccg ggagagggag     180
gaagaggatg gcagggccac gccccagccc atgggccagg ctgctcctgg cagccttgat     240
cagcgtcagc ctctctggga ccttggcaaa ccgctgcaag aaggcccag tgaagagctg      300
cacggagtgt gtccgtgtgg ataaggactg cgcctactgc acagacgaga tgttcaggga     360
ccggcgctgc aacacccagg cggagctgct ggccgcgggc tgccagcggg agagcatcgt     420
ggtcatggag agcagcttcc aaatcacaga ggagacccag attgacacca ccctgcggcg     480
cagccagatg tccccccaag gcctgcgggt ccgtctgcgg cccggtgagg agcggcattt     540
tgagctggag gtgtttgagc cactggagag ccccgtggac ctgtacatcc tcatggactt     600
ctccaactcc atgtccgatg atctggacaa cctcaagaag atgggcaga acctggctcg      660
ggtcctgagc cagctcacca gcgactacac tattggattt ggcaagtttg tggacaaagt     720
cagcgtcccg cagacggaca tgaggcctga aagctgaag gagccctggc ccaacagtga      780
cccccccttc tccttcaaga acgtcatcag cctgacagaa gatgtggatg agttccggaa     840
taaactgcag ggagagcgga tctcaggcaa cctggatgct cctgagggcg gcttcgatgc     900
catcctgcag acagctgtgt gcacgaggga cattggctgg cgcccggaca gcacccacct     960
gctggtcttc tccaccgagt cagccttcca ctatgaggct gatggcgcca acgtgctggc    1020
tggcatcatg agccgcaacg atgaacggtg ccacctggac accacgggca cctacaccca    1080
gtacaggaca caggactacc cgtcggtgcc caccctggtg cgcctgctcg ccaagcacaa    1140
catcatcccc atctttgctg tcaccaacta ctcctatagc tactacgaga gcttcacac     1200
ctatttccct gtctcctcac tgggggtgct gcaggaggac tcgtccaaca tcgtggagct    1260
gctggaggag gccttcaatc ggatccgctc caacctggac atccgggccc tagacagccc    1320
ccgaggcctt cggacagagg tcacctccaa gatgttccag aagacgagga ctgggtcctt    1380
tcacatccgg cggggggaag tgggtatata ccaggtgcag ctgcgggccc ttgagcacgt    1440
ggatgggacg cacgtgtgcc agctgccgga ggaccagaag gcaacatcc atctgaaacc     1500
ttccttctcc gacggcctca gatggacgc gggcatcatc tgtgatgtgt gcacctgcga    1560
gctgcaaaaa gaggtgcggt cagctcgctg cagcttcaac ggagacttcg tgtgcggaca    1620
gtgtgtgtgc agcgagggct ggagtggcca gacctgcaac tgctccaccg gctctctgag    1680
tgacattcag ccctgcctgc ggagggcga ggacaagccg tgctccggcc gtggggagtg     1740
ccagtgcggg cactgtgtgt gctacggcga aggccgctac gagggtcagt tctgcgagta    1800
tgacaacttc cagtgtcccc gcacttccgg gttcctgtgc aatgaccgag acgctgctc     1860
catgggccag tgtgtgtgtg agcctggttg gacaggccca agctgtgact gtcccctcag    1920
caatgccacc tgcatcgaca gcaatggggg catctgtaat ggacgtggcc actgtgagtg    1980
tggccgctgc cactgccacc agcagtcgct ctacacggac accatctgcg agatcaacta    2040

```
ctcggcgatc cacccgggcc tctgcgagga cctacgctcc tgcgtgcagt gccaggcgtg   2100
gggcaccggc gagaagaagg ggcgcacgtg tgaggaatgc aacttcaagg tcaagatggt   2160
ggacgagctt aagagagccg aggaggtggt ggtgcgctgc tccttccggg acgaggatga   2220
cgactgcacc tacagctaca ccatggaagg tgacggcgcc cctgggccca acagcactgt   2280
cctggtgcac aagaagaagg actgccctcc gggctccttc tggtggctca tcccctgct    2340 cctcctcctc ctgccgctcc tggccctgct actgctgcta tgctgaagt  actgtgcctg   2400 ctgcaaggcc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggcttgtcca tcatgccgc cagcatcaac cccacagagc tggtgccta   2640 cgggctgtcc ttgcgcctgg cccgccttg caccgagaac ctgctgaagc ctgacactcg   2700
ggagtgcgcc cagctgcgcc aggaggtgga ggagaacctg aacgaggtct acaggcagat   2760
ctccggtgta cacaagctcc agcagaccaa gttccggcag cagcccaatg ccgggaaaaa   2820
gcaagaccac accattgtgg acacagtgct gatggcgccc cgctcggcca agccggccct   2880
gctgaagctt acagagaagc aggtggaaca gagggccttc cacgacctca aggtggcccc   2940
cggctactac accctcactg cagaccagga cgcccgggc atggtggagt tccaggaggg   3000
cgtggagctg gtggacgtac gggtgcccct ctttatccgg cctgaggatg acgacgagaa   3060
gcagctgctg gtggaggcca tcgacgtgcc cgcaggcact gccaccctcg gccgccgcct   3120
ggtaaacatc accatcatca aggagcaagc cagagacgtg gtgtcctttg agcagcctga   3180
gttctcggtc agccgcgggg accaggtggc ccgcatccct gtcatccggc gtgtcctgga   3240
cggcgggaag tcccaggtct cctaccgcac acaggatggc accgcgcagg gcaaccggga   3300
ctacatcccc gtggagggtg agctgctgtt ccagcctggg gaggcctgga aagagctgca   3360
ggtgaagctc ctggagctgc aagaagttga ctccctcctg cggggccgcc aggtccgccg   3420
tttccacgtc cagctcagca accctaagtt tggggcccac ctgggccagc ccactccac    3480 caccatcatc atcagggacc cagatgaact ggaccggagc ttcacgagtc agatgttgtc   3540
atcacagcca cccctcacg cgacctggg cgccccgcag aacccaatg ctaaggccgc     3600 tgggtccagg aagatccatt tcaactggct gccccttct ggcaagccaa tggggtacag    3660
ggtaaagtac tggattcagg gcgactccga atccgaagcc cacctgctcg acagcaaggt   3720
gccctcagtg gagctcacca acctgtaccc gtattgcgac tatgagatga aggtgtgcgc   3780 ctacgggct cagggcgagg gaccctcag  ctccctggtg tcctgccgca cccaccagga    3840
agtgcccagc gagccagggc gtctggcctt caatgtcgtc tcctccacgg tgacccagct   3900
gagctgggct gagccggctg agaccaacgg tgagatcaca gcctacgagg tctgctatgg   3960
cctggtcaac gatgacaacc gaccatttgg gcccatgaag aaagtgctgg ttgacaaccc   4020
taagaaccgg atgctgctta ttgagaacct tcggagtcc cagccctacc gctacacggt    4080
gaaggcgcgc aacggggccg gctgggggcc tgagcgggag ccatcatca acctggccac    4140 ccagcccaag aggcccatgt ccatccccat catccctgac atccctatcg tggacgccca   4200
gagcggggag gactacgaca gcttccttat gtacagcgat gacgttctac gctctccatc   4260
gggcagccag aggcccagcg tctccgatga cactggctgc ggctggaagt tcgagcccct   4320 gctggggag gagctggacc tgcggcgcgt cacgtggcgg ctgcccccgg agctcatccc    4380
gcgcctgtcg gccagcagcg ggcgctcctc cgacgccgag gccccacgg cccccggac    4440
```

-continued

```
gacggcggcg cgggcgggaa gggcggcagc cgtgccccgc agtgcgacac ccgggccccc    4500
cggagagcac ctggtgaatg gccggatgga ctttgccttc ccgggcagca ccaactccct    4560
gcacaggatg accacgacca gtgctgctgc ctatggcacc cacctgagcc acacgtgcc     4620 ccaccgcgtg ctaagcacat cctccaccct cacacgggac tacaactcac tgacccgctc    4680
agaacactca cactcgacca cactgcccag ggactactcc accctcacct ccgtctcctc    4740
ccacgactct cgcctgactg ctggtgtgcc cgacacgccc acccgcctgg tgttctctgc    4800
cctggggccc acatctctca gagtgagctg gcaggagccg cggtgcgagc ggccgctgca    4860
gggctacagt gtggagtacc agctgctgaa cggcggtgag ctgcatcggc tcaacatccc    4920
caaccctgcc cagacctcgg tggtggtgga agacctcctg cccaaccact cctacgtgtt    4980
ccgcgtgcgg gcccagagcc aggaaggctg gggccgagag cgtgagggtg tcatcaccat    5040
tgaatcccag gtgcacccgc agagcccact gtgtccctg ccaggctccg ccttcacttt     5100
gagcactccc agtgccccag gcccgctggt gttcactgcc ctgagcccag actcgctgca    5160
gctgagctgg gagcggccac ggaggcccaa tggggatatc gtcggctacc tggtgacctg    5220
tgagatggcc caaggaggag ggccagccac cgcattccgg gtggatggag acagccccga    5280
gagccggctg accgtgccgg gcctcagcga aacgtgccc tacaagttca aggtgcaggc      5340
caggaccact gagggcttcg ggccagagcg cgagggcatc atcaccatag agtcccagga    5400
tggaggaccc ttcccgcagc tgggcagccg tgccgggctc ttccagcacc cgctgcaaag    5460
cgagtacagc agcatcacca ccacccacac cagcgccacc gagcccttcc tagtggatgg    5520
gctgaccctg ggggcccagc acctggaggc aggcggctcc ctcacccggc atgtgaccca    5580
ggagtttgtg agcggacac tgaccaccag cggaacccctt agcacccaca tggaccaaca     5640
gttcttccaa acttgaccgc accctgcccc acccccgcca tgtcccacta ggcgtcctcc    5700
cgactcctct cccggagcct cctcagctac tccatccttg caccctgggg gcccagccc     5760 acccgcatgc acagagcagg ggctaggtgt ctcctgggag gcatgaaggg ggcaaggtcc    5820
gtcctctgtg ggcccaaacc tatttgtaac caaagagctg ggagcagcac aaggacccag    5880
cctttgttct gcacttaata aatggttttg ctactgctaa aaaaaaaaa aaaaaaaaa      5940 aaaaaaaaaa aaaaaaaaaa aaaaaaaaaa aaaaaaaaaa aaaaaaaaaa aaaa          5994
```

<210> SEQ ID NO 14
<211> LENGTH: 1898
<212> TYPE: DNA
<213> ORGANISM: Homo sapiens

<400> SEQUENCE: 14

```
ccgccgggct ggccatggag ctgctgtgcc acgaggtgga cccggtccgc agggccgtgc      60
gggaccgcaa cctgctccga gacgaccgcg tcctgcagaa cctgctcacc atcgaggagc    120
gctaccttcc gcagtgctcc tacttcaagt gcgtgcagaa ggacatccaa ccctacatgc    180
gcagaatggt ggccacctgg atgctggagg tctgtgagga acagaagtgc gaagaagagg    240
tcttccctct ggccatgaat tacctggacc gtttcttggc tggggtcccg actccgaagt    300
cccatctgca actcctgggt gctgtctgca tgttcctggc ctccaaactc aaagagacca    360
gcccgctgac cgcggagaag ctgtgcattt acaccgacaa ctccatcaag cctcaggagc    420
tgctggagtg ggaactggtg gtgctgggga agttgaagtg gaacctggca gctgtcactc    480
ctcatgactt cattgagcac atcttgcgca agctgcccca gcagcgggag aagctgtctc    540
```

| | |
|---|---|
| tgatccgcaa gcatgctcag accttcattg ctctgtgtgc caccgacttt aagtttgcca | 600 |
| tgtacccacc gtcgatgatc gcaactggaa gtgtgggagc agccatctgt gggctccagc | 660 |
| aggatgagga agtgagctcg ctcacttgtg atgccctgac tgagctgctg gctaagatca | 720 |
| ccaacacaga cgtggattgt ctcaaagctt gccaggagca gattgaggcg gtgctcctca | 780 |
| atagcctgca gcagtaccgt caggaccaac gtgacggatc caagtcggag gatgaactgg | 840 |
| accaagccag caccccctaca gacgtgcggg atatcgacct gtgaggatgc cagttgggcc | 900 |
| gaaagagaga gacgcgtcca taatctggtc tcttcttctt tctggttgtt tttgttcttt | 960 |
| gtgttttagg gtgaaactta aaaaaaaaat tctgccccca cctagatcat atttaaagat | 1020 |
| cttttagaag tgagagaaaa aggtcctacg aaaacggaat aataaaaagc atttggtgcc | 1080 |
| tatttgaagt acagcataag ggaatccctt gtatatgcga acagttattg tttgattatg | 1140 |
| taaaagtaat agtaaaatgc ttacaggaaa acctgcagag tagttagaga atatgtatgc | 1200 |
| ctgcaatatg ggaacaaatt agaggagact ttttttttc atgttatgag ctagcacata | 1260 |
| caccccttg tagtataatt tcaaggaact gtgtacgcca tttatggcat gattagattg | 1320 |
| caaagcaatg aactcaagaa ggaattgaaa taaggaggga catgatgggg aaggagtaca | 1380 |
| aaacaatctc tcaacatgat tgaaccattt gggatggaga agcacctttg ctctcagcca | 1440 |
| cctgttacta agtcaggagt gtagttggat ctctacatta atgtcctctt gctgtctaca | 1500 |
| gtagctgcta cctaaaaaaa gatgttttat tttgccagtt ggacacaggt gattggctcc | 1560 |
| tgggtttcat gttctgtgac atcctgcttc ttcttccaaa tgcagttcat tgcagacacc | 1620 |
| accatattgc tatctaatgg ggaaatgtag ctatgggcca taaccaaaac tcacatgaaa | 1680 |
| cggaggcaga tggagaccaa gggtgggatc cagaatggag tcttttctgt tattgtattt | 1740 |
| aaaagggtaa tgtggccttg gcatttcttc ttagaaaaaa actaattttt ggtgctgatt | 1800 |
| ggcatgtctg gttcacagtt tagcattgtt ataaaccatt ccattcgaaa agcactttga | 1860 |
| aaaattgttc ccgagcgata gatgggatgg tttatgca | 1898 |

<210> SEQ ID NO 15
<211> LENGTH: 4286
<212> TYPE: DNA
<213> ORGANISM: Homo sapiens

<400> SEQUENCE: 15

| | |
|---|---|
| gagacattcc ggtgggggac tctggccagc ccgagcaacg tggatcctga gagcactccc | 60 |
| aggtaggcat ttgccccggt gggacgcctt gccagagcag tgtgtggcag gccccgtgg | 120 |
| aggatcaaca cagtggctga acactgggaa ggaactggta cttggagtct ggacatctga | 180 |
| aacttggctc tgaaactgcg cagcggccac cggacgcctt ctggagcagg tagcagcatg | 240 |
| cagccgcctc caagtctgtg cggacgcgcc ctggttgcgc tggttcttgc ctgcggcctg | 300 |
| tcgcggatct ggggagagga gagaggcttc ccgcctgaca gggccactcc gcttttgcaa | 360 |
| accgcagaga taatgacgcc acccactaag accttatggc ccaagggttc caacgccagt | 420 |
| ctggcgcggt cgttggcacc tgcggaggtg cctaaaggag acaggacggc aggatctccg | 480 |
| ccacgcacca tctcccctcc cccgtgccaa ggacccatcg agatcaagga gactttcaaa | 540 |
| tacatcaaca cggttgtgtc ctgccttgtg ttcgtgctgg ggatcatcgg aactccaca | 600 |
| cttctgagaa ttatctacaa gaacaagtgc atgcgaaacg tcccaatat cttgatcgcc | 660 |
| agcttggctc tgggagacct gctgcacatc gtcattgaca tccctatcaa tgtctacaag | 720 |
| ctgctggcag aggactggcc atttggagct gagatgtgta agctggtgcc tttcatacag | 780 |

```
aaagcctccg tgggaatcac tgtgctgagt ctatgtgctc tgagtattga cagatatcga    840
gctgttgctt cttggagtag aattaaagga attggggttc caaaatggac agcagtagaa    900
attgttttga tttgggtggt ctctgtggtt ctggctgtcc ctgaagccat aggttttgat    960
ataattacga tggactacaa aggaagttat ctgcgaatct gcttgcttca tcccgttcag   1020
aagacagctt tcatgcagtt ttacaagaca gcaaaagatt ggtggctgtt cagtttctat   1080
ttctgcttgc cattggccat cactgcattt ttttatacac taatgacctg tgaaatgttg   1140
agaaagaaaa gtggcatgca gattgcttta aatgatcacc taaagcagag acgggaagtg   1200
gccaaaaccg tcttttgcct ggtccttgtc tttgccctct gctggcttcc ccttcacctc   1260
agcaggattc tgaagctcac tctttataat cagaatgatc ccaatagatg tgaacttttg   1320
agctttctgt tggtattgga ctatattggt atcaacatgg cttcactgaa ttcctgcatt   1380
aacccaattg ctctgtattt ggtgagcaaa agattcaaaa actgctttaa gtcatgctta   1440
tgctgctggt gccagtcatt tgaagaaaaa cagtccttgg aggaaaagca gtcgtgctta   1500
aagttcaaag ctaatgatca cggatatgac aacttccgtt ccagtaataa atacagctca   1560
tcttgaaaga agaactattc actgtatttc attttcttta tattggaccg aagtcattaa   1620
aacaaaatga aacatttgcc aaaacaaaac aaaaaactat gtatttgcac agcacactat   1680
taaaatatta agtgtaatta ttttaacact cacagctaca tatgacattt tatgagctgt   1740
ttacggcatg gaaagaaaat cagtgggaat taagaaagcc tcgtcgtgaa agcacttaat   1800
tttttacagt tagcacttca acatagctct taacaacttc caggatattc acacaacact   1860
taggcttaaa aatgagctca ctcagaattt ctattctttc taaaaagaga tttattttta   1920
aatcaatggg actctgatat aaaggaagaa taagtcactg taaaacagaa cttttaaatg   1980
aagcttaaat tactcaattt aaaattttaa aatcctttaa aacaactttt caattaatat   2040
tatcacacta ttatcagatt gtaattagat gcaaatgaga gagcagttta gttgttgcat   2100
ttttcggaca ctggaaacat ttaaatgatc aggagggagt aacagaaaga gcaaggctgt   2160
ttttgaaaat cattacactt tcactagaag cccaaacctc agcattctgc aatatgtaac   2220
caacatgtca caaacaagca gcatgtaaca gactggcaca tgtgccagct gaatttaaaa   2280
tataatactt ttaaaaagaa aattattaca tcctttacat tcagttaaga tcaaacctca   2340
caaagagaaa tagaatgttt gaaaggctat cccaaaagac ttttttgaat ctgtcattca   2400
catccctgt gaagacaata ctatctcaaa tttttttcagg attattaaaa tcttcttttt   2460
tcactatcgt agcttaaact ctgtttggtt ttgtcatctg taaatactta cctacataca   2520
ctgcatgtag atgattaaat gagggcaggc cctgtgctca tagctttacg atggagagat   2580
gccagtgacc tcataataaa gactgtgaac tgcctggtgc agtgtccaca tgacaagggg   2640
gcaggtagca ccctctctca cccatgctgt ggttaaaatg gtttctagca tatgtataat   2700
gctatagtta aaatactatt tttcaaaatc atacagatta gtacatttaa cagctacctg   2760
taaagcttat tactaatttt tgtattattt ttgtaaatag ccaatagaaa agtttgcttg   2820
acatggtgct tttctttcat ctagaggcaa aactgctttt tgagaccgta agaacctctt   2880
agctttgtgc gttcctgcct aattttttata tcttctaagc aaagtgcctt aggatagctt   2940
gggatgagat gtgtgtgaaa gtatgtacaa agagaaacgg aagagagagg aaatgaggtg   3000
gggttggagg aaacccatgg ggacagattc ccattcttag cctaacgttc gtcattgcct   3060
cgtcacatca atgcaaaagg tcctgatttt gttccagcaa aacacagtgc aatgttctca   3120
```

```
gagtgacttt cgaaataaat tgggcccaag agctttaact cggtcttaaa atatgcccaa    3180
atttttactt tgttttctt ttaataggct gggccacatg ttggaaataa gctagtaatg    3240
ttgttttctg tcaatattga atgtgatggt acagtaaacc aaaacccaac aatgtggcca    3300
gaaagaaaga gcaataataa ttaattcaca caccatatgg attctattta taaatcaccc    3360
acaaacttgt tctttaattt catcccaatc acttttcag aggcctgtta tcatagaagt    3420
cattttagac tctcaatttt aaattaattt tgaatcacta atattttcac agtttattaa    3480
tatatttaat ttctatttaa atttagatt attttatta ccatgtactg aattttaca    3540 tcctgatacc ctttccttct ccatgtcagt atcatgttct ctaattatct tgccaaattt    3600
tgaaactaca cacaaaaagc atacttgcat tatttataat aaaattgcat tcagtggctt    3660
tttaaaaaaa atgtttgatt caaaacttta acatactgat aagtaagaaa caattataat    3720
ttctttacat actcaaaacc aagatagaaa aaggtgctat cgttcaactt caaaacatgt    3780
ttcctagtat taaggacttt aatatagcaa cagacaaaat tattgttaac atggatgtta    3840
cagctcaaaa gatttataaa agattttaac ctattttctc ccttattatc cactgctaat    3900
gtggatgtat gttcaaacac cttttagtat tgatagctta catatggcca aaggaataca    3960
gtttatagca aaacatgggt atgctgtagc taactttata aaagtgtaat ataacaatgt    4020
aaaaaattat atatctggga ggattttttg gttgcctaaa gtggctatag ttactgatt    4080 tttattatgt aagcaaaacc aataaaaat taagtttttt taacaactac cttatttttc    4140
actgtacaga cactaattca ttaaaatacta attgattgtt taaagaaat ataaatgtga    4200 caagtggaca ttatttatgt taaatataca attatcaagc aagtatgaag ttattcaatt    4260
aaaatgccac atttctggtc tctggg                                         4286

<210> SEQ ID NO 16
<211> LENGTH: 3148
<212> TYPE: DNA
<213> ORGANISM: Homo sapiens

<400> SEQUENCE: 16
gaattcccgc ggagcagcgt gcgcggggcc ccgggagacg gcggcggtag cggcgcgggc      60
agagcaagga cgcggcggat cccactcgca cagcagcgca ctcggtgccc cgcgcagggt     120
cgcgatgctg cccggtttgg cactgctcct gctggccgcc tggacggctc gggcgctgga     180 ggtaccccact gatggtaatg ctggcctgct ggctgaaccc cagattgcca tgttctgtgg     240
cagactgaac atgcacatga atgtccagaa tgggaagtgg gattcagatc catcagggac     300
caaaacctgc attgatacca aggaaggcat cctgcagtat tgccaagaag tctaccctga     360
actgcagatc accaatgtgg tagaagccaa ccaaccagtg accatccaga actggtgcaa     420
gcggggccgc aagcagtgca agacccatcc ccactttgtg attccctacc gctgcttagt     480
tggtgagttt gtaagtgatg cccttctcgt tcctgacaag tgcaaattct acaccaggaa     540
gaggatggat gtttgcgaaa ctcatcttca ctggcacacc gtcgccaaag agacatgcag     600
tgagaagagt accaacttgc atgactacgg catgttgctg ccctgcggaa ttgacaagtt     660
ccgaggggta gagtttgtgt gttgcccact ggctgaagaa agtgacaatg tggattctgc     720
tgatgcggag gaggatgact cggatgtctg gtgggcgga gcagacacag actatgcaga     780
tgggagtgaa gacaaagtag tagaagtagc agaggaggaa gaagtggctg aggtggaaga     840
agaagaagcc gatgatgacg aggacgatga ggatggtgat gaggtagagg aagaggctga     900
ggaaccctac gaagaagcca cagagagaac caccagcatt gccaccacca ccaccaccac     960
```

```
cacagagtct gtggaagagg tggttcgaga ggtgtgctct gaacaagccg agacggggcc     1020
gtgccgagca atgatctccc gctggtactt tgatgtgact gaagggaagt gtgccccatt     1080
cttttacggc ggatgtggcg gcaaccggaa caactttgac acagaagagt actgcatggc     1140
cgtgtgtggc agcgccattc ctacaacagc agccagtacc cctgatgccg ttgacaagta     1200
tctcgagaca cctggggatg agaatgaaca tgcccatttc cagaaagcca aagagaggct     1260
tgaggccaag caccgagaga gaatgtccca ggtcatgaga gaatgggaag aggcagaacg     1320
tcaagcaaag aacttgccta agctgataaa gaaggcagtt atccagcatt ccaggagaa      1380 agtggaatct ttggaacagg aagcagccaa cgagagacag cagctggtgg agacacacat     1440
ggccagagtg gaagccatgc tcaatgaccg ccgccgcctg ccctggaga actacatcac      1500 cgctctgcag gctgttcctc ctcggcctcg tcacgtgttc aatatgctaa agaagtatgt     1560
ccgcgcagaa cagaaggaca gacagcacac cctaaagcat ttcgagcatg tgcgcatggt     1620
ggatcccaag aaagccgctc agatccggtc ccaggttatg acacacctcc gtgtgattta     1680
tgagcgcatg aatcagtctc tctccctgct ctacaacgtg cctgcagtgg ccgaggagat     1740
tcaggatgaa gttgatgagc tgcttcagaa agagcaaaac tattcagatg acgtcttggc     1800
caacatgatt agtgaaccaa ggatcagtta cggaaacgat gctctcatgc catctttgac     1860
cgaaacgaaa accaccgtgg agctccttcc cgtgaatgga gagttcagcc tggacgatct     1920
ccagccgtgg cattcttttg gggctgactc tgtgccagcc aacacagaaa acgaagttga     1980
gcctgttgat gcccgccctg ctgccgaccg aggactgacc actcgaccag gttctgggtt     2040
gacaaatatc aagacggagg agatctctga agtgaagatg gatgcagaat tccgacatga     2100
ctcaggatat gaagttcatc atcaaaaatt ggtgttcttt gcagaagatg tgggttcaaa     2160
caaaggtgca atcattggac tcatggtggg cggtgttgtc atagcgacag tgatcgtcat     2220
caccttggtg atgctgaaga gaaacagta cacatccatt catcatgtg tggtggaggt      2280 tgacgccgct gtcaccccag aggagcgcca cctgtccaag atgcagcaga acggctacga     2340
aaatccaacc tacaagttct ttgagcagat gcagaactag accccgcca cagcagcctc     2400 tgaagttgga cagcaaaacc attgcttcac tacccatcgg tgtccattta tagaataatg     2460
tgggaagaaa caaacccgtt ttatgattta ctcattatcg ccttttgaca gctgtgctgt     2520
aacacaagta gatgcctgaa cttgaattaa tccacacatc agtaatgtat tctatctctc     2580
tttacatttt ggtctctata ctacattatt aatgggtttt gtgtactgta aagaatttag     2640
ctgtatcaaa ctagtgcatg aatagattct ctcctgatta tttatcacat agccccttag     2700
ccagttgtat attattcttg tggtttgtga cccaattaag tcctacttta catatgcttt     2760
aagaatcgat gggggatgct tcatgtgaac gtgggagttc agctgcttct cttgcctaag     2820
tattcctttc ctgatcacta tgcattttaa agttaaacat ttttaagtat ttcagatgct     2880
ttagagagat ttttttttcca tgactgcatt ttactgtaca gattgctgct tctgctatat     2940
ttgtgatata ggaattaaga ggatacacac gtttgtttct tcgtgcctgt tttatgtgca     3000
cacattaggc attgagactt caagcttttc ttttttttgtc cacgtatctt tgggtctttg     3060
ataaagaaaa gaatccctgt tcattgtaag cacttttacg gggcgggtgg ggaggggtgc     3120
tctgctggtc ttcaattacc aagaattc                                        3148

<210> SEQ ID NO 17
<211> LENGTH: 4434
<212> TYPE: DNA
```

<213> ORGANISM: Homo sapiens

<400> SEQUENCE: 17

| | | | | | |
|---|---|---|---|---|---|
| gccgccctcg | ccaccgctcc | cggccgccgc | gctccggtac | acacaggatc | cctgctgggc | 60 |
| accaacagct | ccaccatggg | gctggcctgg | ggactaggcg | tcctgttcct | gatgcatgtg | 120 |
| tgtggcacca | accgcattcc | agagtctggc | ggagacaaca | gcgtgtttga | catctttgaa | 180 |
| ctcaccgggg | ccgcccgcaa | ggggtctggg | cgccgactgg | tgaagggccc | cgacccttcc | 240 |
| agcccagctt | tccgcatcga | ggatgccaac | ctgatccccc | ctgtgcctga | tgacaagttc | 300 |
| caagacctgg | tggatgctgt | gcggacagaa | aagggtttcc | tccttctggc | atccctgagg | 360 |
| cagatgaaga | gacccggggg | cacgctgctg | gccctggagc | ggaaagacca | ctctggccag | 420 |
| gtcttcagcg | tggtgtccaa | tggcaaggcg | ggcaccctgg | acctcagcct | gaccgtccaa | 480 |
| ggaaagcagc | acgtggtgtc | tgtggaagaa | gctctcctgg | caaccggcca | gtggaagagc | 540 |
| atcaccctgt | ttgtgcagga | agacagggcc | cagctgtaca | tcgactgtga | aaagatggag | 600 |
| aatgctgagt | tggacgtccc | catccaaagc | gtcttcacca | gagacctggc | cagcatcgcc | 660 |
| agactccgca | tcgcaaaggg | gggcgtcaat | gacaatttcc | aggggggtgct | gcagaatgtg | 720 |
| aggtttgtct | ttggaaccac | accagaagac | atcctcagga | acaaaggctg | ctccagctct | 780 |
| accagtgtcc | tcctcaccct | tgacaacaac | gtggtgaatg | gttccagccc | tgccatccgc | 840 |
| actaactaca | ttggccacaa | gacaaaggac | ttgcaagcca | tctgcggcat | ctcctgtgat | 900 |
| gagctgtcca | gcatggtcct | ggaactcagg | ggcctgcgca | ccattgtgac | cacgctgcag | 960 |
| gacagcatcc | gcaaagtgac | tgaagagaac | aaagagttgg | ccaatgagct | gaggcggcct | 1020 |
| cccctatgct | atcacaacgg | agttcagtac | agaaataacg | aggaatggac | tgttgatagc | 1080 |
| tgcactgagt | gtcactgtca | gaactcagtt | accatctgca | aaaaggtgtc | ctgccccatc | 1140 |
| atgcctgct | ccaatgccac | agttcctgat | ggagaatgct | gtcctcgctg | tttggcccagc | 1200 |
| gactctgcgg | acgatggctg | gtctccatgg | tccgagtgga | cctcctgttc | tacgagctgt | 1260 |
| ggcaatggaa | ttcagcagcg | cggccgctcc | tgcgatagcc | tcaacaaccg | atgtgagggc | 1320 |
| tcctcggtcc | agacacggac | ctgccacatt | caggagtgtg | acaagagatt | taaacaggat | 1380 |
| ggtggctgga | gccactggtc | cccgtggtca | tcttgttctg | tgacatgtgg | tgatggtgtg | 1440 |
| atcacaagga | tccggctctg | caactctccc | agccccagaa | tgaacgggaa | accctgtgaa | 1500 |
| ggcgaagcgc | gggagaccaa | agcctgcaag | aaagacgcct | gccccatcaa | tggaggctgg | 1560 |
| ggtccttggt | caccatggga | catctgttct | gtcacctgtg | aggagggggt | acagaaacgt | 1620 |
| agtcgtctct | gcaacaaccc | cacacccccag | tttggaggca | aggactgcgt | tggtgatgta | 1680 |
| acagaaaacc | agatctgcaa | caagcaggac | tgtccaattg | atggatgcct | gtccaatccc | 1740 |
| tgctttgccg | gcgtgaagtg | tactagctac | cctgatggca | gctggaaatg | tggtgcttgt | 1800 |
| cccccctggtt | acagtggaaa | tggcatccag | tgcacagatg | ttgatgagtg | caagaagtg | 1860 |
| cctgatgcct | gcttcaacca | caatggagag | caccggtgtg | agaacacgga | ccccggctac | 1920 |
| aactgcctgc | cctgccccccc | acgcttcacc | ggctcacagc | cttcggcca | gggtgtcgaa | 1980 |
| catgccacgg | ccaacaaaca | ggtgtgcaag | ccccgtaacc | cctgcacgga | tgggacccac | 2040 |
| gactgcaaca | gaacgccaa | gtgcaactac | ctgggccact | atagcgaccc | catgtaccgc | 2100 |
| tgcgagtgca | agcctggcta | cgctggcaat | ggcatcatct | gcggggagga | cacagacctg | 2160 |
| gatgctggc | ccaatgagaa | cctggtgtgc | gtggccaatg | cgacttacca | ctgcaaaag | 2220 |
| gataattgcc | ccaaccttcc | caactcaggg | caggaagact | atgacaagga | tggaattggt | 2280 |

-continued

```
gatgcctgtg atgatgacga tgacaatgat aaaattccag atgacaggga caactgtcca    2340
ttccattaca acccagctca gtatgactat gacagagatg atgtgggaga ccgctgtgac    2400
aactgtccct acaaccacaa cccagatcag gcagacacag acaacaatgg ggaaggagac    2460
gcctgtgctg cagacattga tggagacggt atcctcaatg aacgggacaa ctgccagtac    2520
gtctacaatg tggaccagag agacactgat atggatgggg ttggagatca gtgtgacaat    2580
tgccccttgg aacacaatcc ggatcagctg gactctgact cagaccgcat tggagatacc    2640
tgtgacaaca atcaggatat tgatgaagat ggccaccaga acaatctgga caactgtccc    2700
tatgtgccca atgccaacca ggctgaccat gacaaagatg gcaagggaga tgcctgtgac    2760
cacgatgatg acaacgatgg cattcctgat gacaaggaca actgcagact cgtgcccaat    2820
cccgaccaga aggactctga cggcgatggt cgaggtgatg cctgcaaaga tgattttgac    2880
catgacagtg tgccagacat cgatgacatc tgtcctgaga atgttgacat cagtgagacc    2940
gatttccgcc gattccagat gattcctctg accccaaag ggacatccca aaatgaccct    3000
aactgggttg tacgccatca gggtaaagaa ctcgtccaga ctgtcaactg tgatcctgga    3060
ctcgctgtag gttatgatga gtttaatgct gtggacttca gtggcacctt cttcatcaac    3120
accgaaaggg acgatgacta tgctggattt gtctttggct accagtccag cagccgcttt    3180
tatgttgtga tgtggaagca agtcacccag tcctactggg acaccaaccc cacgagggct    3240
cagggatact cgggcctttc tgtgaaagtt gtaaactcca ccacagggcc tggcgagcac    3300
ctgcggaacg ccctgtggca cacaggaaac acccctggcc aggtgcgcac cctgtggcat    3360
gaccctcgtc acataggctg aaagatttc accgcctaca gatggcgtct cagccacagg    3420
ccaaagacgg gtttcattag agtggtgatg tatgaaggga agaaaatcat ggctgactca    3480
ggacccatct atgataaaac ctatgctggt ggtagactag ggttgtttgt cttctctcaa    3540
gaaatggtgt tcttctctga cctgaaatac gaatgtagag atccctaatc atcaaattgt    3600
tgattgaaag actgatcata aaccaatgct ggtattgcac cttctggaac tatgggcttg    3660
agaaaacccc caggatcact tctccttggc ttccttcttt tctgtgcttg catcagtgtg    3720
gactcctaga acgtgcgacc tgcctcaaga aaatgcagtt ttcaaaaaca gactcagcat    3780
tcagcctcca atgaataaga catcttccaa gcatataaac aattgctttg gtttcctttt    3840
gaaaaagcat ctacttgctt cagttgggaa ggtgcccatt ccactctgcc tttgtcacag    3900
agcagggtgc tattgtgagg ccatctctga gcagtggact caaaagcatt ttcaggcatg    3960
tcagagaagg gaggactcac tagaattagc aaacaaaacc accctgacat cctccttcag    4020
gaacacgggg agcagaggcc aaagcactaa ggggagggcg catacccgag acgattgtat    4080
gaagaaaata tggaggaact gttacatgtt cggtactaag tcatttttcag gggattgaaa    4140
gactattgct ggatttcatg atgctgactg gcgttagctg attaacccat gtaaataggc    4200
acttaaatag aagcaggaaa gggagacaaa gactggcttc tggacttcct ccctgatccc    4260
caccccttact catcacctgc agtggccaga attagggaat cagaatcgaa accagtgtaa    4320
ggcagtgctg gctgccattg cctggtcaca ttgaaattgg tggcttcatt ctagatgtag    4380
cttgtgcaga tgtagcagga aaataggaaa acctaccatc tcagtgagca ccag         4434
```

<210> SEQ ID NO 18
<211> LENGTH: 1377
<212> TYPE: DNA
<213> ORGANISM: Homo sapiens

```
<400> SEQUENCE: 18
atttctcttt agttctttgc aagaaggtag agataaagac acttttttcaa aaatggcaat    60 ggtatcagaa ttcctcaagc aggcctggtt tattgaaaat gaagagcagg aatatgttca   120
aactgtgaag tcatccaaag gtggtcccgg atcagcggtg agcccctatc ctaccttcaa   180
tccatcctcg gatgtcgctg ccttgcataa ggccataatg gttaaaggtg tggatgaagc   240
aaccatcatt gacattctaa ctaagcgaaa caatgcacag cgtcaacaga tcaaagcagc   300
atatctccag gaaacaggaa agcccctgga tgaaacactg aagaaagccc ttacaggtca   360
ccttgaggag gttgttttag ctctgctaaa aactccagcg caatttgatg ctgatgaact   420
tcgtgctgcc atgaagggcc ttggaactga tgaagatact ctaattgaga ttttggcatc   480
aagaactaac aaagaaatca gagacattaa cagggtctac agagaggaac tgaagagaga   540
tctggccaaa gacataacct cagacacatc tggagatttt cggaacgctt gctttctct   600 tgctaagggt gaccgatctg aggactttgg tgtgaatgaa gacttggctg attcagatgc   660
cagggccttg tatgaagcag gagaaaggag aaaggggaca gacgtaaacg tgttcaatac   720
catccttacc accagaagct atccacaact tcgcagagtg tttcagaaat acaccaagta   780
cagtaagcat gacatgaaca aagttctgga cctggagttg aaaggtgaca ttgagaaatg   840
cctcacagct atcgtgaagt gcgccacaag caaaccagct tctctttgcag agaagcttca   900 tcaagccatg aaaggtgttg aactcgcca taaggcattg atcaggatta tggtttcccg   960
ttctgaaatt gacatgaatg atatcaaagc attctatcag aagatgtatg gtatctccct  1020 tgccaagcc atcctggatg aaaccaaagg agattatgag aaaatcctgg tggctctttg  1080
tggaggaaac taaacattcc cttgatggtc tcaagctatg atcagaagac tttaattata  1140
tattttcatc ctataagctt aaataggaaa gtttcttcaa caggattaca gtgtagctac  1200
ctacatgctg aaaaatatag cctttaaatc attttatat tataactctg tataatagag  1260
ataagtccat tttttaaaaa tgttttcccc aaaccataaa accctataca agttgttcta  1320
gtaacaatac atgagaaaga tgtctatgta gctgaaaata aaatgacgtc acaagac     1377

<210> SEQ ID NO 19
<211> LENGTH: 3370
<212> TYPE: DNA
<213> ORGANISM: Homo sapiens

<400> SEQUENCE: 19 gccccgccc ggcccgcccc gctctcctag tcccttgcaa cctggcgctg catccgggcc    60
actgtcccag gtcccaggtc ccggcccgga gctatggagc ggcgctggcc cctgggcta   120 gggctggtgc tgctgctctg cgccccgctg ccccgggg cgcgcgccaa ggaagttact   180
ctgatggaca caagcaaggc acagggagag ctgggctggc tgctggatcc cccaaaagat   240
gggtggagtg aacagcaaca gatactgaat gggacacccc tctacatgta ccaggactgc   300
ccaatgcaag gacgcagaga cactgaccac tggcttcgct ccaattggat ctaccgcggg   360
gaggaggctt cccgcgtcca cgtggagctg cagttcaccg tgcgggactg caagagtttc   420 cctggggag ccgggcctct gggctgcaag gagaccttca accttctgta catggagagt   480 gaccaggat gggcattca gctccgacgg cccttgttcc agaaggtaac cacggtggct   540
gcagaccaga gcttcaccat tcgagacctt tgcgtctggct ccgtgaagct gaatgtggag   600
cgctgctctc tgggccgcct gacccgccgt ggcctctacc tcgctttcca caacccgggt   660
gcctgtgtgg ccctggtgtc tgtccgggtc ttctaccagc gctgtcctga ccctgaat   720
```

```
ggcttggccc aattcccaga cactctgcct ggccccgctg ggttggtgga agtggcgggc    780
acctgcttgc cccacgcgcg ggccagcccc aggccctcag gtgcaccccg catgcactgc    840
agccctgatg gcgagtggct ggtgcctgta ggacggtgcc actgtgagcc tggctatgag    900
gaaggtggca gtggcgaagc atgtgttgcc tgccctagcg gctcctaccg gatggacatg    960
gacacacccc attgtctcac gtgccccag cagagcactg ctgagtctga gggggccacc   1020
atctgtacct gtgagagcgg ccattacaga gctcccgggg agggccccca ggtggcatgc   1080
acaggtcccc cctcggcccc ccgaaacctg agcttctctg cctcagggac tcagctctcc   1140
ctgcgttggg aaccccagc agatacgggg ggacgccagg atgtcagata cagtgtgagg   1200
tgttcccagt gtcagggcac agcacaggac gggggggccct gccagccctg tggggtgggc   1260
gtgcacttct cgccggggc ccgggcgctc accacacctg cagtgcatgt caatggcctt   1320
gaaccttatg ccaactacac ctttaatgtg aagcccaaa atggagtgtc agggctgggc   1380
agctctggcc atgccagcac ctcagtcagc atcagcatgg ggcatgcaga gtcactgtca   1440
ggcctgtctc tgagactggt gaagaaagaa ccgaggcaac tagagctgac ctgggcgggg   1500
tcccggcccc gaagccctgg ggcgaacctg acctatgagc tgcacgtgct gaaccaggat   1560
gaagaacggt accagatggt tctagaaccc agggtcttgc tgacagagct gcagcctgac   1620
accacataca tcgtcagagt ccgaatgctg accccactgg gtcctggccc tttctcccct   1680
gatcatgagt ttcggaccag cccaccagtg tccaggggcc tgactggagg agagattgta   1740
gccgtcatct ttgggctgct gcttggtgca gccttgctgc ttgggattct cgttttccgg   1800
tccaggagag cccagcggca gaggcagcag aggcacgtga ccgcgccacc gatgtggatc   1860
gagaggacaa gctgtgctga agccttatgt ggtacctcca ggcatacgag gaccctgcac   1920
agggagcctt ggactttacc cggaggctgg tctaattttc cttcccggga gcttgatcca   1980
gcgtggctga tggtggacac tgtcatagga gaaggagagt ttggggaagt gtatcgaggg   2040
accctcaggc tccccagcca ggactgcaag actgtggcca ttaagacctt aaaagacaca   2100
tccccaggtg gccagtggtg gaacttcctt cgagaggcaa ctatcatggg ccagtttagc   2160
cacccgcata ttctgcatct ggaaggcgtc gtcacaaagc gaaagccgat catgatcatc   2220
acagaattta tggagaatgc agccctggat gccttcctga gggagcggga ggaccagctg   2280
gtccctgggc agctagtggc catgctgcag ggcatagcat ctggcatgaa ctacctcagt   2340
aatcacaatt atgtccaccg ggacctggct gccagaaaca tcttggtgaa tcaaaacctg   2400
tgctgcaagg tgtctgactt tggcctgact cgcctcctgg atgactttga tggcacatac   2460
gaaacccagg aggaaagat ccctatccgt tggacagccc tgaagccat gcccatcgg   2520
atcttcacca cagccagcga tgtgtggagc tttgggattg tgatgtggga ggtgctgagc   2580
tttgggggaca agccttatgg ggagatgagc aatcaggagg ttatgaagag cattgaggat   2640
gggtaccggt tgccccctcc tgtggactgc cctgcccctc tgtatgagct catgaagaac   2700
tgctgggcat atgaccgtgc ccgccggcca cacttccaga gcttcaggc acatctggag   2760
caactgcttg ccaaccccca ctccctgcgg accattgcca actttgaccc cagggtgact   2820
cttcgcctgc ccagcctgag tggctcagat gggatcccgt atcgaaccgt ctctgagtgg   2880
ctcgagtcca tacgcatgaa acgctacatc ctgcacttcc actcggctgg gctggacacc   2940
atggagtgtg tgctggagct gaccgctgag gacctgacgc agatgggaat cacactgccc   3000
gggcaccaga agcgcattct ttgcagtatt cagggattca aggactgatc cctcctctca   3060
```

| | |
|---|---:|
| ccccatgccc aatcaggtg caaggagcaa ggacggggcc aaggtcgctc atggtcactc | 3120 |
| cctgcgcccc ttcccacaac ctgccagact aggctatcgg tgctgcttct gcccgcttta | 3180 |
| aggagaaccc tgctctgcac cccagaaaac ctctttgttt taaaagggag gtgggggtag | 3240 |
| aagtaaaagg atgatcatgg gagggagctc agggggttaat atatatacat acatacacat | 3300 |
| atatatattg ttgtaaataa acaggaaatg attttctgcc tccatcccac ccatcagggc | 3360 |
| tgcaggcact | 3370 |

```
<210> SEQ ID NO 20
<211> LENGTH: 1913
<212> TYPE: DNA
<213> ORGANISM: Homo sapiens

<400> SEQUENCE: 20
```

| | |
|---|---:|
| ccaagagcta cgcggcggcg gcggagcgca ggcctcgtgc cgttacggcc atcacggcgg | 60 |
| ccgcagtggc gtcctggagc cctcctcagt gctgaagctg ctgaaagatg cagaagaag | 120 |
| tggtggtagt agccaaattt gattatgtgg cccaacaaga acaagagttg gacatcaaga | 180 |
| agaatgagag attatggctt ctggatgatt ctaagtcctg gtggcgagtt cgaaattcca | 240 |
| tgaataaaac aggttttgtg ccttctaact atgtggaaag gaaaaacagt gctcggaaag | 300 |
| catctattgt gaaaaaccta aaggatacct taggcattgg aaaagtgaaa agaaaaccta | 360 |
| gtgtgccaga ttctgcatct cctgctgatg atagttttgt tgacccaggg gaacgtctct | 420 |
| atgacctcaa catgcccgct tatgtgaaat ttaactacat ggctgagaga gaggatgaat | 480 |
| tatcattgat aaaggggaca aaggtgatcg tcatggagaa atgcagtgat gggtggtggc | 540 |
| gtggtagcta caatggacaa gttggatggt tcccttcaaa ctatgtaact gaagaaggtg | 600 |
| acagtccttt gggtgaccat gtgggttctc tgtcagagaa attagcagca gtcgtcaata | 660 |
| acctaaatac tggcaagtg ttgcatgtgg tacaggctct ttacccattc agctcatcta | 720 |
| atgatgaaga acttaatttc gagaaaggag atgtaatgga tgttattgaa aaacctgaaa | 780 |
| atgacccaga gtggtggaaa tgcaggaaga tcaatggtat ggttggtcta gtaccaaaaa | 840 |
| actatgttac cgttatgcag aataatccat taacttcagg tttggaacca tcacctccac | 900 |
| agtgtgatta cattaggcct tcactcactg gaaagttgc tggcaatcct tggtattatg | 960 |
| gcaaagtcac caggcatcaa gcagaaatgg cattaaatga aagaggacat gaaggggatt | 1020 |
| tcctcattcg tgatagtgaa tcttcgccaa atgatttctc agtatcacta aaagcacaag | 1080 |
| ggaaaaacaa gcattttaaa gtccaactaa agagactgt ctactgcatt gggcagcgta | 1140 |
| aattcagcac catggaagaa cttgtagaac attacaaaaa ggcaccaatt tttacaagtg | 1200 |
| aacaaggaga aaaattatat cttgtcaagc atttatcatg atactgctga ccagaagtga | 1260 |
| ctgctgtgta gctgtaattt gtcatgtaat tgaagactga gaaatgttgg gtccagtcg | 1320 |
| tgcttgattg gaaattgttg tttctaaatc tatatgagaa ttgacaataa gtatttttat | 1380 |
| tataactcag cccatacata tatactatgt atgcagtgca tctgcataga acagttcctt | 1440 |
| atccttggcc ttctgtttta ttgtttttt ctttgctgtt ttcccttgc ttctaatatt | 1500 |
| acagttttgt attttgtaaa caaaaatcaa ataatgcata tcagaatctt tatatggaag | 1560 |
| aaatccttta ttgcctttcc tttgtttcct tgtaaaggca ccctgttctg ttatggtttt | 1620 |
| tcattatata aaattattat atctatatat gacatatgct aaaatttctt ggagagtgtt | 1680 |
| aatctttct gtgactaaat agcaataata agtggaaaat tagaaattat ttccaggtat | 1740 |
| tatatttgtc acaggccatt gtaaatacca agtatattgt gtctgccata atttttaaaa | 1800 |

| | |
|---|---:|
| atacattcat tgtcttcagt catacagcaa gacacatgag acatagatta gaaaacatgt | 1860 |
| tgtacaattt taatttacaa ctgttggaaa taaaaatcac ttaatttttt tcc | 1913 |

<210> SEQ ID NO 21
<211> LENGTH: 3257
<212> TYPE: DNA
<213> ORGANISM: Homo sapiens

<400> SEQUENCE: 21

| | |
|---|---:|
| catggcggcg actgcggcaa agcgagagcc tcggagacgc cgctgccgcc agcacagccg | 60 |
| gagacctgag ccgacactgg gggcagtccg cgagccccgc actctctcga tgagtcggag | 120 |
| aagtcccgtt gtatcagagt aagatggacg gtagctttga ttgtgattgt ggtgagctgg | 180 |
| agccacctga tcactaacaa agacatcttc tgttaaccaa cagccgcca gggcttcctg | 240 |
| ttgaaataaa tatatagcaa caaaggaaaa aagaagcaa acggaaata gtgcttacca | 300 |
| gcaccttaga atgatgctgc tcaggaccag tccaacactg aatgtatctg cactgtgagg | 360 |
| agaatgttca tagaagcctg ttgtgtgcat atttattcac attttttgtta aatgttaaat | 420 |
| cgtttagcac ggtaatctga gtgcacagta tgtcatttca ttccgtttga gtttcttgtt | 480 |
| ttcgttaaat gtctgcagag ttgctgcccc tttcttgaac tatgagtact gcaatctttt | 540 |
| taattctcaa tatgaataga gcttttttgag ctttaaatct aaggggaact cgacaggcct | 600 |
| gtttggcata tgcaatgaac atcaagaaac catcttgctg tggaagcata attatttttc | 660 |
| ttctcccttt ttgaaagatc tttccttttg atgccagttt tcttccttgt ttacacaagt | 720 |
| tcaatttgaa aggaaaaggc aatagtaagg gttttcaaaat ggcagagaaa tttgaaagtc | 780 |
| tcatgaacat tcatggtttt gatctgggtt ctaggtatat ggacttaaaa ccattgggtt | 840 |
| gtggaggcaa tggcttggtt ttttctgctg tagacaatga ctgtgacaaa agagtagcca | 900 |
| tcaagaaaat tgtccttact gatccccaga gtgtcaaaca tgctctacgt gaaatcaaaa | 960 |
| ttattagaag acttgaccat gataacattg tgaaagtgtt tgagattctt ggtcccagtg | 1020 |
| gaagccaatt aacagacgat gtgggctctc ttacggaact gaacagtgtt tacattgttc | 1080 |
| aggagtacat ggagacagac ttggctaatg tgctggagca gggcccttta ctggaagagc | 1140 |
| atgccaggct tttcatgtat cagctgctac ggggggctcaa gtatattcac tctgcaaatg | 1200 |
| tactgcacag agatctcaaa ccagctaatc tttttcattaa tacggaagac ttggtgctga | 1260 |
| agataggtga ctttggtctt gcacggatca tggatcctca ttattcccat aagggtcatc | 1320 |
| tttctgaagg attggttact aaatggtaca gatctccacg tctttttactt tctcctaata | 1380 |
| attatactaa agccattgac atgtgggctg caggctgcat ctttgctgaa atgctgactg | 1440 |
| gtaaaacct ttttgcaggt gcacatgaac ttgaacagat gcagctgatt ttagaatcta | 1500 |
| ttcctgttgt acatgaggaa gatcgtcagg agcttctcag cgtaattcca gtttacatta | 1560 |
| gaaatgacat gactgagcca cacaaacctt taactcagct gcttccagga attagtcgag | 1620 |
| aagcactgga tttcctggaa caaattttga catttagccc catggatcgg ttaacagcag | 1680 |
| aagaagcact ctcccatcct tacatgagca tatattcttt tccaatggat gagccaattt | 1740 |
| caagccatcc ttttcatatt gaagatgaag ttgatgatat tttgcttatg gatgaaactc | 1800 |
| acagtcacat ttataactgg gaaaggtatc atgattgtca gttttcagag catgattggc | 1860 |
| ctgtacataa caactttgat attgatgaag ttcagcttga tccaagagct ctgtccgatg | 1920 |
| tcactgatga agaagaagta caagttgatc cccgaaaata tttggatgga gatcgggaaa | 1980 |

```
agtatctgga ggatcctgct tttgatacca attactctac tgagccttgt tggcaatact    2040
cagatcatca tgaaaacaaa tattgtgatc tggagtgtag ccatacttgt aactacaaaa    2100
cgaggtcatc atcatattta gataacttag tttggagaga gagtgaagtt aaccattact    2160
atgaacccaa gcttattata gatctttcca attggaaaga acaaagcaaa gaaaaatctg    2220
ataagaaagg caaatcaaaa tgtgaaagga atggattggt taaagcccag atagcgctag    2280
aggaagcatc acagcaactg ctggaaaag aaagggaaaa gaatcaggga tttgattttg     2340
attcctttat tgcaggaact attcagctta gttcccagca tgagcctact gatgttgttg    2400
ataaattaaa tgacttgaat agctcagtgt cccaactaga attgaaaagt ttgatatcaa    2460
agtcagtaag ccaagaaaaa caggaaaaag gaatggcaaa tctggctcaa ttagaagcct    2520
tgtaccagtc ttcttgggac agccagtttg tgagtggtgg ggaggactgt ttttcataa     2580 atcagttttg tgaggtaagg aaggatgaac aagttgagaa ggaaaacact tacactagtt    2640
acttggacaa gttctttagc aggaaagaag atactgaaat gctagaaact gagccagtag    2700
aggatgggaa gcttggggag agaggacatg aggaaggatt tctgaacaac agtggggagt    2760
tcctctttaa caagcagctc gagtccatag gcatcccaca gtttcacagt ccagttgggt    2820
caccacttaa gtcaatacag gccacattaa caccttctgc tatgaaatct tcccctcaaa    2880
ttcctcatca aacatacagc agcattctga aacatctgaa ctaaaacact cagcagacat    2940
ttatctttgt attcttcatg aaatgtgttt tgtctttttt tattactagt gtttaagtca    3000
ttttttactt gaatcagatg gtgtcattta gtaaggattt tatgagttct tgttttttaa    3060
aatccagact ttcttttct acatgtgaga tagttttcat tttaactggc atgtcatttg     3120
cacacaaaaa taaagactag agcaaaataa tgcaacgcag gaggagaaaa gaaatgcact    3180
aagacaagaa cattctctca tagaacattg atctgtttta caggaaacaa accttgcctt    3240
gaaatttaca cagtgag                                                   3257

<210> SEQ ID NO 22
<211> LENGTH: 2354
<212> TYPE: DNA
<213> ORGANISM: Homo sapiens

<400> SEQUENCE: 22
ggtctttgag cgctaacgtc tttctgtctc cccgcggtgg tgatgacggt gaaaactgag      60
gctgctaagg gcaccctcac ttactccagg atgaggggca tggtggcaat tctcatcgct     120
ttcatgaagc agaggaggat gggtctgaac gactttattc agaagattgc caataactcc     180
tatgcatgca acaccctga agttcagtcc atcttgaaga tctcccaacc tcaggagcct      240
gagcttatga atgccaaccc ttctcctcca ccaagtcctt ctcagcaaat caaccttggc     300
ccgtcgtcca atcctcatgc taaaccatct gactttcact tcttgaaagt gatcggaaag    360
ggcagttttg gaaaggttct tctagcaaga cacaaggcag aagaagtgtt ctatgcagtc     420
aaagttttac agaagaaagc aatcctgaaa aagaaagagg agaagcatat tatgtcggag    480
cggaatgttc tgttgaagaa tgtgaagcac ccttttcctgg tgggccttca cttctctttc    540
cagactgctg acaaattgta ctttgtccta gactacatta tggtggaga ttgttctac     600 catctccaga gggaacgctg cttcctgaa ccacgggctc gtttctatgc tgctgaaata     660
gccagtgcct gggctacct gcattcactg aacatcgttt atagagactt aaaaccagag     720 aatatttgc tagattcaca gggacacatt gtccttactg acttcggact ctgcaaggag    780
aacattgaac acaacagcac aacatccacc ttctgtggca cgccggagta tctcgcacct    840
```

```
gaggtgcttc ataagcagcc ttatgacagg actgtggact ggtggtgcct gggagctgtc        900
ttgtatgaga tgctgtatgg cctgccgcct ttttatagcc gaaacacagc tgaaatgtac        960
gacaacattc tgaacaagcc tctccagctg aaaccaaata ttacaaattc cgcaagacac       1020
ctcctggagg gcctcctgca aaggacagg acaaagcggc tcggggccaa ggatgacttc       1080
atggagatta agagtcatgt cttcttctcc ttaattaact gggatgatct cattaataag       1140
aagattactc ccccttttaa cccaaatgtg agtgggccca acgacctacg cactttgac        1200 cccgagttta ccgaagagcc tgtccccaac tccattggca agtccctga cagcgtcctc       1260 gtcacagcca gcgtcaagga agctgccgag gctttcctag gcttttccta tgcgcctccc       1320
acggactctt tcctctgaac cctgttaggg cttggtttta aaggatttta tgtgtgtttc       1380
cgaatgtttt agttagcctt tggtggagc cgccagctga caggacatct tacaagagaa       1440
tttgcacatc tctggaagct tagcaatctt attgcacact gttcgctgga agcttttga       1500 agagcacatt ctcctcagtg agctcatgag gttttcattt ttattcttcc ttccaacgtg       1560
gtgctatctc tgaaacgagc gttagagtgc cgccttagac ggaggcagga gtttcgttag       1620
aaagcggacg ctgttctaaa aaggtctcc tgcagatctg tctgggctgt gatgacgaat       1680
attatgaaat gtgcctttc tgaagagatt gtgttagctc caaagctttt cctatcgcag       1740
tgtttcagtt ctttattttc ccttgtggat atgctgtgtg aaccgtcgtg tgagtgtggt       1800
atgcctgatc acagatggat tttgttataa gcatcaatgt gacacttgca ggacactaca       1860
acgtgggaca ttgtttgttt cttccatatt tggaagataa atttatgtgt agacttttt       1920 gtaagatacg gttaataact aaaatttatt gaaatggtct tgcaatgact cgtattcaga       1980
tgcttaaaga aagcattgct gctacaaata tttctatttt tagaaagggt ttttatggac       2040
caatgcccca gttgtcagtc agagccgttg gtgttttca ttgtttaaaa tgtcacctgt       2100
aaaatgggca ttatttatgt tttttttttt gcattcctga taattgtatg tattgtataa       2160
agaacgtctg tacattgggt tataacacta gtatatttaa acttacaggc ttatttgtaa       2220
tgtaaaccac cattttaatg tactgtaatt aacatggtta taatacgtac aatccttccc       2280
tcatcccatc acacaacttt ttttgtgtgt gataaactga ttttggtttg caataaaacc       2340
ttgaaaaata ttta                                                         2354

<210> SEQ ID NO 23
<211> LENGTH: 1728
<212> TYPE: DNA
<213> ORGANISM: Homo sapiens

<400> SEQUENCE: 23
gagcagcaga atttcaactc cagtagactt gaatatgcct ctgggcaaag aagcagagct         60
aacgaggaaa gggatttaaa gagttttttct tgggtgtttg tcaaactttt attccctgtc       120
tgtgtgcaga ggggattcaa cttcaatttt tctgcagtgg ctctgggtcc agccccttac       180
ttaaagatct ggaaagcatg aagactgggc ttttttttcct atgtctcttg ggaactgcag       240
ctgcaatccc gacaaatgca agattattat ctgatcattc caaccaact gctgaaacgg        300 tagcaccctga caacactgca atccccagtt taagggctga agctgaagaa atgaaaaag        360 aaacagcagt atccacagaa gacgattccc accataaggc tgaaaaatca tcagtactaa       420
agtcaaaaga ggaaagccat gaacagtcag cagaacaggg caagagttct agccaagagc       480
tgggattgaa ggatcaagag gacagtgatg gtcacttaag tgtgaatttg gagtatgcac       540
```

```
caactgaagg tacattggac ataaaagaag atatgagtga gcctcaggag aaaaaactct    600
cagagaacac tgatttttg gctcctggtg ttagttcctt cacagattct aaccaacaag    660
aaagtatcac aaagagagag gaaaaccaag aacaacctag aaattattca catcatcagt    720
tgaacaggag cagtaaacat agccaaggcc taagggatca aggaaaccaa gagcaggatc    780
caaatatttc aatggagaa gaggaagaag aaaaagagcc aggtgaagtt ggtacccaca    840
atgataacca agaaagaaag acagaattgc ccagggagca tgctaacagc aagcaggagg    900
aagacaatac ccaatctgat gatattttgg aagagtctga tcaaccaact caagtaagca    960
agatgcagga ggatgaattt gatcagggta accaagaaca agaagataac tccaatgcag   1020
aaatggaaga ggaaaatgca tcgaacgtca ataagcacat tcaagaaact gaatggcaga   1080
gtcaagaggg taaaactggc ctagaagcta tcagcaacca aaagagaca gagaaagaaga   1140 ctgtttctga ggctctgctc atggaaccta ctgatgatgg taataccacg cccagaaatc   1200
atggagttga tgatggc gatgatgatg gcgatgatgg cggcactgat ggccccaggc   1260
acagtgcaag tgatgactac ttcatcccaa gccaggcctt tctggaggcc gagagagctc   1320
aatccattgc ctatcacctc aaaattgagg agcaaagaga aaagtacat gaaaatgaaa   1380 atataggtac cactgagcct ggagagcacc aagaggccaa gaaagcagag aactcatcaa   1440
atgaggagga aacgtcaagt gaaggcaaca tgagggtgca tgctgtggat tcttgcatga   1500
gcttccagtg taaaagaggc cacatctgta aggcagacca acagggaaaa cctcactgtg   1560
tctgccagga tccagtgact tgtcctccaa caaaacccct tgatcaagtt tgtggcactg   1620
acaatcagac ctatgctagt tcctgtcatc tattcgctac taaatgcaga ctggagggga   1680
ccaaaaaggg gcatcaactc cagctggatt attttggagc ctgcaaat                1728

<210> SEQ ID NO 24
<211> LENGTH: 1848
<212> TYPE: DNA
<213> ORGANISM: Homo sapiens

<400> SEQUENCE: 24
cggataagga caaaaaacgc cagaagaaaa gaggcatttt ccccaaagta gcaacaaata     60
tcatgagagc atggctcttc cagcatctca cacatccgta cccttccgaa gagcagaaga    120
aacagttagc gcaagacaca ggacttacaa ttctccaagt aaacaactgg tttattaatg    180
ccagaagaag aatagtacag cccatgattg accagtcaaa tcgagcagtg agccaaggag    240
cagcatatag tccagagggt cagcccatgg ggagctttgt gttggatggt cagcaacaca    300
tggggatccg gcctgcagga cctatgagtg gaatgggcat gaatatgggc atggatgggc    360
aatggcacta catgtaacct tcatcatgta aagcaatcgc aaagcaaggg ggaagtttgc    420
agagcatgcc aggggactac gtttctcagg gtggtcctat gggaatgagt atggcacagc    480
caagttacac tcctccccag atgaccccac accctactca attaagacat ggaccccaa    540 tgcattcata tttgccaagc catccccacc acccagccat gatgatgcac ggaggacccc    600
ctacccaccc tggaatgact atgtcagcac agagccccac aatgttaaat tctgtagatc    660
ccaatgttgg cggacaggtt atggacattc atgcccaata gtataaggga actcaaggga    720
aaaggaaaca cacgcaaaaa ctattttaag actttctgaa ctttgaccag atgttgacac    780
ttaatatgaa attccagaca gctgtgatta ttttttactt ttgtcatttt tcatcaagca    840
acagaggacc aatgcaacaa gaacacaaat gtgaaatcat gggctgactg agacaattct    900
gtccatgtaa agatcctctg gaaaaagact ccgagagtta aactactgt agtataaata    960
```

| | |
|---|---|
| taggaactaa gttaaacttg tacatttctg ttgatcacgc cgttatgttg cctcaaatag | 1020 |
| ttttagaaga gaaaaaaaaa tatatccttg ttttccacac tatgtgtgtt gttcccaaaa | 1080 |
| gaatgactgt tttggttcat cagtgaattc accatccagg agagactgtg gtatatattt | 1140 |
| taaacctgtt gggccaatga gaaaagaacc acactggaga tcatgatgaa cttttggctg | 1200 |
| aacctcatca ctcgaactcc agcttcaaga atgtgttttc atgcccggcc tttgttcctc | 1260 |
| cataaatgtg tcctttagtt tcaaacagat ctttatagtt cgtgcttcat aagccaattc | 1320 |
| ttattattat ttttggggga ctcttcttca aagagcttgc caatgaagat ttaaagacag | 1380 |
| agcaggagct tcttccagga gttctgagcc ttggttgtgg acaaaacaat cttaagttgg | 1440 |
| gcagctttcc tcaacacaaa aaaaagttat taatggtcat tgaaccataa ctaggacttt | 1500 |
| atcagaaact caaagcttgg gggataaaaa ggagcaagag aatactgtaa caaacttcgt | 1560 |
| acagagttcg gtctattaat tgtttcatgt tagatattct atgtgtttac ctcaattgaa | 1620 |
| aaaaaaaga atgtttttgc tagtatcaga tctgctgtgg aattggtatt gtatgtccat | 1680 |
| gaattcttct tttctcagca cgtgttcctc actagaagaa aatgctgtta cctttaagct | 1740 |
| ttgtcaaatt tacattaaaa tacttgtatg aggactgtga cgttatgtta aaaaaaaaaa | 1800 |
| ggtgttaagt cacaaaaagc ggtaataaat atttcatttt tgattttt | 1848 |

<210> SEQ ID NO 25
<211> LENGTH: 3164
<212> TYPE: DNA
<213> ORGANISM: Homo sapiens

<400> SEQUENCE: 25

| | |
|---|---|
| agcacactga ggaggcgatc cgccagcagg aggtggagca gctggacttc cgagacctcc | 60 |
| tggggaagaa ggtgagtaca aagaccctat cggaagacga cctgaaggag atcccagccg | 120 |
| agcagatgga tttccgtgcc aacctgcagc ggcaagtgaa gccaaagact gtgtctgagg | 180 |
| aagagaggaa ggtgcacagc ccccagcagg tcgattttcg ctctgtcctg gccaagaagg | 240 |
| ggacttccaa gaccccgtg cctgagaagg tgccaccgcc aaaacctgcc accccggatt | 300 |
| ttcgctcagt gctgggtggc aagaagaaat taccagcaga gaatggcagc agcagtgccg | 360 |
| agaccctgaa tgccaaggca gtggagagtt ccaagcccct gagcaatgca cagccttcag | 420 |
| ggcccttgaa accgtgggc aacgccaagc ctgctgagac cctgaagcca atgggcaacg | 480 |
| ccaagcctgc cgagaccctg aagcccatgg gcaatgccaa gcctgatgag aacctgaaat | 540 |
| ccgctagcaa agaagaactc aagaaagacg ttaagaatga tgtgaactgc aagagaggcc | 600 |
| atgcagggac cacagataat gaaaagagat cagagagcca ggggacagcc ccagccttca | 660 |
| agcagaagct gcaagatgtt catgtggcag agggcaagaa gctgctgctc cagtgccagg | 720 |
| tgtcttctga ccccccagcc accatcatct ggacgctgaa cggaaagacc atcaagacca | 780 |
| ccaagttcat catcctctcc caggaaggct cactctgctc cgtctccatc gagaaggcac | 840 |
| tgcctgagga cagaggctta tacaagtgtg tagccaagaa tgacgctggc caggcggagt | 900 |
| gctcctgcca agtcaccgtg gatgatgctc cagccagtga gaacaccaag gcccagagga | 960 |
| tgaaatcccg gaggcccaag agctctcttc ctcccgtgct aggaactgag agtgatgcga | 1020 |
| ctgtgaaaaa gaaacctgcc cccaagacac ctccgaaggc agcaatgccc cctcagatca | 1080 |
| tccagttccc tgaggaccag aaggtacgcg caggagagtc agtggagctg tttggcaaag | 1140 |
| tgacaggcac tcagcccatc acctgtacct ggatgaagtt ccgaaagcag atccaggaaa | 1200 |

```
gcgagcacat gaaggtggag aacagcgaga atggcagcaa gctcaccatc ctggccgcgc   1260
gccaggagca ctgcggctgc tacacactgc tggtggagaa caagctgggc agcaggcagg   1320
cccaggtcaa cctcactgtc gtggataagc cagaccccc agctggcaca ccttgtgcct   1380
ctgacattcg gagctcctca ctgaccctgt cctggtatgg ctcctcatat gatggggca    1440 gtgctgtaca gtcctacagc atcgagatct gggactcagc caacaagacg tggaaggaac   1500
tagccacatg ccgcagcacc tctttcaacg tccaggacct gctgcctgac cacgaatata   1560
agttccgtgt acgtgcaatc aacgtgtatg aaccagtga ccaagccag gagtctgaac     1620 tcacaacggt aggagagaaa cctgaagagc cgaaggatga agtggaggtg tcagacgatg   1680
atgagaagga gcccgaggtt gattaccgga cagtgacaat caatactgaa caaaaagtat   1740
ctgacttcta cgacattgag gagagattag gatctgggaa atttggacag gtctttcgac   1800
ttgtagaaaa gaaaactcga aaagtctggg cagggaagtt cttcaaggca tattcagcaa   1860
aagagaaaga gaatatccgg caggagatta gcatcatgaa ctgcctccac caccctaagc   1920
tggtccagtg tgtggatgcc tttgaagaaa aggccaacat cgtcatggtc ctggagatcg   1980
tgtcaggagg ggagctgttt gagcgcatca ttgacgagga ctttgagctg acggagcgtg   2040
agtgcatcaa gtacatgcgg cagatctcgg agggagtgga gtacatccac aagcagggca   2100
tcgtgcacct ggacctcaag ccggagaaca tcatgtgtgt caacaagacg ggcaccagga   2160
tcaagctcat cgactttggt ctggccagga ggctggagaa cgcggggtct ctgaaggtcc   2220
tctttggcac cccagaattt gtggctcctg aagtgatcaa ctatgagccc atcggctacg   2280
ccacagacat gtggagcatc ggggtcatct gctacatcct agtcagtggc ctttccccct   2340
tcatgggaga caacgataac gaaaccttgg ccaacgttac ctcagccacc tgggacttcg   2400
acgacgaggc attcgatgag atctccgacg atgccaagga tttcatcagc aatctgctga   2460
agaaagatat gaaaaccgc ctggactgca cgcagtgcct tcagcatcca tggctaatga   2520
aagataccaa gaacatggag gccaagaaac tctccaagga ccggatgaag aagtacatgg   2580
caagaaggaa atggcagaaa acgggcaatg ctgtgagagc cattggaaga ctgtcctcta   2640
tggcaatgat ctcagggctc agtggcagga aatcctcaac agggtcacca accagcccgc   2700
tcaatgcaga aaaactagaa tctgaagaag atgtgtccca agctttcctt gaggctgttg   2760
ctgaggaaaa gcctcatgta aaaccctatt tctctaagac cattcgcgat ttagaagttg   2820
tggagggaag tgctgctaga tttgactgca agattgaagg atacccagac cccgaggttg   2880
tctggttcaa agatgaccag tcaatcaggg agtcccgcca cttccagata gactacgatg   2940
aggacgggaa ctgctcttta attattagtg atgtttgcgg ggatgacgat gccaagtaca   3000
cctgcaaggc tgtcaacagt cttggagaag ccacctgcac agcagagctc attgtggaaa   3060
cgatggagga aggtgaaggg gaaggggaag aggaagaaga gtgaaacaaa gccagagaaa   3120
agcagtttct aagtcatatt aaaaggacta tttctctaaa actc                    3164
```

<210> SEQ ID NO 26
<211> LENGTH: 3851
<212> TYPE: DNA
<213> ORGANISM: Homo sapiens

<400> SEQUENCE: 26

```
ctctcccaac cgcctcgtcg cactcctcag gctgagagca ccgctgcact cgcggccggc     60
gatgcgggac cccggcgcgg ccgctccgct ttcgtccctg ggcctctgtg ccctggtgct    120
ggcgctgctg ggcgcactgt ccgcgggcgc cggggcgcag ccgtaccacg agagaagggg    180
```

```
catctccgtg ccggaccacg gcttctgcca gcccatctcc atcccgctgt gcacggacat    240
cgcctacaac cagaccatcc tgcccaacct gctgggccac acgaaccaag aggacgcggg    300
cctcgaggtg caccagttct acccgctggt gaaggtgcag tgttctcccg aactccgctt    360
tttcttatgc tccatgtatg cgcccgtgtg caccgtgctc gatcaggcca tcccgccgtg    420
tcgttctctg tgcgagcgcg cccgccaggg ctgcgaggcg ctcatgaaca agttcggctt    480
ccagtggccc gagcggctgc gctgcgagaa cttcccggtg caccggtgcgg gcgagatctg    540 cgtgggccag aacacgtcgg acggctccgg gggcccaggc ggcggcccca ctgcctaccc    600
taccgcgccc tacctgccgg acctgccctt caccgcgctg cccccggggg cctcagatgg    660
cagggggcgt cccgccttcc ccttctcatg ccccgtcag ctcaaggtgc cccgtacct     720 gggctaccgc ttcctgggtg agcgcgattg tggcgccccg tgcgaaccgg gccgtgccaa    780
cggcctgatg tactttaagg aggaggagag gcgcttcgcc cgcctctggg tgggcgtgtg    840
gtccgtgctg tgctgcgcct cgacgctctt taccgttctc acctacctgg tggacatgcg    900
gcgcttcagc tacccagagc ggcccatcat cttcctgtcg ggctgctact tcatggtggc    960
cgtggcgcac gtggccggct ccttctaga ggaccgcgcc gtgtgcgtgg agcgcttctc    1020
ggacgatggc taccgcacgg tggcgcaggg caccaagaag gagggctgca ccatcctctt    1080
catggtgctc tacttcttcg gcatggccag ctccatctgg tgggtcattc tgtctctcac    1140
ttggttcctg gcggccggca tgaagtgggg ccacgaggcc atcgaggcca actcgcagta    1200
cttccacctg gccgcgtggg ccgtgcccgc cgtcaagacc atcactatcc tggccatggg    1260
ccaggtagac ggggacctgc tgagcggggt gtgctacgtt ggcctctcca gtgtggacgc    1320
gctgcggggc ttcgtgctgg cgcctctgtt cgtctacctc ttcataggca cgtccttctt    1380
gctggccggc ttcgtgtccc tcttccgtat ccgcaccatc atgaaacacg acggcaccaa    1440
gaccgagaag ctggagaagc tcatggtgcg catcggcgtc ttcagcgtgc tctacacagt    1500
gcccgccacc atcgtcctgg cctgctactt ctacgagcag gccttccgcg agcactggga    1560
gcgcacctgg ctcctgcaga cgtgcaagag ctatgccgtg ccctgcccgc ccggccactt    1620
cccgcccatg agccccgact tcaccgtctt catgatcaag tacctgatga ccatgatcgt    1680
cggcatcacc actggcttct ggatctggtc gggcaagacc ctgcagtcgt ggcgcgccgctt    1740 ctaccacaga cttagccaca gcagcaaggg ggagactgcg gtatgagccc cggcccctcc    1800
ccacctttcc caccccagcc ctcttgcaag aggagaggca cggtagggaa aagaactgct    1860 gggtggggc ctgtttctgt aactttctcc ccctctactg agaagtgacc tggaagtgag    1920
aagttctttg cagatttggg gcgaggggtg atttggaaaa aagacctgg gtggaaagcg    1980 gtttggatga aaagatttca ggcaaagact tgcaggaaga tgatgataac ggcgatgtga    2040
atcgtcaaag gtacgggcca gcttgtgcct aatagaaggt tgagaccagc agagactgct    2100
gtgagtttct cccggctccg aggctgaacg gggactgtga gcgatccccc tgctgcaggg    2160
cgagtggcct gtccagaccc ctgtgaggcc ccgggaaagg tacagccctg tctgcggtgg    2220
ctgctttgtt ggaaagaggg agggcctcct gcggtgtgct tgtcaagcag tggtcaaacc    2280
ataatctctt ttcactgggg ccaaactgga gcccagatgg gttaatttcc agggtcagac    2340
attacggtct ctcctcccct gcccctccc gcctgttttt cctcccgtac tgctttcagg    2400
tcttgtaaaa taagcatttg gaagtcttgg gaggcctgcc tgctagaatc ctaatgtgag    2460
gatgcaaaag aaatgatgat aacatttga gataaggcca aggagacgtg gagtaggtat    2520
```

```
ttttgctact ttttcatttt ctggggaagg caggaggcag aaagacgggt gttttatttg    2580
gtctaatacc ctgaaaagaa gtgatgactt gttgcttttc aaaacaggaa tgcattttc     2640 cccttgtctt tgttgtaaga gacaaaagag gaaacaaaag tgtctccctg tggaaaggca    2700
taactgtgac gaaagcaact tttataggca aagcagcgca aatctgaggt ttcccgttgg    2760
ttgttaattt ggttgagata acattcctt tttaaggaaa agtgaagagc agtgtgctgt     2820
cacacaccgt taagccagag gttctgactt cgctaaagga aatgtaagag gttttgttgt    2880
ctgttttaaa taaatttaat tcggaacaca tgatccaaca gactatgtta aaatattcag    2940
ggaaatctct cccttcattt acttttctt gctataagcc tatatttagg tttcttttct     3000 attttttct cccatttgga tcctttgagg taaaaaaaca taatgtcttc agcctcataa     3060
taaaggaaag ttaattaaaa aaaaaagca aagagccatt ttgtcctgtt ttcttggttc     3120
catcaatctg tttattaaac atcatccata tgctgaccct gtctctgtgt ggttgggttg    3180
ggaggcgatc agcagatacc atagtgaacg aagaggaagg tttgaaccat gggccccatc    3240
tttaaagaaa gtcattaaaa gaaggtaaac ttcaaagtga ttctggagtt ctttgaaatg    3300
tgctggaaga cttaaattta ttaatcttaa atcatgtact ttttttctgt aatagaactc    3360
ggattctttt gcatgatggg gtaaagctta gcagagaatc atgggagcta acctttatcc    3420
cacctttgac actaccctcc aatcttgcaa cactatcctg tttctcagaa cagttttaa    3480 atgccaatca tagagggtac tgtaaagtgt acaagttact ttatatatgt aatgttcact    3540
tgagtggaac tgcttttac attaaagtta aaatcgatct tgtgtttctt caaccttcaa    3600
aactatctca tctgtcagat ttttaaaact ccaacacagg ttttggcatc ttttgtgctg    3660
tatcttttaa gtgcatgtga aatttgtaaa atagagataa gtacagtatg tatattttgt    3720
aaatctccca tttttgtaag aaaatatata ttgtatttat acattttac tttggatttt     3780 tgttttgttg gctttaaagg tctaccccac tttatcacat gtacagatca caaataaatt    3840
tttttaaata c                                                         3851
```

<210> SEQ ID NO 27
<211> LENGTH: 1476
<212> TYPE: DNA
<213> ORGANISM: Homo sapiens

<400> SEQUENCE: 27

```
ggggctcggg acggccgggc tgggagctgg agcccacagc gggaagcggc cgccgcccgg     60
gcctcgcagg gctaggcgag gcgaggggg gcggggccgg gcgctacggg aaggggaggc    120
cgcgcggacc gggagccgca ccgcgccagc cgggctgcag cggccgcgca ccaaggctgc    180 gatgggctg gagacggaga aggcggacgt acagctcttc atggacgacg actcctacag    240
ccaccacagc ggcctcgagt acgccgaccc cgagaagttc gcggactcgg accaggaccg    300
ggatccccac cggctcaact cgcatctcaa gctgggcttc gaggatgtga tcgcagagcc    360
ggtgactacg cactcctttg acaaagtgtg gatctgcagc catgccctct ttgaaatcag    420
caaatacgta atgtacaagt tcctgacggt gttcctggcc attcccctgg ccttcattgc    480
gggaattctc tttgccaccc tcagctgtct gcacatctgg attttaatgc cttttgtaaa    540
gacctgccta atggttctgc cttcagtgca gacaatatgg aagagtgtga cagatgttat    600
cattgctcca ttgtgtacga gcgtaggacg atgcttctct tctgtcagcc tgcaactgag    660
ccaggattga atacttggac cccaggtctg gagattggga tactgtaata cttcttttgtt   720 attataacat aaaagcacca ctgttctgtt catttcctag ctgttctaat taagaaaact    780
```

| | |
|---|---|
| attaagatga gcaaccacat ttagaaatgt ttattgacag gtcttttcaa ataatgcttt | 840 |
| tctaattaat agccaaagat ttcatatcta actttgtaac cagaattata cagtaagttg | 900 |
| acaccactta gatttaaagg cagacagttt tgctttagta caatagtata cattttataa | 960 |
| tgatgaactt ataatgatta agggacattt ctataaaaat actacaatag ttttatgcac | 1020 |
| aacttcccat taaaaatgag atttcttatt tgtttgtctg ttttttactct gggagtaata | 1080 |
| cttttttaaat taccttttaca tatatagtca ctggcatact gagaatatac aatgatcctg | 1140 |
| gaaattgcag taacaaaagc acacaacgat tatagtaact ataagataca ataaaacaaa | 1200 |
| taaatatgaa agtagattca tgaaaatgta ttcctttaaa atattgtttt cctacaggcc | 1260 |
| tatttaacaa gatgtttcat tttactgtat attttgtagt taatataaat gttgctctaa | 1320 |
| tcagattgct taaaagcatt tttattatat ttatgttgtt gaactaatat atgaaataag | 1380 |
| taaatgtagc tcccacaagg taaacttcat tggtaagatt gcactgttct gattatgtaa | 1440 |
| gcatttgtac atcttctttg gaaataaaag ataaaa | 1476 |

<210> SEQ ID NO 28
<211> LENGTH: 4116
<212> TYPE: DNA
<213> ORGANISM: Homo sapiens

<400> SEQUENCE: 28

| | |
|---|---|
| gtttagaaca gcctacagac ccagtggcac gagacgggcc tctctcccaa acatcttcca | 60 |
| agccagatcc tagtcagtgg gaaagcccca gcttcaaccc ctttgggagc cactctgttc | 120 |
| tgcagaactc cccaccccctc tcttctgagg gctcctacca ctttgaccca gataactttg | 180 |
| acgaatccat ggatcccttt aaaccaacta cgaccttaac aagcagtgac ttttgttctc | 240 |
| ccactggtaa tcacgttaat gaaatcttag aatcacccaa aaggcaaag tcgcgtttaa | 300 |
| taacgactac tgaacaagtg aaatttctct gttttctgtt gagtggctgt aaggtgaaga | 360 |
| agcatgaaac tcagtctctc gccctggatg catgttctcg ggatgaaggg gcagtgatct | 420 |
| cccagatttc agacatttct aatagggatg gccatgctac tgatgaggag aaactggcat | 480 |
| ccacgtcatg tggtcagaaa tcagctggtg ccgaggtgaa aggtgagcca gaggaagacc | 540 |
| tggagtactt tgaatgttcc aatgttcctg tgtctaccat aaatcatgcg ttttcatcct | 600 |
| cagaagcagg catagagaag gagacgtgcc agaagatgga agaagacggg tccactgtgc | 660 |
| ttgggctgct ggagtcctct gcagagaagg cccctgtgtc ggtgtcctgt ggaggtgaga | 720 |
| gcccccctgga tgggatctgc ctcagcgaat cagacaagac agccgtgctc accttaataa | 780 |
| gagaagagat aattactaaa gagattgaag caaatgaatg gaagaagaaa tacgaagaga | 840 |
| cccggcaaga agttttggag atgaggaaaa ttgtagctga atatgaaaag actattgctc | 900 |
| aaatgattga tgaacaaagg acaagtatga cctctcagaa gagcttccag caactgacca | 960 |
| tggagaagga acaggccctg gctgacctta actctgtgga aggtcccttt tctgatctct | 1020 |
| tcaggagata tgaacctg aaaggtgttc tggaagggtt caagaagaat gaagaagcct | 1080 |
| tgaagaaatg tgctcaggat tacttagcca gagttaaaca agaggagcag cgataccagg | 1140 |
| ccctgaaaat ccacgcagaa gagaaactgg acaaagccaa tgaagagatt gctcaggttc | 1200 |
| gaacaaaagc aaaggctgag agtgcagctc tccatgctgg actccgcaaa gagcagatga | 1260 |
| aggtggagtc cctggaaagg gccctgcagc agaagaacca agaaattgaa gaactgacaa | 1320 |
| aaatctgtga tgagctgatt gcaaagctgg gaaagactga ctgagacact cccctgttta | 1380 |

```
gctcaacaga tctgcatttg gctgcttctc ttgtgaccac aattatcttg ccttatccag    1440
gaataattgc ccctttgcag agaaaaaaaa aaacttaaaa aaagcacatg cctactgctg    1500
cctgtcccgc tttgctgcca atgcaacagc cctggaagaa acctagagg gttgcatagt     1560
ctagaaagga gtgtgacctg acagtgctgg agcctcctag tttcccccta tgaaggttcc    1620
cttaggctgc tgagtttggg tttgtgattt atctttagtt tgttttaaag tcatctttac    1680
tttcccaaat gtgttaaatt tgtaactcct ctttggggtc ttctccacca cctgtctgat    1740
ttttttgtga tctgtttaat cttttaattt tttagtatca gtggttttat ttaaggagac    1800
agtttggcct attgttactt ccaatttata atcaagaagg ggctctggat cccctttaa     1860
attacacaca ctctcacaca catacatgta tgtttataga tgctgctgct cttttccctg    1920
aagcatagtc aagtaagaac tgctctacag aaggacatat tccttggat gtgagaccct     1980
attttgaaat agagtcctga ctcagaacac caacttaaga atttggggga ttaaagatgt    2040
gaagaccaca gtcttgggtt ttcatatctg gagaagacta tttgccatga cgttttgttg    2100
ccctggtatt tggacactcc tcagctttaa tgggtgtggc cccttaggg ttagtcctca     2160
gactaatgat agtgtctgct ttctgcatga acggcaatat gggactccct ccaagctagg    2220
gtttggcaag tctgccctag agtcatttac tctcctctgc ctccatttgt aatacagaa     2280
tcaacattta gtcttcatta tcttttttt tttttttgag acagagtttc gatctatttt     2340
aagtatgtga agaaaatcta cttgtaaaag gctcagatct taattaaaag gtaattgtag    2400
cacattacca attataaggt gaagaaatgt ttttttccca agtgtgatgc attgttcttc    2460
agatgttgaa aagaaagcaa aaaataccct ctaacttaag acagaatttt taacaaaatg    2520
agcagtaaaa gtcacatgaa ccactccaaa aatcagtgca ttttgcatat ttttaaacaa    2580
agacagcttg ttgaatactg agaagaggag tgcaaggaga aggtctgtac taacaaagcc    2640
aaattcctca agctcttact ggactcagtt cagagtggtg ggccattaac cccaacatgg    2700
aatttttcca tataaatctc aatgaattcc ctttcatttg aataggcaaa cccaaatcca    2760
tgcaagtgtt ttaaagcact gtcctgtctt aatcttacat gctgaaagtc ttcatggtga    2820
tatgcactat attcagtata cgtatgtttt cctacttctc ttgtaaaact gttgcatgat    2880
ccaacttcag caatgaattg tgcctagtgg agaacctcta tagatcttaa aaaatgaatt    2940
attctttagc agtgtattac tcacatgggt gcaatcttta gccccaggga ggtcaataat    3000
gtctttaaaa gccagaagtc acattttacc aatatgcatt tatcataatt ggtgcttagg    3060
ctgtatattc aagcctgttg tcttaacatt ttgtataaaa aagaacaaca gaaattatct    3120
gtcatttgag aagtggcttg acaatcattt gagctttgaa agcagtcact gtggtgtaat    3180
atgaatgctg tcctagtggt catagtacca agggcacgtg tctccccttg gtataactga    3240
tttcctttt agtcctctac tgctaaataa gttaattttg cattttgcag aaagaaacat     3300
tgattgctaa atctttttgc tgctgtgttt tggtgttttc atgtttactt gttttatatt    3360
gatctgtttt aagtatgaga ggcttatagt gccctccatt gtaaatccat agtcatcttt    3420
ttaagcttat tgtgtttaag aaagtagcta tgtgttaaac agaggtgatg gcagcccttc    3480
cctagcacac tggtggaaga gaccccttaa gaacctgacc ccagtgaatg aagctgatgc    3540
acagggagca ccaaaggacc ttcgttaagt gataattgtc ctggcctctc agccatgacc    3600
gttatgagga aatatccccc attcgaactt aacagatgcc tcctctccaa agagaattaa    3660
aatcgtagct tgtacagatc aagagaatat actgggcaga atgaagtatg tttgtttatt    3720
tttctttaaa aataaaggat tttggaactc tggagagtaa gaatatagta tagagtttgc    3780
```

| | |
|---|---|
| ctcaacacat gtgagggcca aataacctgc tagctaggca gtaataaact ctgttacaga | 3840 |
| agagaaaaag ggccgggcac agtggcttat tcctgtaatc ccaacactgt ggaaggccga | 3900 |
| ggcaggagga tcacttgagt ccaggagttt gaaacctacc taggcaacat ggtgaaacct | 3960 |
| tgtctctacc aaaataaaaa ttagctgggc atggtggcac gtgcctgtgg tcccagctac | 4020 |
| ttgggaggct gaggtgggag cctgggaggt caaggctgca gtgagccatg atcatgccac | 4080 |
| tgcactccat cctgggtgac agcaagatct tgtctc | 4116 |

<210> SEQ ID NO 29
<211> LENGTH: 540
<212> TYPE: DNA
<213> ORGANISM: Homo sapiens

<400> SEQUENCE: 29

| | |
|---|---|
| cgagttcccc gaggtgtacg tgcccaccgt cttcgagaac tatgtggccg acattgaggt | 60 |
| ggacggcaag caggtggagc tggcgctgtg ggacacggcg ggccaggagg actacgaccg | 120 |
| cctgcggccg ctctcctacc cggacaccga cgtcattctc atgtgcttct cggtggacag | 180 |
| cccggactcg ctggagaaca tccccgagaa gtgggtcccc gaggtgaagc acttctgtcc | 240 |
| caatgtgccc atcatcctgg tggccaacaa aaaagacctg cgcagcgacg agcatgtccg | 300 |
| cacagagctg gcccgcatga agcaggaacc cgtgcgcacg gatgacggcc gcgccatggc | 360 |
| cgtgcgcatc caagcctacg actacctcga gtgctctgcc aagaccaagg aaggcgtgcg | 420 |
| cgaggtcttc gagacggcca cgcgcgccgc gctgcagaag cgctacggct cccagaacgg | 480 |
| ctgcatcaac tgctgcaagg tgctatgagg gccgcgcccg tcgcgcctgc ccctgccggc | 540 |

<210> SEQ ID NO 30
<211> LENGTH: 1063
<212> TYPE: DNA
<213> ORGANISM: Homo sapiens

<400> SEQUENCE: 30

| | |
|---|---|
| cggggagacc atggggcccc tctcagcccc ttcctgcaca cacctcatca cttggaaggg | 60 |
| ggtcctgctc acagcatcac ttttaaactt ctggaatccg cccaccactg ccgaagtcac | 120 |
| gattgaagcc cagccaccca agtttctga ggggaaggat gttcttctac ttgttcacaa | 180 |
| tttgccccag aatcttcctg gctacttctg gtacaaaggg gaaatgacgg acctctacca | 240 |
| ttacattata tcgtatatag ttgatggtaa aataattata tatgggcctg catacagtgg | 300 |
| aagagaaaca gtatattcca acgcatccct gctgatccag aatgtcaccc ggaaggatgc | 360 |
| aggaacctac accttacaca tcataaagcg aggtgatgag actagagaag aaattcgaca | 420 |
| tttcacCttc accttatact atggtccaga cctccccaga atttacccTt cattcaccta | 480 |
| ttacggttca ggagaaaacc tcgacttgtc ctgcttcacg gaatctaacc caccggcaga | 540 |
| gtattttgg acaattaatg gaagtttca gcaatcagga caaaagctct ttatccccca | 600 |
| aattactaga aatcatagcg ggctctatgt ttgctctgtt cataactcag ccactggcaa | 660 |
| ggaaatctcc aaatccatga cagtcaaagt ctctggtccc tgccatggag acctgacaga | 720 |
| gtttcagtca tgactgcaac aactgagaca ctgagaaaaa gaacaggctg ataccttcat | 780 |
| gaaattcaag acaaagaaga aaaaaactca atgttattgg actaaataat caaaggata | 840 |
| atgttttcat aattttttat tggaaaatgt gctgattctt tgaatgtttt attctccaga | 900 |
| tttatgaact ttttttcttc agcaattggt aaagtatact tttgtaaaca aaaattgaaa | 960 |

| | |
|---|---|
| tatttgctttt tgctgtctat ctgaatgccc cagaattgtg aaactactca tgagtactca | 1020 |
| taggtttatg gtaataaagt tatttgcaca tgttccgtag ttt | 1063 |

<210> SEQ ID NO 31
<211> LENGTH: 1117
<212> TYPE: DNA
<213> ORGANISM: Homo sapiens

<400> SEQUENCE: 31

| | |
|---|---|
| gcaccaacca gcaccatgcc catgatactg gggtactggg acatccgcgg gctggcccac | 60 |
| gccatccgcc tgctcctgga atacacagac tcaagctatg aggaaaagaa gtacacgatg | 120 |
| ggggacgctc ctgattatga cagaagccag tggctgaatg aaaaattcaa gctgggcctg | 180 |
| gactttccca atctgcccta cttgattgat ggggctcaca agatcaccca gagcaacgcc | 240 |
| atcttgtgct acattgcccg caagcacaac ctgtgtgggg agacagaaga ggagaagatt | 300 |
| cgtgtggaca ttttggagaa ccagaccatg acaaccata tgcagctggg catgatctgc | 360 |
| tacaatccag aatttgagaa actgaagcca agtacttgg aggaactccc tgaaaagcta | 420 |
| aagctctact cagagtttct ggggaagcgg ccatggtttg caggaaacaa gatcactttt | 480 |
| gtagattttc tcgtctatga tgtccttgac ctccaccgta tatttgagcc caactgcttg | 540 |
| gacgccttcc caaatctgaa ggacttcatc tcccgctttg agggcttgga gaagatctct | 600 |
| gcctacatga agtccagccg cttcctccca agacctgtgt tctcaaagat ggctgtctgg | 660 |
| ggcaacaagt agggccttga aggcaggagg tgggagtgag gagcccatac tcagcctgct | 720 |
| gcccaggctg tgcagcgcag ctggactctg catcccagca cctgcctcct cgttcctttc | 780 |
| tcctgtttat tccatctttt actcccaaga cttcattgtc cctcttcact cccctaaac | 840 |
| ccctgtccca tgcaggccct ttgaagcctc agctaccac tatccttcgt gaacatcccc | 900 |
| tcccatcatt acccttccct gcactaaagc cagcctgacc ttccttcctg ttagtggttg | 960 |
| tgtctgctttt aaagcctgcc tggccctcg cctgtggagc tcagcccga gctgtccccg | 1020 |
| tgttgcatga aggagcagca ttgactggtt tacaggccct gctcctgcag catggtccct | 1080 |
| gcctaggcct acctgatgga agtaaagcct caaccac | 1117 |

<210> SEQ ID NO 32
<211> LENGTH: 1869
<212> TYPE: DNA
<213> ORGANISM: Homo sapiens

<400> SEQUENCE: 32

| | |
|---|---|
| ttcaggaacc ggtttggtgc tggtgctgga ggcggctatg gctttggagg tggtgccggt | 60 |
| agtggatttg gtttcggcgg tggagctggt ggtggctttg gctcggtgg cggagctggc | 120 |
| tttggaggtg gcttcggtgg ccctggcttt cctgtctgcc ctcctggagg tatccaagag | 180 |
| gtcactgtca accagagtct cctgactccc ctcaacctgc aaatcgaccc cagcatccag | 240 |
| agggtgagga ccgaggagcg cgagcagatc aagaccctca caataagtt tgcctccttc | 300 |
| atcgacaagg tgcggttcct ggagcagcag aacaaggttc tggacaccaa gtggaccctg | 360 |
| ctgcaggagc agggcaccaa gactgtgagg cagaacctgg agccgttgtt cgagcagtac | 420 |
| atcaacaacc tcaggaggca gctggacagc atcgtggggg aacggggccg cctggactca | 480 |
| gagctgagaa acatgcagga cctggtggaa gacttcaaga caagtatga ggatgaaatc | 540 |
| aacaagcgta ccactgctga gaatgagttt gtgatgctga agaaggatgt agatgctgcc | 600 |
| tacatgaaca aggtggagct ggaggccaag gttgatgcac tgatggatga gattaacttc | 660 |

```
atgaagatgt tctttgatgc ggagctgtcc cagatgcaga cgcatgtctc tgacacctca    720
gtggtcctct ccatggacaa caaccgcaac ctggacctgg atagcatcat cgctgaggtc    780
aaggcccagt atgaggagat tgccaaccgc agccggacag aagccgagtc ctggtatcag    840
accaagtatg aggagctgca gcagacagct ggccggcatg gcgatgacct ccgcaacacc    900
aagcatgaga tctctgagat gaaccggatg atccagaggc tgagagccga gattgacaat    960
gtcaagaaac agtgcgccaa tctgcagaac gccattgcgg atgccgagca gcgtggggag   1020
ctggccctca aggatgccag gaacaagctg gccgagctgg aggaggccct gcagaaggcc   1080
aagcaggaca tggcccggct gctgcgtgag taccaggagc tcatgaacac caagctggcc   1140
ctggacgtgg agatcgccac ttaccgcaag ctgctggagg gcgaggaatg cagactcagt   1200
ggagaaggag ttggaccagt caacatctct gttgtcacaa gcagtgtttc ctctggatat   1260
ggcagtggca gtggctatgg cggtggcctc ggtggaggtc ttggcggcgg cctcggtgga   1320
ggtcttgccg gaggtagcag tggaagctac tactccagca gcagtggggg tgtcggccta   1380
ggtggtgggc tcagtgtggg gggctctggc ttcagtgcaa gcagtggccg agggctgggg   1440
gtgggctttg gcagtggcgg gggtagcagc tccagcgtca aatttgtctc caccacctcc   1500
tcctcccgga gagcttcaa gagctaagaa cctgctgcaa gtcactgcct tccaagtgca   1560
gcaacccagc ccatggagat tgcctcttct aggcagttgc tcaagccatg ttttatcctt   1620
ttctggagag tagtctagac caagccaatt gcagaaccac attctttggt tcccaggaga   1680
gccccattcc cagcccctgg tctcccgtgc cgcagttcta tattctgctt caaatcagcc   1740
ttcaggtttc ccacagcatg gcccctgctg acacgagaac ccaaagtttt cccaaatcta   1800
aatcatcaaa acagaatccc caccccaatc ccaaattttg ttttggttct aactacctcc   1860
agaatgtgt                                                            1869

<210> SEQ ID NO 33
<211> LENGTH: 664
<212> TYPE: DNA
<213> ORGANISM: Homo sapiens

<400> SEQUENCE: 33
agtgatcagg gccaaagcgg tcagtgagaa ggaagtggac tctggaaacg acatttatgg     60
caaccctatc aagaggatcc agtatgagat caagcagata aagatgttca aagggcctga    120
gaaggatata gagtttatct acacggcccc ctcctcggca gtgtgtgggg tctcgctgga    180
cgttggagga aagaaggaat atctcattgc aggaaaggcc gagggggacg gcaagatgca    240
catcaccctc tgtgacttca tcgtgccctg ggacaccctg agcaccaccc agaagaagag    300
cctgaaccac aggtaccaga tgggctgcga gtgcaagatc acgcgctgcc ccatgatccc    360
gtgctacatc tcctcccgg acgagtgcct ctggatggca tgggtcacag agaagaacat    420
caacgggcac caggccaagt tcttcgcctg catcaagaga agtgacggct cctgtgcgtg    480
gtaccgcggc gcggcgcccc ccaagcagga gtttctcgac atcgaggacc cataagcagg    540
cctccaacgc ccctgtggcc aactgcaaaa aaagcctcca agggtttcga ctggtccagc    600
tctgacatcc cttcctggaa acagcatgaa taaaacactc atcccatggg tccaaattaa    660
tatg                                                                 664

<210> SEQ ID NO 34
<211> LENGTH: 2598
<212> TYPE: DNA
```

<213> ORGANISM: Homo sapiens

<400> SEQUENCE: 34

| | | | | | |
|---|---|---|---|---|---|
| tgtcgccacc | atggctccgc | accgccccgc | gcccgcgctg | ctttgcgcgc | tgtccctggc | 60 |
| gctgtgcgcg | ctgtcgctgc | ccgtccgcgc | ggccactgcg | tcgcgggggg | cgtcccaggc | 120 |
| gggggcgccc | caggggcggg | tgcccgaggc | gcggcccaac | agcatggtgg | tggaacaccc | 180 |
| cgagttcctc | aaggcaggga | aggagcctgg | cctgcagatc | tggcgtgtgg | agaagttcga | 240 |
| tctggtgccc | gtgccaccca | acctttatgg | agacttcttc | acgggcgacg | cctacgtcat | 300 |
| cctgaagaca | gtgcagctga | ggaacggaaa | tctgcagtat | gacctccact | actggctggg | 360 |
| caatgagtgc | agccaggatg | agagcggggc | ggccgccatc | tttaccgtgc | agctggatga | 420 |
| ctacctgaac | ggccgggccg | tgcagcaccg | tgaggtccag | ggcttcgagt | cggccacctt | 480 |
| cctaggctac | ttcaagtctg | gcctgaagta | caagaaagga | ggtgtggcat | caggattcaa | 540 |
| gcacgtggta | cccaacgagg | tggtggtgca | gagactcttc | caggtcaaag | gcggcgtgt | 600 |
| ggtccgtgcc | accgaggtac | ctgtgtcctg | ggagagcttc | aacaatggcg | actgcttcat | 660 |
| cctggacctg | gcaacaacaa | tccaccagtg | gtgtggttcc | aacagcaatc | ggtatgaaag | 720 |
| actgaaggcc | acacaggtgt | ccaagggcat | ccgggacaac | gagcggagtg | gccgggcccg | 780 |
| agtgcacgtg | tctgaggagg | gcactgagcc | cgaggcgatg | ctccaggtgc | tgggccccaa | 840 |
| gccggctctg | cctgcaggta | ccgaggacac | cgccaaggag | gatgcggcca | accgcaagct | 900 |
| ggccaagctc | tacaaggtct | ccaatggtgc | agggaccatg | tccgtctccc | tcgtggctga | 960 |
| tgagaacccc | ttcgcccagg | gggccctgaa | gtcagaggac | tgcttcatcc | tggaccacgg | 1020 |
| caaagatggg | aaaatctttg | tctggaaagg | caagcaggca | aacacggagg | agaggaaggc | 1080 |
| tgccctcaaa | acagcctctg | acttcatcac | caagatggac | taccccaagc | agactcaggt | 1140 |
| ctcggtcctt | cctgagggcg | gtgagacccc | actgttcaag | cagttcttca | agaactggcg | 1200 |
| ggacccagac | cagacagatg | gcctgggctt | gtcctacctt | tccagccata | tcgccaacgt | 1260 |
| ggagcgggtg | cccttcgacg | ccgccaccct | gcacacctcc | actgccatgg | ccgcccagca | 1320 |
| cggcatggat | gacgatggca | caggccagaa | acagatctgg | agaatcgaag | gttccaacaa | 1380 |
| ggtgcccgtg | gaccctgcca | catatggaca | gttctatgga | ggcgacagct | acatcattct | 1440 |
| gtacaactac | cgccatggtg | gccgccaggg | gcagataatc | tataactggc | agggtgccca | 1500 |
| gtctacccag | gatgaggtcg | ctgcatctgc | catcctgact | gctcagctgg | atgaggagct | 1560 |
| gggaggtacc | cctgtccaga | gccgtgtggt | ccaaggcaag | gagcccgccc | acctcatgag | 1620 |
| cctgtttggt | gggaagccca | tgatcatcta | caagggcggc | acctcccgcg | agggcgggca | 1680 |
| gacagccccc | gccagcaccc | gcctcttcca | ggtccgcgcc | aacagcgctg | gagccacccg | 1740 |
| ggctgttgag | gtattgccta | aggctggtgc | actgaactcc | aacgatgcct | tgttctgaa | 1800 |
| aaccccctca | gccgcctacc | tgtgggtggg | tacaggagcc | agcgaggcag | agaagacggg | 1860 |
| ggcccaggag | ctgctcaggg | tgctgcgggc | ccaacctgtg | caggtggcag | aaggcagcga | 1920 |
| gccagatggc | ttctgggagg | ccctgggcgg | gaaggctgcc | taccgcacat | ccccacggct | 1980 |
| gaaggacaag | aagatggatg | cccatcctcc | tcgcctcttt | gcctgctcca | caagattgg | 2040 |
| acgttttgtg | atcgaagagg | ttcctggtga | gctcatgcag | gaagacctgg | caacggatga | 2100 |
| cgtcatgctt | ctggacacct | gggaccaggt | ctttgtctgg | gttggaaagg | attctcaaga | 2160 |
| agaagaaaag | acagaagcct | tgacttctgc | taagcggtac | atcgagacgg | acccagccaa | 2220 |
| tcgggatcgg | cggacgccca | tcaccgtggt | gaagcaaggc | tttgagcctc | ctccttttgt | 2280 |

```
gggctggttc cttggctggg atgatgatta ctggtctgtg gaccccttgg acagggccat    2340
ggctgagctg gctgcctgag gaggggcagg gcccacccat gtcaccggtc agtgccttt     2400 ggaactgtcc ttccctcaaa gaggccttag agcgagcaga gcagctctgc tatgagtgtg    2460
tgtgtgtgtg tgtgttgttt cttttttttt ttttacagt atccaaaaat agccctgcaa     2520
aaattcagag tccttgcaaa attgtctaaa atgtcagtgt ttgggaaatt aaatccaata    2580
aaaacatttt gaagtgtg                                                  2598
```

<210> SEQ ID NO 35
<211> LENGTH: 329
<212> TYPE: DNA
<213> ORGANISM: Homo sapiens
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 35

```
gaagtaaaag atttttattg ttctatagac acttctgaaa agagatctaa ttgagaaaat    60
atacaaagca tttaagagtt tcatccccag agactgactg aaggcgttac agccctcctc   120
tccaaggctc agggctgaga acggttagca tatcgaatga tcagtaaaaa catgcaaaag   180
tgagaaggaa agggaaaaag gtgcattccc ctaagctgag ggggatggaa tttcagaaca   240
gaggangcag ggtggacaag taccaaggtg gctctccctt tccctctgtg tnatctttca   300
aaaccanttc caagcntgga tnaaagcaa                                     329
```

<210> SEQ ID NO 36
<211> LENGTH: 1555
<212> TYPE: DNA
<213> ORGANISM: Homo sapiens

<400> SEQUENCE: 36

```
caaagtctga gccccgctcc gctgatgcct gtctgcagaa tccgcaccaa ccagcaccat    60
gcccatgact ctggggtact gggacatccg tgggctggcc cacgccatcc gcttgctcct   120
ggaatacaca gactcaagct atgtggaaaa gaagtacacg ctgggggacg ctcctgacta   180
tgacagaagc cagtggctga atgaaaaatt caagctgggc ctggactttc caatctgcc    240 ctacttgatt gatgggggctc acaagatcac ccagagcaat gccatcctgc gctacattgc   300
ccgcaagcac aacctgtgtg gggagacaga agaggagaag attcgtgtgg acattttgga   360
gaaccaggtt atggataacc acatggagct ggtcagactg tgctatgacc cagattttga   420
gaaactgaag ccaaaatact tggaggaact ccctgaaaag ctaaagctct actcagagtt   480
tctggggaag cggccatggt ttgcaggaga caagatcacc tttgtggatt tccttgccta   540
```

```
tgatgtcctt gacatgaagc gtatatttga gcccaagtgc ttggacgcct tcctaaactt    600
gaaggacttc atctcccgct ttgagggttt gaagaagatc tctgcctaca tgaagtccag    660
ccaattcctc cgaggtcttt tgtttggaaa gtcagctaca tggaacagca aatagggccc    720
agtgatgcca gaagatggga gggaggagcc aaccttgctg cctgcgaccc tggaggacag    780
cctgactccc tggacctgcc ttcttccttt ttccttcttt ctactctctt ctcttcccca    840
aggcctcatt ggcttccttt cttctaacat catccctccc cgcatcgagg ctctttaaag    900
cttcagctcc ccactgtcct ccatcaaagt cccctccta acgtcttcct ttccctgcac    960
taacgccaac ctgactgctt ttcctgtcag tgcttttctc ttctttgaga agccagactg   1020
atctctgagc tccctagcac tgtcctcaaa gaccatctgt atgccctgct cccttttgctg  1080 ggtccctacc ccagctccgt gtgatgccca gtaaagcctg aaccatgcct gccatgtctt   1140
gtcttattcc ctgaggctcc cttgactcag gactgtgctc gaattgtggg tggttttttg   1200
tcttctgttg tccacagcca gagcttagtg gatgggtgtg tgtgtgtgtg tgttgggggt   1260
ggtgatcagg caggttcata aatttccttg gtcatttctg ccctctagcc acatccctct   1320
gttcctcact gtggggatta ctacagaaag gtgctctgtg ccaagttcct cactcattcg   1380
cgctcctgta ggccgtctag aactggcatg gttcaaagag gggctaggct gatggggaag   1440
ggggctgagc agctcccagg cagactgcct tctttcaccc tgtcctgata gacttccctg   1500
atctagatat ccttcgtcat gacacttctc aataaaacgt atcccaccgt attgt         1555

<210> SEQ ID NO 37
<211> LENGTH: 4812
<212> TYPE: DNA
<213> ORGANISM: Homo sapiens
<220> FEATURE:
<221> NAME/KEY: misc_feature
<222> LOCATION: (784)..(1133)
<223> OTHER INFORMATION: n is a, c, g, or t

<400> SEQUENCE: 37
ggttgagaat gcttgcacca agcttgtcca ggcagctcag atgcttcagt cagacccta     60 ctcagtgcct gctcgagatt atctaattga tgggtcaagg ggcatcctct ctggaacatc   120
agacctgctc cttaccttcg atgaggctga ggtccgtaaa attattagag tttgcaaagg   180
aattttggaa tatcttacag tggcagaggt ggtggagact atggaagatt tggtcactta   240
cacaaagaat cttgggccag gaatgactaa gatggccaag atgattgacg agagacagca   300
ggagctcact caccaggagc accgagtgat gttggtgaac tcgatgaaca ccgtgaaaga   360
gttgctgcca gttctcattt cagctatgaa gattttgta acaactaaaa actcaaaaaa   420
ccaaggcata gaggaagctt taaaaatcg caatttact gtagaaaaaa tgagtgctga    480
aattaatgag ataattcgtg tgttacaact cacctcttgg gatgaagatg cctgggccag   540
caaggacact gaagccatga agagagcatt ggcctccata gactccaaac tgaaccaggc   600
caaaggttgg ctccgtgacc ctagtgcctc cccaggggat gctggtgagc aggccatcag   660
acagatctta gatgaagctg gaaaagttgg tgaactctgt gcaggcaaag aacgcaggga   720
gattctggga acttgcaaaa tgctagggca gatgactgat caagtggctg acctccgtgc   780 cagnnnnnn nnnnnnnnnn nnnnnnnnnn nnnnnnnnnn nnnnnnnnnn nnnnnnnnnn   840
nnnnnnnnnn nnnnnnnnnn nnnnnnnnnn nnnnnnnnnn nnnnnnnnnn nnnnnnnnnn   900
nnnnnnnnnn nnnnnnnnnn nnnnnnnnnn nnnnnnnnnn nnnnnnnnnn nnnnnnnnnn   960
nnnnnnnnnn nnnnnnnnnn nnnnnnnnnn nnnnnnnnnn nnnnnnnnnn nnnnnnnnnn  1020
```

```
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnaggctcg    1140
agccttggcc aaacaggtgg ccacggccct gcagaacctg cagaccaaaa ccaaccgggc    1200
tgtggccaac agcagaccgg ccaaagcagc tgtacacctt gagggcaaga ttgagcaagc    1260
acagcggtgg attgataatc ccacagtgga tgaccgtgga gtcggtcagg ctgccatccg    1320
ggggcttgtg gccgaagggc atcgtctggc taatgttatg atgggggcctt atcggcaaga   1380
tcttctcgcc aagtgtgacc gagtggacca gctgacagcc cagctggctg acctggctgc    1440
cagaggggaa ggggagagtc ctcaggcacg agcacttgca tctcagctcc aagactcctt    1500
aaaggatcta aaagctcgga tgcaggaggc catgactcag gaagtgtcag atgttttcag    1560
cgataccaca actcccatca agctgttggc agtggcagcc acggcgcctc ctgatgcgcc    1620
taacagggaa gaggtatttg atgagagggc agctaacttt gaaaaccatt caggaaagct    1680
tggtgctacg gccgagaagg cggctgcggt tggtactgct aataaatcaa cagtggaagg    1740
cattcaggcc tcagtgaaga cggcccgaga actcacaccc caggtggtct cggctgctcg    1800
tatcttactt aggaaccctg gaaatcaagc tgcttatgaa cattttgaga ccatgaagaa    1860
ccagtggatc gataatgttg aaaaaatgac agggctggtg gacgaagcca ttgataccaa    1920
atctctgttg gatgcttcag aagaagcaat taaaaaagac ctggacaagt gcaaggtagc    1980
tatggccaac attcagcctc agatgctggt tgctggggca accagtattg ctcgtcgggc    2040
caaccggatc ctgctggtgg ctaagaggga ggtggagaat ccgaggatcc caagttccg    2100
tgaggctgtg aaagctgcct ctgatgaatt gagcaaaacc atctccccga tggtgatgga    2160
tgcaaaagct gtggctggaa acatttccga ccctggactg caaaagagct tcctggactc    2220
aggatatcgg atcctgggag ctgtggccaa ggtcagagaa gccttccaac ctcaggagcc    2280
tgacttcccg ccgcctccac cagaccttga acaactccga ctaacagatg agcttgctcc    2340
tcccaaacca cctctgcctg aaggtgaggt ccctccacct aggcctccac caccagagga    2400
aaaggatgaa gagttccctg agcagaaggc cggggaggtg attaaccagc caatgatgat    2460
ggctgccaga cagctccatg atgaagctcg caaatggtcc agcaagggca atgacatcat    2520
tgcagcagcc aagcgcatgg ctctgctgat ggctgagatg tctcggctgg taagaggggg    2580
cagtggtacc aagcgggcac tcattcagtg tgccaaggac atcgccaagg cctcagatga    2640
ggtgactcgg ttggccaagg aggttgccaa gcagtgcaca gataaacgga ttagaaccaa    2700
cctcttacag gtatgtgagc gaatcccaac cataagcacc cagctcaaaa tcctgtccac    2760
agtgaaggcc accatgctgg gccggaccaa catcagtgat gaggagtctg agcaggccac    2820
agagatgctg gttcacaatg cccagaacct catgcagtct gtgaaggaga ctgtgcggga    2880
agctgaagct gcttcaatca aaattcgaac agatgctgga tttacactgc gctgggttag    2940
aaagactccc tggtaccagt aggcacctgg ctgagcctgg ctggcacaga aacctctact    3000
aaaaagaagg aaaatgatct gagtcccagg agctgcccag agttgctggg agctgaaaaa    3060
tcacatcctg gcctggcaca tcagaaagga atgggggcct cttcaaatta gaagacattt    3120
atactctttt ttcatggaca ctttgaaatg tgtttctgta taaagcctgt attctcaaac    3180
acagttacac ttgtgcaccc tctatcccaa taggcagact gggtttctag cccatggact    3240
tcacataagc tcagaatcca agtgaacact agccagacac tctgctctgc ccttgttccc    3300
tagggacac  ttccctctgt ttctctttcc ttggctccca ttcactcttc cagaatccca    3360
```

```
agacccaggg cccaggcaaa tcagttacta agaagaaaat tgctgtgcct cccaaaattg    3420
ttttgagctt tccatgttgc tgccaaccat accttcttc cctgggctgt gctacctggg    3480
tccttttcag aagtgagctt tgctgctaca ggggaaggtg gcctctgtgg agccccagca    3540 tatggggcc tggattcatt tcctgccctt cctcagttta atccttctag tttcccacaa    3600
tataaaactg tacttcactg tcaggaagaa atcacagaat catatgattc tgcttttacc    3660
atgcccctga gcaatgtctg tgctagggaa acttcccgtc ccatatcctg cctcagcccg    3720
ccaaggtagc catcccatga acacactgtg tcctggtgct ctctgccact ggaagggcag    3780
agtagccagg gtgtggccct gccatcttcc cagcagggcc actcccggca ctccatgctt    3840
agtcactgcc tgcagaggtc tgtgctgagg ccttatcatt cattcttagc tcttaattgt    3900
tcattttgag ctgaaatgct gcattttaat tttaaccaaa acatgtctcc tatcctggtt    3960
tttgtagcct tcctccacat cctttctaaa caagatttta aagacatgta ggtgtttgtt    4020
catctgtaac tctaaaagat ccttttttaaa ttcagtccta agaaaggaga gtgcttgtcc    4080
cctaagagtg tttaatggca aggcagccct gtctgaagga cacttcctgc ctaagggaga    4140
gtggtatttg cagactagaa ttctagtgct gctgaagatg aatcaatggg aaatactact    4200
cctgtaattc ctacctcct gcaaccaact acaaccaagc tctctgcatc tactcccaag    4260 tatgggttc aagagagtaa tgggtttcat atttcttatc accacagtaa gttcctacta    4320
ggcaaaatga gagggcagtg tttccttttt ggtacttatt actgctaagt atttcccagc    4380
acatgaaacc ttatttttc ccaaagccag aaccagatga gtaaaggagt aagaaccttg    4440
cctgaacatc cttccttccc acccatcgct gtgtgttagt tcccaacatc gaatgtgtac    4500
aacttaagtt ggtcctttac actcaggctt tcactatttc ctttataatg aggatgatta    4560
ttttcaaggc cctcagcata tttgtatagt tgcttgcctg atataaatgc aatattaatg    4620
cctttaaagt atgaatctat gccaaagatc acttgttgtt ttactaaaga aagattactt    4680
agaggaaata agaaaaatca tgtttgctct cccggttctt ccagtggttt gagacactgg    4740
tttacacttt atgccggatg tgcttttctc caatatcagt gctcgagaca cagtgaagca    4800
aattaaaaaa aa                                                       4812
```

<210> SEQ ID NO 38
<211> LENGTH: 2038
<212> TYPE: DNA
<213> ORGANISM: Homo sapiens

<400> SEQUENCE: 38

```
atatccagcc tttgccgaat acatcctatc tgccacacat ccagcgtgag gtccctccag     60
ctacaaggtg ggcaccatgg cggagaagtt tgactgccac tactgcaggg atcccttgca    120
ggggaagaag tatgtgcaaa aggatggcca ccactgctgc ctgaaatgct ttgacaagtt    180
ctgtgccaac acctgtgtgg aatgccgcaa gcccatcggt gcggactcca aggaggtgca    240
ctataagaac cgcttctggc atgacacctg cttccgctgt gccaagtgcc ttcaccccttt    300 ggccaatgag acctttgtgg ccaaggacaa caagatcctg tgcaacaagt gcaccactcg    360
ggaggactcc cccaagtgca aggggtgctt caaggccatt gtggcaggag atcaaaacgt    420
ggagtacaag gggaccgtct ggcacaaaga ctgcttcacc tgtagtaact gcaagcaagt    480
catcgggact ggaagcttct tccctaaagg ggaggacttc tactgcgtga cttgccatga    540
gaccaagttt gccaagcatt gcgtgaagtg caacaaggcc atcacatctg aggaatcac    600 ttaccaggat cagccctggc atgccgattg ctttgtgtgt gttacctgct ctaagaagct    660
```

```
ggctgggcag cgtttcaccg ctgtggagga ccagtattac tgcgtggatt gctacaagaa      720
ctttgtggcc aagaagtgtg ctggatgcaa gaaccccatc actgggaaaa ggactgtgtc      780
aagagtgagc cacccagtct ctaaagctag gaagccccca gtgtgccacg ggaaacgctt      840
gcctctcacc ctgtttccca gcgccaacct ccggggcagg catccgggtg gagagaggac      900
ttgtccctcg tgggtggtgg ttctttatag aaaaaatcga agcttagcag ctcctcgagg      960
cccgggtttg gtaaaggctc cagtgtggtg gcctatgaag acaatcctg gcacgactac      1020
tgcttccact gcaaaaaatg ctccgtgaat ctggccaaca agcgctttgt tttccaccag      1080
gagcaagtgt attgtcccga ctgtgccaaa aagctgtaaa ctgacagggg ctcctgtcct      1140
gtaaaatggc atttgaatct cgttctttgt gtccttactt tctgccctat accatcaata      1200
ggggaagagt ggtccttccc ttctttaaag ttctccttcc gtcttttctc ccattttaca      1260
gtattactca aataagggca cacagtgatc atattagcat ttagcaaaaa gcaaccctgc      1320
agcaaagtga atttctgtcc ggctgcaatt taaaaatgaa aacttaggta gattgactct      1380
tctgcatgtt tctcatagag cagaaaagtg ctaatcattt agccacttag tgatgtaagc      1440
aagaagcata ggagataaaa ccccactga gatgcctctc atgcctcagc tgggaccca     1500
cgtgtagaca cacgacatgc aagagttgca gcggctgctc caactcactg ctcaccctct      1560
tctgtgagca ggaaaagaac cctactgaca tgcatggttt aacttcctca tcagaactct      1620
gcccttcctt ctgttctttt gtgctttcaa ataactaaca cgaacttcca gaaaattaac      1680
atttgaactt agctgtaatt ctaaactgac ctttccccgt actaacgttt ggtttccccg      1740
tgtggcatgt tttctgagcg ttcctacttt aaagcatgga acatgcaggt gatttgggaa      1800
gtgtagaaag acctgagaaa acgagcctgt ttcagaggaa catcgtcaca acgaatactt      1860
ctggaagctt aacaaaacta accctgctgt ccttttttatt gttttttaatt aatatttttg      1920
ttttaattga tagcaaaata gtttatgggt ttggaaactt gcatgaaaat attttagccc      1980
cctcagatgt tcctgcagtg ctgaaattca tcctacggaa gtaaccgcaa aactctag       2038
```

<210> SEQ ID NO 39
<211> LENGTH: 691
<212> TYPE: DNA
<213> ORGANISM: Homo sapiens
<220> FEATURE:
<221> NAME/KEY: misc_feature
<222> LOCATION: (37)..(238)
<223> OTHER INFORMATION: The n at this position can be a, c, t, or g.
<220> FEATURE:
<221> NAME/KEY: misc_feature
<222> LOCATION: (240)..(268)
<223> OTHER INFORMATION: The n at this position can be a, c, t, or g.

<400> SEQUENCE: 39

```
tgccgcccta caccgtggtc tatttcccag ttcgagnnnn nnnnnnnnn nnnnnnnnn       60
nnnnnnnnnn nnnnnnnngc tgctggcaga tcagggccag agctggaagg aggaggtggt      120
gaccgtggag acgtggcagg agggctcact caaagcctcc tgcctatacg ggcagctccc      180
caagttccag gacggagacc tcaccctgta ccagtccaat accatcctgc gtcacctggn      240
nnnnnnnnnn nnnnnnnnnn nnnnnnnngg ctctatggga aggaccagca ggaggcagcc      300
ctggtggaca tggtgaatga cggcgtggag gacctccgct gcaaatacat ctccctcatc      360
tacaccaact atgaggcggg caaggatgac tatgtgaagg cactgcccgg gcaactgaag      420
ccttttgaga ccctgctgtc ccagaaccag ggaggcaaga ccttcattgt gggagaccag      480
```

```
atctccttcg ctgactacaa cctgctggac ttgctgctga tccatgaggt cctagcccct    540
ggctgcctgg atgcgttccc cctgctctca gcatatgtgg ggcgcctcag tgcccggccc    600
aagctcaagg ccttcctggc ctcccctgag tacgtgaacc tccccatcaa tggcaacggg    660
aaacagtgag ggttgggggg actctgagcg g                                    691
```

<210> SEQ ID NO 40
<211> LENGTH: 2511
<212> TYPE: DNA
<213> ORGANISM: Homo sapiens
<220> FEATURE:
<221> NAME/KEY: misc_feature
<222> LOCATION: (799)..(953)
<223> OTHER INFORMATION: The n at this position can be a, c, t, or g.

<400> SEQUENCE: 40

```
cttttcacac tggccttaaa gaggatatat tagaagttga agtaggaagg gagccagaga     60
ggccgatggc gcaaaggtac gacgatctac cccattacgg gggcatggat ggagtaggca    120 tccccctccac gatgtatggg gacccgcatg cagccaggtc catgcagccg gtccaccacc  180
tgaaccacgg gcctcctctg cactcgcatc agtacccgca cacagctcat accaacgcca    240
tggcccccag catgggctcc tctgtcaatg acgctttaaa gagagataaa gatgccattt    300
atggacaccc cctcttccct ctcttagcac tgattttga gaaatgtgaa ttagctactt     360
gtaccccccg cgagccgggg gtggcgggcg gggacgtctg ctcgtcagag tcattcaatg    420
aagatatagc cgtgttcgcc aaacagattc gcgcagaaaa acctctattt tcttctaatc    480
cagaactgga taacttgatg attcaagcca tacaagtatt aaggtttcat ctattggaat    540
tagagaaggt acacgaatta tgtgacaatt tctgccaccg gtatattagc tgtttgaaag    600
ggaaaatgcc tatcgatttg gtgatagacg atagagaagg aggatcaaaa tcagacagtg    660
aagatataac aagatcagca aatctaactg accagccctc ttggaacaga gatcatgatg    720
acacggcatc tactcgttca ggaggaaccc caggcccttc cagcggtggc cacacgtcac    780
acagtgggga caacagcann nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnncacccctt   960 acccttctga agaacagaaa aagcagttgg cacaagacac gggactcacc atccttcaag   1020
tgaacaattg gtttattaat gcccggagaa gaatagtgca gcccatgata gaccagtcca   1080
accgagcagt aagtcaagga acaccttata atcctgatga cagcccatg ggaggtttcg    1140 taatggacgg tcagcaacat atgggaatta gagcaccagg acctatgagt ggaatgggca   1200
tgaatatggg catggagggg cagtggcact acatgtaacc ttcatctagt taaccaatcg   1260
caaagcaagg gggaaggctg caaagtatgc caggggagta tgtagcccgg ggtggtccaa   1320
tgggtgtgag tatgggacag ccaagttata cccaacccca gatgccccc catcctgctc   1380 agctgcgtca tgggcccccc atgcatacgt acattcctgg cacccctcac cacccaacag   1440
tgatgatgca tggaggaccg ccccacccctg gaatgccaat gtcagcatca agccccacag  1500
ttcttaatac aggagaccca acaatgagtg acaagtcat ggacattcat gctcagtagc    1560
ttaagggaat atgcattgtc tgcaatggtg actgatttca aatcatgttt ttctgcaat    1620 gactgtggag ttccattctt ggcatctact ctggaccaag gagcatccct aattcttcat   1680
agggaccttt aaaagcagg aaataccaac tgaagtcaat ttgggggaca tgctaaataa    1740
ctatataaga cattaagaga acaaagagtg aaatattgta aatgctatta tactgttatc   1800
```

```
catattacgt tgtttcttat agattttta aaaaaaatgt gaaattttc cacactatgt     1860 gtgttgtttc catagctctt cacttcctcc agaagcctcc ttacattaaa aagccttaca    1920
gttatcctgc aagggacagg aaggtctgat ttgcaggatt tttagagcat taaaataact    1980
atcaggcaga agaatctttc ttctcgccta ggatttcagc catgcgcgcg ctctctctct    2040
ttctctctct tttcctctct ctccctcttt ctagcctggg gcttgaattt gcatgtctaa    2100
ttcatttact caccatattt gaattggcct gaacagatgt aaatcgggaa ggatgggaaa    2160
aactgcagtc atcaacaatg attaatcagc tgttgcaggc agtgtcttaa ggagactggt    2220
aggaggaggc atggaaacca aaggccgtg tgtttagaag cctaattgtc acatcaagca     2280
tcattgtccc catgcaacaa ccaccacctt atacatcact tcctgtttta agcagctcta    2340
aaacatagac tgaagattta tttttaatat gttgacttta tttctgagca aagcatcggt    2400
catgtgtgta ttttttcata gtcccacctt ggagcattta tgtagacatt gtaaataaat    2460
tttgtgcaaa aaggactgga aaatgaact gtattattgc aatttttttt t             2511

<210> SEQ ID NO 41
<211> LENGTH: 441
<212> TYPE: DNA
<213> ORGANISM: Homo sapiens

<400> SEQUENCE: 41
ctcaataagc caaccatgtc tttcaaggat tacatccaag agaggagtga cccagtggag     60
caaggcaaac cagttatacc tgcagctgtg ctggccggct tcacaggaag tggacctatt    120
cagctgtggc agtttctcct ggagctgcta tcagacaaat cctgccagtc attcatcagc    180
tggactggac acggatggga gtttaagctc gccgacccg atgaggtggc ccgccggtgg     240
ggaaagagga aaaataagcc caagatgaac tacgagaagc tgagccgggg cttacgctac    300
tattacgaca agaacatcat ccacaagacg tcggggaagc gctacgtgta ccgcttcgtg    360
tgcgacctcc agaacttgct ggggttcacg cccgaggaac tgcacgccat cctgggcgtc    420 cagccccgaca cggaggactg a                                             441

<210> SEQ ID NO 42
<211> LENGTH: 1531
<212> TYPE: DNA
<213> ORGANISM: Homo sapiens

<400> SEQUENCE: 42
ggacgacaag gcgttcacca aggagctgga ccagtgggtc gagcagctga cgagtgtaa      60 gcagctgaac gagaaccaag tgcggacgct gtgcgagaag gcaaaggaaa ttttaacaaa    120
agaatcaaat gtgcaagagg ttcgttgccc tgttactgtc tgtggagatg tgcatggtca    180
atttcatgat cttatggaac tcttttagaat tggtggaaaa tcaccggata caaactactt    240
attcatgggt gactatgtag acagaggata ttattcagtg gagactgtga ctcttcttgt    300
agcattaaag gtgcgttatc cagaacgcat tacaatattg agaggaaatc acgaaagccg    360
acaaattacc caagtatatg gcttttatga tgaatgtctg cgaaagtatg ggaatgccaa    420
cgtttggaaa tatttacag atctctttga ttatcttcca cttacagctt tagtagatgg     480
acagatattc tgcctccatg gtggcctctc tccatccata gacacactgg atcatataag    540
agccctggat cgtttacagg aagttccaca tgagggccca atgtgtgatc tgttatggtc    600
agatccagat gatcgtggtg gatggggtat ttcaccacgt ggtgctggct acacatttgg    660
```

-continued

```
acaagacatt tctgaaacct ttaaccatgc caatggtctc acactggttt ctcgtgccca      720
ccagcttgta atggagggat acaattggtg tcatgatcgg aatgtggtta ccattttcag      780
tgcacccaat tactgttatc gttgtgggaa ccaggctgct atcatggaat tagatgacac      840
tttaaaatat tccttccttc aatttgaccc agcgcctcgt cgtggtgagc ctcatgttac      900
acggcgcacc ccagactact tcctataaat ttctcctggg aaacctgcct ttgtatgtgg      960
aagtatacct ggcttttaa aatatatgta tttaaaaaca aaaagcaaca gtaatctatg     1020
tgtttctgta acaaattggg atctgtcttg gcattaaacc acatcatgga ccaaatgtgc     1080
catactaatg atgagcattt agcacaattt gagactgaaa tttagtacac tatgttctag     1140
gtcagtctaa cagtttgcct gctgtattta tagtaaccat tttcctttgg actgttcaag     1200
caaaaaaggt aactaactgc ttcatctcct tttgcgctta tttggaaatt ttagtttatag    1260 tgtttaactg gcatggatta atagagttgg agttttattt ttaagaaaaa ttcacaagct     1320
aacttccact aatccattat cctttatttt attgaaatgt ataattaact taactgaaga     1380
aaaggttctt cttgggagta tgttgtcata acatttaaag agatttccct tcatttaaac     1440
taaattactg ttttatgttg atctgcatat ttctgtatat ttgtcatgac agtgcttgca     1500
tcctatttgg tgtactcagc aaataaactt t                                     1531

<210> SEQ ID NO 43
<211> LENGTH: 1260
<212> TYPE: DNA
<213> ORGANISM: Homo sapiens

<400> SEQUENCE: 43
cctgtgagca ccacgtcaac ggctcccggc ccccatgcac gggggaggga gatacccca       60 agtgtagcaa gatctgtgag cctggctaca gcccgaccta caaacaggac aagcactacg     120
gatacaattc ctacagcgtc tccaatagcg agaaggacat catggccgag atctacaaaa     180
acggccccgt ggagggagct ttctctgtgt attcggactt cctgctctac aagtcaggag     240
tgtaccaaca cgtcaccgga gagatgatgg gtggccatgc catccgcatc ctgggctggg     300
gagtggagaa tggcacaccc tactggctgg ttgccaactc ctggaacact gactggggtg     360
acaatggctt ctttaaaata ctcagaggac aggatcactg tggaatcgaa tcagaagtgg     420
tggctggaat tccacgcacc gatcagtact gggaaaagat ctaatctgcc gtgggcctgt     480
cgtgccagtc ctggggggcga gatgggggta gaaatgcatt ttattcttta agttcacgta     540
agatacaagt ttcagacagg gtctgaagga ctggattggc caaacatcag acctgtcttc     600
caaggagacc aagtcctggc tacatcccag cctgtggtta cagtgcagac aggccatgtg     660
agccaccgct gccagcacag agcgtccttc cccctgtaga ctagtgccgt agggagtacc     720
tgttgcccca gctgactgtg gcccctccg tgatccatcc atctccaggg agcaagacag     780
agacccagga atggaaagcg gagttcctaa caggatgaaa gttccccat cagttccccc     840 agtacctcca agcaagtagc tttccacatt tgtcacagaa atcagaggag agatggtgtt    900
gggagccctt tggagaacgc cagtctccca ggcccctgc atctatcgag tttgcaatgt    960
cacaacctct ctgatcttgt gctcagcatg attctttaat agaagttta tttttcgtg     1020 cactctgcta atcatgtggg tgagccagtg aacagcggg agacctgtgc tagttttaca    1080
gattgcctcc ttatgacgcg gctcaaaagg aaaccaagtg gtcaggagtt gtttctgacc    1140
cactgatctc tactaccaca aggagaatag tttaggagaa accagctttt actgtttttg    1200
aaaaattaca gcttcacccct gtcaagttaa caaggaatgc ctgtgccaat aaaaggtttc    1260
```

<210> SEQ ID NO 44
<211> LENGTH: 5418
<212> TYPE: DNA
<213> ORGANISM: Homo sapiens
<220> FEATURE:
<221> NAME/KEY: misc_feature
<222> LOCATION: (1210)..(1219)
<223> OTHER INFORMATION: The "n" at this position can be either "a", "t", "g", or "c".

<400> SEQUENCE: 44

| | | | | | |
|---|---|---|---|---|---|
| gtgtcccata | gtgtttccaa | acttggaaag | ggcggggag | ggcgggagga | tgcggagggc | 60 |
| ggaggtatgc | agacaacgag | tcagagtttc | cccttgaaag | cctcaaaagt | gtccacgtcc | 120 |
| tcaaaagaa | tggaaccaat | ttaagaagcc | agccccgtgg | ccacgtccct | tcccccattc | 180 |
| gctccctcct | ctgcgccccc | gcaggctcct | cccagctgtg | gctgcccggg | ccccagccc | 240 |
| cagccctccc | attggtggag | gcccttttgg | aggcaccta | gggccaggga | aacttttgcc | 300 |
| gtataaatag | ggcagatccg | ggctttatta | ttttagcacc | acggcagcag | gaggtttcgg | 360 |
| ctaagttgga | ggtactggcc | acgactgcat | gcccgcgccc | gccaggtgat | acctccgccg | 420 |
| gtgacccagg | ggctctgcga | cacaaggagt | ctgcatgtct | aagtgctaga | catgctcagc | 480 |
| tttgtggata | cgcggacttt | gttgctgctt | gcagtaacct | tatgcctagc | aacatgccaa | 540 |
| tctttacaag | aggaaactgt | aagaaagggc | ccagccggag | atagaggacc | acgtggagaa | 600 |
| aggggtccac | caggcccccc | aggcagagat | ggtgaagatg | gtcccacagg | ccctcctggt | 660 |
| ccacctggtc | ctcctggccc | ccctggtctc | ggtgggaact | ttgctgctca | gtatgatgga | 720 |
| aaaggagttg | gacttggccc | tggaccaatg | ggcttaatgg | gacctagagg | cccacctggt | 780 |
| gcagctggag | ccccaggccc | tcaaggtttc | caaggacctg | ctggtgagcc | tggtgaacct | 840 |
| ggtcaaactg | gtcctgcagg | tgctcgtggt | ccagctggcc | ctcctggcaa | ggctggtgaa | 900 |
| gatggtcacc | ctggaaaacc | cggacgacct | ggtgagagag | gagttgttgg | accacagggt | 960 |
| gctcgtggtt | tccctggaac | tcctggactt | cctggcttca | aaggcattag | gggacacaat | 1020 |
| ggtctggatg | gattgaaggg | acagcccggt | gctcctggtg | tgaagggtga | acctggtgcc | 1080 |
| cctggtgaaa | atggaactcc | aggtcaaaca | ggagcccgtg | ggcttcctgg | tgagagagga | 1140 |
| cgtgttggtg | cccctggccc | agctggtgcc | cgtggcagtg | atggaagtgt | gggtcccgtg | 1200 |
| ggtcctgctn | nnnnnnnng | gtctgctggc | cctccaggct | tcccaggtgc | ccctggcccc | 1260 |
| aagggtgaaa | ttggagctat | tggtaacgct | ggtcctgctg | gtcccgccgg | tccccgtggt | 1320 |
| gaagtgggtc | ttccaggcct | ctccggcccc | gttggacctc | ctggtaatcc | tggagcaaac | 1380 |
| ggccttactg | gtgccaaggg | tgctgctggc | cttccggcg | ttgctgggc | tcccggcctc | 1440 |
| cctggacccc | gcggtattcc | tggccctgtt | ggtgctgccg | gtgctactgg | tgccagagga | 1500 |
| cttgttggtg | agcctggtcc | agctggctcc | aaaggagaga | gcgtaacaa | gggtgagccc | 1560 |
| ggctctgctg | ggccccaagg | tcctcctggt | cccagtggtg | aagaaggaaa | gagaggccct | 1620 |
| aatggggaag | ctggatctgc | cggccctcca | ggacctcctg | ggctgagagg | tagtcctggt | 1680 |
| tctcgtggtc | ttcctggagc | tgatggcaga | gctggcgtca | tgggccctcc | tggtagtcgt | 1740 |
| ggtgcaagtg | gccctgctgg | agtccgagga | cctaatggaa | atgctggtcg | ccctgggag | 1800 |
| cctggtctca | tgggacccag | aggtcttcct | ggttccctg | gaaatatcgg | ccccgctgga | 1860 |
| aaagaaggtc | ctgtcggcct | ccctggcatc | gacggcaggc | ctggcccaat | ggccccgtt | 1920 |
| ggagcaagag | gagagcctgg | caacattgga | ttccctggac | ccaaaggccc | cactggtgac | 1980 |

```
cctggcaaaa acggtgataa aggtcatgct ggtcttgctg gtgctcgggg tgctccaggt    2040
cctgatggaa acaatggtgc tcagggacct cctggaccac agggtgttca aggtggaaaa    2100
ggtgaacagg gtcccgctgg tcctccaggc ttccagggtc tgcctggccc ctcaggtccc    2160
gctggtgaag ttggcaaacc aggagaaagg ggtctccatg gtgagtttgg tctccctggt    2220
cctgctggtc aagagggga acgcggtccc caggtgagaa gtggtgctgc cggtcctact    2280
ggtcctattg gaagccgagg tccttctgga cccccagggc ctgatggaaa caagggtgaa    2340
cctggtgtgg ttggtgctgt gggcactgct ggtccatctg gtcctagtgg actcccagga    2400
gagagggtg ctgctggcat acctggaggc aagggagaaa aggtgaacc tggtctcaga     2460
ggtgaaattg gtaaccctgg cagagatggt gctcgtggtg ctcatggtgc tgtaggtgcc    2520
cctggtcctg ctggagccac aggtgaccgg ggcgaagctg gggctgctgg tcctgctggt    2580
cctgctggtc ctcggggaag ccctggtgaa cgtggcgagg tcggtcctgc tggccccaac    2640
ggatttgctg gtccggctgg tgctgctggt caaccgggtg ctaaaggaga aagaggaggc    2700
aaagggccta agggtgaaaa cggtgttgtt ggtcccacag gcccgttgg agctgctggc     2760
ccagctggtc caaatggtcc cccggtcct gctggaagtc gtggtgatgg aggcccccct    2820
ggtatgactg gtttcctgg tgctgctgga cggactggtc cccaggacc ctctggtatt     2880
tctggccctc ctggtccccc tggtcctgct gggaagaag gcttcgtgg tcctcgtggt     2940
gaccaaggtc cagttggccg aactggagaa gtaggtgcag ttggtccccc tggcttcgct    3000
ggtgagaagg gtccctctgg agaggctggt actgctggac ctcctggcac tccaggtcct    3060
cagggtcttc ttggtgctcc tggtattctg ggtctccctg gctcgagagg tgaacgtggt    3120
ctacctggtg ttgctggtgc tgtgggtgaa cctggtcctc ttggcattgc cggccctcct    3180
ggggcccgtg gtcctcctgg tgctgtgggt agtcctggag tcaacggtgc tcctggtgaa    3240
gctggtcgtg atggcaaccc tgggaacgat ggtccccag tcgcgatgg tcaacccgga     3300
cacaagggag agcgcggtta ccctggcaat attggtcccg ttggtgctgc aggtgcacct    3360
ggtcctcatg gccccgtggg tcctgctggc aaacatggaa accgtggtga aactggtcct    3420
tctggtcctg ttggtcctgc tggtgctgtt ggcccaagag gtcctagtgg cccacaaggc    3480
attcgtggcg ataagggaga gcccggtgaa aaggggccca gaggtcttcc tggcttcaag    3540
ggacacaatg gattgcaagg tctgcctggt atcgctggtc accatggtga tcaaggtgct    3600
cctggctccg tggtcctgc tggtcctagg ggccctgctg gtccttctgg ccctgctgga    3660
aaagatggtc gcactggaca tcctggtacg gttggacctg ctggcattcg aggccctcag    3720
ggtcaccaag gccctgctgg ccccctggt ccccctggcc ctcctggacc tcaggtgta    3780
agcggtggtg gttatgactt tggttacgat ggagacttct acaggctga ccagcctcgc     3840
tcagcacctt ctctcagacc caaggactat gaagttgatg ctactctgaa gtctctcaac    3900
aaccagattg agaccttct tactcctgaa ggctctagaa agaaccagc tcgcacatgc     3960
cgtgacttga gactcagcca cccagagtgg agcagtggtt actactgat tgaccccaac     4020
caaggatgca ctatggaagc catcaaagta tactgtgatt tccctaccgg cgaaacctgt    4080
atccggcccc aacctgaaaa catcccagcc aagaactggt ataggagctc caaggacaag    4140
aaacacgtct ggctaggaga actatcaat gctggcagcc agtttgaata taatgttgaa     4200
ggagtgactt ccaaggaaat ggctaccaa cttgccttca tgcgcctgct ggccaactat     4260
gcctctcaga acatcaccta ccactgcaag aacagcattg catacatgga tgaggagact    4320
```

```
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac catgaattct ttgtggacat ggcccagtc    4560 tgtttcaaat aaatgaactc aatctaaatt aaaaaagaaa gaaatttgaa aaaactttct   4620
ctttgccatt tcttcttctt cttttttaac tgaaagctga atccttccat ttcttctgca   4680
catctacttg cttaaattgt gggcaaaaga gaaaagaag gattgatcag agcattgtgc    4740
aatacagttt cattaactcc ttcccccgct cccccaaaaa tttgaatttt tttttcaaca   4800
ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac tacctcaaaa cactttccca tgagtgtgat   4980
ccacattgtt aggtgctgac ctagacagag atgaactgag gtccttgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat tttttaaaaa   5160
atttgattta gcattcatat tttccatctt attcccaatt aaaagtatgc agattatttg   5220
cccaaagttg tcctcttctt cagattcagc atttgttctt tgccagtctc attttcatct   5280
tcttccatgg ttccacagaa gctttgtttc ttgggcaagc agaaaaatta aattgtacct   5340
attttgtata tgtgagatgt ttaaataaat tgtgaaaaaa atgaaataaa gcatgtttgg   5400
ttttccaaaa gaacatat                                                5418

<210> SEQ ID NO 45
<211> LENGTH: 2566
<212> TYPE: DNA
<213> ORGANISM: Homo sapiens

<400> SEQUENCE: 45
cagaccacag gaatacctaa tgccttttt ctcttcctgt ctttgtccct cacactacag      60
caggcccctc ccttccctct tcaacctcat cctccctccc cacaggccca gagaaccagt    120
tgggctttgt tctcctgcag gctatggttc atcatgcaaa tagctcctgt gtcagaaatg    180 cttttttggct tcaaataaca gaaaagctaa caccagcttt atcaataata atatcggtgg    240
tttacttaag gtgtccagag atggtggaga acaggattgg tttcctcctc aatgtcaagg    300
actcaaagac tctttctgtg gtagggccac atcctaaacc ctgtatcctg tgattattta    360
cctgacaggg caaaagagat tttgcagatg caattaaggt taaggacctt gacgtgggaa    420
gattgtgatt atttacctga cagggcaaaa gagattttgc agatgcaatt aaggttaagg    480
accttgacgt gggaagatta ttctggatta tctaggtggg cgcaatttga tcacatgggt    540
ccccagaagt ggagaacctt tcccacctgt agaaagccag agagctggca cctgagaagg    600
acagaactgt cactgcagga tttgaagatg aaggggccca tgagccaagg aatgccagtg    660
acctatagag gctaaaaaac agcaaggaaa tggactctcc ccagagcctc cagaggaatg    720
cagccctgtt gatcacatga tcaccagatg gctgccccag agccaaatgt cgcttcctga    780
gcaccatact caaaggcagg ggaagtggat ggagggcagg agctccattc ttgtttgcca    840
ctctcctttt gtcaattggg aaaaaattcc agaaactctg ggagccctcc ccttacatttt    900 cctgggtcat ggggccagcc ctagctgctg gagggactga gaactgctgt tgagcagtttt    960 acctgacggc atctgccatg gcttggcagg aactctggct ttgggagaga gcagcagcaa   1020
```

```
ggtattcaag caccacctcc acccagcccc tcccacattt cactcaggac tgagtaaagg    1080
agacactcag atgctactca gatgctggct tcagctaagt attttgcaaa gcctctcgtg    1140
ttcttacaag tttgtggcta tcatgacaaa atggagcagc ctactatatc tacatataca    1200
actatggggg acctagtttt atctcattta ccacaatgtt ttcaatcatt ttttggatga    1260
cataattttt agcctcttct ctaaatgctt cctcaagctt tccttgcctt ccagccactg    1320
caaatgactt gcagtttccc ctacatggca cctgacccct gtgcctccct ccctctgccc    1380
atggcccaga aagcccttc ctgtgccctc tggcttcctg ataaactcct atcatcttca    1440
agagccagtt cccatgccag ctctccccaa gtgctccact gaggcttccg taacacctct    1500
gttcccacat cgggttgact gtctttgttt tgtcattgct tgctctggct gtgtctccct    1560
cattagactg ggatgccttc aaggtaggga ccctatctgg gtcagcttgg caccccaaag    1620
cgtaccacag cacctgattc tgaggaggct ctcagtagat atctgttgag taaccagaat    1680
gtagggtggt cctgatggtt tctgacattg aatagaaaac agctccctat ttgatcttaa    1740
aataatcact ataacctgga catactgtac tagatgctgt ttttgtctga cttctactct    1800
gtcaatctct ttgcacctcc atttgttcat ctgtgaaatg aagaaaatgc tcatggagtt    1860
cagtgaagat taaatgaatg aatataggta gactgcctaa tctggcactt gccacgcagc    1920
tgacttcaat atagtagctc taatattatg gtccttgagg atcttactgt cttatggccc    1980
agaactgcat ttgattaaag aaggctcccc taaaaaaaga gtcatacata ttccatttgt    2040
cctttcagaa ggccgtgaag catttacact ctttaagaca aattcccatc caaaaatagt    2100
taagatttct aaaatatttt gatgctgaaa gaggtgtgct tcagttgggt ggcaaatttg    2160
cttctatgga agattttaa tacaggttgt ttctatttta ctttttctgg ctgaaaggat    2220
tttacattta ttcaaagtca aagggaaaa gaaatccaag aactacagaa gagcagttga    2280
agtgatttat gcttgatttc taaatgcaac ttatgtttat acataattta aaactcaaag    2340
aaagcatgct tatacaatca tgtgcaactt taaactttaa gaactctgga tgaatacatg    2400
gtggcaacag tccatgacac ctgaaaacat catttgtgga gtggcgtaga gttcagtgtt    2460
cgcagtcgca tattacaacc atgtttcaca cagccctgct cggtttgatt ttctccacgt    2520
ggttgataat tgtcttcagt tgctgctaag tgattttgca aatttc                  2566
```

<210> SEQ ID NO 46
<211> LENGTH: 1847
<212> TYPE: DNA
<213> ORGANISM: Homo sapiens
<400> SEQUENCE: 46

```
gtccccgcgc cagagacgca gccgcgctcc caccaccac acccaccgcg ccctcgttcg      60
cctcttctcc gggagccagt ccgcgccacc gccgccgccc aggccatcgc caccctccgc    120
agccatgtcc accaggtccg tgtcctcgtc ctcctaccgc aggatgttcg gcggcccggg    180
caccgcgagc cggccgagct ccagccggag ctacgtgact acgtccaccc gcacctacag    240
cctgggcagc gcgctgcgcc ccagcaccag ccgcagcctc tacgcctcgt ccccgggcgg    300
cgtgtatgcc acgcgctcct ctgccgtgcg cctgcggagc agcgtgcccg gggtgcggct    360
cctgcaggac tcggtggact ctctcgctgg cgacgccatc aacaccgagt tcaagaacac    420
ccgcaccaac gagaaggtgg agctgcagga gctgaatgac cgcttcgcca actacatcga    480
caaggtgcgc ttcctggagc agcagaataa gatcctgctg gccgagctcg agcagctcaa    540
```

```
gggccaaggc aagtcgcgcc tgggggacct ctacgaggag gagatgcggg agctgcgccg      600
gcaggtggac cagctaacca acgacaaagc ccgcgtcgag gtggagcgcg acaacctggc      660
cgaggacatc atgcgcctcc gggagaaatt gcaggaggag atgcttcaga gagaggaagc      720
cgaaaacacc ctgcaatctt tcagacagga tgttgacaat gcgtctctgg cacgtcttga      780
ccttgaacgc aaagtggaat ctttgcaaga gagagattgcc tttttgaaga aactccacga      840
agaggaaatc caggagctgc aggctcagat tcaggaacag catgtccaaa tcgatgtgga      900
tgtttccaag cctgacctca cggctgccct gcgtgacgta cgtcagcaat atgaaagtgt      960
ggctgccaag aacctgcagg aggcagaaga atggtacaaa tccaagtttg ctgacctctc     1020
tgaggctgcc aaccggaaca atgacgccct gcgccaggca aagcaggagt ccactgagta     1080
ccggagacag gtgcagtccc tcacctgtga agtggatgcc cttaaaggaa ccaatgagtc     1140
cctggaacgc cagatgcgtg aaatggaaga gaactttgcc gttgaagctg ctaactacca     1200
agacactatt ggccgcctgc aggatgagat tcagaatatg aaggaggaaa tggctcgtca     1260
ccttcgtgaa taccaagacc tgctcaatgt taagatggcc cttgacattg agattgccac     1320
ctacaggaag ctgctggaag gcgaggagag caggatttct ctgcctcttc caaacttttc     1380
ctccctgaac ctgagggaaa ctaatctgga ttcactccct ctggttgata cccactcaaa     1440
aaggacactt ctgattaaga cggttgaaac tagagatgga caggttatca acgaaacttc     1500
tcagcatcac gatgaccttg aataaaaatt gcacacactc agtgcagcaa tatattacca     1560
gcaagaataa aaaagaaatc catatcttaa agaaacagct ttcaagtgcc tttctgcagt     1620 tttttcaggag cgcaagatag atttggaata ggaataagct ctagttctta acaaccgaca     1680
ctcctacaag atttagaaaa aagtttacaa cataatctag tttacagaaa atcttgtgc      1740 tagaatactt tttaaaaggt attttgaata ccattaaaac tgctttttt tttccagcaa      1800 gtatccaacc aacttggttc tgcttcaata aatctttgga aaaactc                    1847
```

<210> SEQ ID NO 47
<211> LENGTH: 3864
<212> TYPE: DNA
<213> ORGANISM: Homo sapiens

<400> SEQUENCE: 47

```
ggccagccga atccaagccg tgtgtactgc gtgctcagca ctgcccgaca gtcctagcta       60
aacttcgcca actccgctgc ctttgccgcc accatgccca aaacgatcag tgtgcgtgtg      120
accaccatgg atgcagagct ggagtttgcc atccagccca acaccaccgg gaagcagcta      180
tttgaccagg tggtgaaaac tattggcttg agggaagttt ggttctttgg tctgcagtac      240
caggacacta aaggtttctc cacctggctg aaactcaata agaaggtgac tgcccaggat      300
gtgcggaagg aaagccccct gctctttaag ttccgtgcca gttctaccc tgaggatgtg      360 tccgaggaat tgattcagga catcactcag cgcctgttct ttctgcaagt gaaagagggc      420
attctcaatg atgatatttta ctgcccgcct gagaccgctg tgctgctggc ctcgtatgct      480
gtccagtcta agtatggcga cttcaataag gaagtgcata agtctggcta cctggccgga      540
gacaagttgc tcccgcagag agtcctggaa cagcacaaac tcaacaagga ccagtgggag      600
gagcggatcc aggtgtggca tgaggaacac cgtggcatgc tcagggagga tgctgtcctg      660
gaatatctga agattgctca agatctggag atgtatggtg tgaactactt cagcatcaag      720
aacaagaaag gctcagagct gtggctgggg gtggatgccc tgggtctcaa catctatgag     780
cagaatgaca gactaactcc caagataggc ttcccctgga gtgaaatcag gaacatctct      840
```

```
ttcaatgata agaaatttgt catcaagccc attgacaaaa aagccccgga cttcgtcttc      900
tatgctcccc ggctgcggat taacaagcgg atcttggcct tgtgcatggg gaaccatgaa      960
ctatacatgc gccgtcgcaa gcctgatacc attgaggtgc agcagatgaa ggcacaggcc     1020
cgggaggaga agcaccagaa gcagatggag cgtgctatgc tggaaaatga agaagaag       1080
cgtgaaatgg cagagaagga gaaagagaag attgacggg agaaggagga gctgatggag      1140
aggctgaagc agatcgagga acagactaag aaggctcagc aagaactgga gaacagacc      1200
cgtagggctc tggaacttga gcaggaacgg aagcgtgccc agagcgaggc tgaaaagctg     1260
gccaaggagc gtcaagaagc tgaagaggcc aaggaggcct tgctgcaggc ctcccgggac     1320
cagaaaaaga ctcaggaaca gctggccttg gaaatggcag agctgacagc tcgaatctcc     1380
cagctggaga tggcccgaca gaagaaggag agtgaggctg tggagtggca gcagaaggcc     1440
cagatggtac aggaagactt ggagaagacc cgtgctgagc tgaagactgc catgagtaca     1500
cctcatgtgg cagagcctgc tgagaatgag caggatgagc aggatgagaa tggggcagag     1560
gctagtgctg acctacgggc tgatgctatg gccaaggacc gcagtgagga ggaacgtacc     1620
actgaggcag agaagaatga gcgtgtgcag aagcacctga aggccctcac ttcggagctg     1680
gccaatgcca gagatgagtc caagaagact gccaatgaca tgatccatgc tgagaacatg     1740
cgactgggcc gagacaaata caagaccctg cgccagatcc ggcagggcaa caccaagcag     1800
cgcattgacg aatttgagtc tatgtaatgg gcacccagcc tctagggacc cctcctccct     1860
ttttccttgt ccccacactc ctacacctaa ctcacctaac tcatactgtg ctggagccac     1920
taactagagc agccctggag tcatgccaag catttaatgt agccatggga ccaaacctag     1980
cccctagcc cccacccact tccctgggca atgaatggc tcactatggt gccaatggaa      2040
cctcctttct cttctctgtt ccattgaatc tgtatggcta aatatccta cttctccagc     2100
ctagaggtac tttccacttg attttgcaaa tgcccttaca cttactgttg tcctatggga     2160
gtcaagtgtg gagtaggttg gaagctagct cccctcctct cccctaccac tgtcttcttc     2220
agggtcctga gatttacacg gttggagtgt tatgcggtct agggaatgag acaggaccta     2280
ggatatcttc tccaggatgt caactgacct aaaatttgcc ctcccatccc gtttagagtt     2340
atttaggctt tgtaacgatt gggggataaa agatgttca gtcattttg tttctacctc       2400
ccagatcgga tctgttgcaa actcagcctc aataagcctt gtcgttgact ttagggactc     2460
aatttctccc cagggtggat gggggaaatg gtgccttcaa gaccttcacc aaacatacta     2520
gaagggcatt ggccattcta ttgtggcaag gctgagtaga agatcctacc ccaattcctt     2580
gtaggagtat aggccggtct aaagtgagct ctatgggcag atctacccct tacttattat     2640
tccagatctg cagtcacttc gtgggatctg cccctccctg cttcaatacc caaatcctct     2700
ccagctataa cagtagggat gagtacccaa aagctcagcc agcccatca ggactcttgt      2760
gaaaagagag gatatgttca cacctagcgt cagtattttc cctgctaggg gttttaggtc     2820
tcttcccctc tcagagctac ttgggccata gctcctgctc cacagccatc ccagccttgg     2880
catctagagc ttgatgccag taggctcaac tagggagtga gtgcaaaaag ctgagtatgg     2940
tgagagaagc ctgtgccctg atccaagttt actcaaccct ctcaggtgac caaaatcccc     3000
ttctcatcac tcccctccaa agaggtgact gggccctgcc tctgtttgac aaacctctaa     3060
cccaggtctt gacaccagct gttcgtccc ttggagctgt aaaccagaga gctgctgggg      3120
attctggcct agtcccttcc acaccccac ccttgctct caacccagga gcatccacct       3180
```

```
ccttctctgt ctcatgtgtg ctcttcttct ttctacagta ttatgtactc tactgatatc    3240
taaatattga tttctgcctt ccttgctaat gcaccattag aagatattag tcttggggca    3300
ggatgatttt ggcctcatta ctttaccacc cccacacctg gaaagcatat actatattac    3360
aaaatgacat tttgccaaaa ttattaatat aagaagcttt cagtattagt gatgtcatct    3420
gtcactatag gtcatacaat ccattcttaa agtacttgtt atttgttttt attattactg    3480
tttgtcttct ccccagggtt cagtcctcaa ggggccatcc tgtcccacca tgcagtgccc    3540
ctagcttaga gcctccctca attcccctg gccaccaccc cccactctgt gcctgacctt     3600
gaggagtctt gtgtgcattg ctgtgaatta gctcacttgg tgatatgtcc tatattggct    3660
aaattgaaac ctggaattgt ggggcaatct attaatagct gccttaaagt cagtaactta    3720
cccttaggga ggctggggga aaaggttaga ttttgtattc aggggttttt tgtgtacttt    3780
ttgggttttt taaaaattgt ttttggaggg gtttatgctc aatccatgtt ctatttcagt    3840
gccaataaaa tttaggaaga cttc                                          3864

<210> SEQ ID NO 48
<211> LENGTH: 2270
<212> TYPE: DNA
<213> ORGANISM: Homo sapiens

<400> SEQUENCE: 48
ggtgtgcccg agaggctga gcagcctgcg cctgagctgg tggaggtgga agtgggcagc      60
acagcccttc tgaagtgcgg cctctcccag tcccaaggca acctcagcca tgtcgactgg    120
ttttctgtcc acaaggagaa gcggacgctc atcttccgtg tgcgccaggg ccagggccag    180
agcgaacctg gggagtacga gcagcggctc agcctccagg acagaggggc tactctggcc    240
ctgactcaag tcaccccca agacgagcgc atcttcttgt gccagggcaa gcgccctcgg    300
tcccaggagt accgcatcca gctccgcgtc tacaaagctc cggaggagcc aaacatccag    360
gtcaaccccc tgggcatccc tgtgaacagt aaggagcctg aggaggtcgc tacctgtgta    420
gggaggaacg ggtacccat tcctcaagtc atctggtaca gaatggccg gcctctgaag     480 gaggagaaga accgggtcca cattcagtcg tcccagactg tggagtcgag tggtttgtac    540
accttgcaga gtattctgaa ggcacagctg gttaaagaag acaaagatgc ccagttttac    600
tgtgagctca actaccggct gcccagtggg aaccacatga aggagtccag ggaagtcacc    660
gtccctgttt tctacccgac agaaaaagtg tggctggaag tggagcccgt gggaatgctg    720
aaggaagggg accgcgtgga aatcaggtgt ttggctgatg gcaaccctcc accacacttc    780
agcatcagca gcagaaccc cagcaccagg gaggcagagg aagagacaac caacgacaac    840
ggggtcctgg tgctggagcc tgcccggaag gaacacagtg ggcgctatga atgtcagggc    900
ctggacttgg acaccatgat atcgctgctg agtgaaccac aggaactact ggtgaactat    960
gtgtctgacg tccgagtgag tcccgcagca cactgagaga caggaaggca gcagcctcac   1020
cctgacctgt gaggcagaga gtagccagga cctcgagttc cagtggctga gagaagagac   1080
aggccaggtg ctggaaaggg ggcctgtgct tcagttgcat gacctgaaac gggaggcagg   1140
aggcggctat cgctgcgtgg cgtctgtgcc cagcataccc ggcctgaacc gcacacagct   1200
ggtcaacgtg gcctttttg gcccccttg gatggcattc aaggagagga aggtgtgggt    1260
gaaagagaat atggtgttga atctgtcttg tgaagcgtca gggcacccc ggcccaccat    1320 ctcctggaac gtcaacggca cggcaagtga acaagaccaa gatccacagc gagtcctgag    1380
caccctgaat gtcctcgtga ccccggagct gttggagaca ggtgttgaat gcacggcctc   1440
```

| | |
|---|---|
| caacgacctg ggcaaaaaca ccagcatcct cttcctggag ctggtcaatt taaccaccct | 1500 |
| cacaccagac tccaacacaa ccactggcct cagcacttcc actgccagtc ctcataccag | 1560 |
| agccaacagc acctccacag agagaaagct gccggagccg gagagccggg gcgtggtcat | 1620 |
| cgtggctgtg attgtgtgca tcctggtcct ggcggtgctg ggcgctgtcc tctatttcct | 1680 |
| ctataagaag ggcaagctgc cgtgcaggcg ctcaggaag caggagatca cgctgccccc | 1740 |
| gtctcgtaag agcgaacttg tagttgaagt taagtcagat aagctcccag aagagatggg | 1800 |
| cctcctgcag ggcagcagcg gtgacaagag ggctccggga gaccagggag agaaatacat | 1860 |
| cgatctgagg cattagcccc gaatcacttc agctcccttc cctgcctgga ccattcccag | 1920 |
| ctccctgctc actcttctct cagccaaagc ctccaaaggg actagagaga agcctcctgc | 1980 |
| tcccctcgcc tgcacacccc ctttcagagg gccactgggt taggacctga ggacctcact | 2040 |
| tggccctgca aggcccgctt tcagggacc agtccaccac catctccacg ttgagtgaag | 2100 |
| ctcatcccaa gcaaggagcc ccagtctccc gagcgggtag gagagtttct tgtagaacgt | 2160 |
| gttttttctt tacacacatt atggctgtaa atacctggct cctgccagca gctgagctgg | 2220 |
| gtagcctctc tgagctggga ttacaggtgt gagccactgc gcccagccaa | 2270 |

<210> SEQ ID NO 49
<211> LENGTH: 2127
<212> TYPE: DNA
<213> ORGANISM: Homo sapiens

<400> SEQUENCE: 49

| | |
|---|---|
| caaacttggt ggcaacttgc ctcccggtgc gggcgtctct ccccaccgt ctcaacatgc | 60 |
| ttaggggtcc ggggcccggg ctgctgctgc tggccgtcct gtgcctgggg acagcggtgc | 120 |
| cctccacggg agcctcgaag agcaagaggc aggctcagca aatggttcag ccccagtccc | 180 |
| cggtggctgt cagtcaaagc aagcccggtt gttatgacaa tggaaaacac tatcagataa | 240 |
| atcaacagtg ggagcggacc tacctaggca atgcgttggt ttgtacttgt tatggaggaa | 300 |
| gccgaggttt taactgcgag agtaaacctg aagctgaaga gacttgcttt gacaagtaca | 360 |
| ctgggaacac ttaccgagtg ggtgacactt atgagcgtcc taaagactcc atgatctggg | 420 |
| actgtacctg catcggggct gggcgaggga aataagctg taccatcgca aaccgctgcc | 480 |
| atgaaggggg tcagtcctac aagattggtg acacctggag gagaccacat gagactggtg | 540 |
| gttacatgtt agagtgtgtg tgtcttggta atggaaaagg agaatggacc tgcaagccca | 600 |
| tagctgagaa gtgttttgat catgctgctg ggacttccta tgtggtcgga gaaacgtggg | 660 |
| agaagcccta ccaaggctgg atgatggtag attgtacttg cctgggagaa ggcagcggac | 720 |
| gcatcacttg cacttctaga aatagatgca acgatcagga cacaaggaca tcctatagaa | 780 |
| ttggagacac ctggagcaag aaggataatc gaggaaacct gctccagtgc atctgcacag | 840 |
| gcaacggccg aggagagtgg aagtgtgaga ggcacacctc tgtgcagacc acatcgagcg | 900 |
| gatctggccc cttcaccgat gttcgtgcag ctgtttacca accgcagcct caccccagc | 960 |
| ctcctcccta tggccactgt gtcacagaca gtggtgtggt ctactctgtg gggatgcagt | 1020 |
| ggctgaagac acaaggaaat aagcaaatgc tttgcacgtg cctgggcaac ggagtcagct | 1080 |
| gccaagagac agctgtaacc cagacttacg gtggcaactc aaatggagag ccatgtgtct | 1140 |
| taccattcac ctacaatggc aggacgtgca gcacaacttc gaattatgag caggaccaga | 1200 |
| aatactcttt ctgcacagac cacactgttt tggttcagac tcgaggagga aattccaatg | 1260 |

```
gtgccttgtg ccacttcccc ttcctataca acaaccacaa ttacactgat tgcacttctg   1320
agggcagaag agacaacatg aagtggtgtg ggaccacaca gaactatgat gccgaccaga   1380
agtttgggtt ctgccccatg gctgcccacg aggaaatctg cacaaccaat gaagggtca    1440 tgtaccgcat tggagatcag tgggataagc agcatgacat gggtcacatg atgaggtgca   1500
cgtgtgttgg gaatggtcgt ggggaatgga catgcattgc ctactcgcag cttcgagatc   1560
agtgcattgt tgatgacatc acttacaatg tgaacgacac attccacaag cgtcatgaag   1620
aggggcacat gctgaactgt acatgcttcg gtcagggtcg gggcaggtgg aagtgtgatc   1680
ccgtcgacca atgccaggat tcagagactg ggacgtttta tcaaattgga gattcatggg   1740
agaagtatgt gcatggtgtc agataccagt gctactgcta tggccgtggc attggggagt   1800
ggcattgcca acctttacag acctatccaa gctcaagtgg tcctgtcgaa gtatttatca   1860
ctgagactcc gagtcagccc aactcccacc ccatccagtg gaatgcacca cagccatctc   1920
acatttccaa gtacattctc aggtggagac ctgtgagtat cccacccaga aaccttggat   1980
actgagtctc ctaatcttat caattctgat ggtttctttt tttcccagct tttgagccaa   2040
caactctgat taactattcc tatagcattt actatatttg tttagtgaac aaacaatatg   2100
tggtcaatta aattgacttg tagactg                                       2127

<210> SEQ ID NO 50
<211> LENGTH: 1918
<212> TYPE: DNA
<213> ORGANISM: Homo sapiens

<400> SEQUENCE: 50 accccccgcac ccagctccgc aggaccggcg ggcgcgcgcg ggctctggag gccacgggca    60
tgatgcttcg ggtcctggtg ggggctgtcc tccctgccat gctactggct gccccaccac   120
ccatcaacaa gctggcactg ttcccagata agagtgcctg gtgcgaagcc aagaacatca   180
cccagatcgt gggccacagc ggctgtgagg ccaagtccat ccagaacagg gcgtgcctag   240
gacagtgctt cagctacagc gtccccaaca ccttcccaca gtccacagag tccctggttc   300
actgtgactc ctgcatgcca gcccagtcca tgtgggagat tgtgacgctg gagtgccgg    360 gccacgagga ggtgcccagg gtggacaagc tggtggagaa gatcctgcac tgtagctgcc   420
aggcctgcgg caaggagcct agtcacgagg ggctgagcgt ctatgtgcag ggcgaggacg   480
ggccgggatc ccagcccggc acccaccctc acccccatcc ccaccccat cctggcgggc   540 agaccctga gccgaggac cccctgggg cccccacac agaggaagag ggggctgagg   600
actgaggccc ccccaactct tcctccctc tcatcccct gtggaatgtt gggtctcact   660
ctctggggaa gtcaggggag aagctgaagc cccccttgg cactgatgg acttggcttc   720 agactcggac ttgaatgctg cccggttgcc atggagatct gaaggggcgg ggttagagcc   780
aagctgcaca atttaatata ttcaagagtg ggggaggaa gcagaggtct tcagggctct   840
tttttggggg ggggtggtct cttcctgtct ggcttctaga gatgtgcctg tgggagggg    900 aggaagttgg ctgagccatt gagtgctggg ggaggccatc caagatggca tgaatcgggc   960
taaggtccct gggggtgcag atggtactgc tgaggtcccg ggcttagtgt gagcatcttg  1020
ccagcctcag gcttgaggga gggctgggct agaaagacca ctggcagaaa caggaggctc  1080
cggcccacag gtttccccaa ggcctctcac cccacttccc atctccaggg aagcgtcgcc  1140
ccagtggcac tgaagtggcc ctccctcagc ggaggggttt gggagtcagg cctgggcagg  1200
accctgctga ctcgtggcgc gggagctggg agccaggctc tccgggcctt tctctggctt  1260
```

-continued

```
ccttggcttg cctggtgggg gaagggggag aggggaagaa ggaaagggaa gagtcttcca    1320
aggccagaag gaggggggaca accccccaag accatccctg aagacgagca tcccctcct    1380 ctccctgtta gaaatgttag tgccccgcac tgtgccccaa gttctaggcc ccccagaaag    1440
ctgccagagc cggccgcctt ctcccctctc ccagggatgc tctttgtaaa tatcggatgg    1500
gtgtgggagt gaggggttac ctccctcgcc ccaaggttcc agaggcccta ggcgggatgg    1560
gctcgctgaa cctcgaggaa ctccaggacg aggaggacat gggacttgcg tggacagtca    1620
gggttcactt gggctctctc tagctcccca attctgcctg cctcctccct cccagctgca    1680 ctttaacccct agaaggtggg gacctggggg gagggacagg gcaggcgggc ccatgaagaa    1740
agcccctcgt tgcccagcac tgtctgcgtc tgctcttctg tgcccagggt ggctgccagc    1800
ccactgcctc ctgcctgggg tggcctggcc ctcctggctg ttgcgacgcg ggcttctgga    1860
gcttgtcacc attggacagt ctccctgatg gaccctcagt cttctcatga ataaattc     1918
```

<210> SEQ ID NO 51
<211> LENGTH: 1222
<212> TYPE: DNA
<213> ORGANISM: Homo sapiens

<400> SEQUENCE: 51

```
atccgtcccg gataagaccc gctgtctggc cctgagtagg gtgtgacctc cgcagccgca     60
gaggaggagc gcagcccggc ctcgaagaac ttctgcttgg gtggctgaac tctgatcttg    120
acctagagtc atggccatgg caaccaaagg aggtactgtc aaagctgctt caggattcaa    180
tgccatggaa gatgcccaga ccctgaggaa ggccatgaaa gggctcggca ccgatgaaga    240
cgccattatt agcgtccttg cctaccgcaa caccgcccag cgccaggaga tcaggacagc    300
ctacaagagc accatcggca gggacttgat agacgacctg aagtcagaac tgagtggcaa    360
cttcgagcag gtgattgtgg ggatgatgac gcccacggtg ctgtatgacg tgcaagagct    420
gcgaagggcc atgaagggag ccggcactga tgagggctgc ctaattgaga tcctggcctc    480 ccggaccccct gaggagatcc ggcgcataag ccaaacctac cagcagcaat atggacggag    540
ccttgaagat gacattcgct ctgacacatc gttcatgttc cagcgagtgc tggtgtctct    600
gtcagctggt gggagggatg aaggaaatta tctggacgat gctctcgtga caggatgc     660 ccaggacctg tatgaggctg agagaagaa atggggaca gatgaggtga aatttctaac     720
tgttctctgt tcccggaacc gaaatcacct gttgcatggt ttgatgaata caaaaggata    780
tcacagaagg atattgaaca gagtattaaa tctgaaacat ctggtagctt tgaagatgct    840
ctgctggcta tagtaaagtg catgaggaac aaatctgcat attttgctga aaagctctat    900
aaatcgatga agggcttggg caccgatgat aacaccctca tcagagtgat ggtttctcga    960
gcagaaattg acatgttgga tatccgggca cacttcaaga gactctatgg aaagtctctg   1020
tactcgttca tcaagggtga cacatctgga gactacagga agtactgct tgttctctgt   1080 ggaggagatg attaaaataa aaatcccaga aggacaggag gattctcaac actttgaatt   1140
tttttaactt cattttttcta cactgctatt atcattatct cagaatgctt atttccaatt   1200
aaaacgccta cagctgcctc ct                                            1222
```

<210> SEQ ID NO 52
<211> LENGTH: 2468
<212> TYPE: DNA
<213> ORGANISM: Homo sapiens

<400> SEQUENCE: 52

```
tggggcagcc gcgcccgcgg tgttttccgc ccggcgctgg cggctgctgc gcccgcggct    60
ccccagtgcc ccgagtgccc cgcgggcccc gcgagcggga gtgggaccca gcccctaggc   120
agaacccagg cgccgcgccc gggacgcccg cggagagagc cactcccgcc cacgtcccat   180
ttcgcccctc gcgtccggag tcctcgtggc cagatctaac catgagctac cctggctatc   240
ccccgccccc aggtggctac ccaccagctg caccaggtgg tggtccctgg ggaggtgctg   300
cctaccctcc tccgcccagc atgccccca tcgggctgga taacgtggcc acctatgcgg    360
ggcagttcaa ccaggactat ctctcgggaa tggcggccaa catgtctggg acatttggag   420
gagccaacat gcccaacctg taccctgggg cccctggggc tggctaccca ccagtgcccc   480
ctggcggctt tgggcagccc cctctgccc agcagcctgt tcctccctat gggatgtatc    540
cacccccagg aggaaaccca ccctccagga tgccctcata tccgccatac caggggccc    600
ctgtgccggg ccagcccatg ccaccccccg gacagcagcc cccaggggcc taccctgggc   660
agccaccagt gacctaccct ggtcagcctc cagtgccact ccctgggcag cagcagccag   720
tgccgagcta cccaggatac ccggggtctg ggactgtcac ccccgctgtg ccccaaccc    780
agtttggaag ccgaggcacc atcactgatg ctcccggctt tgaccccctg cgagatgccg   840
aggtcctgcg gaaggccatg aaaggcttcg gacggatga gcaggccatc attgactgcc    900
tggggagtcg ctccaacaag cagcggcagc agatcctact ttccttcaag acggcttacg   960
gcaaggattt gatcaaagat ctgaaatctg aactgtcagg aaactttgag aagacaatct  1020
tggctctgat gaagacccca gtcctctttg acatttatga gataaaggaa gccatcaagg  1080
gggttggcac tgatgaagcc tgcctgattg agatcctcgc ttcccgcagc aatgagcaca  1140
tccgagaatt aaacagagcc tacaaagcag aattcaaaaa gaccctggaa gaggccattc  1200
gaagcgacac atcagggcac ttccagcggc tcctcatctc tctctctcag ggaaaccgtg  1260
atgaaagcac aaacgtggac atgtcactcg cccagagaga tgcccaggag ctgtatgcgg  1320
ccggggagaa ccgcctggga acagacgagt ccaagttcaa tgcggttctg tgctcccgga  1380
gccgggccca cctggtagca gttttcaatg agtaccagag aatgacaggc cgggacattg  1440
agaagagcat ctgccgggag atgtccgggg acctggagga gggcatgctg gccgtggtga  1500
aatgtctcaa gaatacccca gccttctttg cggagaggct caacaaggcc atgagggggg  1560
caggaacaaa ggaccggacc ctgattcgca tcatggtgtc tcgcagcgag accgacctcc  1620
tggacatcag atcagagtat aagcggatgt acggcaagtc gctgtaccac gacatctcgg  1680
gagatacttc aggggattac cggaagattc tgctgaagat ctgtggtggc aatgactgaa  1740
cagtgactgg tggctcactt ctgcccacct gccggcaaca ccagtgccag gaaaaggcca  1800
aaagaatgtc tgtttctaac aaatccacaa atagccccga gattcaccgt cctagagctt  1860
aggcctgtct tccaccctc ctgacccgta tagtgtgcca caggacctgg gtcggtctag   1920
aactctctca ggatgccttt tctacccca ccctcacagc ctcttgctgc taaaatagat   1980
gtttcatttt tctgactcat gcaatcattc ccctttgcct gtggctaaga cttggcttca  2040
tttcgtcatg taattgtata ttttatttg gaggcatatt ttcttttctt acagtcattg   2100
ccagacagag gcatacaagt ctgtttgctg catacacatt tctggtgagg gcgactgggt  2160
gggtgaagca ccgtgtcctc gctgaggaga gaaagggagg cgtgcctgag aaggtagcct  2220
gtgcatctgg tgagtgtgtc acgagctttg ttactgccaa actcactcct ttttagaaaa  2280
aacaaaaaaa aagggccaga aagtcattcc ttccatcttc cttgcagaaa ccacgagaac  2340
```

| | |
|---|---|
| aaagccagtt ccctgtcagt gacagggctt cttgtaattt gtggtatgtg ccttaaacct | 2400 |
| gaatgtctgt agccaaaact tgtttccaca ttaagagtca gccagctctg gaatggtctg | 2460 |
| gaaatgtc | 2468 |

<210> SEQ ID NO 53
<211> LENGTH: 4907
<212> TYPE: DNA
<213> ORGANISM: Homo sapiens

<400> SEQUENCE: 53

| | |
|---|---|
| tagacgcacc ctctgaagat ggtgactccc tcctgagaag ctggacccct tggtaaaaga | 60 |
| caaggccttc tccaagaaga atatgaaagt gttactcaga cttatttgtt tcatagctct | 120 |
| actgatttct tctctggagg ctgataaatg caaggaacgt gaagaaaaaa taattttagt | 180 |
| gtcatctgca aatgaaattg atgttcgtcc ctgtcctctt aacccaaatg aacacaaagg | 240 |
| cactataact tggtataaag atgacagcaa gacacctgta tctacagaac aagcctccag | 300 |
| gattcatcaa cacaaagaga aactttggtt tgttcctgct aaggtggagg attcaggaca | 360 |
| ttactattgc gtggtaagaa attcatctta ctgcctcaga attaaaataa gtgcaaaatt | 420 |
| tgtggagaat gagcctaact tatgttataa tgcacaagcc atatttaagc agaaactacc | 480 |
| cgttgcagga gacggaggac ttgtgtgccc ttatatggag ttttttaaaa atgaaaataa | 540 |
| tgagttacct aaattacagt ggtataagga ttgcaaacct ctacttcttg acaatataca | 600 |
| ctttagtgga gtcaaagata ggctcatcgt gatgaatgtg ctgaaaagc atagagggaa | 660 |
| ctatacttgt catgcatcct acacatactt gggcaagcaa tatcctatta cccgggtaat | 720 |
| agaatttatt actctagagg aaaacaaacc cacaaggcct gtgattgtga gcccagctaa | 780 |
| tgagacaatg aagtagact tgggatccca gatacaattg atctgtaatg tcaccggcca | 840 |
| gttgagtgac attgcttact ggaagtggaa tgggtcagta attgatgaag atgacccagt | 900 |
| gctaggggaa gactattaca gtgtggaaaa tcctgcaaac aaaagaagga gtaccctcat | 960 |
| cacagtgctt aatatatcgg aaattgaaag tagattttat aaacatccat ttacctgttt | 1020 |
| tgccaagaat acacatggta tagatgcagc atatatccag ttaatatatc cagtcactaa | 1080 |
| tttccagaag cacatgattg gtatatgtgt cacgttgaca gtcataattg tgtgttctgt | 1140 |
| tttcatctat aaaatcttca gattgacat tgtgctttgg tacagggatt cctgctatga | 1200 |
| ttttctccca ataaaagctt cagatggaaa gacctatgac gcatatatac tgtatccaaa | 1260 |
| gactgttggg gaagggtcta cctctgactg tgatatttt gtgtttaaag tcttgcctga | 1320 |
| ggtcttggaa aaacagtgtg gatataagct gttcatttat ggaagggatg actacgttgg | 1380 |
| ggaagacatt gttgaggtca ttaatgaaaa cgtaaagaaa gcagaagac tgattatcat | 1440 |
| tttagtcaga gaaacatcag gcttcagctg gctgggtggt tcatctgaag gcaaatagc | 1500 |
| catgtataat gctcttgttc aggatggaat taaagttgtc ctgcttgagc tggagaaaat | 1560 |
| ccaagactat gagaaaatgc cagaatcgat taaattcatt aagcagaaac atggggctat | 1620 |
| ccgctggtca ggggacttta cacagggacc acagtctgca aagacaaggt tctggaagaa | 1680 |
| tgtcaggtac cacatgccag tccagcgacg gtcaccttca tctaaacacc agttactgtc | 1740 |
| accagccact aaggagaaac tgcaaagaga ggctcacgtg cctctcgggt agcatggaga | 1800 |
| agttgccaag agttctttag gtgcctcctg tcttatggcg ttgcaggcca ggttatgcct | 1860 |
| catgctgact tgcagagttc atggaatgta actatatcat cctttatccc tgaggtcacc | 1920 |

```
tggaatcaga ttattaaggg aataagccat gacgtcaata gcagcccagg gcacttcaga    1980
gtagagggct tgggaagatc tttttaaaaag gcagtaggcc cggtgtggtg gctcacgcct    2040
ataatcccag cactttggga ggctgaagtg ggtggatcac cagaggtcag gagttcgaga    2100
ccagcccagc caacatggca aaaccccatc tctactaaaa atacaaaaat gagctaggca    2160
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaagggcaa taaatgccct ctctgaatgt ttgaactgcc    2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgaccct ggagcggctc tcctgagagg tgctgcaggc aaagtgagac    2520
tgacacctca ctgaggaagg gagacatatt cttggagaac tttccatctg cttgtatttt    2580
ccatacacat ccccagccag aagttagtgt ccgaagaccg aatttttattt tacagagctt    2640 gaaaactcac ttcaatgaac aaagggattc tccaggattc caaagttttg aagtcatctt    2700
agctttccac aggaggggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc ctccgtctgc aatgtccctt gcacagccca    2880
cacatgaacc atccttccca tgatgccgct cttctgtcat cccgctcctg ctgaaacacc    2940 tcccagggge tccacctgtt caggagctga agcccatgct ttcccaccag catgtcactc    3000
ccagaccacc tccctgccct gtcctccagc ttcccctcgc tgtcctgctg tgtgaattcc    3060
caggttggcc tggtggccat gtcgcctgcc cccagcactc ctctgtctct gctcttgcct    3120
gcacccttcc tcctccttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttttgc aattattcta    3480 attttatata tagagaaagt gacctatttt ttaaaaaaat cacactctaa gttctattga    3540
acctaggact tgagcctcca tttctggctt ctagtctggt gttctgagta cttgatttca    3600
ggtcaataac ggtccccct cactccacac tggcacgttt gtgagaagaa atgacatttt    3660
gctaggaagt gaccgagtct aggaatgctt ttattcaaga caccaaattc caaacttcta    3720
aatgttggaa tttttcaaaaa ttgtgtttag atttttatgaa aaactcttct actttcatct    3780
attctttccc tagaggcaaa catttcttaa aatgtttcat tttcattaaa aatgaaagcc    3840
aaatttatat gccaccgatt gcaggacaca agcacagttt taagagttgt atgaacatgg    3900
agaggacttt tggtttttat atttctcgta tttaatatgg gtgaacacca acttttatttt    3960 ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
```

-continued

```
aagaattaca agtagaatgg cagctggaat ttaaggaggg acaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
ccactaaaac aaaacaaaaa acttttaatg ccttccacat taattagatt ttcttgcagt    4560
ttttttatgg catttttta aagatgccct aagtgttgaa gaagagtttg caaatgcaac    4620
aaaatattta attaccggtt gttaaaactg gtttagcaca atttatattt tccctctctt    4680
gcctttctta tttgcaataa aaggtattga gccattttt aaatgacatt tttgataaat     4740
tatgtttgta ctagttgatg aaggagtttt ttttaacctg tttatataat tttgcagcag    4800
aagccaaatt ttttgtatat taaagcacca aattcatgta cagcatgcat cacggatcaa    4860
tagactgtac ttattttcca ataaaatttt caaactttgt actgtta                  4907
```

<210> SEQ ID NO 54
<211> LENGTH: 1004
<212> TYPE: DNA
<213> ORGANISM: Homo sapiens

<400> SEQUENCE: 54

```
ccctgcactc tcgctctcct gccccacccc gaggtaaagg gggcgactaa gagaagatgg      60
tgttgctcac cgcggtcctc ctgctgctgg ccgcctatgc ggggccggcc cagagcctgg     120
gctccttcgt gcactgcgag ccctgcgacg agaaagccct ctccatgtgc cccccagcc      180 ccctgggctg cgagctggtc aaggagccgg gctgcggctg ctgcatgacc tgcgccctgg    240 ccgagggggca gtcgtgcggc gtctacaccg agcgctgcgc ccaggggctg cgctgcctcc    300
cccggcagga cgaggagaag ccgctgcacg ccctgctgca cggccgcggg gtttgcctca    360
acgaaaagag ctaccgcgag caagtcaaga tcgagagaga ctcccgtgag cacgaggagc    420
ccaccacctc tgagatggcc gaggagacct actcccccaa gatcttccgg cccaaacaca    480
cccgcatctc cgagctgaag gctgaagcag tgaagaagga ccgcagaaag aagctgaccc    540
agtccaagtt tgtcggggga gccgagaaca ctgcccaccc ccggatcatc tctgcacctg    600
agatgagaca ggagtctgag cagggcccct gccgcagaca catggaggct tccctgcagg    660
agctcaaagc cagcccacgc atggtgcccc gtgctgtgta cctgcccaat tgtgaccgca    720
aaggattcta caagagaaag cagtgcaaac cttcccgtgg ccgcaaacgt ggcatctgct    780
ggtgcgtgga caagtacggg atgaagctgc caggcatgga gtacgttgac ggggactttc    840
agtgccacac cttcgacagc agcaacgttg agtgatgcgt cccccccaa cctttccctc     900 accccctccc accccagcc ccgactccag ccagcgcctc cctccacccc aggacgccac     960
tcatttcatc tcatttaagg gaaaaatata tatctatcta tttg                    1004
```

<210> SEQ ID NO 55
<211> LENGTH: 772
<212> TYPE: DNA
<213> ORGANISM: Homo sapiens

<400> SEQUENCE: 55

```
cgcagcgggt cctctctatc tagctccagc ctctcgcctg cgccccactc cccgcgtccc      60
gcgtcctagc cgaccatggc cgggcccctg cgcgccccgc tgctcctgct ggccatcctg    120 gccgtgccc tggccgtgag ccccgcggcc ggctccagtc ccggcaagcc gccgcgccta    180
gtgggaggcc ccatggacgc cagcgtggag gaggaggggtg tgcggcgtgc actggacttt    240
```

-continued

| | |
|---|---|
| gccgtcggcg agtacaacaa agccagcaac gacatgtacc acagccgcgc gctgcaggtg | 300 |
| gtgcgcgccc gcaagcagat cgtagctggg gtgaactact tcttggacgt ggagctgggc | 360 |
| cgaaccacgt gtaccaagac ccagcccaac ttgacaact gccccttcca tgaccagcca | 420 |
| catctgaaaa ggaaagcatt ctgctctttc cagatctacg ctgtgccttg gcagggcaca | 480 |
| atgaccttgt cgaaatccac ctgtcaggac gcctagggggt ctgtaccggg ctggcctgtg | 540 |
| cctatcacct cttatgcaca cctcccaccc cctgtattcc caccccctgga ctggtggccc | 600 |
| ctgccttggg gaaggtctcc ccatgtgcct gcaccaggag acagacagag aaggcagcag | 660 |
| gcggcctttg ttgctcagca aggggctctg ccctccctcc ttccttcttg cttctcatag | 720 |
| ccccggtgtg cggtgcatac accccccacct cctgcaataa aatagtagca tc | 772 |

```
<210> SEQ ID NO 56
<211> LENGTH: 2128
<212> TYPE: DNA
<213> ORGANISM: Homo sapiens

<400> SEQUENCE: 56
```

| | |
|---|---|
| gaaagatgga tcactccagc tcaaagagaa catgtgggaa tgaaaggaca ggctgggccc | 60 |
| aaaggagaaa agggtgatgc tggggaggag cttcctggcc ctcctgaacc ttctgggcct | 120 |
| gttggaccca cggcaggagc agaagcagag ggctctggcc taggctgggg ctcggacgtc | 180 |
| ggctctggct ctggtgacct ggtgggcagt gagcagctgc tgagaggtcc tccaggaccc | 240 |
| ccagggccac ctggcttacc tgggattcca ggaaaaccag gaactgatgt tttcatggga | 300 |
| cccccctggat ctcctggaga ggatggacct gctggtgaac ctgggccccc gggccctgag | 360 |
| ggacagcctg gagttgatgg agccaccggc cttcccggga tgaaagggga aagggagca | 420 |
| agagggccta atggctcagt tggtgaaaag ggtgaccctg caacagagg cttacctgga | 480 |
| cccccgggga aaagggaca agctggccct cctggggtca tgggaccccc agggcctcct | 540 |
| ggaccccctg ggccccaggg ccctggatgc acaatgggac ttggattcga ggataccgaa | 600 |
| ggctctggaa gcacccagct attgaatgaa cccaaactct ccagaccaac ggctgcaatt | 660 |
| ggtctcaaag gagagaaagg agaccgggga cccaaggag aaagggggat ggatggagcc | 720 |
| agtattgtgg gaccccctgg gccgagaggg ccacctgggc acatcaaggt cttgtctaat | 780 |
| tccttgatca atatcaccca tggattcatg aatttctcgg acattcctga gctggtgggg | 840 |
| cctccggggc cggacgggtt gcctgggctg ccaggatttc caggggtccta gaggaccaaa | 900 |
| aggtgacact ggtttacctg gctttccagg actaaaagga gaacagggcg agaagggaga | 960 |
| gccgggtgcc atcctgacag aggacattcc tctggaaagg ctgatgggga aaagggtga | 1020 |
| acctggaatg catggagccc caggaccaat ggggcccaaa ggaccaccag acataaagg | 1080 |
| agaatttggc cttcccgggc gacctggtcg cccaggactg aatggcctca agggtaccaa | 1140 |
| aggagatcca ggggtcatta tgcagggccc acctggctta cctggccctc caggcccccc | 1200 |
| tgggccacct ggagctgtga ttaacatcaa aggagccatt ttcccaatac ccgtccgacc | 1260 |
| acactgcaaa atgccagttg atactgctca tcctgggagt ccagagctca tcactttttca | 1320 |
| cggtgttaaa ggagagaaag gatcctgggg tcttcctggc tcaaagggag aaaaaggcga | 1380 |
| ccagggagcc cagggaccac caggtcctcc acttgatcta gcttacctga gacactttct | 1440 |
| gaacaacttg aagggggaga atggagacaa ggggttcaaa ggtgaaaaag gagaaaaagg | 1500 |
| agacattaat ggcagcttcc ttatgtctgg gcctccaggc ctgccggaa atccaggccc | 1560 |
| ggctggccaa aaagggggaga cagtcgttgg gccccaagga cccccaggtg ctcctggtct | 1620 |

-continued

```
gcctgggcca cctggctttg aagacctgg tgatcctggg ccaccggggc ccccggggcc      1680
accaggacct ccagctatcc tgggagcagc tgtggcccct tccaggtcccc ctggccctcc     1740 aggacagcca gggcttcccg gatccagaaa cctggtcaca gcattcagca acatggatga     1800
catgctgcag aaagcgcatt tggttataga aggaacattc atctacctga gggacagcac     1860 tgagttttc attcgtgtta gagatggctg gaaaaaatta cagctgggag aactgatccc      1920
cattcctgcc gacagccctc caccccctgc gctttccagc aacccacatc agcttctgcc     1980
tccaccaaac cctatttcaa gtgccaatta tgagaagcct gctctgcatt tggctgctct     2040
gaacatgcca ttttctgggg acattcgagc tgattttcag tgcttcaagc aggccagagc     2100
tgcaggactg ttgtccacct accgagca                                          2128

<210> SEQ ID NO 57
<211> LENGTH: 4309
<212> TYPE: DNA
<213> ORGANISM: Homo sapiens

<400> SEQUENCE: 57
tagaaattgt taattttaac aatccagagc aggccaacga ggctttgctc tcccgacccg       60
aactaaaggt ccctcgctcc gtgcgctgct acgagcggtg tctcctgggg ctccaatgca     120
gcgagctgtg cccgaggggt tcggaaggcg caagctgggc agcgacatgg gaacgcggga     180
gcgggctccg gggtctcgga gctttgggcc agtacccacg ctgctgctgc tcgccgcggc     240
gctactggcc gtgtcggacg cactcgggcg cccctccgag gaggacgagg agctagtggt     300
gccggagctg gagcgcgccc cgggacacgg gaccacgcgc ctccgcctgc acgcctttga     360
ccagcagctg gatctggagc tgcggcccga cagcagcttt ttggcgcccg gcttcacgct     420
ccagaacgtg gggcgcaaat ccgggtccga gacgccgctt ccggaaaccg acctggcgca     480
ctgcttctac tccggcaccg tgaatggcga tcccagctcg gctgccgccc tcagcctctg     540
cgagggcgtg cgcggcgcct tctacctgct gggggaggcg tatttcatcc agccgctgcc     600
cgccgccagc gagcgcctcg ccaccgccgc cccaggggag aagccgccgg caccactaca     660
gttccacctc ctgcggcgga atcggcaggg cgacgtcggc ggcacgtgcg gggtcgtgga     720
cgacgagccc cggccgactg ggaaagcgga gaccgaagac gaggacgaag ggactgaggg     780
cgaggacgaa ggggctcagt ggtcgccgca ggacccggca ctgcaaggcg taggacagcc     840
cacaggaact ggaagcataa gaagaagcg atttgtgtcc agtcaccgct atgtggaaac     900
catgcttgtg gcagaccagt cgatggcaga attccacggc agtggtctaa agcattacct     960
tctcacgttg ttttcggtgg cagccagatt gtacaaacac cccagcattc gtaattcagt    1020
tagcctggtg gtggtgaaga tcttggtcat ccacgatgaa cagaaggggc ggaagtgac     1080 ctccaatgct gccctcactc tgcggaactt ttgcaactgg cagaagcagc acaacccacc    1140
cagtgaccgg gatgcagagc actatgacac agcaattctt ttcaccagac aggacttgtg    1200
tgggtcccag acatgtgata ctcttgggat ggctgatgtt ggaactgtgt gtgatccgag    1260
cagaagctgc tccgtcatag aagatgatgg tttacaagct gccttcacca cagcccatga    1320
attaggccac gtgtttaaca tgccacatga tgatgcaaag cagtgtgcca gccttaatgg    1380
tgtgaaccag gattcccaca tgatggcgtc aatgcttcc aacctggacc acagccagcc    1440
ttggtctcct tgcagtgcct acatgattac atcatttctg gataatgtc atggggaatg    1500 tttgatggac aagcctcaga atcccatacc gctcccaggc gatctccctg gcacctcgta    1560
```

```
cgatgccaac cggcagtgcc agtttacatt tggggaggac tccaaacact gccccgatgc   1620
agccagcaca tgtagcacct tgtggtgtac cggcacctct ggtggggtgc tggtgtgtca   1680
aaccaaacac ttcccgtggg cggatggcac cagctgtgga aagggaaat ggtgtatcaa    1740 cggcaagtgt gtgaacaaaa ccgacagaaa gcattttgat acgccttttc atggaagctg   1800
gggaatgtgg gggccttggg gagactgttc gagaacgtgc ggtggaggag tccagtacac   1860
gatgagggaa tgtgacaacc cagtcccaaa gaatggaggg aagtactgtg aaggcaaacg   1920
agtgcgctac agatcctgta accttgagga ctgtccagac aataatggaa aaacctttag   1980
agaggaacaa tgtgaagcac acaacgagtt ttcaaaagct tcctttggga gtgggcctgc   2040
ggtggaatgg attcccaagt acgctggcgt ctcaccaaag gacaggtgca agctcatctg   2100
ccaagccaaa ggcattggct acttcttcgt tttgcagccc aaggttgtag atggtactcc   2160
atgtagccca gattccacct ctgtctgtgt gcaaggacag tgtgtaaaag ctggttgtga   2220
tcgcatcata gactccaaaa agaagtttga taaatgtggt gtttgcgggg gaaatggatc   2280
tacttgtaaa aaatatcag gatcagttac tagtgcaaaa cctggatatc atgatatcat    2340
cacaattcca actggagcca ccaacatcga agtgaaacag cggaaccaga ggggatccag   2400
gaacaatggc agctttcttg ccatcaaagc tgctgatggc acatatattc ttaatggtga   2460
ctacactttg tccaccttag agcaagacat tatgtacaaa ggtgttgtct tgaggtacag   2520
cggctcctct gcggcattgg aaagaattcg cagctttagc cctctcaaag agcccttgac   2580
catccaggtt cttactgtgg gcaatgccct tcgacctaaa attaaataca cctacttcgt   2640
aaagaagaag aaggaatctt tcaatgctat ccccactttt tcagcatggg tcattgaaga   2700
gtggggcgaa tgttctaagt catgtgaatt gggttggcag agaagactgg tagaatgccg   2760
agacattaat ggacagcctg cttccgagtg tgcaaaggaa gtgaagccag ccagcaccag   2820
accttgtgca gaccatccct gccccagtg gcagctgggg gagtggtcat catgttctaa    2880
gacctgtggg aagggttaca aaaaagaag cttgaagtgt ctgtcccatg atggaggggt    2940
gttatctcat gagagctgtg atcctttaaa gaaacctaaa catttcatag acttttgcac   3000
aatggcagaa tgcagttaag tggtttaagt ggtgttagct ttgagggcaa ggcaaagtga   3060
ggaagggctg gtgcagggaa agcaagaagg ctggagggat ccagcgtatc ttgccagtaa   3120
ccagtgaggt gtatcagtaa ggtgggatta tgggggtaga tagaaaagga gttgaatcat   3180
cagagtaaac tgccagttgc aaatttgata ggatagttag tgaggattat taacctctga   3240
gcagtgatat agcataataa agccccgggc attattatta ttatttcttt tgttacatct   3300
attacaagtt tagaaaaaac aaagcaattg tcaaaaaaag ttagaactat tacaacccct   3360
gtttcctggt acttatcaaa tacttagtat catgggggtt gggaaatgaa agtaggaga    3420 aaagtgagat tttactaaga cctgttttac tttacctcac taacaatggg gggagaaagg   3480
agtacaaata ggatctttga ccagcactgt ttatggctgc tatggtttca gagaatgttt   3540
atacattatt tctaccgaga attaaaactt cagattgttc aacatgagag aaaggctcag   3600
caacgtgaaa taacgcaaat ggcttcctct ttccttttt ggaccatctc agtctttatt    3660
tgtgtaattc attttgagga aaaacaact ccatgtattt attcaagtgc attaaagtct    3720
acaatggaaa aaaagcagtg aagcattaga tgctggtaaa agctagagga gacacaatga   3780
gcttagtacc tccaacttcc tttctttcct accatgtaac cctgctttgg gaatatggat   3840
gtaaagaagt aacttgtgtc tcatgaaaat cagtacaatc acacaaggag gatgaaacgc   3900
cggaacaaaa atgaggtgtg tagaacaggg tcccacaggt ttggggacat tgagatcact   3960
```

| | |
|---|---|
| tgtcttgtgg tggggaggct gctgaggggt agcaggtcca tctccagcag ctggtccaac | 4020 |
| agtcgtatcc tggtgaatgt ctgttcagct cttctgtgag aatatgattt tttccatatg | 4080 |
| tatatagtaa aatatgttac tataaattac atgtacttta taagtattgg tttgggtgtt | 4140 |
| ccttccaaga aggactatag ttagtaataa atgcctataa taacatattt attttatac | 4200 |
| atttatttct aatgaaaaaa acttttaaat tatatcgctt ttgtggaagt gcatataaaa | 4260 |
| tagagtattt atacaatata tgttactaga aataaaagaa cacttttgg | 4309 |

<210> SEQ ID NO 58
<211> LENGTH: 3488
<212> TYPE: DNA
<213> ORGANISM: Homo sapiens

<400> SEQUENCE: 58

| | |
|---|---|
| gggcccgggc gcgcgggagc gggagcggcc ggggagccg agcgcacca tggaggcggc | 60 |
| ggcaggcggc cgcggctgtt ccagccgca cccggggctg cagaagacgc tggagcagtt | 120 |
| ccacctgagc tccatgagct cgctgggcgg cccggccgct ttctcggcgc gctgggcgca | 180 |
| ggaggcctac aagaaggaga gcgccaagga ggcgggcgcg gccgcggtgc cggcgccggt | 240 |
| gcccgcagcc accgagccgc cgcccgtgct gcacctgccc gccatccagc cgccgccgcc | 300 |
| cgtgctgccc gggcccttct tcatgccgtc cgaccgctcc accgagcgct gcgagaccgt | 360 |
| actggaaggc gagaccatct cgtgcttcgt ggtgggaggc gagaagcgcc tgtgtctgcc | 420 |
| gcagattctc aactcggtgc tgcgcgactt ctcgctgcag cagatcaacg cggtgtgcga | 480 |
| cgagctccac atctactgct cgcgctgcac ggccgaccag ctggagatcc tcaaagtcat | 540 |
| gggcatcctg cccttctcgg cgcctcgtg cgggctcatc accaagacgg acgccgagcg | 600 |
| cctgtgcaac gcgctgctct acggcggcgc ctacccgccg ccctgcaaga aggagctggc | 660 |
| cgccagcctg gcgctgggcc tggagctcag cgagcgcagc gtccgcgtgt accacgagtg | 720 |
| cttcggcaag tgtaaggggc tgctggtgcc cgagctctac agcagcccga gcgccgcctg | 780 |
| catccagtgc ctggactgcc gcctcatgta cccgccgcac aagttcgtgg tgcactcgca | 840 |
| caaggccctg gagaaccgga cctgccactg gggcttcgac tcggccaact ggcgggccta | 900 |
| catcctgctg agccaggatt acacgggcaa ggaggagcag gcgcgcctcg gccgctgcct | 960 |
| ggacgacgtg aaggagaaat cgactatggg caacaagtac aagcggcggg tgccccgggt | 1020 |
| ctcctctgag cctccggcct ccataagacc caaaacagat gacacctctt cccagtcccc | 1080 |
| cgcgccttcc gaaaaggaca gccgtccag ctggctgcgg accttggccg ctctcttccaa | 1140 |
| taagagcctg ggctgtgttc accctcgcca gcgcctctct gctttccgac cctggtcccc | 1200 |
| cgcagtgtca gcgagtgaga aagagctctc cccacacctc ccggccctca tccgagacag | 1260 |
| cttctactcc tacaagagct ttgagacagc cgtggcgccc aacgtggccc tcgcaccgcc | 1320 |
| ggcccagcag aaggttgtga gcagccctcc gtgtgccgcc gccgtctccc gggcccccga | 1380 |
| gcctctcgcc acttgcaccc agcctcggaa gcggaagctg actgtggaca ccccaggagc | 1440 |
| cccagagacg ctggcgcccg tggctgcccc agaggaggac aaggactcgg aggcggaggt | 1500 |
| ggaagttgaa agcaggggagg aattcacctc ctccttgtcc tcgctctctt ccccgtcctt | 1560 |
| tacctcatcc agctccgcca aggacctggg ctcccccggt gcgcgtgccc tgccctcggc | 1620 |
| cgtccctgat gctgcggccc ctgccgacgc cccagtgggg ctggaggcgg agctggagca | 1680 |
| cctgcggcag gcactggagg gcggcctgga caccaaggaa gccaaagaga agttcctgca | 1740 |

```
tgaggtggtc aagatgcgcg tgaagcagga ggagaagctc agcgcagccc tgcaggccaa    1800
gcgcagcctc caccaggagc tggagttcct acgcgtggcc aagaaggaga agctgcggga    1860
ggccacggag gccaagcgta acctgcggaa ggagatcgag cgtctccgcg ccgagaacga    1920
gaagaagatg aaagaggcca acgagtcacg gctgcgcctg aagcgggagc tggagcaggc    1980
gcggcaggcc cgggtgtgcg caagggctg cgaggcgggc cgcctgcgcg ccaagtactc    2040
ggcccagatc gaagacctgc aggtgaagct gcagcacgcg gaggcggacc gggagcagct    2100
gcgggccgac ctgctgcggg agcgcgaggc ccgggagcac ctggagaagg tggtgaagga    2160
gctgcaggaa cagctgtggc cgcgggcccg ccccgaggct gcgggcagcg agggcgctgc    2220
ggagctggag ccgtagattc cgtgcctgcc gccgcagcgc cgccgacaac gcgggtgcag    2280
gggggcgcgg ctgggcggtg cagctccgcc cggctccgcc cctgcagccc acacagcaca    2340
acgtcttacc gtgcctatta ccaagcgagt gtttgtaacc atgtagtttt ggaacccact    2400
gcaaaatttt ctactggcca agttcaagtg agtaagccgc gtcccccaac tacagctgga    2460
gacggggcca gctcggcggc ctgctggtcc tctgcttgct ggaacattct aacatttaca    2520
cttttgttat aagctattta aaaccagtaa ggagacttga aattcagaaa atcaacacat    2580
ttttaaatga ctaacttcta aaagccccaa cacatgacgc catctgaaga cccgcaacgg    2640
agtgggggtg gcgccgcc cacccctccc acccggggaa gccatcacag ctcatctgcc    2700
cgcggctgcg tgaggacagc aggggttttt cttcagagtc tattttttca gcgacaagga    2760
cccaggtctt cctgctgctg ccaggggagag cagggacagt gccgcgtgcg agatgagctc    2820
gaacactgcc cgccttactg ccgcctaccc cgcccgccac gccgccgtcg atgccagcgc    2880
tgtccccacg ggtaccagga agtgcagagc cgcacaggag ctgccccgga gctgagggga    2940
cggtcttcgg ctcctctgca ccccgtgatt ctgcccacgc tcctccacca cgaggcactg    3000
acctgcgtcg ggtggtgacc gtggctggcg gtcacgccct cagcccctcc gggcacacgt    3060
gccgcctgac cgggcgaccc ttttcagttc ggcaaacgtc gctcccttca ttttgggact    3120
gaggctgcag cattggaaca aaagagcatt atttcaattt ttctttcttt ttttttgttc    3180
gttcatttaa acgtatattt agaactgcac tttgtccaca accttccctt ctctttctat    3240
tccccagtga actgaggttt ttaccgattt atagagcagt caaatccgaa gtgctcgagt    3300
gcttagaaac cccctctggt gcttggttga acaagggaat cacaagaaaa cgaaaatgca    3360
aaaactgaac ttcgggggtc gttctgtgcc ttccagcatc ttgtacagca aatcctgact    3420
cgtgtctttt taccccaag atatctgtct tcagtagcga ctgaatctgc cactctcaga    3480
ataagttc                                                             3488
```

<210> SEQ ID NO 59
<211> LENGTH: 3108
<212> TYPE: DNA
<213> ORGANISM: Homo sapiens

<400> SEQUENCE: 59

```
gccgccgccg ccatccgccg ccgcagccag cttccgccgc cgcaggaccg gcccctgccc      60
cagcctccgc agccgcggcg cgtccacgcc cgcccgcgcc cagggcgagt cggggtcgcc     120
gcctgcacgc ttctcagtgt tccccgcgcc ccgcatgtaa cccggccagg cccccgcaac     180
tgtgtcccct gcagctccag ccccgggctg catcccccg ccccgacacc agctctccag     240
cctgctcgtc caggatggcc gcggccaagg ccgagatgca gctgatgtcc ccgctgcaga     300
tctctgaccc gttcggatcc tttcctcact cgcccaccat ggacaactac cctaagctgg     360
```

-continued

```
aggagatgat gctgctgagc aacgggctc cccagttcct cggcgccgcc ggggcccag      420 agggcagcgg cagcaacagc agcagcagca gcagcggggg cggtggaggc ggcggggcg      480 gcagcaacag cagcagcagc agcagcacct tcaaccctca ggcggacacg ggcgagcagc    540
cctacgagca cctgaccgca gagtctttc ctgacatctc tctgaacaac gagaaggtgc     600
tggtggagac cagttacccc agccaaacca ctcgactgcc ccccatcacc tatactggcc   660
gcttttccct ggagcctgca cccaacagtg gcaacacctt gtggcccgag ccctcttca     720 gcttggtcag tggcctagtg agcatgacca acccaccggc ctcctcgtcc tcagcaccat    780
ctccagcggc ctcctccgcc tccgcctccc agagcccacc cctgagctgc gcagtgccat    840
ccaacgacag cagtcccatt tactcagcgg cacccacctt ccccacgccg aacactgaca    900 tttttccctga gccacaaagc caggccttcc cgggctcggc agggacagcg ctccagtacc   960
cgcctcctgc ctaccctgcc gccaagggtg gcttccaggt tcccatgatc cccgactacc  1020
tgtttccaca gcagcagggg gatctgggcc tgggcacccc agaccagaag cccttccagg  1080
gcctggagag ccgcacccag cagccttcgc taacccctct gtctactatt aaggcctttg  1140
ccactcagtc gggctcccag gacctgaagg ccctcaatac cagctaccag tcccagctca  1200
tcaaacccag ccgcatgcgc aagtacccca accggcccag caagacgccc ccccacgaac  1260
gcccttacgc ttgcccagtg gagtcctgtg atcgccgctt ctcccgctcc gacgagctca  1320
cccgccacat ccgcatccac acaggccaga agcccttcca gtgccgcatc tgcatgcgca  1380
acttcagccg cagcgaccac ctcaccaccc acatccgcac ccacacaggc gaaaagccct  1440
tcgcctgcga catctgtgga agaaagtttg ccaggagcga tgaacgcaag aggcatacca  1500
agatccactt gcggcagaag gacaagaaag cagacaaaag tgttgtggcc tcttcggcca  1560
cctcctctct ctcttcctac ccgtccccgg ttgctacctc ttaccgtcc ccggttacta  1620 cctcttatcc atccccggcc accacctcat acccatcccc tgtgcccacc tccttctcct  1680
ctcccggctc ctcgacctac ccatccctg tgcacagtgg cttccctcc ccgtcggtgg  1740 ccaccacgta ctcctctgtt ccccctgctt tcccggccca ggtcagcagc ttccttcct  1800 cagctgtcac caactccttc agcgcctcca cagggctttc ggacatgaca gcaaccttt  1860 ctcccaggac aattgaaatt tgctaaaggg aaaggggaaa gaaagggaaa agggagaaaa  1920
agaaacacaa gagacttaaa ggacaggagg aggagatggc cataggagag gagggttcct  1980
cttaggtcag atggaggttc tcagagccaa gtcctccctc tctactggag tggaaggtct  2040
attggccaac aatcctttct gcccacttcc ccttcccaa ttactattcc ctttgacttc    2100
agctgcctga acagccatg tccaagttct tcacctctat ccaaagaact tgatttgcat    2160
ggattttgga taaatcattt cagtatcatc tccatcatat gcctgacccc ttgctccctt   2220
caatgctaga aaatcgagtt ggcaaaatgg ggtttgggcc cctcagagcc ctgccctgca  2280
cccttgtaca gtgtctgtgc catggatttc gttttcttg gggtactctt gatgtgaaga    2340
taatttgcat attctattgt attatttgga gttaggtcct cacttggggg aaaaaaaaaa   2400
aagaaaagcc aagcaaacca atggtgatcc tctattttgt gatgatgctg tgacaataag  2460
tttgaacctt ttttttttgaa acagcagtcc cagtattctc agagcatgtg tcagagtgtt 2520
gttccgttaa ccttttttgta aatactgctt gaccgtactc tcacatgtgg caaaatatgg  2580
tttggttttt cttttttttt tttttgaaa gtgtttttc ttcgtccttt tggtttaaaa     2640
agtttcacgt cttggtgcct tttgtgtgat gcgccttgct gatggcttga catgtgcaat   2700
```

| | |
|---|---:|
| tgtgagggac atgctcacct ctagccttaa gggggcagg gagtgatgat ttggggagg | 2760 |
| ctttgggagc aaaataagga agagggctga gctgagcttc ggttctccag aatgtaagaa | 2820 |
| aacaaaatct aaaacaaaat ctgaactctc aaaagtctat ttttttaact gaaaatgtaa | 2880 |
| atttataaat atattcagga gttggaatgt tgtagttacc tactgagtag gcggcgattt | 2940 |
| ttgtatgtta tgaacatgca gttcattatt ttgtggttct attttacttt gtacttgtgt | 3000 |
| ttgcttaaac aaagtgactg tttggcttat aaacacattg aatgcgcttt attgcccatg | 3060 |
| ggatatgtgg tgtatatcct tccaaaaaat taaaacgaaa ataaagta | 3108 |

<210> SEQ ID NO 60
<211> LENGTH: 3775
<212> TYPE: DNA
<213> ORGANISM: Homo sapiens
<400> SEQUENCE: 60

| | |
|---|---:|
| cattcataag actcagagct acggccacgg cagggacacg cggaaccaag acttggaaac | 60 |
| ttgattgttg tggttcttct tgggggttat gaaatttcat taatcttttt ttttttccggg | 120 |
| gagaaagttt ttggaaagat tcttccagat atttcttcat tttctttttgg aggaccgact | 180 |
| tactttttt ggtcttcttt attactcccc tcccccgtg ggacccgccg gacgcgtgga | 240 |
| ggagaccgta gctgaagctg attctgtaca gcgggacagc gctttctgcc cctgggggag | 300 |
| caaccctcc ctcgcccctg gtcctacgg agcctgcact ttcaagaggt acagcggcat | 360 |
| cctgtggggg cctgggcacc gcaggaagac tgcacagaaa cttttgccatt gttggaacgg | 420 |
| gacgttgctc cttccccgag cttccccgga cagcgtactt tgaggactcg ctcagctcac | 480 |
| cggggactcc cacggctcac cccggacttg caccttactt ccccaacccg gccatagcct | 540 |
| tggcttcccg gcgacctcag cgtggtcaca ggggcccccc tgtgcccagg gaaatgtttc | 600 |
| aggctttccc cggagactac gactccggct cccggtgcag ctcctcaccc tctgccgagt | 660 |
| ctcaatatct gtcttcggtg gactccttcg gcagtccacc caccgccgcg gcctcccagg | 720 |
| agtgcgccgg tctcggggaa atgcccggtt ccttcgtgcc cacggtcacc gcgatcacaa | 780 |
| ccagccagga cctccagtgg cttgtgcaac ccaccctcat ctcttccatg gcccagtccc | 840 |
| aggggcagcc actggcctcc cagcccccgg tcgtcgaccc ctacgacatg ccgggaacca | 900 |
| gctactccac accaggcatg agtggctaca gcagtggcgg agcgagtggc agtggtgggc | 960 |
| cttccaccag cggaactacc agtgggcctg ggcctgcccg cccagcccga gcccggccta | 1020 |
| ggagaccccg agaggagacg ctcaccccag aggaagagga gaagcgaagg gtgcgccggg | 1080 |
| aacgaaataa actagcagca gctaaatgca ggaaccggcg gagggagctg accgaccgac | 1140 |
| tccaggcgga gacagatcag ttggaggaag aaaaagcaga gctggagtcg agatcgccg | 1200 |
| agctccaaaa ggagaaggaa cgtctggagt ttgtgctggt ggcccacaaa ccgggctgca | 1260 |
| agatccccta cgaagagggg cccgggccgg gcccgctggc ggaggtgaga gatttgccgg | 1320 |
| gctcagcacc ggctaaggaa gatggcttca gctggctgct gccgccccg ccaccaccgc | 1380 |
| ccctgccctt ccagaccagc caagacgcac ccccaacct gacggcttct ctctttacac | 1440 |
| acagtgaagt tcaagtcctc ggcgacccct tccccgttgt taacccttcg tacacttctt | 1500 |
| cgtttgtcct cacctgcccg gaggtctccg cgttcgccgg cgcccaacgc accagcggca | 1560 |
| gtgaccagcc ttccgatccc ctgaactcgc cctccctcct cgctcggtga actctttaga | 1620 |
| cacacaaaac aaacaaacac atgggggaga gagacttgga agaggaggag gaggaggaga | 1680 |
| aggaggagag agaggggaag agacaaagtg ggtgtgtggc ctccctggct cctccgtctg | 1740 |

-continued

```
accctctgcg gccactgcgc cactgccatc ggacaggagg attccttgtg ttttgtcctg    1800
cctcttgttt ctgtgccccg gcgaggccgg agagctggtg actttgggga caggggggtgg   1860 gaaggggatg gacaccccca gctgactgtt ggctctctga cgtcaaccca agctctgggg    1920
atgggtgggg aggggggcgg gtgacgccca ccttcgggca gtcctgtgtg aggatgaagg    1980 gacggggtg ggaggtaggc tgtgggggtgg gctggagtcc tctccagaga ggctcaacaa    2040
ggaaaaatgc cactccctac ccaatgtctc ccacacccac ccttttttttg gggtgcccag   2100 gttggttttcc cctgcactcc cgaccttagc ttattgatcc cacatttcca tggtgtgaga   2160
tcctctttac tctgggcaga agtgagcccc cccttaaagg gaattcgatg ccccccctaga  2220 ataatctcat ccccccaccc gacttctttt gaaatgtgaa cgtccttcct tgactgtcta   2280
gccactccct cccagaaaaa ctggctctga ttggaatttc tggcctccta aggctcccca   2340
ccccgaaatc agccccagc cttgtttctg atgacagtgt tatcccaaga ccctgccccc    2400
tgccagccga ccctcctggc cttcctcgtt gggccgctct gatttcaggc agcagggct    2460 gctgtgatgc cgtcctgctg gagtgattta tactgtgaaa tgagttggcc agattgtggg   2520
gtgcagctgg gtgggggcagc acacctctgg ggggataatg tccccactcc cgaaagcctt  2580
tcctcggtct ccccttccgtc catccccctt cttcctcccc tcaacagtga gttagactca   2640 aggggggtgac agaaccgaga aggggggtgac agtcctccat ccacgtggcc tctctctctc  2700
tcctcaggac cctcagccct ggcctttttc tttaaggtcc cccgaccaat ccccagccta   2760
ggacgccaac ttctcccacc ccttggcccc tcacatcctc tccaggaagg cagtgagggg   2820
ctgtgacatt tttccggaga agatttcaga gctgaggctt tggtaccccc aaaccccccaa  2880 tattttttgga ctggcagact caaggggctg gaatctcatg attccatgcc cgagtccgcc   2940
catccctgac catggttttg gctctcccac cccgccgttc cctgcgcttc atctcatgag    3000 gatttctttta tgaggcaaat ttatattttt taatatcggg gggtggacca cgccgccctc   3060
catccgtgct gcatgaaaaa cattccacgt gccccttgtc gcgcgtctcc catcctgatc   3120
ccagacccat tccttagcta tttatccctt tcctggtttc cgaaaggcaa ttatatctat    3180
tatgtataag taaatatatt atatatggat gtgtgtgtgt gcgtgcgcgt gagtgtgtga   3240
gcgcttctgc agcctcggcc taggtcacgt tggccctcaa agcgagccgt tgaattggaa   3300
actgcttcta gaaactctgg ctcagcctgt ctcgggctga cccttttctg atcgtctcgg    3360
cccctctgat tgttcccgat ggtctctctc cctctgtctt ttctcctccg cctgtgtcca   3420
tctgaccgtt ttcacttgtc tcctttctga ctgtccctgc caatgctcca gctgtcgtct   3480
gactctgggt tcgttgggga catgagattt tattttttgt gagtgagact gagggatcgt    3540 agattttta aatctgtatc tttgacaatt ctgggtgcga gtgtgagagt gtgagcaggg    3600
cttgctcctg ccaaccacaa ttcaatgaat ccccgacccc cctacccat gctgtacttg    3660 tggttctctt tttgtatttt gcatctgacc ccggggggct gggacagatt ggcaatgggc   3720
cgtcccctct ccccttggtt ctgcactgtt gccaataaaa agctcttaaa aacgc         3775
```

<210> SEQ ID NO 61
<211> LENGTH: 2021
<212> TYPE: DNA
<213> ORGANISM: Homo sapiens

<400> SEQUENCE: 61

```
agcgagcttg cagcctcacc gacgagtctc aactaaaagg gactcccgga gctaggggtg    60
```

```
gggactcggc ctcacacagt gagtgccggc tattggactt ttgtccagtg acagctgaga      120
caacaaggac cacgggagga ggtgtaggag agaagcgccg cgaacagcga tcgcccagca      180
ccaagtccgc ttccaggctt tcggtttctt tgcctccatc ttgggtgcgc cttcccggcg      240
tctaggggag cgaaggctga ggtggcagcg gcaggagagt ccggccgcga caggacgaac      300
tcccccactg gaaggattc tgaaagaaat gaagtcagcc ctcagaaatg aagttgactg       360
cctgctggct ttctgttgac tggcccggag ctgtactgca agaccttgt gagcttccct      420 agtctaagag taggatgtct gctgaagtca tccatcaggt tgaagaagca cttgatacag      480
atgagaagga gatgctgctc ttttgtgcc gggatgttgc tatagatgtg gttccaccta      540
atgtcaggga ccttctggat attttacggg aaagaggtaa gctgtctgtc ggggacttgg      600
ctgaactgct ctacagagtg aggcgatttg acctgctcaa acgtatcttg aagatggaca      660
gaaaagctgt ggagacccac ctgctcagga accctcacct tgtttcggac tatagagtgc      720
tgatggcaga gattggtgag gatttggata aatctgatgt gtcctcatta attttcctca      780
tgaaggatta catgggccga ggcaagataa gcaaggagaa ggtttcttgg accttgtggt      840
tgagttggag aaactaaatc tggttgcccc agatcaactg gatttattag aaaaatgcct      900
aaagaacatc cacagaatag acctgaagac aaaaatccag aagtacaagc agtctgttca      960
aggagcaggg acaagttaca ggaatgttct ccaagcagca atccaaaaga gtctcaagga     1020
tccttcaaat aacttcaggc tccataatgg gagaagtaaa gaacaaagac ttaaggaaca     1080
gcttggcgct caacaagaac cagtgaagaa atccattcag gaatcagaag cttttttgcc     1140
tcagagcata cctgaagaga gatacaagat gaagagcaag cccctaggaa tctgcctgat     1200
aatcgattgc attggcaatg agacagagct tcttcgagac accttcactt ccctgggcta     1260
tgaagtccag aaattcttgc atctcagtat gcatggtata tcccagattc ttggccaatt     1320
tgcctgtatg cccgagcacc gagactacga cagctttgtg tgtgtcctgg tgagccgagg     1380
aggctcccag agtgtgtatg gtgtggatca gactcactca gggctccccc tgcatcacat     1440
caggaggatg ttcatgggag attcatgccc ttatctagca gggaagccaa agatgttttt     1500
tattcagaac tatgtggtgt cagagggcca gctggaggac agcagcctct ggaggtgga     1560 tgggccagcg atgaagaatg tggaattcaa ggctcagaag cgagggctgt gcacagttca     1620
ccgagaagct gacttcttct ggagcctgtg tactgcggac atgtccctgc tggagcagtc     1680
tcacagctca ccatccctgt acctgcagtg cctctcccag aaactgagac aagaaagaaa     1740
acgcccactc ctggatcttc acattgaact caatggctac atgtatgatt ggaacagcag     1800
agtttctgcc aaggagaaat attatgtctg gctgcagcac actctgagaa agaaacttat     1860
cctctcctac acataagaaa ccaaaaggct gggcgtagtg gctcacacct gtaatcccag     1920
cactttggga ggccaaggag ggcagatcac ttcaggtcag gagttcgaga ccagcctggc     1980
caacatggta aacgctgtcc ctagtaaaaa tacaaaaatt a                         2021
```

<210> SEQ ID NO 62
<211> LENGTH: 3254
<212> TYPE: DNA
<213> ORGANISM: Homo sapiens

<400> SEQUENCE: 62

```
agagttgcac tgagtgtggc tgaagcagcg aggcgggagt ggaggtgcgc ggagtcaggc       60
agacagacag acacagccag ccagccaggt cggcagtata gtccgaactg caaatcttat      120
tttcttttca ccttctctct aactgcccag agctagcgcc tgtggctccc gggctggtgt      180
```

-continued

```
ttcgggagtg tccagagagc ctggtctcca gccgccccg ggaggagagc cctgctgccc      240
aggcgctgtt gacagcggcg gaaagcagcg gtacccacgc gcccgccggg ggaagtcggc      300
gagcggctgc agcagcaaag aactttcccg gctgggagga ccggagacaa gtggcagagt      360
cccggagcca acttttgcaa gcctttcctg cgtcttaggc ttctccacgg cggtaaagac      420
cagaaggcgg cggagagcca cgcaagagaa gaaggacgtg cgctcagctt cgctcgcacc      480
ggttgttgaa cttgggcgag cgcgagccgc ggctgccggg cgcccctcc ccctagcagc       540
ggaggagggg acaagtcgtc ggagtccggg cggccaagac ccgccgccgg ccggccactg      600
cagggtccgc actgatccgc tccgcgggga gagccgctgc tctgggaagt gagttcgcct      660
gcggactccg aggaaccgct gcgcacgaag agcgctcagt gagtgaccgc gacttttcaa      720
agccgggtag cgcgcgcgag tcgacaagta agagtgcggg aggcatctta attaaccctg      780
cgctccctgg agcgagctgg tgaggagggc gcagcgggga cgacagccag cgggtgcgtg      840
cgctcttaga gaaactttcc ctgtcaaagg ctccgggggg cgcgggtgtc cccgcttgc       900
cacagccctt ttgcggcccc gaaacttgtg cgcgcagccc aaactaacct cacgtgaagt      960
gacggactgt tctatgactg caaagatgga aacgaccttc tatgacgatg ccctcaacgc     1020
ctcgttcctc ccgtccgaga gcggaccttca tggctacagt aaccccaaga tcctgaaaca     1080
gagcatgacc ctgaacctgg ccgacccagt ggggagcctg aagccgcacc tccgcgccaa     1140
gaactcggac ctcctcacct cgcccgacgt ggggctgctc aagctggcgt cgcccgagct     1200
ggagcgcctg ataatccagt ccagcaacgg gcacatcacc accacgccga ccccccaccca     1260
gttcctgtgc cccaagaacg tgacagatga gcaggagggc ttcgccgagg gcttcgtgcg     1320
cgccctggcc gaactgcaca gccagaacac gctgcccagc gtcacgtcgg cggcgcagcc     1380
ggtcaacggg gcaggcatgg tggctcccgc ggtagcctcg gtggcagggg gcagcggcag     1440
cggcggcttc agcgccagcc tgcacagcga gccgccggtc tacgcaaacc tcagcaactt     1500
caacccaggc gcgctgagca gcggcggcgg ggcgccctcc tacggcgcgg ccggcctggc     1560
cttttcccgcg caacccccagc agcagcagca gccgccgcac cacctgcccc agcagatgcc     1620
cgtgcagcac ccgcggctgc aggccctgaa ggaggagcct cagacagtgc ccgagatgcc     1680
cggcgagaca ccgccctgt cccccatcga catggagtcc caggagcgga tcaaggcgga     1740
gaggaagcgc atgaggaacc gcatcgctgc ctccaagtgc cgaaaaagga agctggagag     1800
aatcgcccgg ctggaggaaa aagtgaaaac cttgaaagct cagaactcgg agctggcgtc     1860
cacggccaac atgctcaggg aacaggtggc acagcttaaa cagaaagtca tgaaccacgt     1920
taacagtggg tgccaactca tgctaacgca gcagttgcaa acattttgaa gagagaccgt     1980
cgggggctga ggggcaacga agaaaaaaaa taacacagag agacagactt gagaacttga     2040
caagttgcga cggagagaaa aagaagtgt ccgagaacta agccaagggg tatccaagtt      2100
ggactgggtt gcgtcctgac ggcgccccca gtgtgcacga gtgggaagga cttggcgcgc     2160
cctcccttgg cgtggagcca gggagcggcc gcctgcgggc tgcccgcttt gcggacgggg     2220
ctgtccccgc gcgaacggaa cgttggactt ttcgttaaca ttgaccaaga actgcatgga     2280
cctaacattc gatctcattc agtattaaag gggagggg gaggggtta caaactgcaa     2340
tagagactgt agattgcttc tgtagtactc cttaagaaca caaagcgggg ggagggttgg     2400
ggaggggcgg caggagggag gtttgtgaga gcgaggctga gcctacagat gaactctttc     2460
tggcctgcct tcgttaactg tgtatgtaca tatatatatt ttttaatttg atgaaagctg     2520
```

```
attactgtca ataaacagct tcatgccttt gtaagttatt tcttgtttgt ttgtttgggt    2580
atcctgccca gtgttgtttg taaataagag atttggagca ctctgagttt accatttgta    2640
ataaagtata taatttttt atgttttgtt tctgaaaatt ccagaaagga tatttaagaa     2700
aatacaataa actattggaa agtactcccc taacctcttt tctgcatcat ctgtagatac    2760
tagctatcta ggtggagttg aaagagttaa gaatgtcgat taaaatcact ctcagtgctt    2820
cttactatta agcagtaaaa actgttctct attagacttt agaaataaat gtacctgatg    2880
tacctgatgc tatggtcagg ttatactcct cctcccccag ctatctatat ggaattgctt    2940
accaaaggat agtgcgatgt ttcaggaggc tggaggaagg ggggttgcag tggagaggga    3000
cagcccactg agaagtcaaa catttcaaag tttggattgt atcaagtggc atgtgctgtg    3060
accatttata atgttagtag aaattttaca ataggtgctt attctcaaag caggaattgg    3120
tggcagattt tacaaaagat gtatccttcc aatttggaat cttctctttg acaattccta    3180
gataaaaaga tggccctttgc ttatgaatat ttataacagc attcttgtca cataaaatgt    3240
attcaaatac caat                                                      3254

<210> SEQ ID NO 63
<211> LENGTH: 3254
<212> TYPE: DNA
<213> ORGANISM: Homo sapiens

<400> SEQUENCE: 63
agagttgcac tgagtgtggc tgaagcagcg aggcgggagt ggaggtgcgc ggagtcaggc      60
agacagacag acacagccag ccagccaggt cggcagtata gtccgaactg caaatcttat    120
tttcttttca ccttctctct aactgcccag agctagcgcc tgtggctccc gggctggtgt    180
ttcgggagtg tccagagagc ctggtctcca gccgcccccg ggaggagagc cctgctgccc    240
aggcgctgtt gacagcggcg gaaagcagcg gtacccacgc gcccgccggg ggaagtcggc    300
gagcggctgc agcagcaaag aactttcccg gctgggagga ccggagacaa gtggcagagt    360
cccggagcca acttttgcaa gccttttcctg cgtcttaggc ttctccacgg cggtaaagac    420
cagaaggcgg cggagagcca cgcaagagaa gaaggacgtg cgctcagctt cgctcgcacc    480
ggttgttgaa cttgggcgag cgcgagccgc ggctgccggg cgccccctcc ccctagcagc    540
ggaggagggg acaagtcgtc ggagtccggg cggccaagac ccgccgccgg ccggccactg    600
cagggtccgc actgatccgc tccgcgggga gagccgctgc tctgggaagt gagttcgcct    660
gcggactccg aggaaccgct gcgcacgaag agcgctcagt gagtgaccgc gacttttcaa    720
agccgggtag cgcgcgcgag tcgacaagta agagtgcggg aggcatctta attaaccctg    780
cgctccctgg agcgagctgg tgaggagggc gcagcgggga cgacagccag cgggtgcgtg    840
cgctcttaga gaaactttcc ctgtcaaagg ctccgggggg cgcgggtgtc cccgcttgc     900 cacagccctg ttgcggcccc gaaacttgtg cgcgcagccc aaactaacct cacgtgaagt    960
gacggactgt tctatgactg caaagatgga acgaccttc tatgacgatg ccctcaacgc    1020
ctcgttcctc ccgtccgaga gcggaccta tggctacagt aacccaaga tcctgaaaca    1080 gagcatgacc ctgaacctgg ccgacccagt ggggagcctg aagccgcacc tccgcgccaa    1140
gaactcggac ctcctcacct cgcccgacgt ggggctgctc aagctggcgt cgcccgagct    1200
ggagcgcctg ataatccagt ccagcaacgg gcacatcacc accacgccga ccccacccca    1260
gttcctgtgc cccaagaacg tgacagatga gcaggaggc ttcgccgagg cttcgtgcg     1320 cgccctggcc gaactgcaca gccagaacac gctgcccagc gtcacgtcgg cggcgcagcc    1380
```

-continued

```
ggtcaacggg gcaggcatgg tggctcccgc ggtagcctcg gtggcagggg gcagcggcag    1440
cggcggcttc agcgccagcc tgcacagcga gccgccggtc tacgcaaacc tcagcaactt    1500
caacccaggc gcgctgagca gcggcggcgg ggcgccctcc tacggcgcgg ccggcctggc    1560 cttctcccgcg caaccccagc agcagcagca gccgccgcac cacctgcccc agcagatgcc    1620
cgtgcagcac ccgcggctgc aggccctgaa ggaggagcct cagacagtgc ccgagatgcc    1680
cggcgagaca ccgcccctgt cccccatcga catggagtcc caggagcgga tcaaggcgga    1740
gaggaagcgc atgaggaacc gcatcgctgc ctccaagtgc cgaaaaagga agctggagag    1800
aatcgcccgg ctggaggaaa aagtgaaaac cttgaaagct cagaactcgg agctggcgtc    1860
cacggccaac atgctcaggg aacaggtggc acagcttaaa cagaaagtca tgaaccacgt    1920
taacagtggg tgccaactca tgctaacgca gcagttgcaa acattttgaa gagagaccgt    1980
cgggggctga ggggcaacga agaaaaaaaa taacacagag agacagactt gagaacttga    2040
caagttgcga cggagagaaa aagaagtgt ccgagaacta agccaaggg tatccaagtt    2100 ggactgggtt gcgtcctgac ggcgccccca gtgtgcacga gtgggaagga cttggcgcgc    2160
cctcccttgg cgtggagcca gggagcggcc gcctgcgggc tgccccgctt gcggacgggg    2220
ctgtccccgc gcgaacggaa cgttggactt tcgttaaca ttgaccaaga actgcatgga    2280
cctaacattc gatctcattc agtattaaag gggggagggg gagggggtta caaactgcaa    2340
tagagactgt agattgcttc tgtagtactc cttaagaaca caaagcgggg ggagggttgg    2400
ggaggggcgg caggagggag gtttgtgaga gcgaggctga gcctacagat gaactctttc    2460
tggcctgcct tcgttaactg tgtatgtaca tatatatatt ttttaatttg atgaaagctg    2520
attactgtca ataaacagct tcatgccttt gtaagttatt tcttgtttgt ttgtttgggt    2580
atcctgccca gtgttgtttg taaataagag atttggagca ctctgagttt accatttgta    2640
ataaagtata taattttttt atgttttgtt tctgaaaatt ccagaaagga tatttaagaa    2700
aatacaataa actattggaa agtactcccc taacctcttt tctgcatcat ctgtagatac    2760
tagctatcta ggtggagttg aaagagttaa gaatgtcgat taaaatcact ctcagtgctt    2820
cttactatta agcagtaaaa actgttctct attagacttt agaaataaat gtacctgatg    2880
tacctgatgc tatggtcagg ttatactcct cctcccccag ctatctatat ggaattgctt    2940
accaaaggat agtgcgatgt tcaggaggc tggaggaagg ggggttgcag tggagaggga    3000
cagcccactg agaagtcaaa catttcaaag tttggattgt atcaagtggc atgtgctgtg    3060
accatttata atgttagtag aaattttaca ataggtgctt attctcaaag caggaattgg    3120
tggcagattt tacaaaagat gtatccttcc aatttggaat cttctctttg acaattccta    3180
gataaaaaga tggcctttgc ttatgaatat ttataacagc attcttgtca cataaatgt    3240 attcaaatac caat                                                      3254
```

<210> SEQ ID NO 64
<211> LENGTH: 1832
<212> TYPE: DNA
<213> ORGANISM: Homo sapiens

<400> SEQUENCE: 64

```
gtgccgctcc ttggtggggg ctgttcatgg cggttccggg gtctccaaca ttttttcccgg     60 ctgtggtcct aaatctgtcc aaagcagagg cagtggagct tgaggttctt gctggtgtga    120
aatgactgag tacaaactgg tggtggttgg agcaggtggt gttgggaaaa gcgcactgac    180
```

| | |
|---|---|
| aatccagcta atccagaacc actttgtaga tgaatatgat cccaccatag aggattctta | 240 |
| cagaaaacaa gtggttatag atggtgaaac ctgtttgttg acatactgg atacagctgg | 300 |
| acaagaagag tacagtgcca tgagagacca atacatgagg acaggcgaag gcttcctctg | 360 |
| tgtatttgcc atcaataata gcaagtcatt tgcggatatt aacctctaca gggagcagat | 420 |
| taagcgagta aaagactcgg atgatgtacc tatggtgcta gtgggaaaca agtgtgattt | 480 |
| gccaacaagg acagttgata caaaacaagc ccacgaactg ccaagagtt acgggattcc | 540 |
| attcattgaa acctcagcca agaccagaca gggtgttgaa gatgcttttt acacactggt | 600 |
| aagagaaata cgccagtacc gaatgaaaaa actcaacagc agtgatgatg ggactcaggg | 660 |
| ttgtatggga ttgccatgtg tggtgatgta acaagatact tttaaagttt tgtcagaaaa | 720 |
| gagccacttt caagctgcac tgacaccctg gtcctgactt ccctggagga gaagtattcc | 780 |
| tgttgctgtc ttcagtctca cagagaagct cctgctactt ccccagctct cagtagttta | 840 |
| gtacaataat ctctatttga gaagttctca gaataactac ctcctcactt ggctgtctga | 900 |
| ccagagaatg cacctcttgt tactccctgt tatttttctg ccctgggttc ttccacagca | 960 |
| caaacacacc tctgccaccc caggttttc atctgaaaag cagttcatgt ctgaaacaga | 1020 |
| gaaccaaacc gcaaacgtga attctattg aaaacagtgt cttgagctct aaagtagcaa | 1080 |
| ctgctggtga tttttttttt ctttttactg ttgaacttag aactatgcta attttggag | 1140 |
| aaatgtcata aattactgtt tgccaagaa tatagttatt attgctgttt ggtttgttta | 1200 |
| taatgttatc ggctctattc tctaaactgg catctgctct agattcataa atacaaaaat | 1260 |
| gaatactgaa ttttgagtct atcctagtct tcacaacttt gacgtaatta aatccaactt | 1320 |
| tcacagtgaa gtgccttttt cctagaagtg gtttgtagac ttcctttata atatttcagt | 1380 |
| ggaatagatg tctcaaaaat ccttatgcat gaaatgaatg tctgagatac gtctgtgact | 1440 |
| tatctaccat tgaaggaaag ctatatctat ttgagagcag atgccatttt gtacatgtat | 1500 |
| gaaattggtt ttccagaggc ctgttttggg gctttcccag gagaaagatg aaactgaaag | 1560 |
| cacatgaata atttcactta ataattttta cctaatctcc acttttttca taggttacta | 1620 |
| cctatacaat gtatgtaatt tgtttcccct agcttactga taaacctaat attcaatgaa | 1680 |
| cttccatttg tattcaaatt tgtgtcatac cagaaagctc tacatttgca gatgttcaaa | 1740 |
| tattgtaaaa ctttggtgca ttgttattta atagctgtga tcagtgattt tcaaacctca | 1800 |
| aatatagtat attaacaaat tacattttca ct | 1832 |

<210> SEQ ID NO 65
<211> LENGTH: 3890
<212> TYPE: DNA
<213> ORGANISM: Homo sapiens

<400> SEQUENCE: 65

| | |
|---|---|
| atgaaggtga taagcttatt cattttggtg ggatttatag gagagttcca aagtttttca | 60 |
| agtgcctcct ctccagtcaa ctgccagtgg gacttctatg ccccttggtc agaatgcaat | 120 |
| ggctgtacca agactcagac tcgcaggcgg tcagttgctg tgtatgggca gtatggaggc | 180 |
| cagccttgtg ttggaaatgc ttttgaaaca cagtcctgtg aacctacaag aggatgtcca | 240 |
| acagaggagg atgtggaga gcgtttcagg tgcttttcag gtcagtgcat cagcaaatca | 300 |
| ttggtttgca atgggattc tgactgtgat gaagacagtg ctgatgaaga cagatgtgag | 360 |
| gactcagaaa ggagaccttc ctgtgatatc gataaacctc ctcctaacat agaacttact | 420 |
| ggaaatggtt acaatgaact cactggccag tttaggaaca gagtcatcaa taccaaaagt | 480 |

```
tttggtggtc aatgtagaaa ggtgtttagt ggggatggaa aagatttcta caggctgagt    540
ggaaatgtcc tgtcctatac attccaggtg aaaataaata atgattttaa ttatgaattt    600
tacaatagta cttggtctta tgtaaaacat acgtcgacag aacacacatc atctagtcgg    660
aagcgctcct tttttagatc ttcatcatct tcttcacgca gttatacttc acataccaat    720
gaaatccata aaggaaagag ttaccaactg ctggttgttg agaacactgt tgaagtggct    780
cagttcatta ataacaatcc agaatttta caacttgctg agccattctg gaaggagctt     840
tcccacctcc cctctctgta tgactacagt gcctaccgaa gattaatcga ccagtacggg    900
acacattatc tgcaatctgg gtcgttagga ggagaataca gagttctatt ttatgtggac    960
tcagaaaaat aaaacaaaa tgattttaat tcagtcgaag aaaagaaatg taaatcctca    1020
ggttggcatt ttgtcgttaa attttcaagt catggatgca aggaactgga aaacgcttta    1080
aaagctgctt caggaaccca gaacaatgta ttgcgaggag aaccgttcat cagagggga    1140
ggtgcaggct tcatatctgg ccttagttac ctagagctgg acaatcctgc tggaaacaaa    1200
aggcgatatt ctgcctgggc agaatctgtg actaatcttc ctcaagtcat aaaacaaaag    1260
ctgacacctt tatatgagct ggtaaaggaa gtaccttgtg cctctgtgaa aaaactatac    1320
ctgaaatggg ctcttgaaga gtatctggat gaatttgacc cctgtcattg ccggccttgt    1380
caaaatggtg gtttggctac tgttgagggg acccattgtc tgtgccattg caaaccgtac    1440
acatttggtg cggcgtgtga gcaaggagtc ctcgtaggga atcaagcagg agggggttgat   1500
ggaggttgga gttgctggtc ctcttggagc ccctgtgtcc aagggaagaa aacaagaagc    1560
cgtgaatgca ataacccacc tcccagtggg ggtgggagat cctgcgttgg agaaacgaca    1620
gaaagcacac aatgcgaaga tgaggagctg gagcacttga ggttgcttga accacattgc    1680
tttcctttgt ctttggttcc aacagaattc tgtccatcac ctcctgcctt gaaagatgga    1740
tttgttcaag atgaaggtcc aatgtttcct gtggggaaaa atgtagtgta cacttgcaat    1800
gaaggatact ctcttattgg aaacccagtg gccagatgtg agaagatttt acggtggctt    1860
gttggggaaa tgcattgtca gaaaattgcc tgtgttctac ctgtactgat ggatggcata    1920
cagagtcacc cccaaaaacc tttctacaca gttggtgaga aggtgactgt tcctgttca    1980
ggtggcatgt ccttagaagg tccttcagca tttctctgtg ctccagcct taagtggagt    2040
cctgagatga agaatgcccg ctgtgtacaa aaagaaaatc cgttaacaca ggcagtgcct    2100
aaatgtcagc gctgggagaa actgcagaat tcaagatgtg tttgtaaaat gccctacgaa    2160
tgtggacctt ccttggatgt atgtgctcaa gatgagagaa gcaaaggat actgcctctg    2220
acagtttgca agatgcatgt tctccactgt cagggtagaa attacaccct tactggtagg    2280
gacagctgta ctctgcctgc ctcagctgag aaagcttgtg gtgcctgccc actgtgggga    2340
aaatgtgatg ctgagagcag caaatgtgtc tgccgagaag catcggagtg cgaggaagaa    2400
gggtttagca tttgtgtgga agtgaacggc aaggagcaga cgatgtctga gtgtgaggcg    2460
ggcgctctga gatgcagagg gcagagcatc tctgtcacca gcataaggcc ttgtgctgcg    2520
gaaacccagt aggctcctgg aggccatggt cagcttgctt ggaatccagc aggcagctgg    2580
ggctgagtga aaacatctgc acaactgggc actggacagc ttttccttct tctccagtgt    2640
ctaccttcct cctcaactcc cagccatctg tataaacaca atcctttgtt ctcccaaatc    2700
tgaatcgaat tactcttttg cctccttttt aatgtcagta aggatatgag cctttgcaca    2760
ggctggctgc gtgttcttga aataggtgtt accttctctg ggccttggtt ttttaaaatc    2820
```

```
tgtaaaatta gaggattgca ctagagaaac ttgaatgctc cattcaggcc tatcatttta    2880
ttaagtatga ttgacacagc ccatgggcca gaacacactc tacaaaatga ctaggataac    2940
agaaagaacg tgatctcctg attagagagg gtggttttcc tcaatggaac caaatataaa    3000
gaggacttga acaaaatga cagatacaaa ctatttctat cctgagtagt aatctcacac     3060
ttcatcctat agagtcaacc accacagata ggaattcctt attcttttt taatttttt      3120 aagacagagt ctcactttgt tgcccaggct ggagcgcagt ggggtgatct catctccctg    3180
caacctccgc ctcctgggtt gaagcgattc ttgtgcctca gcttcccaag cagctgggat    3240
tacaggtgcc cgccaccacg cccagctaat ttttgcattt ttagtagaga tgggtttcac    3300
catgttggcc atgctcgtct ccaactcctg acctcaggta atccgtctgc cttggcctcc    3360
caaatgctgg gattacagac atgaaccacc acgcctggct ggaatactta ctcttgtcgg    3420
gagattgaac cactaaaatg ttagagcaga attcattatg ctgtggtcac aggggtgtct    3480
tgtctgagaa caaatacaat tcagtcttct ctttggggtt ttagtatgtg tcaaacatag    3540
gactggaagt ttgcccctgt tcttttttct tttgaaagaa catcagttca tgcctgaggc    3600
atgagtgact gtgcatttga gatagttttc cctattctgt ggatacagtc ccagagtttt    3660
cagggagtac acaggtagat tagtttgaag cattgacctt ttatttattc cttatttctc    3720
tttcatcaaa acaaaacagc agctgtggga ggagaaatga gagggcttaa atgaaattta    3780
aaataagcta tattatacaa atactatctc tgtattgttc tgaccctggt aaatatattt    3840
caaaacttca gatgacaagg attagaacac tcattaagat gctattcttc                3890
```

<210> SEQ ID NO 66
<211> LENGTH: 725
<212> TYPE: DNA
<213> ORGANISM: Homo sapiens

<400> SEQUENCE: 66

```
ctaacccaga aacatccaat tctcaaactg aagctcgcac tctcgcctcc agcatgaaag      60
tctctgccgc ccttctgtgc ctgctgctca tagcagccac cttcattccc caagggctcg    120
ctcagccaga tgcaatcaat gccccagtca cctgctgtta aacttcacc aataggaaga     180 tctcagtgca gaggctcgcg agctatagaa gaatcaccag cagcaagtgt cccaaagaag    240
ctgtgatctt caagaccatt gtggccaagg agatctgtgc tgaccccaag cagaagtggg    300
ttcaggattc catggaccac ctggacaagc aaacccaaac tccgaagact tgaacactca    360
ctccacaacc caagaatctg cagctaactt attttcccct agctttcccc agacaccctg    420
ttttatttta ttataatgaa ttttgtttgt tgatgtgaaa cattatgcct taagtaatgt    480
taattcttat ttaagttatt gatgttttaa gtttatcttt catggtacta gtgtttttta    540
gatacagaga cttggggaaa ttgctttcc tcttgaacca cagttctacc cctgggatgt     600
tttgagggtc tttgcaagaa tcattaatac aaagaattt ttttaacatt ccaatgcatt     660
gctaaaatat tattgtggaa atgaatattt tgtaactatt acaccaaata aatatatttt    720
tgtac                                                                725
```

<210> SEQ ID NO 67
<211> LENGTH: 3451
<212> TYPE: DNA
<213> ORGANISM: Homo sapiens
<220> FEATURE:
<221> NAME/KEY: misc_feature
<222> LOCATION: (841)..(1225)
<223> OTHER INFORMATION: The "n" at this position can be either "a", "t", "g", or "c".

<400> SEQUENCE: 67

```
ttcaatgttg atgtgaaaaa ttcaatgact ttcagcggcc cggtggaaga catgtttgga      60
tatactgttc aacaatatga aaatgaagaa ggaaaatggg tgcttattgg ttctccgtta     120
gttggccaac ccaaaaacag aactggagat gtctataagt gtccagttgg gagaggtgaa     180
tcattacctt gcgtaaagtt ggatctacca gttaatacat caattcccaa tgtcacagaa     240
gtaaaggaga acatgacatt tggatcaact ttagtcacca acccaaatgg aggatttctg     300
gcttgtgggc ccttatatgc ctatagatgt ggacatttgc attacacaac tggaatctgt     360
tctgacgtca gccccacatt tcaagtcgtg aattccattg ccctgtaca agaatgcagc      420
actcaactgg acatagtcat agtgctggat ggttccaaca gtatttaccc atgggacagt     480
gttacagctt ttttaaatga ccttcttgaa agaatggata ttggtcctaa acagacacag     540
gttgaattg tacagtatgg agaaaacgtg acccatgagt tcaacctcaa taagtattct      600
tccaccgaag aggtacttgt tgcagcaaag aaaatagtcc agagaggtgg ccgccagact     660
atgacagctc ttggaataga cacagcaaga aaggaggcat tcacggaagc ccggggtgcc     720
cgaagaggag ttaaaaaagt catggttatt gtgacagatg gagagtctca tgacaatcat     780
cgactgaaga aggtcatcca agactgtgaa gatgaaaaca ttcaacggtt ttccatagct     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnctt catatgaaat ggaaatgtct cagactggct tcagtgctca ttattcacag    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnngttac actgtaaact ctgctactgc ttcttctgga    1260
gatgtgctct atattgctgg acagcctcgg tacaatcata caggccaggt cattatctac    1320
aggatggaag atgaaacat caaaattctc cagacgctca gtggagaaca gattggttcc     1380
tactttggca gtattttaac aacaactgac attgacaagg attctaatac tgacattctt    1440
ctagtcggag cccctatgta catgggaaca gagaaggagg agcaaggaaa agtgtatgtg    1500
tatgctctca atcagacaag gtttgaatat caaatgagcc tggaacctat taagcagacg    1560
tgctgttcat ctcggcagca caattcatgc acaacagaaa acaaaaatga gccatgcggg    1620
gctcgttttg gaactgcaat tgctgctgta aaagacctca atcttgatgg atttaatgac    1680
atcgtgatag gagctccgct ggagatgatc acggggagc tgtgtacatt tatcatggaa     1740
gtggcaagac tataaggaaa gagtatgcac aacgtattcc atcaggtggg gatggtaaga    1800
cactgaaatt ttttggccag tctatccacg gagaaatgga tttaaatggt gacggtctga    1860
cagatgtgac tattggggc cttggtggtg ctgccctctt ctggtcccga gatgtggccg     1920
tagttaaagt gaccatgaat tttgagccaa ataaagtgaa tattcaaaag aaaaactgcc    1980
atatggaggg aaaggaaaca gtatgcataa atgctacagt gtgttttgat gtgaaattaa    2040
agtctaaaga agacacgatt tatgaagctg atttgcagta ccgtgtcacc ctagattcac    2100
taagacaaat atcacgaagt ttttctctg gaactcaaga gagaaaggtt caaaggaaca     2160
tcacagttcg aaaatcagaa tgcactaagc actccttcta catgttgaca agcatgactt    2220
tcaggactct gtgagaataa cgttggactt taatcttacc gatccagaaa atgggcctgt    2280
```

```
tcttgatgat tctctaccaa actcagtaca tgaatatatt cccttttgcca aagattgtgg    2340 aaataaggaa aaatgtatct cagacctcag cctgcatgtc gccaccactg aaaaggacct    2400
gctgattgtc cgatcccaga atgataagtt caacgttagc ctcacagtca aaaatacaaa    2460
ggacagtgcc tataacacca ggacaatagt gcattattct ccaaatctag tttttttcagg   2520 aattgaggct atccaaaaag acagttgtga atcaatcat aatatcacat gtaaagttgg     2580
atatcccttc ctgagaagag gagagatggt aactttcaaa atattgtttc agtttaacac    2640
atcctatctc atggaaaatg tgaccatttta tttaagtgca acaagtgaca gcgaagaacc   2700
tcctgaaacc ctttctgata atgtagtaaa catttctatc ccggtaaaat atgaagttgg    2760
actacagttt tacagctctg caagtgaata ccacatttca attgctgcca atgagacagt    2820
ccctgaagtt attaattcta ctgaggacat tggaaatgaa attaatatct tctacttgat    2880
tagaaaaagt ggatcttttc caatgccaga gcttaagctg tcaatttcat tcccccaatat  2940 gacatcaaat ggttaccctg tgctgtaccc aactggattg tcatcttctg agaatgcaaa    3000
ctgcagaccc catatctttg aggatccttt cagtatcaac tctggaaaga aaatgactac    3060
atcaactgac catctcaaac gaggcacaat tctggactgc aatacatgta aatttgctac    3120
catcacatgt aatctcactt cttctgacat cagccaagtc aatgtttcgc ttatcttgtg    3180
gaaaccaact tttataaaat catattttc cagcttaaat cttactataa ggggagaact    3240
tcggagtgaa aatgcatctc tggttttaag tagcagcaat caaaaaagag agcttgctat    3300
tcaaatatcc aaagatgggc taccgggcag agtgccatta tgggtcatcc tgctgagtgc    3360
ttttgccgga ttgttgctgt taatgctgct cattttagca ctgtggaaga ttggattctt    3420
caaaagacca ctgaaaaaga aaatggagaa a                                   3451

<210> SEQ ID NO 68
<211> LENGTH: 1772
<212> TYPE: DNA
<213> ORGANISM: Homo sapiens

<400> SEQUENCE: 68
gtatcactca gaatctggca gccagttccg tcctgacaga gttcacagca tatattggtg     60
gattcttgtc catagtgcat ctgctttaag aattaacgaa agcagtgtca agacagtaag    120
gattcaaacc atttgccaaa aatgagtcta agtgcattta ctctcttcct ggcattgatt    180
ggtggtacca gtggccagta ctatgattat gattttcccc tatcaattta tgggcaatca    240
tcaccaaact gtgcaccaga atgtaactgc cctgaaagct acccaagtgc catgtactgt    300
gatgagctga aattgaaaag tgtaccaatg gtgcctcctg aatcaagta tctttacctt    360 aggaataacc agattgacca tattgatgaa aaggcctttg agaatgtaac tgatctgcag    420
tggctcattc tagatcacaa ccttctagaa aactccaaga taaaagggag agttttctct    480
aaattgaaac aactgaagaa gctgcatata aaccacaaca cctgacagaa gtctgtgggc    540
ccacttccca aatctctgga ggatctgcag cttactcata acaagatcac aaagctgggc    600
tcttttgaag gattggtaaa cctgaccttc atccatctcc agcacaatcg gctgaaagag    660
gatgctgttt cagctgcttt taaaggtctt aaatcactcg aataccttga cttgagcttc    720
aatcagatag ccagactgcc ttctggtctc cctgtctctc ttctaactct ctacttagac    780
aacaataaga tcagcaacat ccctgatgag tatttcaagc gttttaatgc attgcagtat    840
ctgcgtttat ctcacaacga actggctgat agtggaatac ctggaaattc tttcaatgtg    900
```

```
tcatccctgg ttgagctgga tctgtcctat aacaagctta aaaacatacc aactgtcaat      960
gaaaaccttg aaaactatta cctggaggtc aatcaacttg agaagtttga cataaagagc     1020
ttctgcaaga tcctggggcc attatcctac tccaagatca agcatttgcg tttggatggc     1080
aatcgcatct cagaaaccag tcttccaccg gatatgtatg aatgtctacg tgttgctaac     1140
gaagtcactc ttaattaata tctgtatcct ggaacaatat tttatggtta tgttttctg     1200 tgtgtcagtt ttcatagtat ccatatttta ttactgttta ttacttccat gaattttaaa     1260
atctgaggga aatgttttgt aaacatttat tttttttaaa gaaagatga aaggcaggcc     1320 tatttcatca caagaacaca cacatataca cgaatagaca tcaaactcaa tgctttattt     1380
gtaaatttag tgttttttta tttctactgt caaatgatgt gcaaaacctt ttactggttg     1440
catgaaaatc agccaagttt tataatcctt aaatcttaat gttcctcaaa gcttggatta     1500
aatacatatg gatgttactc tcttgcacca aattatcttg atacattcaa atttgtctgg     1560
ttaaaaaata ggtggtagat attgaggcca agaatattgc aaaatacatg aagcttcatg     1620
cacttaaaga agtattttta gaataagaat ttgcatactt acctagtgaa acttttctag     1680
aattattttt cactctaagt catgtatgtt tctctttgat tatttgcatg ttatgtttaa     1740
taagctacta gcaaaataaa acatagcaaa tg                                   1772

<210> SEQ ID NO 69
<211> LENGTH: 2198
<212> TYPE: DNA
<213> ORGANISM: Homo sapiens

<400> SEQUENCE: 69
tggacagagg agcagtaaca atccccactc tccaattgtg gaagagttcc aagtcccata       60
caacaaactc caggtgatct ttaagtcaga ctttttccaat gaagagcgtt ttacggggtt      120
tgctgcatac tatgttgcca cagacataaa tgaatgcaca gattttgtag atgtcccttg      180
tagccacttc tgcaacaatt tcattggtgg ttacttctgc tcctgccccc cggaatattt      240
cctccatgat gacatgaaga attgcggagt taattgcagt ggggatgtat tcactgcact      300
gattggggag attgcaagtc ccaattatcc caaaccatat ccagagaact caaggtgtga      360
ataccagatc cggttggaga aagggttcca agtggtggtg accttgcgga gagaagattt      420
tgatgtggaa gcagctgact cagcgggaaa ctgccttgac agtttagttt ttgttgcagg      480
agatcggcaa tttggtccctt actgtggtca tggattccct gggcctctaa atattgaaac      540
caagagtaat gctcttgata tcatcttcca aactgatcta acagggcaaa aaagggctg      600 gaaacttcgc tatcatggag atccaatgcc ctgccctaag gaagacactc ccaattctgt      660
ttgggagcct gcgaaggcaa aatatgtctt tagagatgtg gtgcagataa cctgtctgga      720
tgggtttgaa gttgtggagg gacgtgttgg tgcaacatct ttctattcga cttgtcaaag      780
caatggaaag tggagtaatt ccaaactgaa atgtcaacct gtggactgtg gcattcctga      840
atccattgag aatggtaaag ttgaagaccc agagagcact ttgtttggtt ctgtcatccg      900
ctacacttgt gaggagccat attactacat ggaaaatgga ggaggtgggg agtatcactg      960
tgctggtaac gggagctggg tgaatgaggt gctgggcccg gagctgccga atgtgttcc     1020 aggtctgtgg agtccccaga gaacccttg aagaaaaaca gaggataatt ggaggatccg     1080
atgcagatat taaaaacttc ccctggcaag tcttctttga caacccatgg gctggtggag     1140
cgctcattaa tgagtactgg gtgctgacgg ctgctcatgt tgtggaggga acagggagc     1200 caacaatgta tgttgggtcc acctcagtgc agacctcacg gctggcaaaa tccaagatgc     1260
```

```
tcactcctga gcatgtgttt attcatccgg gatggaagct gctggaagtc ccagaaggac    1320
gaaccaattt tgataatgac attgcactgg tgcggctgaa agacccagtg aaaatgggac    1380
ccaccgtctc tcccatctgc ctaccaggca cctcttccga ctacaacctc atggatgggg    1440
acctgggact gatctcaggc tggggccgaa cagagaagag agatcgtgct gttcgcctca    1500
aggcggcaag gttacctgta gctccttaa gaaaatgcaa agaagtgaaa gtggagaaac     1560
ccacagcaga tgcagaggcc tatgttttca ctcctaacat gatctgtgct ggaggagaga    1620
agggcatgga tagctgtaaa ggggacagtg gtggggcctt tgctgtacag gatcccaatg    1680
acaagaccaa attctacgca gctggcctgg tgtcctgggg gccccagtgt gggacctatg    1740
ggctctacac acgggtaaag aactatgttg actggataat gaagactatg caggaaaata    1800
gcaccccccg tgaggactaa tccagataca tcccaccagc ctctccaagg gtggtgacca    1860
atgcattacc ttctgttcct tatgatattc tcattatttc atcatgactg aaagaagaca    1920
cgagcgaatg atttaaatag aacttgattg ttgagacgcc ttgctagagg tagagtttga    1980
tcatagaatt gtgctggtca tacatttgtg gtctgactcc ttggggtcct ttccccggag    2040
tacctattgt agataacact atgggtgggg cactcctttc ttgcactatt ccacagggat    2100
accttaattc tttgtttcct ctttacctgt tcaaaattcc atttacttga tcattctcag    2160
tatccactgt ctatgtacaa taaaggatgt ttataagc                             2198

<210> SEQ ID NO 70
<211> LENGTH: 2177
<212> TYPE: DNA
<213> ORGANISM: Homo sapiens

<400> SEQUENCE: 70
aaactctgat ctggggagga accaggacta catagatcaa ggcagttttc ttctttgaga    60
aactatccca gatatcatca tagagtcttc tgctcttcct caactaccaa agaaaaacat    120
cagcgaagca gcaggccatg cacccccaa aaactccatc tggggctctt catagaaaaa     180
ggaaaatggc agcctggccc ttctccaggc tgtggaaagt ctctgatcca attctcttcc    240
aaatgacctt gatcgctgct ctgttgcctg ctgttcttgg caattgtggt cctccaccca    300
ctttatcatt tgctgccccg atggatatta cgttgactga gacacgcttc aaaactggaa    360
ctactctgaa atacacctgc ctccctggct acgtcagatc ccattcaact cagacgctta    420
cctgtaattc tgatggcgaa tgggtgtata acaccttctg tatctacaaa cgatgcagac    480
acccaggaga gttacgtaat gggcaagtag agattaagac agatttatct tttggatcac    540
aaatagaatt cagctgttca gaaggatttt tcttaattgg ctcaaccact agtcgttgtg    600
aagtccaaga tagaggagtt ggctggagtc atcctctccc acaatgtgaa attgtcaagt    660
gtaagcctcc tccagacatc aggaatgaa ggcacagcgg tgaagaaaat ttctacgcat     720
acggcttttc tgtcacctac agctgtgacc cccgcttctc actcttgggc catgcctcca    780
tttcttgcac tgtggagaat gaaacaatag gtgtttggag accaagccct cctacctgtg    840
aaaaaatcac ctgtcgcaag ccagatgttt cacatgggga atggtctct ggatttggac     900 ccatctataa ttacaaagac actattgtgt ttaagtgcca aaaaggtttt gttctcagag    960
gcagcagtgt aattcattgt gatgctgata gcaaatggaa tccttctcct cctgcttgtg    1020
agcccaatag ttgtattaat ttaccagaca ttccacatgc ttcctgggaa acatatccta    1080
ggccgacaaa agaggatgtg tatgttgttg ggactgtgtt aaggtaccgc tgtcatcctg    1140
```

-continued

```
gctacaaacc cactacagat gagcctacga ctgtgatttg tcagaaaaat ttgagatgga    1200
ccccatacca aggatgtgag gcgttatgtt gccctgaacc aaagctaaat aatggtgaaa    1260
tcactcaaca caggaaaagt cgtcctgcca atcactgtgt ttatttctat ggagatgaga    1320
tttcattttc atgtcatgag accagtaggt tttcagctat atgccaagga gatggcacgt    1380
ggagtccccg aacaccatca tgtggagaca tttgcaattt tcctcctaaa attgcccatg    1440
ggcattataa acaatctagt tcatacagct ttttcaaaga agagattata tatgaatgtg    1500
ataaaggcta cattctggtc ggacaggcga aactctcctg cagttattca cactggtcag    1560
ctccagcccc tcaatgtaaa gctctgtgtc ggaaaccaga attagtgaat ggaaggttgt    1620
ctgtggataa ggatcagtat gttgagcctg aaaatgtcac catccaatgt gattctggct    1680
atggtgtggt tggtccccaa agtatcactt gctctgggaa cagaacctgg tacccagagg    1740
tgcccaagtg tgagtgggag accccgaag gctgtgaaca agtgctcaca ggcaaaagac    1800
tcatgcagtg tctcccaaac ccagaggatg tgaaaatggc cctggaggta tataagctgt    1860
ctctggaaat tgaacaactg gaactacaga gagacagcgc aagacaatcc actttggata    1920
aagaactata atttttctca aaagaaggag gaaaaggtgt cttgctggct tgcctcttgc    1980
aattcaatac agatcagttt agcaaatcta ctgtcaattt ggcagtgata ttcatcataa    2040
taaatatcta gaaatgataa tttgctaaag tttagtgctt tgagattgtg aaattattaa    2100
tcatcctctg tgtggctcat gttttttgctt ttcaacacac aaagcacaaa ttttttttcg    2160
attaaaaatg tatgtat                                                  2177
```

<210> SEQ ID NO 71
<211> LENGTH: 387
<212> TYPE: DNA
<213> ORGANISM: Homo sapiens
<220> FEATURE:
<221> NAME/KEY: misc_feature
<222> LOCATION: (27)..(53)
<223> OTHER INFORMATION: The "n" at this position can be either "a", "t", "g", or "c".

<400> SEQUENCE: 71

```
gccctgctgg ccctgctggt gctcccnnnn nnnnnnnnnn nnnnnnnnnn nnnggtcctc      60
aaggcccacg tggtgacaaa ggtgaaacag gtgaacgtgg agctgctggc atcaaaggac    120
atcgaggatt ccctggtaat ccaggtgccc caggttctcc agggccctgc tggtcagcag    180
ggtgcaatcg gcagtccagg acctgcaggc cccagaggac ctgttggacc cagtggacct    240
cctggcaaag atggaaccag tggacatcca ggtcccattg gaccaccagg gcctcgaggt    300
aacagaggtg aaagaggatc tgagggctcc ccaggccacc cagggcaacc aggccctcct    360
ggacctcctg gtgcccctgg tccttgc                                        387
```

<210> SEQ ID NO 72
<211> LENGTH: 14749
<212> TYPE: DNA
<213> ORGANISM: Homo sapiens
<220> FEATURE:
<221> NAME/KEY: misc_feature
<222> LOCATION: (4989)..(4997)
<223> OTHER INFORMATION: n is a, c, g, or t
<220> FEATURE:
<221> NAME/KEY: misc_feature
<222> LOCATION: (10041)..(10537)
<223> OTHER INFORMATION: n is a, c, g, or t
<220> FEATURE:
<221> NAME/KEY: misc_feature
<222> LOCATION: (11852)..(11893)

<223> OTHER INFORMATION: n is a, c, g, or t

<400> SEQUENCE: 72

```
gggcgcgggg agagggcgcg ggagcggctc gcgcggcagg taccatgcgg acgcgcgagc      60
ccggcgaggg ccccggcagg cccggtccct gctcggggc gcgctgagac ggcgggtgag      120
ctccacgaga gcgccgtcgc cacttcgggc caactttgcg attcccgaca gttaagcaat     180
ggggagacat ttggctttgc tcctgcttct gctccttctc ttccaacatt ttggagacag     240
tgatggcagc caacgacttg aacagactcc tctgcagttt acacacctcg agtacaacgt     300
caccgtgcag gagaactctg cagctaagac ttatgtgggg catcctgtca agatgggtgt     360
ttacattaca catccagcgt gggaagtaag gtacaaaatt gtttccggag acagtgaaaa     420
cctgttcaaa gctgaagagt acattctcgg agacttttgc tttctaagaa taaggaccaa     480
aggaggaaat acagctattc ttaatagaga agtgaaggat cactacacat tgatagtgaa     540
agcacttgaa aaaatacta atgtggaggc gcgaacaaag gtcagggtgc aggtgctgga     600
tacaaatgac ttgagaccgt tattctcacc cacctcatac agcgtttctt tacctgaaaa     660
cacagctata aggaccagta tcgcaagagt cagcgccacg gatgcagaca taggaaccaa     720
cggggaattt tactacagtt ttaaagatcg aacagatatg tttgctattc acccaaccag     780
tggtgtgata tgttaactg gtagacttga ttacctagag accaagctct atgagatgga     840
aatcctcgct gcggaccgtg gcatgaagtt gtatgggagc agtggcatca gcagcatggc     900
caagctaacg gtgcacatcg aacaggccaa tgaatgtgct ccggtgataa cagcagtgac     960
attgtcacca tcagaactgg acagggaccc agcatatgca attgtgacag tggatgactg    1020
cgatcagggt gccaatggtg acatagcatc tttaagcatc gtggcaggtg accttctcca    1080
gcagtttaga acagtgaggt cctttccagg gagtaaggag tataaagtca aagccatcgg    1140
tggcattgat tgggacagtc atcctttcgg ctacaatctc acactacagg ctaaagataa    1200
aggaactccg ccccagttct cttctgttaa agtcattcac gtgacttctc cacagttcaa    1260
agccgggcca gtcaagtttg aaaaggatgt ttacagagca gaaataagtg aatttgctcc    1320
tcccaacaca cctgtggtca tggtaaaggc cattcctgct tattcccatt tgaggtatgt    1380
ttttaaaagt acacctggaa aagctaaatt cagtttaaat tacaacactg gtctcatttc    1440
tattttagaa ccagttaaaa gacagcaggc agcccatttt gaacttgaag taacaacaag    1500
tgacagaaaa gcgtccacca aggtcttggt gaaagtctta ggtgcaaata gcaatccccc    1560
tgaatttacc cagacagcgt acaaagctgc ttttgatgag aacgtgccca ttggtactac    1620
tgtcatgagc ctgagtgccg tagaccctga tgagggtgag aacgggtacg tgacatacag    1680
tatcgcaaat ttaaatcatg tgccgtttgc gattgaccat ttcactggtg ccgtgagtac    1740
gtcagaaaac ctggactacg aactgatgcc tcgggtttat actctgagga ttcgtgcatc    1800
agactggggc ttgccgtacc gccgggaagt cgaagtcctt gctacaatta ctctcaataa    1860
cttgaatgac aacacaccett tgtttgagaa aataaattgt gaagggacaa ttcccagaga    1920
tctaggcgtg ggagagcaaa taaccactgt ttctgctatt gatgcagatg aacttcagtt    1980
ggtacagtat cagattgaag ctggaaatga actggatttc tttagtttaa accccaactc    2040
gggggtattg tcattaaagc gatcgctaat ggatggctta ggtgcaaagg tgtctttcac    2100
agtctgagaa tcacagctac agatggagaa aattttgcca caccattata tatcaacata    2160
acagtggctg ccagtcacaa gctggtaaac ttgcagtgtg aagagactgg tgttgccaaa    2220
atgctggcag agaagctcct gcaggcaaat aaattacaca accagggaga ggtggaggat    2280
```

```
attttcttcg attctcactc tgtcaatgct cacataccgc agtttagaag cactcttccg    2340
actggtattc aggtaaagga aaaccagcct gtgggttcca gtgtaatttt catgaactcc    2400
actgaccttg acactggctt caatggaaaa ctggtctatg ctgtttctgg aggaaatgag    2460
gatagttgct tcatgattga tatggaaaca ggaatgctga aaattttatc tcctcttgac    2520
cgtgaaacaa cagacaaata cacccctgaat attaccgtct atgaccttgg atacccccag    2580
aaggctgcgt ggcgtcttct acatgtcgtg gttgtcgatg ccaatgataa tccacccgag    2640
tttttacagg agagctattt tgtggaagtg agtgaagaca aggaggtaca tagtgaaatc    2700
atccaggttg aagccacaga taaagacctg gggcccaacg gacacgtgac gtactcaatt    2760
gttacagaca cagacacatt ttcaattgac agcgtgacgg gtgttgttaa catcgcacgc    2820
cctctggatc gagagctgca gcatgagcac tccttaaaga ttgaggccag ggaccaagcc    2880
agagaagagc ctcagctgtt ctccactgtc gttgtgaaag tatcactaga agatgttaat    2940
gacaacccac ctacatttat tccacctaat tatcgtgtga aagtccgaga ggatcttcca    3000
gaaggaaccg tcatcatgtg gttagaagcc cacgatcctg atttaggtca gtctggtcag    3060
gtcagcacac agccttctgg accacggaga aggaaacttc gatgtggata aactcagtgg    3120
agcagttagg atcgtccagc agttggactt tgagaagaag caagtgtata atctcactgt    3180
gagggccaaa gacaagggaa agccagtttc tctgtcttct acttgctatg ttgaagttga    3240
ggtggttgat gtgaatgaga acctgcaccc acccgtgttt tccagctttg tggaaaaggg    3300
gacagtgaaa aagatgcac ctgttggttc attggtaatg acggtgtcgg ctcatgatga    3360
ggacgccaga agagatgggg agatccgata ctccattaga gatggctctg gcgttggtgt    3420
tttcaaaata ggtgaagaga caggtgtcat agagacgtca gatcgactgg accgtgaatc    3480
gacctcccat tattggctaa cagtcttttgc aaccgatcag ggtgtcgtgc ctctttcatc    3540
gttcatagag atctacatag aggttgagga tgtcaatgac aatgcaccac agacatcaga    3600
gcctgtttat tacccagaaa tcatggaaaa ttctcctaaa gatgtatctg tggtccagat    3660
cgaggcattt gatccagatt cgagctctaa tgacaagctc atgtacaaaa ttacaagtgg    3720
aaatccacaa ggattctttt caatacatcc taaaacaggt ctcatcacaa ctacgtcaag    3780
gaagctagac cgagaacagc aagatgaaca catattagag gttactgtga cagacaatgg    3840
tagtcccccc aaatcaacca ttgcaagagt cattgtgaaa atccttgatg aaaatgacaa    3900
caaacctcag tttctgcaaa agttctacaa aatcagactc cctgagcggg aaaagccaga    3960
ccgagaaaga aatgccagac gggagccgct ctatcgcgtc atagccaccg acaaggatga    4020 gggcccccaat gcagaaatct cctacagcat cgaagacggg aatgagcatg caaattttt    4080 catcgaaccg aaaactggag tggtttcgtc caagaggttt tcagcagctg gagaatatga    4140
tattctttca attaaggcag ttgacaatgg tcgcccctcaa aagtcatcaa ccaccagact    4200
ccatattgaa tggatctcca gcccaaaacc gtccctggag cccatttcat ttgaagaatc    4260 atttttttacc tttactgtga tggaaagtga ccccgttgct cacatgattg gagtaatatc    4320
tgtggagcct cctggcatac cccttttggtt tgacatcact ggtggcaact acgacagtca    4380
cttcgatgtg gacaagggaa ctggaaccat cattgttgcc aaacctctg atgcagaaca    4440 gaagtcaaac tacaacctca cagtcgaggc tacagatgga accaccacta tcctcactca    4500
ggtattcatc aaagtaatag acacaaatga ccatcgtcct cagttttcta catcaaagta    4560
tgaagttgtt attcctgaag atacagcgcc agaaacagaa attttgcaaa tcagtgctgt    4620
```

```
ggatcaggat gagaaaaaca aactaatcta cactctgcag agcagtagag atccactgag    4680
tctcaagaaa tttcgtcttg atcctgcaac cggctctctc tatacttctg agaaactgga    4740
tcatgaagct gttcaccagc acaccctcac ggtcatggta cgagatcaag atgtgcctgt    4800
aaaacgcaac tttgcaagga ttgtggtcaa tgtcagcgac acgaatgacc acgcccgtg     4860
gttcaccgct tcctcctaca aagggcgggt ttatgaatcg gcagccgttg gctcagttgt    4920
gttgcaggtg acggctctgg acaaggacaa agggaaaaat gctgaagtgc tgtactcgat    4980
cgagtcagnn nnnnnnngaa atattggaaa ttcttttatg attgatcctg tcttgggctc    5040
tattaaaact gccaaagaat tagatcgaag taaccaagcg gagtatgatt taatggtaaa    5100
agctacagat aagggcagtc caccaatgag tgaaataact tctgtgcgta tctttgtcac    5160
aattgctgac aacgcctctc cgaagtttac atcaaaagaa tattctgttg aacttagtga    5220
aactgtcagc attgggagtt tcgttgggat ggttacagcc catagtcaat catcagtggt    5280
gtatgaaata aaagatggaa atacaggtga tgcttttgat attaatccac attctggaac    5340
tatcatcact cagaaagccc tggactttga aactttgccc atttacacat tgataataca    5400
aggaactaac atggctggtt tgtccactaa tacaacggtt ctagttcact tgcaggatga    5460
gaatgacaac gcgccagttt ttatgcaggc agaatataca ggactcatta gtgaatcagc    5520
ctcaattaac agcgtggtcc taacagacag gaatgtccca ctggtgattc gagcagctga    5580
tgctgataaa gactcaaatg ctttgcttgt atatcacatt gttgaaccat ctgtacacac    5640
atattttgct attgattcta gcactggtgc tattcataca gtactaagtc tggactatga    5700
agaaacaagt attttcact ttaccgtcca agtgcatgac atgggaaccc cacgtttatt     5760
tgctgagtat gcagcgaatg taacagtaca tgtaattgac attaatgact gccccctgt     5820
gtttgccaag ccattatatg aagcatctct tttgttacca acatacaaag gagtaaaagt    5880
catcacagta aatgctacag atgctgattc aagtgcattc tcacagttga tttactccat    5940
caccgaaggc aacatcgggg agaagttttc tatggactac aagactggtg ctctcactgt    6000
ccaaaacaca actcagttaa gaagccgcta cgagctaacc gttagagctt ccgatggcag    6060
atttgccggc cttacctctg tcaaaattaa tgtgaaagaa agcaaagaaa gtcacctaaa    6120
gtttacccag gatgtctact ctgcggtagt gaaagagaat tccaccgagg ccgaaacatt    6180
agctgtcatt actgctattg ggaatccaat caatgagcct ttgttttatc acatcctcaa    6240
cccagatcgc agatttaaaa taagccgcac ttcaggagtt ctgtcaacca ctggcacgcc    6300
cttcgatcgt gagcagcagg aggcgtttga tgtggttgta gaagtgacag aggaacataa    6360
gccttctgca gtggcccacg ttgtcgtgaa ggtcattgta gaagaccaaa atgataatgc    6420
gccggtgttt gtcaaccttc cctactacgc cgttgttaaa gtggacactg aggtgggcca    6480
tgtcattcgc tatgtcactg ctgtagacag agacagtggc agaaacgggg aagtgcatta    6540
ctacctcaag gaacatcatg aacactttca aattggaccc ttgggtgaaa tttcactgaa    6600
aaagcaattt gagcttgaca ccttaaataa agaatatctt gttacagtgg ttgcaaaaga    6660
tggagggaac ccggcctttt cagcggaagt tatcgttccg atcactgtca tgaataaagc    6720
catgcctgtg tttgaaaaac ctttctacag tgcagagatt gcagagagca tccaggtgca    6780
cagccctgtg gtccacgtgc aggctaacag cccggaaggc ctgaaagtgt tctacagcat    6840
cacagacgga gacccttttca gccagttcac tattaacttc aatactggag ttatcaatgt    6900
catagctcct ctggactttg aggcccacc ggcatataag ctgagcatac gcgcaactga     6960
ctccttgacg ggcgctcatg ctgaagtatt tgtggacatc atagtagacg acatcaatga    7020
```

```
taaccctcct gtgtttgctc agcagtctta tgcggtgacc ctgtctgagg catctgtaat      7080
tggaacgtct gttgttcaag ttagagccac cgattctgat tcagaaccaa atagaggaat      7140
ctcataccag atgtttggga atcacagcaa gagtcatgat cattttcatg tagacagcag      7200
cactggcctc atctcactac tcagaaccct ggattacgag cagtcccggc agcacacgat      7260
ttttgtgagg gcagttgatg gtggtatgcc cacgctgagc agtgatgtga ttgtcacggt      7320
ggacgttacc gacctcaatg ataatccacc actctttgaa caacagattt atgaagccag      7380
aattagcgag cacgcccctc atgggcattt cgtgacctgt gtaaaagcct atgatgcaga      7440
cagttcagac atagacaagt tgcagtattc cattctgtct ggcaatgatc ataaacattt      7500
tgtcattgac agtgcaacag ggattatcac cctctcaaac ctgcaccggc acgccctgaa      7560 gccatttac agtcttaacc tgtcagtgtc tgatggagtt tttagaagtt ccacccaggt      7620
tcatgtaact gtaattggag gcaatttgca cagtcctgct ttccttcaga acgaatatga      7680
agtggaacta gctgaaaacg ctcccctaca taccctggtg atggaggtga aaactacgga      7740
tggggattct ggtatttatg gtcacgttac ttaccatatt gtaaatgact ttgccaaaga      7800
cagattttac ataaatgaga gaggacagat atttactttg gaaaaacttg atcgagaaac      7860
cccggcggag aaagtgatct cagtccgttt aatggctaag gatgctggag gaaaagttgc      7920
tttctgcacc gtgaatgtca tccttacaga tgacaatgac aatgcaccac aatttcgagc      7980
aaccaaatac gaagtgaata tcgggtccag tgctgctaaa gggacttcag tcgttaaagt      8040
tcttgcaagt gatgccgatg agggctccaa tgccgacatc acctatgcca ttgaagcaga      8100
ctctgaaagt gtaaaagaga atttggaaat taacaaactg tccggcgtaa tcactacaaa      8160
ggagagcctc attggcttgg aaaatgaatt cttcactttc tttgttagag ctgtggataa      8220
tgggtctcca tcaaaagaat ctgttgttct tgtctatgtt aaaatccttc caccggaaat      8280
gcagcttcca aaattttcag aacctttcta tacctttaca gtgtcagagg acgtgcctat      8340
tggaacagag atagatctca tccgagcaga acatagtggg actgttcttt acagcctggt      8400
caaagggaat actccagaaa gcaatagggga tgagtccttt gtgattgaca gacagagcgg      8460
gagactgaag ttggagaaga gtcttgatca tgagacaact aagtggtatc agttttccat      8520
actggccagg tgcactcaag atgaccatga gatggtggct tctgtagatg ttagtatcca      8580
agtgaaagat gcaaatgaca acagcccggt ctttgaatct agtccatatg aggcattcat      8640
tgttgaaaac ctgccaggggg gaagtagagt aattcagatc agggcatctg atgctgactc      8700
aggaaccaac ggccaagtta tgtatagcct ggatcagtca caaagtgtgg aagtcattga      8760
atcctttgcc attaacatgg aaacaggctg gattacaact ttaaaggaac ttgaccatga      8820
aaagagagac aattaccaga ttaaagtggt tgcatcagat catggtgaaa agatccagct      8880
atcctccaca gccattgtgg atgttaccgt caccgatgtc aacgatagtc caccacgatt      8940
cacggccgag atctataaag ggactgtgag tgaggatgac ccccaaggtg gggtgattgc      9000
catcttaagt accacggatg ctgattctga agagatcaac agacaagtta catatttcat      9060
aacaggaggg gatcctttag acagtttgc cgttgaaact atacagaatg aatggaaggt      9120
atatgtgaag aaacctctag acagggaaaa aaggggcaat taccttctta ctatcacggc      9180
aactgatggc accttctcat caaaagcgat agttgaagtg aaagttctgg atgcaaatga      9240
caacagtcca gtttgtgaaa agactttata ttcagacact attcctgaag acgtccttcc      9300
tggaaaattg atcatgcaga tctctgctac agacgcagac atccgctcta acgctgaaat      9360
```

```
tacttacacg ttattgggtt caggtgcaga aaaattcaaa ctaaatccag acacaggtga   9420
actgaaaacg tcaaccccccc ttgatcgtga ggagcaagct gtttatcatc ttctcgtcag   9480
ggccacagat ggaggaggaa gattctgcca agccagtatt gtgctcacgc tagaagatgt   9540
gaacgataac gcccccgaat tctctgccga tccttatgcc atcaccgtgt ttgaaaacac   9600
agagccggga acgctgctga caagagtgca ggccacagat gccgacgcag gattaaatcg   9660
gaagatttta tactcactga ttgactctgc tgatgggcag ttctccatta acgaattatc   9720
tggaattatt cagttagaaa aacctttgga cagagaactc caggcagtat acaccctctc   9780
tttgaaagct gtggatcaag gcttgccaag gaggctgact gccactggca ctgtgattgt   9840
atcagttctt gacataaatg acaaccccccc tgtgtttgag taccgtgaat atggtgccac   9900
cgtgtctgag gacattcttg ttggaactga agttcttcaa gtgtatgcag caagtcggga   9960
tattgaagca aatgcagaaa tcacctactc aataataagt ggaaatgaac atgggaaatt  10020
cagcatagat tctaaaacag nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn nnnnnnnnnn nnnnnnnnnn  10260
nnnnnnnnnn nnnnnnnnnn nnnnnnnnnn nnnnnnnnnn nnnnnnnnnn nnnnnnnnnn  10320
nnnnnnnnnn nnnnnnnnnn nnnnnnnnnn nnnnnnnnnn nnnnnnnnnn nnnnnnnnnn  10380
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnnnnnnnn nnnnnnnnnn nnnnnnnnnn  10500
nnnnnnnnnn nnnnnnnnnn nnnnnnnnnn nnnnnnngaa aataagccag tgggcttcag  10560
cgtgctgcag ctggtagtaa cagatgagga ttcttcccat aacggtccac ccttcttctt  10620
tactattgta actggaaatg atgagaaggc ttttgaagtt aacccgcaag gagtcctcct  10680
gacatcatct gccatcaaga ggaaggagaa agatcattac ttactgcagg tgaaggtggc  10740
agataatgga aagcctcagt tgtcatcttt gacatacatt gacattaggg taattgagga  10800
gagcatctat ccgcctgcga ttttgcccct ggagattttc atcacctctt ctggagaaga  10860
atactcaggt ggcgtcattg ggaagatcca tgccacagac caggacgtgt atgatactct  10920
aacctacagt ctcgaccctc agatggacaa cctgttctct gtttccagca caggggggcaa  10980 gctgatagca cacaaaaagc tagacatagg gcaatacctt ctcaatgtca gcgtaacaga  11040
tgggaagttc acgacggtgg ccgacatcac agtgcatatc agacaagtca cacaggagat  11100
gttgaaccac accatcgcga tccgctttgc caacctcact ccggaagaat tcgttggtga  11160
ctactggcgc aacttccagc gagctttacg gaacatcctg ggtgtgagga ggaacgacat  11220
acagattgtt agtttgcagt cctctgaacc tcacccacat ctggacgtct acttttttgt  11280
agagaaacca ggtagtgctc agatctcaac aaaacaactt ctgcacaaga ttaactcttc  11340
cgtgactgac attgaggaaa tcattggagt taggatactg aatgtattcc agaaactctg  11400
cgcgggactg gactgcccct ggaagttctg cgatgaaaag gtgtctgtgg atgaaagtgt  11460
gatgtcaaca cacagcacag ccagactgag ttttgtgact ccccgccacc acagggcagc  11520
ggtgtgtctc tgcaaagagg gaaggtgccc acctgtccac catggctgtg aagatgatcc  11580
gtgccctgag ggatccgaat gtgtgtctga tccctgggag gagaaacaca cctgtgtctg  11640
tcccagcggc aggtttggtc agtgcccagg gagttcatct atgacactga ctggaaacag  11700
ctacgtgaaa taccgtctga cggaaaatga aaacaaatta gagatgaaac tgaccatgag  11760
```

```
gctcagaaca tattccacgc atgcggttgt catgtatgct cgaggaactg actatagcat   11820
cttggagatt catcatggaa ggtgcagtca annnnnnnnn nnnnnnnnnn nnnnnnnnnn   11880
nnnnnnnnnn nnncattcag gtcaatgatg ggcagtggca cgcagtggcc ctggaagtga   11940
atggaaacta tgctcgcttg gttctagacc aagttcatac tgcatcgggc acagccccag   12000
ggactctgaa aaccctgaac ctggataact atgtgttttt tggtggccac atccgtcagc   12060
agggaacaag gcatggaaga agtcctcaag ttggtaatgg tttcaggggt tgtatggact   12120
ccatttattt gaatgggcag gagctcccct taaacagcaa acccagaagc tatgcacaca   12180
tcgaagagtc ggtggatgta tctccaggct gcttcctgac ggccacggaa gactgcgcca   12240
gcaacccttg ccagaatgga ggcgtttgca atccgtcacc tgctgaggt tattactgca   12300
aatgcagtgc cttgtacata gggacccact gtgagataag cgtcaatccg tgttcctcca   12360
agccatgcct ctatgggggc acgtgtgttg tcgacaacgg aggctttgtt tgccagtgta   12420
gaggattata tactggtcag aggtgtcagc ttagtccata ctgcaaagat gaaccctgta   12480
agaatgcgg aacatgcttt gacagtttgg atggcgccgt ttgtcagtgt gattcgggtt   12540
ttaggggaga aaggtgtcag agtgatatcg acgagtgctc tggaaaccct tgcctgcacg   12600
gggccctctg tgagaacacg cacggctcct atcactgcaa ctgcagccac gagtacaggg   12660
gacgtcactg cgaggatgct cgcccaacc agtatgtgtc cacgccgtgg aacattgggt   12720
tggcggaagg aattggaatc gttgtgtttg ttgcagggat atttttactg gtggtggtgt   12780
tgttctctg ccgtaagatg attagtcgga aaaagaagca tcaggctgaa cctaaagaca   12840
agcacctggg acccgctacg gctttcttgc aaagaccgta ttttgattcc aagctaaata   12900
agaacattta ctcagacata ccaccccagg tgcctgtccg gcctatttcc tacacccga   12960
gtattccaag tgactcaaga aacaatctgg accgaaattc cttcgaagga tctgctatcc   13020
cagagcatcc cgaattcagc actttttaacc ccgagtctgt gcacgggcac cgaaaagcag   13080
tggcggtctg cagcgtggcg ccaaacctgc ctcccccacc cccttcaaac tccccttctg   13140
acagcgactc catccagaag cctagctggg actttgacta tgacacaaaa gtggtggatc   13200
ttgatccctg tctttccaag aagcctctag aggaaaagcc ttcccagcca tacagtgccc   13260
gggaaagcct gtctgaagtg cagtctctga gctccttcca gtccgaatcg tgcgatgaca   13320
atgggtatca ctgggataca tcagattgga tgccaagcgt tcctctgccg gacatacaag   13380
agttccccaa ctatgaggtg attgatgagc agacacccct gtactcagca gatcaaacg   13440
ccatcgatac ggactattac cctggaggct acgacatcga aagtgatttt cctccacccc   13500
cagaagactt ccccgcagct gatgagctac caccgttacc gcccgaattc agcaatcagt   13560
ttgaatccat ccaccctcct agagacatgc ctgccgcggg tagcttgggt tcttcatcaa   13620
gaaaccggca gaggttcaac ttgaatcagt atttgcccaa tttttatccc ctcgatatgt   13680
ctgaacctca acaaaaggc actggtgaga atagtacttg tagagaaccc catgcccctt   13740
acccgccagg gtatcaaaga cacttcgagg cgcccgctgt cgagagcatg cccatgtctg   13800
tgtacgcctc caccgcctcc tgtctctgacg tgtcagcctg ctgcgaagtg gagtccgagg   13860
tcatgatgag tgactatgag agcggggacg acggccactt cgaagaggtg acgatccgc   13920
ccctggattc ccagcagcac acggaagtct gactctcaac tcccccaaa gtgcctgact   13980
ttagtgaacc tagaggtgat gtgagtaatc cgcgctgttc tttgcagcag tgcttccaag   14040
cttttttttgg tgagccgaat gggcatggct gcgctggatc ctgcgcctct ggacgtgcta   14100
```

```
gccatttcca gtgtcccaac tactgtcatc gtgaggtttt catcggctgt gccatttccc    14160
aacgtctttt gggatttaca tctgtctgtg ttaaaataat caaacgaaaa atcagtcctg    14220
tgttgtcagc atgattcatg tatttatata gatttgatta ttttaatttt cctgtctctt    14280
ttttttgtaa attttatgta cagatttgat ttttcatagt tttaactaga tttccaagat    14340
attttgtgca tttgtttcaa ctgaattttg gtggtgtcag tgccattatc tagcaccctg    14400
attttttttt ttttactata accagggttt cattctgtct ttttccactg aagtgtgaca    14460
ttttgttagt acatttcagt gtagtcattc atttctagct gtacatagga tgaaggagag    14520
atcagataca tgaacatgtc ttacatgggt tgctgtattt agaattataa acatttttca    14580
ttattggaaa gtgtaacggg gaccttctgc atacctgttt agaaccaaaa ccaccatgac    14640
acagttttta tagtgtctgt atatttgtga tgcaatggtc ttgtaaaggt ttttaatgaa    14700
aactaccatt agccagtctt tcttactgac aataaattat taataaaat                14749
```

<210> SEQ ID NO 73
<211> LENGTH: 5508
<212> TYPE: DNA
<213> ORGANISM: Homo sapiens
<400> SEQUENCE: 73

```
gattttaggt gatgggcaag tcagaaagtc agatggatat aactgatatc aacactccaa      60
agccaaagaa gaaacagcga tggactccac tggagatcag cctctcggtc cttgtcctgc     120
tcctcaccat catagctgtg acaatgatcg cactctatgc aacctacgat gatggtatt      180 gcaagtcatc agactgcata aaatcagctg ctcgactgat ccaaaacatg gatgccacca     240
ctgagccttg tacagacttt ttcaaatatg cttgcggagg ctggttgaaa cgtaatgtca     300
ttcccgagac cagctcccgt tacggcaact ttgacatttt aagagatgaa ctagaagtcg     360
ttttgaaaga tgtccttcaa gaacccaaaa ctgaagatat agtagcagtg cagaaagcaa     420
aagcattgta caggtcttgt ataaatgaat ctgctattga tagcagaggt ggagaacctc     480
tactcaaact gttaccagac atatatgggt ggccagtagc aacagaaaac tgggagcaaa     540
aatatggtgc ttcttggaca gctgaaaaag ctattgcaca actgaattct aaatatggga     600
aaaaagtcct tattaatttg tttgttggca ctgatgataa gaattctgtg aatcatgtaa     660
ttcatattga ccaacctcga cttggcctcc cttctagaga ttactatgaa tgcactggaa     720
tctataaaga ggcttgtaca gcatatgtgg attttatgat ttctgtggcc agattgattc     780
gtcaggaaga aagattgccc atcgatgaaa accagcttgc tttggaaatg aataaagtta     840
tggaattgga aaaagaaatt gccaatgcta cggctaaacc tgaagatcga atgatccaa      900 tgcttctgta taacaagatg acattggccc agatccaaaa taactttctca ctagagatca     960 atgggaagcc attcagctgg ttgaatttca aaatgaaat catgtcaact gtgaatatta     1020
gtattacaaa tgaggaagat gtggttgttt atgctccaga atatttaacc aaacttaagc     1080
ccattcttac caaatattct gccagagatc ttcaaaattt aatgtcctgg agattcataa     1140
tggatcttgt aagcagcctc agccgaacct acaaggagtc cagaaatgct ttccgcaagg     1200
ccctttatgg tacaacctca gaaacagcaa cttggagacg ttgtgcaaac tatgtcaatg     1260
ggaatatgga aaatgctgtg gggaggcttt atgtggaagc agcatttgct ggagagagta     1320
aacatgtggt cgaggatttg attgcacaga tccgagaagt ttttattcag actttagatg     1380
acctcacttg gatggatgcc gagacaaaaa agagagctga agaaaggcc ttagcaatta     1440 aagaaaggat cggctatcct gatgacattg tttcaaatga taacaaactg aataatgagt     1500
```

```
acctcgagtt gaactacaaa gaagatgaat acttcgagaa cataattcaa aatttgaaat    1560
tcagccaaag taaacaactg aagaagctcc gagaaaaggt ggacaaagat gagtggataa    1620
gtggagcagc tgtagtcaat gcattttact cttcaggaag aaatcagata gtcttcccag    1680
ccggcattct gcagccccccc ttctttagtg cccagcagtc caactcattg aactatgggg    1740
gcatcggcat ggtcatagga cacgaaatca cccatggctt cgatgacaat ggcagaaact    1800
ttaacaaaga tggagacctc gttgactggt ggactcaaca gtctgcaagt aactttaagg    1860
agcaatccca gtgcatggtg tatcagtatg gaaacttttc ctgggacctg gcaggtggac    1920
agcaccttaa tggaattaat acactgggag aaaacattgc tgataatgga ggtcttggtc    1980
aagcatacag agcctatcag aattatatta aaaagaatgg cgaagaaaaa ttacttcctg    2040
gacttgacct aaatcacaaa caactatttt tcttgaactt tgcacaggtg tggtgtggaa    2100
cctataggcc agagtatgcg gttaactcca ttaaaacaga tgtgcacagt ccaggcaatt    2160
tcaggattat tgggactttg cagaactctg cagagttttc agaagccttt cactgccgca    2220
agaattcata catgaatcca gaaaagaagt gccgggtttg gtgatcttca aaagaagcat    2280
tgcagccctt ggctagactt gccaacacca cagaaatggg gaattctcta atcgaaagaa    2340
aatgggccct aggggtcact gtactgactt gagggtgatt aacagagagg gcaccatcac    2400
aatacagata acattaggtt gtcctagaaa gggtgtggag ggaggaaggg ggtctaaggt    2460
ctatcaagtc aatcatttct cactgtgtac ataatgctta atttctaaag ataatattac    2520
tgtttatttc tgtttctcat atggtctacc agtttgctga tgtccctaga aaacaatgca    2580
aaacctttga ggtagaccag gatttctaat caaaagggaa aagaagatgt tgaagaatac    2640
agttaggcac cagaagaaca gtaggtgaca ctatagttta aaacacattg cctaactact    2700 agttttact tttatttgca acatttacag tccttcaaaa tccttccaaa gaattcttat    2760
acacattggg gccttggagc ttacatagtt ttaaactcat ttttgccata catcagttat    2820
tcattctgtg atcatttatt ttaagcactc ttaaagcaaa aaatgaatgt ctaaaattgt    2880
tttttgttgt acctgctttg actgatgctg agattcttca ggcttcctgc aattttctaa    2940
gcaatttctt gctctatctc tcaaaacttg gtattttttca gagatttata taaatgtaaa    3000
aataataatt tttatattta attattaact acatttatga gtaactatta ttataggtaa    3060
tcaatgaata ttgaagtttc agcttaaaat aaacagttgt gaaccaagat ctataaagcg    3120
atatacagat gaaaatttga gactatttaa acttataaat catattgatg aaaagattta    3180
agcacaaact ttagggtaaa aattgccatt ggacagttgt ctagagatat atatacttgt    3240
ggttttcaaa ttggactttc aaaattaaat ctgtccctga gagtgtctct gataaaaggg    3300
caaatctgca cctatgtagc tctgcatctc ctgtcttttc aggtttgtca tcagatggaa    3360
atattttgat aataaattga aattgtgaac tcattgctcc ctaagactgt gacaactgtc    3420
taactttaga agtgcatttc tgaatagaaa tgggaggcct ctgatggacc ttctagaatt    3480
ataagtcaca aagagttctg gaaaagaact gtttactgct tgataggaat tcatcttttg    3540
aggcttctgt tcctctcttt tcctgttgta ttgactattt tcgttcatta cttgattaag    3600
attttacaaa agaggagcac ttccaaaatt cttattttttc ctaacaaaag atgaaagcag    3660
ggaatttcta tctaaatgat gagtattagt tccctgtctc ttgaaaaatg cccatttgcc    3720
tttaaaaaaa aaagttacag aaatactata acatatgtac ataaattgca taaagcataa    3780
gtatacagtt caataaactt aacttttaact gaacaatggc cctgtagcca gcacctgtaa    3840
```

```
gaaacagagc agtaccagcg ctctaaaagc acctccttgt cactttatta ctcccagaac    3900
aacaactatc ctgacttcta atatcattca ctagctttgc ctggttttgt cttttatgca    3960
gatagaatca atcagtatgt attcttttgt gcctggcttc tttctctcag ccttacattt    4020
gtgagattcc tctgtattgt gctgattgtg gatcttttca ttctcattgc agaataatgt    4080
tctattgtgg gacttattac aatttgttca tcctattgtt gatgggcact tgagaacttt    4140
ccattttggc gctattacaa atagtgcaac tatgaatgta ctgcatgtta ccatcttact    4200
tgagccttta atggacttat ttcttcaaat ccttccaaaa attattataa gcattgaaat    4260
tatagtttca agccaactgt ggatacccct acccttcct cctttatcac aaccaccgtt    4320
acaagtatac ttatatttcc ctaaaataca tttaaaactt acctaagtga catttgtagt    4380
tggagtaata ggagcttcca gctctaataa aacagctgtc tctaacttat tttatttcca    4440
tcatgtcaga gcaggtgaag agccagaagt gaagagtgac tagtacaaat tataaaaagc    4500
cactagactc ttcactgtta gcttttaaa acattaggct cccatcccta tggaggaaca    4560
actctccagt gcctggatcc cctctgtcta caaatataag attttctggg cctaaaggat    4620
agatcaaagt caaaaatagc aatgcctccc tatccctcac acatccagac atcatgaatt    4680
ttacatggta ctcttgttga gttctgtaga gccttctgat gtctctaaag cactaccgat    4740
tctttggagt tgtcacatca gataagacat atctctaatt ccatccataa atccagttct    4800
actatggctg agttctggtc aaagaaagaa agtttagaag ctgagacaca aagggttggg    4860
agctgatgaa actcacaaat gatggtagga agaagctctc gacaataccc gttggcaagg    4920
agtctgcctc catgctgcag tgttcgagtg gattgtaggt gcaagatgga aaggattgta    4980
ggtgcaagct gtccagagaa aagagtcctt gttccagccc tattctgcca ctcctgacag    5040
ggtgaccttg ggtatttgca atattccttt gggcctctgc ttctctcacc taaaaaaaga    5100
gaattagatt atattggtgg ttctcagcaa gagaaggagt atgtgtccaa tgctgccttc    5160
ccatgaatct gtctcccagt tatgaatcag tgggcaggat aaactgaaaa ctcccatttta    5220
cgtgtctgaa tcgagtgaga caaaatttta gtccaaataa caagtaccaa agttttatca    5280
agtttgggtc tgtgctgctg ttactgttaa ccatttaagt ggggcaaaac cttgctaatt    5340
ttctcaaaag catttatcat tcttgttgcc acagctggag ctctcaaact aaaagacatt    5400
tgttattttg gaagaagaa agactctatt ctcaaagttt cctaatcaga aattttatc     5460
agtttccagt ctcaaaaata caaataaaa acaaacgttt ttaatact                 5508
```

<210> SEQ ID NO 74
<211> LENGTH: 1495
<212> TYPE: DNA
<213> ORGANISM: Homo sapiens

<400> SEQUENCE: 74

```
atgtccaatc agggaagtaa gtacgtcaat aaggaaattc aaaatgctgt caacggggtg      60
aaacagataa agactctcat agaaaaaaca aacgaagagc gcaagacact gctcagcaac     120
ctagaagaag ccaagaagaa gaaagaggat gccctaaatg agaccaggga atcagagaca     180
aagctgaagg agctcccagg agtgtgcaat gagaccatga tggccctctg gaagagtgt      240
aagccctgcc tgaaacagac ctgcatgaag ttctacgcac gcgtctgcag aagtggctca     300
ggcctggttg gccgccagct tgaggagttc ctgaaccaga gctcgcccttct ctacttctgg     360
atgaatggtg accgcatcga ctccctgctg gagaacgacc ggcagcagac gcacatgctg     420
gatgtcatgc aggaccactt cagccgcgcg tccagcatca tagacgagct cttccaggac     480
```

```
aggttcttca cccgggagcc ccaggatacc taccactacc tgcccttcag cctgccccac    540
cggaggcctc acttcttctt tcccaagtcc cgcatcgtcc gcagcttgat gcccttctct    600
ccgtacgagc ccctgaactt ccacgccatg ttccagccct ccttgagat gatacacgag     660 gctcagcagg ccatggacat ccacttccat agcccggcct tccagcaccc gccaacagaa    720
ttcatacgag aaggcgacga tgaccggact gtgtgccggg agatccgcca caactccacg    780
ggctgcctgc ggatgaagga ccagtgtgac aagtgccggg agatcttgtc tgtggactgt    840
tccaccaaca ccctccca ggctaagctg cggcgggagc tcgacgaatc cctccaggtc      900
gctgagaggt tgaccaggaa atacaacgag ctgctaaagt cctaccagtg aagatgctc     960 aacacctcct ccttgctgga gcagctgaac gagcagttta ctgggtgtc ccggctggca    1020 aacctcacgc aaggcgaaga ccagtactat ctgcgggtca ccacggtggc ttcccacact   1080
tctgactcgg acgttccttc cggtgtcact gaggtggtcg tgaagctctt tgactctgat   1140
cccatcactg tgacggtccc tgtagaagtc tccaggaaga accctaaatt tatggagacc   1200
gtggcggaga aagcgctgca ggaataccgc aaaaagcacc gggaggagtg agatgtggat   1260
gttgcttttg cacctacggg ggcatctgag tccagctccc cccaagatga gctgcagccc   1320
cccagagaga gctctgcacg tcaccaagta accaggcccc agcctccagg cccccaactc   1380
cgcccagcct ctccccgctc tggatcctgc actctaacac tcgactctgc tgctcatggg   1440
aagaacagaa ttgctcctgc atgcaactaa ttcaataaaa ctgtcttgtg agctg         1495

<210> SEQ ID NO 75
<211> LENGTH: 967
<212> TYPE: DNA
<213> ORGANISM: Homo sapiens

<400> SEQUENCE: 75
gaaggaaaaa gagcaacaga tccagggagc attcacctgc cctgtctcca aacagccttg     60
tgcctcacct accccaacc tcccagaggg agcagctatt taaggggagc aggagtgcag      120
aacaaacaag acggcctggg gatacaactc tggagtcctc tgagagagcc accaaggagg    180
agcaggggag cgacggccgg ggcagaagtt gagaccaccc agcagaggag ctaggccagt    240
ccatctgcat ttgtcaccca agaactctta ccatgaagac cctcctactg ttggcagtga    300
tcatgatctt tggcctactg caggcccatg ggaatttggt gaatttccac agaatgatca    360
agttgacgac aggaaaggaa gccgcactca gttatggctt ctacggctgc cactgtggcg    420
tgggtggcag aggatccccc aaggatgcaa cggatcgctg ctgtgtcact catgactgtt    480
gctacaaacg tctggagaaa cgtggatgtg caccaaatt tctgagctac aagtttagca    540
actcggggag cagaatcacc tgtgcaaaac aggactcctg cagaagtcaa ctgtgtgagt    600
gtgataaggc tgctgccacc tgttttgcta gaaacaagac gacctacaat aaaaagtacc    660
agtactattc caataaacac tgcagaggga caccctcg ttgctgagtc ccctcttccc       720
tggaaacctt ccacccagtg ctgaatttcc ctctctcata ccctccctcc ctaccctaac    780
caagttcctt ggccatgcag aaagcatccc tcacccatcc tagaggccag gcaggagccc    840
ttctataccc acccagaatg agacatccag cagatttcca gccttctact gctctcctcc    900
acctcaactc cgtgcttaac caaagaagct gtactccggg gggtctcttc tgaataaagc    960
aattagc                                                              967

<210> SEQ ID NO 76
```

<211> LENGTH: 2515
<212> TYPE: DNA
<213> ORGANISM: Homo sapiens

<400> SEQUENCE: 76

```
gctccatcaa gtatgatggt gaaggatgaa tatgtgcatg actttgaggg acagccatcg      60
ttgtccactg aaggacattc aattcaaacc atccagcatc caccaagtaa tcgtgcatcg     120
acagagacat acagcacccc agctctgtta gccccatctg agtctaatgc taccagcact     180
gccaactttc ccaacattcc tgtggcttcc acaagtcagc ctgccagtat actgggggc     240
agccatagtg aaggactgtt gcagatagca tcagggcctc agccaggaca gcagcagaat     300
ggatttactg gtcagccagc tacttaccat cataacagca ctaccacctg gactggaagt     360
aggactgcac catacacacc taatttgcct caccaccaaa acggccatct tcagcaccac     420
ccgcctatgc cgccccatcc cggacattac tggcctgttc acaatgagct tgcattccag     480
cctcccattt ccaatcatcc tgctcctgag tattggtgtt ccattgctta ctttgaaatg     540
gatgttcagg taggagagac atttaaggtt ccttcaagct gccctattgt tactgttgat     600
ggatacgtgg acccttctgg aggagatcgc ttttgtttgg gtcaactctc caatgtccac     660
aggacagaag ccattgagag agcaaggttg cacataggca aaggtgtgca gttggaatgt     720
aaaggtgaag gtgatgtttg ggtcaggtgc cttagtgacc acgcggtctt tgtacagagt     780
tactacttag acagagaagc tgggcgtgca cctggagatg ctgttcataa gatctaccca     840
agtgcatata taaaggtctt tgatttgcgt cagtgtcatc gacagatgca gcagcaggcg     900
gctactgcac aagctgcagc agctgcccag gcagcagccg tggcaggaaa catccctggc     960
ccaggatcag taggtggaat agctccagct atcagtctgt cagctgctgc tggaattggt    1020
gttgatgacc ttcgtcgctt atgcatactc aggatgagtt ttgtgaaagg ctggggaccg    1080
gattacccaa gacagagcat caaagaaaca ccttgctgga ttgaaattca cttacaccgg    1140
gccctccagc tcctagacga agtacttcat accatgccga ttgcagaccc caacccttta    1200
gactgaggtc ttttaccgtt ggggccctta accttatcag gatggtggac tacaaaatac    1260
aatcctgttt ataatctgaa gatatatttc acttttgttc tgctttatct tttcataaag    1320
ggttgaaaat gtgtttgctg ccttgctcct agcagacaga aactggatta aaacaatttt    1380
ttttttcctc ttcagaactt gtcaggcatg gctcagagct tgaagattag gagaaacaca    1440
ttccttattaa ttcttcacct gttatgtatg aaggaatcat tccagtgcta gaaaatttag    1500
cccctttaaaa cgtcttagag ccttttatct gcagaacatc gatatgtata tcattctaca    1560
gaataatcca gtattgctga ttttaaaggc agagaagttc tcaaagttaa ttcacctatg    1620
ttatttttgtg tacaagttgt tattgttgaa catacttcaa aaataatgtg ccatgtgggt    1680
gagttaattt taccaagagt aactttactc tgtgtttaaa agtaagtta ataatgtatt     1740
gtaatctttc atccaaaata ttttttgcaa gttatattag tgaagatggt ttcaattcag    1800
attgtcttgc aacttcagtt ttatttttgc caaggcaaaa aactcttaat ctgtgtgtat    1860
attgagaatc ccttaaaatt accagacaaa aaaatttaaa attacgtttg ttattcctag    1920
tggatgactg ttgatgaagt atacttttcc cctgttaaac agtagttgta ttcttctgta    1980
tttctaggca caaggttggt tgctaagaag cctataagag gaatttcttt tccttcattc    2040
atagggaaag gttttgtatt ttttaaaaca ctaaaagcag cgtcactcta cctaatgtct    2100
cactgttctg caaggtggc aatgcttaaa ctaaataatg aataaactga atattttgga     2160
aactgctaaa ttctatgtta aatactgtgc agaataatgg aaacattaca gttcataata    2220
```

| | |
|---|---:|
| ggtagtttgg atattttgt acttgatttg atgtgacttt ttttggtata atgtttaaat | 2280 |
| catgtatgtt atgatattgt ttaaaattca gttttgtat cttggggcaa gactgcaaac | 2340 |
| ttttttatat cttttggtta ttctaagccc tttgccatca atgatcatat caattggcag | 2400 |
| tgactttgta tagagaattt aagtagaaaa gttgcagatg tattgactgt accacagaca | 2460 |
| caatatgtat gcttttacc tagctggtag cataaataaa actgaatctc aacat | 2515 |

<210> SEQ ID NO 77
<211> LENGTH: 2017
<212> TYPE: DNA
<213> ORGANISM: Homo sapiens

<400> SEQUENCE: 77

| | |
|---|---:|
| gcaggcccgt tggaagtggt tgtgacaacc ccagcaatgt ggagaagcct ggggcttgcc | 60 |
| ctggctctct gtctcctccc atcgggagga acagagagcc aggaccaaag ctccttatgt | 120 |
| aagcaacccc cagcctggag cataagagat caagatccaa tgctaaactc caatggttca | 180 |
| gtgactgtgg ttgctcttct tcaagccagc tgatacctgt gcatactgca ggcatctaaa | 240 |
| ttagaagacc tgcgagtaaa actgaagaaa gaaggatatt ctaatatttc ttatattgtt | 300 |
| gttaatcatc aaggaatctc ttctcgatta aaatacacac atcttaagaa taaggtttca | 360 |
| gagcatattc ctgtttatca acaagaagaa accaaacag atgtctggac tcttttaaat | 420 |
| ggaagcaaag atgacttcct catatatgat agatgtggcc gtcttgtata tcatcttggt | 480 |
| ttgcctttt ccttcctaac tttcccatat gtagaagaag ccattaagat tgcttactgt | 540 |
| gaaaagaaat gtggaaactg ctctctcacg actctcaaag atgaagactt ttgtaaacgt | 600 |
| gtatctttgg ctactgtgga taaaacagtt gaaactccat cgcctcatta ccatcatgag | 660 |
| catcatcaca atcatggaca tcagcacctt ggcagcagtg agctttcaga gaatcagcaa | 720 |
| ccaggagcac caaatgctcc tactcatcct gctcctccag gccttcatca ccaccataag | 780 |
| cacaagggtc agcataggca gggtcaccca gagaaccgag atatgccagc aagtgaagat | 840 |
| ttacaagatt tacaaagaa gctctgtcga agagatgta taaatcaatt actctgtaaa | 900 |
| ttgcccacag attcagagtt ggctcctagg agctgatgct gccattgtcg acatctgata | 960 |
| tttgaaaaaa cagggtctgc aatcacctga cagtgtaaag aaaacctccc atctttatgt | 1020 |
| agctgacagg gacttcgggc agaggagaac ataactgaat cttgtcagtg acgtttgcct | 1080 |
| ccagctgcct gacaaataag tcagcagctt atacccacag aagccagtgc cagttgacgc | 1140 |
| tgaaagaatc aggcaaaaaa gtgagaatga ccttcaaact aaatatttaa aataggacat | 1200 |
| actccccaat ttagtctaga cacaatttca tttccagcat ttttataaac taccaaatta | 1260 |
| gtgaaccaaa aatagaaatt agatttgtgc aaacatggag aaatctactg aattggcttc | 1320 |
| cagattttaa attttatgtc atagaaatat tgactcaaac catatttttt atgatggagc | 1380 |
| aactgaaagg tgattgcagc ttttggttaa tatgtctttt tttttctttt tccagtgttc | 1440 |
| tatttgcttt aatgagaata gaaacgtaaa ctatgaccta ggggtttctg ttggataatt | 1500 |
| agcagtttag aatggaggaa gaacaacaaa gacatgcttt ccatttttt ctttacttat | 1560 |
| ctctcaaaac aatattactt tgtcttttca atcttctact tttaactaat aaaataagtg | 1620 |
| gattttgtat tttaagatcc agaaatactt aacacgtgaa tattttgcta aaaaagcata | 1680 |
| tataactatt ttaaatatcc atttatcttt tgtatatcta agactcatcc tgatttttac | 1740 |
| tatcacacat gaataaagcc tttgtatctt tctttctcta atgttgtatc atactcttct | 1800 |

| | |
|---|---|
| aaaacttgag tggctgtctt aaaagatata aggggaaaga taatattgtc tgtctctata | 1860 |
| ttgcttagta agtatttcca tagtcaatga tggtttaata ggtaaaccaa accctataaa | 1920 |
| cctgacctcc tttatggtta atactattaa gcaagaatgc agtacagaat tggatacagt | 1980 |
| acggatttgt ccaaataaat tcaataaaaa ccttaaa | 2017 |

<210> SEQ ID NO 78
<211> LENGTH: 1468
<212> TYPE: DNA
<213> ORGANISM: Homo sapiens

<400> SEQUENCE: 78

| | |
|---|---|
| caaccacttg acaacctggt tagaagatgc ccgccagcat tccaattcca acatggtcat | 60 |
| tatgcttatt ggaaataaaa gtgatttaga atctagaaga gaagtaaaaa agaagaagg | 120 |
| tgaagctttt gcacgagaac atggactcat cttcatggaa acgtctgcta agactgcttc | 180 |
| caatgtagaa gaggcattta ttaatacagc aaaagaaatt tatgaaaaaa ttcaagaagg | 240 |
| agtctttgac attaataatg aggcaaatgg cattaaaatt ggccctcagc atgctgctac | 300 |
| caatgcaaca catgcaggca atcagggagg acagcaggcg gggggcggct gctgttgagt | 360 |
| ctgtttttac tgtctagctg cccaacgggg cctactcact tattctttca cccctctcc | 420 |
| tcctgctcag ctgagacatg aaactatttg aaatggcttt atgtcacaga gactttaat | 480 |
| ccgtcaaatt cttgtataac tttgaataaa tggttaatgt tcacttaaaa gacagatttt | 540 |
| ggagattgta ttcatatcta tttgcatttg atttctaggt caattgatgt gattattttt | 600 |
| gttaaatgtt gtcttgtgcc cttaactacg aactgaattg tattaaacac tacaaagtca | 660 |
| tcttgagtat tttaaatcgg tttgtgtagt taggtttccc aacatctgtg gttacctaat | 720 |
| gtttaatatt atagaactgt cctcagaaac tttgtcaatt ttcacggcta taaggaaaca | 780 |
| gaaggactct tttaattctg tatttatcat ttactttctg tatatatagt ttaataacct | 840 |
| gcttgggtgt aatttgccaa gcttgaattc tttaatgcat ttgcataaat tctatactgt | 900 |
| ttagagctta aagctacaga agcattgtta ggaattgctt ggacactgaa ttttaaactt | 960 |
| tttgacattg ttaacaagca tgttcatctt ttcttgtcac tagtccaaga aaaatatgct | 1020 |
| taatgtatat tacaaaggct ttgtatatgt taacctgttt taatgccaaa agtttgcttt | 1080 |
| gtccacaatt tccttaagac ctcttcagaa agggatttgt ttgccttaat gaatactgtt | 1140 |
| gggaaaaaac acagtataat gagtgaaaag ggcagaagca agaaatttct acatcttagc | 1200 |
| gactccaaga agaatgagta tccacattta gatggcacat tatgaggact ttaatctttc | 1260 |
| cttaaacaca ataatgtttt cttttttctt ttattcacat gatttctaag tatattttc | 1320 |
| atgcaggaca gttttcaac cttgatgtac agtgactgtg taaaattttt ctttcagtgg | 1380 |
| caacctctat aatctttaaa atatggtgag catcttgtct gttttgaagg ggatatgaca | 1440 |
| ataaatctat cagatggaaa atcctgtt | 1468 |

<210> SEQ ID NO 79
<211> LENGTH: 3590
<212> TYPE: DNA
<213> ORGANISM: Homo sapiens

<400> SEQUENCE: 79

| | |
|---|---|
| cctgggtctg acgcggccct gttcgagggg gcctctcttg tttatttatt tattttccgt | 60 |
| gggtgcctcc gagtgtgcgc gcgctctcgc tacccggcgg ggagggggtg ggggagggc | 120 |
| ccgggaaaag ggggagttgg agccggggtc gaaacgccgc gtgacttgta ggtgagagaa | 180 |

-continued

```
cgccgagccg tcgccgcagc ctccgccgcc gagaagccct tgttcccgct gctgggaagg      240
agagtctgtg ccgacaagat ggcggacggg gagctgaacg tggacagcct catcacccgg      300
ctgctggagg tacagggatg tcgtccagga aagattgtgc agatgactga agcagaagtt      360
cgaggcttat gtatcaagtc tcgggagatc tttctcagcc agcctattct tttggaattg      420
gaagcaccgc tgaaaatttg tggagatatt catggacaat atacagattt actgagatta      480
tttgaatatg gaggtttccc accagaagcc aactatcttt tcttaggaga ttatgtggac      540
agaggaaagc agtcttttgga aaccatttgt ttgctattgg cttataaaat caaatatcca      600
gagaacttct ttctcttaag aggaaaccat gagtgtgcta gcatcaatcg catttatgga      660
ttctatgatg aatgcaaacg aagatttaat attaaattgt ggaagacctt cactgattgt      720
tttaactgtc tgcctatagc agccattgtg gatgagaaga tcttctgttg tcatggagga      780
ttgtcaccag acctgcaatc tatggagcag attcggagaa ttatgagacc tactgatgtc      840
cctgatacag gtttgctctg tgatttgcta tggtctgatc cagataagga tgtgcaaggc      900
tggggagaaa atgatcgtgg tgtttccttt acttttggag ctgatgtagt cagtaaattt      960
ctgaatcgtc atgatttaga tttgatttgt cgagctcatc aggtggtgga agatggatat      1020
gaattttttg ctaaacgaca gttggtaacc ttattttcag ccccaaatta ctgtggcgag      1080
tttgataatg ctggtggaat gatgagtgtg gatgaaactt tgatgtgttc atttcagata      1140
ttgaaaccat ctgaaaagaa agctaaatac cagtatggtg gactgaattc tggacgtcct      1200
gtcactccac ctcgaacagc taatccgccg aagaaaaggt gaagaaagga attctgtaaa      1260
gaaaccatca gatttgttaa ggacatactt cataatatat aagtgtgcac tgtaaaacca      1320
tccagccatt tgacaccctt tatgatgtca ccctttaac ttaaggagac gggtaaagga      1380
tcttaaattt ttttctaata gaaagatgtg ctacactgta ttgtaataag tatactctgt      1440
tatagtcaac aaagttaaat ccaaattcaa aattatccat taaagttaca tcttcatgta      1500
tcacaatttt taaagttgaa aagcatccca gttaaactag atgtgatagt taaaccagat      1560
gaaagcatga tgatccatct gtgtaatgtg gttttagtgt tgcttggttg tttaattatt      1620
ttgagcttgt tttgtttttg tttgttttca ctagaataat ggcaaatact tctaattttt      1680
ttccctaaac attttaaaa gtgaaatatg ggaagagctt tacagacatt caccaactat      1740 tatttccct tgtttatcta cttagatatc tgtttaatct tactaagaaa actttcgcct      1800
cattacatta aaaggaatt ttagagattg attgttttaa aaaaaaatac gcacattgtc      1860
caatccagtg attttaatca tacagtttga ctgggcaaac tttacagctg atagtgaata      1920
ttttgcttta tacaggaatt gacactgatt tggatttgtg cactctaatt tttaacttat      1980
tgatgctcta ttgtgcagta gcatttcatt taagataagg ctcatatagt attacccaac      2040
tagttggtaa tgtgattatg tggtaccttg gctttaggtt ttcattcgca cggaacacct      2100
tttggcatgc ttaacttcct ggtaacacct tcacctgcat tggttttctt tttctttttt      2160
ctttcttttt tttttttttt tttttttga gttgttgttt gttttagat ccacagtaca      2220 tgagaatcct ttttgacaa gccttggaaa gctgacactg tctcttttttc ctccctctat      2280 acgaaggatg tatttaaatg aatgctggtc agtgggacat tttgtcaact atgggtattg      2340
ggtgcttaac tgtctaatat tgccatgtga atgttgtata cgattgtaag gcttatgtca      2400
ctaaagattt ttattctgat ttttcataa tcaaaggtca tatgatactg tatagacaag      2460 cttttgtagtg aagtatagta gcaataattt ctgtacctga tcaagtttat tgcagccttt      2520
```

```
cttttcctat ttctttttttt taagggttag tattaacaaa tggcaatgag tagaaaagtt    2580
aacatgaaga ttttagaagg agagaactta caggacacag atttgtgatt ctttgactgt    2640
gacactattg gatgtgattc taaaagcttt tattgagcat tgtcaaattt gtaagcttca    2700
tagggatgga catcatatct ataatgccct tctatatgtg ctaccataga tgtgacattt    2760
ttgaccttaa tatcgtcttt gaaaatgtta aattgagaaa cctgttaact tacatttat    2820 gaattggcac attgtattac ttactgcaag agatatttca ttttcagcac agtgcaaaag    2880
ttctttaaaa tgcatatgtc ttttttttcta attccgtttt gttttaaagc acattttaaa    2940
tgtagttttc tcatttagta aaagttgtct aattgatatg aagcctgact gattttttt    3000 ttccttacag tgagacattt aagcacacat tttattcaca tagatactat gtccttgaca    3060
tattgaaatg attcttttct gaaagtattc atgatctgca tatgatgtat taggttaggt    3120
cacaaaggtt ttatctgagg tgatttaaat aacttcctga ttggagtgtg taagctgagc    3180
gatttctaat aaaattttag ttgtacactt ttagtagtca tagtgaagca ggtctagaaa    3240
ataagccttt ggcagggaaa aagggcaatg ttgattaatc tcagtattaa accacattaa    3300
tctgtatccc attgtctggc ttttgtaaat tcatccaggt caagactaag tatgttggtt    3360
aataggaatc cttttttttt tttaaagact aaatgtgaaa aaataatcac tacttaagct    3420
aattaatatt ggtcattaaa tttaaaggat ggaaatttat catgtttaaa aattattcaa    3480
gcactcttaa aaccacttaa acagcctcca gtcataaaaa tgtgttcttt acaaatattt    3540
gcttggcaac acgacttgaa ataaataaaa ctttgtttct taggagaaaa              3590

<210> SEQ ID NO 80
<211> LENGTH: 1750
<212> TYPE: DNA
<213> ORGANISM: Homo sapiens

<400> SEQUENCE: 80
gcaacctgcc ccattatccc tggctgcgaa acaaccatcg agatttccaa agggcgaaca      60
gggctgggcc tgagcatcgt tgggggttca gacacgctgc tgggtgccat tattatccat     120
gaagtttatg aagaaggagc agcatgtaaa gatggaagac tctgggctgg agatcagatc     180
ttagaggtga atggaattga cttgagaaag gccacacatg atgaagcaat caatgtcctg     240
agacagacgc cacagagagt gcgcctgaca ctctacagag atgaggcccc atacaaagag     300
gaggaagtgt gtgacaccct cactattgag ctgcagaaga gcccgggaaa aggcctagga     360
ttaagtattg ttggtaaaag aaacgatact ggagtatttg tgtcagacat tgtcaaagga     420
ggaattgcag atgccgatgg aagactgatg cagggagacc agatattaat ggtgaatggg     480
gaagacgttc gtaatgccac ccaagaagcg gttgccgctt tgctaaagtg ttccctaggc     540
acagtaacct tggaagttgg aagaatcaaa gctggtccat tccattcaga gaggaggcca     600
tctcaaagca gccaggtgag tgaaggcagc ctgtcatctt tcactttcc actctctgga     660 tccagtacat ctgagtcact ggaaagtagc tcaaagaaga atgcattggc atctgaaata    720
cagggattaa gaacagtcga atgaaaaaag ggccctactg actcactggg aatcagcatt    780
gctggaggag taggcagccc acttggtgat gtgcctatat ttattgcaat gatgcaccca    840
actggagttg cagcacagac ccaaaaactc agagttgggg ataggattgt caccatctgt    900
ggcacatcca ctgagggcat gactcacacc caagcagtta acctactgaa aaatgcatct    960
ggctccattg aaatgcaggt ggttgctgga ggagacgtga gtgtggtcac aggtcatcag   1020
caggagcctg caagttccag tctttcttc actgggctga cgtcaagcag tatatttcag   1080
```

| | |
|---|---|
| gatgatttag gacctcctca atgtaagtct attacactag agcgaggacc agatggctta | 1140 |
| ggcttcagta tagttggagg atatggcagc cctcatggag acttacccat ttatgttaaa | 1200 |
| acagtgtttg caagggagc agcctctgaa gacggacgtc tgaaaagggg cgatcagatc | 1260 |
| attgctgtca atgggcagag tctagaagga gtcacccatg aagaagctgt tgccatcctt | 1320 |
| aaacggacaa aaggcactgt cactttgatg gttctctctt gaattggctg ccagaattga | 1380 |
| accaacccaa cccctagctc acctcctact gtaaagagaa tgcactggtc ctgacaattt | 1440 |
| ttatgctgtg ttcagccggg tcttcaaaac tgtaggggg aaataacact taagtttctt | 1500 |
| tttctcatct agaaatgctt tccttactga caacctaaca tcattttct tttcttcttg | 1560 |
| cattttgtga acttaaagag aaggaatatt tgtgtaggtg aatctcgttt ttatttgtgg | 1620 |
| agatatctaa tgttttgtag tcacatgggc aagaattatt acatgctaag ctggttagta | 1680 |
| taaagaaga taattctaaa gctaaccaaa gaaaatggct tcagtaaatt aggatgaaaa | 1740 |
| atgaaaatat | 1750 |

```
<210> SEQ ID NO 81
<211> LENGTH: 3254
<212> TYPE: DNA
<213> ORGANISM: Homo sapiens

<400> SEQUENCE: 81
```

| | |
|---|---|
| ggagcgcaat ggcgtccaac cccgaacggg gggagattct gctcacggaa ctgcaggggg | 60 |
| attcccgaag tcttccgttt tctgagaatg tgagtgctgt tcaaaaatta gacttttcag | 120 |
| atacaatggt gcagcagaaa ttggatgata tcaaggatcg aattaagaga gaaataagga | 180 |
| aagaactgaa atcaaagaa ggagctgaaa atctgaggaa agtcacaaca gataaaaaaa | 240 |
| gtttggctta tgtagacaac attttgaaaa aatcaaataa aaattagaa gaactacatc | 300 |
| acaagctgca ggaattaaat gcacatattg ttgtatcaga tccagaagat attacagatt | 360 |
| gcccaaggac tccagatact ccaaataatg accctcgttg ttctactagc aacaatagat | 420 |
| tgaaggcctt acaaaaacaa ttggatatag aacttaaagt aaaacaaggt gcagagaata | 480 |
| tgatacagat gtattcaaat ggatcttcaa aggatcggaa actccatggt acagctcagc | 540 |
| aactgctcca ggacagcaag acaaaaatag aagtcatacg aatgcagatt cttcaggcag | 600 |
| tccagactaa tgaattggct tttgataatg caaaacctgt gataagtcct cttgaacttc | 660 |
| ggatggaaga attaaggcat cattttagga tagagtttgc agtagcagaa ggtgcaaaga | 720 |
| atgtaatgaa attacttggc tcaggaaaag taacagacag aaaagcactt tcagaagctc | 780 |
| aagcaagatt taatgaatca agtcagaagt tggacctttt aaagtattca ttagagcaaa | 840 |
| gattaaacga agtccccaag aatcatccca aaagcaggat tattattgaa gaactttcac | 900 |
| ttgttgctgc atcaccaaca ctaagtccac gtcaaagtat gatatctacg caaaatcaat | 960 |
| atagtacact atccaaacca gcagcactaa caggtacttt ggaagttcgt cttatgggct | 1020 |
| gccaagatat cctagagaat gtccctggac ggtcaaaagc aacatcagtt gcactgcctg | 1080 |
| gttggagtcc aagtgaaacc agatcatctt tcatgagcag aacgagtaaa agtaaaagcg | 1140 |
| gaagtagtcg aaatcttcta aaaaccgatg acttgtccaa tgatgtctgt gctgttttga | 1200 |
| agctcgataa tactgtggtt ggccaaacta gctggaaacc catttccaat cagtcatggg | 1260 |
| accagaagtt tacactggaa ctggacaggt cacgtgaact ggaaatttca gtttattggc | 1320 |
| gtgattggcg gtctctgtgt gctgtaaaat ttctgaggtt agaagatttt ttagacaacc | 1380 |

-continued

```
aacggcatgg catgtgtctc tatttggaac cacagggtac tttatttgca gaggttacct      1440
tttttaatcc agttattgaa agaagaccaa aacttcaaag acaaaagaaa attttttcaa      1500
agcaacaagg caaaacattt ctcagagctc ctcaaatgaa tattaatatt gccacttggg      1560
gaaggctagt aagaagagct attcctacag taaatcattc tggcaccttc agccctcaag      1620
ctcctgtgcc tactacagtg ccagtggttg atgtacgcat ccctcaacta gcacctccag      1680
ctagtgattc tacagtaacc aaattggact ttgatcttga gcctgaacct cctccagccc      1740
caccacgagc ttcttctctt ggagaaatag atgaatcttc tgaattaaga gttttggata      1800
taccaggaca ggattcagag actgtttttg atattcagaa tgacagaaat agtatacttc      1860
caaaatctca atctgaatac aagcctgata ctcctcagtc aggcctagaa tatagtggta      1920
ttcaagaact tgaggacaga gatctcagc aaaggtttca gtttaatcta caagatttca      1980
ggtgttgtgc tgtcttggga agaggacatt ttggaaaggt gcttttagct gaatataaaa      2040
acacaaatga gatgtttgct ataaaagcct aaagaaagg agatattgtg gctcgagatg      2100
aagtagacag cctgatgtgt gaaaaagaa ttttgaaac tgtgaatagt gtaaggcatc      2160 ccttttttggt gaacctttt gcatgtttcc aaaccaaaga gcatgtttgc tttgtaatgg      2220
aatatgctgc cggtggggac ctaatgatgc acattcatac tgatgtcttt tctgaaccaa      2280
gagctgtatt ttatgctgct tgtgtagttc ttgggttgca gtatttacat gaacacaaaa      2340
ttgtttatag agatttgaaa ttggataact tattgctaga tacagagggc tttgtgaaaa      2400
ttgctgattt tggtctttgc aaagaaggaa tgggatatgg agatagaaca agcacatttt      2460
gtggcactcc tgaatttctt gccccagaag tattaacaga aacttcttat acaagggctg      2520
tagattggtg gggccttggc gtgcttatat atgaaatgct tgttggtgag tctcccttc      2580 ctggtgatga tgaagaggaa gttttttgaca gtattgtaaa tgatgaagta aggtatccaa      2640
ggttcttatc tacagaagcc atttctataa tgagaaggct gttaagaaga atcctgaac      2700 ggcgccttgg ggctagcgag aaagatgcag aggatgtaaa aaagcaccca tttttccggc      2760
taattgattg gagcgctctg atggacaaaa agtaaagcc accatttata cctaccataa      2820
gaggacgaga agatgttagt aattttgatg atgaatttac ctcagaagca cctattctga      2880
ctccacctcg agaaccaagg atactttcgg aagaggagca ggaaatgttc agagattttg      2940
actacattgc tgattggtgt taagttgcta gacactgcga aaccaagctg actcacaaga      3000
agacctctta aaaatagcaa cccttcattt gctctctgtg ccaccaatag cttctgagtt      3060
ttttgttgtt gttgttttta ttgaaacacg tgaagatttg tttaaaagta ccattctaat      3120
acttcttcaa aagtggctcc tcattgtact tcagcgtaaa tatgagcact ggaaacagtt      3180
tcatggagtt aagttgagt gaacatcggc catgaaaatc catcacgaat acttttggat      3240
caatagtcta tttt                                                         3254
```

<210> SEQ ID NO 82
<211> LENGTH: 509
<212> TYPE: DNA
<213> ORGANISM: Homo sapiens

<400> SEQUENCE: 82

```
atgaaattca agttacatgt gaattctgcc aggcaataca aggacctgtg gaatatgagt       60
gatgacaaac ccttttctatg tactgcgcct ggatgtggcc agagtgaagt cacccctgctg     120 agaaatgaag tggcacagct gaaacagctt cttctggctc ataaagattg ccctgtaacc      180
gccatgcaga gaaatctgg ctatcatact gctgataaag atgatagttc agaagacatt      240
```

```
tcagtgccga gtagtccaca tacagaagct atacagcata gttcggtcag cacatccaat    300
ggagtcagtt caacctccaa ggcagaagct gtagccactt cagtcctcac ccagatggcg    360
gaccagagta cagagcctgc tctttcacag atcgttatgg ctccttcctc ccagtcacag    420
ccctcaggaa gttgattaaa aacctgcagt acaacagttt tagatactca ttagtgactt    480
caaagggaaa tcaaggaaag accagtttc                                     509

<210> SEQ ID NO 83
<211> LENGTH: 719
<212> TYPE: DNA
<213> ORGANISM: Homo sapiens

<400> SEQUENCE: 83
gaattctgga agttcattga agagtctgaa attagggact tatttcaaat ttggacatgg     60
ctagtcgagg cgcaacaaga cccaacggcc caaatactgg aaataaaata tgccagttca    120
aactagtact tctgggagag tccgctgttg gcaaatcaag cctagtgctt cgttttgtga    180
aaggccaatt tcatgaattt caagagagta ccattggggc tgcttttcta acccaaactg    240
tatgtcttga tgacactaca gtaaagtttg aaatctggga tacagctggt caagaaggat    300
accatagcct agcaccaatg tactacagag gagcacaagc agccatagtt gtatatgata    360
tcacaaatga ggagtccttt gcaagagcaa aaaattgggt taaagaactt cagaggcaag    420
caagtcctaa cattgtaata gctttatcgg gaaacaaggc cgacctagca ataaaagag     480 cagtagattt ccaggaagca cagtcctatg cagatgacaa tagtttatta ttcatggaga    540
catccgctaa aacatcaatg aatgtaaatg aaatattcat ggcaatagct aaaaaattgc    600
caaagaatga accacaaaat ccaggagcaa attctgccag aggaggagga gtagacctta    660
ccgaacccac acaaccaacc aggaatcagt gttgtagtaa ctaaacctct agtttgaac     719

<210> SEQ ID NO 84
<211> LENGTH: 1433
<212> TYPE: DNA
<213> ORGANISM: Homo sapiens

<400> SEQUENCE: 84
gacgctctgg gccgccacct ccgcggaccc tgagcgcaag agccaagccg ccagcgctgc     60
gatgtgggcc acgctgccgc tgctctgcgc cggggcctgg ctcctgggag tcccgtctg    120 cggtgccgcc gaactgtgcg tgaactcctt agagaagttt cacttcaagt catggatgtc    180
taagcaccgt aagacctaca gtacggagga gtaccaccac aggctgcaga cgtttgccag    240
caactggagg aagataaacg cccacaacaa tgggaaccac acatttaaaa tggcactgaa    300
ccaattttca gacatgagct ttgctgaaat aaaacacaag tatctctggt cagagcctca    360
gaattgctca gccaccaaaa gtaactacct tcgaggtact ggtccctacc cacttccgt     420 ggactggcgg aaaaaaggaa attttgtctc acctgtgaaa aatcagggtg cctgcggcag    480
ttgctggact ttctccacca ctgggggccct ggagtctgcg atcgccatcg caaccggaaa    540
gatgctgtcc ttggcggaac agcagctggt ggactgcgcc caggacttca ataatcacgg    600
ctgccaaggg gtctccccca gccaggcttt cgagtatatc ctgtacaaca gggggatcat    660
gggtgaagac acctaccccct accagggcaa ggatggttat tgcaagttcc aacctggaaa    720
ggccatcggc tttgtcaagg atgtagccaa catcacaatc tatgacgagg aagcgatggt    780
ggaggctgtg gccctctaca acctgtgag ctttgccttt gaggtgactc aggacttcat    840
```

| | |
|---|---|
| gatgtataga accggcatct actccagtac ttcctgccat aaaactccag ataaagtaaa | 900 |
| ccatgcagta ctggctgttg ggtatggaga aaaaaatggg atcccttact ggatcgtgaa | 960 |
| aaactcttgg ggtccccagt ggggaatgaa cgggtacttc ctcatcgagc gcggaaagaa | 1020 |
| catgtgtggc ctgcctgcct cgcctcccta ccccatccct ctggtgtgag ccgtggcagc | 1080 |
| cgcagcgcag actggcggag aaggagagga acgggcagcc tgggcctggg tggaaatcct | 1140 |
| gccctggagg aagttgtggg gagatccact gggaccccca acattctgcc ctcacctctg | 1200 |
| tgcccagcct ggaaacctac agacaaggag gagttccacc atgagctcac ccgtgtctat | 1260 |
| gacgcaaaga tcaccagcca tgtgccttag tgtccttctt aacagactca aaccacatgg | 1320 |
| accacgaata ttcttctgt ccagaagggc tactttccac atatagagct ccagggactg | 1380 |
| tcttttctgt attcgctgtt caataaacat tgagtgagca cctccccaga tgg | 1433 |

<210> SEQ ID NO 85
<211> LENGTH: 2093
<212> TYPE: DNA
<213> ORGANISM: Homo sapiens

<400> SEQUENCE: 85

| | |
|---|---|
| ggtcggggcc cgcggccgct cgcgcctctc gatgggcagc tcgcacttgc tcaacaaggg | 60 |
| cctgccgctt ggcgtccgac ctccgatcat gaacgggccc ctgcacccgc ggcccctggt | 120 |
| ggcattgctg gatggccggg actgcacagt ggagatgccc atcctgaagg acgtggccac | 180 |
| tgtggccttc tgcgacgcgc agtccacgca ggagatccat gagaaggtcc tgaacgaggc | 240 |
| tgtgggggcc ctgatgtacc acaccatcac tctcaccagg gaggacctgg agaagttcaa | 300 |
| agccctccgc atcatcgtcc ggattggcag tggttttgac aacatcgaca tcaagtcggc | 360 |
| cggggattta ggcattgccg tctgcaacgt gcccgcggcg tctgtggagg agacggccga | 420 |
| ctcgacgctg tgccacatcc tgaacctgta ccggcgggcc acctggctgc accaggcgct | 480 |
| gcgggagggc acacgagtcc agagcgtcga gcagatccgc gaggtggcgt ccggcgctgc | 540 |
| caggatccgc ggggagacct tgggcatcat cggacttgtc gcgtggggca ggcagtggcg | 600 |
| ctgcgggcca aggccttcgg cttcaacgtg ctcttctacg acccttactt gtcggatggc | 660 |
| gtggagcggg cgctggggct gcagcgtgtc agcaccctgc aggacctgct cttccacagc | 720 |
| gactgcgtga ccctgcactg cggcctcaac gagcacaacc accacctcat caacgacttc | 780 |
| accgtcaagc agatgagaca aggggccttc ctggtgaaca cagcccgggg tggcctggtg | 840 |
| gatgagaagg cgctggccca ggccctgaag gagggccgga tccgcggcgc ggccctggat | 900 |
| gtgcacgagt cggaacccctt cagctttagc cagggccctc tgaaggatgc acccaacctc | 960 |
| atctgcaccc ccatgctgc atggtacagc gagcaggcat ccatcgagat gcgagaggag | 1020 |
| gcggcacggg agatccgcag agccatcaca ggccggatcc cagacagcct gaagaactgt | 1080 |
| gtcaacaagg accatctgac agccgccacc cactgggcca gcatggaccc cgccgtcgtg | 1140 |
| caccctgagc tcaatggggc tgcctatagg taccctccgg gcgtggtggg cgtggccccc | 1200 |
| actggcatcc cagctgctgt ggaaggtatc gtccccagcg ccatgtccct gtcccacggc | 1260 |
| ctgccccctg tggcccaccc gccccacgcc ccttctcctg gccaaaccgt caagcccgag | 1320 |
| gcggatagag accacgccag tgaccagttg agcccgggaa ggagctctcc agcctcggcg | 1380 |
| cctgggcaga gggcccggaa accctcggac cagagtgtgt ggaggaggca tctgtgtggt | 1440 |
| ggccctggca ctgcagagac tggtccgggc tgtcaggagg cggagggggg cagcgctggg | 1500 |
| cctcgtgtcg cttgtcgtcg tccgtcctgt gggcgctctg ccctgtgtcc ttcgcgttcc | 1560 |

| | |
|---|---:|
| tcgttaagca gaagaagtca gtagttattc tcccatgaac gttcttgtct gtgtacagtt | 1620 |
| tttagaacat tacaaaggat ctgtttgctt agctgtcaac aaaaagaaaa cctgaaggag | 1680 |
| catttggaag tcaatttgag gtttttttt ttgttttttt ttttttttgta tgttggaacg | 1740 |
| tgccccagaa tgaggcagtt ggcaaacttc tcaggacaat gaatccttcc cgttttctt | 1800 |
| tttatgccac acagtgcatt gtttttctta cctgcttgtc ttatttag aataatttag | 1860 |
| aaaaacaaaa caaaggctgt ttttcctaat tttggcatga acccccctt gttccaaatg | 1920 |
| aagacggcat cacgaagcag ctccaaaagg aaaagcttgg gcggtgccca gcgtgcccgc | 1980 |
| tgcccatcga cgtctgtcct ggggacgtgg agggtggcag cgtccccgcc tgcaccagtg | 2040 |
| ccgtcctgct gatgtggtag gctagcaata ttttggttaa aatcatgttt gtg | 2093 |

<210> SEQ ID NO 86
<211> LENGTH: 3435
<212> TYPE: DNA
<213> ORGANISM: Homo sapiens

<400> SEQUENCE: 86

| | |
|---|---:|
| cgcgcggcca ggccctctta gccctctgcc gtttgggggg cacgggtgaa cctgccgccc | 60 |
| cactcccacc ccgccccgcc ccgcccgtac agccaaatcg gaagggacga gcctgccctt | 120 |
| tgaaagggtt ttttttcttg ctcctgcgga gggcgcccca gccatggccc tcaggagctc | 180 |
| cctagacccc gcaggggactg ccctccatcc cggccgccgg ggccgccct ctgcatcccg | 240 |
| cgggcagcct gtgtgaagcg gcctcccgca gccccggcc cctccccat ggaggaggag | 300 |
| gaggggggcgg tggccaagga gtggggcacg accccgcgg ggcccgtctg gaccgcggtg | 360 |
| ttcgactacg aggcggcggg cgacgaggag ctgaccctgc ggagggggcga tcgcgtccag | 420 |
| gtgctttccc aagactgtgc ggtgtccggc gacgagggct ggtggaccgg gcagctcccc | 480 |
| agcggccgcg tgggcgtctt ccccagcaac tacgtggccc ccggcgcccc cgctgcaccc | 540 |
| gcgggcctcc agctgcccca ggagatcccc ttccacgagc tgcagctaga ggagatcatc | 600 |
| ggtgtggggg gctttggcaa ggtctatcgg gccctgtggc gtggcgagga ggtggcagtc | 660 |
| aaggccgccc ggctggaccc tgagaaggac ccggcagtga cagcggagca ggtgtgccag | 720 |
| gaagcccggc tctttggagc cctgcagcac cccaacataa ttgcccttag ggcgcctgc | 780 |
| ctcaaccccc cacacctctg cctagtgatg gagtatgccc gggggtggtgc actgagcagg | 840 |
| gtgctggcag gtcgccgggt gccacctcac gtgctggtca actgggctgt gcaggtggcc | 900 |
| cggggcatga actacctaca caatgatgcc cctgtgccca tcatccaccg ggacctcaag | 960 |
| tccatcaaca tcctgatcct ggaggccatc gagaaccaca acctcgcaga cacggtgctc | 1020 |
| aagatcacgg acttcggcct cgcccgcgag tggcacaaga ccaccaagat gagcgctgcg | 1080 |
| gggacctacg cctggatggc gccggaggtt atccgtctct ccctcttctc caaaagcagt | 1140 |
| gatgtctgga gcttcggggt gctgctgtgg gagctgctga cggggggaggt cccctaccgt | 1200 |
| gagatcgacg cctggccgt ggcgtatggc gtggctatga taagctgac gctgcccatt | 1260 |
| ccctccacgt gccccgagcc ctttgcccgc ctcctggagg aatgctggga cccagacccc | 1320 |
| cacgggcggc cagatttcgg tagcatcttg aagcggcttg aagtcatcga acagtcagcc | 1380 |
| ctgttccaga tgccactgga gtccttccac tcgctgcagg aagactggaa gctggagatt | 1440 |
| cagcacatgt ttgatgacct tcggaccaag gagaaggagc ttcggagccg tgaggaggag | 1500 |
| ctgctgcggg cggcacagga gcagcgcttc caggaggagc agctgcggcg gcgggagcag | 1560 |

| | |
|---|---|
| gagctggcag aacgtgagat ggacatcgtg gaacgggagc tgcacctgct catgtgccag | 1620 |
| ctgagccagg agaagccccg ggtccgcaag cgcaagggca acttcaagcg cagccgcctg | 1680 |
| ctcaagctgc gggaaggcgg cagccacatc agcctgccct ctggctttga gcataagatc | 1740 |
| acagtccagg cctctccaac tctggataag cggaaaggat ccgatggggc cagccccct | 1800 |
| gcaagcccca gcatcatccc ccggctgagg gccattcgcc tgactcccgt ggactgtggt | 1860 |
| ggcagcagca gtggcagcag cagtggagga agtgggacat ggaccgcgg tgggccccca | 1920 |
| aagaaggaag aactggtcgg gggcaagaag aagggacgaa cgtgggggcc cagctccacc | 1980 |
| ctgcagaagg agcgggtggg aggagaggag aggctgaagg ggctggggga aggaagcaaa | 2040 |
| cagtggtcat caagtgcccc caacctgggc aagtcccca aacacacacc cagtcgccgc | 2100 |
| tggcttcgcc agcctcaatg agatggagga gttcgcggag cagaggatg gaggcagcag | 2160 |
| cgtgcccct tccccctact cgaccccgtc ctacctctca gtgccactgc tgccgagcc | 2220 |
| ctccccgggg gcgcgggcgc cgtgggagcc gacgccgtcc gcgccccg ctcggtgggg | 2280 |
| acacggcgcc cggcggcgct gcgacctggc gctgctaggc tgcgccacgc tgctggggc | 2340 |
| tgtgggcctg ggcgccgacg tggccgaggc gcgcgcggcc gacggtgagg agcagcggcg | 2400 |
| ctggctcgac ggcctcttct ttccccgcgc cggccgcttc ccgcggggcc tcagcccacc | 2460 |
| cgcgcgtccc cacggccgcc gcgaagacgt gggcccggc ctgggcctgg cgccctcggc | 2520 |
| caccctcgtg tcgctgtcgt ccgtgtccga ctgcaactcc acgcgttcac tgctgcgctc | 2580 |
| tgacagtgac gaggccgcac cggccgcgcc ctccccacca ccctcccgc ccgcgcccac | 2640 |
| acccacgccc tcgcccagca ccaaccccct ggtggacctg gagctggaga gcttcaagaa | 2700 |
| ggaccccgc cagtcgctca cgcccaccca cgtcacggct gcatgcgctg tgagccgcgg | 2760 |
| gcaccggcgg acgccatcgg atggggcgct ggggcagcgg gggccgcccg agcccgcggg | 2820 |
| ccatggccct ggccctcgtg accttctgga cttcccccgc ctgccgacc ccaggccct | 2880 |
| gttcccagcc cgccgccggc ccctgagtt cccaggccgc cccaccaccc tgaccttgc | 2940 |
| cccgagacct cggccggctg ccagtcgccc ccgcttggac ccctggaaac tggtctcctt | 3000 |
| cggccggaca ctcaccatct cgcctcccag caggccagac actccggaga gccctgggcc | 3060 |
| ccccagcgtg cagcccacac tgctggacat ggacatggag gggcagaacc aagacagcac | 3120 |
| agtgcccctg tgcggggccc acggctccca ctaaggcctg cccaccaccg cccgcctggg | 3180 |
| cagccatgaa tgtagcgccc caggccctgc cccagcccgc catgccacaa ggtgggggag | 3240 |
| gccctgggca ggatgttcac tctatttatt ggggaaggag ggaggggggg gacacttaac | 3300 |
| ttattccttt gtaccccagg gggtggagcc ctgtgcccac cctgcactgg ggggagggtg | 3360 |
| ggcagggata ctcagggaca gggcatcatg ggggatttgg cacaaaatgg agcattaaag | 3420 |
| gtaacccctg ccccc | 3435 |

<210> SEQ ID NO 87
<211> LENGTH: 2227
<212> TYPE: DNA
<213> ORGANISM: Homo sapiens

<400> SEQUENCE: 87

| | |
|---|---|
| gggcccgccc ctggtcacag ccagactgac tcagtttccc tgggaggtcc cgctcgagcc | 60 |
| cgtccttccc ctccctctgc ccgcccccag ccctcgcccc accctcggcg cccgcacatc | 120 |
| tgcctgctca gctccagacg cgcgcccgac ccccgggcgc gggatccagc caggtgggag | 180 |
| ccccgcagat gaggtctctg aaggtgtgcc tgaaccagtg ccagcctgcc ctgtctgcag | 240 |

| | |
|---|---|
| catcggcctg atggggtggt gactgatccc tcagggctcc ggagccatgt ggcccaacgg | 300 |
| cagttccctg gggccctgtt tccggcccac aaacattacc ctggaggaga gacggctgat | 360 |
| cgcctcgccc tggttcgccg cctccttctg cgtggtgggc ctggcctcca acctgctggc | 420 |
| cctgagcgtg ctggcgggcg cgcggcaggg gggttcgcac acgcgctcct ccttcctcac | 480 |
| cttcctctgc ggcctcgtcc tcaccgactt cctggggctg ctggtgaccg gtaccatcgt | 540 |
| ggtgtcccag cacgccgcgc tcttcgagtg gcacgccgtg gaccctggct gccgtctctg | 600 |
| tcgcttcatg ggcgtcgtca tgatcttctt cggcctgtcc ccgctgctgc tgggggccgc | 660 |
| catggcctca gagcgctacc tgggtatcac ccggcccttc tcgcgcccgg cggtcgcctc | 720 |
| gcagcgccgc gcctgggcca ccgtggggct ggtgtgggcg gccgcgctgg cgctgggcct | 780 |
| gctgcccctg ctgggcgtgg gtcgctacac cgtgcaatac ccggggtcct ggtgcttcct | 840 |
| gacgctgggc gccgagtccg gggacgtggc cttcgggctg ctcttctcca tgctgggcgg | 900 |
| cctctcggtc gggctgtcct tcctgctgaa cacggtcagc gtggccaccc tgtgccacgt | 960 |
| ctaccacggg caggaggcgg cccagcagcg tccccgggac tccgaggtgg agatgatggc | 1020 |
| tcagctcctg gggatcatgg tggtggccag cgtgtgttgg ctgccccttc tggtcttcat | 1080 |
| cgcccagaca gtgctgcgaa acccgcctgc catgagcccc gccgggcagc tgtcccgcac | 1140 |
| cacggagaag gagctgctca tctacttgcg cgtggccacc tggaaccaga tcctggaccc | 1200 |
| ctgggtgtat atcctgttcc gccgcgccgt gctccggcgt ctccagcctc gcctcagcac | 1260 |
| ccggcccagg tcgctgtccc tccagcccca gctcacgcag cgctccgggc tgcagtagga | 1320 |
| agtggacaga gcgcccctcc cgcgcctttc cgcggagccc ttggcccctc ggacagccca | 1380 |
| tctgcctgtt ctgaggattc aggggctggg ggtgctggat ggacagtggg catcagcagc | 1440 |
| agggttttgg gttgacccca atccaacccg ggacccccca actcctccct gatcctttta | 1500 |
| ccaagcactc tccttcctc ggccccttt tcccatccag agctcccacc ccttctctgc | 1560 |
| gtccctccca accccaggaa gggcatgcag acattggaag agggtcttgc attgctattt | 1620 |
| tttttttag acggagtctt gctctgtccc ccaggctgga gtgcagtggc gcaatctcag | 1680 |
| ctcactgcaa cctccacctc ccgggttcaa gcgattctcc tgcctcagcc tcctgagtag | 1740 |
| ctgggactat aggcgcgcgc caccacgccc ggctaatttt tgtattttta gtagagacgg | 1800 |
| ggtttcaccg tgttggccag gctggtcttg aactcctgac ctcaggtgat tcaccagcct | 1860 |
| cagcctccca aagtgctggg atcacaggca tgaaccacca cacctggcca ttttttttt | 1920 |
| tttttttaga cggagtctca ctctgtggcc cagcctggag tacagtggca cgatctcggc | 1980 |
| tcactgcaac ctccgcctcc cgggttcaag cgattctcgt gcctcagcct cccgagcagc | 2040 |
| tgggattaca ggcgtaagcc actgcgcccg gccttgcatg ctctttgacc ctgaatttga | 2100 |
| cctacttgct ggggtacagt tgcttccttt tgaacctcca acagggaagg ctctgtccag | 2160 |
| aaaggattga atgtgaacgg gggcaccccc tttcttgcc aaaatatatc tctgcctttg | 2220 |
| gttttat | 2227 |

<210> SEQ ID NO 88
<211> LENGTH: 2662
<212> TYPE: DNA
<213> ORGANISM: Homo sapiens

<400> SEQUENCE: 88

| | |
|---|---|
| cccggacatg gccgccaaca tgtacagggt cggagactac gtctactttg agaactcctc | 60 |

```
cagcaaccca tacctgatcc ggagaatcga ggagctcaac aagacggcca atgggaacgt    120
ggaggccaaa gtggtgtgct tctaccggag gcgggacatc tccagcaccc tcatcgccct    180
ggccgacaag cacgcaaccc tgtcagtctg ctataaggcc ggaccggggg cggacaacgg    240
cgaggaaggg gaaatagaag aggaaatgga gaatccggaa atggtggacc tgcccgagaa    300
actaaagcac cagctgcggc atcgggagct gttcctctcc cggcagctgg agtctctgcc    360
cgccacgcac atcaggggca agtgcagcgt caccctgctc aacgaccgc agtcgctcaa    420 gtcctacctg gagcgggagg atttcttctt ctattctcta gtctacgacc cacagcagaa    480
gaccctgctg gcagataaag gagagattcg agtaggaaac cggtaccagg cagacatcac    540
cgacttgtta aaagaaggcg aggaggatgg ccgagaccag tccaggttgg agacccaggt    600
gtgggaggcg cacaacccac tcacagacaa gcagatcgac cagttcctgg tggtggcccg    660
ctctgtgggc accttcgcac gggccctgga ctgcagcagc tccgtccgac agcccagcct    720
gcacatgagc gccgcagctg cctcccgaga catcaccctg ttccacgcca tggatactct    780
ccacaagaac atctacgaca tctccaaggc catctcggcg ctggtgccgc agggcgggcc    840
cgtgctctgc agggacgaga tggaggagtg gtctgcatca gaggccaacc ttttcgagga    900
agccctggaa aaatatggga aggatttcac ggacattcag caagattttc tcccgtggaa    960
gtcgctgacc agcatcattg agtactacta catgtggaag accacgaca gatacgtgca   1020 gcagaaacgc ttgaaagcag ctgaagctga gagcaagtta aagcaagttt atattcccaa   1080
ctataacaag ccaaatccga accaaatcag cgtcaacaac gtcaaggccg gtgtggtgaa   1140
cggcacgggg gcgccgggcc agagccctgg ggctggccgg gcctgcgaga gctgttacac   1200
cacacagtct taccagtggt attcttgggg tccccctaac atgcagtgtc gtctctgcgc   1260
atcttgttgg acatattgga gaaatatgg tggcttgaaa atgccaaccc ggttagatgg   1320
agagaggcca ggaccaaaacc gcagtaacat gagtccccac ggcctcccag cccggagcag   1380
cgggagcccc aagtttgcca tgaagaccag gcaggctttc tatctgcaca cgacgaagct   1440
gacgcggatc gccccggcgcc tgtgccgtga tcctgcgc ccgtggcacg ctgcgcggaa   1500
cccctacctg cccatcaaca gcgcggccat caaggccgag tgcacggcgc ggctgcccga   1560
agcctcccag agcccgctgg tgctgaagca ggcggtacgc aagccgctgg aagccgtgct   1620
tcggtatctt gagacccacc cccgcccccc caagcctgac cccgtgaaaa gcgtgtccag   1680
cgtgctcagc agcctgacgc ccgccaaggt ggccccccgtc atcaacaacg gctcccccac   1740
catcctgggc aagcgcagct acgagcagca caacggggtg gacggcaaca tgaagaagcg   1800
cctcttgatg cccagtaggg gtctggcaaa ccacggacag accaggcaca tgggaccaag   1860
ccggaacctc ctgctcaacg ggaagtccta ccccaccaaa gtgcgcctga tccggggggg   1920
ctccctgccc ccagtcaagc ggcggcggat gaactggatc gacgcccgg gtgacgtgtt   1980 ctacatgccc aaagaggaga ccaggaagat ccgcaagctc tctcatcct cggaaaccaa   2040 gcgtgctgcc cgccggccct acaagcccat cgccctgcgc cagagccagg ccctgccgcc   2100
gcggccaccg ccacctgcgc ccgtcaacga cgagcccatc gtcatcgagg actaggggcc   2160
gcccccacct gcggccgccc ccgccccctc gcccgcccac acggcccctt cccagccagc   2220
ccgccgcccg cccctcagtt tggtagtgcc ccacctcccg ccctcacctg aagagaaacg   2280
cgctccttgg cggacactgg gggaggagag gaagaagcgc ggctaactta ttccgagaat   2340
gccgaggagt tgtcgttttt agctttgtgt ttacttttg gctggagcgg agatgagggg   2400
ccaccccgtg cccctgtgct gcggggcctt ttgcccggag gccgggccct aaggttttgt   2460
```

```
tgtgttctgt tgaaggtgcc attttaaatt ttatttttat tactttttt gtagatgaac    2520 ttgagctctg taacttacac ctggaatgtt aggatcgtgc ggccgcggcc ggccgagctg    2580
cctggcgggg ttggcccttg tcttttcaag taattttcat attaaacaaa aacaaagaaa    2640
aaaaatctta taaaaggaa aa                                              2662

<210> SEQ ID NO 89
<211> LENGTH: 552
<212> TYPE: DNA
<213> ORGANISM: Homo sapiens

<400> SEQUENCE: 89
atgagagagt acaaagtggt ggtgctgggc tcgggcggcg tgggcaagtc cgcgctcacc      60
gtgcagttcg tgacgggctc cttcatcgag aagtacgacc cgaccatcga agacttttac    120
cgcaaggaga ttgaggtgga ctcgtcgccg tcggtgctgg agatcctgga tacggcgggc    180
accgagcagt tcgcgtccat gcgggacctg tacatcaaga acggccaggg cttcatcctg    240
gtctacagcc tcgtcaacca gcagagcttc caggacatca gcccatgcg ggaccagatc    300 atccgcgtga agcggtacga gcgcgtgccc atgatcctgg tgggcaacaa ggtggacctg    360
gagggtgagc gcgaggtctc gtacggggag ggcaaggccc tggctgagga gtggagctgc    420
cccttcatgg agacgtcggc caaaaacaaa gcctcggtag acgagctatt tgccgagatc    480
gtgcggcaga tgaactacgc ggcgcagtcc aacggcgatg agggctgctg ctcggcctgc    540
gtgatcctct ga                                                        552

<210> SEQ ID NO 90
<211> LENGTH: 2198
<212> TYPE: DNA
<213> ORGANISM: Homo sapiens

<400> SEQUENCE: 90
gagctgcggg cgctgctgct gtggggccgc cgcctgcggc ctttgctgcg ggcgccggcg      60
ctggcggccg tgccgggagg aaaaccaatt ctgtgtcctc ggaggaccac agcccagttg    120
ggccccaggc gaaacccagc ctggagcttg caggcaggac gactgttcag cacgcagacc    180
gccgaggaca aggaggaacc cctgcactcg attatcagca gcacagagag cgtgcagggt    240
tccacttcca acatgagtt ccaggccgag acaaagaagc ttttggacat tgttgcccgg    300
tccctgtact cagaaaaaga ggtgtttata cgggagctga tctccaatgc cagcgatgcc    360
ttggaaaaac tgcgtcacaa actggtgtct gacggccaag cactgccaga atggagatt    420 cacttgcaga ccaatgccga gaaaggcacc atcaccatcc aggatactgg tatcgggatg    480
acacaggaag agctggtgtc caacctgggg acgattgcca gatcggggtc aaaggccttc    540
ctggatgctc tgcagaacca ggctgaggcc agcagcaaga tcatcggcca gtttggagtg    600
ggtttctact cagcttcat ggtggctgac agagtggagg tctattcccg ctcggcagcc    660
ccggggagcc tgggttacca gtggcttca gatggttctg gagtgtttga atcgccgaa    720 gcttcgggag ttagaaccgg acaaaaatc atcatccacc tgaaatccga ctgcaaggag    780
ttttccagcg aggcccgggt gcgagatgtg gtaacgaagt acagcaactt cgtcagcttc    840
cccttgtact tgaatggaag gcggatgaac accttgcagg ccatctggat gatggaccc    900 aaggatgtcc gtgagtggca acatgaggag ttctaccgct acgtcgcgca ggctcacgac    960
aagccccgct acaccctgca ctataagacg gacgcaccgc tcaacatccg cagcatcttc   1020
```

```
tacgtgcccg acatgaaacc gtccatgttt gatgtgagcc gggagctggg ctccagcgtt    1080
gcactgtaca gccgcaaagt cctcatccag accaaggcca cggacatcct gcccaagtgg    1140
ctgcgcttca tccgaggtgt ggtggacagt gaggacattc ccctgaacct cagccgggag    1200
ctgctgcagg agagcgcact catcaggaaa ctccgggacg ttttacagca gaggctgatc    1260
aaattcttca ttgaccagag taaaaaagat gctgagaagt atgcaaagtt ttttgaagat    1320
tacggcctgt tcatgcggga gggcattgtg accgccaccg agcaggaggt caaggaggac    1380
atagcaaagc tgctgcgcta cgagtcctcg gcgctgccct ccgggcagct aaccagcctc    1440
tcagaatacg ccagccgcat gcgggccggc acccgcaaca tctactacct gtgcgccccc    1500
aaccgtcacc tggcagagca ctcaccctac tatgaggcca tgaagaagaa agacacagag    1560
gttctcttct gctttgagca gtttgatgag ctcaccctgc tgcaccttcg tgagtttgac    1620
aagaagaagc tgatctctgt ggagacggac atagtcgtgg atcactacaa ggaggagaag    1680
tttgaggaca ggtccccagc cgccgagtgc ctatcagaga aggagacgga ggagctcatg    1740
gcctggatga gaaatgtgct ggggtcgcgt gtcaccaacg tgaaggtgac cctccgactg    1800
gacacccacc ctgccatggt caccgtgctg gagatggggg ctgcccgcca cttcctgcgc    1860
atgcagcagc tggccaagac ccaggaggag cgcgcacagc tcctgcagcc cacgctggag    1920 atcaaccccca ggcacgcgct catcaagaag ctgaatcagc tgcgcgcaag cgagcctggc    1980
ctggctcagc tgctggtgga tcagatatac gagaacgcca tgattgctgc tggacttgtt    2040
gacgacccta gggccatggt gggccgcttg aatgagctgc ttgtcaaggc cctggagcga    2100
cactgacagc caggggggcca aaggactga caccacagat gacagcccca cctccttgag    2160
ctttatttac ctaaatttaa aggtatttct taacccga                            2198

<210> SEQ ID NO 91
<211> LENGTH: 1790
<212> TYPE: DNA
<213> ORGANISM: Homo sapiens

<400> SEQUENCE: 91
agtgatgtcc ttgcattgcc cattttttaag caagaagagt cgagtttgcc tcctgataat     60
gagaataaaa tcctgccttt tcaatatgtg ctttgtgctg ctacctctcc agcagtgaaa    120
ctccatgatg aaaccctaac gtatctcaat caaggacagt cttatgaaat tcgaatgcta    180
gacaatagga aacttggaga acttccagaa attaatggca aattggtgaa gagtatattc    240
cgtgtggtgt tccatgacag aaggcttcag tacactgagc atcagcagct agagggctgg    300
aggtggaacc gacctggaga cagaattctt gacatagata tcccgatgtc tgtgggtata    360
atcgatccta gggctaatcc aactcaacta atacagtgg agttcctgtg ggaccctgca    420
aagaggacat ctgtgtttat tcaggtgcac tgtattagca cagagttcac tatgaggaaa    480
catggtggag aaaaggtggt gccattccga gtacaaatag ataccttcaa ggagaatgaa    540
aacggggaat atactgagca cttacactcg gccagctgcc agatcaaagt tttcaagcca    600
aaggtgcaga cagaaagcaa aaaacggata gggaaaaaat ggagaaacga acacctcatg    660
aaaaggagaa atatcagcct tcctatgaga caaccatact cacagagtgt tctccatggc    720
ccgagatcac gtatgtcaat aactccccat cacctggctt caacgttcc catagcagtt    780 tttctcttgg ggaaggaaat ggttcaccaa accaccagcc agagccaccc cctccagtca    840
cagataacct cttaccaaca accacacctc aggaagctca gcagtggttg catcgaaatc    900 gttttttctac attcacaagg ctttttcacaa acttctcagg ggcagattta ttgaaattaa    960
```

```
ctagagatga tgtgatccaa atctgtggcc ctgcagatgg aatcagactt tttaatgcat    1020
taaaaggccg gatggtgcgt ccaaggttaa ccatttatgt ttgtcaggaa tcactgcagt    1080
tgagggagca gcaacaacag cagcagcaac agcagcagaa gcatgaggat ggagactcaa    1140
atggtacttt cttcgtttac catgctatct atctagaaga actaacagct gttgaattga    1200
cagaaaaaat tgctcagctt ttcagcattt ccccttgcca gatcagccag atttacaagc    1260
aggggccaac aggaattcat gtgctcatca gtgatgagat gatacagaac tttcaggaag    1320
aagcatgttt tattctggac acaatgaaag cagaaaccaa tgatagctat catatcatac    1380
tgaagtagga gtgcggcgtt tcgtgcccag tggctgctcc ttccttcacc tctgaaaacg    1440
gccctcttga aggggatat gaatggagat ttgaaggtct gcaagaacct gactcgtctg     1500
actgtgtgtg gaggagtcca ggccatggag gcagaatcct ggccctctgt gttggcccaa    1560
gctcttgtgg tacacacaga ttactgccca atatgcagtt ctgcagctgt tttagttaaa    1620
tttctggacc ttgttgttgt taaatatcag tagaaactct acataattta gagtgtatgt    1680
agggcataat gatgatggga attgtgtgat gtttaacagg aagatcttaa attttgtgat    1740
atggagccct gtaattttt tcttatataa aaatgggtat ctatattcat               1790

<210> SEQ ID NO 92
<211> LENGTH: 652
<212> TYPE: DNA
<213> ORGANISM: Homo sapiens

<400> SEQUENCE: 92
aggtctgttc cgcatgaaac tcctgctggg gaaggacttc cctgcctccc cacccaaggg     60
ctacttcctg accaagatct tccacccgaa cttgggcgcc aatggcgaga gtgcgtcaa    120 cgtgctcaag agggactgga cggctgagct gggcatccga cacgtactgc tgaccatcaa    180
gtgcctgctg atccacccta accccgagtc tgcactcaac gaggaggcgg gccgcctgct    240
cttggagaac tacgaggagt atgcggctcg ggcccgtctg ctcacagaga tccacggggg    300
cgccggcggg cccagcggca gggccaaagc cgggcgggcc ctggccagtg gcactgcagc    360
ttcctccacc gactctgggg cccaggggg cttgggaggg gctgagggtc ccatggccaa    420
gaagcatgct ggcgagcgcg ataagaagct ggcggccaag aaaaagacgg acaagaagcg    480
ggcgctacgg cggctgtagt gggctctctt cctccttcca ccgtgacccc aacctctcct    540
gtcccctccc tccaactctg tctctaagtt atttaaatta tggctggggt cggggaggt    600 acaggggca ctgagacctg gatttgtttt tttaaataaa gttggaaaag ca             652

<210> SEQ ID NO 93
<211> LENGTH: 771
<212> TYPE: DNA
<213> ORGANISM: Homo sapiens

<400> SEQUENCE: 93
gtcgtgttct ccgagttcct gtctctctgc caacgccgcc cggatggctt cccaaaaccg     60
cgacccagcc gccactagcg tcgccgccgc ccgtaaagga gctgagccga gcgggggcgc    120
cgcccggggt ccggtgggca aaaggctaca gcaggagctg atgaccctca tgatgtctgg    180
cgataaaggg atttctgcct tccctgaatc agacaacctt ttcaaatggg tagggaccat    240
ccatggagca gctggaacag tatatgaaga cctgaggtat aagctctcgc tagagttccc    300
cagtggctac ccttacaatg cgcccacagt gaagttcctc acgccctgct atcaccccaa    360
```

| | |
|---|---:|
| cgtggacacc cagggtaaca tatgcctgga catcctgaag gaaaagtggt ctgccctgta | 420 |
| tgatgtcagg accattctgc tctccatcca gagccttcta ggagaaccca acattgatag | 480 |
| tcccttgaac acacatgctg ccgagctctg gaaaaacccc acagctttta agaagtacct | 540 |
| gcaagaaacc tactcaaagc aggtcaccag ccaggagccc tgacccaggc tgcccagcct | 600 |
| gtccttgtgt cgtcttttta atttttcctt agatggtctg tccttttgt gatttctgta | 660 |
| taggactctt tatcttgagc tgtggtattt ttgttttgtt tttgtctttt aaattaagcc | 720 |
| tcggttgagc ccttgtatat taaataaatg cattttgtc ctttttaga c | 771 |

<210> SEQ ID NO 94
<211> LENGTH: 2527
<212> TYPE: DNA
<213> ORGANISM: Homo sapiens

<400> SEQUENCE: 94

| | |
|---|---:|
| ctccagcagc acccgagagg gtcaggagaa aagcggagga agctgggtag gccctgaggg | 60 |
| gcctcggtaa gccatcatga ccacccggca agccacgaag gatcccctcc tccggggtgt | 120 |
| atctcctacc cctagcaaga ttccggtacg ctctcagaaa cgcacgcctt tccccactgt | 180 |
| tacatcgtgc gccgtggacc aggagaacca agatccaagg agatgggtgc agaaaccacc | 240 |
| gctcaatatt caacgccccc tcgttgattc agcaggcccc aggccgaaag ccaggcacca | 300 |
| ggcagagaca tcacaaagat tggtggggat cagtcagcct cggaaccct tggaagagct | 360 |
| caggcctagc cctaggggtc aaaatgtggg gcctgggccc cctgcccaga cagaggctcc | 420 |
| agggaccata gagtttgtgg ctgaccctgc agccctggcc accatcctgt caggtgaggg | 480 |
| tgtgaagagc tgtcacctgg ggcgccagcc tagtctggct aaaagagtac tggttcgagg | 540 |
| aagtcaggga ggcaccaccc agagggtcca gggtgttcgg gcctctgcat atttggcccc | 600 |
| cagaaccccc acccaccgac tggacccgtc cagggcttcc tgcttctcta ggctggaggg | 660 |
| accaggacct cgaggccgga cattgtgtcc ccagaggcta caggctctga tttcaccttc | 720 |
| aggaccttcc tttcacccett ccactcgccc cagtttccag gagctaagaa gggagacagc | 780 |
| tggcagcagc cggacttcag tgagccaggc ctcaggattg ctcctggaga ccccagtcca | 840 |
| gcctgctttc tctcttccta aaggagaacg cgaggttgtc actcactcag atgaaggagg | 900 |
| tgtggcctct cttggtctgg cccagcgagt accattaaga gaaaaccgag aaatgtcaca | 960 |
| taccagggac agccatgact cccacctgat gccctcccct gccctgtgg cccagccctt | 1020 |
| gcctggccat gtggtgccat gtccatcacc ctttggacgg gctcagcgtg taccctcccc | 1080 |
| aggccctcca actctgacct catattcagt gttgcggcgt ctcaccgttc aacctaaaac | 1140 |
| ccggttcaca cccatgccat caaccccag agttcagcag gcccagtggc tgcgtggtgt | 1200 |
| ctcccctcag tcctgctctg aagatcctgc cctgccctgg gagcaggttg ccgtccggtt | 1260 |
| gtttgaccag gagagttgta taaggtcact ggagggttct gggaaaccac cggtggccac | 1320 |
| tccttctgga ccccactcta acagaacccc cagcctccag gaggtgaaga ttcaacgcat | 1380 |
| cggtatcctg caacagctgt tgagacagga agtagagggg ctggtagggg gccagtgtgt | 1440 |
| ccctcttaat ggaggctctt ctctggatat ggttgaactt cagcccctgc tgactgagat | 1500 |
| ttctagaact ctgaatgcca cagagcataa ctctgggact tcccaccttc ctggactgtt | 1560 |
| aaaacactca gggctgccaa agccctgtct tccagaggag tgcggggaac cacagccctg | 1620 |
| ccctccggca gagcctgggc ccccagaggc cttctgtagg agtgagcctg agataccaga | 1680 |
| gccctccctc caggaacagc ttgaagtacc agagccctac cctccagcag aacccaggcc | 1740 |

-continued

```
cctagagtcc tgctgtagga gtgagcctga gataccggag tcctctcgcc aggaacagct      1800
tgaggtacct gagccctgcc ctccagcaga acccaggccc ctagagtcct actgtaggat      1860
tgagcctgag ataccggagt cctctcgcca ggaacagctt gaggtacctg agccctgccc      1920
tccagcagaa cccgggcccc ttcagcccag cacccagggg cagtctggac ccccagggcc      1980
ctgccctagg gtagagctgg gggcatcaga gccctgcacc ctggaacata gaagtctaga      2040
gtccagtcta ccaccctgct gcagtcagtg ggctccagca accaccagcc tgatcttctc      2100
ttcccaacac ccgctttgtg ccagcccccc tatctgctca ctccagtctt tgagaccccc      2160
agcaggccag gcaggcctca gcaatctggc ccctcgaacc ctagccctga gggagcgcct      2220
caaatcgtgt ttaaccgcca tccactgctt ccacgaggct cgtctggacg atgagtgtgc      2280
cttttacacc agccgagccc ctccctcagg ccccacccgg gtctgcacca accctgtggc      2340
tacattactc gaatggcagg atgccctgtg tttcattcca gttggttctg ctgccccca       2400 gggctctcca tgatgagaca accactcctg ccctgccgta cttcttcctt ttagcccta       2460 tttattgtcg gtctgcccat gggactggga gccgcccact tttgtcctca ataaagtttc      2520
taaagta                                                                 2527

<210> SEQ ID NO 95
<211> LENGTH: 2512
<212> TYPE: DNA
<213> ORGANISM: Homo sapiens

<400> SEQUENCE: 95
agaataatca tgggccagac tgggaagaaa tctgagaagg gaccagtttg ttggcggaag        60
cgtgtaaaat cagagtacat gcgactgaga cagctcaaga ggttcagacg agctgatgaa       120
gtaaaggtat gtttagttcc aatcgtcaga aaattttgga agaacggaa atcttaaacc        180 aagaatggaa acagcgaagg atacagcctg tgcacatcct gacttctgtg agctcattgc       240
gcgggactag ggagtgttcg gtgaccagtg acttggattt tccaacacaa gtcatcccat       300
taaagactct gaatgcagtt gcttcagtac ccataatgta ttcttggtct cccctacagc       360
agaattttat ggtggaagat gaaactgttt tacataacat tccttatatg ggagatgaag       420
ttttagatca ggatggtact ttcattgaag aactaataaa aaattatgat gggaaagtac       480
acggggatag agaatgtggg tttataaatg atgaaatttt tgtggagttg gtgaatgccc       540
ttggtcaata taatgatgat gacgatgatg atgatggaga cgatcctgaa gaaagagaag       600
aaaagcagaa agatctggag gatcaccgag atgataaaga aagccgccca cctcggaaat       660
ttccttctga taaatttttt gaagccattt cctcaatgtt tccagataag ggcacagcag       720
aagaactaaa ggaaaaatat aaagaactca ccgaacagca gctcccaggc gcacttcctc       780
ctgaatgtac ccccaacata gatggaccaa atgctaaatc tgttcagaga gagcaaagct       840
tacactcctt tcatacgctt ttctgtaggc gatgttttaa atatgactgc ttcctacatc       900 ctttcatgc aacacccaac acttataagc ggaagaacac agaaacagct ctagacaaca       960
aaccttgtgg accacagtgt taccagcatt tggagggagc aaaggagttt gctgctgctc      1020
tcaccgctga gcggataaag accccaccaa aacgtccagg aggccgcaga agaggacggc      1080
ttcccaataa cagtagcagg cccagcaccc ccaccattaa tgtgctggaa tcaaaggata      1140
cagacagtga tagggaagca gggactgaaa cgggggggaga gaacaatgat aaagaagaag      1200
aagagaagaa agatgaaact tcgagctcct ctgaagcaaa ttctcggtgt caaacaccaa      1260
```

| | | | | |
|---|---|---|---|---|
| taaagatgaa | gccaaatatt | gaacctcctg | agaatgtgga gtggagtggt | gctgaagcct | 1320 |
| caatgtttag | agtcctcatt | ggcacttact | atgacaattt ctgtgccatt | gctaggttaa | 1380 |
| ttgggaccaa | acatgtaga | caggtgtatg | agtttagagt caaagaatct | agcatcatag | 1440 |
| ctccagctcc | cgctgaggat | gtggatactc | ctccaaggaa aaagaagagg | aaacaccggt | 1500 |
| tgtgggctgc | acactgcaga | aagatacagc | tgaaaaagga cggctcctct | aaccatgttt | 1560 |
| acaactatca | accctgtgat | catccacggc | agccttgtga cagttcgtgc | ccttgtgtga | 1620 |
| tagcacaaaa | ttttttgtgaa | aagttttgtc | aatgtagttc agagtgtcaa | aaccgctttc | 1680 |
| cgggatgccg | ctgcaaagca | cagtgcaaca | ccaagcagtg cccgtgctac | ctggctgtcc | 1740 |
| gagagtgtga | ccctgacctc | tgtcttactt | gtggagccgc tgaccattgg | acagtaaaa | 1800 |
| atgtgtcctg | caagaactgc | agtattcagc | ggggctccaa aaagcatcta | ttgctggcac | 1860 |
| catctgacgt | ggcaggctgg | gggattttta | tcaaagatcc tgtgcagaaa | aatgaattca | 1920 |
| tctcagaata | ctgtgggagag | attatttctc | aagatgaagc tgacagaaga | gggaaagtgt | 1980 |
| atgataaata | catgtgcagc | tttctgttca | acttgaacaa tgattttgtg | gtggatgcaa | 2040 |
| cccgcaaggg | taacaaaatt | cgttttgcaa | atcattcggt aaatccaaac | tgctatgcaa | 2100 |
| aagttatgat | ggttaacggt | gatcacagga | taggtatttt tgccaagaga | gccatccaga | 2160 |
| ctggcgaaga | gctgttttttt | gattacagat | acagccaggc tgatgccctg | aagtatgtcg | 2220 |
| gcatcgaaag | agaaatggaa | atcccttgac | atctgctacc tcctcccccc | tcctctgaaa | 2280 |
| cagctgcctt | agcttcagga | acctcgagta | ctgtgggcaa tttagaaaaa | gaacatgcag | 2340 |
| tttgaaattc | tgaatttgca | agtactgta | agaataattt atagtaatga | gtttaaaaat | 2400 |
| caacttttta | ttgccttctc | accagctgca | aagtgttttg taccagtgaa | tttttgcaat | 2460 |
| aatgcagtat | ggtacatttt | tcaactttga | ataaagaata cttgaacttg | tc | 2512 |

<210> SEQ ID NO 96
<211> LENGTH: 3403
<212> TYPE: DNA
<213> ORGANISM: Homo sapiens

<400> SEQUENCE: 96

| | | | | |
|---|---|---|---|---|
| caggtctgag | gcgaagctag | gtgagccgtg | ggaagaaaag agggagcagc | tagggcgcgg | 60 |
| gtctccctcc | tcccggagtt | tggaacggct | gaagttcacc ttccagcccc | tagcgccgtt | 120 |
| cgcgccgcta | ggcctggctt | ctgaggcggt | tgcggtgctc ggtcgccgcc | taagcggggc | 180 |
| agggtgcgaa | caggggcttc | gggccacgct | tctcttggcg acaggatttt | gctgtgaagt | 240 |
| ccgtccggga | acggaggaa | aaaagagtt | gcgggaggct gtctgctaat | aacggttctt | 300 |
| gatacatatt | tgccagactt | caagatttca | gaaaaggggt gaaagagaag | attgcaactt | 360 |
| tgagtcagac | ctgtaggcct | gatagactga | ttaaaccaca gaaggtgacc | tgctgagaaa | 420 |
| agtggtacaa | atactgggaa | aaacctgctc | ttctgcgtta agtgggagac | aatgtcacaa | 480 |
| gttaaaagct | cttattccta | tgatgccccc | tcggatttca tcaattttc | atccttggat | 540 |
| gatgaaggag | atactcaaaa | catagattca | tggtttgagg agaaggccaa | tttggagaat | 600 |
| aagttactgg | ggaagaatgg | aactggaggg | cttttttcagg gcaaaactcc | tttgagaaag | 660 |
| gctaatcttc | agcaagctat | tgtcacacct | ttgaaccag ttgacaacac | ttactacaaa | 720 |
| gaggcagaaa | aagaaaatct | tgtggaacaa | tccattccgt caaatgcttg | ttcttccctg | 780 |
| gaagttgagg | cagccatatc | aagaaaaact | ccagcccagc tcagagaag | atctcttagg | 840 |
| ctttctgctc | agaaggattt | ggaacagaaa | gaaaagcatc atgtaaaaat | gaaagccaag | 900 |

-continued

```
agatgtgcca ctcctgtaat catcgatgaa attctaccct ctaagaaaat gaaagtttct    960
aacaacaaaa agaagccaga ggaagaaggc agtgctcatc aagatactgc tgaaaacaat   1020
gcatcttccc cagagaaagc caagggtaga catactgtgc cttgtatgcc acctgcaaag   1080
cagaagtttc taaaaagtac tgaggagcaa gagctggaga agagtatgaa aatgcagcaa   1140
gaggtggtgg agatgcggaa aaagaatgaa gaattcaaga aacttgctct ggctggaata   1200
gggcaacctg tgaagaaatc agtgagccag gtcaccaaat cagttgactt ccacttccgc   1260
acagatgagc gaatcaaaca acatcctaag aaccaggagg aatataagga agtgaacttt   1320
acatctgaac tacgaaagca tccttcatct cctgcccgag tgactaaggg atgtaccatt   1380
gttaagcctt tcaacctgtc caaggaaag aaaagaacat ttgatgaaac agtttctaca   1440
tatgtgcccc ttgcacagca agttgaagac ttccataaac gaaccccta cagatatcat    1500
ttgaggagca agaaggatga tattaacctg ttaccctcca aatcttctgt gaccaagatt   1560
tgcagagacc cacagactcc tgtactgcaa accaaacacc gtgcacgggc tgtgacctgc   1620
aaaagtacag cagagctgga ggctgaggag ctcgagaaat tgcaacaata caaattcaaa   1680
gcacgtgaac ttgatcccag aatacttgaa ggtgggccca tcttgcccaa gaaaccacct   1740
gtgaaaccac ccaccgagcc tattggcttt gatttggaaa ttgagaaaag aatccaggag   1800
cgagaatcaa agaagaaaac agaggatgaa cactttgaat ttcattccag accttgccct   1860
actaagattt ggaagatgt tgtgggtgtt cctgaaaaga aggtacttcc aatcaccgtc    1920
cccaagtcac cagcctttgc attgaagaac agaattcgaa tgcccaccaa agaagatgag   1980
gaagaggacg aaccggtagt gataaaagct caacctgtgc cacattatgg ggtgcctttt   2040
aagcccccaaa tccagaggc aagaactgtg gaaatatgcc ctttctcgtt tgattctcga    2100
gacaaagaac gtcagttaca gaaggagaag aaaataaaag aactgcagaa aggggaggtg   2160
cccaagttca aggcacttcc cttgcctcat tttgacacca ttaacctgcc agagaagaag   2220
gtaaagaatg tgacccagat tgaacctttc tgcttggaga ctgacagaag aggtgctctg   2280
aaggcacaga cttggaagca ccagctggaa gaagaactga gacagcagaa agaagcagct   2340
tgtttcaagg ctcgtccaaa caccgtcatc tctcaggagc cctttgttcc caagaaagag   2400
aagaaatcag ttgctgaggg cctttctggt tctctagttc aggaaccttt tcagctggct   2460
actgagaaga gagccaaaga gcggcaggag ctggagaaga gaatggctga ggtagaagcc   2520
cagaaagccc agcagttgga ggaggccaga ctacaggagg aagagcagaa aaaagaggag   2580
ctggccaggc tacggagaga actggtgcat aaggcaaatc caatacgcaa gtaccagggt   2640
ctggagataa agtcaagtga ccagcctctg actgtgcctg tatctcccaa attctccact   2700
cgattccact gctaaactca gctgtgagct gcggataccg cccggcaatg ggacctgctc   2760
ttaacctcaa acctaggacc gtcttgcttt gtcattgggc atggagagaa cccatttctc   2820
cagactttta cctacccgtg cctgagaaag catacttgac aactgtggac tccagttttg   2880
ttgagaattg ttttcttaca ttactaaggc taataatgag atgtaactca tgaatgtctc   2940
gattagactc catgtagtta cttcctttaa accatcagcc ggccttttat atgggtcttc   3000
actctgacta gaatttagtc tctgtgtcag cacagtgtaa tctctattgc tattgccct    3060
tacgactctc accctctccc cactttttt aaaaatttta accagaaaat aaagatagtt    3120
aaatcctaag atagagatta agtcatggtt taaatgagga acaatcagta aatcagattc   3180
tgtcctcttc tctgcatacc gtgaatttat agttaaggat ccctttgctg tgagggtaga   3240
```

| | |
|---|---|
| aaacctcacc aactgcacca gtgaggaaga agactgcgtg gattcatggg gagcctcaca | 3300 |
| gcagccacgc agcaggctct gggtggggct gccgttaagg cacagttctt tccttactgg | 3360 |
| tgctgataac aacagggaac cgtgcagtgt gcattttaag acc | 3403 |

<210> SEQ ID NO 97
<211> LENGTH: 2688
<212> TYPE: DNA
<213> ORGANISM: Homo sapiens

<400> SEQUENCE: 97

| | |
|---|---|
| cttcaacccg cgccggcggc gactgcagtt cctgcgagcg aggagcgcgg gacctgctga | 60 |
| cacgctgacg ccttcgagcg cggcccgggg cccggagcgg ccggagcagc ccgggtcctg | 120 |
| accccggccc ggctcccgct ccgggctctg ccggcgggcg ggcgagcgcg cgcggtccg | 180 |
| ggccgggggg atgtctcggc ggacgcgctg cgaggatctg gatgagctgc actaccagga | 240 |
| cacagattca gatgtgccgg agcagaggga tagcaagtgc aaggtcaaat ggacccatga | 300 |
| ggaggacgag cagctgaggg ccctggtgag gcagtttgga cagcaggact ggaagttcct | 360 |
| ggccagccac ttccctaacc gcactgacca gcaatgccag tacaggtggc tgagagtttt | 420 |
| gaatccagac cttgtcaagg ggccatggac caaagaggaa gaccaaaaag tcatcgagct | 480 |
| ggttaagaag tatggcacaa agcagtggac actgattgcc aagcacctga agggccggct | 540 |
| ggggaagcag tgccgtgaac gctggcacaa ccacctcaac cctgaggtga agaagtcttg | 600 |
| ctggaccgag gaggaggacc gcatcatctg cgaggcccac aaggtgctgg caaccgctg | 660 |
| ggccgagatc gccaagatgt tgccagggag acagacaat gctgtgaaga atcactggaa | 720 |
| ctctaccatc aaaaggaagg tggacacagg aggcttcttg agcgagtcca agactgcaa | 780 |
| gcccccagtg tacttgctgc tggagctcga ggacaaggac ggcctccaga gtgcccagcc | 840 |
| cacgaaggc cagggaagtc ttctgaccaa ctggccctcc gtccctccta ccataaagga | 900 |
| ggaggaaaac agtgaggagg aacttgcagc agccaccaca tcgaaggaac aggagcccat | 960 |
| cggtacagat ctggacgcag tgcgaacacc agagcccttg gaggaattcc cgaagcgtga | 1020 |
| ggaccaggaa ggctccccac cagaaacgag cctgccttac aagtgggtgg tggaggcagc | 1080 |
| taacctcctc atccctgctg tgggttctag cctctctgaa gccctggact tgatcgagtc | 1140 |
| ggaccctgat gcttggtgtg acctgagtaa atttgacctc cctgaggaac catctgcaga | 1200 |
| ggacagtatc aacaacagcc tagtgcagct gcaagcgtca catcagcagc aagtcctgcc | 1260 |
| accccgccag ccttccgccc tggtgcccag tgtgaccgag taccgcctgg atggccacac | 1320 |
| catctcagac ctgagccgga gcagccgggg cgagctgatc ccatctcccc ccagcactga | 1380 |
| agtcggggc tctggcattg gcacaccgcc ctctgtgctc aagcggcaga ggaagaggcg | 1440 |
| tgtggctctg tccctgtca ctgagaatag caccagtctg tccttcctgg attcctgtaa | 1500 |
| cagcctcacg cccaagagca cacctgttaa gaccctgccc ttctcgccct cccagttct | 1560 |
| gaacttctgg aacaaacagg acacattgga gctggagagc ccctcgctga catccacccc | 1620 |
| agtgtgcagc cagaaggtgg tggtcaccac accactgcac cgggacaaga cacccctgca | 1680 |
| ccagaaacat gctgcgtttg taaccccaga tcagaagtac tccatggaca acactcccca | 1740 |
| cacgccaacc ccgttcaaga cgccctgga gaagtacgga ccctgaagc cctgccaca | 1800 |
| gaccccgcac ctggaggagg acttgaagga ggtgctgcgt tctgaggctg gcatcgaact | 1860 |
| catcatcgag gacgacatca ggcccgagaa gcagaagagg aagcctgggc tgcggcggag | 1920 |
| ccccatcaag aaagtccgga agtctctggc tcttgacatt gtggatgagg atgtgaagct | 1980 |

```
gatgatgtcc acactgccca agtctctatc cttgccgaca actgcccctt caaactcttc    2040
cagcctcacc ctgtcaggta tcaaagaaga caacagcttg ctcaaccagg gcttcttgca    2100
ggccaagccc gagaaggcag cagtggccca gaagccccga agccacttca cgacacctgc    2160
ccctatgtcc agtgcctgga agacggtggc ctgcgggggg accagggacc agcttttcat    2220
gcaggagaaa gcccggcagc tcctgggccg cctgaagccc agccacacat ctcggaccct    2280
catcttgtcc tgaggtgttg agggtgtcac gagcccattc tcatgtttac aggggttgtg    2340
ggggcagagg gggtctgtga atctgagagt cattcaggtg acctcctgca gggagccttc    2400
tgccaccagc ccctccccag actctcaggt ggaggcaaca gggccatgtg ctgccctgtt    2460
gccgagccca gctgtgggcg gctcctggtg ctaacaacaa agttccactt ccaggtctgc    2520
ctggttccct ccccaaggcc acaggagct ccgtcagctt ctcccaagcc cacgtcaggc    2580
ctggcctcat ctcagaccct gcttaggatg ggggatgtgg ccaggggtgc tcctgtgctc    2640
accctctctt ggtgcatttt tttggaagaa taaaattgcc tctctctt              2688

<210> SEQ ID NO 98
<211> LENGTH: 1883
<212> TYPE: DNA
<213> ORGANISM: Homo sapiens

<400> SEQUENCE: 98
atgaggttga cgctactttg ttgcacctgg agggaagaac gtatgggaga ggaaggaagc      60
gagttgcccg tgtgtgcaag ctgcggccag aggatctatg atggccagta cctccaggcc     120
ctgaacgcgg actggcacgc agactgcttc aggtgttgtg actgcagtgc ctccctgtcg     180
caccagtact atgagaagga tgggcagctc ttctgcaaga aggactactg ggcccgctat     240
ggcgagtcct gccatgggtg ctctgagcaa atcaccaagg gactggttat ggtggctggg     300
gagctgaagt accaccccga gtgtttcatc tgcctcacgt gtgggacctt tatcggtgac     360
ggggacacct acacgctggt ggagcactcc aagctgtact gcgggcactg ctactaccag     420
actgtggtga cccccgtcat cgagcagatc ctgcctgact ccctggctc ccacctgccc     480 cacaccgtca ccctggtgtc catcccagcc tcatctcatg gcaagcgtgg actttcagtc     540
tccattgacc ccccgcacgg cccaccgggc tgtggcaccg agcactcaca caccgtccgc     600
gtccagggag tggatccggg ctgcatgagc ccagatgtga agaattccat ccacgtcgga     660
gaccggatct tggaaatcaa tggcacgccc atccgaaatg tgcccctgga cgagattgac     720
ctgctgattc aggaaaccag ccgcctgctc cagctgaccc tcgagcatga ccctcacgat     780
acactgggcc acgggctggg gcctgagacc agcccctga gctctccggc ttatactccc     840
agcggggagg cgggcagctc tgcccggcag aaacctgtct tcgcaaggac ctgggtcgct     900
ctgagtccct ccgcgtagtc tgccggccac accgcatctt ccggccgtcg gacctcatcc     960
acggggaggt gctgggcaag gctgcttcg gccaggctat caaggtgaca caccgtgaga    1020
caggtgaggt gatggtgatg aaggagctga tccggttcga cgaggagacc cagaggacgt    1080
tcctcaagga ggtgaaggtc atgcgatgcc tggaacaccc caacgtgctc aagttcatcg    1140
gggtgctcta caaggacaag aggctcaact tcatcactga gtacatcaag gcggcacgc    1200 tccggggcat catcaagagc atggacagcc agtacccatg gagccagaga gtgagctttg    1260
ccaaggacat cgcatcaggg atggcctacc tccactccat gaacatcatc caccgagacc    1320
tcaactccca caactgcctg gtccgcgaga caagaatgt ggtggtggct gacttcgggc    1380
```

-continued

| | |
|---|---|
| tggcgcgtct catggtggac gagaagactc agcctgaggg cctgcggagc ctcaagaagc | 1440 |
| cagaccgcaa gaagcgctac accgtggtgg gcaacccta ctggatggca cctgagatga | 1500 |
| tcaacggccg cagctatgat gagaaggtgg atgtgttctc ctttgggatc gtcctgtgcg | 1560 |
| agatcatcgg gcgggtgaac gcagaccctg actacctgcc ccgcaccatg gactttggcc | 1620 |
| tcaacgtgcg aggattcctg gaccgctact gcccccaaa ctgcccccg agcttcttcc | 1680 |
| ccatcaccgt gcgctgttgc gatctggacc ccgagaagag gccatccttt gtgaagctgg | 1740 |
| aacactggct ggagaccctc cgcatgcacc tggccggcca cctgccactg ggcccacagc | 1800 |
| tggagcagct ggacagaggt ttctgggaga cctaccggcg cggcgagagc ggactgcctg | 1860 |
| cccacccctga ggtccccgac tga | 1883 |

<210> SEQ ID NO 99
<211> LENGTH: 597
<212> TYPE: DNA
<213> ORGANISM: Homo sapiens

<400> SEQUENCE: 99

| | |
|---|---|
| atgcctggct tcgactacaa gttcctggag aagcccaagc gacggctgct gtgcccactg | 60 |
| tgcgggaagc ccatgcgcga gcctgtgcag gtttccacct gcggccaccg tttctgcgat | 120 |
| acctgcctgc aggagttcct cagtgaagga gtcttcaagt gccctgagga ccagcttcct | 180 |
| ctggactatg ccaagatcta cccagacccg gagctggaag tacaagtatt gggcctgcct | 240 |
| atccgctgca tccacagtga ggagggctgc cgctggagtg ggccactacg tcatctacag | 300 |
| ggccacctga atacctgcag cttcaatgtc attccctgcc ctaatcgctg ccccatgaag | 360 |
| ctgagccgcc gtgatctacc tgcacacttg cagcatgact gccccaagcg cgcgcctcaag | 420 |
| tgcgagtttt gtggctgtga cttcagtggg gaggcctatg aggtggatga gagttctctg | 480 |
| ggctttggtt atcccaagtt catctcccac caggacattc gaaagcgaaa ctatgtgcgg | 540 |
| gatgatgcag tcttcatccg tgctgctgtt gaactgcccc ggaagatcct cagctga | 597 |

<210> SEQ ID NO 100
<211> LENGTH: 23
<212> TYPE: DNA
<213> ORGANISM: Artificial
<220> FEATURE:
<223> OTHER INFORMATION: Synthetic

<400> SEQUENCE: 100

| | |
|---|---|
| cgtatgcccc gctgaatctc gtg | 23 |

<210> SEQ ID NO 101
<211> LENGTH: 24
<212> TYPE: DNA
<213> ORGANISM: Artificial
<220> FEATURE:
<223> OTHER INFORMATION: Synthetic

<400> SEQUENCE: 101

| | |
|---|---|
| tggccaatca tccgtgctca tctg | 24 |

<210> SEQ ID NO 102
<211> LENGTH: 24
<212> TYPE: DNA
<213> ORGANISM: Artificial
<220> FEATURE:
<223> OTHER INFORMATION: Synthetic

<400> SEQUENCE: 102

-continued

```
cggagtcaac ggatttggtc gtat                                            24
```

<210> SEQ ID NO 103
<211> LENGTH: 24
<212> TYPE: DNA
<213> ORGANISM: Artificial
<220> FEATURE:
<223> OTHER INFORMATION: Synthetic

<400> SEQUENCE: 103

```
agccttctcc atggtggtga agac                                            24
```

<210> SEQ ID NO 104
<211> LENGTH: 2005
<212> TYPE: DNA
<213> ORGANISM: Homo sapiens

<400> SEQUENCE: 104

```
ttgcaggctg ctgggctggg gctaagggct gctcagtttc cttcagcggg gcactgggaa      60
gcgccatggc actgcagggc atctcggtcg tggagctgtc cggcctggcc ccggccccgt     120
tctgtgctat ggtcctggct gacttcgggg cgcgtgtggt acgcgtggac cggcccggct     180
cccgctacga cgtgagccgc ttgggccggg gcaagcgctc gctagtgctg gacctgaagc     240
agccgcgggg agccgccgtg ctgcggcgtc tgtgcaagcg gtcggatgtg ctgctggagc     300
ccttccgccg cggtgtcatg gagaaactcc agctgggccc agagattctg cagcgggaaa     360
atccaaggct tatttatgcc aggctgagtg gatttggcca gtcaggaagc ttctgccggt     420
tagctggcca cgatatcaac tatttggctt tgtcaggtgt tctctcaaaa attggcagaa     480
gtggtgagaa tccgtatgcc ccgctgaatc tcctggctga ctttgctggt ggtggcctta     540
tgtgtgcact gggcattata atggctcttt ttgaccgcac acgcactggc aagggtcagg     600
tcattgatgc aaatatggtg gaaggaacag catatttaag ttcttttctg tggaaaactc     660
agaaatcgag tctgtgggaa gcacctcgag acagaacat gttggatggt ggagcacctt     720
tctatacgac ttcaggaca gcagatgggg aattcatggc tgttggagca atagaacccc     780
agttctacga gctgctgatc aaaggacttg gactaaagtc tgatgaactt cccaatcaga     840
tgagcatgga tgattggcca gaaatgaaga agaagttttgc agatgtattt gcaaagaaga     900
cgaaggcaga gtggtgtcaa atctttgacg gcacagatgc ctgtgtgact ccggttctga     960
cttttgagga ggttgttcat catgatcaca acaaggaacg gggctcgttt atcaccagtg    1020
aggagcagga cgtgagcccc cgccctgcac ctctgctgtt aaacacccca gccatccctt    1080
cttttcaaaag ggatcctttc ataggagaac acactgagga gatacttgaa gaatttggat    1140
tcagccgcga agagatttat cagcttaact cagataaaat cattgaaagt aataaggtaa    1200
aagctagtct ctaacttcca ggcccacggc tcaagtgaat ttgaatactg catttacagt    1260
gtagagtaac ataacatt gtatgcatgg aaacatggag gaacagtatt acagtgtcct    1320
accactctaa tcaagaaaag aattacagac tctgattcta cagtgatgat tgaattctaa    1380
aaatggttat cattagggct tttgattat aaaactttgg gtacttatac taaattatgg    1440
tagttattct gccttccagt ttgcttgata tatttgttga tattaagatt cttgacttat    1500
attttgaatg ggttctagtg aaaaaggaat gatatattct tgaagacatc gatatacatt    1560
tatttacact cttgattcta caatgtagaa aatgaggaaa tgccacaaat tgtatggtga    1620
taaaagtcac gtgaaacaga gtgattggtt gcatccaggc cttttgtctt ggtgttcatg    1680
```

```
atctccctct aagcacattc caaactttag caacagttat cacactttgt aatttgcaaa   1740
gaaaagtttc acctgtattg aatcagaatg ccttcaactg aaaaaaacat atccaaaata   1800
atgaggaaat gtgttggctc actacgtaga gtccagaggg acagtcagtt ttagggttgc   1860
ctgtatccag taactcgggg cctgtttccc cgtgggtctc tgggctgtca gctttccttt   1920
ctccatgtgt ttgatttctc ctcaggctgg tagcaagttc tggatcttat acccaacaca   1980
cagcaacatc cagaaataaa gatct                                        2005
```

<210> SEQ ID NO 105
<211> LENGTH: 24
<212> TYPE: DNA
<213> ORGANISM: Artificial
<220> FEATURE:
<223> OTHER INFORMATION: Synthetic

<400> SEQUENCE: 105
tggccaatca tccgtgctca tctg    24

<210> SEQ ID NO 106
<211> LENGTH: 24
<212> TYPE: DNA
<213> ORGANISM: Artificial
<220> FEATURE:
<223> OTHER INFORMATION: Synthetic

<400> SEQUENCE: 106
agccttctcc atggtggtga agac    24

<210> SEQ ID NO 107
<211> LENGTH: 24
<212> TYPE: DNA
<213> ORGANISM: Artificial
<220> FEATURE:
<223> OTHER INFORMATION: Synthetic

<400> SEQUENCE: 107
agccttctcc atggtggtga agac    24

<210> SEQ ID NO 108
<211> LENGTH: 21
<212> TYPE: DNA
<213> ORGANISM: Artificial
<220> FEATURE:
<223> OTHER INFORMATION: Synthetic

<400> SEQUENCE: 108
gccagactgg aagaaatct g    21

<210> SEQ ID NO 109
<211> LENGTH: 21
<212> TYPE: DNA
<213> ORGANISM: Artificial
<220> FEATURE:
<223> OTHER INFORMATION: Synthetic

<400> SEQUENCE: 109
tgtgctggaa aatccaagtc a    21

<210> SEQ ID NO 110
<211> LENGTH: 24
<212> TYPE: DNA
<213> ORGANISM: Artificial
<220> FEATURE:
<223> OTHER INFORMATION: Synthetic

<400> SEQUENCE: 110
cggagtcaac ggatttggtc gtat                                          24

<210> SEQ ID NO 111
<211> LENGTH: 24
<212> TYPE: DNA
<213> ORGANISM: Artificial
<220> FEATURE:
<223> OTHER INFORMATION: Synthetic

<400> SEQUENCE: 111
agccttctcc atggtggtga agac                                          24

<210> SEQ ID NO 112
<211> LENGTH: 35
<212> TYPE: DNA
<213> ORGANISM: Artificial
<220> FEATURE:
<223> OTHER INFORMATION: Synthetic

<400> SEQUENCE: 112
ggggtaccat gggcggccgc gaacaaaagt tgatt                              35

<210> SEQ ID NO 113
<211> LENGTH: 33
<212> TYPE: DNA
<213> ORGANISM: Artificial
<220> FEATURE:
<223> OTHER INFORMATION: Synthetic

<400> SEQUENCE: 113
ggggaattct catgccagca atagatgctt ttt                                33

<210> SEQ ID NO 114
<211> LENGTH: 3042
<212> TYPE: DNA
<213> ORGANISM: Homo sapiens

<400> SEQUENCE: 114
cggaggcgct gggcgcacgg cgcggagccg ccggagctc gaggccggcg gcggcgggag     60
agcgacccgg gcggcctcgt agcggggccc cggatccccg agtggcggcc ggagcctcga   120
aaagagattc tcagcgctga ttttgagatg atgggcttgg gaaacgggcg tcgcagcatg   180
aagtcgccgc ccctcgtgct ggccgccctg gtggcctgca tcatcgtctt gggcttcaac   240
tactggattg cgagctcccg gagcgtggac ctccagacac ggatcatgga gctggaaggc   300
agggtccgca gggcggctgc agagagaggc gccgtggagc tgaagaagaa cgagttccag   360
ggagagctgg agaagcagcg ggagcagctt gacaaaatcc agtccagcca caacttccag   420
ctggagagcg tcaacaagct gtaccaggac gaaaaggcgg ttttggtgaa taacatcacc   480
acaggtgaga ggctcatccg agtgctgcaa gaccagttaa agaccctgca gaggaattac   540
ggcaggctgc agcaggatgt cctccagttt cagaagaacc agaccaacct ggagaggaag   600
ttctcctacg acctgagcca gtgcatcaat cagatgaagg aggtgaagga acagtgtgag   660
gagcgaatag aagaggtcac caaaaagggg aatgaagctg tagcttccag agacctgagt   720
gaaaacaacg accagagaca gcagctccaa gccctcagtg agcctcagcc aggctgcag   780 gcagcaggcc tgccacacac agaggtgcca caagggaagg gaaacgtgct tggtaacagc   840
aagtcccaga caccagcccc cagttccgaa gtggttttgg attcaaagag acaagttgag   900

```
aaagaggaaa ccaatgagat ccaggtggtg aatgaggagc ctcagaggga caggctgccg    960
caggagccag gccgggagca ggtggtggaa gacagacctg taggtggaag aggcttcggg   1020
ggagccggag aactgggcca gaccccacag gtgcaggctg ccctgtcagt gagccaggaa   1080
aatccagaga tggagggccc tgagcgagac cagcttgtca tccccgacgg acaggaggag   1140
gagcaggaag ctgccgggga agggagaaac cagcagaaac tgagaggaga agatgactac   1200
aacatggatg aaaatgaagc agaatctgag acagacaagc aagcagccct ggcagggaat   1260
gacagaaaca tagatgtttt taatgttgaa gatcagaaaa gagacaccat aaatttactt   1320
gatcagcgtg aaaagcggaa tcatacactc tgaattgaac tggaatcaca tatttcacaa   1380
cagggccgaa gagatgacta taaaatgttc atgagggact gaatactgaa aactgtgaaa   1440
tgtactaaat aaaatgtaca tctgaagatg attattgtga aatttttagta tgcactttgt   1500 gtaggaaaaa atggaatggt cttttaaaca gcttttgggg gggtactttg gaagtgtcta   1560
ataaggtgtc acaatttttg gtagtaggta tttcgtgaga agttcaacac caaaactgga   1620
acatagttct ccttcaagtg ttggcgacag cggggcttcc tgattctgga atataacttt   1680
gtgtaaatta acagccacct atagaagagt ccatctgctg tgaaggagag acagagaact   1740
ctgggttccg tcgtcctgtc cacgtgctgt accaagtgct ggtgccagcc tgttacctgt   1800
tctcactgaa aagtctggct aatgctcttg tgtagtcact tctgattctg acaatcaatc   1860
aatcaatggc ctagagcact gactgttaac acaaacgtca ctagcaaagt agcaacagct   1920
ttaagtctaa atacaaagct gttctgtgtg agaattttttt aaaaggctac ttgtataata   1980
acccttgtca ttttttaatgt acaaaacgct attaagtggc ttagaatttg aacatttgtg   2040 gtctttatttt acttttgcttc gtgtgtgggc aaagcaacat cttccctaaa tatatattac   2100
caagaaaagc aagaagcaga ttaggttttt gacaaaacaa acaggccaaa aggggggctga   2160 cctggagcag agcatggtga gaggcaaggc atgagagggc aagtttgttg tggacagatc   2220
tgtgcctact ttattactgg agtaaaagaa aacaaagttc attgatgtcg aaggatatat   2280
acagtgttag aaattaggac tgtttagaaa aacaggaata caatggttgt ttttatcata   2340
gtgtacacat ttagcttgtg gtaaatgact cacaaaactg attttaaaat caagttaatg   2400
tgaattttga aaattactac ttaatcctaa ttcacaataa caatggcatt aaggtttgac   2460
ttgagttggt tcttagtatt atttatggta aataggctct taccacttgc aaataactgg   2520
ccacatcatt aatgactgac ttcccagtaa ggctctctaa ggggtaagta ggaggatcca   2580
caggatttga gatgctaagg ccccagagat cgtttgatcc aaccctctta ttttcagagg   2640
ggaaaatggg gcctagaagt tacagagcat ctagctggtg cgctggcacc cctggcctca   2700
cacagactcc cgagtagctg ggactacagg cacacagtca ctgaagcagg ccctgtttgc   2760
aattcacgtt gccacctcca acttaaacat tcttcatatg tgatgtcctt agtcactaag   2820
gttaaacttt cccacccaga aaaggcaact tagataaaat cttagagtac tttcatactc   2880
ttctaagtcc tcttccagcc tcactttgag tcctccttgg ggttgatagg aattttctct   2940
tgctttctca ataagtctc tattcatctc atgtttaatt tgtacgcata gaattgctga   3000
gaaataaaat gttctgttca acttaaaaaa aaaaaaaaa aa                       3042
```

<210> SEQ ID NO 115
<211> LENGTH: 2368
<212> TYPE: DNA
<213> ORGANISM: Homo sapiens
<400> SEQUENCE: 115

-continued

```
cgggcgatgc cgcgctgcgg gggggccgca cagccgccgc caccgccacc gccgccgggt      60
ggggtgggag gggcgggaac gcgcgccgcc gcctccaggg tgggcgcctt cgccgtggga    120
cgccgaccgt ccgggacgag ggtttcatca ccttaaatgg ttttgaacca atgaaggtgt    180
attcccttaa aaagacggac agcccatcgt gtgaactata gagtttgtgg acagatttat    240
attgggttca tagtggcgtc atgcacgcag actcctgcaa gttcccctaa gttcttagag    300
gactgctttg cctttgatc tgagagttgc aaagttccat aaagaatggc ccttgtggat    360
aagcacaaag tcaagagaca gcgattggac agaatttgtg aaggtatccg cccccagatc    420
atgaacggcc ccctgcaccc ccgcccctg gtggcgctgc tggacggccg cgactgcact    480
gtggagatgc ccatcctgaa ggacctggcc actgtggcct tctgtgacgc gcagtcgacg    540
caggaaatcc acgagaaggt tctaaacgaa gccgtgggcg ccatgatgta ccacaccatc    600
accctcacca gggaggacct ggagaagttc aaggccctga gagtgatcgt gcggataggc    660
agtggctatg acaacgtgga catcaaggct gccggcgagc tcggaattgc cgtgtgcaac    720
atcccgtctg cagccgtgga agagacagcg gactctacca tctgccacat cctcaacctg    780
taccggagga acacgtggct gtaccaggca ctgcgggaag gcacgcgggt tcagagcgtg    840
gagcagatcc gcgaggtggc ctcgggagcg gcccgcatcc gtggggagac gctgggcctc    900
attggctttg gtcgcacggg gcaggcggtt gcagttcgag ccaaggcctt tggattcagc    960
gtcatatttt atgacccta cttgcaggat gggatcgagc ggtccctggg cgtgcagagg   1020
gtctacaccc tgcaggattt gctgtatcag agcgactgcg tctccttgca ctgcaatctc   1080
aacgaacata accaccacct catcaatgac tttaccataa agcagatgag gcagggagca   1140
ttccttgtga acgcagcccg tggcggcctg gtggacgaga aagccttagc acaagccctc   1200
aaggagggca ggatacgagg ggcagccctc gacgtgcatg agtcagagcc cttcagcttt   1260
gctcagggtc cgttgaaaga tgccccgaat ctcatctgca ctcctcacac tgcctggtac   1320
agtgagcagg cgtcactgga gatgagggag gcagctgcca ccgagatccg ccgagccatc   1380
acaggtcgca tcccagaaag cttaagaaat tgtgtgaaca aggaattctt tgtcacatca   1440
gcgccttggt cagtaataga ccagcaagca attcatcctg agctcaatgg tgccacatac   1500
agatatccgc caggcatcgt gggtgtggct ccaggaggac ttcctgcagc catgaaggg    1560
atcatccctg gaggcatccc agtgactcac aacctcccga cagtggcaca tccttcccaa   1620
gcgccctctc ccaaccagcc cacaaaaac ggggacaatc gagagcaccc caacgagcaa   1680
tagcagagaa tgccagaagg taatcactca gatacacttg gaccaagag acagtgaaaa    1740
atagatgaac taagagaaaa agaatcggat ggtctttgta actgattctg gacatatgca    1800
tcattgatgt tgcagtgttg aaactacaag agctagaaaa ctgaagatgt cgtctgctta   1860
cggaagcgct gaaagactag gatgtgattt attaacgacc aacttctgtt attgtgtgtt    1920
aagtttttca tctgtgcatc aaatcacaaa aagaataaat agagcttttt cctttatcag    1980
tcccttgggc acagcaggtc ctgaacaccc tgctctacaa tgttgcatca agagttcaaa    2040
caacaaaata aaaaatatta agaggaaatc cccatcctgt gacttgagtc ccttaagtct    2100
acaggggctg gtgacctctt tttgctaata ggaaaatcac attactacaa aatgggagaa   2160
aaactgtttg cctgtggtag acacctgcac gcataggatt gaagacagta caggctgctg    2220
tacagagaag cgcctctcac atctgaactg catactgagc gggcaagtcg gttgtaagtt   2280
cagtaaaacc ctctgatgat gcaaaaaaaa aaaaaagta ttaagtttca caagctgttt   2340
```

```
gtactcaaat atattttctc agtttcag                                    2368
```

<210> SEQ ID NO 116
<211> LENGTH: 1362
<212> TYPE: DNA
<213> ORGANISM: Homo sapiens

<400> SEQUENCE: 116

```
catttgggga cgctctcagc tctcggcgca cggcccagct tccttcaaaa tgtctactgt    60
tcacgaaatc ctgtgcaagc tcagcttgga gggtgatcac tctacacccc caagtgcata   120
tgggtctgtc aaagcctata ctaactttga tgctgagcgg gatgctttga acattgaaac   180
agccatcaag accaaggtg tggatgaggt caccattgtc aacattttga ccaaccgcag   240
caatgcacag agacaggata ttgccttcgc ctaccagaga aggaccaaaa aggaacttgc   300
atcagcactg aagtcagcct tatctggcca cctggagacg gtgattttgg gcctattgaa   360
gacacctgct cagtatgacg cttctgagct aaaagcttcc atgaaggggc tgggaaccga   420
cgaggactct ctcattgaga tcatctgctc cagaaccaac caggagctgc aggaaattaa   480
cagagtctac aaggaaatgt acaagactga tctggagaag acattatttt cggacacatc   540
tggtgacttc cgcaagctga tggttgccct ggcaaagggt agaagagcag aggatggctc   600
tgtcattgat tatgaactga ttgaccaaga tgctcgggat ctctatgacg ctggagtgaa   660
gaggaaagga actgatgttc ccaagtggat cagcatcatg accgagcgga gcgtgcccca   720
cctccagaaa gtatttgata ggtacaagag ttacagccct tatgacatgt tggaaagcat   780
caggaaagag gttaaaggag acctggaaaa tgctttcctg aacctggttc agtgcattca   840
gaacaagccc ctgtattttg ctgatcggct gtatgactcc atgaagggca aggggacgcg   900
agataaggtc ctgatcagaa tcatggtctc ccgcagtgaa gtggacatgt tgaaaattag   960
gtctgaattc aagagaaagt acggcaagtc cctgtactat tatatccagc aagacactaa  1020
gggcgactac cagaaagcgc tgctgtacct gtgtggtgga gatgactgaa gcccgacacg  1080
gcctgagcgt ccagaaatgg tgctcaccat gcttccagct aacaggtcta gaaaaccagc  1140
ttgcgaataa cagtccccgt ggccatccct gtgagggtga cgttagcatt accccccaacc  1200
tcattttagt tgcctaagca ttgcctggcc ttcctgtcta gtctctcctg taagccaaag  1260
aaatgaacat tccaaggagt tggaagtgaa gtctatgatg tgaaacactt tgcctcctgt  1320
gtactgtgtc ataaacagat gaataaactg aatttgtact tt                     1362
```

<210> SEQ ID NO 117
<211> LENGTH: 2137
<212> TYPE: DNA
<213> ORGANISM: Homo sapiens

<400> SEQUENCE: 117

```
gccccaggtg cgcttcccct agagagggat tttccggtct cgtgggcaga ggaacaacca    60
ggaacttggg ctcagtctcc accccacagt ggggcggatc cgtcccggat aagacccgct   120
gtctggccct gagtagggtg tgacctccgc agccgcagag gaggagcgca gcccggcctc   180
gaagaacttc tgcttgggtg gctgaactct gatcttgacc tagagtcatg gccatggcaa   240
ccaaaggagg tactgtcaaa gctgcttcag gattcaatgc catggaagat gcccagaccc   300
tgaggaaggc catgaaaggg ctcggcaccg atgaagacgc cattattagc gtccttgcct   360
accgcaacac cgcccagcgc caggagatca ggacagccta caagagcacc atcggcaggg   420
acttgatagat cgacctgaag tcagaactga gtggcaactt cgagcaggtg attgtgggga   480
```

-continued

```
tgatgacgcc cacggtgctg tatgacgtgc aagagctgcg aagggccatg aagggagccg        540
gcactgatga gggctgccta attgagatcc tggcctcccg gacccctgag gagatccggc        600
gcataagcca aacctaccag cagcaatatg acggagcct tgaagatgac attcgctctg         660
acacatcgtt catgttccag cgagtgctgg tgtctctgtc agctggtggg agggatgaag        720
gaaattatct ggacgatgct ctcgtgagac aggatgccca ggacctgtat gaggctggag        780
agaagaaatg ggggacagat gaggtgaaat ttctaactgt tctctgttcc cggaaccgaa        840
atcacctgtt gcatgtgttt gatgaataca aaggatatc acagaaggat attgaacaga         900
gtattaaatc tgaaacatct ggtagctttg aagatgctct gctggctata gtaaagtgca        960
tgaggaacaa atctgcatat tttgctgaaa agctctataa atcgatgaag gcttgggca        1020 ccgatgataa caccctcatc agagtgatgg tttctcgagc agaaattgac atgttggata       1080
tccgggcaca cttcaagaga ctctatggaa agtctctgta ctcgttcatc aagggtgaca       1140
catctggaga ctacaggaaa gtactgcttg ttctctgtgg aggagatgat taaaataaaa       1200
atcccagaag acaggagga ttctcaacac tttgaatttt tttaacttca ttttttctaca        1260 ctgctattat cattatctca gaatgctat ttccaattaa aacgcctaca gctgcctcct         1320
agaatataga ctgtctgtat tattattcac ctataattag tcattatgat gctttaaagc       1380
tgtacttgca tttcaaagct tataagatat aaatggagat tttaaagtag aaataaatat       1440
gtattccatg ttttaaaag attactttct actttgtgtt tcacagacat tgaatatatt        1500
aaattattcc atattttctt ttcagtgaaa attttttaa atggaagact gttctaaaat        1560 cactttttc cctaatccaa ttttagagt ggctagtagt ttcttcattt gaaattgtaa         1620
gcatccggtc agtaagaatg cccatccagt ttctatatt tcatagtcaa agccttgaaa       1680
gcatctacaa atctcttttt ttaggttttg tccatagcat cagttgatcc ttactaagtt       1740
tttcatggga gacttccttc atcacatctt atgttgaaat cactttctgt agtcaaagta       1800
taccaaaacc aatttatctg aactaaattc taaagtatgg ttatacaaac catatacatc       1860
tggttaccaa acataaatgc tgaacattcc atattttat agttaatgtc ttaatccagc        1920
ttgcaagtga atggaaaaaa aaataagctt caaactaggt attctgggaa tgatgtaatg       1980
ctctgaattt agtatgatat aaagaaaact ttttgtgct aaaaatactt tttaaaatca        2040 atttttgttga ttgtagtaat ttctatttgc actgtgcctt tcaactccag aaacattctg      2100
aagatgtact tggatttaat taaaaagttc actttgt                                2137
```

<210> SEQ ID NO 118
<211> LENGTH: 1958
<212> TYPE: DNA
<213> ORGANISM: Homo sapiens

<400> SEQUENCE: 118

```
gctgctgcgc ccgcggctcc ccagtgcccc gagtgccccg cgggccccgc gagcgggagt         60
gggacccagc cctaggcaga acccaggcgc gcgcccgggg acgcccgcgg agagagccac        120
tcccgcccac gtcccatttc gcccctcgcg tccggagtcc ccgtggccag atctaaccat        180
gagctaccct ggctatcccc cgcccccagg tggctaccca ccagctgcac caggtggtgg        240
tccctgggga ggtgctgcct accctcctcc gcccagcatg ccccccatcg ggctggataa        300
cgtggccacc tatgcgggc agttcaacca ggactatctc tcgggaatgg cggccaacat        360 gtctggggaca tttggaggag ccaacatgcc caacctgtac cctggggccc ctggggctgg        420
```

```
ctacccacca gtgcccctg gcggctttgg gcagccccc tctgcccagc agcctgttcc      480
tccctatggg atgtatccac ccccaggagg aaacccaccc tccaggatgc cctcatatcc    540
gccataccca ggggcccctg tgccgggcca gccatgcca cccccggac agcagccccc     600 aggggcctac cctgggcagc caccagtgac ctaccctggt cagcctccag tgccactccc   660
tgggcagcag cagccagtgc cgagctaccc aggatacccg gggtctggga ctgtcaccc   720 cgctgtgccc ccaacccagt ttggaagccg aggcaccatc actgatgctc ccggctttga   780 cccctgcga gatgccgagg tcctgcggaa ggccatgaaa ggcttcggga cggatgagca   840
ggccatcatt gactgcctgg ggagtcgctc aacaagcag cggcagcaga tcctactttc    900
cttcaagacg gcttacggca aggatttgat caaagatctg aaatctgaac tgtcaggaaa   960 cttgagaag acaatcttgg ctctgatgaa gaccccagtc ctctttgaca tttatgagat    1020
aaaggaagcc atcaaggggg ttggcactga tgaagcctgc ctgattgaga tcctcgcttc   1080
ccgcagcaat gagcacatcc gagaattaaa cagagcctac aaagcagaat caaaagac     1140 cctggaagag gccattcgaa gcgacacatc agggcacttc cagcggctcc tcatctctct   1200
ctctcaggga aaccgtgatg aaagcacaaa cgtggacatg tcactcgccc agagagatgc   1260
ccaggagctg tatgcggccg gggagaaccg cctgggaaca gacgagtcca gttcaatgc    1320 ggttctgtgc tcccggagcc gggcccacct ggtagcagtt ttcaatgagt accagagaat   1380
gacaggccgg gacattgaga agagcatctg ccgggagatg tccggggacc tggaggaggg   1440
catgctggcc gtggtgaaat gtctcaagaa tacccagcc ttctttgcgg agaggctcaa    1500
caaggccatg agggggcag gaacaaagga ccggaccctg attcgcatca tggtgtctcg    1560
cagcgagacc gacctcctgg acatcagatc agagtataag cggatgtacg gcaagtcgct   1620
gtaccacgac atctcgggag atacttcagg ggattaccgg aagattctgc tgaagatctg   1680
tggtggcaat gactgaacag tgactggtgg ctcacttctg cccacctgcc ggcaacacca   1740
gtgccaggaa aaggccaaaa gaatgtctgt ttctaacaaa tccacaaata gccccgagat   1800
tcaccgtcct agagcttagg cctgtcttcc acccctcctg accgtatag tgtgccacag    1860 gacctgggtc ggtctagaac tctctcagga tgccttttct accccatccc tcacagcctc   1920
ttgctgctaa aatagatgtt tcattttct gaaaaaaa                            1958
```

<210> SEQ ID NO 119
<211> LENGTH: 5791
<212> TYPE: DNA
<213> ORGANISM: Homo sapiens

<400> SEQUENCE: 119

```
ggctcatgct cgggagcgtg gttgagcggc tggcgcggtt gtcctggagc aggggcgcag    60
gaattctgat gtgaaactaa cagtctgtga gccctggaac ctccactcag agaagatgaa   120
ggatatcgac ataggaaaag agtatatcat ccccagtcct gggtatagaa gtgtgaggaa   180
gagaaccagc acttctggga cgcacagaga ccgtgaagat tccaagttca ggagaactcg   240
accgttggaa tgccaagatg ccttggaaac agcagcccga gccgagggcc tctctcttga   300
tgcctccatg cattctcagc tcagaatcct ggatgaggag catcccaagg gaaagtacca   360
tcatggcttg agtgctctga gcccatccg gactacttcc aaacaccagc cccagtgga    420 caatgctggg ctttttttcct gtatgacttt ttcgtggctt tcttctctgg cccgtgtggc   480
ccacaagaag gggagctct caatggaaga cgtgtggtct ctgtccaagc acgagtcttc    540
tgacgtgaac tgcagaagac tagagagact gtggcaagaa gagctgaatg aagttgggcc   600
```

```
agacgctgct tccctgcgaa gggttgtgtg gatcttctgc cgcaccaggc tcatcctgtc      660
catcgtgtgc ctgatgatca cgcagctggc tggcttcagt ggaccagcct tcatggtgaa      720
acacctcttg gagtataccc aggcaacaga gtctaacctg cagtacagct tgttgttagt      780
gctgggcctc ctcctgacgg aaatcgtgcg gtcttggtcg cttgcactga cttgggcatt      840
gaattaccga accggtgtcc gcttgcgggg ggccatccta accatggcat ttaagaagat      900
ccttaagtta aagaacatta aagagaaatc cctgggtgag ctcatcaaca tttgctccaa      960
cgatgggcag agaatgtttg aggcagcagc cgttggcagc ctgctggctg gaggacccgt     1020
tgttgccatc ttaggcatga tttataatgt aattattctg ggaccaacag gcttcctggg     1080
atcagctgtt tttatcctct tttacccagc aatgatgttt gcatcacggc tcacagcata     1140
tttcaggaga aaatgcgtgg ccgccacgga tgaacgtgtc cagaagatga atgaagttct     1200
tacttacatt aaatttatca aaatgtatgc ctgggtcaaa gcattttctc agagtgttca     1260
aaaaatccgc gaggaggagc gtcggatatt ggaaaaagct gggtacttcc agagcatcac     1320
tgtgggtgtg ctcccattg tggtggtgat tgccagcgtg gtgaccttct ctgttcatat     1380
gaccctgggc ttcgatctga cagcagcaca ggcttttcaca gtggtgacag tcttcaattc     1440
catgactttt gctttgaaag taacaccgtt ttcagtaaag tccctctcag aagcctcagt     1500
ggctgttgac agatttaaga gtttgtttct aatggaagag gttcacatga taaagaacaa     1560
accagccagt cctcacatca agatagagat gaaaaatgcc accttggcat gggactcctc     1620
ccactccagt atccagaact cgcccaagct gaccccccaaa atgaaaaaag acaagagggc     1680
ttccaggggc aagaaagaga aggtgaggca gctgcagcgc actgagcatc aggcggtgct     1740
ggcagagcag aaaggccacc tcctcctgga cagtgacgag cggcccagtc ccgaagagga     1800
agaaggcaag cacatccacc tgggccacct gcgcttacag aggacactgc acagcatcga     1860
tctggagatc aagagggta aactggttgg aatctgtggc agtgtgggaa gtggaaaaac     1920
ctctctcatt tcagccattt taggccagat gacgcttcta gagggcagca ttgcaatcag     1980
tggaaccttc gcttatgtgg cccagcaggc ctggatcctc aatgctactc tgagagacaa     2040
catcctgttt gggaaggaat atgatgaaga aagatacaac tctgtgctga acagctgctg     2100
cctgaggcct gacctggcca ttcttcccag cagcgacctg acggagattg agagcgagg     2160
agccaacctg agcggtgggc agcgccagag gatcagcctt gcccgggcct tgtatagtga     2220
caggagcatc tacatcctgg acgacccct cagtgcctta gatgcccatg tgggcaacca     2280
catcttcaat agtgctatcc ggaaacatct caagtccaag acagttctgt tgttaccca     2340
ccagttacag tacctggttg actgtgatga agtgatcttc atgaaagagg ctgtgattac     2400
ggaaagaggc acccatgagg aactgatgaa tttaaatggt gactatgcta ccattttaa     2460
taacctgttg ctgggagaga caccgccagt tgagatcaat tcaaaaaagg aaaccagtgg     2520
ttcacagaag aagtcacaag acaagggtcc taaaacagga tcagtaaaga aggaaaaagc     2580
agtaaagcca gaggaaggc agcttgtgca gctggaagag aaagggcagg ttcagtgcc     2640
ctggtcagta tatggtgtct acatccaggc tgctgggggc cccttggcat tcctggttat     2700
tatgcccctt ttcatgctga atgtaggcag caccgcctc agcacctggt ggttgagtta     2760
ctggatcaag caaggaagcg ggaacaccac tgtgactcga gggaacgaga cctcggtgag     2820
tgacagcatg aaggacaatc ctcatatgca gtactatgcc agcatctacg ccctctccat     2880
ggcagtcatg ctgatcctga aagccattcg aggagttgtc tttgtcaagg gcacgctgcg     2940
```

```
agcttcctcc cggctgcatg acgagctttt ccgaaggatc cttcgaagcc ctatgaagtt   3000
ttttgacacg accccacag ggaggattct caacaggttt tccaaagaca tggatgaagt   3060
tgacgtgcgg ctgccgttcc aggccgagat gttcatccag aacgttatcc tggtgttctt   3120
ctgtgtggga atgatcgcag gagtcttccc gtggttcctt gtggcagtgg ggccccttgt   3180
catcctcttt tcagtcctgc acattgtctc cagggtcctg attcgggagc tgaagcgtct   3240
ggacaatatc acgcagtcac cttcctctc ccacatcacg tccagcatac agggccttgc   3300
caccatccac gcctacaata aagggcagga gtttctgcac agataccagg agctgctgga   3360
tgacaaccaa gctcctttt ttttgtttac gtgtgcgatg cggtggctgg ctgtgcggct   3420
ggacctcatc agcatcgccc tcatcaccac cacggggctg atgatcgttc ttatgcacgg   3480
gcagattccc ccagcctatg cgggtctcgc catctcttat gctgtccagt taacggggct   3540
gttccagttt acggtcagac tggcatctga acagaagct cgattcacct cggtggagag   3600
gatcaatcac tacattaaga ctctgtcctt ggaagcacct gccagaatta gaacaaggc   3660
tccctcccct gactggcccc aggagggaga ggtgaccttt gagaacgcag agatgaggta   3720
ccgagaaaac ctccctctcg tcctaaagaa agtatccttc acgatcaaac ctaaagagaa   3780
gattggcatt gtggggcgga caggatcagg gaagtcctcg ctggggatgg ccctcttccg   3840
tctggtggag ttatctggag gctgcatcaa gattgatgga gtgagaatca gtgatattgg   3900
ccttgccgac ctccgaagca aactctctat cattcctcaa gagccggtgc tgttcagtgg   3960
cactgtcaga tcaaatttgg accccttcaa ccagtacact gaagaccaga tttgggatgc   4020
cctggagagg acacacatga aagaatgtat tgctcagcta cctctgaaac ttgaatctga   4080
agtgatggaa aatggggata acttctcagt ggggaacgg cagctcttgt gcatagctag   4140
agccctgctc cgccactgta agattctgat tttagatgaa gccacagctg ccatggacac   4200
agagacagac ttattgattc aagagaccat ccgagaagca tttgcagact gtaccatgct   4260
gaccattgcc catcgcctgc acacggttct aggctccgat aggattatgg tgctggccca   4320
gggacaggtg gtggagtttg acacccccatc ggtccttctg tccaacgaca gttcccgatt   4380
ctatgccatg tttgctgctg cagagaacaa ggtcgctgtc aagggctgac tcctccctgt   4440
tgacgaagtc tcttttcttt agagcattgc cattccctgc ctggggcggg ccctcatcg   4500
cgtcctccta ccgaaacctt gccttctcg attttatctt tcgcacagca gttccggatt   4560
ggcttgtgtg tttcactttt agggagagtc atatttgat tatttgtattt attccatatt   4620
catgtaaaca aaatttagtt tttgttctta attgcactct aaaaggttca gggaaccgtt   4680
attataattg tatcagaggc ctataatgaa gctttatacg tgtagctata tctatatata   4740
attctgtaca tagcctatat ttacagtgaa aatgtaagct gtttattta tattaaaata   4800
agcactgtgc taataacagt gcatattcct ttctatcatt tttgtacagt ttgctgtact   4860
agagatctgt ttttgctatt agactgtagg aagagtagca tttcattctt ctctagctgg   4920
tggtttcacg gtgccaggtt ttctgggtgt ccaaaggaag acgtgtggca atagtgggcc   4980
ctccgacagc cccctctgcc gcctcccac ggccgctcca gggtggctg gagacgggtg   5040
ggcggctgga gaccatgcag agcgccgtga gttctcaggg ctcctgcctt ctgtcctggt   5100
gtcacttact gtttctgtca ggagagcagc ggggcgaagc ccaggccct tttcactccc   5160
tccatcaaga atggggatca cagagacatt cctccgagcc ggggagtttc tttcctgcct   5220
tcttcttttt gctgttgttt ctaaacaaga atcagtctat ccacagagag tcccactgcc   5280
tcaggttcct atggctggcc actgcacaga gctctccagc tccaagacct gttggttcca   5340
```

-continued

| | |
|---|---|
| agccctggag ccaactgctg cttttttgagg tggcactttt tcatttgcct attcccacac | 5400 |
| ctccacagtt cagtggcagg gctcaggatt tcgtgggtct gttttccttt ctcaccgcag | 5460 |
| tcgtcgcaca gtctctctct ctctctcccc tcaaagtctg caactttaag cagctcttgc | 5520 |
| taatcagtgt ctcacactgg cgtagaagtt tttgtactgt aaagagacct acctcaggtt | 5580 |
| gctggttgct gtgtggtttg gtgtgttccc gcaaacccccc tttgtgctgt ggggctggta | 5640 |
| gctcaggtgg gcgtggtcac tgctgtcatc aattgaatgg tcagcgttgc atgtcgtgac | 5700 |
| caactagaca ttctgtcgcc ttagcatgtt tgctgaacac cttgtggaag caaaaatctg | 5760 |
| aaaatgtgaa taaaattatt ttggattttg t | 5791 |

<210> SEQ ID NO 120
<211> LENGTH: 1992
<212> TYPE: DNA
<213> ORGANISM: Homo sapiens

<400> SEQUENCE: 120

| | |
|---|---|
| aaacttcccg cacgcgttac aggagccagg tcggtataag cgccacgcct cgccgcccgt | 60 |
| caagctgtcc acatccctgg cctcagcccg ccacatcacc ctgacctgct tacgcccaga | 120 |
| tttttcttcaa tcacatctga ataaatcact tgaagaaagc ttatagcttc attgcaccat | 180 |
| gtgtggcatt tgggcgctgt ttggcagtga tgattgcctt tctgttcagt gtctgagtgc | 240 |
| tatgaagatt gcacacagag gtccagatgc attccgtttt gagaatgtca atggatacac | 300 |
| caactgctgc tttggatttc accggttggc ggtagttgac ccgctgtttg gaatgcagcc | 360 |
| aattcgagtg aagaaatatc cgtatttgtg gctctgttac aatggtgaaa tctacaacca | 420 |
| taagaagatg caacagcatt tgaatttga ataccagacc aaagtggatg gtgagataat | 480 |
| ccttcatctt tatgacaaag gaggaattga gcaaacaatt tgtatgttgg atggtgtgtt | 540 |
| tgcatttgtt ttactggata ctgccaataa gaaagtgttc ctgggtagag atacatatgg | 600 |
| agtcagacct tgtttaaag caatgacaga agatggattt ttggctgtat gttcagaagc | 660 |
| taaaggtctt gttacattga agcactccgc gactcccttt ttaaaagtgg agccttttct | 720 |
| tcctggacac tatgaagttt tggatttaaa gccaaatggc aaagttgcat ccgtggaaat | 780 |
| ggttaaaatat catcactgtc gggatgtacc cctgcacgcc ctctatgaca atgtggagaa | 840 |
| actctttcca ggttttgaga tagaaactgt gaagaacaac ctcaggatcc tttttaataa | 900 |
| tgctgtaaag aaacgtttga tgacagacag aaggattggc tgccttttat cagggggctt | 960 |
| ggactccagc ttggttgctg ccactctgtt gaagcagctg aaagaagccc aagtacagta | 1020 |
| tcctctccag acatttgcaa ttggcatgga agacagcccc gatttactgg ctgctagaaa | 1080 |
| ggtggcagat catattggaa gtgaacatta tgaagtcctt tttaactctg aggaaggcat | 1140 |
| tcaggctctg gatgaagtca tattttcctt ggaaacttat gacattacaa cagttcgtgc | 1200 |
| ttcagtaggt atgtatttaa tttccaagta tattcggaag aacacagata gcgtggtgat | 1260 |
| cttctctgga gaaggatcag atgaacttac gcagggttac atatattttc acaaggctcc | 1320 |
| ttctcctgaa aaagccgagg aggagagtga gaggcttctg agggaactct atttgtttga | 1380 |
| tgttctccgc gcagatcgaa ctactgctgc ccatggtctt gaactgagag tcccatttct | 1440 |
| agatcatcga tttttttcct attacttgtc tctgccacca gaaatgagaa ttccaaagaa | 1500 |
| tgggatagaa aaacatctcc tgagagagac gtttgaggat tccaatctga tacccaagga | 1560 |
| gattctctgg cgaccaaaag aagccttcag tgatggaata acttcagtta agaattcctg | 1620 |

-continued

| | |
|---|---|
| gtttaagatt ttacaggaat acgttgaaca tcaggttgat gatgcaatga tggcaaatgc | 1680 |
| agcccagaaa tttcccttca atactcctaa aaccaaagaa ggatattact accgtcaagt | 1740 |
| ctttgaacgc cattacccag gccgggctga ctggctgagc cattactgga tgcccaagtg | 1800 |
| gatcaatgcc actgacccct ctgcccgcac gctgacccac tacaagtcag ctgtcaaagc | 1860 |
| ttaggtggtc tttatgctgt aatgtgaaag caaatatttc ttcgtgttgg atggggactg | 1920 |
| tgggtagata ggggaacaat gagagtcaac tcaggctaac ttgggtttga aaaaataaa | 1980 |
| attcctaaat tt | 1992 |

<210> SEQ ID NO 121
<211> LENGTH: 5698
<212> TYPE: DNA
<213> ORGANISM: Homo sapiens

<400> SEQUENCE: 121

| | |
|---|---|
| aggttcaagt ggagctctcc taaccgacgc gcgtctgtgg agaagcggct tggtcggggg | 60 |
| tggtctcgtg gggtcctgcc tgtttagtcg ctttcagggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aagaaaaca | 240 |
| caattggaac atattttgct ccgcccagac acctacattg gttctgtgga attagtgacc | 300 |
| cagcaaatgt gggtttacga tgaagatgtt ggcattaact atagggaagt cacttttgtt | 360 |
| cctggttttgt acaaaatctt tgatgagatt ctagttaatg ctgcggacaa caaacaaagg | 420 |
| gacccaaaaa tgtcttgtat tagagtcaca attgatccgg aaaacaattt aattagtata | 480 |
| tggaataatg aaaaggtat tcctgttgtt gaacacaaag ttgaaaagat gtatgtccca | 540 |
| gctctcatat ttggacagct cctaacttct agtaactatg atgatgatga aagaaagtg | 600 |
| acaggtggtc gaaatggcta tggagccaaa ttgtgtaaca tattcagtac caaatttact | 660 |
| gtggaaacag ccagtagaga atacaagaaa atgttcaaac agacatggat ggataatatg | 720 |
| ggaagagctg gtgagatgga actcaagccc ttcaatggag aagattatac atgtatcacc | 780 |
| tttcagcctg atttgtctaa gtttaaaatg caaagcctgg acaaagatat tgttgcacta | 840 |
| atggtcagaa gagcatatga tattgctgga tccaccaaag atgtcaaagt ctttcttaat | 900 |
| ggaaataaac tgccagtaaa aggatttcgt agttatgtgg acatgtattt gaaggacaag | 960 |
| ttggatgaaa ctggtaactc cttgaaagta atacatgaac aagtaaacca caggtgggaa | 1020 |
| gtgtgtttaa ctatgagtga aaaaggcttt cagcaaatta gctttgtcaa cagcattgct | 1080 |
| acatccaagg gtggcagaca tgttgattat gtagctgatc agattgtgac taaacttgtt | 1140 |
| gatgttgtga agaagaagaa caagggtggt gttgcagtaa aagcacatca ggtgaaaaat | 1200 |
| cacatgtgga tttttgtaaa tgccttaatt gaaaacccaa cctttgactc tcagacaaaa | 1260 |
| gaaaacatga ctttacaacc caagagcttt ggatcaacat gccaattgag tgaaaaattt | 1320 |
| atcaaagctg ccattggctg tggtattgta gaaagcatac taaactgggt gaagtttaag | 1380 |
| gcccaagtcc agtaaacaa gaagtgttca gctgtaaaac ataatagaat caagggaatt | 1440 |
| cccaaactcg atgatgccaa tgatgcaggg ggccgaaact ccactgagtg tacgcttatc | 1500 |
| ctgactgagg gagattcagc caaaactttg gctgtttcag gccttggtgt ggttgggaga | 1560 |
| gacaaatatg gggttttccc tcttagagga aaaatactca atgttcgaga agcttctcat | 1620 |
| aagcagatca tggaaaatgc tgagattaac aatatcatca agattgtggg tcttcagtac | 1680 |
| aagaaaaact atgaagatga agattcattg aagacgcttc gttatgggaa gataatgatt | 1740 |

```
atgacagatc aggaccaaga tggttcccac atcaaaggct tgctgattaa ttttatccat    1800
cacaactggc cctctcttct gcgacatcgt tttctggagg aatttatcac tcccattgta    1860
aaggtatcta aaaacaagca agaaatggca ttttacagcc ttcctgaatt tgaagagtgg    1920
aagagttcta ctccaaatca taaaaaatgg aaagtcaaat attacaaagg tttgggcacc    1980
agcacatcaa aggaagctaa agaatacttt gcagatatga aaagacatcg tatccagttc    2040
aaatattctg gtcctgaaga tgatgctgct atcagcctgg cctttagcaa aaacagata    2100
gatgatcgaa aggaatggtt aactaatttc atggaggata aagacaacg aaagttactt    2160
gggcttcctg aggattactt gtatggacaa actaccacat atctgacata taatgacttc    2220
atcaacaagg aacttatctt gttctcaaat tctgataacg agagatctat cccttctatg    2280
gtggatggtt tgaaaccagg tcagagaaag gttttgttta cttgcttcaa acggaatgac    2340
aagcgagaag taaggttgc ccaattagct ggatcagtgg ctgaaatgtc ttcttatcat    2400
catggtgaga tgtcactaat gatgaccatt atcaatttgg ctcagaattt tgtgggtagc    2460
aataatctaa acctcttgca gcccattggt cagtttggta ccaggctaca tggtggcaag    2520
gattctgcta gtccacgata catctttaca atgctcagct ctttggctcg attgttattt    2580
ccaccaaaag atgatcacac gttgaagttt ttatatgatg acaaccagcg tgttgagcct    2640
gaatggtaca ttcctattat tcccatggtg ctgataaatg gtgctgaagg aatcggtact    2700
gggtggtcct gcaaaatccc caactttgat gtgcgtgaaa ttgtaaataa catcaggcgt    2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaaacatgga cccagacata caaagaacaa    2940
gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc ttttgacca cgtaggctgt ttaaagaaat atgacacggt gttggatatt    3180
ctaagagact ttttttgaact cagacttaaa tattatggat taagaaaaga atggctccta    3240
ggaatgcttg gtgctgaatc tgctaaactg aataatcagg ctcgctttat cttagagaaa    3300
atagatggca aaataatcat tgaaaataag cctaagaaag aattaattaa agttctgatt    3360
cagaggggat atgattcgga tcctgtgaag gcctggaaaa aagcccagca aaaggttcca    3420
gatgaagaag aaaatgaaga gagtgacaac gaaaaggaaa ctgaaaagag tgactccgta    3480
acagattctg gaccaacctt caactatctt cttgatatgc cccttttggta tttaaccaag    3540
gaaaagaaag atgaactctg caggctaaga aatgaaaaag aacaagagct ggacacatta    3600
aaaagaaaga gtccatcaga tttgtggaaa aagacttgg ctacatttat tgaagaattg    3660
gaggctgttg aagccaagga aaacaagat gaacaagtcg acttcctgg gaaagggggg    3720
aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa    3840
attaagaatg aaaatactga aggaagccct caagaagatg gtgtggaact agaaggccta    3900
aaacaaagat tagaaaagaa acagaaaaga gaaccaggta caaagacaaa gaaacaaact    3960
acattggcat ttaagccaat caaaaaagga aagaagagaa atccctggtc tgattcagaa    4020
tcagatagga gcagtgacga aagtaatttt gatgtccctc cacgagaaac agagccacgg    4080
```

| | |
|---|---|
| agagcagcaa caaaaacaaa attcacaatg gatttggatt cagatgaaga tttctcagat | 4140 |
| tttgatgaaa aaactgatga tgaagatttt gtcccatcag atgctagtcc acctaagacc | 4200 |
| aaaacttccc caaaacttag taacaaagaa ctgaaaccac agaaaagtgt cgtgtcagac | 4260 |
| cttgaagctg atgatgttaa gggcagtgta ccactgtctt caagccctcc tgctacacat | 4320 |
| ttcccagatg aaactgaaat tacaaaccca gttcctaaaa agaatgtgac agtgaagaag | 4380 |
| acagcagcaa aaagtcagtc ttccacctcc actaccggtg ccaaaaaaag ggctgcccca | 4440 |
| aaaggaacta aagggatcc agctttgaat tctggtgtct ctcaaaagcc tgatcctgcc | 4500 |
| aaaaccaaga atcgccgcaa aaggaagcca tccacttctg atgattctga ctctaatttt | 4560 |
| gagaaaattg tttcgaaagc agtcacaagc aagaaatcca aggggagag tgatgacttc | 4620 |
| catatggact ttgactcagc tgtggctcct cgggcaaaat ctgtacgggc aaagaaacct | 4680 |
| ataaagtacc tggaagagtc agatgaagat gatctgtttt aaaatgtgag gcgattattt | 4740 |
| taagtaatta tcttaccaag cccaagactg gttttaaagt tacctgaagc tcttaacttc | 4800 |
| ctcccctctg aatttagttt ggggaaggtg ttttagtac aagacatcaa agtgaagtaa | 4860 |
| agcccaagtg ttctttagct ttttataata ctgtctaaat agtgaccatc tcatgggcat | 4920 |
| tgttttcttc tctgctttgt ctgtgttttg agtctgcttt cttttgtctt taaaacctga | 4980 |
| tttttaagtt cttctgaact gtagaaatag ctatctgatc acttcagcgt aaagcagtgt | 5040 |
| gtttattaac catccactaa gctaaaacta gagcagtttg atttaaaagt gtcactcttc | 5100 |
| ctccttttct actttcagta gatatgagat agagcataat tatctgtttt atcttagttt | 5160 |
| tatacataat ttaccatcag atagaacttt atggttctag tacagatact ctactacact | 5220 |
| cagcctctta tgtgccaagt ttttctttaa gcaatgagaa attgctcatg ttcttcatct | 5280 |
| tctcaaatca tcagaggcca aagaaaaaca ctttggctgt gtctataact tgacacagtc | 5340 |
| aatagaatga agaaaattag agtagttatg tgattatttc agctcttgac ctgtcccctc | 5400 |
| tggctgcctc tgagtctgaa tctcccaaag agagaaacca atttctaaga ggactggatt | 5460 |
| gcagaagact cggggacaac atttgatcca agatcttaaa tgttatattg ataaccatgc | 5520 |
| tcagcaatga gctattagat tcattttggg aaatctccat aatttcaatt tgtaaacttt | 5580 |
| gttaagacct gtctacattg ttatatgtgt gtgacttgag taatgttatc aacgttttg | 5640 |
| taaatattta ctatgttttt ctattagcta aattccaaca attttgtact ttaataaa | 5698 |

<210> SEQ ID NO 122
<211> LENGTH: 2753
<212> TYPE: DNA
<213> ORGANISM: Homo sapiens

<400> SEQUENCE: 122

| | |
|---|---|
| gcgccatgga gcagtggcgg cagtgcggcc gctggctcat cgattgcaag gtcctgccgc | 60 |
| ccaaccaccg ggtggtgtgg ccctcggccg tggtcttcga cctggcgcag gcgctgcgcg | 120 |
| acggggtcct tctgtgccag ctgctgcaca acctctcccc cggctccatc gacctcaagg | 180 |
| acatcaactt ccgccgcag atgtcccagt ttctgtgttt gaagaacata cgcaccttcc | 240 |
| tgaaagtctg ccacgataaa tttggattaa ggaacagcga gctgtttgac ccctttgacc | 300 |
| tcttcgatgt gcgagacttt ggaaaggtca tctccgcggt gtcgaggctc tccctgcaca | 360 |
| gcatcgcgca gaacaaaggg atcaggcctt ttccctcaga ggagaccaca gagaatgacg | 420 |
| atgacgtcta ccgcagcctg gaggagctgg ccgacgagca tgacctgggg gaggacatct | 480 |
| acgactgcgt cccgtgtgag gatggagggg acgacatcta cgaggacatc atcaaggtgg | 540 |

-continued

```
aggtgcagca gcccatgatt agatacatgc agaaaatggg catgactgaa gatgacaaga    600
ggaactgctg cctgctggag atccaggaga ccgaggccaa gtactaccgc accctggagg    660
acattgagaa gaactacatg agcccccctgc ggctggtgct gagcccggcg acatggcag    720
ctgtcttcat taacctggag gacctgatca aggtgcatca cagcttcctg agggccatcg    780
acgtgtccgt gatggtgggg ggcagcacgc tggccaaggt cttcctcgat ttcaaggaaa    840
ggcttctgat ctacggggag tactgcagcc acatggagca cgcccagaac acactgaacc    900
agctcctggc cagccgggag gacttcaggc agaaagtcga ggagtgcaca ctgaaggtcc    960
aggatggaaa atttaagctg caagacctgc tggtggtccc catgcagagg gtgctcaaat    1020
accacctgct cttgaaggag cttctgagcc attctgcgga acggcctgag aggcagcagc    1080
tcaaagaagc actggaagcc atgcaggact tggcgatgta catcaatgaa gttaaacggg    1140
acaaggagac cttgaggaaa atcagcgaat tcagagttc tatagaaaat ttgcaagtga    1200
aactggagga atttggaaga ccaaagattg acggggaact gaaagtccgg tccatagtca    1260
accacaccaa gcaggacagg tacttgttcc tgtttgacaa ggtggtcatc gtctgcaagc    1320
ggaagggcta cagctacgag ctcaaggaga tcatcgagct gctgttccac aagatgaccg    1380
acgacccat gaacaacaag gacgtcaaga agtctcacgg gaaaatgtgg tcctacggct    1440
tctacctaat tcaccttcaa ggaaagcagg gcttccagtt tttctgcaaa acagaagata    1500
tgaagaggaa gtggatggag cagtttgaga tggccatgtc aaacatcaag ccagacaaag    1560
ccaatgccaa ccaccacagt ttccagatgt acacgtttga caagaccacc aactgcaaag    1620
cctgcaaaat gttcctcagg ggcaccttct accagggata catgtgtacc aagtgtggcg    1680
tcggggcaca caaggagtgc ctggaagtga tacctccctg caagttcact ctctcctgcag    1740
atctggacgc ctccggagcg ggaccaggtc ccaagatggt ggccatgcag aattaccatg    1800
gcaacccagc ccctcccggg aagcctgtgc tgaccttcca gacgggcgac gtgcttgagc    1860
tgctgagggg cgaccctgag tctccgtggt gggagggtcg tctggtacaa accaggaagt    1920
cagggtatt ccccagctca tctgtgaagc cctgccctgt ggatggaagg ccgcccatca    1980
gccggccgcc atcccgggag atcgactaca ctgcataccc ctggtttgca ggtaacatgg    2040
agaggcagca gacggacaac ctgctcaagt cccacgccag cgggacctac ctgatcaggg    2100
agcggcctgc cgaggctgag cgctttgcaa taagcatcaa gttcaatgat gaggtgaagc    2160
acatcaaggt ggtggagaag gacaactgga tccacatcac agaggccaag aaattcgaca    2220
gcctcctgga gttggtggag tactaccagt gccactcact gaaggagagc ttcaagcagc    2280
tggacaccac actcaagtac ccctacaagt cccgggaacg ttcggcctcc agggcctcca    2340
gccggtcccc agcttcctgt gcttcctaca actttctt tctcagtcct cagggcctca    2400
gctttgcttc tcagggcccc tccgctccct tctggtcagt gttcacgccc cgcgtcatcg    2460
gcacagctgt ggccaggtat aactttgccg cccgagatat gagggagctt tcgctgcggg    2520
aggtgacgt ggtgaggatc tacagccgca tcggcggaga ccagggctgg tggaagggcg    2580
agaccaacgg acggattggc tggtttcctt caacgtacgt agaagaggag ggcatccagt    2640
gacggcagga acgtggacaa gactcgcaga ttttcttggg agagtcactc cagccctgaa    2700
gtctgtctct agctcctctg tgactcagag gggaaatacc aacctcccag tct           2753
```

<210> SEQ ID NO 123
<211> LENGTH: 23
<212> TYPE: DNA

```
-continued

<213> ORGANISM: Artificial
<220> FEATURE:
<223> OTHER INFORMATION: Synthetic

<400> SEQUENCE: 123
cgtatgcccc gctgaatctc gtg                                              23
```